(12) United States Patent
Haas et al.

(10) Patent No.: US 9,326,513 B2
(45) Date of Patent: May 3, 2016

(54) FUNGICIDAL COMPOSITIONS

(75) Inventors: Ulrich Johannes Haas, Stein (CH); Dietrich Hermann, Stein (CH); Gabriel Didier Scalliet, Stein (CH); Kurt Nebel, Stein (CH); Long Lu, Shanghai (CN); Qiang Lu, Shanghai (CN); Jianzhong Yang, Shanghai (CN); Thomas James Hoffman, Stein (CH); Renaud Beaudegnies, Stein (CH); Werner Zambach, Stein (CH); Olivier Jacob, Stein (CH)

(73) Assignee: Syngenta Participations AG, Basel (CH)

( * ) Notice: Subject to any disclaimer, the term of this patent is extended or adjusted under 35 U.S.C. 154(b) by 236 days.

(21) Appl. No.: 14/362,709

(22) PCT Filed: Apr. 9, 2012

(86) PCT No.: PCT/CN2012/073665
§ 371 (c)(1),
(2), (4) Date: Jun. 4, 2014

(87) PCT Pub. No.: WO2012/146125
PCT Pub. Date: Nov. 1, 2012

(65) Prior Publication Data
US 2014/0335201 A1    Nov. 13, 2014

(30) Foreign Application Priority Data

Apr. 26, 2011  (EP) .................................... 11163731
Dec. 14, 2011  (WO) ................ PCT/CN2011/084016

(51) Int. Cl.
| | |
|---|---|
| *A01N 43/40* | (2006.01) |
| *A01N 35/06* | (2006.01) |
| *A01N 37/10* | (2006.01) |
| *A01N 37/18* | (2006.01) |
| *A01N 41/10* | (2006.01) |
| *A01N 43/22* | (2006.01) |
| *C07D 213/74* | (2006.01) |
| *C07F 7/08* | (2006.01) |
| *A01N 59/20* | (2006.01) |
| *A01N 57/20* | (2006.01) |
| *A01N 55/00* | (2006.01) |
| *A01N 53/00* | (2006.01) |
| *A01N 47/40* | (2006.01) |
| *A01N 47/42* | (2006.01) |
| *A01N 43/36* | (2006.01) |
| *A01N 43/38* | (2006.01) |
| *A01N 43/52* | (2006.01) |
| *A01N 43/54* | (2006.01) |
| *A01N 43/56* | (2006.01) |
| *A01N 43/653* | (2006.01) |
| *A01N 43/80* | (2006.01) |
| *A01N 43/82* | (2006.01) |
| *A01N 43/84* | (2006.01) |
| *A01N 43/88* | (2006.01) |
| *A01N 59/16* | (2006.01) |

(52) U.S. Cl.
CPC ............... *A01N 43/40* (2013.01); *A01N 35/06* (2013.01); *A01N 37/10* (2013.01); *A01N 37/18* (2013.01); *A01N 41/10* (2013.01); *A01N 43/22* (2013.01); *A01N 43/36* (2013.01); *A01N 43/38* (2013.01); *A01N 43/52* (2013.01); *A01N 43/54* (2013.01); *A01N 43/56* (2013.01); *A01N 43/653* (2013.01); *A01N 43/80* (2013.01); *A01N 43/82* (2013.01); *A01N 43/84* (2013.01); *A01N 43/88* (2013.01); *A01N 47/40* (2013.01); *A01N 47/42* (2013.01); *A01N 53/00* (2013.01); *A01N 55/00* (2013.01); *A01N 57/20* (2013.01); *A01N 59/16* (2013.01); *A01N 59/20* (2013.01); *C07D 213/74* (2013.01); *C07F 7/0812* (2013.01); *Y02P 60/218* (2015.11)

(58) Field of Classification Search
CPC ....... A01N 43/40; A01N 35/06; A01N 37/10; A01N 37/18; A01N 41/10; A01N 43/22; A01N 43/36; A01N 43/38; A01N 43/52; A01N 43/54; A01N 43/56; A01N 43/653; A01N 43/80; A01N 43/82; A01N 43/84; A01N 43/88; A01N 47/40; A01N 47/42; A01N 53/00; A01N 55/00; A01N 57/20; A01N 59/16; A01N 59/20; C07D 213/74; C07F 7/0812
See application file for complete search history.

(56) References Cited

U.S. PATENT DOCUMENTS

2007/0155802 A1*  7/2007  Labourdette ........... A01N 37/52
                                                    514/355

FOREIGN PATENT DOCUMENTS

| WO | 2008/101682 | | 8/2008 | | |
|---|---|---|---|---|---|
| WO | WO2008101682 A2 | * | 8/2008 | .......... | C07D 213/16 |
| WO | 2009/088103 | | 7/2009 | | |
| WO | WO2009088103 A1 | * | 7/2009 | .............. | A01N 43/40 |

OTHER PUBLICATIONS

International Search Report dated Jul. 19, 2012 for International Patent Application No. PCT/CN2012/073665.

* cited by examiner

*Primary Examiner* — Jane C Osweckí
(74) *Attorney, Agent, or Firm* — R. Kody Jones

(57) ABSTRACT

The present invention provides a composition comprising a combination of components A) and B), wherein component A) is a compound of formula (I) and the component (B) is a further fungicide, insecticide or herbicide.

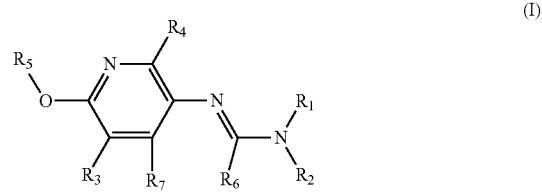

(I)

16 Claims, No Drawings

FUNGICIDAL COMPOSITIONS

RELATED APPLICATION INFORMATION

This application is a 371 of International Application No. PCT/CN2012/073665, filed 9 Apr. 2012, which claims priority to International Application No. PCT/CN2011/084016, filed 14 Dec. 2011, the contents of which are incorporated herein by reference.

The present invention relates to novel fungicidal compositions which comprise fungicidally active pyridylamidine compounds for the treatment of phytopathogenic diseases of useful plants, especially phytopathogenic fungi, and to a method of controlling phytopathogenic diseases on useful plants.

Certain phenylamidine derivatives are described in WO2008/101682 as microbicidally active ingredients in pesticides.

The present invention provides a composition comprising a combination of components A) and B), wherein component A) is a compound of formula (I)

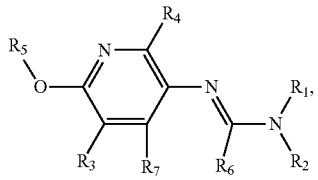

(I)

wherein $R_1$ and $R_2$ are each independently selected from hydrogen, $C_1$-$C_4$ alkyl, $C_3$-$C_4$ alkenyl, $C_3$-$C_4$ alkynyl, $(R_{10})$carbonyl and $(R_{10})$oxycarbonyl;

or $R_1$ and $R_2$ together with the nitrogen atom to which they are attached form a 5- or 6 membered cyclic group which may be saturated or unsaturated and may contain a further heteroatom selected from S or O;

$R_3$ represents hydrogen, halogen, cyano, nitro, mercapto, hydroxy, —C(=S)NH$_2$, —SF$_5$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ cycloalkyl, amino, $C_1$-$C_2$ alkylamino, di($C_1$-$C_6$ alkyl)amino, a 5-membered heterocycle containing 1-4 nitrogen atoms, piperidino, morpholino, thiomorpholino, formyl, hydroxycarbonyl, $C_2$-$C_7$ alkoxycarbonyl, $C_2$-$C_7$ haloalkoxycarbonyl, $C_4$-$C_7$ alkenyloxycarbonyl, $C_4$-$C_7$ haloalkenyloxycarbonyl, $C_2$-$C_7$ alkylcarbonyl, $C_2$-$C_7$ haloalkylcarbonyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ hydroxyalkyl, phenyl or benzyl wherein the phenyl and benzyl are optionally substituted by one or more groups independently selected from the group consisting of halogen, cyano, hydroxy, mercapto, amino, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl;

$R_4$ represents hydrogen, halogen, cyano, amino, $C_1$-$C_4$alkyl, $C_1$-$C_4$ haloalkyl, $C_3$-$C_6$ cycloalkyl, $C_2$-$C_4$ alkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, methylamino and dimethylamino;

$R_5$ is hydrogen, $C_1$-$C_{12}$alkyl, $C_3$-$C_{12}$alkenyl, $C_3$-$C_{12}$alkynyl, $C_1$-$C_{12}$alkylsulfonyl, $C_2$-$C_{12}$alkenylsulfonyl, phenylsulfonyl or benzylsulfonyl, or is $C_1$-$C_{12}$alkyl, $C_2$-$C_{12}$alkenyl, $C_2$-$C_{12}$alkynyl, $C_1$-$C_{12}$alkylsulfonyl, $C_2$-$C_{12}$alkenylsulfonyl, phenylsulfonyl or benzylsulfonyl mono- to polysubstituted by substituents independently selected from the group consisting of halogen, cyano, nitro, hydroxy, mercapto, azido, formyl, $C_2$-$C_7$alkylcarbonyl, $C_2$-$C_7$haloalkylcarbonyl, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or $R_5$ is formyl, $C_2$-$C_{12}$ alkylcarbonyl, $C_3$-$C_{12}$ alkenylcarbonyl, $C_3$-$C_{12}$ alkynylcarbonyl, $C_4$-$C_{12}$ cycloalkylcarbonyl, benzylcarbonyl, phenylcarbonyl, $C_2$-$C_{12}$ alkoxycarbonyl, $C_4$-$C_{12}$ alkenyloxycarbonyl, $C_4$-$C_{12}$ alkynyloxycarbonyl, $C_4$-$C_{12}$ cycloalkoxycarbonyl, benzyloxycarbonyl or phenoxycarbonyl, or is $C_2$-$C_{12}$ alkylcarbonyl, $C_3$-$C_{12}$ alkenylcarbonyl, $C_3$-$C_{12}$ alkynylcarbonyl, $C_4$-$C_{12}$ cycloalkylcarbonyl, benzylcarbonyl, phenylcarbonyl, $C_2$-$C_{12}$ alkoxycarbonyl, $C_4$-$C_{12}$ alkenyloxycarbonyl, $C_4$-$C_{12}$ alkynyloxycarbonyl, $C_4$-$C_{12}$ cycloalkoxycarbonyl, benzyloxycarbonyl or phenoxycarbonyl mono- to polysubstituted by substituents independently selected from the group consisting of halogen, cyano, $C_1$-$C_6$ alkyl, $C_1$-$C_6$ haloalkyl and $C_1$-$C_6$ alkoxy; or $R_5$ is $(R_{51})(R_{52})(R_{53})$Si—, $(R_{51})(R_{52})(R_{53})$Si—$(C_1$-$C_{12}$alkyl)-, $(R_{51})(R_{52})(R_{53})$Si—$(C_3$-$C_8$cycloalkyl)-, $(R_{54}O)(R_{55}O)(R_{56}O)$Si—, $(R_{54}O)(R_{55}O)(R_{56}O)$Si—$(C_1$-$C_{12}$alkyl)- or $(R_{54}O)(R_{55}O)(R_{56}O)$Si—$(C_3$-$C_8$cycloalkyl)-; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl, $C_2$-$C_{12}$alkenyl-, $C_3$-$C_8$cycloalkyl-N—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl- or phenyl-B—$C_3$-$C_{12}$cycloalkyl-, wherein the group B is selected from —C(=O)—, —C(=S)—, —C(=NOR$_{59}$)—, —C(R$_{60}$) =NO—, —ON=C(R$_{60}$)—, —O—C(=O)—, —C(=O)— O—, —O—, —S—, —S(=O)—, —S(=O)$_2$—, —S(=O) (=NR$_{13}$)—, —S(=O)(R$_{14}$)=N—, —N=S(=O)(R$_{14}$)—, —N(R$_{62}$)—C(=O)—, —C(=O)—N(R$_{62}$)—, —N(R$_{62}$)— SO$_2$— or —SO$_2$—N(R$_{62}$)—; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl-, phenyl-B—$C_3$-$C_{12}$cycloalkyl-, all of which, in turn, are mono- to poly-substituted by substituents independently selected from the group consisting of halogen, cyano, hydroxy, mercapto, $C_1$-$C_6$ haloalkyl, $C_1$-$C_6$ alkoxy, formyl, $C_2$-$C_6$ alkylcarbonyl, $C_1$-$C_6$ alkylthio, $C_1$-$C_6$ alkylsulfinyl and $C_1$-$C_6$ alkylsulfonyl; or $R_5$ is A-, A-($C_1$-$C_6$alkyl)-, A-O—($C_1$-$C_6$alkyl)-, A-($C_3$-$C_6$alkenyl)-, A-O—($C_4$-$C_6$alkenyl)-, A-($C_3$-$C_6$-alkynyl)-, A-O—($C_4$-$C_6$alkynyl)-, A-($C_3$-$C_8$cycloalkyl)- or A-O—($C_3$-$C_8$cycloalkyl)-;

wherein A is a three- to ten-membered monocyclic or fused bicyclic ring system which can be aromatic, partially saturated or fully saturated and can contain 1 to 4 hetero atoms selected from the group consisting of nitrogen, oxygen and sulphur, it not being possible for each ring system to contain —O—O—, —S—S— and —O—S— fragments, and it being possible for the three- to ten-membered ring system to be itself mono- or polysubstituted A1) by substituents independently selected from the group consisting of halogen, cyano, nitro, hydroxy, mercapto, azido, formyl, carboxy, =O, =S, $C_1$-$C_6$ alkyl, $C_2$-$C_6$ alkenyl, $C_2$-$C_6$ alkynyl, $C_3$-$C_8$ cycloalkyl, $C_1$-$C_6$ haloalkyl, $C_2$-$C_6$ haloalkenyl, $C_2$-$C_6$ haloalkynyl, $C_3$-$C_8$ halocycloalkyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_8$ cycloalkyloxy, benzyl, benzyloxy, phenyl and phenoxy, where the benzyl, benzyloxy, phenyl and phenoxy, in turn, may be mono- to polysubstituted by substituents independently selected from the group consisting of halogen, cyano, nitro, hydroxy, mercapto, amino, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or A2) by substituents independently selected form the group consisting of $(R_{14})S(=O)(=NR_{13})—$, $(R_{14})(R_{15})S(=O)=N—$; $—Si(R_{51})(R_{52})(R_{53})$, $—NR_{57}R_{58}$, $—C(=O)NR_{57}R_{58}$, $C(=S)NR_{57}R_{58}$, $HC(=NOR_{59})—$, $(C_1$-$C_6alkyl)C(=NOR_{59})—$, $(C_1$-$C_6haloalkyl)C(=NOR_{59})—$, $(C_1$-$C_6alkyl)C(=NOR_{59})C_1$-$C_6alkyl$-, $(C_1$-$C_6haloalkyl)C(=NOR_{59})C_1$-$C_6alkyl$-, $N(C_1$-$C_6alkyl)aminosulfonyl$ and $N,N$-$di(C_1$-$C_6alkyl)aminosulfonyl$; or A3) by substituents independently selected from the group consisting of formyl, $C_2$-$C_7$ alkylcarbonyl, $C_2$-$C_7$ haloalkylcarbonyl, $C_3$-$C_7$ alkenylcarbonyl, $C_3$-$C_7$ haloalkenylcarbonyl, $C_4$-$C_9$ cycloalkylcarbonyl, $C_4$-$C_9$ halocycloalkylcarbonyl, $C_2$-$C_7$ alkoxycarbonyl, $C_2$-$C_7$ haloalkoxycarbonyl, $C_3$-$C_7$ alkenyloxycarbonyl, $C_3$-$C_7$ alkynyloxycarbonyl, $C_4$-$C_9$ cycloalkoxycarbonyl, $C_2$-$C_7$ alkylthiocarbonyl and benzyloxycarbonyl, and benzyloxycarbonyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy; or A4) by substituents independently selected from the group consisting of hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl, phenyl, $=C(R^{36})_2$, $=N—OH$, $=N—O—C_1$-$C_4$-alkyl, $=N—O—C_3$-$C_4$ alkenyl, $=N—O—C_3$-$C_4$ alkynyl, $=N—O—C_1$-$C_4$ haloalkyl, $=N—O—C_3$-$C_4$ haloalkenyl, $=N—O$-benzyl and $=N—O$-phenyl, wherein the $=N—O$-benzyl and $=N—O$-phenyl are optionally substituted by one or more group selected from the group consisting of halogen, methyl, halomethyl; or $R_5$ is $—N=C(R_8)(R_9)$; or $R_5$ is a $C_8$-$C_{11}$ spirobicyclic system containing 0, 1 or 2 O or N atoms, wherein there are no adjacent O atoms, which is optionally substituted by one or more groups independently selected from halogen, CN, $NO_2$, OH, SH, CHO, COOH, tri($C_1$-$C_6$-alkyl)silyl, $C_1$-$C_6$ alkyl, $—CH(CH_3)—CH_2—CH_2—CH_3$, $—CH—CH(CH_3)—CH_2—CH_3$, $—CH_2—CH_2—CH(CH_3)—CH_3$, $—CH_2—CH_2—CH(CH_3)_2$, $—CH(CH_3)—CH(CH_3)_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$-alkylcarbonyl, $C_2$-$C_7$-alkoxycarbonyl, $C_4$-$C_7$-alkenyloxycarbonyl, $C_4$-$C_7$-alkynyloxycarbonyl, $C_1$-$C_6$ alkylthio, $C_1$-$C_6$ alkylsulfinyl, $C_1$-$C_6$ alkylsulfonyl, $=O$, $—C(=O)NH_2$, $—C(=O)NH(CH_3)$, $—C(=O)N(CH_3)_2$ and $—C(=S)NH_2$;

$R_6$ is selected from hydrogen and SH;

$R_7$ is hydrogen, halogen or $C_1$-$C_4$ alkyl;

$R_8$ and $R_9$, independently from each other, are hydrogen, halogen, cyano, $C_1$-$C_{12}$ alkyl, $C_2$-$C_{12}$ alkenyl, $C_2$-$C_{12}$ alkynyl, $C_1$-$C_{12}$ alkoxy, formyl, $C_2$-$C_{12}$ alkylcarbonyl, $C_3$-$C_{12}$ alkenylcarbonyl, carboxy, $C_2$-$C_{12}$ alkoxycarbonyl and $C_4$-$C_{12}$ alkenyloxycarbonyl, or $C_1$-$C_{12}$ alkyl, $C_2$-$C_{12}$ alkenyl, $C_2$-$C_{12}$ alkynyl, $C_1$-$C_{12}$ alkoxy, $C_2$-$C_{12}$ alkylcarbonyl, $C_3$-$C_{12}$ alkenylcarbonyl, $C_2$-$C_{12}$ alkoxycarbonyl and $C_4$-$C_{12}$ alkenyloxycarbonyl mono- to polysubstituted by substituents independently selected from the group consisting of halogen, cyano, nitro, hydroxy, mercapto, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or $R_8$ and $R_9$ together from a $C_2$-$C_8$ alkylene bridge which may optionally be mono- to polysubstituted by substituents independently selected from the group consisting of halogen, cyano, $C_1$-$C_6$ alkyl and $C_1$-$C_6$ haloalkyl; or $R_8$ and $R_9$, independently from each other, are the groups A-, A-O— or A-($C_1$-$C_6alkyl$)-;

$R_{10}$ is H, $C_1$-$C_4$ alkyl, $C_2$-$C_4$ alkenyl or $C_1$-$C_4$ haloalkyl;

$R_{13}$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_8$ cycloalkyl, $C_3$-$C_8$ halocycloalkyl, phenyl and benzyl, or is phenyl and benzyl mono- to polysubstituted by halogen, cyano, hydroxy, $C_1$-$C_6$ alkyl, $C_1$-$C_6$ haloalkyl or $C_1$-$C_6$ alkoxy;

$R_{14}$ and $R_{15}$, independently of each other, are $C_1$-$C_6$ alkyl, $C_3$-$C_8$ cycloalkyl, $C_1$-$C_6$ haloalkyl, $C_3$-$C_8$ halocycloalkyl, $C_2$-$C_6$ alkenyl, $C_2$-$C_6$ haloalkenyl, $C_2$-$C_6$ alkynyl, benzyl or phenyl, or benzyl or phenyl independently of each other, substituted by substituents selected from the group consisting of halogen, cyano, hydroxy, $C_1$-$C_6$ alkyl, $C_1$-$C_6$ haloalkyl and $C_1$-$C_6$ alkoxy;

$R_{51}$, $R_{52}$, $R_{63}$, independently of each other, are halogen, cyano, $C_1$-$C_6$ alkyl, $C_2$-$C_6$alkenyl, $C_3$-$C_8$ cycloalkyl, $C_5$-$C_8$ cycloalkenyl, $C_2$-$C_6$ alkynyl, $C_1$-$C_6$ alkoxy, benzyl or phenyl;

$R_{54}$, $R_{55}$, $R_{66}$, independently of each other, are $C_1$-$C_6$ alkyl, $C_3$-$C_6$ alkenyl, $C_3$-$C_8$ cycloalkyl, $C_3$-$C_6$ alkynyl, benzyl or phenyl;

$R_{57}$ and $R_{68}$, independently of each other, are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_8$ cycloalkyl, $C_3$-$C_8$ halocycloalkyl, phenyl or benzyl, where phenyl or benzyl for their part may be mono- to polysubstituted on the phenyl ring by substituents independently selected from the group consisting of halogen, cyano, hydroxy, $C_1$-$C_6$ alkyl, $C_1$-$C_6$ haloalkyl and $C_1$-$C_6$ alkoxy, or $R_{57}$ and $R_{58}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano;

$R_{59}$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_8$ cycloalkyl, $C_3$-$C_8$ halocycloalkyl, benzyl and phenyl, and benzyl and phenyl mono- to polysubstituted by halogen, cyano, hydroxy, $C_1$-$C_6$ alkyl, $C_1$-$C_6$ haloalkyl or $C_1$-$C_6$ alkoxy;

$R_{60}$ is hydrogen, $C_1$-$C_6$ alkyl, $C_3$-$C_8$ cycloalkyl, $C_1$-$C_6$ haloalkyl, $C_3$-$C_8$ halocycloalkyl, $C_2$-$C_6$ alkenyl, $C_2$-$C_6$ haloalkenyl, $C_2$-$C_6$ alkynyl, benzyl or phenyl, or benzyl or phenyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy;

$R_{62}$ is hydrogen, $C_1$-$C_6$ alkyl, $C_3$-$C_8$ cycloalkyl, $C_1$-$C_6$ haloalkyl, $C_3$-$C_8$ halocycloalkyl, $C_3$-$C_6$ alkenyl, $C_3$-$C_6$ alkynyl, benzyl or phenyl, or benzyl or phenyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy;

each $R^{36'}$ is independently selected from hydrogen, halogen and $C_1$-$C_4$ alkyl;

and agronomically acceptable salts/metallic complexes/metalloidic complexes/isomers/structural isomers/stereoisomers/diastereoisomers/enantiomers/tautomers/N-oxides of those compounds;

and component B) is a strobilurin fungicide, a sterol biosynthesis inhibitor fungicide, a triazole fungicide, or a pro-triazole fungicide, or a DMI fungicide, or a SDHI fungicide, or a compound selected from the group consisting of Chlorothalonil, Fludioxonil, Cyprodinil, Mandipropamid, Fluazinam, Procymedone, Carbendazim, Abamectin, Clothianidin, Emamectin benzoate, Imidacloprid, Tefluthrin, Mefenoxam, Orocymedone, Thiamethoxam, Lambda-cyhalothrin, Gamma-cyhalothrin, Profenofos, Lufenuron, Diflubenzuron, Cypermethrin, Novaluron, Bifenthrin, Methomyl, Chlopyrifos, Methamidophos, Endosulfan, Betacyfluthrin, Triflumuron, Teflubenzuron, SulcotrioneAcephat, Glyphosate, Glufosinate, Mesotrione, Bicyclopyrone, Tembotrione, Sulcotrione, Sulcotrione, Auxins, Trinexapac-ethyl, Prohexadione-Ca, Paclobutrazol, Acibenzolar-S-methyl, Methyl-Jasmonate, Cis-Jasmone, Manganese, Cyflufenamid, Tebufloquin and Copper.

A further aspect of present invention provides a composition comprising a combination of components A) and B) in a synergistically effective ratio between the component A) and component B).

A further aspect of the present invention provides a method of controlling phytopathogenic diseases on useful plants or on propagation material thereof, which comprises applying to the useful plants, the locus thereof or propagation material thereof a combination of components A) and B) in as synergistically effective amount and ratio between the component A) and component B).

A further aspect of the present invention relates to novel compounds according to formula (I).

A further aspect of the present invention relates to novel intermediates to provide compounds according to formula (I).

Preferably, component B is a strobilurin fungicide, a sterol biosynthesis inhibitor fungicide, a triazole fungicide, a pro-triazole fungicide, a DMI fungicide, a SDHI fungicide, or is a compound selected from Chlorothalonil, Fludioxonil, Cyprodinil, Mandipropamid, Mefenoxam, Orocymedone, Fluazinam, Procymedone, Carbendazim, Abamectin, Clothianidin, Emamectin benzoate, Imidacloprid, Tefluthrin, Thiamethoxam, Lambda-cyhalothrin, Gamma-cyhalothrin, Profenofos, Lufenuron, Diflubenzuron, Cypermethrin, Novaluron, Bifenthrin, Methomyl, Chlopyrifos, Methamidophos, Endosulfan, Betacyfluthrin, Triflumuron, Teflubenzuron, SulcotrioneAcephat, Glyphosate, Glufosinate, Mesotrione, Bicyclopyrone, Tembotrione, Sulcotrione, Auxins, Trinexapac-ethyl, Prohexadione-Ca, Paclobutrazol, Acibenzolar-S-methyl, Methyl-Jasmonate, Cis-Jasmone, Manganese and Copper.

Preferably, component B is a strobilurin fungicide, a sterol biosynthesis inhibitor fungicide, a triazole fungicide, a pro-triazole fungicide, a DMI fungicide, a SDHI fungicide, or is a compound selected from the group consisting of Chlorothalonil, Fludioxonil, Cyprodinil, Mandipropamid, Mefenoxam, Orocymedone, Fluazinam, Carbendazim, Thiamethoxam, Glyphosate, 2,4-D, Trinexapac-ethyl, Prohexadione-Ca, Paclobutrazol and cis-Jasmone.

In one group of mixtures, component B is a strobilurin fungicide.

In another group of mixtures, component B is a Sterol biosynthesis inhibitor

In another group of mixtures, component B is a triazole fungicide or a protriazole compound.

In another group of mixtures, component B is a DMI fungicide.

In another group of mixtures, component B is a SDHI fungicide.

In another group of mixtures, component B is a compound of formula (III)

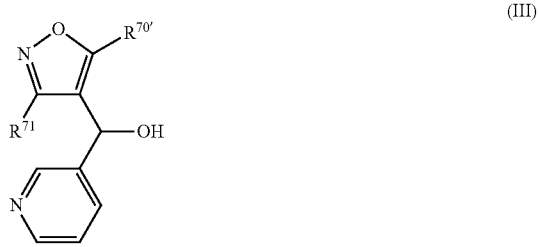

wherein $R^{70'}$ is phenyl, which is unsubstituted or substituted with 1, 2 or 3 substituents selected from halogen, haloalkyl, haloalkoxy and cyano, and;

$R^{71'}$ is phenyl, which is unsubstituted or substituted with 1, 2 or 3 substituents selected from halogen, haloalkyl, haloalkoxy and cyano.

Preferred compounds of formula (III) are (S)-[3-(4-Chloro-2-fluoro-phenyl)-5-(2,4-difluoro-phenyl)-isoxazol-4-yl]-pyridin-3-yl-methanol and 3-(4-Chloro-2-fluoro-phenyl)-5-(2,4-difluoro-phenyl)-isoxazol-4-yl]-pyridin-3-yl-methanol.

In another group of mixtures, component B is selected from the group consisting of Chlorothalonil, Fludioxonil, Cyprodinil, Mandipropamid, Fluazinam, Procymedone, Carbendazim, Abamectin, Clothianidin, Emamectin benzoate, Imidacloprid, Tefluthrin, Mefenoxam, Orocymedone, Thiamethoxam, Lambda-cyhalothrin, Gamma-cyhalothrin, Profenofos, Lufenuron, Diflubenzuron, Cypermethrin, Novaluron, Bifenthrin, Methomyl, Chlopyrifos, Methamidophos, Endosulfan, Betacyfluthrin, Triflumuron, Teflubenzuron, SulcotrioneAcephat, Glyphosate, Glufosinate, Mesotrione, Bicyclopyrone, Tembotrione, Sulcotrione, Auxins (e.g. 2,4-D and MCPA), Trinexapac-ethyl, Prohexadione-Ca, Paclobutrazol, Acibenzolar-S-methyl, Methyl-Jasmonate, Cis-Jasmone, Manganese and Copper, preferably from the group consisting of Chlorothalonil, Fludioxonil, Cyprodinil, Fenpropidin, Mandipropamid, Mefenoxam, Orocymedone, Fluazinam, Procymedone, Carbendazim, Abamectin, Clothianidin, Emamectin benzoate, Imidacloprid, Tefluthrin, Thiamethoxam, Lambda-cyhalothrin, Gamma-cyhalothrin, Profenofos, Lufenuron, Diflubenzuron, Cypermethrin, Novaluron, Bifenthrin, Methomyl, Chlopyrifos, Methamidophos, Endosulfan, Betacyfluthrin, Triflumuron, Teflubenzuron, SulcotrioneAcephat, Glyphosate, Glufosinate, Mesotrione, Bicyclopyrone, Tembotrione, Sulcotrione, Auxins, Trinexapac-ethyl, Prohexadione-Ca, Paclobutrazol, Acibenzolar-S-methyl, Methyl-Jasmonate, Cis-Jasmone, Manganese and Copper, more preferably from the group consisting of Chlorothalonil, Fludioxonil, Cyprodinil, Fenpropidin, Mandipropamid, Mefenoxam, Orocymedone, Fluazinam, Carbendazim, Thiamethoxam, Glyphosate, 2,4-D, Trinexapac-ethyl, Prohexadione-Ca, Paclobutrazol and cis-Jasmone.

In a preferred embodiment the component B) is a compound selected from Chlorothalonil, Fludioxonil, Cyprodinil, Fenpropidin, Mandipropamid, Fenpropimorph, Fluazinam, Procymedone, Carbendazim, Abamectin, Clothianidin, Emamectin benzoate, Imidacloprid, Tefluthrin, Mefenoxam, Orocymedone, Thiamethoxam, Lambda-cyhalothrin, Gamma-cyhalothrin, Profenofos, Lufenuron, Diflubenzuron, Cypermethrin, Novaluron, Bifenthrin, Methomyl, Chlopyrifos, Methamidophos, Endosulfan, Betacyfluthrin, Triflumuron, Teflubenzuron, Acephat, Glyphosate, Glufosinate, Mesotrione, Bicyclopyrone, Tembotrione, Sulcotrione, 2,4-D, MCPA, Trinexapac-ethyl, Prohexadione-Ca, Paclobutrazol, Acibenzolar-S-methyl, Methyl-Jasmonate, Cis-Jasmone, Manganese, Copper, Coumoxystrobin, Dicloaminostrobin, Flufenoxystrobin, Pyrametostrobin, Pyraoxystrobin, Trifloxystrobin, Azoxystrobin, Pyraclostrobin, Picoxystrobin, Jiaxiangjunzhi, Enoxastrobin, Triclopyricarb, the compound of formula II, Cyproconazole, Difenoconazole, Metconazole, Propiconazole, Epoxiconazole, Tebuconazole, Flutriafol, Ipconazole, prothioconazole, (S)-[3-(4-Chloro-2-fluoro-phenyl)-5-(2,4-difluoro-phenyl)-isoxazol-4-yl]-pyridin-3-yl-methanol, 3-(4-Chloro-2-fluoro-phenyl)-5-(2,4-difluoro-phenyl)-isoxazol-4-yl]-pyridin-3-yl-methanol, Pyrisoxazole, 3-(Difluoromethyl)-N-methoxy-1-methyl-N-[1-methyl-2-(2,4,6-trichlorophenyl)ethyl]-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, Isopyrazam, Sedaxane, Boscalid, Fluxapyroxad, Penthiopyrad, Penflufen, Bixafen and Fluopyram.

The term strobilurin fungicide is well known to the person skilled in the art, and includes, for example, Coumoxystrobin, Dicloaminostrobin, Flufenoxystrobin, Pyrametostrobin, Pyraoxystrobin, Trifloxystrobin, Azoxystrobin, Pyraclostrobin, Picoxystrobin, Jiaxiangjunzhi, Enoxastrobin, Triclopyricarb, Fluoxastrobin, Dimoxystrobin, Fenaminostrobin and the compound of formula (II). Preferred strobilurin fungicides are Azoxystrobin, Pyraclostrobin and Picoxystrobin. Even more preferred strobilurin fungicides are Azoxystrobin and Pyraclostrobin.

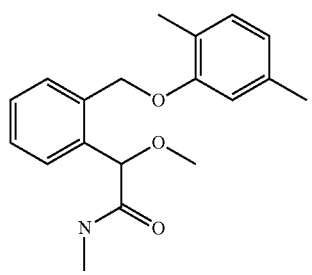

(II)

The term sterol biosynthesis inhibitor fungicide is well known to the person skilled in the art, and includes, for example, Spiroxamine, Fenpropimorph, Tridemorph, Fenpropidin, Fenhexamid, Terbinafine, Naftifine The term triazole fungicide is well known to the person skilled in the art, and includes, for example, Cyproconazole, Difenoconazole, Metconazole, Propiconazole, Epoxiconazole, Tebuconazole, Flutriafol, Ipconazole and 1-(2-chlorophenyl)-2-(1-chlorocycloprop-1-yl)-3-(1,2,4-triazol-1-yl)propan-2-ol [CAS number 120983-64-4]. Preferred triazole fungicide compounds are Cyproconazole, Difenoconazole, Metconazole and Tebuconazole. Even more preferred is Cyproconazole.

The term pro-triazole fungicide is well known to the person skilled in the art and includes, for example, prothioconazole.

The term DMI fungicides is well known to the person skilled in the art and includes, for example, (S)-[3-(4-Chloro-2-fluoro-phenyl)-5-(2,4-difluoro-phenyl)-isoxazol-4-yl]-pyridin-3-yl-methanol, 3-(4-Chloro-2-fluoro-phenyl)-5-(2,4-difluoro-phenyl)isoxazol-4-yl]-pyridin-3-yl-methanol and Pyrisoxazole. Preferred DMI fungicides are (S)-[3-(4-Chloro-2-fluoro-phenyl)-5-(2,4-difluoro-phenyl)-isoxazol-4-yl]-pyridin-3-yl-methanol and 3-(4-Chloro-2-fluoro-phenyl)-5-(2,4-difluoro-phenyl)-isoxazol-4-yl]-pyridin-3-yl-methanol.

The term SDHI fungicide is well known to the person skilled in the art and includes, for example, N-[9-(dichloromethylene)-1,2,3,4-tetrahydro-1,4-methanonaphthalen-5-yl]-3-(difluoromethyl)-1-methyl-1H-pyrazole-4-carboxamide, Isopyrazam, Sedaxane, Boscalid Fluxapyroxad, Penthiopyrad, Penflufen, Bixafen, Fluopyram, 3-(Difluoromethyl)-N-methoxy-1-methyl-N-[1-methyl-2-(2,4,6-trichlorophenyl)ethyl]-1H-pyrazole-4-carboxamide, Preferred SDHI fungicides are N-[9-(dichloromethylene)-1,2,3,4-tetrahydro-1,4-methanonaphthalen-5-yl]-3-(difluoromethyl)-1-methyl-1H-pyrazole-4-carboxamide, Isopyrazam, 3-(Difluoromethyl)-N-methoxy-1-methyl-N-[1-methyl-2-(2,4,6-trichlorophenyl)ethyl]-1H-pyrazole-4-carboxamide and Fluxapyroxad.

The term Auxins is well known to the person skilled in the art and includes, for example, 2,4-D, MCPA and Dicamba In a further preferred embodiment the component B is Chlorothalonil. In a further preferred embodiment the component B is Fludioxonil. In a further preferred embodiment the component B is Cyprodinil. In a further preferred embodiment the component B is Fenpropidin. In a further preferred embodiment the component B is Mandipropamid. In a further preferred embodiment the component B is Fluazinam. In a further preferred embodiment the component B is Procymedone. In a further preferred embodiment the component B is Carbendazim. In a further preferred embodiment the component B is Abamectin. In a further preferred embodiment the component B is Clothianidin. In a further preferred embodiment the component B is Emamectin benzoate. In a further preferred embodiment the component B is Imidacloprid. In a further preferred embodiment the component B is Tefluthrin. In a further preferred embodiment the component B is Mefenoxam. In a further preferred embodiment the component B is Orocymedone. In a further preferred embodiment the component B is Thiamethoxam. In a further preferred embodiment the component B is Lambda-cyhalothrin. In a further preferred embodiment the component B is Gamma-cyhalothrin. In a further preferred embodiment the component B is Profenofos. In a further preferred embodiment the component B is Lufenuron. In a further preferred embodiment the component B is Diflubenzuron. In a further preferred embodiment the component B is Cypermethrin. In a further preferred embodiment the component B is Novaluron. In a further preferred embodiment the component B is Bifenthrin. In a further preferred embodiment the component B is Methomyl. In a further preferred embodiment the component B is Chlopyrifos. In a further preferred embodiment the component B is Methamidophos. In a further preferred embodiment the component B is Endosulfan. In a further preferred embodiment the component B is Betacyfluthrin. In a further preferred embodiment the component B is Triflumuron. In a further preferred embodiment the component B is Teflubenzuron. In a further preferred embodiment the component B is Acephat. In a further preferred embodiment the component B is Glyphosate. In a further preferred embodiment the component B is Glufosinate. In a further preferred embodiment the component B is Mesotrione. In a further preferred embodiment the component B is Bicyclopyrone. In a further preferred embodiment the component B is Tembotrione. In a further preferred embodiment the component B is Sulcotrione. In a further preferred embodiment the component B is 2,4-D. In a further preferred embodiment the component B is MCPA. In a further preferred embodiment the component B is Trinexapac-ethyl. In a further preferred embodiment the component B is Prohexadione-Ca. In a further preferred embodiment the component B is Paclobutrazol. In a further preferred embodiment the component B is Acibenzolar-5-methyl. In a further preferred embodiment the component B is Methyl-Jasmonate. In a further preferred embodiment the component B is Cis-Jasmone. In a further preferred embodiment the component B is Manganese. In a further preferred embodiment the component B is Copper. In a further preferred embodiment the component B is Cyflufenamid. In a further preferred embodiment the component B is Tebufloquin. In a further preferred embodiment the component B is Coumoxystrobin. In a further preferred embodiment the component B is Dicloaminostrobin. In a further preferred embodiment the component B is Flufenoxystrobin. In a further preferred embodiment the component B is Pyrametostrobin. In a further preferred embodiment the component B is Pyraoxystrobin. In a further preferred embodiment the component B is Trifloxystrobin. In a further preferred embodiment the component B is Azoxystrobin. In a further preferred embodiment the component B is Pyraclostrobin. In a further preferred embodiment the component B is Picoxystrobin. In a further preferred embodiment the component B is Jiaxiangjunzhi. In a further preferred embodiment the component B is Enoxastrobin. In a further preferred embodiment the component B is Triclopyricarb. In a further preferred embodiment the component B is Fluoxastrobin. In a further preferred embodiment the component B is Dimoxystrobin. In a further preferred embodiment the component B is Fenaminostrobin In a further preferred embodiment the component B is the compound of formula II. In a further preferred embodiment the component B is Cyproconazole. In a further preferred embodiment the component B is Difenoconazole. In a further preferred embodiment the component B is Metconazole. In a further preferred embodiment the component B is Propiconazole. In a further preferred embodiment the component B is Epoxiconazole. In a further preferred embodiment the component B is Tebuconazole. In a further preferred embodiment the component B is Flutriafol. In a further preferred embodiment the component B is Ipconazole. In a further preferred embodiment the component B is 1-(2-chlorophenyl)-2-(1-chlorocycloprop-1-yl)-3-(1,2,4-triazol-1-yl) propan-2-ol [CAS number 120983-64-4]. In a further preferred embodiment the component B is prothioconazole. In a further preferred embodiment the component B is (S)-[3-(4-Chloro-2-fluoro-phenyl)-5-(2,4-difluoro-phenyl)isoxazol-4-yl]-pyridin-3-yl-methanol. In a further preferred embodiment the component B is 3-(4-Chloro-2-fluoro-phenyl)-5-(2,4-difluoro-phenyl)-isoxazol-4-yl]-pyridin-3-yl-methanol. In a further preferred embodiment the component B is Pyrisoxazole. In a further preferred embodiment the component B is 3-(difluoromethyl)-N-methoxy-1-methyl-N-[1-methyl-2-(2,4,6-trichlorophenyl)ethyl]-1H-Pyrazole-4-carboxamide. In a further preferred embodiment the component B is N-[9-(dichloromethylene)-1,2,3,4-tetrahydro-1,4-methanonaphthalen-5-yl]-3-(difluoromethyl)-1-methyl-1H-pyrazole-4-carboxamide. In a further preferred embodiment the component B is Isopyrazam. In a further preferred embodiment the component B is Sedaxane. In a further preferred embodiment the component B is Boscalid, In a further preferred embodiment the component B is Fluxapyroxad. In a further preferred embodiment the component B is Penthiopyrad. In a further preferred embodiment the component B is Penflufen. In a further preferred embodiment the component B is Bixafen. In a further preferred embodiment the component B is Fluopyram. In a further preferred embodiment the component B is 1-(2-chlorophenyl)-2-(1-chlorocycloprop-1-yl)-3-(1,2,4-triazol-1-yl)propan-2-ol.

The active ingredient mixture according to the invention may bring about the additive enhancement of the spectrum of action with respect to the phytopathogen to be controlled that may in principle be expected but achieves a synergistic effect which extends the range of action of the component (A) and of the component (B) in two ways. Firstly, the rates of application of the component (A) and of the component (B) may be lowered whilst the action remains equally good. Secondly, the active ingredient mixture may still achieve a high degree of phytopathogen control even where the two individual components have become totally ineffective in such a low application rate range. This allows, on the one hand, a substantial broadening of the spectrum of phytopathogens that can be controlled and, on the other hand, increased safety in use.

However, besides the actual synergistic action with respect to fungicidal activity, the pesticidal compositions according to the invention may also have further surprising advantageous properties which can also be described, in a wider sense, as synergistic activity. Examples of such advantageous properties that may be mentioned are: a broadening of the spectrum of fungicidal activity to other phytopathogens, for example to resistant strains; a reduction in the rate of application of the active ingredients; synergistic activity against animal pests, such as insects or representatives of the order Acarina; a broadening of the spectrum of pesticidal activity to other animal pests, for example to resistant animal pests; adequate pest control with the aid of the compositions according to the invention, even at a rate of application at which the individual compounds are totally ineffective; advantageous behaviour during formulation and/or upon application, for example upon grinding, sieving, emulsifying, dissolving or dispensing; increased storage stability; improved stability to light; more advantageous degradability; improved toxicological and/or ecotoxicological behaviour; improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination; or any other advantages familiar to a person skilled in the art.

Substituents at a nitrogen atom are always different from halogen. A hydroxy, mercapto or amino substituent is not to be placed on an α-carbon relative to a heteroatom of a core fragment.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, heptyl and octyl and their branched isomers. Alkoxy, alkenyl and alkynyl radicals are derived from the alkyl radicals mentioned. The alkenyl and alkynyl groups can be mono- or polyunsaturated.

The cycloalkyl groups occurring in the definitions of the substituents are, for example, cyclopropyl, cyclobutyl, cyclopentyl or cyclohexyl.

Halogen is generally fluorine, chlorine, bromine or iodine, preferably fluorine, bromine or chlorine. This also applies, correspondingly, to halogen in combination with other meanings, such as haloalkyl or haloalkoxy.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl, 2,2,2-trichloroethyl, 5,5,5-trifluoropentan-1-yl, 5,5-difluoro-pentan-1-yl, 6,6,6-trifluorohexan-1-yl, 6,6-difluoro-hexan-1-yl, heptafluoro-prop-2-yl and 2-fluoro-prop-2-yl; preferably trichloromethyl, difluorochloromethyl, difluoromethyl, trifluoromethyl and dichlorofluoromethyl.

Suitable haloalkenyl groups are alkenyl groups which are mono- di- or trisubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl. Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl.

$C_2$-$C_6$ alkylcarbonyl is, for example, methylcarbonyl, ethylcarbonyl, propylcarbonyl, isopropylcarbonyl, n-butylcarbonyl, isobutylcarbonyl, sec-butylcarbonyl, tert-butylcarbonyl or n-pentylcarbonyl and their branched isomers, preferably methylcarbonyl and ethylcarbonyl. Haloalkylcarbonyl radicals are derived from the alkyl radicals mentioned.

In the context of the present invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

According to the present invention, a three- to ten-membered monocyclic or fused bicyclic ring system which may be aromatic, partially saturated or fully saturated is, depending of the number of ring members, for example, selected from the group consisting of

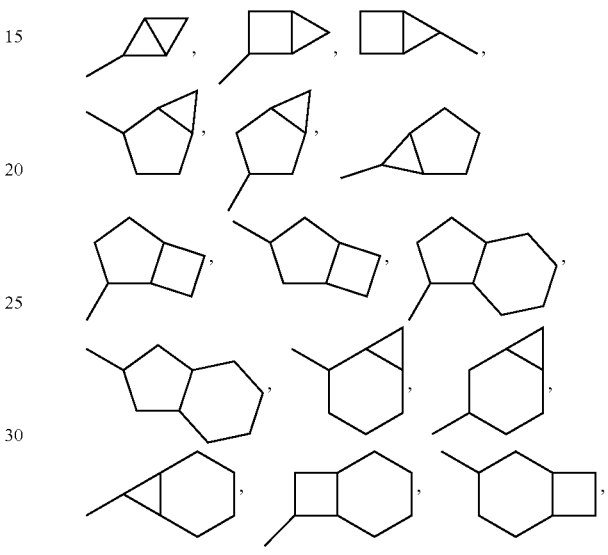

cyclopropyl, cyclobutyl, cyclopentyl, cyclohexyl, where said cycloalkylgroups for their part may be preferably unsubstituted or substituted by $C_1$-$C_6$alkyl or halogen, or is phenyl, benzyl, naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4- oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

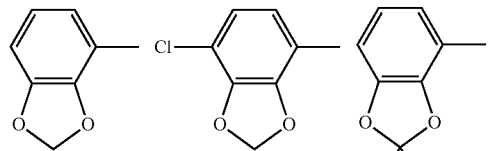

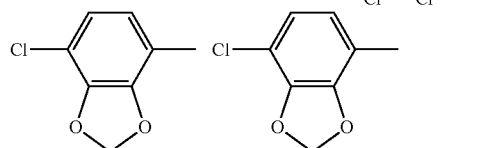

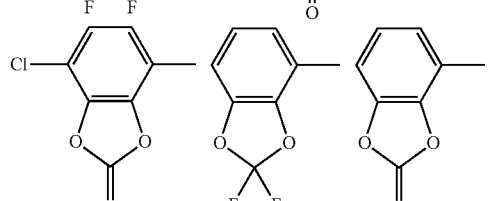

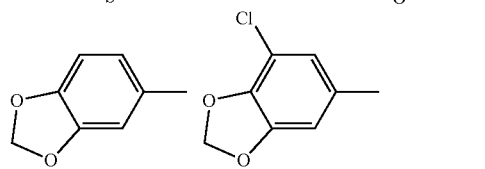

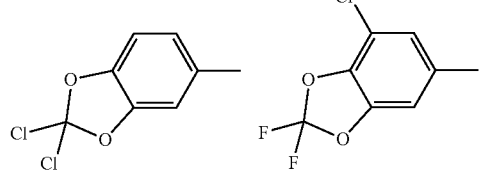

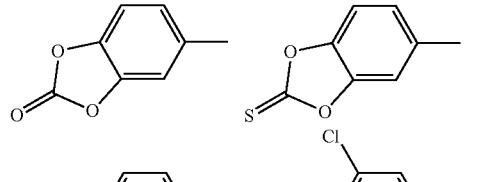

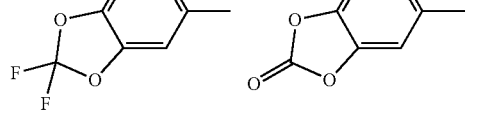

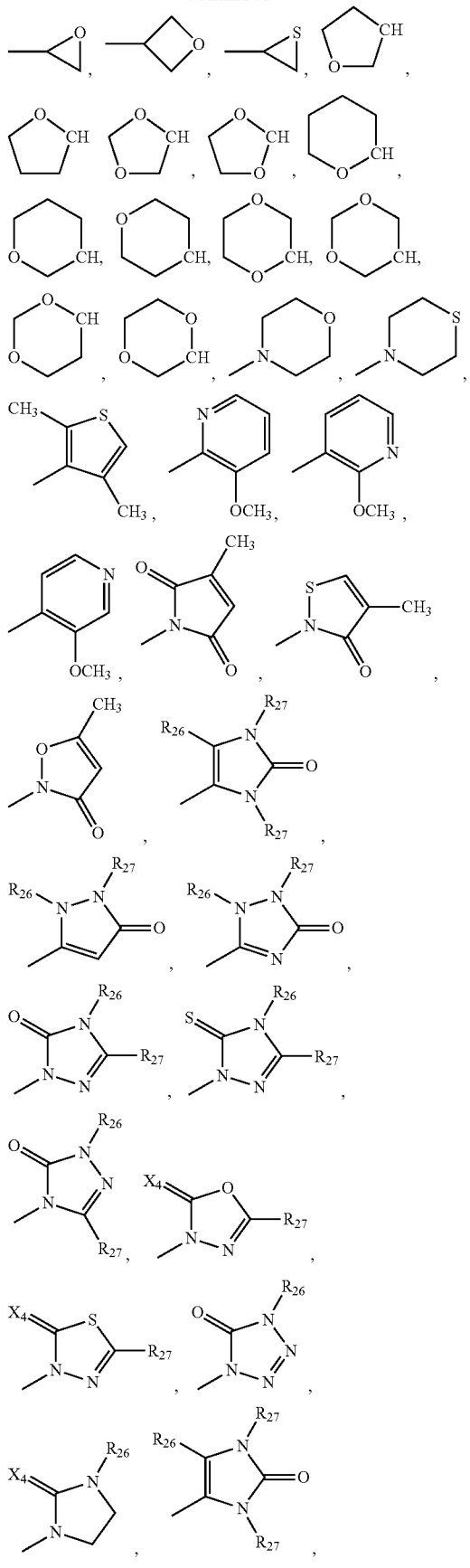

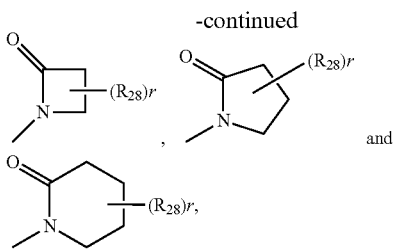

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r=1, 2, 3 or 4.

There no free valency is indicated in those definitions, for example as in

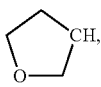

the linkage site is located at the carbon atom labelled "CH" or in a case such as, for example,

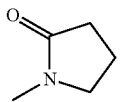

at the bonding site indicated at the bottom left.

The following substituents definitions, including preferred definitions, may be combined in any combination:

$R_1$ and $R_2$ are each independently selected from hydrogen, $C_1$-$C_4$ alkyl, $C_3$-$C_4$ alkenyl, $C_3$-$C_4$ alkynyl, ($R_{10}$)carbonyl and ($R_{10}$)oxycarbonyl;

or $R_1$ and $R_2$ together with the nitrogen atom to which they are attached form a 5- or 6 membered cyclic group which may be saturated or unsaturated and may contain a further heteroatom selected from S or O.

Preferably, $R_1$ and $R_2$ are each independently selected from hydrogen, $C_1$-$C_4$ alkyl, $C_3$-$C_4$ alkenyl and $C_3$-$C_4$ alkynyl;

or $R_1$ and $R_2$ together with the nitrogen atom to which they are attached form a pyrrolidine or piperidine.

More preferably, $R_1$ and $R_2$ are each independently selected from hydrogen or $C_1$-$C_4$ alkyl;

or $R_1$ and $R_2$ together with the nitrogen atom to which they are attached form a pyrrolidine or piperidine.

Even more preferably, $R_1$ and $R_2$ are each independently selected from hydrogen or $C_1$-$C_4$ alkyl.

More preferably again, $R_1$ and $R_2$ are each $C_1$-$C_4$ alkyl.

More favourably again, $R_1$ and $R_2$ are each independently selected from methyl, ethyl and isopropyl.

Yet more favourably, $R_1$ is methyl and $R_2$ is selected from methyl, ethyl and isopropyl.

Yet more favourably still, $R_1$ is methyl and $R_2$ is selected from ethyl and isopropyl.

Most preferably, $R_1$ is methyl and $R_2$ is ethyl.

$R_3$ represents hydrogen, halogen, cyano, nitro, mercapto, hydroxy, —C(=S)NH$_2$, —SF$_5$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ cycloalkyl, amino, $C_1$-$C_2$ alkylamino, di($C_1$-$C_6$alkyl)amino, a 5-membered heterocycle containing 1-4 nitrogen atoms, piperidino, morpholino, thiomorpholino, formyl, hydroxycarbonyl, $C_2$-$C_7$alkoxycarbonyl, $C_2$-$C_7$ haloalkoxycarbonyl, $C_4$-$C_7$ alkenyloxycarbonyl, $C_4$-$C_7$ haloalkenyloxycarbonyl, $C_2$-$C_7$ alkylcarbonyl, $C_2$-$C_7$ haloalkylcarbonyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ hydroxyalkyl, phenyl or benzyl wherein the phenyl and benzyl are optionally substituted by one or more groups independently selected from the group consisting of halogen, cyano, hydroxy, mercapto, amino, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl.

Preferably, $R_3$ represents hydrogen, halogen, cyano, mercapto, hydroxy, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_3$-$C_6$ cycloalkyl, amino, $C_1$-$C_2$ alkylamino, di($C_1$-$C_6$alkyl)amino, pyrrolidino, imidazolino, triazolino, tetrazolino, formyl, $C_2$-$C_5$ alkylcarbonyl, $C_2$-$C_5$ haloalkylcarbonyl, $C_1$-$C_6$alkylthio, $C_1$-$C_6$ alkylsulfinyl, $C_1$-$C_6$alkylsulfonyl, $C_1$-$C_6$ haloalkylthio, $C_1$-$C_6$ haloalkylsulfinyl, $C_1$-$C_6$ haloalkylsulfonyl or $C_1$-$C_6$ hydroxyalkyl.

More preferably, $R_3$ represents hydrogen, halogen, cyano, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_3$-$C_6$ cycloalkyl, amino, $C_1$-$C_2$alkylamino, di($C_1$-$C_6$alkyl)amino, pyrrolidino, imidazolino, triazolino, formyl, phenyl, $C_2$-$C_4$ alkylcarbonyl, $C_1$-$C_6$ alkylthio, $C_1$-$C_6$ alkylsulfinyl, $C_1$-$C_6$ alkylsulfonyl or $C_1$-$C_6$ hydroxyalkyl.

Even more preferably, $R_3$ represents hydrogen, halogen, cyano, $C_1$-$C_4$ alkyl, $C_2$-$C_4$ alkenyl, $C_2$-$C_4$ alkynyl, $C_1$-$C_4$ alkoxy, $C_3$-$C_6$ cycloalkyl, amino, $C_1$-$C_2$ alkylamino, di($C_1$-$C_6$alkyl)amino, pyrrolidino, imidazolino, triazolino, formyl, $C_2$-$C_4$alkylcarbonyl, $C_1$-$C_4$alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl or $C_1$-$C_4$ haloalkylsulfonyl or $C_1$-$C_6$ hydroxyalkyl.

More preferably again, $R_3$ represents hydrogen, halogen, cyano, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_3$-$C_6$ cycloalkyl, $C_1$-$C_4$ alkylthio, $C_1$-$C_4$ alkylsulfinyl or $C_1$-$C_4$ alkylsulfonyl.

Favourably, $R_3$ represents hydrogen, halogen, cyano, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_3$-$C_6$ cycloalkyl, $C_1$-$C_4$ alkylthio, $C_1$-$C_4$ alkylsulfinyl or $C_1$-$C_4$ alkylsulfonyl.

Even more favourably, $R_3$ represents hydrogen, halogen, cyano, $C_1$-$C_4$ alkyl, $C_1$-$C_4$ haloalkyl, $C_2$-$C_4$ alkynyl, $C_1$-$C_4$ alkoxy or $C_3$-$C_6$ cycloalkyl.

More favourably again, $R_3$ represents hydrogen, halogen, $C_1$-$C_4$ alkyl, $C_1$-$C_4$ haloalkyl, cyclopropyl, ethynyl or $C_1$-$C_4$ alkoxy.

Yet more favourably, $R_3$ is selected from hydrogen, bromine, iodine, methyl, CHF$_2$, cyclopropyl, ethynyl and methoxy.

Yet more favourably still, $R_3$ represents hydrogen, bromine, iodine, methyl, difluoromethyl or methoxy.

Most preferably, $R_3$ represents bromine or methyl.

$R_4$ represents hydrogen, halogen, cyano, amino, $C_1$-$C_4$ alkyl, $C_1$-$C_4$ haloalkyl, $C_3$-$C_6$ cycloalkyl, $C_2$-$C_4$ alkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, methylamino or dimethylamino.

Preferably, $R_4$ is selected from hydrogen, fluorine, chlorine, bromine, $C_1$-$C_4$ alkyl, $C_1$-$C_4$ alkenyl, $C_1$-$C_4$ haloalkyl, $C_1$-$C_4$ alkoxy and $C_3$-$C_6$ cycloalkyl.

More preferably, $R_4$ is selected from fluorine, chlorine, bromine, $C_1$-$C_4$ alkyl, $C_1$-$C_4$ alkenyl, $C_1$-$C_4$ haloalkyl, $C_1$-$C_4$ alkoxy and $C_3$-$C_6$ cycloalkyl.

Even more preferably, $R_4$ is selected from fluorine, chlorine, methyl, ethyl, ethenyl, propyl, propenyl, isopropyl, isopropenyl, cyclopropanyl, methoxy, ethoxy, monofluoromethyl, polyfluoromethyl, monofluoroethyl and polyfluoromethyl.

More preferably again, $R_4$ is selected from methyl, ethyl, methoxy, fluorine and chlorine.

More favourably again, $R_4$ is selected from methyl, methoxy, fluorine and chlorine.

Most preferably, $R_4$ is methyl.

In another group of compounds, $R_4$ is selected from methoxy, fluorine and chlorine.

$R_5$ is hydrogen, $C_1$-$C_{12}$alkyl, $C_3$-$C_{12}$alkenyl, $C_3$-$C_{12}$alkynyl, $C_1$-$C_{12}$alkylsulfonyl, $C_2$-$C_{12}$alkenylsulfonyl, phenylsulfonyl or benzylsulfonyl, or is $C_1$-$C_{12}$alkyl, $C_2$-$C_{12}$alkenyl, $C_2$-$C_{12}$alkynyl, $C_1$-$C_{12}$alkylsulfonyl, $C_2$-$C_{12}$alkenylsulfonyl, phenylsulfonyl or benzylsulfonyl mono- to polysubstituted by substituents independently selected from the group consisting of halogen, cyano, nitro, hydroxy, mercapto, azido, formyl, $C_2$-$C_7$alkylcarbonyl, $C_2$-$C_7$haloalkylcarbonyl, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or $R_5$ is formyl, $C_2$-$C_{12}$ alkylcarbonyl, $C_3$-$C_{12}$ alkenylcarbonyl, $C_3$-$C_{12}$ alkynylcarbonyl, $C_4$-$C_{12}$ cycloalkylcarbonyl, benzylcarbonyl, phenylcarbonyl, $C_2$-$C_{12}$ alkoxycarbonyl, $C_4$-$C_{12}$alkenyloxycarbonyl, $C_4$-$C_{12}$ alkynyloxycarbonyl, $C_4$-$C_{12}$ cycloalkoxycarbonyl, benzyloxycarbonyl or phenoxycarbonyl, or is $C_2$-$C_{12}$ alkylcarbonyl, $C_3$-$C_{12}$ alkenylcarbonyl, $C_3$-$C_{12}$ alkynylcarbonyl, $C_4$-$C_{12}$ cycloalkylcarbonyl, benzylcarbonyl, phenylcarbonyl, $C_2$-$C_{12}$ alkoxycarbonyl, $C_4$-$C_{12}$ alkenyloxycarbonyl, $C_4$-$C_{12}$ alkynyloxycarbonyl, $C_4$-$C_{12}$ cycloalkoxycarbonyl, benzyloxycarbonyl or phenoxycarbonyl mono- to polysubstituted by substituents independently selected from the group consisting of halogen, cyano, $C_1$-$C_6$ alkyl, $C_1$-$C_6$ haloalkyl and $C_1$-$C_6$ alkoxy; or $R_5$ is $(R_{51})(R_{52})(R_{53})Si-$, $(R_{51})(R_{52})(R_{53})Si-(C_1$-$C_{12}$alkyl)-, $(R_{51})(R_{52})(R_{53})Si-(C_3$-$C_8$cycloalkyl)-, $(R_{54}O)(R_{55}O)(R_{56}O)Si-$, $(R_{54}O)(R_{55}O)(R_{56}O)Si-(C_1$-$C_{12}$alkyl)- or $(R_{54}O)(R_{55}O)(R_{56}O)Si-(C_3$-$C_8$cycloalkyl)-; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl-, phenyl-B—$C_3$-$C_{12}$cycloalkyl-, wherein the group B is selected from —C(=O)—, —C(=S)—, —C(=NOR$_{59}$)—, —C(R$_{60}$)=NO—, —ON=C(R$_{60}$)—, —O—C(=O)—, —C(=O)—O—, —O—, —S—, —S(=O)—, —S(=O)$_2$—, —S(=O)(=NR$_{13}$)—, —S(=O)(R$_{14}$)=N—, —N=S(=O)(R$_{14}$)—, —N(R$_{62}$)—C=O)—, —C=O)—N(R$_{62}$)—, —N(R$_{62}$)—SO$_2$— or —SO$_2$—N(R$_{62}$)—; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl- or phenyl-B—$C_3$-$C_{12}$cycloalkyl-, all of which, in turn, are mono- to poly-substituted by substituents independently selected from the group consisting of halogen, cyano, hydroxy, mercapto, $C_1$-$C_6$ haloalkyl, $C_1$-$C_6$ alkoxy, formyl, $C_2$-$C_6$ alkylcarbonyl, $C_1$-$C_6$ alkylthio, $C_1$-$C_6$ alkylsulfinyl and $C_1$-$C_6$ alkylsulfonyl; or $R_5$ is A-, A-($C_1$-$C_6$alkyl)-, A-O—($C_1$-$C_6$alkyl)-, A-($C_3$-$C_6$alkenyl)-, A-O—($C_4$-$C_6$alkenyl)-, A-($C_3$-$C_6$-alkynyl)-, A-O—($C_4$-$C_6$alkynyl)-, A-($C_3$-$C_8$cycloalkyl)- or A-O—($C_3$-$C_8$cycloalkyl)-; or wherein A is a three- to ten-membered monocyclic or fused bicyclic ring system which can be aromatic, partially saturated or fully saturated and can contain 1 to 4 hetero atoms selected from the group consisting of nitrogen, oxygen and sulphur, it not being possible for each ring system to contain —O—O—, —S—S— and —O—S— fragments, and it being possible for the three- to ten-membered ring system to be itself mono- or polysubstituted A1) by substituents independently selected from the group consisting of halogen, cyano, nitro, hydroxy, mercapto, nitro, azido, formyl, carboxy, =O, =S, $C_1$-$C_6$ alkyl, $C_2$-$C_6$ alkenyl, $C_2$-$C_6$ alkynyl, $C_3$-$C_8$ cycloalkyl, $C_1$-$C_6$ haloalkyl, $C_2$-$C_6$ haloalkenyl, $C_2$-$C_6$ haloalkynyl, $C_3$-$C_8$ halocycloalkyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_8$ cycloalkyloxy, benzyl, benzyloxy, phenyl and phenoxy, where the benzyl, benzyloxy, phenyl and phenoxy, in turn, may be mono- to polysubstituted by substituents independently selected from the group consisting of halogen, cyano, nitro, hydroxy, mercapto, amino, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or A2) by substituents independently selected form the group consisting of $(R_{14})S(=O)(=NR_{13})$—, $(R_{14})(R_{15})S(=O)=N$—; —Si$(R_{51})(R_{52})(R_{53})$, —NR$_{57}$R$_{58}$, —C(=O)NR$_{57}$R$_{58}$, C(=S)NR$_{57}$R$_{58}$, HC(=NOR$_{59}$)—, ($C_1$-$C_6$alkyl)C(=NOR$_{59}$)—, ($C_1$-$C_6$haloalkyl)C(=NOR$_{59}$)—, ($C_1$-$C_6$alkyl)C(=NOR$_{59}$)$C_1$-$C_6$alkyl-, ($C_1$-$C_6$haloalkyl)C(=NOR$_{59}$)$C_1$-$C_6$alkyl-, N($C_1$-$C_6$alkyl)aminosulfonyl and N,N-di($C_1$-$C_6$alkyl)aminosulfonyl; or A3) by substituents independently selected from the group consisting of formyl, $C_2$-$C_7$ alkylcarbonyl, $C_2$-$C_7$ haloalkylcarbonyl, $C_3$-$C_7$ alkenylcarbonyl, $C_3$-$C_7$ haloalkenylcarbonyl, $C_4$-$C_9$ cycloalkylcarbonyl, $C_4$-$C_9$ halocycloalkylcarbonyl, $C_2$-$C_7$ alkoxycarbonyl, $C_2$-$C_7$ haloalkoxycarbonyl, $C_3$-$C_7$ alkenyloxycarbonyl, $C_3$-$C_7$ alkynyloxycarbonyl, $C_4$-$C_9$ cycloalkoxycarbonyl, $C_2$-$C_7$ alkylthiocarbonyl and benzyloxycarbonyl, and benzyloxycarbonyl mono- to polysubstituted by substituents independently selected from the group consisting of halogen, cyano, hydroxy, $C_1$-$C_6$alkyl, $C_1$-$C_6$ haloalkyl and $C_1$-$C_6$ alkoxy; or A4) by substituents independently selected from the group consisting of hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl, phenyl, =C(R$^{36'}$)$_2$, =N—OH, =N—O—$C_1$-$C_4$-alkyl, =N—O—$C_3$-$C_4$ alkenyl, =N—O—$C_3$-$C_4$ alkynyl, =N—O—$C_1$-$C_4$ haloalkyl, =N—O—$C_3$-$C_4$ haloalkenyl, =N—O-benzyl and =N—O-phenyl, wherein the =N—O-benzyl and =N—O-phenyl are optionally substituted by one or more group selected from the group consisting of halogen, methyl, halomethyl; or $R_5$ is —N=C($R_8$)($R_9$); or $R_5$ is a $C_8$-$C_{11}$ spirobicyclic system containing 0, 1 or 2 O, S or N atoms, wherein there are no adjacent O atoms, which is optionally substituted by one or more groups independently selected from halogen, CN, $NO_2$, OH, SH, CHO, COOH, tri($C_1$-$C_6$-alkyl)silyl, $C_1$-$C_6$ alkyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$-alkylcarbonyl, $C_2$-$C_7$-alkoxycarbonyl, $C_4$-$C_7$-alkenyloxycarbonyl, $C_4$-$C_7$-alkynyloxycarbonyl, $C_1$-$C_6$ alkylthio, $C_1$-$C_6$ alkylsulfinyl, $C_1$-$C_6$ alkylsulfonyl, =O, —C(=O)$NH_2$, —C(=O)NH($CH_3$), —C(=O)N($CH_3$)$_2$ and —C(=S)$NH_2$.

Preferably, $R_5$ represents hydrogen, $C_1$-$C_{12}$ alkylsulfonyl, $C_1$-$C_{12}$ alkyl, $C_3$-$C_{12}$ alkenyl, $C_3$-$C_{12}$ alkynyl, or is $C_1$-$C_{12}$ alkyl, $C_2$-$C_{12}$ alkenyl, $C_2$-$C_{12}$ alkynyl mono- to polysubstituted by substituents independently selected from the group consisting of halogen, cyano, nitro, hydroxy, mercapto, azido, formyl, $C_2$-$C_7$ alkylcarbonyl, $C_2$-$C_7$ haloalkylcarbonyl, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or $R_5$ is ($R_{51}$)($R_{52}$)($R_{53}$)Si—, ($R_{61}$)($R_{62}$)($R_{63}$)Si—($C_1$-$C_{12}$alkyl)-, ($R_{51}$)($R_{52}$)($R_{53}$)Si—($C_3$-$C_8$cycloalkyl)-, ($R_{54}$O)($R_{55}$O)($R_{56}$O)Si—, ($R_{54}$O)($R_{55}$O)($R_{56}$O)Si—($C_1$-$C_{12}$alkyl)- or ($R_{54}$O)($R_{55}$O)($R_{56}$O)Si—($C_3$-$C_8$cycloalkyl)-; or $R_5$ is $C_1$-$C_6$alkyl-B—$C_1$-$C_2$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkylB—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl- or phenyl-B—$C_3$-$C_{12}$cycloalkyl-, wherein the group B is selected from —C(=O)—, —C(=S)—, —C(=NOR$_{59}$)—, —C(R$_{60}$)=NO—, —ON=C(R$_{60}$)—, —O—C(=O)—, —C(=O)—O—, —O—, —S—, —S(=O)—, —S(=O)$_2$—, —S(=O)(=NR$_{13}$)—, —S(=O)(R$_{14}$)=N—, —N=S(=O)(R$_{14}$)—, —N(R$_{62}$)—C(=O)—, —C(=O)—N(R$_{62}$)—, —N(R$_{62}$)—SO$_2$— or —SO$_2$—N(R$_{62}$)—; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkylB—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl-, phenyl-B—$C_3$-$C_{12}$cycloalkyl-, all of which, in turn, are mono- to polysubstituted by substituents independently selected from the group consisting of halogen, cyano, hydroxy, mercapto, $C_1$-$C_6$ haloalkyl, $C_1$-$C_6$ alkoxy, formyl, $C_2$-$C_6$ alkylcarbonyl, $C_1$-$C_6$ alkylthio, $C_1$-$C_6$ alkylsulfinyl and $C_1$-$C_6$ alkylsulfonyl; or $R_5$ is selected from A-, A-($C_1$-$C_6$alkyl)-, A-O—($C_1$-$C_6$alkyl)-, A-($C_3$-$C_6$alkenyl)-, A-O—($C_4$-$C_6$alkenyl)-, A-($C_3$-$C_6$-alkynyl)-, A-O—($C_4$-$C_6$alkynyl)-, A-($C_3$-$C_8$cycloalkyl)- and A-O—($C_3$-$C_8$cycloalkyl)-;

wherein A is a three- to ten-membered monocyclic or fused bicyclic ring system which can be aromatic, partially saturated or fully saturated and can contain 1 to 4 hetero atoms selected from the group consisting of nitrogen, oxygen and sulphur, it not being possible for each ring system to contain —O—O—, —S—S— and —O—S— fragments, and it being possible for the three- to ten-membered ring system to be itself mono- or polysubstituted A1) by substituents independently selected from the group consisting of halogen, cyano, nitro, hydroxy, mercapto, nitro, azido, formyl, carboxy, =O, =S, $C_1$-$C_6$ alkyl, $C_2$-$C_6$ alkenyl, $C_2$-$C_6$ alkynyl, $C_3$-$C_8$ cycloalkyl, $C_1$-$C_6$ haloalkyl, $C_2$-$C_6$ haloalkenyl, $C_2$-$C_6$ haloalkynyl, $C_3$-$C_8$ halocycloalkyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_8$ cycloalkyloxy, $C_3$-$C_8$ halocycloalkyloxy, $C_3$-$C_8$ cycloalkenyloxy, $C_3$-$C_8$ halocycloalkenyloxy, benzyl, benzyloxy, phenyl and phenoxy, where the benzyl, benzyloxy, phenyl and phenoxy, in turn, may be mono- to polysubstituted by substituents independently selected from the group consisting of halogen, cyano, nitro, hydroxy, mercapto, amino, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or A3) by substituents independently selected from the group consisting of formyl, $C_2$-$C_7$ alkylcarbonyl, $C_2$-$C_7$ haloalkylcarbonyl, $C_3$-$C_7$ alkenylcarbonyl, $C_3$-$C_7$ haloalkenylcarbonyl, $C_4$-$C_9$ cycloalkylcarbonyl, $C_2$-$C_7$ alkoxycarbonyl, $C_4$-$C_7$ alkenyloxycarbonyl, $C_4$-$C_7$ alkynyloxycarbonyl, $C_4$-$C_9$ cycloalkoxycarbonyl and benzyloxycarbonyl, and benzyloxycarbonyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy; or A4) by substituents independently selected from the group consisting of hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl, phenyl, =C($R^{36'}$)$_2$, =N—OH, =N—O—$C_1$-$C_4$-alkyl, =N—O—$C_3$-$C_4$ alkenyl, =N—O—$C_3$-$C_4$ alkynyl, =N—O—$C_1$-$C_4$ haloalkyl, =N—O—$C_3$-$C_4$ haloalkenyl, =N—O-benzyl and =N—O-phenyl, wherein the =N—O-benzyl and =N—O-phenyl are optionally substituted by one or more group selected from the group consisting of halogen, methyl, halomethyl; or $R_5$ is a $C_8$-$C_{11}$ spirobicyclic system containing 0, 1 or 2 O, S or N atoms, wherein there are no adjacent O atoms, which is optionally substituted by one or more groups independently selected from halogen, CN, $NO_2$, OH, SH, CHO, COOH, tri($C_1$-$C_6$-alkyl)silyl, $C_1$-$C_6$ alkyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$alkylcarbonyl, $C_2$-$C_7$alkoxycarbonyl, $C_4$-$C_7$-alkenyloxycarbonyl, $C_4$-$C_7$alkynyloxycarbonyl, $C_1$-$C_6$ alkylthio, $C_1$-$C_6$ alkylsulfinyl, $C_1$-$C_6$ alkylsulfonyl, =O, —C(=O)NH$_2$, —C(=O)NH (CH$_3$), —C(=O)N(CH$_3$)$_2$ and —C(=S)NH$_2$.

More preferably, $R_5$ is selected from $G^1$, $G^2$, $G^3$-$G^4$, $G^5$, $G^6$-$G^7$, $G^8$, $G^9$, $G^{10}$-$G^{11}$, $G^{12}$, $G^{13}$, $G^{14}$, $G^{15}$ and $G^{16}$.

More preferably again, $R_5$ is selected from $G^1$, $G^2$, $G^5$, $G^6$-$G^8$, $G^9$, $G^{10}$-$G^{11}$, $G^{12}$, $G^{14}$, $G^{15}$ and $G^{16}$.

More favourably again, $R_5$ is selected from $G^2$, $G^5$, $G^6$-$G^7$, $G^8$, $G^9$, $G^{10}$-$G^{11}$, $G^{14}$, $G^{16}$.

Most preferably, $R_5$ is selected from $G^2$, $G^5$, $G^8$ and $G^{10}$-$G^{11}$.

$R_6$ is selected from hydrogen and SH.

Most preferably, $R_6$ is hydrogen.

In one group of compounds, $R_6$ is SH.

$R_7$ is hydrogen, halogen or $C_1$-$C_4$ alkyl.

Preferably, $R_7$ is hydrogen or $C_1$-$C_4$ alkyl.

Most preferably, $R_7$ is hydrogen.

$R_8$ and $R_9$, independently from each other, are hydrogen, halogen, cyano, $C_1$-$C_{12}$ alkyl, $C_2$-$C_{12}$ alkenyl, $C_2$-$C_{12}$ alkynyl, $C_1$-$C_{12}$ alkoxy, formyl, $C_2$-$C_{12}$ alkylcarbonyl, $C_3$-$C_{12}$ alkenylcarbonyl, carboxy, $C_2$-$C_{12}$ alkoxycarbonyl and $C_4$-$C_{12}$ alkenyloxycarbonyl, or $C_1$-$C_{12}$ alkyl, $C_2$-$C_{12}$ alkenyl, $C_2$-$C_{12}$ alkynyl, $C_1$-$C_{12}$ alkoxy, $C_2$-$C_{12}$ alkylcarbonyl, $C_3$-$C_{12}$ alkenylcarbonyl, $C_2$-$C_{12}$ alkoxycarbonyl and $C_4$-$C_{12}$ alkenyloxycarbonyl mono- to polysubstituted by substituents independently selected from the group consisting of halogen, cyano, nitro, hydroxy, mercapto, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or $R_8$ and $R_9$ together from a $C_2$-$C_8$ alkylene bridge which may optionally be mono- to polysubstituted by substituents independently selected from the group consisting of halogen, cyano, $C_1$-$C_6$ alkyl and $C_1$-$C_6$ haloalkyl; or $R_8$ and $R_9$, independently from each other, are the groups A-, A-O— or A-($C_1$-$C_6$alkyl)-.

$R_{10}$ is H, $C_1$-$C_4$ alkyl, $C_2$-$C_4$ alkenyl or $C_1$-$C_4$ haloalkyl.

$R_{13}$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_8$ cycloalkyl, $C_3$-$C_8$ halocycloalkyl, phenyl and benzyl, or is phenyl and benzyl mono- to polysubstituted by halogen, cyano, hydroxy, $C_1$-$C_6$ alkyl, $C_1$-$C_6$ haloalkyl or $C_1$-$C_6$ alkoxy.

$R_{14}$ and $R_{15}$, independently of each other, are $C_1$-$C_6$ alkyl, $C_3$-$C_8$ cycloalkyl, $C_1$-$C_6$ haloalkyl, $C_3$-$C_8$ halocycloalkyl, $C_2$-$C_6$ alkenyl, $C_2$-$C_6$ haloalkenyl, $C_2$-$C_6$ alkynyl, benzyl or phenyl, or benzyl or phenyl independently of each other, substituted by substituents selected from the group consisting of halogen, cyano, hydroxy, $C_1$-$C_6$ alkyl, $C_1$-$C_6$ haloalkyl and $C_1$-$C_6$ alkoxy.

$R_{51}$, $R_{52}$, $R_{53}$, independently of each other, are halogen, cyano, $C_1$-$C_6$ alkyl, $C_2$-$C_6$alkenyl, $C_3$-$C_8$ cycloalkyl, $C_5$-$C_8$ cycloalkenyl, $C_2$-$C_6$ alkynyl, $C_1$-$C_6$ alkoxy, benzyl or phenyl.

$R_{54}$, $R_{55}$, $R_{56}$, independently of each other, are $C_1$-$C_6$ alkyl, $C_3$-$C_6$ alkenyl, $C_3$-$C_8$ cycloalkyl, $C_3$-$C_6$ alkynyl, benzyl or phenyl.

$R_{57}$ and $R_{58}$, independently of each other, are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_8$ cycloalkyl, $C_3$-$C_8$ halocycloalkyl, phenyl or benzyl, where phenyl or benzyl for their part may be mono- to polysubstituted on the phenyl ring by substituents independently selected from the group consisting of halogen, cyano, hydroxy, $C_1$-$C_6$ alkyl, $C_1$-$C_6$ haloalkyl and $C_1$-$C_6$ alkoxy, or $R_{57}$ and $R_{58}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano.

$R_{59}$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_8$ cycloalkyl, $C_3$-$C_8$ halocycloalkyl, benzyl and phenyl, and benzyl and phenyl mono- to polysubstituted by halogen, cyano, hydroxy, $C_1$-$C_6$ alkyl, $C_1$-$C_6$ haloalkyl or $C_1$-$C_6$ alkoxy.

$R_{60}$ is hydrogen, $C_1$-$C_6$ alkyl, $C_3$-$C_8$ cycloalkyl, $C_1$-$C_6$ haloalkyl, $C_3$-$C_8$ halocycloalkyl, $C_2$-$C_6$ alkenyl, $C_2$-$C_6$ haloalkenyl, $C_2$-$C_6$ alkynyl, benzyl or phenyl, or benzyl or phenyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy;

$R_{62}$ is hydrogen, $C_1$-$C_6$ alkyl, $C_3$-$C_8$ cycloalkyl, $C_1$-$C_6$ haloalkyl, $C_3$-$C_8$ halocycloalkyl, $C_3$-$C_6$ alkenyl, $C_3$-$C_6$ alkynyl, benzyl or phenyl, or benzyl or phenyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy.

$G^1$ is a $C_8$-$C_{10}$ fused bicyclic ring system which may be saturated or comprise one carbon-carbon double bond and is optionally substituted by one or more groups independently selected from hydroxyl, $C_1$-$C_4$ alkyl, $C_1$-$C_4$ alkoxy, halogen, $C_1$-$C_4$ haloalkyl and cyano.

More preferably, $G^1$ is a $C_9$-$C_{10}$ fused bicyclic ring system which may be saturated or comprise one carbon-carbon double bond and is optionally substituted by one or more groups independently selected from hydroxyl, $C_1$-$C_4$ alkyl, $C_1$-$C_4$ alkoxy, halogen, $C_1$-$C_4$ haloalkyl and cyano.

More preferably again, $G^1$ is a $C_9$-$C_{10}$ fused bicyclic ring system which may be saturated or comprise one carbon-carbon double bond and is optionally substituted by one or more groups independently selected from $C_1$-$C_4$ alkyl, fluorine, methoxy and $C_1$-$C_4$ fluoroalkyl.

More favourably, $G^1$ is a saturated $C_9$-$C_{10}$ fused bicyclic ring system which is optionally substituted by one or more groups independently selected from $C_1$-$C_4$ alkyl, fluoro, methoxy and $C_1$-$C_4$ fluoroalkyl.

More favourably again, $G^1$ is a saturated $C_{10}$ fused bicyclic ring system which is optionally substituted by one or more groups independently selected from $C_1$-$C_4$ alkyl, fluorine, methoxy and $C_1$-$C_4$ fluoroalkyl.

Most preferably, $G^1$ is a saturated $C_{10}$ fused bicyclic ring system.

$G^2$ is $C_3$-$C_6$ cycloalkenyl, which is optionally substituted by one or more groups independently selected from halogen, CN, NO$_2$, OH, SH, CHO, COOH, tri($C_1$-$C_6$-alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH═CH (CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, —C(=O)NH$_2$, —C(=O)NH(CH$_3$), —C(=O)N(CH$_3$)$_2$ and —C(=S)NH$_2$;

More preferably again, $G^2$ is $C_3$-$C_6$ cycloalkenyl, which is optionally substituted by one or more groups independently selected from halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH═CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl, $C_1$-$C_6$ alkoxy and $C_1$-$C_6$ alkylthio.

Favourably, $G^2$ is $C_5$-$C_6$ cycloalkenyl, which is optionally substituted by one or more groups independently selected from halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl and $C_1$-$C_6$ alkoxy.

More favourably, $G^2$ is a $C_5$-$C_6$ cycloalkenyl group optionally substituted by one or more groups independently selected from fluorine, ethyl, n-propyl, iso-propyl, n-butyl, iso-butyl, sec-butyl, tert-butyl.

More favourably again, $G^2$ is a $C_5$-$C_6$ cycloalkenyl group optionally substituted by one or more fluorine atoms.

Most preferably, $G^2$ is a $C_5$-$C_6$ cycloalkenyl group.

In one group of compounds, $G^2$ is a $C_5$-$C_6$ cycloalkenyl group optionally substituted one or more groups selected from ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl and $C_1$-$C_6$ alkoxy.

Preferably in this group of compounds, $G^2$ is a $C_5$-$C_6$ cycloalkenyl group optionally substituted one or more groups selected from ethyl, n-propyl, iso-propyl, n-butyl, iso-butyl, sec-butyl, tert-butyl.

$G^3$ is phenyl, which is optionally substituted by one or more groups independently selected from hydroxyl, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen.

More preferably again, $G^3$ is phenyl, which is optionally substituted by one or more groups independently selected from hydroxyl, $C_1$-$C_4$ alkyl, $C_1$-$C_4$ fluoroalkyl, $C_1$-$C_4$ alkoxy and halogen.

More favourably again, $G^3$ is phenyl, which is optionally substituted by one or more groups independently selected from hydroxyl, $C_1$-$C_4$ alkyl, CHF$_2$, CF$_3$, $C_1$-$C_4$ alkoxy and halogen.

Yet more favourably, $G^3$ is phenyl, which is optionally substituted by one or more groups independently selected from $C_1$-$C_4$ alkyl, CHF$_2$, CF$_3$, $C_1$-$C_4$ alkoxy and halogen.

Most preferably, $G^3$ is phenyl.

$G^4$ is $C_3$-$C_{12}$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen.

More preferably again, $G^4$ is $C_5$-$C_6$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen.

More favourably again, $G^4$ is $C_5$-$C_6$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy and halogen.

Yet more favourably, $G^4$ is $C_5$-$C_6$ cycloalkyl which is optionally substituted by one or more groups independently selected from $C_1$-$C_4$ alkyl, $C_1$-$C_4$ alkoxy and halogen.

Yet more favourably still, $G^4$ is cyclohexyl or cyclopentyl.

Most preferably, $G^4$ is cyclohexyl.

$G^5$ is $C_3$-$C_7$ cycloalkyl, which is optionally substituted by one or more groups independently selected from halogen, CN, NO$_2$, OH, SH, CHO, COOH, tri($C_1$-$C_6$-alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_3$-$C_6$-alkenyloxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, phenoxy, —C(=O)NH$_2$, —C(=O)NH(CH$_3$), —C(=O)N(CH$_3$)$_2$ and —C(=S)NH$_2$.

More preferably, $G^5$ is $C_3$-$C_7$ cycloalkyl, which is optionally substituted by one or more groups independently selected from halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl, $C_1$-$C_6$ alkoxy, $C_3$-$C_4$-alkenyloxy, phenoxy and $C_1$-$C_6$ alkylthio.

More preferably again, $G^5$ is $C_3$-$C_7$ cycloalkyl, which is substituted by one or more groups independently selected from ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl, $C_1$-$C_6$ alkoxy, $C_3$-$C_4$-alkenyloxy, phenoxy and $C_1$-$C_6$ alkylthio.

More preferably still, $G^5$ is $C_5$-$C_7$ cycloalkyl, which is substituted by one or more groups independently selected from ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_4$ alkoxy, $C_3$-$C_4$-alkenyloxy, phenoxy and $C_2$-$C_6$ haloalkyl.

More favourably again, $G^5$ is $C_5$-$C_6$ cycloalkyl, which is substituted by one or more groups independently selected from ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$ and $C_2$-$C_6$ haloalkyl.

Yet more favourably, $G^5$ is $C_5$-$C_6$ cycloalkyl, which is substituted by one or more groups independently selected from ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$—CH(CH$_3$)—CH(CH$_3$)$_2$, CHF$_2$ and CF$_3$.

Most preferably, $G^5$ is $C_6$ cycloalkyl, which is substituted by one or more groups independently selected from ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$ and —CH(CH$_3$)—CH(CH$_3$)$_2$.

In another group of compounds, $G^5$ is a $C_5$-$C_6$ cycloalkyl, which is optionally substituted by one or more halogen.

More preferably in this group, $G^5$ is a $C_5$-$C_6$ cycloalkyl, which is optionally substituted by one or more fluorine.

Even more preferably in this group, $G^5$ is an unsubstituted $C_5$-$C_6$ cycloalkyl.

In another group of compounds, $G^5$ is a $C_5$-$C_6$ cycloalkyl, which is optionally substituted by one or more groups selected from the group consisting of $C_1$-$C_4$ alkoxy, $C_3$-$C_4$-alkenyloxy or phenoxy.

Preferably in this group of compounds, $G^5$ is a $C_5$-$C_6$ cycloalkyl, which is optionally substituted by one or more groups selected from the group consisting of methoxy, ethoxy, $C_3$-$C_4$ alkenyloxy and phenoxy.

$G^6$ is phenyl, which must be substituted by at least one fluorine and is optionally further substituted by one or more groups independently selected from halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl.

More preferably again, $G^6$ is phenyl, which must be substituted by at least one fluorine and is optionally further substituted by one or more groups independently selected from halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_1$-$C_6$ alkylthio, $C_1$-$C_6$ alkylsulfinyl and $C_1$-$C_6$ alkylsulfonyl.

Yet more preferably, $G^6$ is phenyl, which must be substituted by at least one fluorine and is optionally further substituted by one or more groups independently selected from halogen, CN, $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, $C_1$-$C_6$ alkoxy, $C_3$-$C_6$ alkenyloxy, $C_3$-$C_6$ alkynyloxy and $C_1$-$C_6$ alkylthio.

Favourably, $G^6$ is phenyl, which must be substituted by at least one fluorine and is optionally further substituted by one or more groups independently selected from halogen, CN, $C_1$-$C_6$ alkyl, $C_1$-$C_6$ haloalkyl and $C_1$-$C_6$ alkoxy.

More favourably again, $G^6$ is phenyl, which must be substituted by at least one fluorine and is optionally further substituted by one or more groups independently selected from halogen, CN, $C_1$-$C_4$ alkyl, $C_1$-$C_4$ haloalkyl and $C_1$-$C_4$ alkoxy.

Yet more favourably, $G^6$ is phenyl, which must be substituted by at least one fluorine and is optionally further substituted by one or more halogen, $CHF_2$, $CF_3$ and $C_1$-$C_4$ alkyl.

Most preferably, $G^6$ is phenyl, which must be substituted by at least one fluorine and is optionally further substituted by one or more methyl, bromine, iodine or chlorine.

In one group of compounds, $G^6$ is phenyl substituted at the para-position by fluorine and further substituted as in the above paragraphs.

In one group of compounds, $G^6$ is phenyl substituted at the ortho-position by fluorine and further substituted as in the above paragraphs.

In one group of compounds, $G^6$ is phenyl substituted at the meta-position by fluorine and further substituted as in the above paragraphs.

$G^7$ is methylene.

$G^8$ is

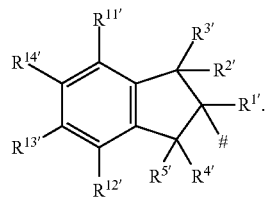

$G^9$ is

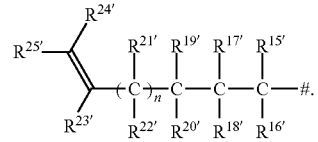

$G^{10}$ is phenyl, which is optionally substituted by one or more groups independently selected from halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, phenyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, phenyl, 2-phenyl-ethynyl and 2-phenyl-ethyl.

Preferably, $G^{10}$ is phenyl, which is optionally substituted by one or more groups independently selected from halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_3$-$C_6$ cycloalkoxy, $C_3$-$C_6$ halocycloalkoxy, phenyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl.

More preferably, $G^{10}$ is phenyl, which is optionally substituted by one or more groups independently selected from halogen, CN, OH, SH, CHO, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_3$-$C_6$ cycloalkoxy, phenyl, $C_1$-$C_6$ alkylthio, $C_1$-$C_6$ alkylsulfinyl and $C_1$-$C_6$ alkylsulfonyl.

More preferably again, $G^{10}$ is phenyl, which is optionally substituted by one or more groups independently selected from halogen, CN, OH, SH, CHO, methyl, ethyl, n-propyl, iso-propyl, phenyl, $CH_2F$, $CHF_2$, $CF_3$, CHF—$CH_3$, $CF_2$—$CH_3$, $CF_2$—$CF_3$, cyclopropyl, CH=$CH_2$, C($CH_3$)=$CH_2$, CH=CH($CH_3$), C($CH_3$)=CH($CH_3$), CH=C($CH_3$)$_2$, C($CH_3$)=C($CH_3$)$_2$, CH=$CF_2$, CH=$CCl_2$, C≡CH, methoxy, ethoxy, iso-propyloxy, $OCHF_2$, $OCH_2$—C≡CH, OCH($CH_3$)—C≡CH, $SCH_3$, $SCH_2CH_3$, S(=O)$CH_3$, S(=O)$CH_2CH_3$, S(=O)$_2CH_3$ and S(=O)$_2CH_2CH_3$ More favourably again, $G^{10}$ is phenyl, which is optionally substituted by one or more groups independently selected from halogen, CN, OH, methyl, ethyl, n-propyl, iso-propyl, $CH_2F$, $CHF_2$, $CF_3$, CHF—$CH_3$, $CF_2$—$CH_3$, $CF_2$—$CF_3$, CH=$CH_2$, C($CH_3$)=$CH_2$, CH=CH($CH_3$), C($CH_3$)=CH($CH_3$), CH=C($CH_3$)$_2$, C($CH_3$)=C($CH_3$)$_2$, CH=$CF_2$, CH=$CCl_2$, C≡CH, methoxy, phenyl, ethoxy, iso-propyloxy and $OCHF_2$.

Yet more favourably, $G^{10}$ is phenyl, which is optionally substituted by one or more groups independently selected from halogen, CN, methyl, ethyl, n-propyl, iso-propyl, ethenyl, methoxy, ethoxy, iso-propyloxy, phenyl, $CHF_2$, $CF_3$, CHF—$CH_3$ and $OCHF_2$.

Most preferably, $G^{10}$ is phenyl, which is optionally substituted by one or more groups independently selected from halogen, CN, methyl, ethyl, n-propyl, iso-propyl, ethenyl, methoxy, phenyl, $CHF_2$, $CF_3$ and $CHF-CH_3$.

$G^{11}$ is methylene substituted by at least one group independently selected from $C_1$-$C_4$ alkyl, $C_1$-$C_4$ haloalkyl, CN, $C_1$-$C_4$ alkoxy and $C_1$-$C_4$ haloalkoxy.

More preferably again, $G^{11}$ is methylene substituted by at least one group independently selected from $C_1$-$C_4$ alkyl, $C_1$-$C_4$ haloalkyl, $C_1$-$C_4$ alkoxy and $C_1$-$C_4$ haloalkoxy.

More favourably again, $G^{11}$ is methylene substituted by at least one group independently selected from $C_1$-$C_4$ alkyl, $C_1$-$C_4$ haloalkyl and $C_1$-$C_4$ alkoxy.

Yet more favourably, $G^{11}$ is methylene substituted by at least one group independently selected from methyl, ethyl, $CHF_2$ and $CF_3$.

More favourably still, $G^{11}$ is methylene substituted by at least one group independently selected from methyl, $CF_3$ and ethyl.

Most preferably, $G^{11}$ is methylene substituted by at least one group independently selected from methyl and ethyl.

$G^{12}$ is

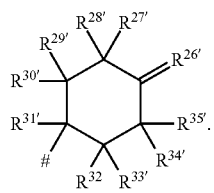

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, CN, $NO_2$, OH, SH, CHO, COOH, tri($C_1$-$C_6$-alkyl)silyl, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, =O, $-C(=O)NH_2$, $-C(=O)NH(CH_3)$, $-C(=O)N(CH_3)_2$ and $-C(=S)NH_2$.

More preferably again, $G^{13}$ is a $C_8$-$C_{11}$ spirobicyclic system containing 0, 1 or 2 O or N atoms, wherein there are no adjacent O atoms, which is optionally substituted by one or more groups independently selected from halogen, $C_1$-$C_6$ alkyl, $C_1$-$C_6$ haloalkyl, $C_1$-$C_6$ alkoxy, $C_1$-$C_6$ alkylthio and =O.

Most preferably, $G^{13}$ is a $C_8$-$C_{11}$ spirobicyclic system containing 0, 1 or 2 O or N atoms, wherein there are no adjacent O atoms, which is optionally substituted by one or more groups independently selected from halogen, $C_1$-$C_4$ alkyl, $C_1$-$C_4$ alkoxy and =O.

$G^{14}$ is

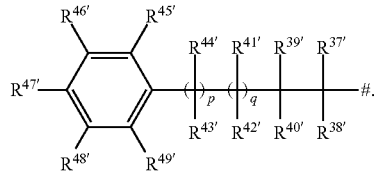

$G^{15}$ is

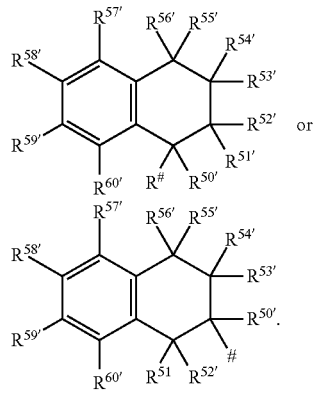

$G^{16}$ is

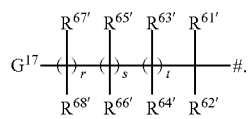

$G^{17}$ is a five- to six-membered monocyclic heteroaromatic ring system which can contain 1 to 4 members selected from the group consisting of N, N($R^{69'}$), O and S (for example, pyridine, pyrimidine, furan, pyrrole, thiazole, oxazole, pyrazole, imidazole, oxadiazole, thiadiazole or tetrazole), it not being possible for each ring system to contain —O—O—, —S—S— and —O—S-fragments, and it being possible for the five- to six-membered ring system to be itself mono- or polysubstituted by groups selected from the group consisting of halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl.

More favourably again, $G^{17}$ is a five- to six-membered monocyclic heteroaromatic ring system which can contain 1 to 4 members selected from the group consisting of N, N($R^{69'}$), O and S, it not being possible for each ring system to contain —O—O—, —S—S— and —O—S— fragments, and it being possible for the five- to six-membered-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or benzyl, wherein the phenyl or benzyl are optionally substituted by halogen, CN, $C_1$-$C_4$ alkyl or $C_1$-$C_4$ haloalkyl.

Yet more favourably, $G^{17}$ is a five- to six-membered monocyclic heteroaromatic ring system which can contain 1 or 2 members selected from the group consisting of N, N($R^{69'}$), O and S, it not being possible for each ring system to contain —O—O—, —S—S— and —O—S— fragments, and it being possible for the five- to six-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or benzyl, wherein the phenyl or benzyl are optionally substituted by halogen, CN, $C_1$-$C_4$ alkyl, $C_1$-$C_4$ haloalkyl.

Most preferably, $G^{17}$ is a five- to six-membered monocyclic heteroaromatic ring system which can contain 1 or 2 members selected from the group consisting of N, O and S, it not being possible for each ring system to contain —O—O—, —S—S— and —O—S— fragments, and it being possible for the five- to six-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or fluorophenyl. In one group of compounds, $G^{17}$ is selected from pyridine, pyrimidine, furan, pyrrole, thiazole, oxazole, pyrazole, imidazole, oxadiazole, thiadiazole or tetrazole each of which may be substituted by one or more groups selected from the group consisting of halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl.

More favourably again in this group, $G^{17}$ is selected from pyridine, pyrimidine, furan, pyrrole, thiazole, oxazole, pyrazole, imidazole, oxadiazole, thiadiazole or tetrazole each of which may be substituted by one or more groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or benzyl, wherein the phenyl or benzyl are optionally substituted by halogen, CN, $C_1$-$C_4$ alkyl, $C_1$-$C_4$ haloalkyl.

Yet more favourably in this group, $G^{17}$ is selected from pyridine, pyrimidine, furan, pyrrole, thiazole, oxazole, pyrazole, or imidazole each of which may be substituted by one or more groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or benzyl, wherein the phenyl or benzyl are optionally substituted by halogen, CN, $C_1$-$C_4$ alkyl, $C_1$-$C_4$ haloalkyl.

Most preferably in this group, $G^{17}$ is selected from pyridine, furan, pyrrole, thiazole or oxazole or imidazole each of which may be substituted by one or more groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or fluorophenyl.

In another group of compounds, $G^{17}$ is a five- to six-membered monocyclic heteroaromatic ring system which can contain 1 member selected from the group consisting of N and O (for example, pyridine, furan or pyrrole), it being possible for the five- to six-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy or $C_1$-$C_4$ haloalkoxy.

Preferably in this group, $G^{17}$ is pyridine, furan or pyrrole each of which may be mono- or polysubstituted by groups selected from the group consisting of halogen, CN, $C_1$-$C_4$ alkyl, $C_1$-$C_4$ haloalkyl, $C_1$-$C_4$ alkoxy or $C_1$-$C_4$ haloalkoxy.

In another group of compounds, $G^{17}$ is a five- to six-membered monocyclic heteroaromatic ring system which can contain 2 members selected from the group consisting of N, O and S, (for example oxazole or thiazole) it not being possible for each ring system to contain —O—O—, —S—S— and —O—S— fragments, and it being possible for the five- to six-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or fluorophenyl.

Preferably in this group, $G^{17}$ is oxazole or thiazole each of which may be mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or fluorophenyl.

$R^{1'}$ is selected from the group consisting of hydrogen, fluorine, $C_1$-$C_4$ alkyl, $C_1$-$C_4$ haloalkyl;

$R^{2'}$, $R^{3'}$, $R^{4'}$ and $R^{5'}$ are selected, independently of each other, from the group consisting of hydrogen, fluorine, $C_1$-$C_4$ alkyl, $C_1$-$C_4$ haloalkyl, $C_1$-$C_4$ alkoxy and $C_1$-$C_4$ alkylthio.

More preferably again, $R^{1'}$ is selected from the group consisting of hydrogen, fluorine, $C_1$-$C_4$ alkyl and $C_1$-$C_4$ fluoroalkyl;

$R^{2'}$, $R^{3'}$, $R^{4'}$ and $R^{5'}$ are selected, independently of each other, from the group consisting of hydrogen, fluorine, $C_1$-$C_4$ alkyl, $C_1$-$C_4$ haloalkyl, $C_1$-$C_4$ alkoxy and $C_1$-$C_4$ alkylthio.

Yet more preferably, $R^{1'}$, $R^{2'}$, $R^{3'}$, $R^{4'}$ and $R^{5'}$ are selected, independently of each other, from the group consisting of hydrogen, fluorine, methyl, ethyl, $CH_2F$, $CHF_2$, $CF_3$, CHF—$CH_3$, $CF_2$—$CH_3$, methoxy, ethoxy and S—$CH_3$ S—$CH_2CH_3$.

More favourably again, $R^{1'}$ is selected from the group consisting of hydrogen, fluorine, methyl, $CH_2F$ and $CF_3$;

$R^{2'}$, $R^{3'}$, $R^{4'}$ and $R^{5'}$ are selected, independently of each other, from the group consisting of hydrogen, fluorine, methyl, $CH_2F$, $CF_3$ and methoxy.

Most preferably, $R^{1'}$, $R^{2'}$, $R^{3'}$, $R^{4'}$ and $R^{5'}$ are each hydrogen.

$R^{11'}$, $R^{12'}$, $R^{13'}$ and $R^{14'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, phenyl, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, benzyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl.

More preferably again, $R^{11'}$, $R^{12'}$, $R^{13'}$ and $R^{14'}$ are selected, independently of each other, from the group consisting of hydrogen, cyano, halogen, $C_1$-$C_6$ alkyl, $C_1$-$C_6$ haloalkyl, $C_1$-$C_6$ alkoxy and $C_1$-$C_6$ alkylthio.

More favourably again, $R^{11'}$, $R^{12'}$, $R^{13'}$ and $R^{14'}$ are selected, independently of each other, from the group consisting of hydrogen, halogen, cyano, $C_1$-$C_4$ alkyl, $CHF_2$, $CF_3$ and $C_1$-$C_4$ alkoxy.

Most preferably, $R^{11'}$, $R^{12'}$, $R^{13'}$ and $R^{14'}$ are selected, independently of each other, from the group consisting of hydrogen, halogen, cyano, $C_1$-$C_4$ alkyl and $C_1$-$C_4$ alkoxy.

$R^{15'}$ and $R^{16'}$ are independently selected from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio.

More preferably again, $R^{15'}$, $R^{16'}$, $R^{17'}$, $R^{18'}$, $R^{19'}$, $R^{20'}$, $R^{21'}$ and $R^{22'}$ are independently selected from the group consisting of hydrogen, halogen, methyl, ethyl, isopropyl, $CH_2F$, $CHF_2$, $CF_3$, $CHF-CH_3$, $CF_2-CH_3$ and $CF_2CF_3$;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio.

Favourably, $R^{15'}$, $R^{16'}$, $R^{17'}$, $R^{18'}$, $R^{19'}$, $R^{20'}$, $R^{21'}$ and $R^{22'}$ are independently selected from the group consisting of hydrogen, fluorine, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio.

More favourably, $R^{15'}$, $R^{16'}$, $R^{17'}$, $R^{18'}$, $R^{19'}$, $R^{20'}$, $R^{21'}$ and $R^{22'}$ are each independently selected from hydrogen, fluorine, methyl, ethyl, $CH_2F$, $CHF_2$ and $CF_3$ and isopropyl;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio.

More favourably again, $R^{15'}$, $R^{16'}$, $R^{17'}$, $R^{18'}$, $R^{19'}$, $R^{20'}$, $R^{21'}$ and $R^{22'}$ are each independently selected from hydrogen, fluorine, methyl, ethyl, $CH_2F$, $CHF_2$, $CF_3$ and isopropyl;

$R^{23'}$, $R^{24'}$ and $R^{25'}$ are independently selected from the group consisting of hydrogen, methyl, fluorine, chlorine, bromine, ethyl, $CH_2F$, $CHF_2$ and $CF_3$ and isopropyl.

Yet more favourably, $R^{15'}$, $R^{16'}$, $R^{17'}$, $R^{18'}$, $R^{19'}$, $R^{20'}$, $R^{21'}$ and $R^{22'}$ are each independently selected from hydrogen, fluorine, methyl, ethyl, $CH_2F$, $CHF_2$, $CF_3$ and isopropyl;

$R^{23'}$, $R^{24'}$ and $R^{25'}$ are each independently selected from hydrogen, fluorine, chlorine, bromine, methyl, ethyl and isopropyl.

Most preferably, $R^{15'}$, $R^{16'}$, $R^{17'}$, $R^{18'}$, $R^{19'}$, $R^{20'}$, $R^{21'}$, $R^{22'}$, $R^{23'}$, $R^{24'}$ and $R^{25'}$ are each independently selected from hydrogen, methyl, ethyl and isopropyl.

In one group of compounds, $R^{15'}$ and $R^{16'}$ are each independently selected from the group consisting of hydrogen, methyl, F and $CF_3$ In this group, $R^{15'}$, $R^{16'}$, $R^{17'}$, $R^{18'}$, $R^{19'}$, $R^{20'}$, $R^{21'}$ and $R^{22'}$ are most preferably each hydrogen.

In another preferred group of compounds, $R^{15'}$ is as described above and $R^{16'}$, $R^{17'}$, $R^{18'}$, $R^{19'}$, $R^{20'}$, $R^{21'}$ and $R^{22'}$ are each hydrogen.

In another group of compounds, $R^{23'}$, $R^{24'}$ and $R^{25'}$ are independently selected from the group consisting of hydrogen, fluorine, chlorine, bromine, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$.

$R^{26'}$ is $C(R^{36'})_2$, $N-O-C_1$-$C_4$-alkyl, $N-O-C_2$-$C_4$-alkenyl, $N-O-C_2$-$C_4$ alkynyl, $N-O-C_1$-$C_4$ haloalkyl, $N-O-C_2$-$C_4$ haloalkenyl, N—O-benzyl, N—O-phenyl, N—O-halophenyl, O wherein the N—O-benzyl and N—O-phenyl may be substituted by one or more groups independently selected from the group consisting of halogen, methyl and halomethyl.

Most preferably, $R^{26'}$ is N—OH, $N-O-C_1$-$C_4$ alkyl, $N-O-C_2$-$C_4$ alkenyl, $N-O-C_2$-$C_4$ alkynyl, $N-O-C_1$-$C_4$ haloalkyl, $N-O-C_2$-$C_4$ haloalkenyl, N—O-benzyl, N—O-phenyl, N—O-halophenyl, O or $C(R^{36'})$.

$R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl and phenyl;

or $R^{28'}$ and $R^{29'}$ together with the two carbon atoms to which they are attached form a double bond.

More preferably, $R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, hydroxyl, $C_1$-$C_4$ alkyl, $C_1$-$C_4$ alkoxy and halogen;

or $R^{28'}$ and $R^{29'}$ together with the two carbon atoms to which they are attached form a double bond.

More favourably again, $R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, $C_1$-$C_4$ alkyl and halogen;

or $R^{28'}$ and $R^{29'}$ together with the two carbon atoms to which they are attached form a double bond.

Yet more favourably $R^{27'}$, $R^{28'}$, $R^{29'}$, $R^{30'}$, $R^{31'}$, $R^{32'}$, $R^{33'}$, $R^{34'}$ and $R^{35'}$ are each hydrogen or methyl;

or $R^{28'}$ and $R^{29'}$ together with the two carbon atoms to which they are attached form a double bond.

Most preferably $R^{27'}$ is hydrogen or methyl;

$R^{28'}$, $R^{29'}$, $R^{30'}$, $R^{31'}$, $R^{32'}$, $R^{33'}$, $R^{34'}$ and $R^{35'}$ are each hydrogen; or $R^{28'}$ and $R^{29'}$ together with the two carbon atoms to which they are attached form a double bond.

Each $R^{36'}$ is independently selected from hydrogen, halogen and $C_1$-$C_4$ alkyl.

$R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio.

More preferably again, $R^{37'}$, $R^{38'}$, $R^{39'}$, $R^{40'}$, $R^{41'}$, $R^{42'}$, $R^{43'}$ and $R^{44'}$ are selected independently of each other from a group consisting of hydrogen, halogen, methyl, ethyl, isopropyl, monofluoromethyl, polyfluoromethyl, monofluoroethyl, and polyfluoroethyl.

Favourably, $R^{37'}$, $R^{38'}$, $R^{39'}$, $R^{40'}$, $R^{41'}$, $R^{42'}$, $R^{43'}$ and $R^{44'}$ are selected independently of each other from a group consisting of hydrogen, fluorine, methyl, ethyl, isopropyl, $CH_2F$, $CHF_2$, $CF_3$, $CHF-CH_3$, $CF_2-CH_3$, $CH_2-CH_2F$ $CH_2-CHF_2$, and $CH_2-CF_3$.

More favourably again, $R^{37'}$, $R^{38'}$, $R^{39'}$, $R^{40'}$, $R^{41'}$, $R^{42'}$, $R^{43'}$ and $R^{44'}$ are independently selected from the group consisting of hydrogen, fluorine, methyl and trifluoromethyl.

Yet more favourably, $R^{37'}$, $R^{38'}$, $R^{39'}$, $R^{40'}$, $R^{41'}$, $R^{42'}$, $R^{43'}$ and $R^{44'}$ are hydrogen or methyl.

Most preferably, $R^{37'}$, $R^{38'}$, $R^{39'}$, $R^{40'}$, $R^{41'}$, $R^{42'}$, $R^{43'}$ and $R^{44'}$ are hydrogen.

In one group of compounds, $R^{38'}$, $R^{39'}$, $R^{40'}$, $R^{41'}$, $R^{42'}$, $R^{43'}$ and $R^{44'}$ are each hydrogen, and $R^{37'}$ is as defined above.

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl.

More preferably again, $R^{45'}$, $R^{46'}$, $R^{47'}$, $R^{48'}$ and $R^{49'}$ are independently selected from the group consisting of hydrogen, fluorine, chlorine, bromine, iodine, methyl, ethyl, isopropyl, cyclopropyl, C≡CH, $CH=CH_2$, $C(CH_3)=CH_2$, $CF_3$, $CHF_2$, $CH_2F$, —$CHF-CH_3$, —$CF_2-CH_3$, methoxy, ethoxy, difluoromethoxy, trifluoromethoxy, methlythio, methylsulfinyl and methylsulfonyl.

Most preferably, $R^{45'}$, $R^{46'}$, $R^{47'}$, $R^{48'}$ and $R^{49'}$ are independently selected from the group consisting of hydrogen, fluorine, chlorine, methyl, $CF_3$, $CHF_2$, $CH_2F$, methoxy, difluoromethoxy and trifluoromethoxy.

$R^{50'}$ is selected from the group consisting of hydrogen, fluorine, $C_1$-$C_4$ alkyl, $C_1$-$C_4$ haloalkyl;

$R^{51'}$, $R^{52'}$, $R^{53'}$, $R^{54'}$, $R^{55'}$ and $R^{56'}$ are selected, independently of each other, from the group consisting of hydrogen, fluorine, $C_1$-$C_4$ alkyl, $C_1$-$C_4$ haloalkyl, $C_2$-$C_4$ alkoxy and $C_1$-$C_4$ alkylthio.

More preferably again, $R^{50'}$, is selected from the group consisting of hydrogen, fluorine, $C_1$-$C_4$ alkyl, $C_1$-$C_4$ haloalkyl;

$R^{51'}$, $R^{52'}$, $R^{53'}$, $R^{54'}$, $R^{55'}$ and $R^{56'}$ are selected, independently of each other, from the group consisting of hydrogen, fluorine, $C_1$-$C_4$ alkyl, $C_1$-$C_4$ haloalkyl, $C_2$-$C_4$ alkoxy and $C_1$-$C_4$ haloalkoxy.

Favourably, $R^{50'}$, $R^{51'}$, $R^{52'}$, $R^{53'}$, $R^{54'}$, $R^{55'}$ and $R^{56'}$ are selected, independently of each other, from the group consisting of hydrogen, fluorine, methyl, ethyl, $CH_2F$, $CHF_2$, $CF_3$, $CHF—CH_3$ and $CF_2—CH_3$.

More favourably again, $R^{50'}$, $R^{51'}$, $R^{52'}$, $R^{53'}$, $R^{54'}$, $R^{55'}$ and $R^{56'}$ are selected, independently of each other, from the group consisting of hydrogen, fluorine, methyl, $CH_2F$ and $CF_3$.

Most preferably, $R^{50'}$, $R^{51'}$, $R^{52'}$, $R^{53'}$, $R^{54'}$, $R^{55'}$ and $R^{56'}$ are each hydrogen.

$R^{57'}$, $R^{58'}$, $R^{59'}$ and $R^{60'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxy, $C_2$-$C_6$ haloalkoxy, phenyl, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, benzyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

provided that at least one of $R^{57'}$, $R^{58'}$, $R^{59'}$ and $R^{60'}$ is not hydrogen.

More preferably again, $R^{57'}$, $R^{58'}$, $R^{59'}$ and $R^{60'}$ are selected, independently of each other, from the group consisting of hydrogen, cyano, halogen, $C_1$-$C_6$ alkyl and $C_1$-$C_6$ haloalkyl;

provided that at least one of $R^{57'}$, $R^{58'}$, $R^{59'}$ and $R^{60'}$ is not hydrogen.

More favourably again, $R^{57'}$, $R^{58'}$, $R^{59'}$ and $R^{60'}$ are selected, independently of each other, from the group consisting of hydrogen, halogen, cyano, $C_1$-$C_4$ alkyl, $CHF_2$ and $CF_3$;

provided that at least one of $R^{57'}$, $R^{58'}$, $R^{59'}$ and $R^{60'}$ is not hydrogen.

Most preferably, $R^{57'}$, $R^{58'}$, $R^{59'}$ and $R^{60'}$ are selected, independently of each other, from the group consisting of hydrogen and halogen;

provided that at least one of $R^{57'}$, $R^{58'}$, $R^{59'}$ and $R^{60'}$ is not hydrogen.

In another group of compounds, $R^{57'}$, $R^{58'}$, $R^{59'}$ and $R^{60'}$ are selected, independently of each other, from the group consisting of hydrogen, phenyl and halophenyl;

provided that at least one of $R^{57'}$, $R^{58'}$, $R^{59'}$ and $R^{60'}$ is not hydrogen.

In another group of compounds, $R^{57'}$, $R^{58'}$, $R^{59'}$ and $R^{60'}$ are selected, independently of each other, from the group consisting of hydrogen, methy, ethyl and hydroxy-$C_2$-$C_4$-alkyl;

provided that at least one of $R^{57'}$, $R^{58'}$, $R^{59'}$ and $R^{60'}$ is not hydrogen.

Preferably in this group, $R^{57'}$, $R^{58'}$, $R^{59'}$ and $R^{60'}$ are selected, independently of each other, from the group consisting of hydrogen and hydroxyethyl;

provided that at least one of $R^{57'}$, $R^{58'}$, $R^{59'}$ and $R^{60'}$ is not hydrogen.

$R^{61'}$ and $R^{62'}$ are selected independently of each other from the group consisting of hydrogen, fluorine, cyano, $C_1$-$C_4$ alkyl and $C_1$-$C_4$ haloalkyl;

$R^{63'}$, $R^{64'}$, $R^{65'}$, $R^{66'}$, $R^{67'}$ and $R^{68'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio.

More preferably again, $R^{61'}$ and $R^{62'}$ are selected independently of each other from the group consisting of hydrogen, fluorine, cyano, $C_1$-$C_4$ alkyl and $C_1$-$C_4$ haloalkyl;

$R^{63'}$, $R^{64'}$, $R^{65'}$, $R^{66'}$, $R^{67'}$ and $R^{68'}$ are selected independently of each other from the group consisting of hydrogen, fluorine, cyano, $C_1$-$C_4$ alkyl, $C_1$-$C_4$ haloalkyl, $C_1$-$C_4$ alkoxy and $C_1$-$C_4$ haloalkoxy.

More favourably again, $R^{61'}$ and $R^{62'}$ are selected independently of each other from the group consisting of hydrogen, fluorine, methyl, ethyl, $CHF_2$ and $CF_3$;

$R^{62'}$, $R^{63'}$, $R^{64'}$, $R^{65'}$, $R^{66'}$, $R^{67'}$ and $R^{68'}$ are selected independently of each of there from the group consisting of hydrogen, fluorine, methyl, ethyl, methoxy, difluoromethoxy, trifluoromethoxy, $CHF_2$ and $CF_3$.

Yet more favourably, $R^{61'}$, $R^{62'}$, $R^{63'}$, $R^{64'}$, $R^{65'}$, $R^{66'}$, $R^{67'}$ and $R^{68'}$ are hydrogen, $CHF_2$, $CF_3$ or methyl.

Yet more favourably still, $R^{61'}$, $R^{62'}$, $R^{63'}$, $R^{64'}$, $R^{65'}$, $R^{66'}$, $R^{67'}$ and $R^{68'}$ are hydrogen or methyl.

Most preferably, $R^{61'}$, $R^{62'}$, $R^{63'}$, $R^{64'}$, $R^{65'}$, $R^{66'}$, $R^{67'}$ and $R^{68'}$ are hydrogen.

$R^{69'}$ is selected from hydrogen, $C_1$-$C_4$ alkyl, $C_3$-$C_4$ alkenyl and $C_1$-$C_4$ alkylcarboxy.

More preferably again, $R^{69'}$ is selected from hydrogen, $C_1$-$C_4$ alkyl and $C_1$-$C_4$ alkylcarboxy.

More favourably again, $R^{69'}$ is selected from hydrogen and $C_1$-$C_4$ alkyl.

Most preferably, $R^{69'}$ is hydrogen.

n is 0 or 1.

In one preferred group of compounds, n is 0.

In another preferred group of compounds, n is 1.

p and q are independently selected from 0 and 1.

In one group of compounds, p and q are 0.

In another group of compounds, p and q are 1

In another group of compounds, p is 1 and q is 0.

r, s and t are independently selected from 0 and 1.

More preferably again, r and s are 0 and t is 1 or 0.

Most preferably, r, s and t are each 0.

In a group of compounds of formula I, $R_1$ and $R_2$ are each independently selected from hydrogen, $C_1$-$C_4$ alkyl, $C_3$-$C_4$ alkenyl and $C_3$-$C_4$ alkynyl;

or $R_1$ and $R_2$ together with the nitrogen atom to which they are attached form a pyrrolidine or piperidine;

$R_3$ represents hydrogen, halogen, cyano, mercapto, hydroxy, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_3$-$C_6$ cycloalkyl, amino, $C_1$-$C_2$ alkylamino, di($C_1$-$C_6$alkyl)amino, pyrrolidino, imidazolino, triazolino, tetrazolino, formyl, $C_2$-$C_5$ alkylcarbonyl, $C_2$-$C_5$ haloalkylcarbonyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl or $C_1$-$C_6$ hydroxyalkyl;

$R_4$ represents hydrogen, halogen, cyano, amino, $C_1$-$C_4$ alkyl, $C_1$-$C_4$ haloalkyl, $C_3$-$C_6$ cycloalkyl, $C_2$-$C_4$ alkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, methylamino and dimethylamino;

$R_5$ represents hydrogen, $C_1$-$C_{12}$-alkylsulfonyl, $C_1$-$C_{12}$ alkyl, $C_3$-$C_{12}$ alkenyl, $C_3$-$C_{12}$ alkynyl, or is $C_1$-$C_{12}$ alkyl, $C_2$-$C_{12}$ alkenyl, $C_2$-$C_{12}$ alkynyl mono- to polysubstituted by substituents independently selected from the group consisting of halogen, cyano, nitro, hydroxy, mercapto, azido, formyl, $C_2$-$C_7$ alkylcarbonyl, $C_2$-$C_7$ haloalkylcarbonyl, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or $R_5$ is $(R_{51})(R_{52})(R_{53})Si—$, $(R_{51})(R_{52})(R_{53})Si—(C_1$-$C_{12}alkyl)-$, $(R_{51})(R_{52})(R_{53})Si—(C_3$-$C_8 cycloalkyl)-$, $(R_{54}O)(R_{55}O)(R_{56}O)Si—$, $(R_{54}O)(R_{55}O)(R_{56}O)Si—(C_1$-$C_{12}alkyl)-$ or $(R_{54}O)(R_{55}O)(R_{56}O)Si—(C_3$-$C_8 cycloalkyl)-$; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_{12}$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl- or phenyl-B—$C_3$-$C_{12}$cycloalkyl-, wherein the group B is selected from $—C(=O)—$, $—C(=S)—$, $—C(=NOR_{59})—$, $—C(R_{60})=NO—$, $—ON=C(R_{60})—$, $—O—C(=O)—$, $—C(=O)—O—$, $—O—$, $—S—$, $—S(=O)—$, $—S(=O)_2—$, $—S(=O)(=NR_{13})—$, $—S(=O)(R_{14})=N—$, $—N=S(=O)(R_{14})—$, $—N(R_{62})—C=O)—$, $—C=O)—N(R_{62})—$, $—N(R_{62})—SO_2—$ or $—SO_2—N(R_{62})—$; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl-, phenyl-B—$C_3$-$C_{12}$cycloalkyl-, all of which, in turn, are mono- to polysubstituted by substituents independently selected from the group consisting of halogen, cyano, hydroxy, mercapto, $C_1$-$C_6$ haloalkyl, $C_1$-$C_6$ alkoxy, formyl, $C_2$-$C_6$ alkylcarbonyl, $C_1$-$C_6$ alkylthio, $C_1$-$C_6$ alkylsulfinyl and $C_1$-$C_6$ alkylsulfonyl; or $R_5$ is selected from A-, A-($C_1$-$C_6$alkyl)-, A-O—($C_1$-$C_6$alkyl)-, A-($C_3$-$C_6$alkenyl)-, A-O—($C_4$-$C_6$alkenyl)-, A-($C_3$-$C_6$-alkynyl)-, A-O—($C_4$-$C_6$alkynyl)-, A-($C_3$-$C_8$cycloalkyl)- and A-O—($C_3$-$C_8$cycloalkyl)-;

wherein A is a three- to ten-membered monocyclic or fused bicyclic ring system which can be aromatic, partially saturated or fully saturated and can contain 1 to 4 hetero atoms selected from the group consisting of nitrogen, oxygen and sulphur, it not being possible for each ring system to contain $—O—O—$, $—S—S—$ and $—O—S—$ fragments, and it being possible for the three- to ten-membered ring system to be itself mono- or polysubstituted A1) by substituents independently selected from the group consisting of
halogen, cyano, nitro, hydroxy, mercapto, nitro, azido, formyl, carboxy, $=O$, $=S$, $C_1$-$C_6$ alkyl, $C_2$-$C_6$ alkenyl, $C_2$-$C_6$ alkynyl, $C_3$-$C_8$ cycloalkyl, $C_1$-$C_6$ haloalkyl, $C_2$-$C_6$ haloalkenyl, $C_2$-$C_6$ haloalkynyl, $C_3$-$C_8$ halocycloalkyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_8$ cycloalkyloxy, $C_3$-$C_8$ halocycloalkyloxy, $C_3$-$C_8$ cycloalkenyloxy, $C_3$-$C_8$ halocycloalkenyloxy, benzyl, benzyloxy, phenyl and phenoxy, where the benzyl, benzyloxy, phenyl and phenoxy, in turn, may be mono- to polysubstituted by substituents independently selected from the group consisting of halogen, cyano, nitro, hydroxy, mercapto, amino, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or A3) by substituents independently selected from the group consisting of
formyl, $C_2$-$C_7$ alkylcarbonyl, $C_2$-$C_7$ haloalkylcarbonyl, $C_3$-$C_7$ alkenylcarbonyl, $C_3$-$C_7$ haloalkenylcarbonyl, $C_4$-$C_9$ cycloalkylcarbonyl, $C_2$-$C_7$ alkoxycarbonyl, $C_4$-$C_7$ alkenyloxycarbonyl, $C_4$-$C_7$ alkynyloxycarbonyl, $C_4$-$C_8$ cycloalkoxycarbonyl and benzyloxycarbonyl, and benzyloxycarbonyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy; or A4) by substituents independently selected from the group consisting of hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl, phenyl, $=C(R^{36'})_2$, $=N—OH$, $=N—O—C_1$-$C_4$-alkyl, $=N—O—C_3$-$C_4$ alkenyl, $=N—O—C_3$-$C_4$ alkynyl, $=N—O—C_1$-$C_4$ haloalkyl, $=N—O—C_3$-$C_4$ haloalkenyl, $=N—O$-benzyl and $=N—O$-phenyl, wherein the $=N—O$-benzyl and $=N—O$-phenyl are optionally substituted by one or more group selected from the group consisting of halogen, methyl, halomethyl; or $R_5$ is a $C_8$-$C_{11}$ spirobicyclic system containing 0, 1 or 2 O, S or N atoms, wherein there are no adjacent O atoms, which is optionally substituted by one or more groups independently selected from halogen, CN, $NO_2$, OH, SH, CHO, COOH, tri($C_1$-$C_6$-alkyl)silyl, $C_1$-$C_6$ alkyl, $—CH(CH_3)—CH_2—CH_2—CH_3$, $—CH—CH(CH_3)—CH_2—CH_3$, $—CH_2—CH_2—CH(CH_3)—CH_3$, $—CH_2—CH_2—CH(CH_3)_2$, $—CH(CH_3)—CH(CH_3)_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$alkylcarbonyl, $C_2$-$C_7$alkoxycarbonyl, $C_4$-$C_7$-alkenyloxycarbonyl, $C_4$-$C_7$alkynyloxycarbonyl, $C_1$-$C_6$ alkylthio, $C_1$-$C_6$ alkylsulfinyl, $C_1$-$C_6$ alkylsulfonyl, $=O$, $—C(=O)NH_2$, $—C(=O)NH(CH_3)$, $—C(=O)N(CH_3)_2$ and $—C(=S)NH_2$;

$R_6$ is hydrogen;
$R_7$ is hydrogen or $C_1$-$C_4$ alkyl.

In another group of compounds of formula I, $R_1$ and $R_2$ are each independently selected from hydrogen or $C_1$-$C_4$ alkyl;
or $R_1$ and $R_2$ together with the nitrogen atom to which they are attached form a pyrrolidine or piperidine;

$R_3$ represents hydrogen, halogen, cyano, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_3$-$C_6$ cycloalkyl, amino, $C_1$-$C_2$ alkylamino, di($C_1$-$C_6$alkyl)amino, pyrrolidino, imidazolino, triazolino, formyl, phenyl, $C_2$-$C_4$ alkylcarbonyl, $C_1$-$C_6$ alkylthio, $C_1$-$C_6$ alkylsulfinyl, $C_1$-$C_6$ alkylsulfonyl or $C_1$-$C_6$ hydroxyalkyl;

$R_4$ is selected from fluorine, chlorine, bromine, $C_1$-$C_4$ alkyl, $C_1$-$C_4$ alkenyl, $C_1$-$C_4$ haloalkyl, $C_1$-$C_4$ alkoxy, and $C_3$-$C_6$ cycloalkyl;

$R_5$ is selected from $G^1$, $G^2$, $G^3$-$G^4$, $G^5$, $G^6$-$G^7$, $G^8$, $G^9$, $G^{10}$-$G^{11}$, $G^{12}$, $G^{13}$, $G^{14}$, $G^{15}$ and $G^{16}$;

$R_6$ is hydrogen;

$R_7$ is selected from hydrogen or $C_1$-$C_4$ alkyl;

$G^1$ is a $C_8$-$C_{10}$ fused bicyclic ring system which may be saturated or comprise one carbon-carbon double bond and is optionally substituted by one or more groups independently selected from hydroxyl, $C_1$-$C_4$ alkyl, $C_1$-$C_4$ alkoxy, halogen, $C_1$-$C_4$ haloalkyl and cyano;

$G^2$ is $C_3$-$C_6$ cycloalkenyl, which is optionally substituted by one or more groups independently selected from halogen, CN, $NO_2$, OH, SH, CHO, COOH, tri($C_1$-$C_6$-alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH═CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, —C(═O)NH$_2$, —C(═O)NH(CH$_3$), —C(═O)N(CH$_3$)$_2$ and —C(═S)NH$_2$;

$G^3$ is phenyl, which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen;

$G^4$ is $C_3$-$C_{12}$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen;

$G^5$ is $C_3$-$C_7$ cycloalkyl, which is optionally substituted by one or more groups independently selected from halogen, CN, $NO_2$, OH, SH, CHO, COOH, tri($C_1$-$C_6$-alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH═CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_3$-$C_6$-alkenyloxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, phenoxy, —C(═O)NH$_2$, —C(═O)NH(CH$_3$), —C(═O)N(CH$_3$)$_2$ and —C(═S)NH$_2$;

$G^6$ is phenyl, which must be substituted by at least one fluorine and is optionally further substituted by one or more groups independently selected from halogen, CN, $NO_2$, OH, SH, CHO, C(═O)NH$_2$, C(═O)NH(CH$_3$), C(═O)N(CH$_3$)$_2$, C(═S)NH$_2$, C(═S)NH(CH$_3$), C(═S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$G^7$ is methylene;

$G^8$ is

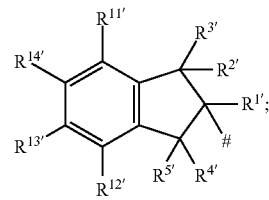

$G^9$ is

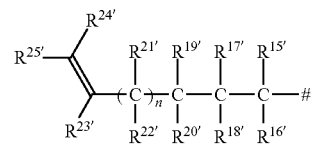

$G^{10}$ is phenyl, which is optionally substituted by one or more groups independently selected from hydrogen, halogen, CN, $NO_2$, OH, SH, CHO, C(═O)NH$_2$, C(═O)NH(CH$_3$), C(═O)N(CH$_3$)$_2$, C(═S)NH$_2$, C(═S)NH(CH$_3$), C(═S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, phenyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, phenyl, 2-phenyl-ethynyl and 2-phenyl-ethyl;

$G^{11}$ is methylene substituted by at least one group independently selected from $C_1$-$C_4$ alkyl, $C_1$-$C_4$ haloalkyl, CN, $C_1$-$C_4$ alkoxy and $C_1$-$C_4$ haloalkoxy;

$G^{12}$ is

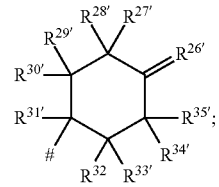

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, CN, $NO_2$, OH, SH, CHO, COOH, tri($C_1$-$C_6$ alkyl)silyl, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, ═O, —C(═O)NH$_2$, —C(═O)NH(CH$_3$), —C(═O)N(CH$_3$)$_2$ and —C(═S)NH$_2$;

$G^{14}$ is

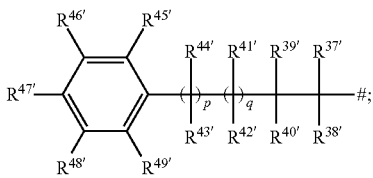

$G^{15}$ is

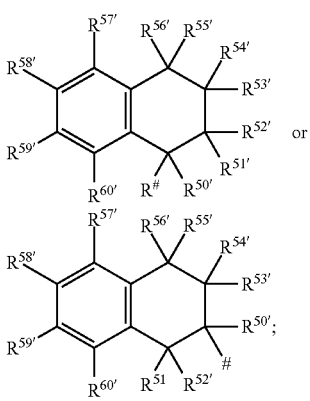

$G^{16}$ is

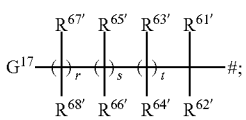

$G^{17}$ is a five- to six-membered monocyclic heteroaromatic ring system which can contain 1 to 4 members selected from the group consisting of N, N($R^{69'}$), O and S (for example, pyridine, pyrimidine, furan, pyrrole, thiazole, oxazole, pyrazole, imidazole, oxadiazole, thiadiazole or tetrazole), it not being possible for each ring system to contain —O—O—, —S—S— and —O—S-fragments, and it being possible for the five- to six-membered ring system to be itself mono- or polysubstituted by groups selected from the group consisting of halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{1'}$ is selected from the group consisting of hydrogen, fluorine, $C_1$-$C_4$-alkyl, $C_1$-$C_4$-haloalkyl;

$R^{2'}$, $R^{3'}$, $R^{4'}$ and $R^{5'}$ are selected, independently of each other, from the group consisting of hydrogen, fluorine, $C_1$-$C_4$ alkyl, $C_1$-$C_4$ haloalkyl, $C_1$-$C_4$ alkoxy and $C_1$-$C_4$ alkylthio;

$R^{11'}$, $R^{12'}$, $R^{13'}$ and $R^{14'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, phenyl, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, benzyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{15'}$ and $R^{16'}$ are independently selected from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

$R^{26'}$ is C($R^{36'}$)$_2$, N—OH, N—O—$C_1$-$C_4$-alkyl, N—O—$C_2$-$C_4$-alkenyl, N—O—$C_2$-$C_4$ alkynyl, N—O—$C_1$-$C_4$ haloalkyl, N—O—$C_2$-$C_4$ haloalkenyl, N—O-benzyl, N—O-phenyl, N—O-halophenyl, O wherein the N—O-benzyl and N—O-phenyl may be substituted by one or more groups independently selected from the group consisting of halogen, methyl and halomethyl;

$R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl and phenyl;

or $R^{28'}$ and $R^{29'}$ together with the two carbon atoms to which they are attached form a double bond;

each $R^{36'}$ is independently selected from hydrogen, halogen and $C_1$-$C_4$ alkyl;

$R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{50'}$ is selected from the group consisting of hydrogen, fluorine, $C_1$-$C_4$ alkyl, $C_1$-$C_4$ haloalkyl;

$R^{51'}$, $R^{52'}$, $R^{53'}$, $R^{54'}$, $R^{55'}$ and $R^{56'}$ are selected, independently of each other, from the group consisting of hydrogen, fluorine, $C_1$-$C_4$ alkyl, $C_1$-$C_4$ haloalkyl, $C_2$-$C_4$ alkoxy and $C_1$-$C_4$ alkylthio;

$R^{57'}$, $R^{58'}$, $R^{59'}$ and $R^{60'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxy, $C_2$-$C_6$ haloalkoxy, phenyl, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, benzyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

provided that at least one of $R^{57'}$, $R^{58'}$, $R^{59'}$ and $R^{60'}$ is not hydrogen;

$R^{61'}$ and $R^{62'}$ are selected independently of each other from the group consisting of hydrogen, fluorine, cyano, $C_1$-$C_4$ alkyl and $C_1$-$C_4$ haloalkyl;

$R^{63'}$, $R^{64'}$, $R^{65'}$, $R^{66'}$, $R^{67'}$ and $R^{68'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy and $C_1$-$C_4$ haloalkoxy and $C_1$-$C_4$ alkylthio;

$R^{69'}$ is selected from hydrogen, $C_1$-$C_4$ alkyl and $C_1$-$C_4$ alkylcarboxy;

n is 0 or 1;

p and q are independently selected from 0 and 1;

r, s and t are independently selected from 0 and 1.

In another group of compounds of formula I, $R_1$ and $R_2$ are each $C_1$-$C_4$ alkyl;

$R_3$ represents hydrogen, halogen, cyano, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_3$-$C_6$ cycloalkyl, $C_1$-$C_4$ alkylthio, $C_1$-$C_4$ alkylsulfinyl or $C_1$-$C_4$ alkylsulfonyl;

$R_4$ is selected from methyl, ethyl, methoxy, fluorine and chlorine;

$R_6$ is hydrogen;

$R_7$ is hydrogen or $C_1$-$C_4$ alkyl.

In another group of compounds, $R_1$ and $R_2$ are each independently selected from methyl, ethyl and isopropyl;

$R_3$ represents hydrogen, halogen, $C_1$-$C_4$ alkyl, $C_1$-$C_4$ haloalkyl, cyclopropyl, ethynyl or $C_1$-$C_4$ alkoxy;

$R_4$ is selected from methyl, methoxy, fluorine and chlorine;

$R_6$ is hydrogen;

$R_7$ is hydrogen.

In another group of compounds, $R_1$ is methyl;

$R_2$ is ethyl;

$R_3$ is selected from hydrogen, bromine, iodine, methyl, $CHF_2$, cyclopropyl, ethynyl and methoxy;

$R_4$ is methyl;

$R_6$ is hydrogen;

$R_7$ is hydrogen.

In another group of compounds, $G^1$ is a $C_9$-$C_{10}$ fused bicyclic ring system which may be saturated or comprise one carbon-carbon double bond and is optionally substituted by one or more groups independently selected from $C_1$-$C_4$ alkyl, fluorine, methoxy and $C_1$-$C_4$ fluoroalkyl;

$G^2$ is $C_3$-$C_6$ cycloalkenyl, which is optionally substituted by one or more groups independently selected from halogen, ethyl, n-propyl, iso-propyl, n-butyl, iso-butyl, sec-butyl, tert-butyl, n-pentyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$, $C_2$-$C_6$ haloalkyl, $C_1$-$C_6$ alkoxy and $C_1$-$C_6$ alkylthio;

$G^3$ is phenyl, which is optionally substituted by one or more groups independently selected from hydroxyl, $C_1$-$C_4$ alkyl, $C_1$-$C_4$ fluoroalkyl, $C_1$-$C_4$ alkoxy and halogen;

$G^4$ is $C_5$-$C_6$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen;

$G^5$ is $C_3$-$C_7$ cycloalkyl, which is substituted by one or more groups independently selected from ethyl, n-propyl, iso-propyl, n-butyl, iso-butyl, sec-butyl, tert-butyl, n-pentyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$, $C_2$-$C_6$ haloalkyl, $C_1$-$C_6$ alkoxy, $C_3$-$C_4$-alkenyloxy, phenoxy and $C_1$-$C_6$ alkylthio;

$G^6$ is phenyl, which must be substituted by at least one fluorine and is optionally further substituted by one or more groups independently selected from halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_1$-$C_6$ alkylthio, $C_1$-$C_6$ alkylsulfinyl and $C_1$-$C_6$ alkylsulfonyl;

$G^{10}$ is phenyl, which is optionally substituted by one or more groups independently selected from halogen, CN, OH, SH, CHO, methyl, ethyl, n-propyl, iso-propyl, phenyl, $CH_2F$, $CHF_2$, $CF_3$, CHF—$CH_3$, $CF_2$—$CH_3$, $CF_2$—$CF_3$, cyclopropyl, CH=$CH_2$, C($CH_3$)=$CH_2$, CH=CH($CH_3$), C($CH_3$)=CH($CH_3$), CH=C($CH_3$)$_2$, C($CH_3$)=C($CH_3$)$_2$, CH=$CF_2$, CH=$CCl_2$, C≡CH, methoxy, ethoxy, iso-propyloxy, $OCHF_2$, $OCH_2$—C≡CH, OCH($CH_3$)—C≡CH, $SCH_3$, $SCH_2CH_3$, S(=O)$CH_3$, S(=O)$CH_2CH_3$, S(=O)$_2CH_3$ and S(=O)$_2CH_2CH_3$;

$G^{11}$ is methylene substituted by at least one group independently selected from $C_1$-$C_4$ alkyl, $C_1$-$C_4$ haloalkyl, CN, $C_1$-$C_4$ alkoxy and $C_1$-$C_4$ haloalkoxy;

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, $C_1$-$C_6$ alkyl, $C_1$-$C_6$ haloalkyl, $C_1$-$C_6$ alkoxy, $C_1$-$C_6$ alkylthio and =O;

$G^{17}$ is a five- to six-membered monocyclic heteroaromatic ring system which can contain 1 to 4 members selected from the group consisting of N, N($R^{69'}$), O and S (for example, pyridine, pyrimidine, furan, pyrrole, thiazole, oxazole, pyrazole, imidazole, oxadiazole, thiadiazole or tetrazole), it not being possible for each ring system to contain —O—O—, —S—S— and —O—S-fragments, and it being possible for the five- to six-membered ring system to be itself mono- or polysubstituted by groups selected from the group consisting of halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{1'}$ is selected from the group consisting of hydrogen, fluorine, $C_1$-$C_4$ alkyl and $C_1$-$C_4$ fluoroalkyl;

$R^{2'}$, $R^{3'}$, $R^{4'}$ and $R^{5'}$ are selected, independently of each other, from the group consisting of hydrogen, fluorine, $C_1$-$C_4$ alkyl, $C_1$-$C_4$ haloalkyl, $C_1$-$C_4$ alkoxy and $C_1$-$C_4$ alkylthio;

$R^{11'}$, $R^{12'}$, $R^{13'}$ and $R^{14'}$ are selected, independently of each other, from the group consisting of hydrogen, cyano, halogen, $C_1$-$C_6$ alkyl, $C_1$-$C_6$ haloalkyl, $C_1$-$C_6$ alkoxy and $C_1$-$C_6$ alkylthio;

$R^{15'}$, $R^{16'}$, $R^{17'}$, $R^{18'}$, $R^{19'}$, $R^{20'}$, $R^{21'}$ and $R^{22'}$ are independently selected from the group consisting of hydrogen, halogen, methyl, ethyl, isopropyl, $CH_2F$, $CHF_2$, $CF_3$, CHF—$CH_3$, $CF_2$—$CH_3$ and $CF_2CF_3$;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

$R^{26'}$ is N—OH, N—O—$C_1$-$C_4$ alkyl, N—O—$C_2$-$C_4$ alkenyl, N—O—$C_2$-$C_4$ alkynyl, N—O—$C_1$-$C_4$ haloalkyl, N—O—$C_2$-$C_4$ haloalkenyl, N—O-benzyl, N—O-phenyl, N—O-halophenyl, O, or $C(R^{36'})_2$;

$R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, hydroxyl, $C_1$-$C_4$ alkyl, $C_1$-$C_4$ alkoxy and halogen;

or $R^{28'}$ and $R^{29'}$ together with the two carbon atoms to which they are attached form a double bond;

each $R^{36'}$ is independently selected from hydrogen, halogen and $C_1$-$C_4$ alkyl;

$R^{37'}$, $R^{38'}$, $R^{39'}$, $R^{40'}$, $R^{41'}$, $R^{42'}$, $R^{43'}$ and $R^{44'}$ are selected independently of each other from a group consisting of hydrogen, halogen, methyl, ethyl, isopropyl, monofluoromethyl, polyfluoromethyl, monofluoroethyl, and polyfluoroethyl;

$R^{45'}$, $R^{46'}$, $R^{47'}$, $R^{48'}$ and $R^{49'}$ are independently selected from the group consisting of hydrogen, fluorine, chlorine, bromine, iodine, methyl, ethyl, isopropyl, cyclopropyl, C≡CH, CH=$CH_2$, C($CH_3$)=$CH_2$, $CF_3$, $CHF_2$, $CH_2F$, —CHF—$CH_3$, —$CF_2$—$CH_3$, methoxy, difluoromethoxy, trifluoromethoxy, ethoxy, methlythio, methylsulfinyl and methylsulfonyl;

$R^{50'}$ is selected from the group consisting of hydrogen, fluorine, $C_1$-$C_4$ alkyl, $C_1$-$C_4$ haloalkyl;

$R^{51'}$, $R^{52'}$, $R^{53'}$, $R^{54'}$, $R^{55'}$ and $R^{56'}$ are selected, independently of each other, from the group consisting of hydrogen, fluorine, $C_1$-$C_4$ alkyl, $C_1$-$C_4$ haloalkyl, $C_2$-$C_4$ alkoxy and $C_1$-$C_4$ haloalkoxy;

$R^{57'}$, $R^{58'}$, $R^{59'}$ and $R^{60'}$ are selected, independently of each other, from the group consisting of hydrogen, cyano, halogen, $C_1$-$C_6$ alkyl and $C_1$-$C_6$ haloalkyl;

provided that at least one of $R^{57'}$, $R^{58'}$, $R^{59'}$ and $R^{60'}$ is not hydrogen;

$R^{61'}$ and $R^{62'}$ are selected independently of each other from the group consisting of hydrogen, fluorine, cyano, $C_1$-$C_4$ alkyl and $C_1$-$C_4$ haloalkyl;

$R^{63'}$, $R^{64'}$, $R^{65'}$, $R^{66'}$, $R^{67'}$ and $R^{68'}$ are selected independently of each other from the group consisting of hydrogen, fluorine, cyano, $C_1$-$C_4$ alkyl, $C_1$-$C_4$ haloalkyl, $C_1$-$C_4$ alkoxy and $C_1$-$C_4$ haloalkoxy;

$R^{69'}$ is selected from hydrogen, $C_1$-$C_4$ alkyl and $C_1$-$C_4$ alkylcarboxy;

n is 0 or 1;

p and q are independently selected from 0 and 1;

r and s are 0 and t is 1 or 0.

In another group of compounds, $G^1$ is a saturated $C_{10}$ fused bicyclic ring system which is optionally substituted by one or more groups independently selected from $C_1$-$C_4$ alkyl, fluorine, methoxy and $C_1$-$C_4$ fluoroalkyl;

$G^2$ is a $C_5$-$C_6$ cycloalkenyl group optionally substituted by one or more fluorine atoms;

$G^3$ is phenyl, which is optionally substituted by one or more groups independently selected from $C_1$-$C_4$ alkyl, $CHF_2$, $CF_3$, $C_1$-$C_4$ alkoxy and halogen;

$G^4$ is $C_5$-$C_6$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy and halogen;

$G^5$ is $C_5$-$C_6$ cycloalkyl, which is substituted by one or more groups independently selected from ethyl, n-propyl, iso-propyl, n-butyl, iso-butyl, sec-butyl, tert-butyl, n-pentyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$ and $C_2$-$C_6$ haloalkyl;

$G^6$ is phenyl, which must be substituted by at least one fluorine and is optionally further substituted by one or more groups independently selected from halogen, CN, $C_1$-$C_4$ alkyl, $C_1$-$C_4$ haloalkyl and $C_1$-$C_4$ alkoxy.

$G^7$ is methylene;

$G^{10}$ is phenyl, which is optionally substituted by one or more groups independently selected from hydrogen, halogen, CN, OH, methyl, ethyl, n-propyl, iso-propyl, $CH_2F$, $CHF_2$, $CF_3$, CHF—$CH_3$, $CF_2$—$CH_3$, $CF_2$—$CF_3$, CH=$CH_2$, C($CH_3$)=$CH_2$, CH=CH($CH_3$), C($CH_3$)=CH($CH_3$), CH=C($CH_3$)$_2$, C($CH_3$)=C($CH_3$)$_2$, CH=$CF_2$, CH=$CCl_2$, C≡CH, methoxy, ethoxy, iso-propyloxy, phenyl and $OCHF_2$;

$G^{11}$ is methylene substituted by at least one group independently selected from $C_1$-$C_4$ alkyl, $C_1$-$C_4$ haloalkyl and $C_1$-$C_4$ alkoxy;

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, $C_1$-$C_6$ alkyl, $C_1$-$C_6$ haloalkyl, $C_1$-$C_6$ alkoxy, $C_1$-$C_6$ alkylthio and =O;

$G^{17}$ is a five- to six-membered monocyclic heteroaromatic ring system which can contain 1 to 4 members selected from the group consisting of N, N($R^{69'}$), O and S it not being possible for each ring system to contain —O—O—, —S—S— and —O—S— fragments, and it being possible for the five- to six-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or benzyl, wherein the phenyl or benzyl are optionally substituted by halogen, CN, $C_1$-$C_4$ alkyl, $C_1$-$C_4$ haloalkyl;

$R^{1'}$ is selected from the group consisting of hydrogen, fluorine, methyl, $CH_2F$ and $CF_3$;

$R^{2'}$, $R^{3'}$, $R^{4'}$ and $R^{5'}$ are selected, independently of each other, from the group consisting of hydrogen, fluorine, methyl, $CH_2F$, $CF_3$ and methoxy;

$R^{11'}$, $R^{12'}$, $R^{13'}$ and $R^{14'}$ are selected, independently of each other, from the group consisting of hydrogen, halogen, cyano, $C_1$-$C_4$ alkyl, $CHF_2$, $CF_3$ and $C_1$-$C_4$ alkoxy;

$R^{15'}$, $R^{16'}$, $R^{17'}$, $R^{18'}$, $R^{19'}$, $R^{20'}$, $R^{21'}$ and $R^{22'}$ are each independently selected from hydrogen, fluorine, methyl, ethyl, $CH_2F$, $CHF_2$, $CF_3$ and isopropyl;

$R^{23'}$, $R^{24'}$ and $R^{25'}$ are independently selected from the group consisting of hydrogen, methyl, fluorine, chlorine, bromine, ethyl, $CH_2F$, $CHF_2$ and $CF_3$ and isopropyl;

$R^{26'}$ is N—OH, N—O—$C_1$-$C_4$ alkyl, N—O—$C_2$-$C_4$ alkenyl, N—O—$C_2$-$C_4$ alkynyl, N—O—$C_1$-$C_4$ haloalkyl, N—O—$C_2$-$C_4$ haloalkenyl, N—O-benzyl, N—O-phenyl, N—O-halophenyl, O, $C_2$-$C_4$ alkenyloxy or $C(R^{36'})$;

$R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, $C_1$-$C_4$ alkyl and halogen;

or $R^{28'}$ and $R^{29'}$ together with the two carbon atoms to which they are attached form a double bond;

each $R^{36'}$ is independently selected from hydrogen, halogen and $C_1$-$C_4$ alkyl;

$R^{37'}$, $R^{38'}$, $R^{39'}$, $R^{40'}$, $R^{41'}$, $R^{42'}$, $R^{43'}$ and $R^{44'}$ are independently selected from the group consisting of hydrogen, fluorine, methyl and trifluoromethyl;

$R^{45'}$, $R^{46'}$, $R^{47'}$, $R^{48'}$ and $R^{49'}$ are independently selected from the group consisting of hydrogen, fluorine, chlorine, bromine, iodine, methyl, ethyl, isopropyl, cyclopropyl, C≡CH, CH=$CH_2$, C($CH_3$)=$CH_2$, $CF_3$, $CHF_2$, $CH_2F$, —CHF—$CH_3$, —$CF_2$—$CH_3$, methoxy, trifluoromethoxy, ethoxy, methlythio, methylsulfinyl and methylsulfonyl;

$R^{50'}$, $R^{51'}$, $R^{52'}$, $R^{53'}$, $R^{54'}$, $R^{55'}$ and $R^{56'}$ are selected, independently of each other, from the group consisting of hydrogen, fluorine, methyl, $CH_2F$ and $CF_3$;

$R^{57'}$, $R^{58'}$, $R^{59'}$ and $R^{60'}$ are selected, independently of each other, from the group consisting of hydrogen, halogen, cyano, $C_1$-$C_4$ alkyl, $CHF_2$ and $CF_3$;

provided that at least one of $R^{57'}$, $R^{58'}$, $R^{59'}$ and $R^{60'}$ is not hydrogen;

$R^{61'}$ and $R^{62'}$ are selected independently of each other from the group consisting of hydrogen, fluorine, methyl, ethyl, $CHF_2$ and $CF_3$;

$R^{62'}$, $R^{63'}$, $R^{64'}$, $R^{65'}$, $R^{66'}$, $R^{67'}$ and $R^{68'}$ are selected independently of each of there from the group consisting of hydrogen, fluoro, methyl, ethyl, methoxy, difluoromethoxy, trifluoromethoxy, $CHF_2$ and $CF_3$;

$R^{69'}$ is selected from hydrogen and $C_1$-$C_4$ alkyl;

n is 0 or 1;

p and q are independently selected from 0 and 1;

r and s are 0 and t is 1 or 0.

In another group of compounds, $G^1$ is a saturated $C_{10}$ fused bicyclic ring system;

$G^2$ is a $C_5$-$C_6$ cycloalkenyl group;

$G^3$ is phenyl;

$G^4$ is cyclohexyl or cyclopentyl;

$G^5$ is $C_6$ cycloalkyl, which is substituted by one or more groups independently selected from ethyl, n-propyl, iso-propyl, n-butyl, iso-butyl, sec-butyl, tert-butyl, n-pentyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$ and —CH($CH_3$)—CH($CH_3$)$_2$;

$G^6$ is phenyl, which must be substituted by at least one fluorine and is optionally further substituted by one or more methyl, bromine, iodine or chlorine;

$G^7$ is methylene;

$G^{10}$ is phenyl, which is optionally substituted by one or more groups independently selected from halogen, CN, methyl, ethyl, n-propyl, iso-propyl, ethenyl, methoxy, ethoxy, iso-propyloxy, phenyl, $CHF_2$, $CF_3$, CHF—$CH_3$ and $OCHF_2$;

$G^{11}$ is methylene substituted by at least one group independently selected from methyl, $CF_3$ and ethyl;

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, $C_1$-$C_4$ alkyl, $C_1$-$C_4$ alkoxy and =O;

$G^{17}$ is a five- to six-membered monocyclic heteroaromatic ring system which can contain 1 or 2 members selected from the group consisting of N, O and S, it not being possible for each ring system to contain —O—O—, —S—S— and —O—S— fragments, and it being possible for the five- to six-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or fluorophenyl;

$R^{1'}$, $R^{2'}$, $R^{3'}$, $R^{4'}$ and $R^{5'}$ are each hydrogen;

$R^{11'}$, $R^{12'}$, $R^{13'}$ and $R^{14'}$ are selected, independently of each other, from the group consisting of hydrogen, halogen, cyano, $C_1$-$C_4$ alkyl and $C_1$-$C_4$ alkoxy;

$R^{15'}$, $R^{16'}$, $R^{17'}$, $R^{18'}$, $R^{19'}$, $R^{20'}$, $R^{21'}$, $R^{22'}$, $R^{23'}$, $R^{24'}$ and $R^{25'}$ are each independently selected from hydrogen, methyl, ethyl and isopropyl;

$R^{23'}$, $R^{24'}$ and $R^{25'}$ are each independently selected from hydrogen, fluorine, chlorine, bromine, methyl, ethyl and isopropyl;

$R^{26'}$ is N—OH, N—O—$C_1$-$C_4$ alkyl, N—O—$C_2$-$C_4$ alkenyl, N—O—$C_2$-$C_4$ alkynyl, N—O—$C_1$-$C_4$ haloalkyl, N—O—$C_2$-$C_4$ haloalkenyl, N—O-benzyl, N—O-phenyl, N—O-halophenyl, O, $C_2$-$C_4$ alkenyloxy and C($R^{36'}$);

$R^{27'}$, $R^{28'}$, $R^{29'}$, $R^{30'}$, $R^{31'}$, $R^{32'}$, $R^{33'}$, $R^{34'}$ and $R^{35'}$ are each hydrogen or methyl; or $R^{27'}$ and $R^{28'}$ together with the two carbon atoms to which they are attached form a double bond;

each $R^{36'}$ is independently selected from hydrogen, halogen and $C_1$-$C_4$ alkyl;

$R^{37'}$, $R^{38'}$, $R^{39'}$, $R^{40'}$, $R^{41'}$, $R^{42'}$, $R^{43'}$ and $R^{44'}$ are hydrogen;

$R^{45'}$, $R^{46'}$, $R^{47'}$, $R^{48'}$ and $R^{49'}$ are independently selected from the group consisting of hydrogen, fluorine, chlorine, methyl, $CF_3$, $CHF_2$, $CH_2F$, methoxy, difluoromethoxy and trifluoromethoxy;

$R^{50'}$, $R^{51'}$, $R^{52'}$, $R^{53'}$, $R^{54'}$, $R^{55'}$ and $R^{56'}$ are each hydrogen;

$R^{57'}$, $R^{58'}$, $R^{59'}$ and $R^{60'}$ are selected, independently of each other, from the group consisting of hydrogen and halogen;

provided that at least one of $R^{57'}$, $R^{58'}$, $R^{59'}$ and $R^{60'}$ is not hydrogen;

$R^{61'}$, $R^{62'}$, $R^{63'}$, $R^{64'}$, $R^{65'}$, $R^{66'}$, $R^{67'}$ and $R^{68'}$ are hydrogen;

$R^{69'}$ is hydrogen;

n is 0 or 1;

p and q are independently selected from 0 and 1;

r, s and t are each 0.

In another preferred group of compounds, $R^5$ is $G^1$.
In another preferred group of compounds, $R^5$ is $G^2$.
In another preferred group of compounds, $R^5$ is $G^3$-$G^4$.
In another preferred group of compounds, $R^5$ is $G^5$.
In another preferred group of compounds, $R^5$ is $G^6$-$G^7$.
In another preferred group of compounds, $R^5$ is $G^8$.
In another preferred group of compounds, $R^5$ is $G^9$.
In another preferred group of compounds, $R^5$ is $G^{10}$-$G^{11}$.
In another preferred group of compounds, $R^5$ is $G^{12}$.
In another preferred group of compounds, $R^5$ is $G^{13}$.
In another preferred group of compounds, $R^5$ is $G^{14}$.
In another preferred group of compounds, $R^5$ is $G^{15}$.
In another preferred group of compounds, $R^5$ is $G^{16}$.

In a further group of compounds, $R_1$ is selected from $R^{1a}$ and $R^{1b}$;

$R_2$ is methyl;

$R_3$ is selected from $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$, $R^{3m}$, $R^{3n}$, $R^{3o}$, $R^{3p}$, $R^{3q}$, $R^{3r}$, $R^{3s}$, $R^{3t}$;

$R_4$ is selected from $R_{4a}$, $R_{4b}$, $R_{4c}$, $R_{4d}$, $R_{4e}$, $R_{4f}$;

$R_5$ is selected from $R^{5a}$, $R^{5b}$, $R^{5c}$, $R^{5d}$, $R^{5e}$, $R^{5f}$, $R^{5g}$, $R^{5h}$, $R^{5i}$, $R^{5j}$, $R^{5k}$, $R^{5l}$, $R^{5m}$, $R^{5n}$, $R^{5o}$, $R^{5p}$, $R^{5q}$, $R^{5r}$, $R^{5s}$, $R^{5t}$, $R^{5u}$, $R^{5v}$, $R^{5x}$, $R^{5y}$, $R^{5z}$, $R^{5ab}$, $R^{5ac}$, $R^{5ad}$, $R^{5ae}$, $R^{5af}$, $R^{5ag}$, $R^{5ah}$, $R^{5aj}$, $R^{5ak}$, $R^{5al}$, $R^{5am}$, $R^{5aa}$, $R^{5bb}$, $R^{5cc}$, $R^{5dd}$, $R^{5ee}$, $R^{5ff}$, $R^{5gg}$, $R^{5hh}$, $R^{5jj}$, $R^{5kk}$, $R^{5ll}$, $R^{5mm}$, $R^{5nn}$, $R^{5oo}$, $R^{5pp}$, $R^{5qq}$, $R^{5rr}$, $R^{5ss}$, $R^{5tt}$, $R^{5uu}$, $R^{5vv}$, $R^{5ww}$, $R^{5xx}$, $R^{5zz}$, $R^{5ba}$, $R^{5bc}$, $R^{5bd}$, $R^{5be}$, $R^{5bf}$, $R^{5bg}$, $R^{5bh}$, $R^{5bi}$, $R^{5bj}$, $R^{5bk}$, $R^{5bl}$, $R^{5bm}$, $R^{5bn}$, $R^{5bo}$, $R^{5bp}$, $R^{5bq}$, $R^{5br}$, $R^{5bs}$, $R^{5bt}$, $R^{5bu}$, $R^{5bv}$, $R^{5bw}$, $R^{5bx}$, $R^{5by}$, $R^{5bz}$, $R^{5ca}$, $R^{5cb}$, $R^{5cd}$, $R^{5ce}$, $R^{5cf}$, $R^{5cg}$, $R^{5bh}$, $R^{5ci}$, $R^{5cj}$, $R^{5ck}$, $R^{5cl}$, $R^{5cm}$, $R^{5cn}$, $R^{5co}$, $R^{5cp}$, $R^{5cq}$, $R^{5cr}$, $R^{5cs}$, $R^{5ct}$, $R^{5cu}$, $R^{5cv}$, $R^{5cw}$, $R^{5cx}$, $R^{5cy}$, $R^{5cz}$, $R^{5da}$, $R^{5db}$, $R^{5dc}$, $R^{5de}$, $R^{5df}$, $R^{5dg}$, $R^{5dh}$, $R^{5di}$, $R^{5dj}$, $R^{5dk}$, $R^{5dl}$, $R^{5dm}$, $R^{5dn}$, $R^{5do}$, $R^{5dp}$, $R^{5q}$, $R^{5dr}$, $R^{5ds}$, $R^{5dt}$, $R^{5du}$, $R^{5dv}$, $R^{5dw}$, $R^{5dx}$, $R^{5ea}$, $R^{5eb}$, $R^{5ec}$, $R^{5ed}$, $R^{5ef}$, $R^{5eg}$, $R^{5eh}$, $R^{5ei}$, $R^{5ej}$, $R^{5ek}$, $R^{5ela}$, $R^{5em}$, $R^{5en}$, $R^{5eo}$, $R^{5ep}$, $R^{5eq}$, $R^{5er}$, $R^{5es}$, $R^{5et}$, $R^{5eu}$, $R^{5ev}$, $R^{5ex}$, $R^{5ey}$, $R^{5ez}$, $R^{5fa}$, $R^{5fb}$, $R^{5fc}$, $R^{5fd}$, $R^{5fe}$, $R^{5fg}$, $R^{5fh}$, $R^{5fi}$, $R^{5fj}$, $R^{5fk}$, $R^{5fl}$, $R^{5fm}$, $R^{5fn}$, $R^{5fo}$, $R^{5fp}$, $R^{5fq}$, $R^{5fr}$, $R^{5fs}$, $R^{5ft}$, $R^{5fu}$, $R^{5fv}$, $R^{5fw}$;

$R_6$ is selected from $R^a$, $R^b$ and $R^c$;

$R_7$ is H;

$R^{1a}$ is selected from ethyl and isopropyl;

$R^{1b}$ is ethyl;

$R^{3a}$ is selected from hydrogen, halogen, CN, methyl, ethyl, isopropyl, CCH, CH=$CH_2$, $H_2$C=C—($CH_3$), cyclopropyl, halomethyl, haloethyl, methoxy, halomethoxy, ethoxy, haloethoxy, methlythio, halomethylthio, methylsulfinyl, halomethylsulfinyl, methylsulfonyl, halomethylsulfonyl, amino, methylamino, dimethylamino, ethylamino, diethylamino, ethylmethylamino, pyrrolidino, imidazolino, triazolino, CHO, $CH_2$OH, CH(OH)Me and CO-Me;

$R^{3b}$ is selected from hydrogen, F, Cl, Br, I, cyano, methyl, ethyl, isopropyl, fluoromethyl, difluoromethyl, trifluoromethyl, $(H_3C)$—CHF, methoxy and ethoxy;

$R^{3c}$ is selected from hydrogen, F, Br, I, methyl, ethyl, isopropyl, fluoromethyl, difluoromethyl, trifluoromethyl, $(H_3C)$—CHF, methoxy and ethoxy;

$R^{3d}$ is selected from hydrogen, halogen, cyano, methyl, ethyl, isopropyl, C≡CH, CH=$CH_2$, $H_2C$=C—$(CH_3)$, cyclopropyl, halomethyl, haloethyl, methoxy, ethoxy, methylthio, halomethylthio, methylsulfinyl, halomethylsulfinyl, methylsulfonyl, halomethylsulfonyl, amino, methylamino, dimethylamino, ethylamino, diethylamino, ethylmethylamino, pyrrolidino, imidazolino, triazolino, CHO and CO-Me;

$R^{3b}$ is selected from hydrogen, F, Cl, Br, I, cyano, methyl, ethyl, isopropyl, fluoromethyl, difluoromethyl, trifluoromethyl, $(H_3C)$—CHF, methoxy and ethoxy;

$R^{3c}$ is selected from hydrogen, F, Br, I, methyl, ethyl, isopropyl, fluoromethyl, difluoromethyl, trifluoromethyl, $(H_3C)$—CHF, methoxy and ethoxy;

$R^{3e}$ is selected from hydrogen, halogen, CN, methyl, ethyl, isopropyl, cyclopropyl, C≡CH, CH=$CH_2$, $C(CH_3)$=$CH_2$, halomethyl, haloethyl, methoxy, ethoxy, methlythio, halomethylthio, methylsulfinyl, halomethylsulfinyl, methylsulfonyl, halomethylsulfonyl, amino, methylamino, dimethylamino, ethylamino, diethylamino, ethylmethylamino, pyrrolidino, imidazolino, triazolino, CHO, $CH_2OH$, CH(OH)Me and CO-Me;

$R^{3f}$ is selected from hydrogen, halogen, CN, methyl, ethyl, isopropyl, cyclopropyl, C≡CH, CH=$CH_2$, $C(CH_3)$=$CH_2$, halomethyl, haloethyl, methoxy, ethoxy, methlythio, methylsulfinyl and methylsulfonyl;

$R^{3g}$ is selected from hydrogen, F, Br, I, methyl, ethyl, isopropyl, cyclopropyl, C≡CH, CH=$CH_2$, $C(CH_3)$=$CH_2$, $CF_3$, $CHF_2$, $CH_2F$, —CHF—$CH_3$, —$CF_2$—$CH_3$, methoxy, ethoxy, methlythio, methylsulfinyl and methylsulfonyl;

$R^{3h}$ is selected from hydrogen, Br, I, methyl, ethyl, C≡CH, CH=$CH_2$, $C(CH_3)$=$CH_2$, $CF_3$, $CHF_2$, $CH_2F$ and methoxy;

$R^{3i}$ is selected from hydrogen, halogen, CN, methyl, ethyl, isopropyl, cyclopropyl, C≡CH, CH=$CH_2$, $C(CH_3)$=$CH_2$, halomethyl, haloethyl, methoxy, ethoxy, methlythio, halomethylthio, methylsulfinyl, halomethylsulfinyl, methylsulfonyl, halomethylsulfonyl, amino, methylamino, dimethylamino, ethylamino, diethylamino, ethylmethylamino, pyrrolidino, imidazolino, triazolino, CHO and CO-Me;

$R^{3j}$ is selected from hydrogen, halogen, CN, methyl, ethyl, isopropyl, halomethyl, haloethyl, methoxy and ethoxy;

$R^{3k}$ is selected from hydrogen, halogen, methyl, ethyl, isopropyl, $CH_2F$, $CHF_2$, $CF_3$, CHF—$CH_3$, $CF_2$—$CH_3$, methoxy and ethoxy;

$R^{3l}$ is selected from hydrogen, halogen, methyl, ethyl, isopropyl, $CH_2F$, $CHF_2$, $CF_3$, CHF—$CH_3$, $CF_2$—$CH_3$, methoxy and ethoxy;

$R^{3m}$ is selected from hydrogen, F, Br, I, methyl, ethyl, $CHF_2$ and methoxy;

$R^{3n}$ is selected from hydrogen, halogen, CN, methyl, ethyl, isopropyl, cyclopropyl, C≡CH, CH=$CH_2$, $C(CH_3)$=$CH_2$, halomethyl, haloethyl, methoxy, ethoxy, methlythio, halomethylthio, methylsulfinyl, halomethylsulfinyl, methylsulfonyl, halomethylsulfonyl, amino, methylamino, dimethylamino, ethylamino, diethylamino, ethylmethylamino, pyrrolidino, imidazolino, triazolino, CHO, $CH_2OH$, CH(OH)Me and CO-Me;

$R^{3o}$ is selected from hydrogen, halogen, CN, methyl, ethyl, isopropyl, cyclopropyl, C≡CH, CH=$CH_2$, $C(CH_3)$=$CH_2$, halomethyl, haloethyl, methoxy, ethoxy, methlythio, halomethylthio, methylsulfinyl, halomethylsulfinyl, methylsulfonyl and halomethylsulfonyl;

$R^{3p}$ is selected from hydrogen, F, Br, I, methyl, ethyl, isopropyl, cyclopropyl, C≡CH, CH=$CH_2$, $C(CH_3)$=$CH_2$, halomethyl, haloethyl, methoxy and ethoxy;

$R^{3q}$ is selected from hydrogen, F, Br, I, methyl, ethyl, isopropyl, cyclopropyl, C≡CH, CH=$CH_2$, $C(CH_3)$=$CH_2$, $CF_3$, $CHF_2$, $CH_2F$, —CHF—$CH_3$, —$CF_2$—$CH_3$, methoxy, ethoxy, methylthio, methylsulfinyl and methylsulfonyl;

$R^{3r}$ is selected from hydrogen, Br, I, methyl, cyclopropyl, C≡CH, CH=$CH_2$, $CF_3$, $CHF_2$, $CH_2F$, —CHF—$CH_3$, —$CF_2$—$CH_3$ and methoxy;

$R^{3s}$ is selected from hydrogen, halogen, CN, methyl, ethyl, isopropyl, cyclopropyl, tert-butyl, C≡CH, CH=$CH_2$, $C(CH_3)$=$CH_2$, halomethyl, haloethyl, methoxy, halomethoxy, ethoxy, haloethoxy, methlythio, halomethylthio, methylsulfinyl, halomethylsulfinyl, methylsulfonyl, halomethylsulfonyl, amino, methylamino, dimethylamino, ethylamino, diethylamino, ethylmethylamino, pyrrolidino, imidazolino, triazolino, CHO and C(=O)Me;

$R^{3t}$ is selected from hydrogen, halogen, CN, methyl, ethyl, isopropyl, cyclopropyl, tert-butyl, C≡CH, CH=$CH_2$, $C(CH_3)$=$CH_2$, halomethyl, haloethyl, methoxy, halomethoxy, ethoxy, haloethoxy, methlythio, halomethylthio, methylsulfinyl, halomethylsulfinyl, methylsulfonyl, halomethylsulfonyl, amino, methylamino, dimethylamino, ethylamino, diethylamino, ethylmethylamino, pyrrolidino, imidazolino, triazolino, CHO and C(=O)Me;

$R_{4a}$ is selected from F, Cl, Br, $C_1$-$C_4$ alkyl, $C_1$-$C_4$ alkenyl, $C_1$-$C_4$ haloalkyl and $C_1$-$C_4$ cycloalkyl;

$R_{4b}$ is selected from F, Cl, methyl, ethyl, ethenyl, propyl, propenyl, isopropyl, isopropenyl, cyclopropanyl, methoxy, ethoxy, monofluoromethyl, polyfluoromethyl, monofluoroethyl and polyfluoromethyl $R_{4c}$ is selected from methyl, ethyl, methoxy, F and Cl;

$R_{4d}$ is selected from methyl, methoxy, F and Cl;

$R_{4e}$ is selected from methyl;

$R_{4f}$ is selected from methoxy, F and Cl;

$R^{5a}$ is a 3- to 6-membered cycloalkenyl group, or a 3- to 6-membered cycloalkenyl group that can be mono- to polysubstituted by substituents independently selected from the group consisting of halogen, CN, $NO_2$, OH, SH, CHO, COOH, tri($C_1$-$C_6$alkyl)silyl, ethyl, n-propyl, iso-propyl, n-butyl, iso-butyl, sec-butyl, tert-butyl, n-pentyl, —CH$(CH_3)$—$CH_2$—$CH_2$—$CH_3$, —CH—CH$(CH_3)$—$CH_2$—$CH_3$, —$CH_2$—$CH_2$—CH$(CH_3)$—$CH_3$, —$CH_2$—$CH_2$—CH$(CH_3)_2$, —CH$(CH_3)$—CH$(CH_3)_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, —C(=O)$NH_2$, —C(=O)NH($CH_3$), —C(=O)N$(CH_3)_2$ and —C(=S)$NH_2$;

$R^{5b}$ is a 3- to 6-membered cycloalkenyl group, or a 3- to 6-membered cycloalkenyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH$(CH_3)$—$CH_2$—$CH_2$—$CH_3$, —CH—CH$(CH_3)$—$CH_2$—$CH_3$, —$CH_2$—$CH_2$—CH$(CH_3)$—$CH_3$, —$CH_2$—$CH_2$—CH$(CH_3)_2$, —CH$(CH_3)$—CH$(CH_3)_2$, $C_1$-$C_6$ haloalkyl, $C_1$-$C_6$ alkoxy and $C_1$-$C_6$ alkylthio;

$R^{5c}$ is a 3- to 6-membered cycloalkenyl group, or a 3- to 6-membered cycloalkenyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$-fluoroalkyl, $C_1$-$C_6$ alkoxy and $C_1$-$C_6$ alkylthio;

$R^{5d}$ is a 5-membered cycloalkenyl group, or a 5-membered cycloalkenyl group that can be mono- to polysubstituted by substituents independently selected from the group consisting of halogen, CN, NO$_2$, OH, SH, CHO, COOH, tri($C_1$-$C_6$alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, —C(=O)NH$_2$, —C(=O)NH(CH$_3$), —C(=O)N(CH$_3$)$_2$ and —C(=S)NH$_2$;

$R^{5e}$ is a 5-membered cycloalkenyl group, or a 5-membered cycloalkenyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ haloalkyl, $C_1$-$C_6$ alkoxy and $C_1$-$C_6$ alkylthio;

$R^{5f}$ is a 5-membered cycloalkenyl group, or a 5-membered cycloalkenyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$-fluoroalkyl, $C_1$-$C_6$ alkoxy and $C_1$-$C_6$ alkylthio;

$R^{59g}$ is a 6-membered cycloalkenyl group, or a 6-membered cycloalkenyl group that can be mono- to polysubstituted by substituents independently selected from the group consisting of halogen, CN, NO$_2$, OH, SH, CHO, COOH, tri($C_1$-$C_6$alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$ $C_7$ alkenyloxycarbonyl, $C_4$ $C_7$ alkynyloxycarbonyl, $C_1$-$C_6$ alkylthio, $C_1$-$C_6$ alkylsulfinyl, $C_1$-$C_6$ alkylsulfonyl, —C(=O)NH$_2$, —C(=O)NH(CH$_3$), —C(=O)N(CH$_3$)$_2$ and —C(=S)NH$_2$;

$R^{5h}$ is a 6-membered cycloalkenyl group, or a 6-membered cycloalkenyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ haloalkyl, $C_1$-$C_6$ alkoxy and $C_1$-$C_6$ alkylthio;

$R^{5j}$ is a 6-membered cycloalkenyl group, or a 6-membered cycloalkenyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ fluoroalkyl, $C_1$-$C_6$ alkoxy and $C_1$-$C_6$ alkylthio;

$R^{5k}$ is a 3- to 7-membered cycloalkyl group, or a 3- to 7-membered cycloalkyl group that can be mono- to polysubstituted by substituents independently selected from the group consisting of halogen, CN, NO$_2$, OH, SH, CHO, COOH, tri($C_1$-$C_6$alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, —C(=O)NH$_2$, —C(=O)NH(CH$_3$), —C(=O)N(CH$_3$)$_2$ and —C(=S)NH$_2$;

$R^{5l}$ is a 3- to 7-membered cycloalkyl group, or a 3- to 7-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ haloalkyl, $C_1$-$C_6$ alkoxy and $C_1$-$C_6$ alkylthio;

$R^{5m}$ is a 3- to 7-membered cycloalkyl group, or a 3- to 7-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$-fluoroalkyl, $C_1$-$C_6$ alkoxy and $C_1$-$C_6$ alkylthio;

$R^{5n}$ is a 3-membered cycloalkyl group, or a 3-membered cycloalkyl group that can be mono- to polysubstituted by substituents independently selected from the group consisting of halogen, CN, NO$_2$, OH, SH, CHO, COOH, tri($C_1$-$C_6$alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$alkoxycarbonyl, $C_4$ $C_7$ alkenyloxycarbonyl, $C_4$ $C_7$ alkynyloxycarbonyl, $C_1$-$C_6$ alkylthio, $C_1$-$C_6$ alkylsulfinyl, $C_1$-$C_6$ alkylsulfonyl, —C(=O)NH$_2$, —C(=O)NH(CH$_3$), —C(=O)N(CH$_3$)$_2$ and —C(=S)NH$_2$;

$R^{5o}$ is a 3-membered cycloalkyl group, or a 3-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_1$-$C_6$ haloalkyl, $C_1$-$C_6$ alkoxy and $C_1$-$C_6$ alkylthio;

$R^{5p}$ is a 3-membered cycloalkyl group, or a 3-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH (CH$_3$)—CH$_3$, —CH$_2$—CH$_2$—CH(CH$_3$)$_2$, —CH(CH$_3$)—CH(CH$_3$)$_2$, C$_1$-C$_6$ fluoroalkyl, C$_1$-C$_6$ alkoxy and C$_1$-C$_6$ alkylthio;

R$^{5q}$ is a 4-membered cycloalkyl group, or a 4-membered cycloalkyl group that can be mono- to polysubstituted by substituents independently selected from the group consisting of halogen, CN, NO$_2$, OH, SH, CHO, COOH, tri(C$_1$-C$_6$alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_3$-C$_6$ cycloalkyl, C$_3$-C$_6$ halocycloalkyl, C$_2$-C$_6$ alkenyl, C$_2$-C$_6$ haloalkenyl, C$_1$-C$_6$ alkoxy, C$_1$-C$_6$ haloalkoxy, C$_2$-C$_7$ alkylcarbonyl, C$_2$-C$_7$alkoxycarbonyl, C$_4$-C$_7$ alkenyloxycarbonyl, C$_4$-C$_7$ alkynyloxycarbonyl, C$_1$-C$_6$ alkylthio, C$_1$-C$_6$ alkylsulfinyl, C$_1$-C$_6$ alkylsulfonyl, —C(=O)NH$_2$, —C(=O)NH(CH$_3$), —C(=O)N(CH$_3$)$_2$ and —C(=S)NH$_2$;

R$^{5r}$ is a 4-membered cycloalkyl group, or a 4-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_1$-C$_6$ alkoxy and C$_1$-C$_6$ alkylthio;

R$^{5s}$ is a 4-membered cycloalkyl group, or a 4-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ fluoroalkyl, C$_1$-C$_6$ alkoxy and C$_1$-C$_6$ alkylthio;

R$^{5t}$ is a 5-membered cycloalkyl group, or a 5-membered cycloalkyl group that can be mono- to polysubstituted by substituents independently selected from the group consisting of halogen, CN, NO$_2$, OH, SH, CHO, COOH, tri(C$_1$-C$_6$alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_3$-C$_6$ cycloalkyl, C$_3$-C$_6$ halocycloalkyl, C$_2$-C$_6$ alkenyl, C$_2$-C$_6$ haloalkenyl, C$_1$-C$_6$ alkoxy, C$_1$-C$_6$ haloalkoxy, C$_2$-C$_7$ alkylcarbonyl, C$_2$-C$_7$alkoxycarbonyl, C$_4$-C$_7$ alkenyloxycarbonyl, C$_4$-C$_7$ alkynyloxycarbonyl, C$_1$-C$_6$ alkylthio, C$_1$-C$_6$ alkylsulfinyl, C$_1$-C$_6$ alkylsulfonyl, —C(=O)NH$_2$, —C(=O)NH(CH$_3$), —C(=O)N(CH$_3$)$_2$ and —C(=S)NH$_2$;

R$^{5u}$ is a 5-membered cycloalkyl group, or a 5-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_1$-C$_6$ alkoxy and C$_1$-C$_6$ alkylthio;

R$^{5v}$ is a 5-membered cycloalkyl group, or a 5-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—

R$^{5x}$ is a 6-membered cycloalkyl group, or a 6-membered cycloalkyl group that can be mono- to polysubstituted by substituents independently selected from the group consisting of halogen, CN, NO$_2$, OH, SH, CHO, COOH, tri(C$_1$-C$_6$alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_3$-C$_6$ cycloalkyl, C$_3$-C$_6$ halocycloalkyl, C$_2$-C$_6$ alkenyl, C$_2$-C$_6$ haloalkenyl, C$_1$-C$_6$ alkoxy, C$_1$-C$_6$ haloalkoxy, C$_2$-C$_7$ alkylcarbonyl, C$_2$-C$_7$alkoxycarbonyl, C$_4$-C$_7$ alkenyloxycarbonyl, C$_4$-C$_7$ alkynyloxycarbonyl, C$_1$-C$_6$ alkylthio, C$_1$-C$_6$ alkylsulfinyl, C$_1$-C$_6$ alkylsulfonyl, —C(=O)NH$_2$, —C(=O)NH(CH$_3$), —C(=O)N(CH$_3$)$_2$ and —C(=S)NH$_2$;

R$^{5y}$ is a 6-membered cycloalkyl group, or a 6-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_1$-C$_6$ alkoxy and C$_1$-C$_6$ alkylthio;

R$^{5z}$ is a 6-membered cycloalkyl group, or a 6-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ fluoroalkyl, C$_1$-C$_6$ alkoxy and C$_1$-C$_6$ alkylthio;

R$^{5ab}$ is a 7-membered cycloalkyl group, or a 7-membered cycloalkyl group that can be mono- to polysubstituted by substituents independently selected from the group consisting of halogen, CN, NO$_2$, OH, SH, CHO, COOH, tri(C$_1$-C$_6$ alkyl)silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_3$-C$_6$ cycloalkyl, C$_3$-C$_6$ halocycloalkyl, C$_2$-C$_6$ alkenyl, C$_2$-C$_6$ haloalkenyl, C$_1$-C$_6$ alkoxy, C$_1$-C$_6$ haloalkoxy, C$_2$-C$_7$ alkylcarbonyl, C$_2$-C$_7$ alkoxycarbonyl, C$_4$-C$_7$ alkenyloxycarbonyl, C$_4$-C$_7$ alkynyloxycarbonyl, C$_1$-C$_6$ alkylthio, C$_1$-C$_6$ alkylsulfinyl, C$_1$-C$_6$ alkylsulfonyl, —C(=O)NH$_2$, —C(=O)NH(CH$_3$), —C(=O)N(CH$_3$)$_2$ and —C(=S)NH$_2$;

R$^{5ac}$ is a 7-membered cycloalkyl group, or a 7-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_1$-C$_6$ alkoxy and C$_1$-C$_6$ alkylthio;

R$^{5ad}$ is a 7-membered cycloalkyl group, or a 7-membered cycloalkyl group that can be mono- to polysubstituted by substituents independently selected from the group consisting of halogen, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH (CH$_3$)—CH$_3$, —CH$_2$—CH$_2$—CH(CH$_3$)$_2$, —CH(CH$_3$)—CH(CH$_3$)$_2$, C$_1$-C$_6$ fluoroalkyl, C$_1$-C$_6$ alkoxy and C$_1$-C$_6$ alkylthio;

R$^{5ae}$ is G$^8$ wherein R$^{1'}$, R$^{2'}$, R$^{3'}$, R$^{4'}$ and R$^{5'}$ are each independently selected from hydrogen, fluoro, C$_1$-C$_4$ alkyl, C$_1$-C$_4$ haloalkyl, C$_1$-C$_4$ alkoxy and C$_1$-C$_4$ alkylthio;

and wherein R$^{11'}$, R$^{12'}$, R$^{13'}$ and R$^{14'}$ are each independently selected from hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

R$^{5af}$ is G$^8$ wherein R$^{1'}$, R$^{2'}$, R$^{3'}$, R$^{4'}$ and R$^{5'}$ are each independently selected from hydrogen, fluoro, C$_1$-C$_4$ alkyl, C$_1$-C$_4$ haloalkyl, C$_1$-C$_4$ alkoxy and C$_1$-C$_4$ alkylthio;

and wherein R$^{11'}$, R$^{12'}$, R$^{13'}$ and R$^{14'}$ are each independently selected from hydrogen, halogen, C$_1$-C$_6$ alkyl, C$_1$-C$_6$ haloalkyl, C$_1$-C$_6$ alkoxy and C$_1$-C$_6$ alkylthio;

R$^{5ag}$ is G$^8$ wherein R$^{1'}$, R$^{2'}$, R$^{3'}$, R$^{4'}$ and R$^{5'}$ are each independently selected from hydrogen, fluoro, methyl, ethyl, CH$_2$F, CHF$_2$, CF$_3$, CHF—CH$_3$, CF$_2$—CH$_3$, methoxy, ethoxy, S—CH$_3$ and S—CH$_2$CH$_3$;

and wherein R$^{11'}$, R$^{12'}$, R$^{13'}$ and R$^{14'}$ are each independently selected from hydrogen, halogen, C$_1$-C$_4$ alkyl, C$_1$-C$_4$ haloalkyl, C$_1$-C$_4$ alkoxy and C$_1$-C$_4$ alkylthio;

R$^{5ah}$ is G$^8$ wherein R$^{1'}$, R$^{2'}$, R$^{3'}$, R$^{4'}$ and R$^{5'}$ are each independently selected from hydrogen, fluoro, methyl, CHF$_2$, CF$_3$ and methoxy;

and wherein R$^{11'}$, R$^{12'}$, R$^{13'}$ and R$^{14'}$ are each independently selected from hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

R$^{5aj}$ is G$^8$ wherein R$^{1'}$, R$^{2'}$, R$^{3'}$, R$^{4'}$ and R$^{5'}$ are each independently selected from hydrogen, fluoro, methyl, CHF$_2$, CF$_3$ and methoxy;

and wherein R$^{11'}$, R$^{12'}$, R$^{13'}$ and R$^{14'}$ are each independently selected from hydrogen, halogen, C$_1$-C$_6$ alkyl, C$_1$-C$_6$ haloalkyl, C$_1$-C$_6$ alkoxy and C$_1$-C$_6$ alkylthio;

R$^{5ak}$ is G$^8$ wherein R$^{1'}$, R$^{2'}$, R$^{3'}$, R$^{4'}$ and R$^{5'}$ are each independently selected from hydrogen, fluoro, methyl, CHF$_2$, CF$_3$ and methoxy;

and wherein R$^{11'}$, R$^{12'}$, R$^{13'}$ and R$^{14'}$ are each independently selected from hydrogen, halogen, C$_1$-C$_4$ alkyl, C$_1$-C$_4$ haloalkyl, C$_1$-C$_4$ alkoxy and C$_1$-C$_4$ alkylthio;

R$^{5al}$ is G$^8$ wherein R$^{1'}$, R$^{2'}$, R$^{3'}$, R$^{4'}$ and R$^{5'}$ are each hydrogen;

and wherein R$^{11'}$, R$^{12'}$, R$^{13'}$ and R$^{14'}$ are each independently selected from hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

R$^{5am}$ is G$^8$ wherein R$^{1'}$, R$^{2'}$, R$^{3'}$, R$^{4'}$ and R$^{5'}$ are each hydrogen;

and wherein R$^{11'}$, R$^{12'}$, R$^{13'}$ and R$^{14'}$ are each independently selected from hydrogen, halogen, C$_1$-C$_6$ alkyl, C$_1$-C$_6$ haloalkyl, C$_1$-C$_6$ alkoxy and C$_1$-C$_6$ alkylthio;

R$^{5aa}$ is G$^8$ wherein R$^{1'}$, R$^{2'}$, R$^{3'}$, R$^{4'}$ and R$^{5'}$ are each hydrogen;

and wherein R$^{11'}$, R$^{12'}$, R$^{13'}$ and R$^{14'}$ are each independently selected from hydrogen, halogen, C$_1$-C$_4$ alkyl, C$_1$-C$_4$ haloalkyl, C$_1$-C$_4$ alkoxy and C$_1$-C$_4$ alkylthio;

R$^{5bb}$ is a benzyl group, wherein the phenyl ring is substituted by at least one fluorine and optionally by one or more groups independently selected from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

R$^{5cc}$ is a benzyl group, wherein the phenyl ring is substituted by at least one fluorine and optionally by one or more groups independently selected from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_1$-C$_6$ alkoxy, C$_1$-C$_6$ haloalkoxy, C$_3$-C$_6$ alkenyloxy, C$_3$-C$_6$ alkynyloxy, C$_1$-C$_6$ alkylthio, C$_1$-C$_6$ alkylsulfinyl and C$_1$-C$_6$ alkylsulfonyl;

R$^{5dd}$ is a benzyl group, wherein the phenyl ring is substituted by at least one fluorine and optionally by one or more groups independently selected from the group consisting of hydrogen, halogen, CN, C$_1$-C$_6$ alkyl, C$_1$-C$_6$ haloalkyl, C$_3$-C$_6$ cycloalkyl, C$_2$-C$_6$ alkenyl, C$_2$-C$_6$ alkynyl, C$_1$-C$_6$ alkoxy, C$_3$-C$_6$ alkenyloxy, C$_3$-C$_6$ alkynyloxy and C$_1$-C$_6$ alkylthio;

R$^{5ee}$ is a benzyl group, wherein the phenyl ring is substituted by at least one fluorine and optionally by one or more groups independently selected from the group consisting of hydrogen, halogen, CN, C$_1$-C$_4$ alkyl, C$_1$-C$_4$ haloalkyl, C$_2$-C$_4$ alkenyl, C$_3$-C$_6$ cycloalkyl and C$_1$-C$_4$ alkoxy;

R$^{5ff}$ is a benzyl group, wherein the methylene portion is substituted by at least one group independently selected from the group consisting of hydrogen, C$_1$-C$_4$ alkyl, C$_1$-C$_4$ haloalkyl, CN, C$_1$-C$_4$ alkoxy and C$_1$-C$_4$ haloalkoxy;

and wherein the phenyl ring is optionally substituted by one or more groups independently selected from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

R$^{5gg}$ is a benzyl group, wherein the methylene portion is substituted by at least one group independently selected from the group consisting of hydrogen, C$_1$-C$_4$ alkyl, C$_1$-C$_4$ haloalkyl and C$_1$-C$_4$ alkoxy;

and wherein the phenyl ring is optionally substituted by one or more groups independently selected from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{5hh}$ is a benzyl group, wherein the methylene portion is substituted one group independently selected from the group consisting of $C_1$-$C_4$ alkyl, $C_1$-$C_4$ haloalkyl and $C_1$-$C_4$ alkoxy;

and wherein the phenyl ring is optionally substituted by one or more groups independently selected from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl $R^{5jj}$ is a benzyl group, wherein the methylene portion is substituted by one group independently selected from the group consisting of hydrogen, $C_1$-$C_4$ alkyl, $C_1$-$C_4$ haloalkyl and $C_1$-$C_4$ alkoxy;

and wherein the phenyl ring is optionally substituted by one or more groups independently selected from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{5kk}$ is a benzyl group, wherein the methylene portion is substituted one group independently selected from the group consisting of methyl, ethyl, $CHF_2$, $CF_3$ and methoxy;

and wherein the phenyl ring is optionally substituted by one or more groups independently selected from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{5ll}$ is a benzyl group, wherein the methylene portion is substituted by one group independently selected from the group consisting of methyl, ethyl, $CHF_2$, $CF_3$ and methoxy;

and wherein the phenyl ring is optionally substituted by one or more groups independently selected from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{5mm}$ is a benzyl group, wherein the methylene portion is substituted by at least one group independently selected from the group consisting of hydrogen, $C_1$-$C_4$ alkyl, $C_1$-$C_4$ haloalkyl, CN, $C_1$-$C_4$ alkoxy and $C_1$-$C_4$ haloalkoxy;

and wherein the phenyl ring is optionally substituted by one or more groups independently selected from the group consisting of hydrogen, halogen, CN, OH, SH, CHO $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_3$-$C_6$ cycloalkoxy, $C_1$-$C_6$ alkylthio, $C_1$-$C_6$ alkylsulfinyl and $C_1$-$C_6$ alkylsulfonyl;

$R^{5nn}$ is a benzyl group, wherein the methylene portion is substituted one group independently selected from the group consisting of $C_1$-$C_4$ alkyl, $C_1$-$C_4$ haloalkyl and $C_1$-$C_4$ alkoxy;

and wherein the phenyl ring is optionally substituted by one or more groups independently selected from the group consisting of hydrogen, halogen, CN, OH, SH, CHO $C_r$, $C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_3$-$C_6$ cycloalkoxy, $C_1$-$C_6$ alkylthio, $C_1$-$C_6$ alkylsulfinyl and $C_1$-$C_6$ alkylsulfonyl;

$R^{oo}$ is a benzyl group, wherein the methylene portion is substituted one group independently selected from the group consisting of methyl, ethyl, $CHF_2$, $CF_3$ and methoxy;

and wherein the phenyl ring is optionally substituted by one or more groups independently selected from the group consisting of hydrogen, halogen, CN, OH, SH, CHO $C_r$, $C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_3$-$C_6$ cycloalkoxy, $C_1$-$C_6$ alkylthio, $C_1$-$C_6$ alkylsulfinyl and $C_1$-$C_6$ alkylsulfonyl;

$R^{5pp}$ is a benzyl group, wherein the methylene portion is substituted by at least one group independently selected from the group consisting of hydrogen, $C_1$-$C_4$ alkyl, $C_1$-$C_4$ haloalkyl, CN, $C_1$-$C_4$ alkoxy and $C_1$-$C_4$ haloalkoxy;

and wherein the phenyl ring is optionally substituted by one or more groups independently selected from the group consisting of hydrogen, halogen, CN, OH, SH, CHO, methyl, ethyl, n-propyl, iso-propyl, $CH_2F$, $CHF_2$, $CF_3$, $CHF-CH_3$, $CF_2-CH_3$, $CF_2-CF_3$, cyclopropyl, $CH=CH_2$, $C(CH_3)=CH_2$, $CH=CH(CH_3)$, $C(CH_3)=CH(CH_3)$, $CH=C(CH_3)_2$, $C(CH_3)=C(CH_3)_2$, $CH=CF_2$, $CH=CCl_2$, $C≡CH$, methoxy, ethoxy, iso-propyloxy, $OCHF_2$, $OCH_2-C≡CH$, $OCH(CH_3)-C≡CH$, $SCH_3$, $SCH_2CH_3$, $S(=O)CH_3$, $S(=O)CH_2CH_3$, $S(=O)_2CH_3$ and $S(=O)_2CH_2CH_3$;

$R^{5qq}$ is a benzyl group, wherein the methylene portion is substituted one group independently selected from the group consisting of $C_1$-$C_4$ alkyl, $C_1$-$C_4$ haloalkyl and $C_1$-$C_4$ alkoxy;

and wherein the phenyl ring is optionally substituted by one or more groups independently selected from the group consisting of hydrogen, halogen, CN, OH, SH, CHO, methyl, ethyl, n-propyl, iso-propyl, $CH_2F$, $CHF_2$, $CF_3$, $CHF-CH_3$, $CF_2-CH_3$, $CF_2-CF_3$, cyclopropyl, $CH=CH_2$, $C(CH_3)=CH_2$, $CH=CH(CH_3)$, $C(CH_3)=CH(CH_3)$, $CH=C(CH_3)_2$, $C(CH_3)=C(CH_3)_2$, $CH=CF_2$, $CH=CCl_2$, $C≡CH$, methoxy, ethoxy, iso-propyloxy, $OCHF_2$, $OCH_2-C≡CH$, $OCH(CH_3)-C≡CH$, $SCH_3$, $SCH_2CH_3$, $S(=O)CH_3$, $S(=O)CH_2CH_3$, $S(=O)_2CH_3$ and $S(=O)_2CH_2CH_3$;

$R^{5rr}$ is a benzyl group, wherein the methylene portion is substituted one group independently selected from the group consisting of methyl, ethyl, $CHF_2$, $CF_3$ and methoxy;

and wherein the phenyl ring is optionally substituted by one or more groups independently selected from the group consisting of hydrogen, halogen, CN, OH, SH, CHO, methyl, ethyl, n-propyl, iso-propyl, $CH_2F$, $CHF_2$, $CF_3$, CHF—$CH_3$, $CF_2$—$CH_3$, $CF_2$—$CF_3$, cyclopropyl, CH=$CH_2$, $C(CH_3)$=$CH_2$, CH=CH($CH_3$), $C(CH_3)$=CH($CH_3$), CH=$C(CH_3)_2$, $C(CH_3)$=$C(CH_3)_2$, CH=$CF_2$, CH=$CCl_2$, C≡CH, methoxy, ethoxy, iso-propyloxy, $OCHF_2$, $OCH_2$—C≡CH, $OCH(CH_3)$—C≡CH, $SCH_3$, $SCH_2CH_3$, S(=O)$CH_3$, S(=O)$CH_2CH_3$, S(=O)$_2CH_3$ and S(=O)$_2CH_2CH_3$;

$R^{5ss}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

$R^{5tt}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is either 0 or 1;

$R^{5vv}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, CHF—$CH_3$, $CF_2$—$CH_3$, $CH_2$—$CH_2F$ $CH_2$—$CHF_2$ and $CH_2$—$CF_3$;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is either 0 or 1;

$R^{5vv}$ is $G^9$ wherein $R^{15'}$, $R^{16'}$, $R^{17'}$, $R^{18'}$, $R^{19'}$, $R^{20'}$, $R^{21'}$ and $R^{22'}$ are each hydrogen;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is either 0 or 1;

$R^{5ww}$ is $G^9$ wherein $R^{15'}$ and $R^{16'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is either 0 or 1;

$R^{5xx}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ are hydrogen;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is either 0 or 1;

$R^{5zz}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, cyano, halogen, methyl, ethyl, isopropyl, fluoromethyl and fluoroethyl;

$R^{5ba}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is either 0 or 1;

$R^{5bc}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, CHF—$CH_3$, $CF_2$—$CH_3$, $CH_2$—$CH_2F$ $CH_2$—$CHF_2$ and $CH_2$—$CF_3$;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is either 0 or 1;

$R^{5bd}$ is $G^9$ wherein $R^{15'}$, $R^{16'}$, $R^{17'}$, $R^{18'}$, $R^{19'}$, $R^{20'}$, $R^{21'}$ and $R^{22'}$ are each hydrogen;

$R^{22'}$ to $R^{24'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is either 0 or 1;

$R^{5be}$ is $G^9$ wherein $R^{15'}$ and $R^{16'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is either 0 or 1;

$R^{5bf}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ is hydrogen;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is either 0 or 1;

$R^{5bg}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

$R^{5bh}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

n is either 0 or 1;

$R^{5bi}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

n is either 0 or 1;

$R^{5bj}$ is $G^9$ wherein $R^{15'}$, $R^{16'}$, $R^{17'}$, $R^{18'}$, $R^{19'}$, $R^{20'}$, $R^{21'}$ and $R^{22'}$ are each hydrogen;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

n is either 0 or 1;

$R^{5bk}$ is $G^9$ wherein $R^{15'}$ and $R^{16'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

n is either 0 or 1;

$R^{5bl}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ is hydrogen;

$R^{22'}$ to $R^{24'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

n is either 0 or 1;

$R^{5bm}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 0;

$R^{5bn}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 0;

$R^{5bo}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 0;

$R^{5bp}$ P is $G^9$ wherein $R^{15'}$, $R^{16'}$, $R^{17'}$, $R^{18'}$, $R^{19'}$, $R^{20'}$, $R^{21'}$ and $R^{22'}$ are each hydrogen;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 0;

$R^{5bq}$ is $G^9$ wherein $R^{15'}$ and $R^{16'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$cycloalkyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 0;

$R^{5br}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ is selected independently of each other, from the group consisting of hydrogen;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 0;

$R^{5bs}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 0;

$R^{5bt}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 0;

$R^{5bu}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 0;

$R^{5bv}$ is $G^9$ wherein $R^{15'}$, $R^{16'}$, $R^{17'}$, $R^{18'}$, $R^{19'}$, $R^{20'}$, $R^{21'}$ and $R^{22'}$ are each hydrogen;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 0;

$R^{5bw}$ is $G^9$ wherein $R^{15'}$ and $R^{16'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 0;

$R^{5bx}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ is hydrogen;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 0;

$R^{5by}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 0;

$R^{5bz}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 0;

$R^{5ca}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 0;

$R^{5cb}$ is $G^9$ wherein $R^{15'}$, $R^{16'}$, $R^{17'}$, $R^{18'}$, $R^{19'}$, $R^{20'}$, $R^{21'}$ and $R^{22'}$ and $R^{22'}$ are each hydrogen;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 0;

$R^{5cd}$ is $G^9$ wherein $R^{23'}$, $R^{24'}$ and $R^{25'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 0;

$R^{5ce}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ is hydrogen;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 0;

$R^{5cf}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 1;

$R^{5cg}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 1;

$R^{5ch}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 1;

$R^{5ci}$ is $G^9$ wherein $R^{15'}$, $R^{16'}$, $R^{17'}$, $R^{18'}$, $R^{19'}$, $R^{20'}$, $R^{21'}$ and $R^{22'}$ are each hydrogen;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 1;

$R^{5cj}$ is $G^9$ wherein $R^{15'}$ and $R^{16'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 1;

$R^{5ck}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ is selected independently of each other, from the group consisting of hydrogen;

$R^{23'}$, $R^{24'}$ and $R^{25'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

n is 1;

$R^{5cl}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 1;

$R^{5cm}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 1;

$R^{5cn}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 1;

$R^{5co}$ is $G^9$ wherein $R^{15'}$, $R^{16'}$, $R^{17'}$, $R^{18'}$, $R^{19'}$, $R^{20'}$, $R^{21'}$ and $R^{22'}$ are each hydrogen;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 1;

$R^{5cp}$ is $G^9$ wherein $R^{15'}$ and $R^{16'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 1;

$R^{5cq}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ is hydrogen;

$R^{23'}$, $R^{24'}$ and $R^{25'}$ are selected independently of each other, from the group consisting of hydrogen, cyano, halogen, methyl, ethyl, isopropyl, monofluoromethyl, polyfluoromethyl, monofluoroethyl, and polyfluoroethyl;

n is 1;

$R^{5cr}$ is $G^9$ wherein $R^{15'}$ and $R^{16'}$ are selected independently of each other, from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 1;

$R^{5cs}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, halogen, methyl, ethyl, isopropyl, monofluoromethyl, polyfluoromethyl, monofluoroethyl, and polyfluoroethyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 1;

$R^{5ct}$ is $G^9$ wherein each $R^{15'}$, $R^{16'}$, $R^{17'}$, $R^{18'}$, $R^{19'}$, $R^{20'}$, $R^{21'}$ and $R^{22'}$ are selected independently of each other, from the group consisting of hydrogen, fluorine, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF-CH_3$, $CF_2-CH_3$, $CH_2-CH_2F$ $CH_2-CHF_2$ and $CH_2-CF_3$;

n is 1;

$R^{5cu}$ is $G^9$ wherein $R^{15'}$, $R^{16'}$, $R^{17'}$, $R^{18'}$, $R^{19'}$, $R^{20'}$, $R^{21'}$ and $R^{22'}$ are each hydrogen;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

n is 1;

$R^{5cv}$ is $G^9$ wherein $R^{15'}$ and $R^{16'}$ are selected independently of each other, from the group consisting of methyl, F and $CF_3$;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

n is 1;

$R^{5cw}$ is $G^9$ wherein $R^{15'}$ is selected from the group consisting of hydrogen, halogen, cyano, $C_1$-$C_4$ alkyl, $C_1$-$C_4$ haloalkyl and $C_3$-$C_6$ cycloalkyl;

each $R^{16'}$, $R^{17'}$, $R^{18'}$, $R^{19'}$, $R^{20'}$, $R^{21'}$ and $R^{22'}$ is hydrogen;

$R^{23'}$, $R^{24'}$ and $R^{25'}$ are selected independently of each other, from the group consisting of hydrogen, F, Cl, Br, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

n is 1;

$R^{5cx}$ is $G^{14}$ wherein $G^{14}$ is wherein $R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy and $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are independently selected from 0 and 1;

$R^{5cy}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are independently selected from 0 and 1;

$R^{5cz}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are independently selected from 0 and 1;

$R^{5da}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and $CF_3$;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are independently selected from 0 and 1;

$R^{5db}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are independently selected from 0 and 1;

$R^{5dc}$ is $G^{14}$ wherein $R^{37'}$ is selected independently of each other from the group consisting of hydrogen, halogen, cyano, $C_1$-$C_4$ alkyl and $C_1$-$C_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are independently selected from 0 and 1;

$R^{5de}$ is $G^{14}$ wherein $R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$, and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy and $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are independently selected from 0 and 1;

$R^{5df}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are independently selected from 0 and 1;

$R^{5dg}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, CH$_2$F, CHF$_2$, CF$_3$, CHF—CH$_3$, CF$_2$—CH$_3$, CH$_2$—CH$_2$F CH$_2$—CHF$_2$ and CH$_2$—CF$_3$;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are independently selected from 0 and 1;

$R^{5dh}$ is $G^{14}$ wherein $R^{37'}$, $R^{38'}$, $R^{39'}$, $R^{40'}$, $R^{41'}$, $R^{42'}$, $R^{43'}$ and 44' are selected independently of each other from the group consisting of methyl, ethyl, F and CF$_3$;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are independently selected from 0 and 1;

$R^{5di}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are independently selected from 0 and 1;

$R^{5dj}$ is $G^{14}$ wherein $R^{37'}$ is selected independently of each other from the group consisting of hydrogen, halogen, cyano, $C_1$-$C_4$ alkyl and $C_1$-$C_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are independently selected from 0 and 1;

$R^{5dk}$ is $G^{14}$ wherein $R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy and $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are independently selected from 0 and 1;

$R^{5dl}$ is $G^{14}$ wherein $R^{37'}$, $R^{38'}$, $R^{39'}$, $R^{40'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are independently selected from 0 and 1;

$R^{5dm}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, CH$_2$F, CHF$_2$, CF$_3$, CHF—CH$_3$, CF$_2$—CH$_3$, CH$_2$—CH$_2$F CH$_2$—CHF$_2$ and CH$_2$—CF$_3$;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are independently selected from 0 and 1;

$R^{5dn}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and CF$_3$;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are independently selected from 0 and 1;

$R^{5do}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are independently selected from 0 and 1;

$R^{5dp}$ is $G^{14}$ wherein $R^{37'}$ is selected from the group consisting of hydrogen, halogen, cyano, $C_1$-$C_4$ alkyl and $C_1$-$C_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are independently selected from 0 and 1;

$R^{5dq}$ is $G^{14}$ wherein $R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, and $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are each 0;

$R^{5dr}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are each 0;

$R^{5ds}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are each 0;

$R^{5dt}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and $CF_3$;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are each 0;

$R^{5du}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are each 0;

$R^{5dv}$ is $G^{14}$ wherein $R^{37'}$ is selected from the group consisting of hydrogen, halogen, cyano, $C_1$-$C_4$ alkyl and $C_1$-$C_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p and q are each 0;

$R^{5dw}$ is $G^{14}$ wherein $R^{37'}$ and $R^{37'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, $C\equiv CH$, $CH=CH_2$, $C(CH_3)=CH_2$, $CF_3$, $CHF_2$, $CH_2F$, —$CHF$—$CH_3$, —$CF_2$—$CH_3$, methoxy, trifluoromethoxy, ethoxy, methlythio, methylsulfinyl and methylsulfonyl;

p and q are each 0;

$R^{5dx}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, $C\equiv CH$, $CH=CH_2$, $C(CH_3)=CH_2$, $CF_3$, $CHF_2$, $CH_2F$, —$CHF$—$CH_3$, —$CF_2$—$CH_3$, methoxy, trifluoromethoxy, ethoxy, methlythio, methylsulfinyl and methylsulfonyl;

p and q are each 0;

$R^{5ea}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, $C\equiv CH$, $CH=CH_2$, $C(CH_3)=CH_2$, $CF_3$, $CHF_2$, $CH_2F$, —$CHF$—$CH_3$, —$CF_2$—$CH_3$, methoxy, trifluoromethoxy, ethoxy, methlythio, methylsulfinyl and methylsulfonyl;

p and q are each 0;

$R^{eb}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently from each other from the group consisting of methyl, ethyl, F and $CF_3$;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are each 0;

$R^{5ec}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are each 0;

$R^{5ed}$ is $G^{14}$ wherein $R^{37'}$ is selected from the group consisting of hydrogen, halogen, cyano, C$_1$-C$_4$ alkyl and C$_1$-C$_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p and q are each 0;

$R^{5ef}$ is $G^{14}$ wherein $R^{37'}$ and $R^{38'}$ are selected independently of each other from the group consisting of hydrogen, halogen, cyano, C$_1$-C$_4$ alkyl and C$_1$-C$_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, C$_1$-C$_4$ alkyl, C$_1$-C$_4$ haloalkyl, C$_1$-C$_4$ alkoxy, C$_1$-C$_4$ haloalkoxy and C$_1$-C$_4$ alkylthio;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are each 0;

$R^{5eg}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are each 0;

$R^{5eh}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, CH$_2$F, CHF$_2$, CF$_3$, CHF—CH$_3$, CF$_2$—CH$_3$, CH$_2$—CH$_2$F CH$_2$—CHF$_2$ and CH$_2$—CF$_3$;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are each 0;

$R^{5ei}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and CF$_3$;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are each 0;

$R^{5ej}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p and q are each 0;

$R^{5ek}$ is $G^{14}$ wherein $R^{37'}$ is selected from the group consisting of hydrogen, halogen, cyano, C$_1$-C$_4$ alkyl and C$_1$-C$_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p is 0;

q is 1;

$R^{5el}$ is $G^{14}$ wherein $R^{37'}$ and $R^{38'}$ are selected independently of each other from the group consisting of hydrogen, halogen, cyano, C$_1$-C$_4$ alkyl and C$_1$-C$_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, C$_1$-C$_4$ alkyl, C$_1$-C$_4$ haloalkyl, C$_1$-C$_4$ alkoxy, C$_1$-C$_4$ haloalkoxy and C$_1$-C$_4$ alkylthio;

$R^{45'}$, $R^{46'}$, $R^{47'}$, $R^{48'}$ and $R^{49'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

p is 0;

q is 1;

$R^{5em}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

p is 0;

q is 1;

$R^{5en}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, CH$_2$F, CHF$_2$, CF$_3$, CHF—CH$_3$, CF$_2$—CH$_3$, CH$_2$—CH$_2$F CH$_2$—CHF$_2$ and CH$_2$—CF$_3$;

$R^{45'}$, $R^{46'}$, $R^{47'}$, $R^{48'}$ and $R^{49'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p is 0;
q is 1;
$R^{5eo}$ is $G^{14}$ wherein $R^{37'}$, $R^{38'}$, $R^{39'}$, $R^{40'}$, $R^{41'}$, $R^{42'}$, $R^{43'}$ and $R^{44'}$ are independently selected of each other from the group consisting of methyl, ethyl, F and $CF_3$;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p is 0;
q is 1;
$R^{5ep}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p is 0;
q is 1;
$R^{5eq}$ is $G^{14}$ wherein $R^{37'}$ is selected from the group consisting of hydrogen, halogen, cyano, $C_1$-$C_4$ alkyl and $C_1$-$C_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p is 0;
q is 1;
$R^{5er}$ is $G^{14}$ wherein $R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=$CH_2$, C($CH_3$)=$CH_2$, $CF_3$, $CHF_2$, $CH_2F$, —CHF—$CH_3$, —$CF_2$—$CH_3$, methoxy, trifluoromethoxy, ethoxy, methlythio, methylsulfinyl and methylsulfonyl;

p is 0;
q is 1;
$R^{5es}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=$CH_2$, C($CH_3$)=$CH_2$, $CF_3$, $CHF_2$, $CH_2F$, —CHF—$CH_3$, —$CF_2$—$CH_3$, methoxy, trifluoromethoxy, ethoxy, methlythio, methylsulfinyl and methylsulfonyl;

p is 0;
q is 1;
$R^{5et}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, $CH_2F$, $CHF_2$, $CF_3$, CHF—$CH_3$, $CF_2$—$CH_3$, $CH_2$—$CH_2F$ $CH_2$—$CHF_2$ and $CH_2$—$CF_3$;

$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=$CH_2$, C($CH_3$)=$CH_2$, $CF_3$, $CHF_2$, $CH_2F$, —CHF—$CH_3$, —$CF_2$—$CH_3$, methoxy, trifluoromethoxy, ethoxy, methlythio, methylsulfinyl and methylsulfonyl;

p is 0;
q is 1;
$R^{5eu}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and $CF_3$;

$R^{45'}$, $R^{46'}$, $R^{47'}$, $R^{48'}$, and $R^{49'}$ are selected, independently of each other, from the group consisting of hydrogen, F, Cl, Br, I, methyl, ethyl, isopropyl, cyclopropyl, C≡CH, CH=$CH_2$, C($CH_3$)=$CH_2$, $CF_3$, $CHF_2$, $CH_2F$, —CHF—$CH_3$, —$CF_2$—$CH_3$, methoxy, trifluoromethoxy, ethoxy, methlythio, methylsulfinyl and methylsulfonyl;

p is 0;
q is 1;
$R^{5ev}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected independently of each other, from the group consisting of hydrogen, F, Cl, Br, I, methyl, ethyl, isopropyl, cyclopropyl, C≡CH, CH=$CH_2$, C($CH_3$)=$CH_2$, $CF_3$, $CHF_2$, $CH_2F$, —CHF—$CH_3$, —$CF_2$—$CH_3$, methoxy, trifluoromethoxy, ethoxy, methlythio, methylsulfinyl and methylsulfonyl;

p is 0;
q is 1;
$R^{5ex}$ is $G^{14}$ wherein $R^{37'}$ is selected from the group consisting of hydrogen, halogen, cyano, $C_1$-$C_4$ alkyl and $C_1$-$C_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ selected, independently of each other, from the group consisting of hydrogen, F, Cl, Br, I, methyl, ethyl, isopropyl, cyclopropyl, C≡CH, CH=$CH_2$, C($CH_3$)=$CH_2$, $CF_3$, $CHF_2$, $CH_2F$, —CHF—$CH_3$, —$CF_2$—$CH_3$, methoxy, trifluoromethoxy, ethoxy, methlythio, methylsulfinyl and methylsulfonyl;

p is 0;
q is 1;
$R^{5ey}$ is $G^{14}$ wherein $R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;

p is 0;

q is 1;

$R^{5ez}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoromethyl;

$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;

p is 0;

q is 1;

$R^{5fa}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;

p is 0;

q is 1;

$R^{5fb}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and $CF_3$;

$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;

p is 0;

q is 1;

$R^{5fc}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;

p is 0;

q is 1;

$R^{5fd}$ is $G^{14}$ wherein $R^{37'}$ is selected from the group consisting of hydrogen, halogen, cyano, $C_1$-$C_4$ alkyl and $C_1$-$C_4$ haloalkyl;

$R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;

p is 0;

q is 1;

$R^{5fe}$ is $G^{14}$ wherein $R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p is 1;

q is 1;

$R^{5fg}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p is 1;

q is 1;

$R^{5fh}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, $CH_2F$, $CHF_2$, $CF_3$, $CHF$—$CH_3$, $CF_2$—$CH_3$, $CH_2$—$CH_2F$ $CH_2$—$CHF_2$ and $CH_2$—$CF_3$;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p is 1;

q is 1;

$R^{5fi}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and $CF_3$;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

p is 1;

q is 1;

$R^{5fj}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

p is 1;
q is 1;
$R^{5fk}$ is $G^{14}$ wherein $R^{37'}$ is selected from the group consisting of hydrogen, halogen, cyano, C$_1$-C$_4$ alkyl and C$_1$-C$_4$ haloalkyl;
$R^{38'}$, $R^{39'}$, $R^{40'}$, $R^{41'}$, $R^{42'}$, $R^{43'}$ and $R^{44'}$ are each hydrogen;
$R^{45'}$, $R^{46'}$, $R^{47'}$, $R^{48'}$ and $R^{49'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

p is 1;
q is 1;
$R^{5fl}$ is $G^{14}$ wherein $R^{37'}$ and $R^{38'}$ are selected independently of each other from the group consisting of hydrogen, halogen, cyano, C$_1$-C$_4$ alkyl and C$_1$-C$_4$ haloalkyl;
$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, C$_1$-C$_4$ alkyl, C$_1$-C$_4$ haloalkyl, C$_1$-C$_4$ alkoxy, C$_1$-C$_4$ haloalkoxy and C$_1$-C$_4$ alkylthio;
$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p is 1;
q is 1;
$R^{5fm}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;
$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p is 1;
q is 1;
$R^{5fn}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, CH$_2$F, CHF$_2$, CF$_3$, CHF—CH$_3$, CF$_2$—CH$_3$, CH$_2$—CH$_2$F CH$_2$—CHF$_2$ and CH$_2$—CF$_3$;
$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p is 1;
q is 1;
$R^{5fo}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and CF$_3$;
$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p is 1;
q is 1;
$R^{5fp}$ is $G^{14}$ wherein $R^{37'}$, $R^{38'}$, $R^{39'}$, $R^{40'}$, $R^{41'}$, $R^{41'}$, $R^{42'}$, $R^{43'}$ and $R^{44'}$ are each hydrogen;
$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p is 1;
q is 1;
$R^{5fq}$ is $G^{14}$ wherein $R^{37'}$ is selected from the group consisting of hydrogen, halogen, cyano, C$_1$-C$_4$ alkyl and C$_1$-C$_4$ haloalkyl;
$R^{38'}$, $R^{39'}$, $R^{40'}$, $R^{41'}$, $R^{42'}$, $R^{43'}$ and $R^{44'}$ are hydrogen;
$R^{45'}$, $R^{46'}$, $R^{47'}$, $R^{48'}$ and $R^{49'}$ are selected, independently of each other, from the group consisting of hydrogen, F, Cl, Br, I, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, trifluoromethoxy, ethoxy, methlythio, methylsulfinyl and methylsulfonyl;

p is 1;
q is 1;
$R^{5fr}$ is $G^{14}$ wherein $R^{37'}$ and $R^{38'}$ are selected independently of each other from the group consisting of hydrogen, halogen, cyano, C$_1$-C$_4$ alkyl and C$_1$-C$_4$ haloalkyl;
$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, C$_1$-C$_4$ alkyl, C$_1$-C$_4$ haloalkyl, C$_1$-C$_4$ alkoxy, C$_1$-C$_4$ haloalkoxy and C$_1$-C$_4$ alkylthio;
$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p is 1;
q is 1;
$R^{5fs}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, halogen, methyl, ethyl, isopropyl, monofluoromethyl, polyfluoromethyl, monofluoroethyl and polyfluoroethyl;
$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p is 1;
q is 1;
$R^{5ft}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, CH$_2$F, CHF$_2$, CF$_3$, CHF—CH$_3$, CF$_2$—CH$_3$, CH$_2$—CH$_2$F CH$_2$—CHF$_2$ and CH$_2$—CF$_3$;
$R^{45'}$, $R^{46'}$, $R^{47'}$, $R^{48'}$ and $R^{49'}$ are selected, independently of each other, from the group consisting of hydrogen, F, Cl, methyl, CF$_3$, CHF$_2$, CH$_2$F, methoxy and trifluoromethoxy;

p is 1;
q is 1;
$R^{5fu}$ is $G^{14}$ wherein $R^{37'}$, $R^{38'}$, $R^{39'}$, $R^{40'}$, $R^{41'}$, $R^{42'}$, $R^{43'}$ and $R^{44'}$ are selected independently of each other from the group consisting of methyl, ethyl, F and $CF_3$;

$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;
p is 1;
q is 1;
$R^{5fv}$ is $G^{14}$ wherein $R^{37'}$, $R^{38'}$, $R^{39'}$, $R^{40'}$, $R^{41'}$, $R^{42'}$, $R^{43'}$ and $R^{44'}$ are each hydrogen;
$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;
p is 1;
q is 1;
$R^{5fw}$ is $G^{14}$ wherein $R^{37'}$ is selected from hydrogen, halogen, cyano, $C_1$-$C_4$ alkyl and $C_1$-$C_4$ haloalkyl;
$R^{38'}$, $R^{39'}$, $R^{40'}$, $R^{41'}$, $R^{42'}$, $R^{43'}$ and $R^{44'}$ are selected independently of each other from the group consisting of hydrogen, fluorine, methyl, ethyl, isopropyl, $CH_2F$, $CHF_2$, $CF_3$, $CHF$—$CH_3$, $CF_2$—$CH_3$, $CH_2$—$CH_2F$, $CH_2$—$CHF_2$ and $CH_2$—$CF_3$;
$R^{45'}$, $R^{46'}$, $R^{47'}$, $R^{48'}$ and $R^{49'}$ are selected, independently of each other, from the group consisting of hydrogen, F, Cl, methyl, $CF_3$, $CHF_2$, $CH_2F$, methoxy and trifluoromethoxy;
p is 1;
q is 1;
$R^{6a}$ is selected from hydrogen and SH;
$R^{6b}$ is hydrogen;
$R^{6c}$ is SH.

Each line of Table N describes a preferred sub-group from N1-N757 of this group. For reasons of clarity, note that in these sub-groups, $R_2$ is always methyl and $R_7$ is always hydrogen. For example, sub-group N1 is a group of compounds of formula (I) wherein
$R_1$ is $R^{1b}$;
$R_2$ is methyl;
$R_3$ is $R^{3a}$;
$R_4$ is $R^{4c}$;
$R_5$ is $R^{5a}$;
$R_6$ is $R^{6b}$;
$R_7$ is H.

TABLE N

| | $R_1$ | $R_3$ | $R_4$ | $R_5$ | $R_6$ |
|---|---|---|---|---|---|
| N1 | $R^{1b}$ | $R^{3a}$ | $R^{4c}$ | $R^{5a}$ | $R^{6b}$ |
| N2 | $R^{1b}$ | $R^{3b}$ | $R^{4d}$ | $R^{5a}$ | $R^{6b}$ |
| N3 | $R^{1b}$ | $R^{3c}$ | $R^{4e}$ | $R^{5a}$ | $R^{6b}$ |
| N4 | $R^{1b}$ | $R^{3a}$ | $R^{4c}$ | $R^{5b}$ | $R^{6b}$ |
| N5 | $R^{1b}$ | $R^{3b}$ | $R^{4d}$ | $R^{5b}$ | $R^{6b}$ |
| N6 | $R^{1b}$ | $R^{3c}$ | $R^{4e}$ | $R^{5b}$ | $R^{6b}$ |
| N7 | $R^{1b}$ | $R^{3a}$ | $R^{4c}$ | $R^{5c}$ | $R^{6b}$ |
| N8 | $R^{1b}$ | $R^{3b}$ | $R^{4d}$ | $R^{5c}$ | $R^{6b}$ |
| N9 | $R^{1b}$ | $R^{3c}$ | $R^{4e}$ | $R^{5c}$ | $R^{6b}$ |
| N10 | $R^{1b}$ | $R^{3a}$ | $R^{4c}$ | $R^{5d}$ | $R^{6b}$ |
| N11 | $R^{1b}$ | $R^{3b}$ | $R^{4d}$ | $R^{5d}$ | $R^{6b}$ |
| N12 | $R^{1b}$ | $R^{3c}$ | $R^{4e}$ | $R^{5d}$ | $R^{6b}$ |
| N13 | $R^{1b}$ | $R^{3a}$ | $R^{4c}$ | $R^{5e}$ | $R^{6b}$ |
| N14 | $R^{1b}$ | $R^{3b}$ | $R^{4d}$ | $R^{5e}$ | $R^{6b}$ |
| N15 | $R^{1b}$ | $R^{3c}$ | $R^{4e}$ | $R^{5e}$ | $R^{6b}$ |
| N16 | $R^{1b}$ | $R^{3a}$ | $R^{4c}$ | $R^{5f}$ | $R^{6b}$ |
| N17 | $R^{1b}$ | $R^{3b}$ | $R^{4d}$ | $R^{5f}$ | $R^{6b}$ |
| N18 | $R^{1b}$ | $R^{3c}$ | $R^{4e}$ | $R^{5f}$ | $R^{6b}$ |
| N19 | $R^{1b}$ | $R^{3a}$ | $R^{4c}$ | $R^{5g}$ | $R^{6b}$ |
| N20 | $R^{1b}$ | $R^{3b}$ | $R^{4d}$ | $R^{5g}$ | $R^{6b}$ |
| N21 | $R^{1b}$ | $R^{3c}$ | $R^{4e}$ | $R^{5g}$ | $R^{6b}$ |
| N22 | $R^{1b}$ | $R^{3a}$ | $R^{4c}$ | $R^{5h}$ | $R^{6b}$ |
| N23 | $R^{1b}$ | $R^{3b}$ | $R^{4d}$ | $R^{5h}$ | $R^{6b}$ |
| N24 | $R^{1b}$ | $R^{3c}$ | $R^{4e}$ | $R^{5h}$ | $R^{6b}$ |
| N25 | $R^{1b}$ | $R^{3a}$ | $R^{4c}$ | $R^{5j}$ | $R^{6b}$ |
| N26 | $R^{1b}$ | $R^{3b}$ | $R^{4d}$ | $R^{5j}$ | $R^{6b}$ |
| N27 | $R^{1b}$ | $R^{3c}$ | $R^{4e}$ | $R^{5j}$ | $R^{6b}$ |
| N28 | $R^{1b}$ | $R^{3d}$ | $R^{4c}$ | $R^{5k}$ | $R^{6b}$ |
| N29 | $R^{1b}$ | $R^{3b}$ | $R^{4d}$ | $R^{5k}$ | $R^{6b}$ |
| N30 | $R^{1b}$ | $R^{3c}$ | $R^{4e}$ | $R^{5k}$ | $R^{6b}$ |
| N31 | $R^{1b}$ | $R^{3d}$ | $R^{4c}$ | $R^{5l}$ | $R^{6b}$ |
| N32 | $R^{1b}$ | $R^{3b}$ | $R^{4d}$ | $R^{5l}$ | $R^{6b}$ |
| N33 | $R^{1b}$ | $R^{3c}$ | $R^{4e}$ | $R^{5l}$ | $R^{6b}$ |
| N34 | $R^{1b}$ | $R^{3d}$ | $R^{4c}$ | $R^{5m}$ | $R^{6b}$ |
| N35 | $R^{1b}$ | $R^{3b}$ | $R^{4d}$ | $R^{5m}$ | $R^{6b}$ |
| N36 | $R^{1b}$ | $R^{3c}$ | $R^{4e}$ | $R^{5m}$ | $R^{6b}$ |
| N37 | $R^{1b}$ | $R^{3d}$ | $R^{4c}$ | $R^{5n}$ | $R^{6b}$ |
| N38 | $R^{1b}$ | $R^{3b}$ | $R^{4d}$ | $R^{5n}$ | $R^{6b}$ |
| N39 | $R^{1b}$ | $R^{3c}$ | $R^{4e}$ | $R^{5n}$ | $R^{6b}$ |
| N40 | $R^{1b}$ | $R^{3d}$ | $R^{4c}$ | $R^{5o}$ | $R^{6b}$ |
| N41 | $R^{1b}$ | $R^{3b}$ | $R^{4d}$ | $R^{5o}$ | $R^{6b}$ |
| N42 | $R^{1b}$ | $R^{3c}$ | $R^{4e}$ | $R^{5o}$ | $R^{6b}$ |
| N43 | $R^{1b}$ | $R^{3d}$ | $R^{4c}$ | $R^{5p}$ | $R^{6b}$ |
| N44 | $R^{1b}$ | $R^{3b}$ | $R^{4d}$ | $R^{5p}$ | $R^{6b}$ |
| N45 | $R^{1b}$ | $R^{3c}$ | $R^{4e}$ | $R^{5p}$ | $R^{6b}$ |
| N46 | $R^{1b}$ | $R^{3d}$ | $R^{4c}$ | $R^{5q}$ | $R^{6b}$ |
| N47 | $R^{1b}$ | $R^{3b}$ | $R^{4d}$ | $R^{5q}$ | $R^{6b}$ |
| N48 | $R^{1b}$ | $R^{3c}$ | $R^{4e}$ | $R^{5q}$ | $R^{6b}$ |
| N49 | $R^{1b}$ | $R^{3d}$ | $R^{4c}$ | $R^{5r}$ | $R^{6b}$ |
| N50 | $R^{1b}$ | $R^{3b}$ | $R^{4d}$ | $R^{5r}$ | $R^{6b}$ |
| N51 | $R^{1b}$ | $R^{3c}$ | $R^{4e}$ | $R^{5r}$ | $R^{6b}$ |
| N52 | $R^{1b}$ | $R^{3d}$ | $R^{4c}$ | $R^{5s}$ | $R^{6b}$ |
| N53 | $R^{1b}$ | $R^{3b}$ | $R^{4d}$ | $R^{5s}$ | $R^{6b}$ |
| N54 | $R^{1b}$ | $R^{3c}$ | $R^{4e}$ | $R^{5s}$ | $R^{6b}$ |
| N55 | $R^{1b}$ | $R^{3d}$ | $R^{4c}$ | $R^{5t}$ | $R^{6b}$ |
| N56 | $R^{1b}$ | $R^{3b}$ | $R^{4d}$ | $R^{5t}$ | $R^{6b}$ |
| N57 | $R^{1b}$ | $R^{3c}$ | $R^{4e}$ | $R^{5t}$ | $R^{6b}$ |
| N58 | $R^{1b}$ | $R^{3d}$ | $R^{4c}$ | $R^{5u}$ | $R^{6b}$ |
| N59 | $R^{1b}$ | $R^{3b}$ | $R^{4d}$ | $R^{5u}$ | $R^{6b}$ |
| N60 | $R^{1b}$ | $R^{3c}$ | $R^{4e}$ | $R^{5u}$ | $R^{6b}$ |
| N61 | $R^{1b}$ | $R^{3d}$ | $R^{4c}$ | $R^{5v}$ | $R^{6b}$ |
| N62 | $R^{1b}$ | $R^{3b}$ | $R^{4d}$ | $R^{5v}$ | $R^{6b}$ |
| N63 | $R^{1b}$ | $R^{3c}$ | $R^{4e}$ | $R^{5v}$ | $R^{6b}$ |
| N64 | $R^{1b}$ | $R^{3d}$ | $R^{4c}$ | $R^{5x}$ | $R^{6b}$ |
| N65 | $R^{1b}$ | $R^{3b}$ | $R^{4d}$ | $R^{5x}$ | $R^{6b}$ |
| N66 | $R^{1b}$ | $R^{3c}$ | $R^{4e}$ | $R^{5x}$ | $R^{6b}$ |
| N67 | $R^{1b}$ | $R^{3d}$ | $R^{4c}$ | $R^{5y}$ | $R^{6b}$ |
| N68 | $R^{1b}$ | $R^{3b}$ | $R^{4d}$ | $R^{5y}$ | $R^{6b}$ |
| N69 | $R^{1b}$ | $R^{3c}$ | $R^{4e}$ | $R^{5y}$ | $R^{6b}$ |
| N70 | $R^{1b}$ | $R^{3d}$ | $R^{4c}$ | $R^{5z}$ | $R^{6b}$ |
| N71 | $R^{1b}$ | $R^{3b}$ | $R^{4d}$ | $R^{5z}$ | $R^{6b}$ |
| N72 | $R^{1b}$ | $R^{3c}$ | $R^{4e}$ | $R^{5z}$ | $R^{6b}$ |
| N73 | $R^{1b}$ | $R^{3d}$ | $R^{4c}$ | $R^{5ab}$ | $R^{6b}$ |
| N74 | $R^{1b}$ | $R^{3b}$ | $R^{4d}$ | $R^{5ab}$ | $R^{6b}$ |
| N75 | $R^{1b}$ | $R^{3c}$ | $R^{4e}$ | $R^{5ab}$ | $R^{6b}$ |
| N76 | $R^{1b}$ | $R^{3d}$ | $R^{4c}$ | $R^{5ac}$ | $R^{6b}$ |
| N77 | $R^{1b}$ | $R^{3b}$ | $R^{4d}$ | $R^{5ac}$ | $R^{6b}$ |
| N78 | $R^{1b}$ | $R^{3c}$ | $R^{4e}$ | $R^{5ac}$ | $R^{6b}$ |
| N79 | $R^{1b}$ | $R^{3d}$ | $R^{4c}$ | $R^{5ad}$ | $R^{6b}$ |
| N80 | $R^{1b}$ | $R^{3b}$ | $R^{4d}$ | $R^{5ad}$ | $R^{6b}$ |
| N81 | $R^{1b}$ | $R^{3c}$ | $R^{4e}$ | $R^{5ad}$ | $R^{6b}$ |
| N82 | $R^{1b}$ | $R^{3e}$ | $R^{4c}$ | $R^{5bb}$ | $R^{6b}$ |
| N83 | $R^{1b}$ | $R^{3f}$ | $R^{4c}$ | $R^{5bb}$ | $R^{6b}$ |
| N84 | $R^{1b}$ | $R^{3g}$ | $R^{4e}$ | $R^{5bb}$ | $R^{6b}$ |
| N85 | $R^{1b}$ | $R^{3h}$ | $R^{4e}$ | $R^{5bb}$ | $R^{6b}$ |
| N86 | $R^{1b}$ | $R^{3e}$ | $R^{4c}$ | $R^{5cc}$ | $R^{6b}$ |
| N87 | $R^{1b}$ | $R^{3f}$ | $R^{4c}$ | $R^{5cc}$ | $R^{6b}$ |
| N88 | $R^{1b}$ | $R^{3g}$ | $R^{4e}$ | $R^{5cc}$ | $R^{6b}$ |
| N89 | $R^{1b}$ | $R^{3h}$ | $R^{4e}$ | $R^{5cc}$ | $R^{6b}$ |
| N90 | $R^{1b}$ | $R^{3e}$ | $R^{4c}$ | $R^{5dd}$ | $R^{6b}$ |
| N91 | $R^{1b}$ | $R^{3f}$ | $R^{4c}$ | $R^{5dd}$ | $R^{6b}$ |
| N92 | $R^{1b}$ | $R^{3g}$ | $R^{4e}$ | $R^{5dd}$ | $R^{6b}$ |
| N93 | $R^{1b}$ | $R^{3h}$ | $R^{4e}$ | $R^{5dd}$ | $R^{6b}$ |
| N94 | $R^{1b}$ | $R^{3e}$ | $R^{4c}$ | $R^{5ee}$ | $R^{6b}$ |
| N95 | $R^{1b}$ | $R^{3f}$ | $R^{4c}$ | $R^{5ee}$ | $R^{6b}$ |
| N96 | $R^{1b}$ | $R^{3g}$ | $R^{4e}$ | $R^{5ee}$ | $R^{6b}$ |
| N97 | $R^{1b}$ | $R^{3h}$ | $R^{4e}$ | $R^{5ee}$ | $R^{6b}$ |
| N98 | $R^{1b}$ | $R^{3i}$ | $R^{4c}$ | $R^{5ae}$ | $R^{6a}$ |
| N99 | $R^{1b}$ | $R^{3j}$ | $R^{4c}$ | $R^{5af}$ | $R^{6b}$ |
| N100 | $R^{1b}$ | $R^{3k}$ | $R^{4c}$ | $R^{5ag}$ | $R^{6a}$ |

TABLE N-continued

| | R$_1$ | R$_3$ | R$_4$ | R$_5$ | R$_6$ |
|---|---|---|---|---|---|
| N101 | R$^{1b}$ | R$^{3k}$ | R$^{4c}$ | R$^{5ag}$ | R$^{6b}$ |
| N102 | R$^{1b}$ | R$^{3l}$ | R$^{4c}$ | R$^{5ag}$ | R$^{6c}$ |
| N103 | R$^{1b}$ | R$^{3i}$ | R$^{4e}$ | R$^{5ae}$ | R$^{6a}$ |
| N104 | R$^{1b}$ | R$^{3j}$ | R$^{4e}$ | R$^{5af}$ | R$^{6b}$ |
| N105 | R$^{1b}$ | R$^{3k}$ | R$^{4e}$ | R$^{5ag}$ | R$^{6a}$ |
| N106 | R$^{1b}$ | R$^{3k}$ | R$^{4e}$ | R$^{5ag}$ | R$^{6b}$ |
| N107 | R$^{1b}$ | R$^{3l}$ | R$^{4e}$ | R$^{5ag}$ | R$^{6c}$ |
| N108 | R$^{1b}$ | R$^{3i}$ | R$^{4f}$ | R$^{5ae}$ | R$^{6a}$ |
| N109 | R$^{1b}$ | R$^{3j}$ | R$^{4f}$ | R$^{5af}$ | R$^{6b}$ |
| N110 | R$^{1b}$ | R$^{3k}$ | R$^{4f}$ | R$^{5ag}$ | R$^{6a}$ |
| N111 | R$^{1b}$ | R$^{3k}$ | R$^{4f}$ | R$^{5ag}$ | R$^{6b}$ |
| N112 | R$^{1b}$ | R$^{3l}$ | R$^{4f}$ | R$^{5ag}$ | R$^{6c}$ |
| N113 | R$^{1b}$ | R$^{3m}$ | R$^{4c}$ | R$^{5ae}$ | R$^{6a}$ |
| N114 | R$^{1b}$ | R$^{3m}$ | R$^{4c}$ | R$^{5af}$ | R$^{6b}$ |
| N115 | R$^{1b}$ | R$^{3m}$ | R$^{4c}$ | R$^{5ag}$ | R$^{6a}$ |
| N116 | R$^{1b}$ | R$^{3m}$ | R$^{4c}$ | R$^{5ag}$ | R$^{6b}$ |
| N117 | R$^{1b}$ | R$^{3m}$ | R$^{4c}$ | R$^{5ag}$ | R$^{6c}$ |
| N118 | R$^{1b}$ | R$^{3m}$ | R$^{4e}$ | R$^{5ae}$ | R$^{6a}$ |
| N119 | R$^{1b}$ | R$^{3m}$ | R$^{4e}$ | R$^{5af}$ | R$^{6b}$ |
| N120 | R$^{1b}$ | R$^{3m}$ | R$^{4e}$ | R$^{5ag}$ | R$^{6a}$ |
| N121 | R$^{1b}$ | R$^{3m}$ | R$^{4e}$ | R$^{5ag}$ | R$^{6b}$ |
| N122 | R$^{1b}$ | R$^{3m}$ | R$^{4e}$ | R$^{5ag}$ | R$^{6c}$ |
| N123 | R$^{1b}$ | R$^{3m}$ | R$^{4f}$ | R$^{5ae}$ | R$^{6a}$ |
| N124 | R$^{1b}$ | R$^{3m}$ | R$^{4f}$ | R$^{5af}$ | R$^{6b}$ |
| N125 | R$^{1b}$ | R$^{3m}$ | R$^{4f}$ | R$^{5ag}$ | R$^{6a}$ |
| N126 | R$^{1b}$ | R$^{3m}$ | R$^{4f}$ | R$^{5ag}$ | R$^{6b}$ |
| N127 | R$^{1b}$ | R$^{3m}$ | R$^{4f}$ | R$^{5ag}$ | R$^{6c}$ |
| N128 | R$^{1b}$ | R$^{3i}$ | R$^{4c}$ | R$^{5ah}$ | R$^{6a}$ |
| N129 | R$^{1b}$ | R$^{3j}$ | R$^{4c}$ | R$^{5ai}$ | R$^{6b}$ |
| N130 | R$^{1b}$ | R$^{3k}$ | R$^{4c}$ | R$^{5ak}$ | R$^{6a}$ |
| N131 | R$^{1b}$ | R$^{3k}$ | R$^{4c}$ | R$^{5ak}$ | R$^{6b}$ |
| N132 | R$^{1b}$ | R$^{3l}$ | R$^{4c}$ | R$^{5ak}$ | R$^{6c}$ |
| N133 | R$^{1b}$ | R$^{3i}$ | R$^{4e}$ | R$^{5ah}$ | R$^{6a}$ |
| N134 | R$^{1b}$ | R$^{3j}$ | R$^{4e}$ | R$^{5ai}$ | R$^{6b}$ |
| N135 | R$^{1b}$ | R$^{3k}$ | R$^{4e}$ | R$^{5ak}$ | R$^{6a}$ |
| N136 | R$^{1b}$ | R$^{3k}$ | R$^{4e}$ | R$^{5ak}$ | R$^{6b}$ |
| N137 | R$^{1b}$ | R$^{3l}$ | R$^{4e}$ | R$^{5ak}$ | R$^{6c}$ |
| N138 | R$^{1b}$ | R$^{3i}$ | R$^{4f}$ | R$^{5ah}$ | R$^{6a}$ |
| N139 | R$^{1b}$ | R$^{3j}$ | R$^{4f}$ | R$^{5ai}$ | R$^{6b}$ |
| N140 | R$^{1b}$ | R$^{3k}$ | R$^{4f}$ | R$^{5ak}$ | R$^{6a}$ |
| N141 | R$^{1b}$ | R$^{3k}$ | R$^{4f}$ | R$^{5ak}$ | R$^{6b}$ |
| N142 | R$^{1b}$ | R$^{3l}$ | R$^{4f}$ | R$^{5ak}$ | R$^{6c}$ |
| N143 | R$^{1b}$ | R$^{3m}$ | R$^{4c}$ | R$^{5ah}$ | R$^{6a}$ |
| N144 | R$^{1b}$ | R$^{3m}$ | R$^{4c}$ | R$^{5ai}$ | R$^{6b}$ |
| N145 | R$^{1b}$ | R$^{3m}$ | R$^{4c}$ | R$^{5ak}$ | R$^{6a}$ |
| N146 | R$^{1b}$ | R$^{3m}$ | R$^{4c}$ | R$^{5ak}$ | R$^{6b}$ |
| N147 | R$^{1b}$ | R$^{3m}$ | R$^{4c}$ | R$^{5ak}$ | R$^{6c}$ |
| N148 | R$^{1b}$ | R$^{3m}$ | R$^{4e}$ | R$^{5ah}$ | R$^{6a}$ |
| N149 | R$^{1b}$ | R$^{3m}$ | R$^{4e}$ | R$^{5ai}$ | R$^{6b}$ |
| N150 | R$^{1b}$ | R$^{3m}$ | R$^{4e}$ | R$^{5ak}$ | R$^{6a}$ |
| N151 | R$^{1b}$ | R$^{3m}$ | R$^{4e}$ | R$^{5ak}$ | R$^{6b}$ |
| N152 | R$^{1b}$ | R$^{3m}$ | R$^{4e}$ | R$^{5ak}$ | R$^{6c}$ |
| N153 | R$^{1b}$ | R$^{3m}$ | R$^{4f}$ | R$^{5ah}$ | R$^{6a}$ |
| N154 | R$^{1b}$ | R$^{3m}$ | R$^{4f}$ | R$^{5ai}$ | R$^{6b}$ |
| N155 | R$^{1b}$ | R$^{3m}$ | R$^{4f}$ | R$^{5ak}$ | R$^{6a}$ |
| N156 | R$^{1b}$ | R$^{3m}$ | R$^{4f}$ | R$^{5ak}$ | R$^{6b}$ |
| N157 | R$^{1b}$ | R$^{3m}$ | R$^{4f}$ | R$^{5ak}$ | R$^{6c}$ |
| N158 | R$^{1b}$ | R$^{3i}$ | R$^{4c}$ | R$^{5al}$ | R$^{6a}$ |
| N159 | R$^{1b}$ | R$^{3j}$ | R$^{4c}$ | R$^{5am}$ | R$^{6b}$ |
| N160 | R$^{1b}$ | R$^{3k}$ | R$^{4c}$ | R$^{5an}$ | R$^{6a}$ |
| N161 | R$^{1b}$ | R$^{3k}$ | R$^{4c}$ | R$^{5an}$ | R$^{6b}$ |
| N162 | R$^{1b}$ | R$^{3l}$ | R$^{4c}$ | R$^{5an}$ | R$^{6c}$ |
| N163 | R$^{1b}$ | R$^{3i}$ | R$^{4e}$ | R$^{5al}$ | R$^{6a}$ |
| N164 | R$^{1b}$ | R$^{3j}$ | R$^{4e}$ | R$^{5am}$ | R$^{6b}$ |
| N165 | R$^{1b}$ | R$^{3k}$ | R$^{4e}$ | R$^{5an}$ | R$^{6a}$ |
| N166 | R$^{1b}$ | R$^{3k}$ | R$^{4e}$ | R$^{5an}$ | R$^{6b}$ |
| N167 | R$^{1b}$ | R$^{3l}$ | R$^{4e}$ | R$^{5an}$ | R$^{6c}$ |
| N168 | R$^{1b}$ | R$^{3i}$ | R$^{4f}$ | R$^{5al}$ | R$^{6a}$ |
| N169 | R$^{1b}$ | R$^{3j}$ | R$^{4f}$ | R$^{5am}$ | R$^{6b}$ |
| N170 | R$^{1b}$ | R$^{3k}$ | R$^{4f}$ | R$^{5an}$ | R$^{6a}$ |
| N171 | R$^{1b}$ | R$^{3k}$ | R$^{4f}$ | R$^{5an}$ | R$^{6b}$ |
| N172 | R$^{1b}$ | R$^{3l}$ | R$^{4f}$ | R$^{5an}$ | R$^{6c}$ |
| N173 | R$^{1b}$ | R$^{3n}$ | R$^{4c}$ | R$^{5ff}$ | R$^{6a}$ |
| N174 | R$^{1b}$ | R$^{3o}$ | R$^{4c}$ | R$^{5gg}$ | R$^{6b}$ |
| N175 | R$^{1b}$ | R$^{3o}$ | R$^{4c}$ | R$^{5gg}$ | R$^{6c}$ |
| N176 | R$^{1b}$ | R$^{3p}$ | R$^{4e}$ | R$^{5ff}$ | R$^{6b}$ |
| N177 | R$^{1b}$ | R$^{3p}$ | R$^{4e}$ | R$^{5gg}$ | R$^{6b}$ |
| N178 | R$^{1b}$ | R$^{3q}$ | R$^{4e}$ | R$^{5ff}$ | R$^{6b}$ |
| N179 | R$^{1b}$ | R$^{3q}$ | R$^{4e}$ | R$^{5gg}$ | R$^{6b}$ |
| N180 | R$^{1b}$ | R$^{3r}$ | R$^{4e}$ | R$^{5ff}$ | R$^{6b}$ |
| N181 | R$^{1b}$ | R$^{3r}$ | R$^{4e}$ | R$^{5gg}$ | R$^{6b}$ |
| N182 | R$^{1b}$ | R$^{3n}$ | R$^{4c}$ | R$^{5hh}$ | R$^{6a}$ |
| N183 | R$^{1b}$ | R$^{3o}$ | R$^{4c}$ | R$^{5jj}$ | R$^{6b}$ |
| N184 | R$^{1b}$ | R$^{3o}$ | R$^{4c}$ | R$^{5jj}$ | R$^{6c}$ |
| N185 | R$^{1b}$ | R$^{3p}$ | R$^{4e}$ | R$^{5hh}$ | R$^{6b}$ |
| N186 | R$^{1b}$ | R$^{3p}$ | R$^{4e}$ | R$^{5jj}$ | R$^{6b}$ |
| N187 | R$^{1b}$ | R$^{3q}$ | R$^{4e}$ | R$^{5hh}$ | R$^{6b}$ |
| N188 | R$^{1b}$ | R$^{3q}$ | R$^{4e}$ | R$^{5jj}$ | R$^{6b}$ |
| N189 | R$^{1b}$ | R$^{3r}$ | R$^{4e}$ | R$^{5hh}$ | R$^{6b}$ |
| N190 | R$^{1b}$ | R$^{3r}$ | R$^{4e}$ | R$^{5jj}$ | R$^{6b}$ |
| N191 | R$^{1b}$ | R$^{3n}$ | R$^{4c}$ | R$^{5kk}$ | R$^{6a}$ |
| N192 | R$^{1b}$ | R$^{3o}$ | R$^{4c}$ | R$^{5ll}$ | R$^{6b}$ |
| N193 | R$^{1b}$ | R$^{3o}$ | R$^{4c}$ | R$^{5ll}$ | R$^{6c}$ |
| N194 | R$^{1b}$ | R$^{3p}$ | R$^{4e}$ | R$^{5kk}$ | R$^{6b}$ |
| N195 | R$^{1b}$ | R$^{3p}$ | R$^{4e}$ | R$^{5ll}$ | R$^{6b}$ |
| N196 | R$^{1b}$ | R$^{3q}$ | R$^{4e}$ | R$^{5kk}$ | R$^{6b}$ |
| N197 | R$^{1b}$ | R$^{3q}$ | R$^{4e}$ | R$^{5ll}$ | R$^{6b}$ |
| N198 | R$^{1b}$ | R$^{3r}$ | R$^{4e}$ | R$^{5kk}$ | R$^{6b}$ |
| N199 | R$^{1b}$ | R$^{3r}$ | R$^{4e}$ | R$^{5ll}$ | R$^{6b}$ |
| N200 | R$^{1b}$ | R$^{3n}$ | R$^{4c}$ | R$^{5mm}$ | R$^{6a}$ |
| N201 | R$^{1b}$ | R$^{3o}$ | R$^{4c}$ | R$^{5nn}$ | R$^{6b}$ |
| N202 | R$^{1b}$ | R$^{3o}$ | R$^{4c}$ | R$^{5nn}$ | R$^{6c}$ |
| N203 | R$^{1b}$ | R$^{3p}$ | R$^{4e}$ | R$^{5mm}$ | R$^{6b}$ |
| N204 | R$^{1b}$ | R$^{3p}$ | R$^{4e}$ | R$^{5nn}$ | R$^{6b}$ |
| N205 | R$^{1b}$ | R$^{3q}$ | R$^{4e}$ | R$^{5mm}$ | R$^{6b}$ |
| N206 | R$^{1b}$ | R$^{3q}$ | R$^{4e}$ | R$^{5nn}$ | R$^{6b}$ |
| N207 | R$^{1b}$ | R$^{3r}$ | R$^{4e}$ | R$^{5mm}$ | R$^{6b}$ |
| N208 | R$^{1b}$ | R$^{3r}$ | R$^{4e}$ | R$^{5nn}$ | R$^{6b}$ |
| N209 | R$^{1b}$ | R$^{3n}$ | R$^{4c}$ | R$^{5nn}$ | R$^{6a}$ |
| N210 | R$^{1b}$ | R$^{3o}$ | R$^{4c}$ | R$^{5nn}$ | R$^{6b}$ |
| N211 | R$^{1b}$ | R$^{3o}$ | R$^{4c}$ | R$^{5nn}$ | R$^{6c}$ |
| N212 | R$^{1b}$ | R$^{3p}$ | R$^{4e}$ | R$^{5nn}$ | R$^{6b}$ |
| N213 | R$^{1b}$ | R$^{3p}$ | R$^{4e}$ | R$^{5nn}$ | R$^{6b}$ |
| N214 | R$^{1b}$ | R$^{3q}$ | R$^{4e}$ | R$^{5nn}$ | R$^{6b}$ |
| N215 | R$^{1b}$ | R$^{3q}$ | R$^{4e}$ | R$^{5nn}$ | R$^{6b}$ |
| N216 | R$^{1b}$ | R$^{3r}$ | R$^{4e}$ | R$^{5nn}$ | R$^{6b}$ |
| N217 | R$^{1b}$ | R$^{3r}$ | R$^{4e}$ | R$^{5nn}$ | R$^{6b}$ |
| N218 | R$^{1b}$ | R$^{3n}$ | R$^{4c}$ | R$^{5oo}$ | R$^{6a}$ |
| N219 | R$^{1b}$ | R$^{3o}$ | R$^{4c}$ | R$^{5oo}$ | R$^{6b}$ |
| N220 | R$^{1b}$ | R$^{3o}$ | R$^{4c}$ | R$^{5oo}$ | R$^{6c}$ |
| N221 | R$^{1b}$ | R$^{3p}$ | R$^{4e}$ | R$^{5oo}$ | R$^{6b}$ |
| N222 | R$^{1b}$ | R$^{3p}$ | R$^{4e}$ | R$^{5oo}$ | R$^{6b}$ |
| N223 | R$^{1b}$ | R$^{3q}$ | R$^{4e}$ | R$^{5oo}$ | R$^{6b}$ |
| N224 | R$^{1b}$ | R$^{3q}$ | R$^{4e}$ | R$^{5oo}$ | R$^{6b}$ |
| N225 | R$^{1b}$ | R$^{3r}$ | R$^{4e}$ | R$^{5oo}$ | R$^{6b}$ |
| N226 | R$^{1b}$ | R$^{3r}$ | R$^{4e}$ | R$^{5oo}$ | R$^{6b}$ |
| N227 | R$^{1b}$ | R$^{3n}$ | R$^{4c}$ | R$^{5pp}$ | R$^{6a}$ |
| N228 | R$^{1b}$ | R$^{3o}$ | R$^{4c}$ | R$^{5qq}$ | R$^{6b}$ |
| N229 | R$^{1b}$ | R$^{3o}$ | R$^{4c}$ | R$^{5qq}$ | R$^{6b}$ |
| N230 | R$^{1b}$ | R$^{3p}$ | R$^{4e}$ | R$^{5qq}$ | R$^{6b}$ |
| N231 | R$^{1b}$ | R$^{3p}$ | R$^{4e}$ | R$^{5qq}$ | R$^{6b}$ |
| N232 | R$^{1b}$ | R$^{3q}$ | R$^{4e}$ | R$^{5qq}$ | R$^{6b}$ |
| N233 | R$^{1b}$ | R$^{3q}$ | R$^{4e}$ | R$^{5qq}$ | R$^{6b}$ |
| N234 | R$^{1b}$ | R$^{3r}$ | R$^{4e}$ | R$^{5qq}$ | R$^{6b}$ |
| N235 | R$^{1b}$ | R$^{3r}$ | R$^{4e}$ | R$^{5qq}$ | R$^{6b}$ |
| N236 | R$^{1b}$ | R$^{3n}$ | R$^{4c}$ | R$^{5pp}$ | R$^{6a}$ |
| N237 | R$^{1b}$ | R$^{3o}$ | R$^{4c}$ | R$^{5qq}$ | R$^{6b}$ |
| N238 | R$^{1b}$ | R$^{3o}$ | R$^{4c}$ | R$^{5qq}$ | R$^{6c}$ |
| N239 | R$^{1b}$ | R$^{3p}$ | R$^{4e}$ | R$^{5qq}$ | R$^{6b}$ |
| N240 | R$^{1b}$ | R$^{3p}$ | R$^{4e}$ | R$^{5qq}$ | R$^{6b}$ |
| N241 | R$^{1b}$ | R$^{3q}$ | R$^{4e}$ | R$^{5qq}$ | R$^{6b}$ |
| N242 | R$^{1b}$ | R$^{3q}$ | R$^{4e}$ | R$^{5qq}$ | R$^{6b}$ |
| N243 | R$^{1b}$ | R$^{3r}$ | R$^{4e}$ | R$^{5qq}$ | R$^{6b}$ |
| N244 | R$^{1b}$ | R$^{3r}$ | R$^{4e}$ | R$^{5qq}$ | R$^{6b}$ |
| N245 | R$^{1b}$ | R$^{3n}$ | R$^{4c}$ | R$^{5rr}$ | R$^{6a}$ |
| N246 | R$^{1b}$ | R$^{3o}$ | R$^{4c}$ | R$^{5rr}$ | R$^{6b}$ |
| N247 | R$^{1b}$ | R$^{3o}$ | R$^{4c}$ | R$^{5rr}$ | R$^{6c}$ |
| N248 | R$^{1b}$ | R$^{3p}$ | R$^{4e}$ | R$^{5rr}$ | R$^{6b}$ |
| N249 | R$^{1b}$ | R$^{3p}$ | R$^{4e}$ | R$^{5rr}$ | R$^{6b}$ |
| N250 | R$^{1b}$ | R$^{3q}$ | R$^{4e}$ | R$^{5rr}$ | R$^{6b}$ |
| N251 | R$^{1b}$ | R$^{3q}$ | R$^{4e}$ | R$^{5rr}$ | R$^{6b}$ |
| N252 | R$^{1b}$ | R$^{3r}$ | R$^{4e}$ | R$^{5rr}$ | R$^{6b}$ |
| N253 | R$^{1b}$ | R$^{3r}$ | R$^{4e}$ | R$^{5rr}$ | R$^{6b}$ |
| N254 | R$^{1b}$ | R$^{3s}$ | R$^{4a}$ | R$^{5ss}$ | R$^{6b}$ |
| N255 | R$^{1b}$ | R$^{3t}$ | R$^{4b}$ | R$^{5ss}$ | R$^{6b}$ |
| N256 | R$^{1b}$ | R$^{3g}$ | R$^{4e}$ | R$^{5ss}$ | R$^{6b}$ |

TABLE N-continued

| | $R_1$ | $R_3$ | $R_4$ | $R_5$ | $R_6$ |
|---|---|---|---|---|---|
| N257 | $R^{1b}$ | $R^{3h}$ | $R^{4e}$ | $R^{5ss}$ | $R^{6b}$ |
| N258 | $R^{1b}$ | $R^{3s}$ | $R^{4a}$ | $R^{5tt}$ | $R^{6b}$ |
| N259 | $R^{1b}$ | $R^{3t}$ | $R^{4b}$ | $R^{5tt}$ | $R^{6b}$ |
| N260 | $R^{1b}$ | $R^{3g}$ | $R^{4e}$ | $R^{5tt}$ | $R^{6b}$ |
| N261 | $R^{1b}$ | $R^{3h}$ | $R^{4e}$ | $R^{5tt}$ | $R^{6b}$ |
| N262 | $R^{1b}$ | $R^{3s}$ | $R^{4a}$ | $R^{5uu}$ | $R^{6b}$ |
| N263 | $R^{1b}$ | $R^{3t}$ | $R^{4b}$ | $R^{5uu}$ | $R^{6b}$ |
| N264 | $R^{1b}$ | $R^{3g}$ | $R^{4e}$ | $R^{5uu}$ | $R^{6b}$ |
| N265 | $R^{1b}$ | $R^{3h}$ | $R^{4e}$ | $R^{5uu}$ | $R^{6b}$ |
| N266 | $R^{1b}$ | $R^{3s}$ | $R^{4a}$ | $R^{5vv}$ | $R^{6b}$ |
| N267 | $R^{1b}$ | $R^{3t}$ | $R^{4b}$ | $R^{5vv}$ | $R^{6b}$ |
| N268 | $R^{1b}$ | $R^{3g}$ | $R^{4e}$ | $R^{5vv}$ | $R^{6b}$ |
| N269 | $R^{1b}$ | $R^{3h}$ | $R^{4e}$ | $R^{5vv}$ | $R^{6b}$ |
| N270 | $R^{1b}$ | $R^{3s}$ | $R^{4a}$ | $R^{5ww}$ | $R^{6b}$ |
| N271 | $R^{1b}$ | $R^{3t}$ | $R^{4b}$ | $R^{5ww}$ | $R^{6b}$ |
| N272 | $R^{1b}$ | $R^{3g}$ | $R^{4e}$ | $R^{5ww}$ | $R^{6b}$ |
| N273 | $R^{1b}$ | $R^{3h}$ | $R^{4e}$ | $R^{5ww}$ | $R^{6b}$ |
| N274 | $R^{1b}$ | $R^{3s}$ | $R^{4a}$ | $R^{5xx}$ | $R^{6b}$ |
| N275 | $R^{1b}$ | $R^{3t}$ | $R^{4b}$ | $R^{5xx}$ | $R^{6b}$ |
| N276 | $R^{1b}$ | $R^{3g}$ | $R^{4e}$ | $R^{5xx}$ | $R^{6b}$ |
| N277 | $R^{1b}$ | $R^{3h}$ | $R^{4e}$ | $R^{5xx}$ | $R^{6b}$ |
| N278 | $R^{1b}$ | $R^{3s}$ | $R^{4a}$ | $R^{5zz}$ | $R^{6b}$ |
| N279 | $R^{1b}$ | $R^{3t}$ | $R^{4b}$ | $R^{5zz}$ | $R^{6b}$ |
| N280 | $R^{1b}$ | $R^{3g}$ | $R^{4e}$ | $R^{5zz}$ | $R^{6b}$ |
| N281 | $R^{1b}$ | $R^{3h}$ | $R^{4e}$ | $R^{5zz}$ | $R^{6b}$ |
| N282 | $R^{1b}$ | $R^{3s}$ | $R^{4a}$ | $R^{5ba}$ | $R^{6b}$ |
| N283 | $R^{1b}$ | $R^{3t}$ | $R^{4b}$ | $R^{5ba}$ | $R^{6b}$ |
| N284 | $R^{1b}$ | $R^{3g}$ | $R^{4e}$ | $R^{5ba}$ | $R^{6b}$ |
| N285 | $R^{1b}$ | $R^{3h}$ | $R^{4e}$ | $R^{5ba}$ | $R^{6b}$ |
| N286 | $R^{1b}$ | $R^{3s}$ | $R^{4a}$ | $R^{5bc}$ | $R^{6b}$ |
| N287 | $R^{1b}$ | $R^{3t}$ | $R^{4b}$ | $R^{5bc}$ | $R^{6b}$ |
| N288 | $R^{1b}$ | $R^{3g}$ | $R^{4e}$ | $R^{5bc}$ | $R^{6b}$ |
| N289 | $R^{1b}$ | $R^{3h}$ | $R^{4e}$ | $R^{5bc}$ | $R^{6b}$ |
| N290 | $R^{1b}$ | $R^{3s}$ | $R^{4a}$ | $R^{5bd}$ | $R^{6b}$ |
| N291 | $R^{1b}$ | $R^{3t}$ | $R^{4b}$ | $R^{5bd}$ | $R^{6b}$ |
| N292 | $R^{1b}$ | $R^{3g}$ | $R^{4e}$ | $R^{5bd}$ | $R^{6b}$ |
| N293 | $R^{1b}$ | $R^{3h}$ | $R^{4e}$ | $R^{5bd}$ | $R^{6b}$ |
| N294 | $R^{1b}$ | $R^{3s}$ | $R^{4a}$ | $R^{5be}$ | $R^{6b}$ |
| N295 | $R^{1b}$ | $R^{3t}$ | $R^{4b}$ | $R^{5be}$ | $R^{6b}$ |
| N296 | $R^{1b}$ | $R^{3g}$ | $R^{4e}$ | $R^{5be}$ | $R^{6b}$ |
| N297 | $R^{1b}$ | $R^{3h}$ | $R^{4e}$ | $R^{5be}$ | $R^{6b}$ |
| N298 | $R^{1b}$ | $R^{3s}$ | $R^{4a}$ | $R^{5bf}$ | $R^{6b}$ |
| N299 | $R^{1b}$ | $R^{3t}$ | $R^{4b}$ | $R^{5bf}$ | $R^{6b}$ |
| N300 | $R^{1b}$ | $R^{3g}$ | $R^{4e}$ | $R^{5bf}$ | $R^{6b}$ |
| N301 | $R^{1b}$ | $R^{3h}$ | $R^{4e}$ | $R^{5bf}$ | $R^{6b}$ |
| N302 | $R^{1b}$ | $R^{3s}$ | $R^{4a}$ | $R^{5bg}$ | $R^{6b}$ |
| N303 | $R^{1b}$ | $R^{3t}$ | $R^{4b}$ | $R^{5bg}$ | $R^{6b}$ |
| N304 | $R^{1b}$ | $R^{3g}$ | $R^{4e}$ | $R^{5bg}$ | $R^{6b}$ |
| N305 | $R^{1b}$ | $R^{3h}$ | $R^{4e}$ | $R^{5bg}$ | $R^{6b}$ |
| N306 | $R^{1b}$ | $R^{3s}$ | $R^{4a}$ | $R^{5bh}$ | $R^{6b}$ |
| N307 | $R^{1b}$ | $R^{3t}$ | $R^{4b}$ | $R^{5bh}$ | $R^{6b}$ |
| N308 | $R^{1b}$ | $R^{3g}$ | $R^{4e}$ | $R^{5bh}$ | $R^{6b}$ |
| N309 | $R^{1b}$ | $R^{3h}$ | $R^{4e}$ | $R^{5bh}$ | $R^{6b}$ |
| N310 | $R^{1b}$ | $R^{3s}$ | $R^{4a}$ | $R^{5bi}$ | $R^{6b}$ |
| N311 | $R^{1b}$ | $R^{3t}$ | $R^{4b}$ | $R^{5bi}$ | $R^{6b}$ |
| N312 | $R^{1b}$ | $R^{3g}$ | $R^{4e}$ | $R^{5bi}$ | $R^{6b}$ |
| N313 | $R^{1b}$ | $R^{3h}$ | $R^{4e}$ | $R^{5bi}$ | $R^{6b}$ |
| N314 | $R^{1b}$ | $R^{3s}$ | $R^{4a}$ | $R^{5bj}$ | $R^{6b}$ |
| N315 | $R^{1b}$ | $R^{3t}$ | $R^{4b}$ | $R^{5bj}$ | $R^{6b}$ |
| N316 | $R^{1b}$ | $R^{3g}$ | $R^{4e}$ | $R^{5bj}$ | $R^{6b}$ |
| N317 | $R^{1b}$ | $R^{3h}$ | $R^{4e}$ | $R^{5bj}$ | $R^{6b}$ |
| N318 | $R^{1b}$ | $R^{3s}$ | $R^{4a}$ | $R^{5bk}$ | $R^{6b}$ |
| N319 | $R^{1b}$ | $R^{3t}$ | $R^{4b}$ | $R^{5bk}$ | $R^{6b}$ |
| N320 | $R^{1b}$ | $R^{3g}$ | $R^{4e}$ | $R^{5bk}$ | $R^{6b}$ |
| N321 | $R^{1b}$ | $R^{3h}$ | $R^{4e}$ | $R^{5bk}$ | $R^{6b}$ |
| N322 | $R^{1b}$ | $R^{3s}$ | $R^{4a}$ | $R^{5bl}$ | $R^{6b}$ |
| N323 | $R^{1b}$ | $R^{3t}$ | $R^{4b}$ | $R^{5bl}$ | $R^{6b}$ |
| N324 | $R^{1b}$ | $R^{3g}$ | $R^{4e}$ | $R^{5bl}$ | $R^{6b}$ |
| N325 | $R^{1b}$ | $R^{3h}$ | $R^{4e}$ | $R^{5bl}$ | $R^{6b}$ |
| N326 | $R^{1b}$ | $R^{3s}$ | $R^{4a}$ | $R^{5bm}$ | $R^{6b}$ |
| N327 | $R^{1b}$ | $R^{3t}$ | $R^{4b}$ | $R^{5bm}$ | $R^{6b}$ |
| N328 | $R^{1b}$ | $R^{3g}$ | $R^{4e}$ | $R^{5bm}$ | $R^{6b}$ |
| N329 | $R^{1b}$ | $R^{3h}$ | $R^{4e}$ | $R^{5bm}$ | $R^{6b}$ |
| N330 | $R^{1b}$ | $R^{3s}$ | $R^{4a}$ | $R^{5bn}$ | $R^{6b}$ |
| N331 | $R^{1b}$ | $R^{3t}$ | $R^{4b}$ | $R^{5bn}$ | $R^{6b}$ |
| N332 | $R^{1b}$ | $R^{3g}$ | $R^{4e}$ | $R^{5bn}$ | $R^{6b}$ |
| N333 | $R^{1b}$ | $R^{3h}$ | $R^{4e}$ | $R^{5bn}$ | $R^{6b}$ |
| N334 | $R^{1b}$ | $R^{3s}$ | $R^{4a}$ | $R^{5bo}$ | $R^{6b}$ |
| N335 | $R^{1b}$ | $R^{3t}$ | $R^{4b}$ | $R^{5bo}$ | $R^{6b}$ |
| N336 | $R^{1b}$ | $R^{3g}$ | $R^{4e}$ | $R^{5bo}$ | $R^{6b}$ |
| N337 | $R^{1b}$ | $R^{3h}$ | $R^{4e}$ | $R^{5bo}$ | $R^{6b}$ |
| N338 | $R^{1b}$ | $R^{3s}$ | $R^{4a}$ | $R^{5bp}$ | $R^{6b}$ |
| N339 | $R^{1b}$ | $R^{3t}$ | $R^{4b}$ | $R^{5bp}$ | $R^{6b}$ |
| N340 | $R^{1b}$ | $R^{3g}$ | $R^{4e}$ | $R^{5bp}$ | $R^{6b}$ |
| N341 | $R^{1b}$ | $R^{3h}$ | $R^{4e}$ | $R^{5bp}$ | $R^{6b}$ |
| N342 | $R^{1b}$ | $R^{3s}$ | $R^{4a}$ | $R^{5bq}$ | $R^{6b}$ |
| N343 | $R^{1b}$ | $R^{3t}$ | $R^{4b}$ | $R^{5bq}$ | $R^{6b}$ |
| N344 | $R^{1b}$ | $R^{3g}$ | $R^{4e}$ | $R^{5bq}$ | $R^{6b}$ |
| N345 | $R^{1b}$ | $R^{3h}$ | $R^{4e}$ | $R^{5bq}$ | $R^{6b}$ |
| N346 | $R^{1b}$ | $R^{3s}$ | $R^{4a}$ | $R^{5br}$ | $R^{6b}$ |
| N347 | $R^{1b}$ | $R^{3t}$ | $R^{4b}$ | $R^{5bq}$ | $R^{6b}$ |
| N348 | $R^{1b}$ | $R^{3g}$ | $R^{4e}$ | $R^{5bq}$ | $R^{6b}$ |
| N349 | $R^{1b}$ | $R^{3h}$ | $R^{4e}$ | $R^{5bq}$ | $R^{6b}$ |
| N350 | $R^{1b}$ | $R^{3s}$ | $R^{4a}$ | $R^{5bs}$ | $R^{6b}$ |
| N351 | $R^{1b}$ | $R^{3t}$ | $R^{4b}$ | $R^{5bs}$ | $R^{6b}$ |
| N352 | $R^{1b}$ | $R^{3g}$ | $R^{4e}$ | $R^{5bs}$ | $R^{6b}$ |
| N353 | $R^{1b}$ | $R^{3h}$ | $R^{4e}$ | $R^{5bs}$ | $R^{6b}$ |
| N354 | $R^{1b}$ | $R^{3s}$ | $R^{4a}$ | $R^{5bt}$ | $R^{6b}$ |
| N355 | $R^{1b}$ | $R^{3t}$ | $R^{4b}$ | $R^{5bt}$ | $R^{6b}$ |
| N356 | $R^{1b}$ | $R^{3g}$ | $R^{4e}$ | $R^{5bt}$ | $R^{6b}$ |
| N357 | $R^{1b}$ | $R^{3h}$ | $R^{4e}$ | $R^{5bt}$ | $R^{6b}$ |
| N358 | $R^{1b}$ | $R^{3s}$ | $R^{4a}$ | $R^{5bu}$ | $R^{6b}$ |
| N359 | $R^{1b}$ | $R^{3t}$ | $R^{4b}$ | $R^{5bu}$ | $R^{6b}$ |
| N360 | $R^{1b}$ | $R^{3g}$ | $R^{4e}$ | $R^{5bu}$ | $R^{6b}$ |
| N361 | $R^{1b}$ | $R^{3h}$ | $R^{4e}$ | $R^{5bu}$ | $R^{6b}$ |
| N362 | $R^{1b}$ | $R^{3s}$ | $R^{4a}$ | $R^{5bv}$ | $R^{6b}$ |
| N363 | $R^{1b}$ | $R^{3t}$ | $R^{4b}$ | $R^{5bv}$ | $R^{6b}$ |
| N364 | $R^{1b}$ | $R^{3g}$ | $R^{4e}$ | $R^{5bv}$ | $R^{6b}$ |
| N365 | $R^{1b}$ | $R^{3h}$ | $R^{4e}$ | $R^{5bv}$ | $R^{6b}$ |
| N366 | $R^{1b}$ | $R^{3s}$ | $R^{4a}$ | $R^{5bw}$ | $R^{6b}$ |
| N367 | $R^{1b}$ | $R^{3t}$ | $R^{4b}$ | $R^{5bw}$ | $R^{6b}$ |
| N368 | $R^{1b}$ | $R^{3g}$ | $R^{4e}$ | $R^{5bw}$ | $R^{6b}$ |
| N369 | $R^{1b}$ | $R^{3h}$ | $R^{4e}$ | $R^{5bw}$ | $R^{6b}$ |
| N370 | $R^{1b}$ | $R^{3s}$ | $R^{4a}$ | $R^{5bx}$ | $R^{6b}$ |
| N371 | $R^{1b}$ | $R^{3t}$ | $R^{4b}$ | $R^{5bx}$ | $R^{6b}$ |
| N372 | $R^{1b}$ | $R^{3g}$ | $R^{4e}$ | $R^{5bx}$ | $R^{6b}$ |
| N373 | $R^{1b}$ | $R^{3h}$ | $R^{4e}$ | $R^{5bx}$ | $R^{6b}$ |
| N374 | $R^{1b}$ | $R^{3s}$ | $R^{4a}$ | $R^{5by}$ | $R^{6b}$ |
| N375 | $R^{1b}$ | $R^{3t}$ | $R^{4b}$ | $R^{5by}$ | $R^{6b}$ |
| N376 | $R^{1b}$ | $R^{3g}$ | $R^{4e}$ | $R^{5by}$ | $R^{6b}$ |
| N377 | $R^{1b}$ | $R^{3h}$ | $R^{4e}$ | $R^{5by}$ | $R^{6b}$ |
| N378 | $R^{1b}$ | $R^{3s}$ | $R^{4a}$ | $R^{5bz}$ | $R^{6b}$ |
| N379 | $R^{1b}$ | $R^{3t}$ | $R^{4b}$ | $R^{5bz}$ | $R^{6b}$ |
| N380 | $R^{1b}$ | $R^{3g}$ | $R^{4e}$ | $R^{5bz}$ | $R^{6b}$ |
| N381 | $R^{1b}$ | $R^{3h}$ | $R^{4e}$ | $R^{5bz}$ | $R^{6b}$ |
| N382 | $R^{1b}$ | $R^{3s}$ | $R^{4a}$ | $R^{5ca}$ | $R^{6b}$ |
| N383 | $R^{1b}$ | $R^{3t}$ | $R^{4b}$ | $R^{5ca}$ | $R^{6b}$ |
| N384 | $R^{1b}$ | $R^{3g}$ | $R^{4e}$ | $R^{5ca}$ | $R^{6b}$ |
| N385 | $R^{1b}$ | $R^{3h}$ | $R^{4e}$ | $R^{5ca}$ | $R^{6b}$ |
| N386 | $R^{1b}$ | $R^{3s}$ | $R^{4a}$ | $R^{5cb}$ | $R^{6b}$ |
| N387 | $R^{1b}$ | $R^{3t}$ | $R^{4b}$ | $R^{5cb}$ | $R^{6b}$ |
| N388 | $R^{1b}$ | $R^{3g}$ | $R^{4e}$ | $R^{5cb}$ | $R^{6b}$ |
| N389 | $R^{1b}$ | $R^{3h}$ | $R^{4e}$ | $R^{5cb}$ | $R^{6b}$ |
| N390 | $R^{1b}$ | $R^{3s}$ | $R^{4a}$ | $R^{5cd}$ | $R^{6b}$ |
| N391 | $R^{1b}$ | $R^{3t}$ | $R^{4b}$ | $R^{5cd}$ | $R^{6b}$ |
| N392 | $R^{1b}$ | $R^{3g}$ | $R^{4e}$ | $R^{5cd}$ | $R^{6b}$ |
| N393 | $R^{1b}$ | $R^{3h}$ | $R^{4e}$ | $R^{5cd}$ | $R^{6b}$ |
| N394 | $R^{1b}$ | $R^{3s}$ | $R^{4a}$ | $R^{5ce}$ | $R^{6b}$ |
| N395 | $R^{1b}$ | $R^{3t}$ | $R^{4b}$ | $R^{5ce}$ | $R^{6b}$ |
| N396 | $R^{1b}$ | $R^{3g}$ | $R^{4e}$ | $R^{5ce}$ | $R^{6b}$ |
| N397 | $R^{1b}$ | $R^{3h}$ | $R^{4e}$ | $R^{5ce}$ | $R^{6b}$ |
| N398 | $R^{1b}$ | $R^{3s}$ | $R^{4a}$ | $R^{5cf}$ | $R^{6b}$ |
| N399 | $R^{1b}$ | $R^{3t}$ | $R^{4b}$ | $R^{5cf}$ | $R^{6b}$ |
| N400 | $R^{1b}$ | $R^{3g}$ | $R^{4e}$ | $R^{5cf}$ | $R^{6b}$ |
| N401 | $R^{1b}$ | $R^{3h}$ | $R^{4e}$ | $R^{5cf}$ | $R^{6b}$ |
| N402 | $R^{1b}$ | $R^{3s}$ | $R^{4a}$ | $R^{5cg}$ | $R^{6b}$ |
| N403 | $R^{1b}$ | $R^{3t}$ | $R^{4b}$ | $R^{5cg}$ | $R^{6b}$ |
| N404 | $R^{1b}$ | $R^{3g}$ | $R^{4e}$ | $R^{5cg}$ | $R^{6b}$ |
| N405 | $R^{1b}$ | $R^{3h}$ | $R^{4e}$ | $R^{5cg}$ | $R^{6b}$ |
| N406 | $R^{1b}$ | $R^{3s}$ | $R^{4a}$ | $R^{5ch}$ | $R^{6b}$ |
| N407 | $R^{1b}$ | $R^{3t}$ | $R^{4b}$ | $R^{5ch}$ | $R^{6b}$ |
| N408 | $R^{1b}$ | $R^{3g}$ | $R^{4e}$ | $R^{5ch}$ | $R^{6b}$ |
| N409 | $R^{1b}$ | $R^{3h}$ | $R^{4e}$ | $R^{5ch}$ | $R^{6b}$ |
| N410 | $R^{1b}$ | $R^{3s}$ | $R^{4a}$ | $R^{5ci}$ | $R^{6b}$ |
| N411 | $R^{1b}$ | $R^{3t}$ | $R^{4b}$ | $R^{5ci}$ | $R^{6b}$ |
| N412 | $R^{1b}$ | $R^{3g}$ | $R^{4e}$ | $R^{5ci}$ | $R^{6b}$ |

TABLE N-continued

| | $R_1$ | $R_3$ | $R_4$ | $R_5$ | $R_6$ |
|---|---|---|---|---|---|
| N413 | $R^{1b}$ | $R^{3h}$ | $R^{4e}$ | $R^{5ci}$ | $R^{6b}$ |
| N414 | $R^{1b}$ | $R^{3s}$ | $R^{4a}$ | $R^{5cj}$ | $R^{6b}$ |
| N415 | $R^{1b}$ | $R^{3t}$ | $R^{4b}$ | $R^{5cj}$ | $R^{6b}$ |
| N416 | $R^{1b}$ | $R^{3g}$ | $R^{4e}$ | $R^{5cj}$ | $R^{6b}$ |
| N417 | $R^{1b}$ | $R^{3h}$ | $R^{4e}$ | $R^{5cj}$ | $R^{6b}$ |
| N418 | $R^{1b}$ | $R^{3s}$ | $R^{4a}$ | $R^{5ck}$ | $R^{6b}$ |
| N419 | $R^{1b}$ | $R^{3t}$ | $R^{4b}$ | $R^{5ck}$ | $R^{6b}$ |
| N420 | $R^{1b}$ | $R^{3g}$ | $R^{4e}$ | $R^{5ck}$ | $R^{6b}$ |
| N421 | $R^{1b}$ | $R^{3h}$ | $R^{4e}$ | $R^{5ck}$ | $R^{6b}$ |
| N422 | $R^{1b}$ | $R^{3s}$ | $R^{4a}$ | $R^{5cl}$ | $R^{6b}$ |
| N423 | $R^{1b}$ | $R^{3t}$ | $R^{4b}$ | $R^{5cl}$ | $R^{6b}$ |
| N424 | $R^{1b}$ | $R^{3g}$ | $R^{4e}$ | $R^{5cl}$ | $R^{6b}$ |
| N425 | $R^{1b}$ | $R^{3h}$ | $R^{4e}$ | $R^{5cl}$ | $R^{6b}$ |
| N426 | $R^{1b}$ | $R^{3s}$ | $R^{4a}$ | $R^{5cm}$ | $R^{6b}$ |
| N427 | $R^{1b}$ | $R^{3t}$ | $R^{4b}$ | $R^{5cm}$ | $R^{6b}$ |
| N428 | $R^{1b}$ | $R^{3g}$ | $R^{4e}$ | $R^{5cm}$ | $R^{6b}$ |
| N429 | $R^{1b}$ | $R^{3h}$ | $R^{4e}$ | $R^{5cm}$ | $R^{6b}$ |
| N430 | $R^{1b}$ | $R^{3s}$ | $R^{4a}$ | $R^{5cn}$ | $R^{6b}$ |
| N431 | $R^{1b}$ | $R^{3t}$ | $R^{4b}$ | $R^{5cn}$ | $R^{6b}$ |
| N432 | $R^{1b}$ | $R^{3g}$ | $R^{4e}$ | $R^{5cn}$ | $R^{6b}$ |
| N433 | $R^{1b}$ | $R^{3h}$ | $R^{4e}$ | $R^{5cn}$ | $R^{6b}$ |
| N434 | $R^{1b}$ | $R^{3s}$ | $R^{4a}$ | $R^{5co}$ | $R^{6b}$ |
| N435 | $R^{1b}$ | $R^{3t}$ | $R^{4b}$ | $R^{5co}$ | $R^{6b}$ |
| N436 | $R^{1b}$ | $R^{3g}$ | $R^{4e}$ | $R^{5co}$ | $R^{6b}$ |
| N437 | $R^{1b}$ | $R^{3h}$ | $R^{4e}$ | $R^{5co}$ | $R^{6b}$ |
| N438 | $R^{1b}$ | $R^{3s}$ | $R^{4a}$ | $R^{5cp}$ | $R^{6b}$ |
| N439 | $R^{1b}$ | $R^{3t}$ | $R^{4b}$ | $R^{5cp}$ | $R^{6b}$ |
| N440 | $R^{1b}$ | $R^{3g}$ | $R^{4e}$ | $R^{5cp}$ | $R^{6b}$ |
| N441 | $R^{1b}$ | $R^{3h}$ | $R^{4e}$ | $R^{5cp}$ | $R^{6b}$ |
| N442 | $R^{1b}$ | $R^{3s}$ | $R^{4a}$ | $R^{5cq}$ | $R^{6b}$ |
| N443 | $R^{1b}$ | $R^{3t}$ | $R^{4b}$ | $R^{5cq}$ | $R^{6b}$ |
| N444 | $R^{1b}$ | $R^{3g}$ | $R^{4e}$ | $R^{5cq}$ | $R^{6b}$ |
| N445 | $R^{1b}$ | $R^{3h}$ | $R^{4e}$ | $R^{5cq}$ | $R^{6b}$ |
| N446 | $R^{1b}$ | $R^{3s}$ | $R^{4a}$ | $R^{5cr}$ | $R^{6b}$ |
| N447 | $R^{1b}$ | $R^{3t}$ | $R^{4b}$ | $R^{5cr}$ | $R^{6b}$ |
| N448 | $R^{1b}$ | $R^{3g}$ | $R^{4e}$ | $R^{5cr}$ | $R^{6b}$ |
| N449 | $R^{1b}$ | $R^{3h}$ | $R^{4e}$ | $R^{5cr}$ | $R^{6b}$ |
| N450 | $R^{1b}$ | $R^{3s}$ | $R^{4a}$ | $R^{5cs}$ | $R^{6b}$ |
| N451 | $R^{1b}$ | $R^{3t}$ | $R^{4b}$ | $R^{5cs}$ | $R^{6b}$ |
| N452 | $R^{1b}$ | $R^{3g}$ | $R^{4e}$ | $R^{5cs}$ | $R^{6b}$ |
| N453 | $R^{1b}$ | $R^{3h}$ | $R^{4e}$ | $R^{5cs}$ | $R^{6b}$ |
| N454 | $R^{1b}$ | $R^{3s}$ | $R^{4a}$ | $R^{5ct}$ | $R^{6b}$ |
| N455 | $R^{1b}$ | $R^{3t}$ | $R^{4b}$ | $R^{5ct}$ | $R^{6b}$ |
| N456 | $R^{1b}$ | $R^{3g}$ | $R^{4e}$ | $R^{5ct}$ | $R^{6b}$ |
| N457 | $R^{1b}$ | $R^{3h}$ | $R^{4e}$ | $R^{5ct}$ | $R^{6b}$ |
| N458 | $R^{1b}$ | $R^{3s}$ | $R^{4a}$ | $R^{5cu}$ | $R^{6b}$ |
| N459 | $R^{1b}$ | $R^{3t}$ | $R^{4b}$ | $R^{5cu}$ | $R^{6b}$ |
| N460 | $R^{1b}$ | $R^{3g}$ | $R^{4e}$ | $R^{5cu}$ | $R^{6b}$ |
| N461 | $R^{1b}$ | $R^{3h}$ | $R^{4e}$ | $R^{5cu}$ | $R^{6b}$ |
| N462 | $R^{1b}$ | $R^{3s}$ | $R^{4a}$ | $R^{5cv}$ | $R^{6b}$ |
| N463 | $R^{1b}$ | $R^{3t}$ | $R^{4b}$ | $R^{5cv}$ | $R^{6b}$ |
| N464 | $R^{1b}$ | $R^{3g}$ | $R^{4e}$ | $R^{5cv}$ | $R^{6b}$ |
| N465 | $R^{1b}$ | $R^{3h}$ | $R^{4e}$ | $R^{5cv}$ | $R^{6b}$ |
| N466 | $R^{1b}$ | $R^{3s}$ | $R^{4a}$ | $R^{5cw}$ | $R^{6b}$ |
| N467 | $R^{1b}$ | $R^{3t}$ | $R^{4b}$ | $R^{5cw}$ | $R^{6b}$ |
| N468 | $R^{1b}$ | $R^{3g}$ | $R^{4e}$ | $R^{5cw}$ | $R^{6b}$ |
| N469 | $R^{1b}$ | $R^{3h}$ | $R^{4e}$ | $R^{5cw}$ | $R^{6b}$ |
| N470 | $R^{1b}$ | $R^{3s}$ | $R^{4a}$ | $R^{5cx}$ | $R^{6b}$ |
| N471 | $R^{1b}$ | $R^{3t}$ | $R^{4b}$ | $R^{5cx}$ | $R^{6b}$ |
| N472 | $R^{1b}$ | $R^{3g}$ | $R^{4e}$ | $R^{5cx}$ | $R^{6b}$ |
| N473 | $R^{1b}$ | $R^{3h}$ | $R^{4e}$ | $R^{5cx}$ | $R^{6b}$ |
| N474 | $R^{1b}$ | $R^{3s}$ | $R^{4a}$ | $R^{5cy}$ | $R^{6b}$ |
| N475 | $R^{1b}$ | $R^{3t}$ | $R^{4b}$ | $R^{5cy}$ | $R^{6b}$ |
| N476 | $R^{1b}$ | $R^{3g}$ | $R^{4e}$ | $R^{5cy}$ | $R^{6b}$ |
| N477 | $R^{1b}$ | $R^{3h}$ | $R^{4e}$ | $R^{5cy}$ | $R^{6b}$ |
| N478 | $R^{1b}$ | $R^{3s}$ | $R^{4a}$ | $R^{5cz}$ | $R^{6b}$ |
| N479 | $R^{1b}$ | $R^{3t}$ | $R^{4b}$ | $R^{5cz}$ | $R^{6b}$ |
| N480 | $R^{1b}$ | $R^{3g}$ | $R^{4e}$ | $R^{5cz}$ | $R^{6b}$ |
| N481 | $R^{1b}$ | $R^{3h}$ | $R^{4e}$ | $R^{5cz}$ | $R^{6b}$ |
| N482 | $R^{1b}$ | $R^{3s}$ | $R^{4a}$ | $R^{5da}$ | $R^{6b}$ |
| N483 | $R^{1b}$ | $R^{3t}$ | $R^{4b}$ | $R^{5da}$ | $R^{6b}$ |
| N484 | $R^{1b}$ | $R^{3g}$ | $R^{4e}$ | $R^{5da}$ | $R^{6b}$ |
| N485 | $R^{1b}$ | $R^{3h}$ | $R^{4e}$ | $R^{5da}$ | $R^{6b}$ |
| N486 | $R^{1b}$ | $R^{3s}$ | $R^{4a}$ | $R^{5db}$ | $R^{6b}$ |
| N487 | $R^{1b}$ | $R^{3t}$ | $R^{4b}$ | $R^{5db}$ | $R^{6b}$ |
| N488 | $R^{1b}$ | $R^{3g}$ | $R^{4e}$ | $R^{5db}$ | $R^{6b}$ |
| N489 | $R^{1b}$ | $R^{3h}$ | $R^{4e}$ | $R^{5db}$ | $R^{6b}$ |
| N490 | $R^{1b}$ | $R^{3s}$ | $R^{4a}$ | $R^{5dc}$ | $R^{6b}$ |
| N491 | $R^{1b}$ | $R^{3t}$ | $R^{4b}$ | $R^{5dc}$ | $R^{6b}$ |
| N492 | $R^{1b}$ | $R^{3g}$ | $R^{4e}$ | $R^{5dc}$ | $R^{6b}$ |
| N493 | $R^{1b}$ | $R^{3h}$ | $R^{4e}$ | $R^{5dc}$ | $R^{6b}$ |
| N494 | $R^{1b}$ | $R^{3s}$ | $R^{4a}$ | $R^{5de}$ | $R^{6b}$ |
| N495 | $R^{1b}$ | $R^{3t}$ | $R^{4b}$ | $R^{5de}$ | $R^{6b}$ |
| N496 | $R^{1b}$ | $R^{3g}$ | $R^{4e}$ | $R^{5de}$ | $R^{6b}$ |
| N497 | $R^{1b}$ | $R^{3h}$ | $R^{4e}$ | $R^{5de}$ | $R^{6b}$ |
| N498 | $R^{1b}$ | $R^{3s}$ | $R^{4a}$ | $R^{5df}$ | $R^{6b}$ |
| N499 | $R^{1b}$ | $R^{3t}$ | $R^{4b}$ | $R^{5df}$ | $R^{6b}$ |
| N500 | $R^{1b}$ | $R^{3g}$ | $R^{4e}$ | $R^{5df}$ | $R^{6b}$ |
| N501 | $R^{1b}$ | $R^{3h}$ | $R^{4e}$ | $R^{5df}$ | $R^{6b}$ |
| N502 | $R^{1b}$ | $R^{3s}$ | $R^{4a}$ | $R^{5dg}$ | $R^{6b}$ |
| N503 | $R^{1b}$ | $R^{3t}$ | $R^{4b}$ | $R^{5dg}$ | $R^{6b}$ |
| N504 | $R^{1b}$ | $R^{3g}$ | $R^{4e}$ | $R^{5dg}$ | $R^{6b}$ |
| N505 | $R^{1b}$ | $R^{3h}$ | $R^{4e}$ | $R^{5dg}$ | $R^{6b}$ |
| N506 | $R^{1b}$ | $R^{3s}$ | $R^{4a}$ | $R^{5dh}$ | $R^{6b}$ |
| N507 | $R^{1b}$ | $R^{3t}$ | $R^{4b}$ | $R^{5dh}$ | $R^{6b}$ |
| N508 | $R^{1b}$ | $R^{3g}$ | $R^{4e}$ | $R^{5dh}$ | $R^{6b}$ |
| N509 | $R^{1b}$ | $R^{3h}$ | $R^{4e}$ | $R^{5dh}$ | $R^{6b}$ |
| N510 | $R^{1b}$ | $R^{3s}$ | $R^{4a}$ | $R^{5di}$ | $R^{6b}$ |
| N511 | $R^{1b}$ | $R^{3t}$ | $R^{4b}$ | $R^{5di}$ | $R^{6b}$ |
| N512 | $R^{1b}$ | $R^{3g}$ | $R^{4e}$ | $R^{5di}$ | $R^{6b}$ |
| N513 | $R^{1b}$ | $R^{3h}$ | $R^{4e}$ | $R^{5di}$ | $R^{6b}$ |
| N514 | $R^{1b}$ | $R^{3s}$ | $R^{4a}$ | $R^{5dj}$ | $R^{6b}$ |
| N515 | $R^{1b}$ | $R^{3t}$ | $R^{4b}$ | $R^{5dj}$ | $R^{6b}$ |
| N516 | $R^{1b}$ | $R^{3g}$ | $R^{4e}$ | $R^{5dj}$ | $R^{6b}$ |
| N517 | $R^{1b}$ | $R^{3h}$ | $R^{4e}$ | $R^{5dj}$ | $R^{6b}$ |
| N518 | $R^{1b}$ | $R^{3s}$ | $R^{4a}$ | $R^{5dk}$ | $R^{6b}$ |
| N519 | $R^{1b}$ | $R^{3t}$ | $R^{4b}$ | $R^{5dk}$ | $R^{6b}$ |
| N520 | $R^{1b}$ | $R^{3g}$ | $R^{4e}$ | $R^{5dk}$ | $R^{6b}$ |
| N521 | $R^{1b}$ | $R^{3h}$ | $R^{4e}$ | $R^{5dk}$ | $R^{6b}$ |
| N522 | $R^{1b}$ | $R^{3s}$ | $R^{4a}$ | $R^{5dl}$ | $R^{6b}$ |
| N523 | $R^{1b}$ | $R^{3t}$ | $R^{4b}$ | $R^{5dl}$ | $R^{6b}$ |
| N524 | $R^{1b}$ | $R^{3g}$ | $R^{4e}$ | $R^{5dl}$ | $R^{6b}$ |
| N525 | $R^{1b}$ | $R^{3h}$ | $R^{4e}$ | $R^{5dl}$ | $R^{6b}$ |
| N526 | $R^{1b}$ | $R^{3s}$ | $R^{4a}$ | $R^{5dm}$ | $R^{6b}$ |
| N527 | $R^{1b}$ | $R^{3t}$ | $R^{4b}$ | $R^{5dm}$ | $R^{6b}$ |
| N528 | $R^{1b}$ | $R^{3g}$ | $R^{4e}$ | $R^{5dm}$ | $R^{6b}$ |
| N529 | $R^{1b}$ | $R^{3h}$ | $R^{4e}$ | $R^{5dm}$ | $R^{6b}$ |
| N530 | $R^{1b}$ | $R^{3s}$ | $R^{4a}$ | $R^{5dn}$ | $R^{6b}$ |
| N531 | $R^{1b}$ | $R^{3t}$ | $R^{4b}$ | $R^{5dn}$ | $R^{6b}$ |
| N532 | $R^{1b}$ | $R^{3g}$ | $R^{4e}$ | $R^{5dn}$ | $R^{6b}$ |
| N533 | $R^{1b}$ | $R^{3h}$ | $R^{4e}$ | $R^{5dn}$ | $R^{6b}$ |
| N534 | $R^{1b}$ | $R^{3s}$ | $R^{4a}$ | $R^{5do}$ | $R^{6b}$ |
| N535 | $R^{1b}$ | $R^{3t}$ | $R^{4b}$ | $R^{5do}$ | $R^{6b}$ |
| N536 | $R^{1b}$ | $R^{3g}$ | $R^{4e}$ | $R^{5do}$ | $R^{6b}$ |
| N537 | $R^{1b}$ | $R^{3h}$ | $R^{4e}$ | $R^{5do}$ | $R^{6b}$ |
| N538 | $R^{1b}$ | $R^{3s}$ | $R^{4a}$ | $R^{5dp}$ | $R^{6b}$ |
| N539 | $R^{1b}$ | $R^{3t}$ | $R^{4b}$ | $R^{5dp}$ | $R^{6b}$ |
| N540 | $R^{1b}$ | $R^{3g}$ | $R^{4e}$ | $R^{5dp}$ | $R^{6b}$ |
| N541 | $R^{1b}$ | $R^{3h}$ | $R^{4e}$ | $R^{5dp}$ | $R^{6b}$ |
| N542 | $R^{1b}$ | $R^{3s}$ | $R^{4a}$ | $R^{5dq}$ | $R^{6b}$ |
| N543 | $R^{1b}$ | $R^{3t}$ | $R^{4b}$ | $R^{5dq}$ | $R^{6b}$ |
| N544 | $R^{1b}$ | $R^{3g}$ | $R^{4e}$ | $R^{5dq}$ | $R^{6b}$ |
| N545 | $R^{1b}$ | $R^{3h}$ | $R^{4e}$ | $R^{5dq}$ | $R^{6b}$ |
| N546 | $R^{1b}$ | $R^{3s}$ | $R^{4a}$ | $R^{5dr}$ | $R^{6b}$ |
| N547 | $R^{1b}$ | $R^{3t}$ | $R^{4b}$ | $R^{5dr}$ | $R^{6b}$ |
| N548 | $R^{1b}$ | $R^{3g}$ | $R^{4e}$ | $R^{5dr}$ | $R^{6b}$ |
| N549 | $R^{1b}$ | $R^{3h}$ | $R^{4e}$ | $R^{5dr}$ | $R^{6b}$ |
| N550 | $R^{1b}$ | $R^{3s}$ | $R^{4a}$ | $R^{5ds}$ | $R^{6b}$ |
| N551 | $R^{1b}$ | $R^{3t}$ | $R^{4b}$ | $R^{5ds}$ | $R^{6b}$ |
| N552 | $R^{1b}$ | $R^{3g}$ | $R^{4e}$ | $R^{5ds}$ | $R^{6b}$ |
| N553 | $R^{1b}$ | $R^{3h}$ | $R^{4e}$ | $R^{5ds}$ | $R^{6b}$ |
| N554 | $R^{1b}$ | $R^{3s}$ | $R^{4a}$ | $R^{5dt}$ | $R^{6b}$ |
| N555 | $R^{1b}$ | $R^{3t}$ | $R^{4b}$ | $R^{5dt}$ | $R^{6b}$ |
| N556 | $R^{1b}$ | $R^{3g}$ | $R^{4e}$ | $R^{5dt}$ | $R^{6b}$ |
| N557 | $R^{1b}$ | $R^{3h}$ | $R^{4e}$ | $R^{5dt}$ | $R^{6b}$ |
| N558 | $R^{1b}$ | $R^{3s}$ | $R^{4a}$ | $R^{5du}$ | $R^{6b}$ |
| N559 | $R^{1b}$ | $R^{3t}$ | $R^{4b}$ | $R^{5du}$ | $R^{6b}$ |
| N560 | $R^{1b}$ | $R^{3g}$ | $R^{4e}$ | $R^{5du}$ | $R^{6b}$ |
| N561 | $R^{1b}$ | $R^{3h}$ | $R^{4e}$ | $R^{5du}$ | $R^{6b}$ |
| N562 | $R^{1b}$ | $R^{3s}$ | $R^{4a}$ | $R^{5dv}$ | $R^{6b}$ |
| N563 | $R^{1b}$ | $R^{3t}$ | $R^{4b}$ | $R^{5dv}$ | $R^{6b}$ |
| N564 | $R^{1b}$ | $R^{3g}$ | $R^{4e}$ | $R^{5dv}$ | $R^{6b}$ |
| N565 | $R^{1b}$ | $R^{3h}$ | $R^{4e}$ | $R^{5dv}$ | $R^{6b}$ |
| N566 | $R^{1b}$ | $R^{3s}$ | $R^{4a}$ | $R^{5dw}$ | $R^{6b}$ |
| N567 | $R^{1b}$ | $R^{3t}$ | $R^{4b}$ | $R^{5dw}$ | $R^{6b}$ |
| N568 | $R^{1b}$ | $R^{3g}$ | $R^{4e}$ | $R^{5dw}$ | $R^{6b}$ |

TABLE N-continued

| | $R_1$ | $R_3$ | $R_4$ | $R_5$ | $R_6$ |
|---|---|---|---|---|---|
| N569 | $R^{1b}$ | $R^{3h}$ | $R^{4e}$ | $R^{5dw}$ | $R^{6b}$ |
| N570 | $R^{1b}$ | $R^{3s}$ | $R^{4a}$ | $R^{5dx}$ | $R^{6b}$ |
| N571 | $R^{1b}$ | $R^{3t}$ | $R^{4b}$ | $R^{5dx}$ | $R^{6b}$ |
| N572 | $R^{1b}$ | $R^{3g}$ | $R^{4e}$ | $R^{5dx}$ | $R^{6b}$ |
| N573 | $R^{1b}$ | $R^{3h}$ | $R^{4e}$ | $R^{5dx}$ | $R^{6b}$ |
| N574 | $R^{1b}$ | $R^{3s}$ | $R^{4a}$ | $R^{5ea}$ | $R^{6b}$ |
| N575 | $R^{1b}$ | $R^{3t}$ | $R^{4b}$ | $R^{5ea}$ | $R^{6b}$ |
| N576 | $R^{1b}$ | $R^{3g}$ | $R^{4e}$ | $R^{5ea}$ | $R^{6b}$ |
| N577 | $R^{1b}$ | $R^{3h}$ | $R^{4e}$ | $R^{5ea}$ | $R^{6b}$ |
| N578 | $R^{1b}$ | $R^{3s}$ | $R^{4a}$ | $R^{5eb}$ | $R^{6b}$ |
| N579 | $R^{1b}$ | $R^{3t}$ | $R^{4b}$ | $R^{5eb}$ | $R^{6b}$ |
| N580 | $R^{1b}$ | $R^{3g}$ | $R^{4e}$ | $R^{5eb}$ | $R^{6b}$ |
| N581 | $R^{1b}$ | $R^{3h}$ | $R^{4e}$ | $R^{5eb}$ | $R^{6b}$ |
| N582 | $R^{1b}$ | $R^{3s}$ | $R^{4a}$ | $R^{5ec}$ | $R^{6b}$ |
| N583 | $R^{1b}$ | $R^{3t}$ | $R^{4b}$ | $R^{5ec}$ | $R^{6b}$ |
| N584 | $R^{1b}$ | $R^{3g}$ | $R^{4e}$ | $R^{5ec}$ | $R^{6b}$ |
| N585 | $R^{1b}$ | $R^{3h}$ | $R^{4e}$ | $R^{5ec}$ | $R^{6b}$ |
| N586 | $R^{1b}$ | $R^{3s}$ | $R^{4a}$ | $R^{5ed}$ | $R^{6b}$ |
| N587 | $R^{1b}$ | $R^{3t}$ | $R^{4b}$ | $R^{5ed}$ | $R^{6b}$ |
| N588 | $R^{1b}$ | $R^{3g}$ | $R^{4e}$ | $R^{5ed}$ | $R^{6b}$ |
| N589 | $R^{1b}$ | $R^{3h}$ | $R^{4e}$ | $R^{5ed}$ | $R^{6b}$ |
| N590 | $R^{1b}$ | $R^{3s}$ | $R^{4a}$ | $R^{5ef}$ | $R^{6b}$ |
| N591 | $R^{1b}$ | $R^{3t}$ | $R^{4b}$ | $R^{5ef}$ | $R^{6b}$ |
| N592 | $R^{1b}$ | $R^{3g}$ | $R^{4e}$ | $R^{5ef}$ | $R^{6b}$ |
| N593 | $R^{1b}$ | $R^{3h}$ | $R^{4e}$ | $R^{5ef}$ | $R^{6b}$ |
| N594 | $R^{1b}$ | $R^{3s}$ | $R^{4a}$ | $R^{5eg}$ | $R^{6b}$ |
| N595 | $R^{1b}$ | $R^{3t}$ | $R^{4b}$ | $R^{5eg}$ | $R^{6b}$ |
| N596 | $R^{1b}$ | $R^{3g}$ | $R^{4e}$ | $R^{5eg}$ | $R^{6b}$ |
| N597 | $R^{1b}$ | $R^{3h}$ | $R^{4e}$ | $R^{5eg}$ | $R^{6b}$ |
| N598 | $R^{1b}$ | $R^{3s}$ | $R^{4a}$ | $R^{5eh}$ | $R^{6b}$ |
| N599 | $R^{1b}$ | $R^{3t}$ | $R^{4b}$ | $R^{5eh}$ | $R^{6b}$ |
| N600 | $R^{1b}$ | $R^{3g}$ | $R^{4e}$ | $R^{5eh}$ | $R^{6b}$ |
| N601 | $R^{1b}$ | $R^{3h}$ | $R^{4e}$ | $R^{5eh}$ | $R^{6b}$ |
| N602 | $R^{1b}$ | $R^{3s}$ | $R^{4a}$ | $R^{5ei}$ | $R^{6b}$ |
| N603 | $R^{1b}$ | $R^{3t}$ | $R^{4b}$ | $R^{5ei}$ | $R^{6b}$ |
| N604 | $R^{1b}$ | $R^{3g}$ | $R^{4e}$ | $R^{5ei}$ | $R^{6b}$ |
| N605 | $R^{1b}$ | $R^{3h}$ | $R^{4e}$ | $R^{5ei}$ | $R^{6b}$ |
| N606 | $R^{1b}$ | $R^{3s}$ | $R^{4a}$ | $R^{5ej}$ | $R^{6b}$ |
| N607 | $R^{1b}$ | $R^{3t}$ | $R^{4b}$ | $R^{5ej}$ | $R^{6b}$ |
| N608 | $R^{1b}$ | $R^{3g}$ | $R^{4e}$ | $R^{5ej}$ | $R^{6b}$ |
| N609 | $R^{1b}$ | $R^{3h}$ | $R^{4e}$ | $R^{5ej}$ | $R^{6b}$ |
| N610 | $R^{1b}$ | $R^{3s}$ | $R^{4a}$ | $R^{5ek}$ | $R^{6b}$ |
| N611 | $R^{1b}$ | $R^{3t}$ | $R^{4b}$ | $R^{5ej}$ | $R^{6b}$ |
| N612 | $R^{1b}$ | $R^{3g}$ | $R^{4e}$ | $R^{5ej}$ | $R^{6b}$ |
| N613 | $R^{1b}$ | $R^{3h}$ | $R^{4e}$ | $R^{5ej}$ | $R^{6b}$ |
| N614 | $R^{1b}$ | $R^{3s}$ | $R^{4a}$ | $R^{5el}$ | $R^{6b}$ |
| N615 | $R^{1b}$ | $R^{3t}$ | $R^{4b}$ | $R^{5el}$ | $R^{6b}$ |
| N616 | $R^{1b}$ | $R^{3g}$ | $R^{4e}$ | $R^{5el}$ | $R^{6b}$ |
| N617 | $R^{1b}$ | $R^{3h}$ | $R^{4e}$ | $R^{5el}$ | $R^{6b}$ |
| N618 | $R^{1b}$ | $R^{3s}$ | $R^{4a}$ | $R^{5em}$ | $R^{6b}$ |
| N619 | $R^{1b}$ | $R^{3t}$ | $R^{4b}$ | $R^{5em}$ | $R^{6b}$ |
| N620 | $R^{1b}$ | $R^{3g}$ | $R^{4e}$ | $R^{5em}$ | $R^{6b}$ |
| N621 | $R^{1b}$ | $R^{3h}$ | $R^{4e}$ | $R^{5em}$ | $R^{6b}$ |
| N622 | $R^{1b}$ | $R^{3s}$ | $R^{4a}$ | $R^{5en}$ | $R^{6b}$ |
| N623 | $R^{1b}$ | $R^{3t}$ | $R^{4b}$ | $R^{5en}$ | $R^{6b}$ |
| N624 | $R^{1b}$ | $R^{3g}$ | $R^{4e}$ | $R^{5en}$ | $R^{6b}$ |
| N625 | $R^{1b}$ | $R^{3h}$ | $R^{4e}$ | $R^{5en}$ | $R^{6b}$ |
| N626 | $R^{1b}$ | $R^{3s}$ | $R^{4a}$ | $R^{5eo}$ | $R^{6b}$ |
| N627 | $R^{1b}$ | $R^{3t}$ | $R^{4b}$ | $R^{5eo}$ | $R^{6b}$ |
| N628 | $R^{1b}$ | $R^{3g}$ | $R^{4e}$ | $R^{5eo}$ | $R^{6b}$ |
| N629 | $R^{1b}$ | $R^{3h}$ | $R^{4e}$ | $R^{5eo}$ | $R^{6b}$ |
| N630 | $R^{1b}$ | $R^{3s}$ | $R^{4a}$ | $R^{5ep}$ | $R^{6b}$ |
| N631 | $R^{1b}$ | $R^{3t}$ | $R^{4b}$ | $R^{5ep}$ | $R^{6b}$ |
| N632 | $R^{1b}$ | $R^{3g}$ | $R^{4e}$ | $R^{5ep}$ | $R^{6b}$ |
| N633 | $R^{1b}$ | $R^{3h}$ | $R^{4e}$ | $R^{5ep}$ | $R^{6b}$ |
| N634 | $R^{1b}$ | $R^{3s}$ | $R^{4a}$ | $R^{5eq}$ | $R^{6b}$ |
| N635 | $R^{1b}$ | $R^{3t}$ | $R^{4b}$ | $R^{5eq}$ | $R^{6b}$ |
| N636 | $R^{1b}$ | $R^{3g}$ | $R^{4e}$ | $R^{5eq}$ | $R^{6b}$ |
| N637 | $R^{1b}$ | $R^{3h}$ | $R^{4e}$ | $R^{5eq}$ | $R^{6b}$ |
| N638 | $R^{1b}$ | $R^{3s}$ | $R^{4a}$ | $R^{5er}$ | $R^{6b}$ |
| N639 | $R^{1b}$ | $R^{3t}$ | $R^{4b}$ | $R^{ber}$ | $R^{6b}$ |
| N640 | $R^{1b}$ | $R^{3g}$ | $R^{4e}$ | $R^{ber}$ | $R^{6b}$ |
| N641 | $R^{1b}$ | $R^{3h}$ | $R^{4e}$ | $R^{ber}$ | $R^{6b}$ |
| N642 | $R^{1b}$ | $R^{3s}$ | $R^{4a}$ | $R^{5es}$ | $R^{6b}$ |
| N643 | $R^{1b}$ | $R^{3t}$ | $R^{4b}$ | $R^{5es}$ | $R^{6b}$ |
| N644 | $R^{1b}$ | $R^{3g}$ | $R^{4e}$ | $R^{5es}$ | $R^{6b}$ |
| N645 | $R^{1b}$ | $R^{3h}$ | $R^{4e}$ | $R^{5es}$ | $R^{6b}$ |
| N646 | $R^{1b}$ | $R^{3s}$ | $R^{4a}$ | $R^{bet}$ | $R^{6b}$ |
| N647 | $R^{1b}$ | $R^{3t}$ | $R^{4b}$ | $R^{bet}$ | $R^{6b}$ |
| N648 | $R^{1b}$ | $R^{3g}$ | $R^{4e}$ | $R^{bet}$ | $R^{6b}$ |
| N649 | $R^{1b}$ | $R^{3h}$ | $R^{4e}$ | $R^{bet}$ | $R^{6b}$ |
| N650 | $R^{1b}$ | $R^{3s}$ | $R^{4a}$ | $R^{5eu}$ | $R^{6b}$ |
| N651 | $R^{1b}$ | $R^{3t}$ | $R^{4b}$ | $R^{5eu}$ | $R^{6b}$ |
| N652 | $R^{1b}$ | $R^{3g}$ | $R^{4e}$ | $R^{5eu}$ | $R^{6b}$ |
| N653 | $R^{1b}$ | $R^{3h}$ | $R^{4e}$ | $R^{5eu}$ | $R^{6b}$ |
| N654 | $R^{1b}$ | $R^{3s}$ | $R^{4a}$ | $R^{5ev}$ | $R^{6b}$ |
| N655 | $R^{1b}$ | $R^{3t}$ | $R^{4b}$ | $R^{5ev}$ | $R^{6b}$ |
| N656 | $R^{1b}$ | $R^{3g}$ | $R^{4e}$ | $R^{5ev}$ | $R^{6b}$ |
| N657 | $R^{1b}$ | $R^{3h}$ | $R^{4e}$ | $R^{5ev}$ | $R^{6b}$ |
| N658 | $R^{1b}$ | $R^{3s}$ | $R^{4a}$ | $R^{5ex}$ | $R^{6b}$ |
| N659 | $R^{1b}$ | $R^{3t}$ | $R^{4b}$ | $R^{5ex}$ | $R^{6b}$ |
| N660 | $R^{1b}$ | $R^{3g}$ | $R^{4e}$ | $R^{5ex}$ | $R^{6b}$ |
| N661 | $R^{1b}$ | $R^{3h}$ | $R^{4e}$ | $R^{5ex}$ | $R^{6b}$ |
| N662 | $R^{1b}$ | $R^{3s}$ | $R^{4a}$ | $R^{5ey}$ | $R^{6b}$ |
| N663 | $R^{1b}$ | $R^{3t}$ | $R^{4b}$ | $R^{5ey}$ | $R^{6b}$ |
| N664 | $R^{1b}$ | $R^{3g}$ | $R^{4e}$ | $R^{5ey}$ | $R^{6b}$ |
| N665 | $R^{1b}$ | $R^{3h}$ | $R^{4e}$ | $R^{5ey}$ | $R^{6b}$ |
| N666 | $R^{1b}$ | $R^{3s}$ | $R^{4a}$ | $R^{5ez}$ | $R^{6b}$ |
| N667 | $R^{1b}$ | $R^{3t}$ | $R^{4b}$ | $R^{5ez}$ | $R^{6b}$ |
| N668 | $R^{1b}$ | $R^{3g}$ | $R^{4e}$ | $R^{5ez}$ | $R^{6b}$ |
| N669 | $R^{1b}$ | $R^{3h}$ | $R^{4e}$ | $R^{5ez}$ | $R^{6b}$ |
| N670 | $R^{1b}$ | $R^{3s}$ | $R^{4a}$ | $R^{5fa}$ | $R^{6b}$ |
| N671 | $R^{1b}$ | $R^{3t}$ | $R^{4b}$ | $R^{5fa}$ | $R^{6b}$ |
| N672 | $R^{1b}$ | $R^{3g}$ | $R^{4e}$ | $R^{5fa}$ | $R^{6b}$ |
| N673 | $R^{1b}$ | $R^{3h}$ | $R^{4e}$ | $R^{5fa}$ | $R^{6b}$ |
| N674 | $R^{1b}$ | $R^{3s}$ | $R^{4a}$ | $R^{5fb}$ | $R^{6b}$ |
| N675 | $R^{1b}$ | $R^{3t}$ | $R^{4b}$ | $R^{5fb}$ | $R^{6b}$ |
| N676 | $R^{1b}$ | $R^{3g}$ | $R^{4e}$ | $R^{5fb}$ | $R^{6b}$ |
| N677 | $R^{1b}$ | $R^{3h}$ | $R^{4e}$ | $R^{5fb}$ | $R^{6b}$ |
| N678 | $R^{1b}$ | $R^{3s}$ | $R^{4a}$ | $R^{5fc}$ | $R^{6b}$ |
| N679 | $R^{1b}$ | $R^{3t}$ | $R^{4b}$ | $R^{5fc}$ | $R^{6b}$ |
| N680 | $R^{1b}$ | $R^{3g}$ | $R^{4e}$ | $R^{5fc}$ | $R^{6b}$ |
| N681 | $R^{1b}$ | $R^{3h}$ | $R^{4e}$ | $R^{5fc}$ | $R^{6b}$ |
| N682 | $R^{1b}$ | $R^{3s}$ | $R^{4a}$ | $R^{5fd}$ | $R^{6b}$ |
| N683 | $R^{1b}$ | $R^{3t}$ | $R^{4b}$ | $R^{5fd}$ | $R^{6b}$ |
| N684 | $R^{1b}$ | $R^{3g}$ | $R^{4e}$ | $R^{5fd}$ | $R^{6b}$ |
| N685 | $R^{1b}$ | $R^{3h}$ | $R^{4e}$ | $R^{5fd}$ | $R^{6b}$ |
| N686 | $R^{1b}$ | $R^{3s}$ | $R^{4a}$ | $R^{5fe}$ | $R^{6b}$ |
| N687 | $R^{1b}$ | $R^{3t}$ | $R^{4b}$ | $R^{5fe}$ | $R^{6b}$ |
| N688 | $R^{1b}$ | $R^{3g}$ | $R^{4e}$ | $R^{5fe}$ | $R^{6b}$ |
| N689 | $R^{1b}$ | $R^{3h}$ | $R^{4e}$ | $R^{5fe}$ | $R^{6b}$ |
| N690 | $R^{1b}$ | $R^{3s}$ | $R^{4a}$ | $R^{5fg}$ | $R^{6b}$ |
| N691 | $R^{1b}$ | $R^{3t}$ | $R^{4b}$ | $R^{5fg}$ | $R^{6b}$ |
| N692 | $R^{1b}$ | $R^{3g}$ | $R^{4e}$ | $R^{5fg}$ | $R^{6b}$ |
| N693 | $R^{1b}$ | $R^{3h}$ | $R^{4e}$ | $R^{5fg}$ | $R^{6b}$ |
| N694 | $R^{1b}$ | $R^{3s}$ | $R^{4a}$ | $R^{5fh}$ | $R^{6b}$ |
| N695 | $R^{1b}$ | $R^{3t}$ | $R^{4b}$ | $R^{5fh}$ | $R^{6b}$ |
| N696 | $R^{1b}$ | $R^{3g}$ | $R^{4e}$ | $R^{5fh}$ | $R^{6b}$ |
| N697 | $R^{1b}$ | $R^{3h}$ | $R^{4e}$ | $R^{5fh}$ | $R^{6b}$ |
| N698 | $R^{1b}$ | $R^{3s}$ | $R^{4a}$ | $R^{5fi}$ | $R^{6b}$ |
| N699 | $R^{1b}$ | $R^{3t}$ | $R^{4b}$ | $R^{5fi}$ | $R^{6b}$ |
| N700 | $R^{1b}$ | $R^{3g}$ | $R^{4e}$ | $R^{5fi}$ | $R^{6b}$ |
| N701 | $R^{1b}$ | $R^{3h}$ | $R^{4e}$ | $R^{5fi}$ | $R^{6b}$ |
| N702 | $R^{1b}$ | $R^{3s}$ | $R^{4a}$ | $R^{5fj}$ | $R^{6b}$ |
| N703 | $R^{1b}$ | $R^{3t}$ | $R^{4b}$ | $R^{5fj}$ | $R^{6b}$ |
| N704 | $R^{1b}$ | $R^{3g}$ | $R^{4e}$ | $R^{5fj}$ | $R^{6b}$ |
| N705 | $R^{1b}$ | $R^{3h}$ | $R^{4e}$ | $R^{5fj}$ | $R^{6b}$ |
| N706 | $R^{1b}$ | $R^{3s}$ | $R^{4a}$ | $R^{5fk}$ | $R^{6b}$ |
| N707 | $R^{1b}$ | $R^{3t}$ | $R^{4b}$ | $R^{5fk}$ | $R^{6b}$ |
| N708 | $R^{1b}$ | $R^{3g}$ | $R^{4e}$ | $R^{5fk}$ | $R^{6b}$ |
| N709 | $R^{1b}$ | $R^{3h}$ | $R^{4e}$ | $R^{5fk}$ | $R^{6b}$ |
| N710 | $R^{1b}$ | $R^{3s}$ | $R^{4a}$ | $R^{5fl}$ | $R^{6b}$ |
| N711 | $R^{1b}$ | $R^{3t}$ | $R^{4b}$ | $R^{5fl}$ | $R^{6b}$ |
| N712 | $R^{1b}$ | $R^{3g}$ | $R^{4e}$ | $R^{5fl}$ | $R^{6b}$ |
| N713 | $R^{1b}$ | $R^{3h}$ | $R^{4e}$ | $R^{5fl}$ | $R^{6b}$ |
| N714 | $R^{1b}$ | $R^{3s}$ | $R^{4a}$ | $R^{5fm}$ | $R^{6b}$ |
| N715 | $R^{1b}$ | $R^{3t}$ | $R^{4b}$ | $R^{5fm}$ | $R^{6b}$ |
| N716 | $R^{1b}$ | $R^{3g}$ | $R^{4e}$ | $R^{5fm}$ | $R^{6b}$ |
| N717 | $R^{1b}$ | $R^{3h}$ | $R^{4e}$ | $R^{5fn}$ | $R^{6b}$ |
| N718 | $R^{1b}$ | $R^{3s}$ | $R^{4a}$ | $R^{5fn}$ | $R^{6b}$ |
| N719 | $R^{1b}$ | $R^{3t}$ | $R^{4b}$ | $R^{5fn}$ | $R^{6b}$ |
| N720 | $R^{1b}$ | $R^{3g}$ | $R^{4e}$ | $R^{5fn}$ | $R^{6b}$ |
| N721 | $R^{1b}$ | $R^{3h}$ | $R^{4e}$ | $R^{5fn}$ | $R^{6b}$ |
| N722 | $R^{1b}$ | $R^{3s}$ | $R^{4a}$ | $R^{5fo}$ | $R^{6b}$ |
| N723 | $R^{1b}$ | $R^{3t}$ | $R^{4b}$ | $R^{5fo}$ | $R^{6b}$ |
| N724 | $R^{1b}$ | $R^{3g}$ | $R^{4e}$ | $R^{5fo}$ | $R^{6b}$ |

TABLE N-continued

| | $R_1$ | $R_3$ | $R_4$ | $R_5$ | $R_6$ |
|---|---|---|---|---|---|
| N725 | $R^{1b}$ | $R^{3h}$ | $R^{4e}$ | $R^{5fo}$ | $R^{6b}$ |
| N726 | $R^{1b}$ | $R^{3s}$ | $R^{4a}$ | $R^{5fp}$ | $R^{6b}$ |
| N727 | $R^{1b}$ | $R^{3t}$ | $R^{4b}$ | $R^{5fp}$ | $R^{6b}$ |
| N728 | $R^{1b}$ | $R^{3g}$ | $R^{4e}$ | $R^{5fp}$ | $R^{6b}$ |
| N729 | $R^{1b}$ | $R^{3h}$ | $R^{4e}$ | $R^{5fp}$ | $R^{6b}$ |
| N730 | $R^{1b}$ | $R^{3s}$ | $R^{4a}$ | $R^{5fq}$ | $R^{6b}$ |
| N731 | $R^{1b}$ | $R^{3t}$ | $R^{4b}$ | $R^{5fq}$ | $R^{6b}$ |
| N732 | $R^{1b}$ | $R^{3g}$ | $R^{4e}$ | $R^{5fq}$ | $R^{6b}$ |
| N733 | $R^{1b}$ | $R^{3h}$ | $R^{4e}$ | $R^{5fq}$ | $R^{6b}$ |
| N734 | $R^{1b}$ | $R^{3s}$ | $R^{4a}$ | $R^{5fr}$ | $R^{6b}$ |
| N735 | $R^{1b}$ | $R^{3t}$ | $R^{4b}$ | $R^{5fr}$ | $R^{6b}$ |
| N736 | $R^{1b}$ | $R^{3g}$ | $R^{4e}$ | $R^{5fr}$ | $R^{6b}$ |
| N737 | $R^{1b}$ | $R^{3h}$ | $R^{4e}$ | $R^{5fr}$ | $R^{6b}$ |
| N738 | $R^{1b}$ | $R^{3s}$ | $R^{4a}$ | $R^{5fs}$ | $R^{6b}$ |
| N739 | $R^{1b}$ | $R^{3t}$ | $R^{4b}$ | $R^{5fs}$ | $R^{6b}$ |
| N740 | $R^{1b}$ | $R^{3g}$ | $R^{4e}$ | $R^{5fs}$ | $R^{6b}$ |
| N741 | $R^{1b}$ | $R^{3h}$ | $R^{4e}$ | $R^{5fs}$ | $R^{6b}$ |
| N742 | $R^{1b}$ | $R^{3s}$ | $R^{4a}$ | $R^{5ft}$ | $R^{6b}$ |
| N743 | $R^{1b}$ | $R^{3t}$ | $R^{4b}$ | $R^{5ft}$ | $R^{6b}$ |
| N744 | $R^{1b}$ | $R^{3g}$ | $R^{4e}$ | $R^{5ft}$ | $R^{6b}$ |
| N745 | $R^{1b}$ | $R^{3h}$ | $R^{4e}$ | $R^{5ft}$ | $R^{6b}$ |
| N746 | $R^{1b}$ | $R^{3s}$ | $R^{4a}$ | $R^{5fu}$ | $R^{6b}$ |
| N747 | $R^{1b}$ | $R^{3t}$ | $R^{4b}$ | $R^{5fu}$ | $R^{6b}$ |
| N748 | $R^{1b}$ | $R^{3g}$ | $R^{4e}$ | $R^{5fu}$ | $R^{6b}$ |
| N749 | $R^{1b}$ | $R^{3h}$ | $R^{4e}$ | $R^{5fu}$ | $R^{6b}$ |
| N750 | $R^{1b}$ | $R^{3s}$ | $R^{4a}$ | $R^{5fv}$ | $R^{6b}$ |
| N751 | $R^{1b}$ | $R^{3t}$ | $R^{4b}$ | $R^{5fv}$ | $R^{6b}$ |
| N752 | $R^{1b}$ | $R^{3g}$ | $R^{4e}$ | $R^{5fv}$ | $R^{6b}$ |
| N753 | $R^{1b}$ | $R^{3h}$ | $R^{4e}$ | $R^{5fv}$ | $R^{6b}$ |
| N754 | $R^{1b}$ | $R^{3s}$ | $R^{4a}$ | $R^{5fw}$ | $R^{6b}$ |
| N755 | $R^{1b}$ | $R^{3t}$ | $R^{4b}$ | $R^{5fw}$ | $R^{6b}$ |
| N756 | $R^{1b}$ | $R^{3g}$ | $R^{4e}$ | $R^{5fw}$ | $R^{6b}$ |
| N757 | $R^{1b}$ | $R^{3h}$ | $R^{4e}$ | $R^{5fw}$ | $R^{6b}$ |

Compounds of formula I as well as intermediates and reagents used can be prepared by the methods herein and as described in WO2008/101682 as well as further methods known to a skilled chemist in a variety of ways, or they are commercially available.

In a further preferred embodiment the component A is a specific compound selected from Tables 1 to 164, a specific compound selected from P.1 to P.372 or a specific compound selected from Q.001 to Q.454 and the component B is Chlorothalonil. In a further preferred embodiment the component A is a specific compound selected from Tables 1 to 164, a specific compound selected from P.1 to P.372 or a specific compound selected from Q.001 to Q.454 and the component B is Fludioxonil. In a further preferred embodiment the component A is a specific compound selected from Tables 1 to 164, a specific compound selected from P.1 to P.372 or a specific compound selected from Q.001 to Q.454 and the component B is Cyprodinil. In a further preferred embodiment the component A is a specific compound selected from Tables 1 to 164, a specific compound selected from P.1 to P.372 or a specific compound selected from Q.001 to Q.454 and the component B is Fenpropidin. In a further preferred embodiment the component A is a specific compound selected from Tables 1 to 164, a specific compound selected from P.1 to P.372 or a specific compound selected from Q.001 to Q.454 and the component B is Mandipropamid. In a further preferred embodiment the component A is a specific compound selected from Tables 1 to 164, a specific compound selected from P.1 to P.372 or a specific compound selected from Q.001 to Q.454 and the component B is Fluazinam. In a further preferred embodiment the component A is a specific compound selected from Tables 1 to 164, a specific compound selected from P.1 to P.372 or a specific compound selected from Q.001 to Q.454 and the component B is Procymedone. In a further preferred embodiment the component A is a specific compound selected from Tables 1 to 164, a specific compound selected from P.1 to P.372 or a specific compound selected from Q.001 to Q.454 and the component B is Carbendazim. In a further preferred embodiment the component A is a specific compound selected from Tables 1 to 164, a specific compound selected from P.1 to P.372 or a specific compound selected from Q.001 to Q.454 and the component B is Abamectin. In a further preferred embodiment the component A is a specific compound selected from Tables 1 to 164, a specific compound selected from P.1 to P.372 or a specific compound selected from Q.001 to Q.454 and the component B is Clothianidin. In a further preferred embodiment the component A is a specific compound selected from Tables 1 to 164, a specific compound selected from P.1 to P.372 or a specific compound selected from Q.001 to Q.454 and the component B is Emamectin benzoate. In a further preferred embodiment the component A is a specific compound selected from Tables 1 to 164, a specific compound selected from P.1 to P.372 or a specific compound selected from Q.001 to Q.454 and the component B is Imidacloprid. In a further preferred embodiment the component A is a specific compound selected from Tables 1 to 164, a specific compound selected from P.1 to P.372 or a specific compound selected from Q.001 to Q.454 and the component B is Tefluthrin. In a further preferred embodiment the component A is a specific compound selected from Tables 1 to 164, a specific compound selected from P.1 to P.372 or a specific compound selected from Q.001 to Q.454 and the component B is Mefenoxam. In a further preferred embodiment the component A is a specific compound selected from Tables 1 to 164, a specific compound selected from P.1 to P.372 or a specific compound selected from Q.001 to Q.454 and the component B is Orocymedone. In a further preferred embodiment the component A is a specific compound selected from Tables 1 to 164, a specific compound selected from P.1 to P.372 or a specific compound selected from Q.001 to Q.454 and the component B is Thiamethoxam. In a further preferred embodiment the component A is a specific compound selected from Tables 1 to 164, a specific compound selected from P.1 to P.372 or a specific compound selected from Q.001 to Q.454 and the component B is Lambda-cyhalothrin. In a further preferred embodiment the component A is a specific compound selected from Tables 1 to 164, a specific compound selected from P.1 to P.372 or a specific compound selected from Q.001 to Q.454 and the component B is Gamma-cyhalothrin. In a further preferred embodiment the component A is a specific compound selected from Tables 1 to 164, a specific compound selected from P.1 to P.372 or a specific compound selected from Q.001 to Q.454 and the component B is Profenofos. In a further preferred embodiment the component A is a specific compound selected from Tables 1 to 164, a specific compound selected from P.1 to P.372 or a specific compound selected from Q.001 to Q.454 and the component B is Lufenuron. In a further preferred embodiment the component A is a specific compound selected from Tables 1 to 164, a specific compound selected from P.1 to P.372 or a specific compound selected from Q.001 to Q.454 and the component B is Diflubenzuron. In a further preferred embodiment the component A is a specific compound selected from Tables 1 to 164, a specific compound selected from P.1 to P.372 or a specific compound selected from Q.001 to Q.454 and the component B is Cypermethrin. In a further preferred embodiment the component A is a specific compound selected from Tables 1 to 164, a specific compound selected from P.1 to P.372 or a specific compound selected from Q.001 to Q.454 and the component B is Novaluron. In a further preferred embodiment the component A is a specific compound selected from Tables 1 to 164, a specific compound selected from P.1 to P.372 or a specific compound selected from Q.001 to Q.454 and the component B is Bifenthrin. In a further preferred embodiment the component A is a specific compound selected from Tables 1 to 164, a specific compound selected from P.1 to P.372 or a specific compound selected from Q.001 to Q.454 and the component B is Methomyl. In a further preferred embodiment the component A is a specific compound selected from Tables 1 to 164, a specific compound selected from P.1 to P.372 or a specific compound selected from Q.001 to Q.454 and the component B is Chlopyrifos. In a further preferred embodiment the component A is a specific compound selected from Tables 1 to 164, a specific compound selected from P.1 to P.372 or a specific compound selected from Q.001 to Q.454 and the component B is Methamidophos. In a further preferred embodiment the component A is a specific compound selected from Tables 1 to 164, a specific compound selected from P.1 to P.372 or a specific compound selected from Q.001 to Q.454 and the component B is Endosulfan. In a further preferred embodiment the component A is a specific compound selected from Tables 1 to 164, a specific compound selected from P.1 to P.372 or a specific compound selected from Q.001 to Q.454 and the component B is Betacyfluthrin. In a further preferred embodiment the component A is a specific compound selected from Tables 1 to 164, a specific compound selected from P.1 to P.372 or a specific compound selected from Q.001 to Q.454 and the component B is Triflumuron. In a further preferred embodiment the component A is a specific compound selected from Tables 1 to 164, a specific compound selected from P.1 to P.372 or a specific compound selected from Q.001 to Q.454 and the component B is Teflubenzuron. In a further preferred embodiment the component A is a specific compound selected from Tables 1 to 164, a specific compound selected from P.1 to P.372 or a specific compound selected from Q.001 to Q.454 and the component B is Acephat. In a further preferred embodiment the component A is a specific compound selected from Tables 1 to 164, a specific compound selected from P.1 to P.372 or a specific compound selected from Q.001 to Q.454 and the component B is Glyphosate. In a further preferred embodiment the component A is a specific compound selected from Tables 1 to 164, a specific compound selected from P.1 to P.372 or a specific compound selected from Q.001 to Q.454 and the component B is Glufosinate. In a further preferred embodiment the component A is a specific compound selected from Tables 1 to 164, a specific compound selected from P.1 to P.372 or a specific compound selected from Q.001 to Q.454 and the component B is Mesotrione. In a further preferred embodiment the component A is a specific compound selected from Tables 1 to 164, a specific compound selected from P.1 to P.372 or a specific compound selected from Q.001 to Q.454 and the component B is Bicyclopyrone. In a further preferred embodiment the component A is a specific compound selected from Tables 1 to 164, a specific compound selected from P.1 to P.372 or a specific compound selected from Q.001 to Q.454 and the component B is Tembotrione. In a further preferred embodiment the component A is a specific compound selected from Tables 1 to 164, a specific compound selected from P.1 to P.372 or a specific compound selected from Q.001 to Q.454 and the component B is Sulcotrione. In a further preferred embodiment the component A is a specific compound selected from Tables 1 to 164, a specific compound selected from P.1 to P.372 or a specific compound selected from Q.001 to Q.454 and the component B is 2,4-D. In a further preferred embodiment the component A is a specific compound selected from Tables 1 to 164 or a specific compound selected from P.1 to P.372 or a specific compound selected from Q.001 to Q.454 and the component B is MCPA. In a further preferred embodiment the component A is a specific compound selected from Tables 1 to 164, a specific compound selected from P.1 to P.372 or a specific compound selected from Q.001 to Q.454 and the component B is Trinexapac-ethyl. In a further preferred embodiment the component A is a specific compound selected from Tables 1 to 164, a specific compound selected from P.1 to P.372 or a specific compound selected from Q.001 to Q.454 and the component B is Prohexadione-Ca. In a further preferred embodiment the component A is a specific compound selected from Tables 1 to 164, a specific compound selected from P.1 to P.372 or a specific compound selected from Q.001 to Q.454 and the component B is Paclobutrazol. In a further preferred embodiment the component A is a specific compound selected from Tables 1 to 164, a specific compound selected from P.1 to P.372 or a specific compound selected from Q.001 to Q.454 and the component B is Acibenzolar-5-methyl. In a further preferred embodiment the component A is a specific compound selected from Tables 1 to 164, a specific compound selected from P.1 to P.372 or a specific compound selected from Q.001 to Q.454 and the component B is Methyl-Jasmonate. In a further preferred embodiment the component A is a specific compound selected from Tables 1 to 164, a specific compound selected from P.1 to P.372 or a specific compound selected from Q.001 to Q.454 and the component B is Cis-Jasmone. In a further preferred embodiment the component A is a specific compound selected from Tables 1 to 164, a specific compound selected from P.1 to P.372 or a specific compound selected from Q.001 to Q.454 and the component B is Manganese. In a further preferred embodiment the component A is a specific compound selected from Tables 1 to 164, a specific compound selected from P.1 to P.372 or a specific compound selected from Q.001 to Q.454 and the component B is Cyflufenamid. In a further preferred embodiment the component A is a specific compound selected from Tables 1 to 164, a specific compound selected from P.1 to P.372 or a specific compound selected from Q.001 to Q.454 and the component B is Tebufloquin. In a further preferred embodiment the component A is a specific compound selected from Tables 1 to 164, a specific compound selected from P.1 to P.372 or a specific compound selected from Q.001 to Q.454 and the component B is Copper. In a further preferred embodiment the component A is a specific compound selected from Tables 1 to 164, a specific compound selected from P.1 to P.372 or a specific compound selected from Q.001 to Q.454 and the component B is Coumoxystrobin. In a further preferred embodiment the component A is a specific compound selected from Tables 1 to 164, a specific compound selected from P.1 to P.372 or a specific compound selected from Q.001 to Q.454 and the component B is Dicloaminostrobin. In a further preferred embodiment the component A is a specific compound selected from Tables 1 to 164, a specific compound selected from P.1 to P.372 or a specific compound selected from Q.001 to Q.454 and the component B is Flufenoxystrobin. In a further preferred embodiment the component A is a specific compound selected from Tables 1 to 164, a specific compound selected from P.1 to P.372 or a specific compound selected from Q.001 to Q.454 and the component B is Pyrametostrobin. In a further preferred embodiment the component A is a specific compound selected from Tables 1 to 164, a specific compound selected from P.1 to P.372 or a specific compound selected from Q.001 to Q.454 and the component B is Pyraoxystrobin. In a further preferred embodiment the component A is a specific compound selected from Tables 1 to 164, a specific compound selected from P.1 to P.372 or a specific compound selected from Q.001 to Q.454 and the component B is Trifloxystrobin. In a further preferred embodiment the component A is a specific compound selected from Tables 1 to 164, a specific compound selected from P.1 to P.372 or a specific compound selected from Q.001 to Q.454 and the component B is Azoxystrobin. In a further preferred embodiment the component A is a specific compound selected from Tables 1 to 164, a specific compound selected from P.1 to P.372 or a specific compound selected from Q.001 to Q.454 and the component B is Pyraclostrobin. In a further preferred embodiment the component A is a specific compound selected from Tables 1 to 164, a specific compound selected from P.1 to P.372 or a specific compound selected from Q.001 to Q.454 and the component B is Picoxystrobin. In a further preferred embodiment the component A is a specific compound selected from Tables 1 to 164, a specific compound selected from P.1 to P.372 or a specific compound selected from Q.001 to Q.454 and the component B is Jiaxiangjunzhi. In a further preferred embodiment the component A is a specific compound selected from Tables 1 to 164, a specific compound selected from P.1 to P.372 or a specific compound selected from Q.001 to Q.454 and the component B is Enoxastrobin. In a further preferred embodiment the component A is a specific compound selected from Tables 1 to 164, a specific compound selected from P.1 to P.372 or a specific compound selected from Q.001 to Q.454 and the component B is Triclopyricarb. In a further preferred embodiment the component A is a specific compound selected from Tables 1 to 164, a specific compound selected from P.1 to P.372 or a specific compound selected from Q.001 to Q.454 and the component B is Fluoxastrobin. In a further preferred embodiment the component A is a specific compound selected from Tables 1 to 164, a specific compound selected from P.1 to P.372 or a specific compound selected from Q.001 to Q.454 and the component B is Dimoxystrobin. In a further preferred embodiment the component A is a specific compound selected from Tables 1 to 164, a specific compound selected from P.1 to P.372 or a specific compound selected from Q.001 to Q.454 and the component B is Fenaminostrobin. In a further preferred embodiment the component A is a specific compound selected from Tables 1 to 164, a specific compound selected from P.1 to P.372 or a specific compound selected from Q.001 to Q.454 and the component B is the compound of formula II. In a further preferred embodiment the component A is a specific compound selected from Tables 1 to 164, a specific compound selected from P.1 to P.372 or a specific compound selected from Q.001 to Q.454 and the component B is Cyproconazole. In a further preferred embodiment the component A is a specific compound selected from Tables 1 to 164, a specific compound selected from P.1 to P.372 or a specific compound selected from Q.001 to Q.454 and the component B is Difenoconazole. In a further preferred embodiment the component A is a specific compound selected from Tables 1 to 164, a specific compound selected from P.1 to P.372 or a specific compound selected from Q.001 to Q.454 and the component B is Metconazole. In a further preferred embodiment the component A is a specific compound selected from Tables 1 to 164, a specific compound selected from P.1 to P.372 or a specific compound selected from Q.001 to Q.454 and the component B is Propiconazole. In a further preferred embodiment the component A is a specific compound selected from Tables 1 to 164, a specific compound selected from P.1 to P.372 or a specific compound selected from Q.001 to Q.454 and the component B is Epoxiconazole. In a further preferred embodiment the component A is a specific compound selected from Tables 1 to 164, a specific compound selected from P.1 to P.372 or a specific compound selected from Q.001 to Q.454 and the component B is Tebuconazole. In a further preferred embodiment the component A is a specific compound selected from Tables 1 to 164, a specific compound selected from P.1 to P.372 or a specific compound selected from Q.001 to Q.454 and the component B is Flutriafol. In a further preferred embodiment the component A is a specific compound selected from Tables 1 to 164, a specific compound selected from P.1 to P.372 or a specific compound selected from Q.001 to Q.454 and the component B is Ipconazole. In a further preferred embodiment the component A is a specific compound selected from Tables 1 to 164, a specific compound selected from P.1 to P.372 or a specific compound selected from Q.001 to Q.454 and the component B is 1-(2-chlorophenyl)-2-(1-chlorocycloprop-1-yl)-3-(1,2,4-triazol-1-yl)propan-2-ol [CAS number 120983-64-4]. In a further preferred embodiment the component A is a specific compound selected from Tables 1 to 164, a specific compound selected from P.1 to P.372 or a specific compound selected from Q.001 to Q.454 and the component B is prothioconazole. In a further preferred embodiment the component A is a specific compound selected from Tables 1 to 164, a specific compound selected from P.1 to P.372 or a specific compound selected from Q.001 to Q.454 and the component B is (S)-[3-(4-chloro-2-fluoro-phenyl)-5-(2,4-difluoro-phenyl)-isoxazol-4-yl]-pyridin-3-yl-methanol [CAS number 1229606-46-5]. In a further preferred embodiment the component A is a specific compound selected from Tables 1 to 164 or a specific compound selected from P.1 to P.372 or a specific compound selected from Q.001 to Q.454 and the component B is 3-(4-Chloro-2-fluoro-phenyl)-5-(2,4-difluoro-phenyl)-isoxazol-4-yl]-pyridin-3-yl-methanol [CAS number 1229605-96-2]. In a further preferred embodiment the component A is a specific compound selected from Tables 1 to 164, a specific compound selected from P.1 to P.372 or a specific compound selected from Q.001 to Q.454 and the component B is Pyrisoxazole. In a further preferred embodiment the component A is a specific compound selected from Tables 1 to 164, a specific compound selected from P.1 to P.372 or a specific compound selected from Q.001 to Q.454 and the component B is 3-(difluoromethyl)-N-methoxy-1-methyl-N-[1-methyl-2-(2,4,6-trichlorophenyl)ethyl]-1H-Pyrazole-4-carboxamide [CAS number 1228284-64-7]. In a further preferred embodiment the component A is a specific compound selected from Tables 1 to 164, a specific compound selected from P.1 to P.372 or a specific compound selected from Q.001 to Q.454 and the component B is N-[9-(dichloromethylene)-1,2,3,4-tetrahydro-1,4-methanonaphthalen-5-yl]-3-(difluoromethyl)-1-methyl-1H-pyrazole-4-carboxamide [CAS number 1072957-71-1]. In a further preferred embodiment the component A is a specific compound selected from Tables 1 to 164, a specific compound selected from P.1 to P.372 or a specific compound selected from Q.001 to Q.454 and the component B is Isopyrazam. In a further preferred embodiment the component A is a specific compound selected from Tables 1 to 164, a specific compound selected from P.1 to P.372 or a specific compound selected from Q.001 to Q.454 and the component B is Sedaxane. In a further preferred embodiment the component A is a specific compound selected from Tables 1 to 164, a specific compound selected from P.1 to P.372 or a specific compound selected from Q.001 to Q.454 and the component B is Boscalid. In a further preferred embodiment the component A is a specific compound selected from Tables 1 to 164, a specific compound selected from P.1 to P.372 or a specific compound selected from Q.001 to Q.454 and the component B is Fluxapyroxad. In a further preferred embodiment the component A is a specific compound selected from Tables 1 to 164, a specific compound selected from P.1 to P.372 or a specific compound selected from Q.001 to Q.454 and the component B is Penthiopyrad. In a further preferred embodiment the component A is a specific compound selected from Tables 1 to 164, a specific compound selected from P.1 to P.372 or a specific compound selected from Q.001 to Q.454 and the component B is Penflufen. In a further preferred embodiment the component A is a specific compound selected from Tables 1 to 164, a specific compound selected from P.1 to P.372 or a specific compound selected from Q.001 to Q.454 and the component B is Bixafen. In a further preferred embodiment the component A is a specific compound selected from Tables 1 to 164, a specific compound selected from P.1 to P.372 or a specific compound selected from Q.001 to Q.454 and the component B is Fluopyram. In a further embodiment the invention relates to a specific compound selected from Tables 1 to 164, a specific compound selected from P.1 to P.372 or a specific compound selected from Q.001 to Q.454.

The compounds of formula I, and, where appropriate, the tautomers thereof, can be present in the form of one of the isomers which are possible or as a mixture of these, for example in the form of pure isomers, such as antipodes and/or diastereomers, or as isomer mixtures, such as structural isomer, stereo isomer, diastereoisomer and enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Likewise, where isomers are possible for compounds that may be selected as component B, the invention relates to the pure isomers and also to all isomer mixtures which are possible.

The compositions according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a composition of the invention is applied to the plants, to parts thereof or the locus thereof. The compositions according to the invention are distinguished by excellent activity at low rates of application, by being well tolerated by plants and by being environmentally safe. They have very useful curative, preventive and systemic properties and are used for protecting numerous useful plants. The compositions of the invention can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compositions of the invention as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compositions of the invention may be used for controlling fungi in related areas, for example in the protection of technical materials, including wood and wood related technical products, in food storage or in hygiene management.

The compositions of the invention are, for example, effective against the phytopathogenic fungi of the following classes: Fungi imperfecti (e.g. *Botrytis, Pyricularia, Helminthosporium, Fusarium, Septoria, Cercospora* and *Alternaria*) and *Basidiomycetes* (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the compositions of the invention are effective against phytopathogenic bacteria and viruses (e.g. against *Xanthomonas* spp, *Pseudomonas* spp, *Erwinia amylovora* as well as against the tobacco mosaic virus). Good activity has been observed against rust disease, like leaf rust (*Puccinia* spp.) and soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals and turf and grass species.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9 C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which have been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which have been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/N L/00/10. Genetically modified maize for the expression of the protein Cry1 F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Components A and B can be used in unmodified form or, preferably, together with carriers and adjuvants conventionally employed in the art of formulation.

To this components A and B and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compositions of the invention can be applied to the locus of the plant or plant to be treated, simultaneously or in succession with further compounds. These further compounds can be e.g. fertilizers or micronutrient donors or other preparations which influence the growth of plants. They can also be herbicides as well as insecticides, fungicides, bactericides, nematicides, molluscicides or mixtures of several of these preparations, if desired together with further carriers, surfactants or application promoting adjuvants customarily employed in the art of formulation. Suitable further compounds are described in WO2008/101682.

A preferred method of the invention is foliar application. The frequency of application and the rate of application will depend on the risk of infestation by the corresponding pathogen. However, the compositions of the invention can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compositions of the invention may also be applied to seeds (coating) by impregnating the seeds or tubers either with a liquid formulation of the fungicide or coating them with a solid formulation.

A formulation, i.e. a composition of the invention and, if desired, comprising a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the active ingredients, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 1 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

The compositions of the invention are effective against various microbial species able to cause a microbial infection in an animal. Examples of such microbial species are those causing Aspergillosis such as *Aspergillus fumigatus, A. flavus, A. terrus, A. nidulans* and *A. niger*, those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are Microsporum Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following table provides a selection of compounds of the invention

| Cpd No. | Structure |
|---|---|
| P.01 | 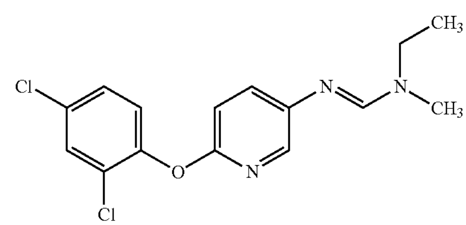 [SMILES: CCN(C)/C=N/c1ccc(Oc2ccc(Cl)cc2Cl)nc1] |
| P.02 | 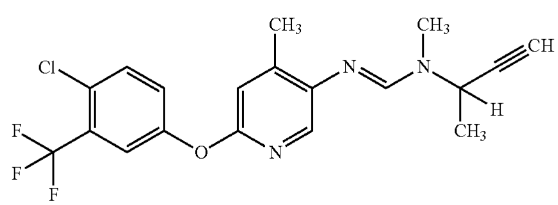 [SMILES: C#CC(C)N(C)/C=N/c1cnc(Oc2ccc(Cl)c(C(F)(F)F)c2)cc1C] |
| P.03 | 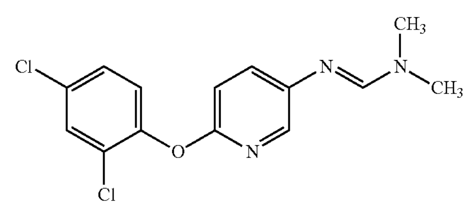 [SMILES: CN(C)/C=N/c1ccc(Oc2ccc(Cl)cc2Cl)nc1] |
| P.04 | 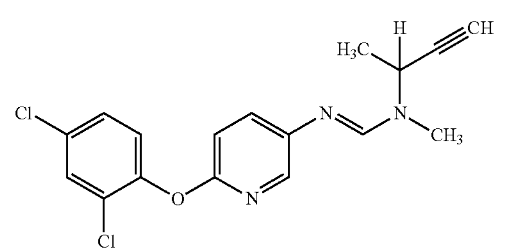 [SMILES: C#CC(C)N(C)/C=N/c1ccc(Oc2ccc(Cl)cc2Cl)nc1] |
| P.05 | 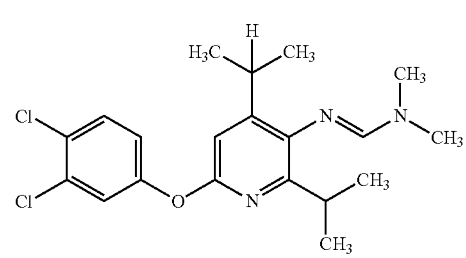 [SMILES: CC(C)c1cc(Oc2ccc(Cl)c(Cl)c2)nc(C(C)C)c1/N=C/N(C)C] |

| Cpd No. | Structure |
|---|---|
| P.06 | 4-chloro-3-(trifluoromethyl)phenoxy-pyridine with 4-methyl and N=CH-N(CH3)2 formamidine substituent |
| P.07 | 4-chloro-3-(trifluoromethyl)phenoxy-pyridine with 2-methyl and N=CH-N(CH3)(C2H5) formamidine substituent |
| P.08 | 4-chloro-3-(trifluoromethyl)phenoxy-pyridine with 3-methyl and N=CH-NH(C2H5) formamidine substituent |
| P.09 | 4-chloro-3-(trifluoromethyl)phenoxy-pyridine with 3-methyl and N=CH-N(CH3)2 formamidine substituent |
| P.10 | 4-chloro-3-(trifluoromethyl)phenoxy-pyridine with 3-methyl and N=CH-N(CH3)(CH(CH3)C≡CH) formamidine substituent |
| P.11 | 4-chloro-3-(trifluoromethyl)phenoxy-pyridine with 4-methyl and N=CH-N(CH3)(C2H5) formamidine substituent |
| P.12 | 3,4-dichlorophenoxy-pyridine with 2,4-diisopropyl and N=CH-N(CH3)(CH(CH3)C≡CH) formamidine substituent |

-continued
| Cpd No. | Structure |
|---|---|
| P.13 | 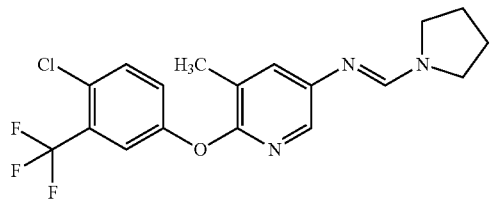 [SMILES: Cc1cc(/N=C/N2CCCC2)cnc1Oc1ccc(Cl)c(C(F)(F)F)c1] |
| P.14 | 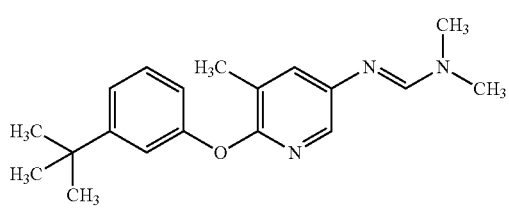 [SMILES: Cc1cc(/N=C/N(C)C)cnc1Oc1cccc(C(C)(C)C)c1] |
| P.15 | 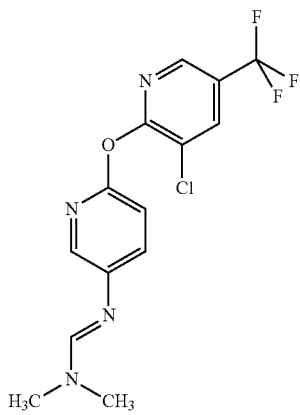 [SMILES: CN(C)/C=N/c1ccc(Oc2ncc(C(F)(F)F)cc2Cl)nc1] |
| P.16 | 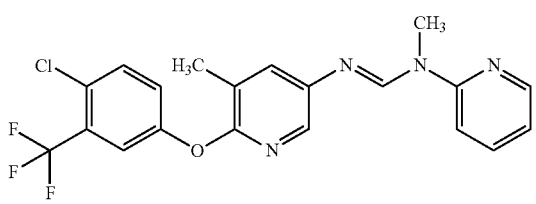 [SMILES: Cc1cc(/N=C/N(C)c2ccccn2)cnc1Oc1ccc(Cl)c(C(F)(F)F)c1] |
| P.17 | 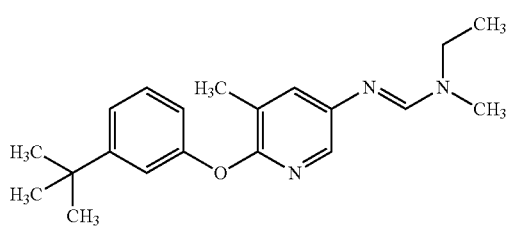 [SMILES: CCN(C)/C=N/c1cnc(Oc2cccc(C(C)(C)C)c2)c(C)c1] |
| P.18 | 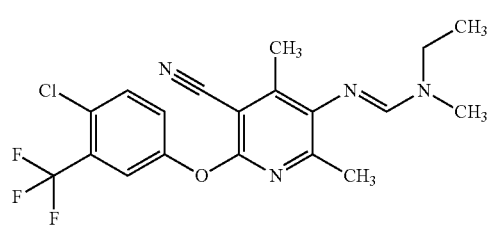 [SMILES: CCN(C)/C=N/c1c(C)nc(Oc2ccc(Cl)c(C(F)(F)F)c2)c(C#N)c1C] |

-continued
| Cpd No. | Structure |
|---|---|
| P.19 | 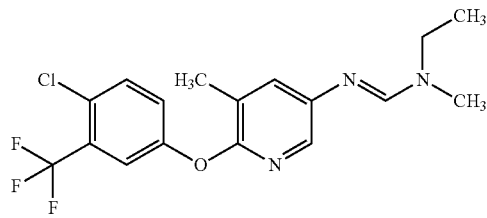 [SMILES: CCN(C)/C=N/c1cnc(Oc2ccc(Cl)c(C(F)(F)F)c2)c(C)c1] |
| P.20 | 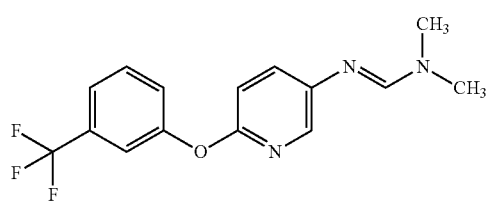 [SMILES: CN(C)/C=N/c1ccc(Oc2cccc(C(F)(F)F)c2)nc1] |
| P.21 | 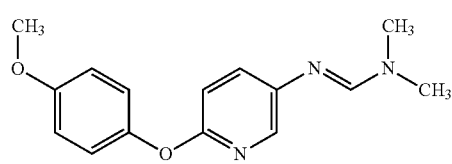 [SMILES: COc1ccc(Oc2ccc(/N=C/N(C)C)cn2)cc1] |
| P.22 | 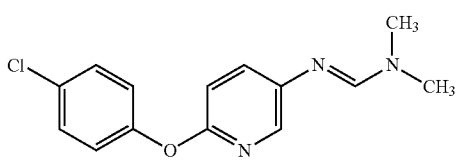 [SMILES: CN(C)/C=N/c1ccc(Oc2ccc(Cl)cc2)nc1] |
| P.23 | 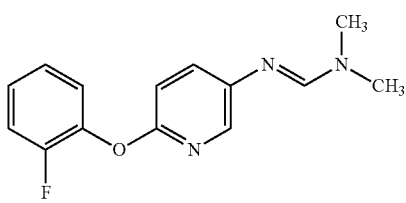 [SMILES: CN(C)/C=N/c1ccc(Oc2ccccc2F)nc1] |
| P.24 | 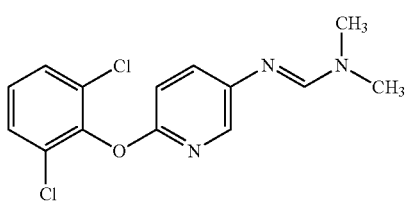 [SMILES: CN(C)/C=N/c1ccc(Oc2c(Cl)cccc2Cl)nc1] |
| P.25 | 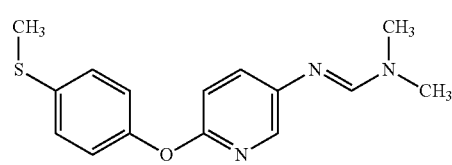 |

-continued
| Cpd No. | Structure |
|---|---|
| P.26 | 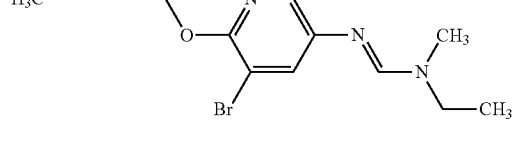 |
| P.27 | 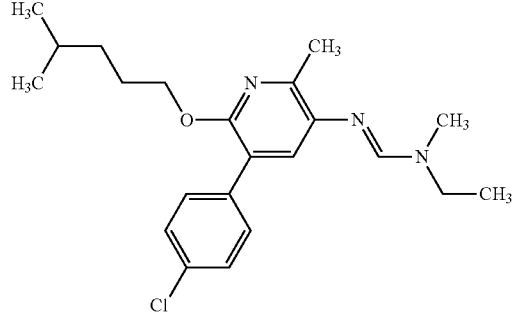 [SMILES: CCN(C)/C=N/c1cc(-c2ccc(Cl)cc2)c(OCCCC(C)C)nc1C] |
| P.28 | 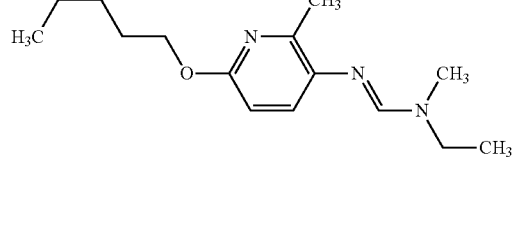 |
| P.29 | 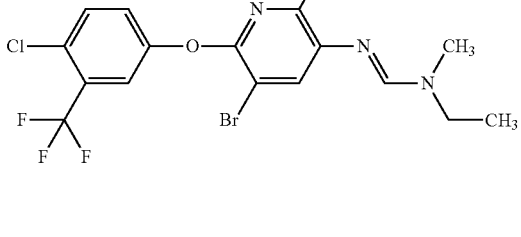 |
| P.30 | 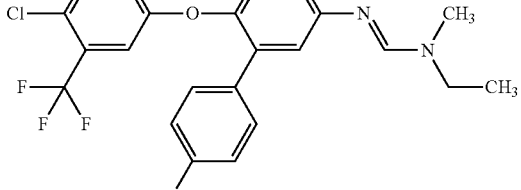 |

| Cpd No. | Structure |
|---|---|
| P.31 | 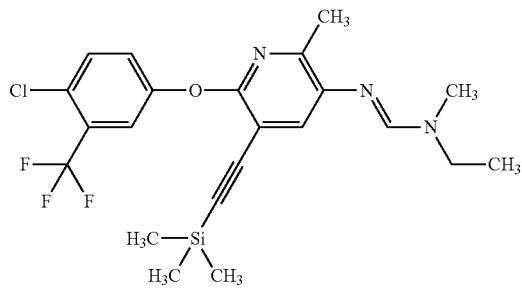 [SMILES: CCN(C)/C=N/c1cc(C#C[Si](C)(C)C)c(Oc2ccc(Cl)c(C(F)(F)F)c2)nc1C] |
| P.32 | 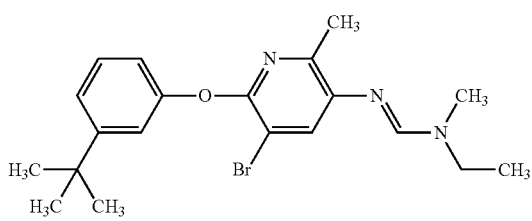 [SMILES: CCN(C)/C=N/c1cc(Br)c(Oc2cccc(C(C)(C)C)c2)nc1C] |
| P.33 | 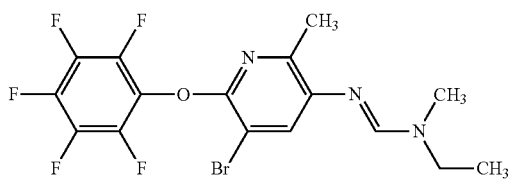 [SMILES: CCN(C)/C=N/c1cc(Br)c(Oc2c(F)c(F)c(F)c(F)c2F)nc1C] |
| P.34 | 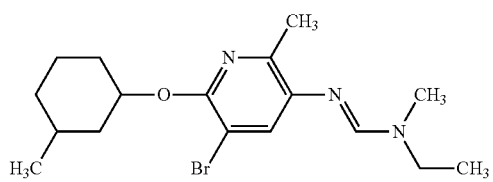 |
| P.35 | 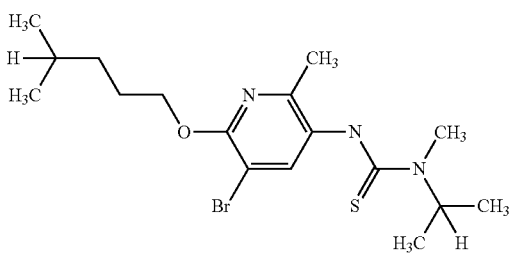 |
| P.36 | 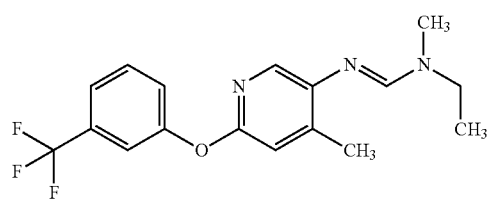 [SMILES: CCN(C)/C=N/c1cnc(Oc2cccc(C(F)(F)F)c2)cc1C] |

-continued
| Cpd No. | Structure |
|---|---|
| P.37 | 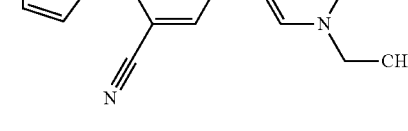 |
| P.38 | 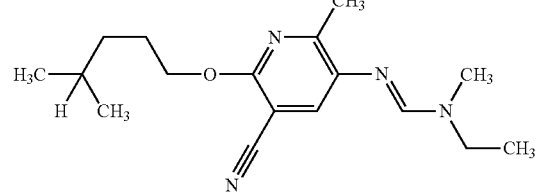 |
| P.39 | 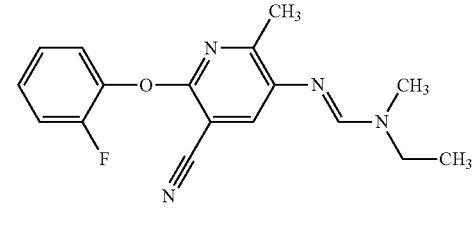 [SMILES: CCN(C)/C=N/c1cc(C#N)c(Oc2ccccc2F)nc1C] |
| P.40 | 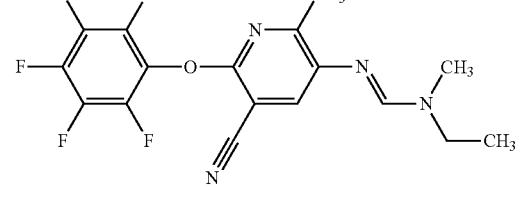 |
| P.41 | 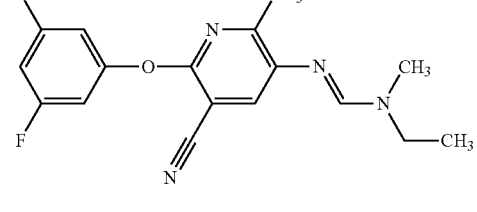 |
| P.42 | 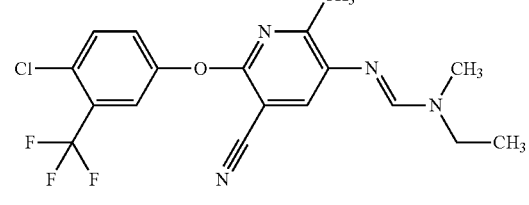 |
| P.43 | 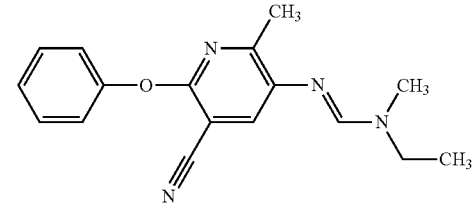 [SMILES: CCN(C)/C=N/c1cc(C#N)c(Oc2ccccc2)nc1C] |

-continued

| Cpd No. | Structure |
|---|---|
| P.44 | 6-chloro-5-cyano-2-methyl-3-pyridyl N'-ethyl-N'-methylformamidine |
| P.45 | 2-(3-methylbutoxy)-3-cyano-6-methyl-5-pyridyl N'-ethyl-N'-methylformamidine |
| P.46 | 2-(3,3-dimethylbutoxy)-5-chloro-6-methyl-3-pyridyl N'-ethyl-N'-methylformamidine |
| P.47 | 2-cyclohexyloxy-5-chloro-6-methyl-3-pyridyl N'-ethyl-N'-methylformamidine |
| P.48 | 2-(cyclopentylmethoxy)-5-chloro-6-methyl-3-pyridyl N'-ethyl-N'-methylformamidine |
| P.49 | 6-[3-(trifluoromethyl)phenoxy]-5-chloro-4-methyl-3-pyridyl N'-ethyl-N'-methylformamidine |
| P.50 | 6-[4-chloro-3-(trifluoromethyl)phenoxy]-5-chloro-4-methyl-3-pyridyl N'-ethyl-N'-methylformamidine |

-continued
| Cpd No. | Structure |
|---|---|
| P.51 | 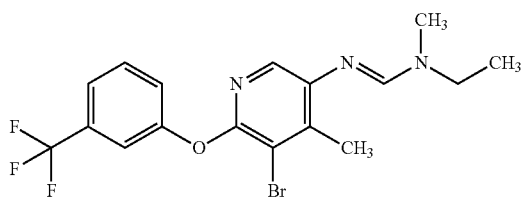 [SMILES: CCN(C)/C=N/c1cnc(Oc2cccc(C(F)(F)F)c2)c(Br)c1C] |
| P.52 | 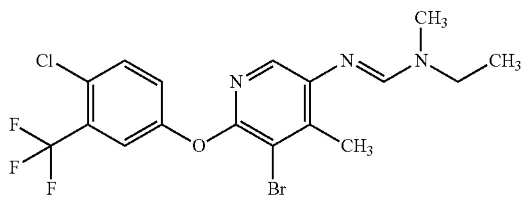 [SMILES: CCN(C)/C=N/c1cnc(Oc2ccc(Cl)c(C(F)(F)F)c2)c(Br)c1C] |
| P.53 | 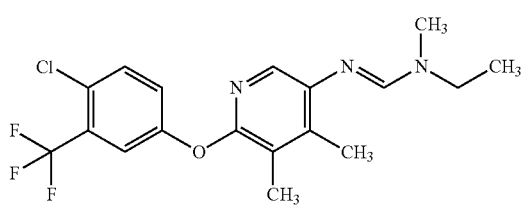 [SMILES: CCN(C)/C=N/c1cnc(Oc2ccc(Cl)c(C(F)(F)F)c2)c(C)c1C] |
| P.54 | 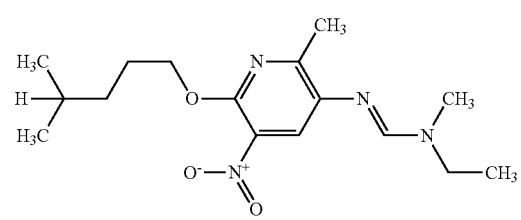 [SMILES: CCN(C)/C=N/c1cc([N+](=O)[O-])c(OCCCC(C)C)nc1C] |
| P.55 | 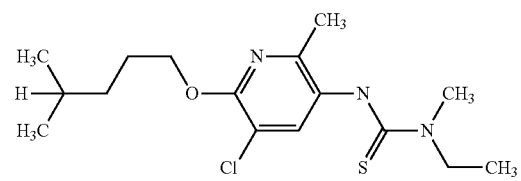 |
| P.56 | 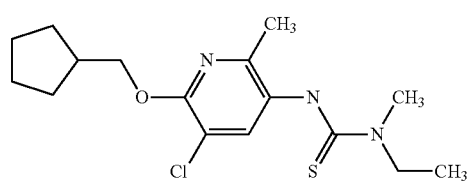 |
| P.57 | 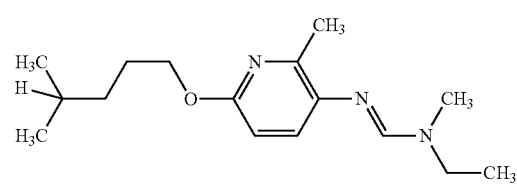 |

-continued
| Cpd No. | Structure |
|---|---|
| P.58 | 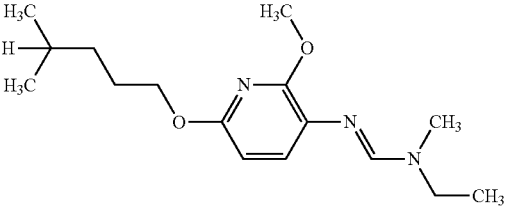 |
| P.59 | 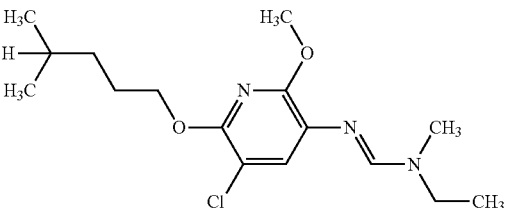 |
| P.60 | 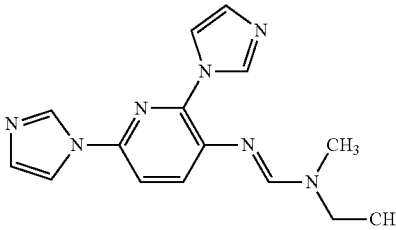 |
| P.61 | 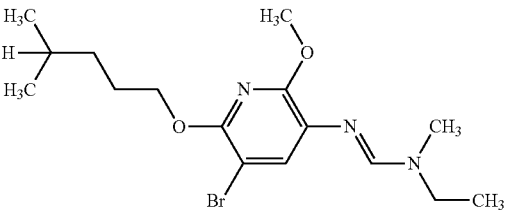 |
| P.62 | 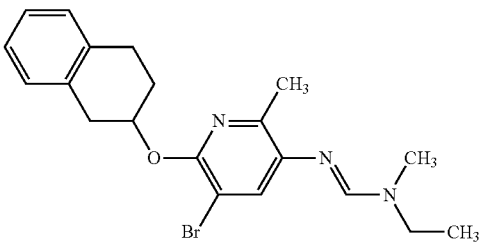 [SMILES: CCN(C)/C=N/c1cc(Br)c(OC2CCc3ccccc3C2)nc1C] |
| P.63 | 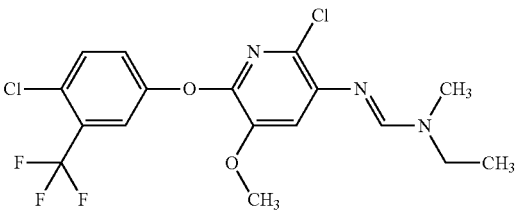 [SMILES: CCN(C)/C=N/c1cc(OC)c(Oc2ccc(Cl)c(C(F)(F)F)c2)nc1Cl] |

| Cpd No. | Structure |
|---|---|
| P.64 | (4-methylpentyl)oxy-bromo-chloro-pyridine with N=CH-N(CH₃)(CH₂CH₃) formamidine |
| P.65 | (4-methylpentyl)oxy-phenyl-pyridine with N=CH-N(CH₃)(CH₂CH₃) formamidine |
| P.66 | (4-chloro-3-trifluoromethylphenoxy)-phenyl-pyridine with N=CH-N(CH₃)(CH₂CH₃) formamidine |
| P.67 | (4-methylpentyl)oxy-methoxy-pyridine with N=CH-N(CH₃)(CH₂CH₃) formamidine |
| P.68 | (4-chloro-3-trifluoromethylphenoxy)-bromo-methoxy-pyridine with N=CH-N(CH₃)(CH₂CH₃) formamidine |
| P.69 | (4-methylpentyl)oxy-2,5-dibromo-pyridine with N=CH-N(CH₃)(CH₂CH₃) formamidine |

-continued

| Cpd No. | Structure |
|---|---|
| P.70 | (structure) |
| P.71 | (structure) |
| P.72 | (structure) |
| P.73 | (structure) |
| P.74 | (structure) |
| P.75 | (structure) |

-continued
| Cpd No. | Structure |
|---|---|
| P.76 | 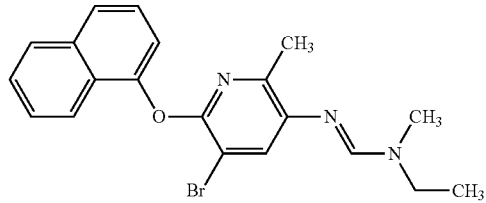 [SMILES: CCN(C)/C=N/c1cc(Br)c(Oc2cccc3ccccc23)nc1C] |
| P.77 | 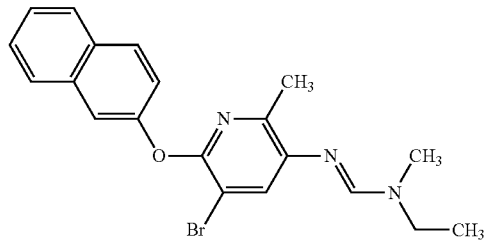 [SMILES: CCN(C)/C=N/c1cc(Br)c(Oc2ccc3ccccc3c2)nc1C] |
| P.78 | 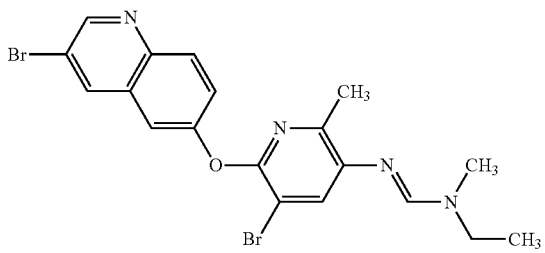 [SMILES: CCN(C)/C=N/c1cc(Br)c(Oc2ccc3ncc(Br)cc3c2)nc1C] |
| P.79 | 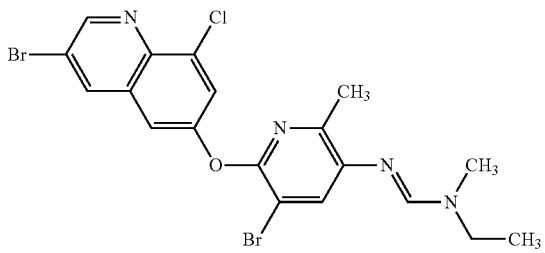 [SMILES: CCN(C)/C=N/c1cc(Br)c(Oc2cc(Cl)c3ncc(Br)cc3c2)nc1C] |
| P.80 | 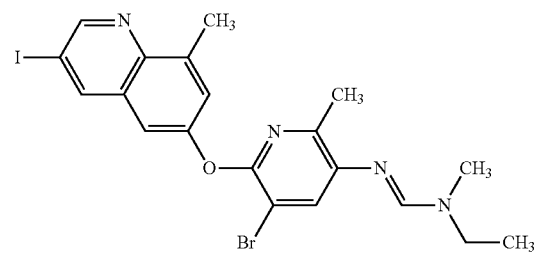 [SMILES: CCN(C)/C=N/c1cc(Br)c(Oc2cc(C)c3ncc(I)cc3c2)nc1C] |
| P.81 | 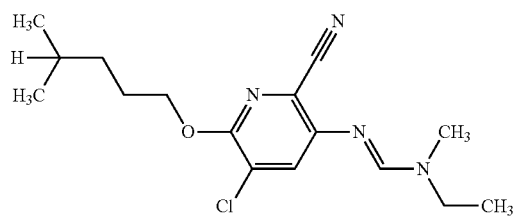 [SMILES: CCN(C)/C=N/c1cc(Cl)c(OCCCC(C)C)nc1C#N] |

-continued

| Cpd No. | Structure |
|---|---|
| P.82 | 6-methoxy-1,2,3,4-tetrahydronaphthalen-2-yl ether of 5-bromo-2-methyl-3-{[(E)-(N-methyl-N-ethylamino)methylidene]amino}pyridine |
| P.83 | 2,3-dihydro-1H-inden-2-yl ether of 5-bromo-2-methyl-3-{[(E)-(N-methyl-N-ethylamino)methylidene]amino}pyridine |
| P.84 | 4-methyl-2,3-dihydro-1H-inden-2-yl ether of 5-bromo-2-methyl-3-{[(E)-(N-methyl-N-ethylamino)methylidene]amino}pyridine |
| P.85 | 5-methoxy-2,3-dihydro-1H-inden-2-yl ether of 5-bromo-2-methyl-3-{[(E)-(N-methyl-N-ethylamino)methylidene]amino}pyridine |
| P.86 | 6-bromo-1,2,3,4-tetrahydronaphthalen-2-yl ether of 5-bromo-2-methyl-3-{[(E)-(N-methyl-N-ethylamino)methylidene]amino}pyridine |

| Cpd No. | Structure |
|---|---|
| P.87 | 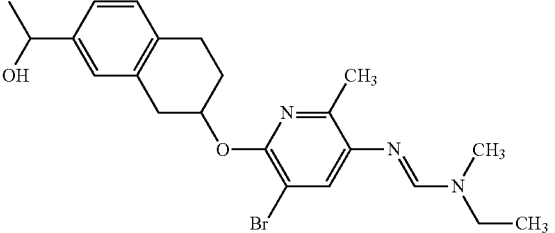 [SMILES: CCN(C)/C=N/c1cc(Br)c(OC2CCc3ccc(C(C)O)cc3C2)nc1C] |
| P.88 | 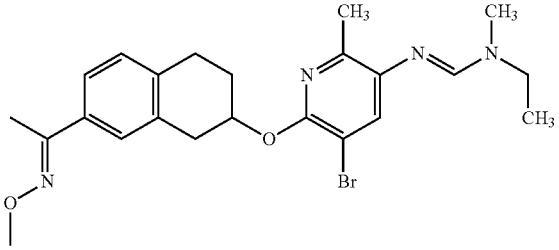 [SMILES: CCN(C)/C=N/c1cc(Br)c(OC2CCc3ccc(/C(C)=N/OC)cc3C2)nc1C] |
| P.89 | 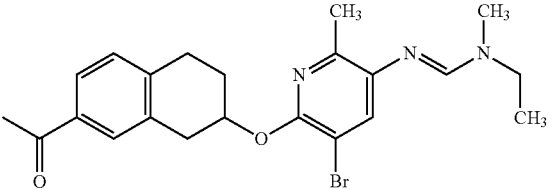 [SMILES: CCN(C)/C=N/c1cc(Br)c(OC2CCc3ccc(C(C)=O)cc3C2)nc1C] |
| P.90 | 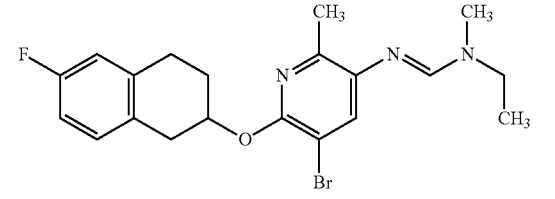 [SMILES: CCN(C)/C=N/c1cc(Br)c(OC2CCc3cc(F)ccc3C2)nc1C] |
| P.91 | 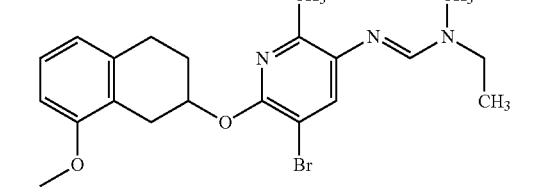 |
| P.92 | 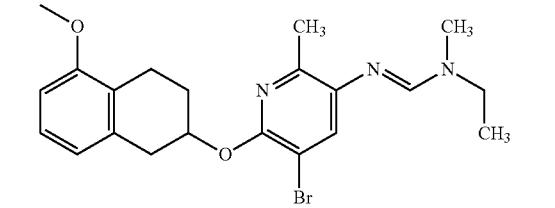 [SMILES: CCN(C)/C=N/c1cc(Br)c(OC2CCc3c(cccc3OC)C2)nc1C] |

-continued
| Cpd No. | Structure |
|---|---|
| P.93 | 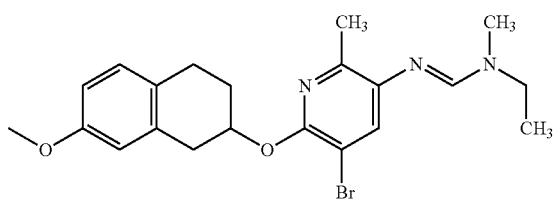 [SMILES: CCN(C)/C=N/c1cc(Br)c(OC2CCc3ccc(OC)cc3C2)nc1C] |
| P.94 | 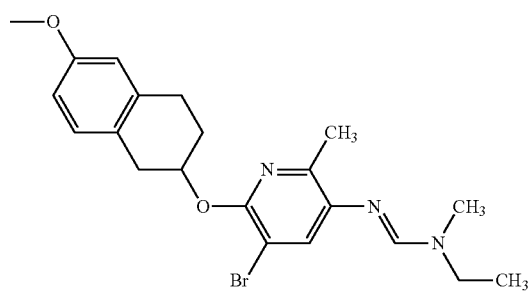 [SMILES: CCN(C)/C=N/c1cc(Br)c(OC2CCc3cc(OC)ccc3C2)nc1C] |
| P.95 | 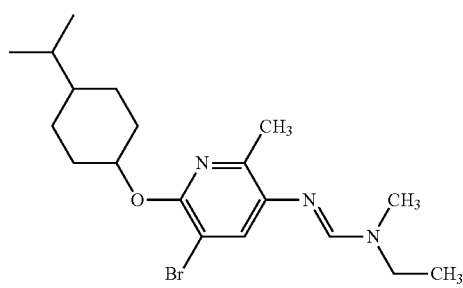 [SMILES: CCN(C)/C=N/c1cc(Br)c(OC2CCC(C(C)C)CC2)nc1C] |
| P.96 | 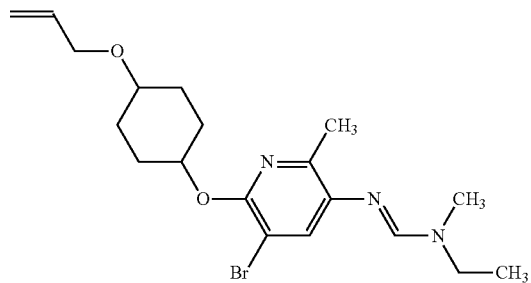 [SMILES: C=CCOC1CCC(Oc2nc(C)c(/N=C/N(C)CC)cc2Br)CC1] |
| P.97 | 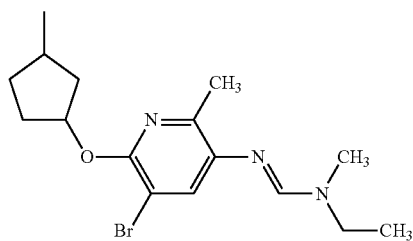 [SMILES: CCN(C)/C=N/c1cc(Br)c(OC2CCC(C)C2)nc1C] |

-continued
| Cpd No. | Structure |
|---|---|
| P.98 | 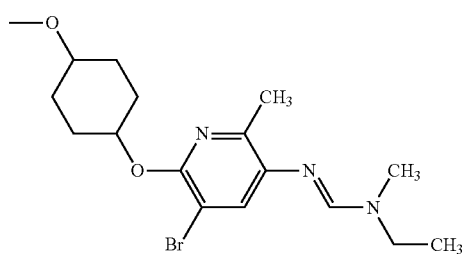 |
| P.99 | 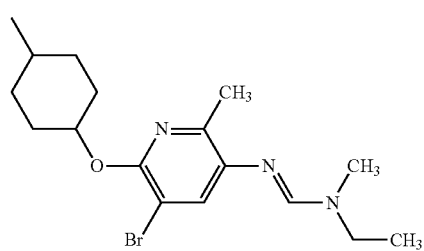 [SMILES: CCN(C)/C=N/c1cc(Br)c(OC2CCC(C)CC2)nc1C] |
| P.100 | 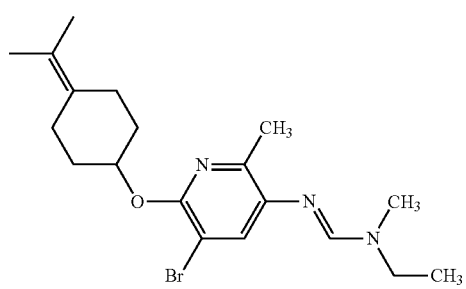 [SMILES: CCN(C)/C=N/c1cc(Br)c(OC2CCC(=C(C)C)CC2)nc1C] |
| P.101 | 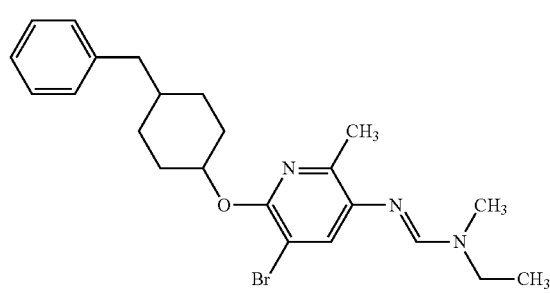 [SMILES: CCN(C)/C=N/c1cc(Br)c(OC2CCC(Cc3ccccc3)CC2)nc1C] |
| P.101a | 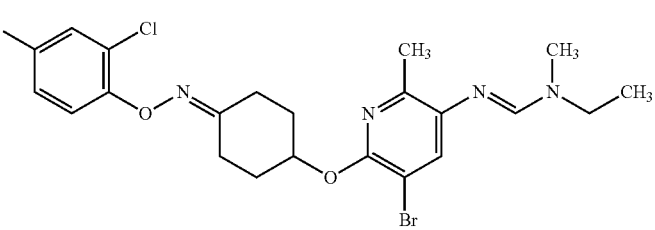 |

-continued

| Cpd No. | Structure |
|---|---|
| P.102 | (structure) |
| P.103 | (structure) |
| P.104 | (structure) |
| P.105 | (structure) |
| P.106 | (structure) |
| P.107 | (structure) |
| P.108 | (structure) |

-continued
| Cpd No. | Structure |
|---|---|
| P.109 | 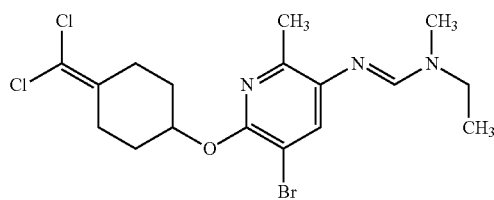 [SMILES: CCN(C)/C=N/c1cc(Br)c(OC2CCC(=C(Cl)Cl)CC2)nc1C] |
| P.110 | 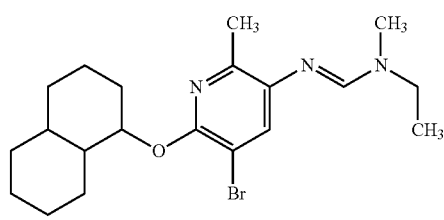 [SMILES: CCN(C)/C=N/c1cc(Br)c(OC2CCCC3CCCCC32)nc1C] |
| P.111 | 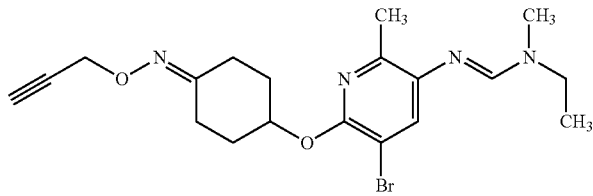 [SMILES: C#CCON=C1CCC(Oc2nc(C)c(/N=C/N(C)CC)cc2Br)CC1] |
| P.112 | 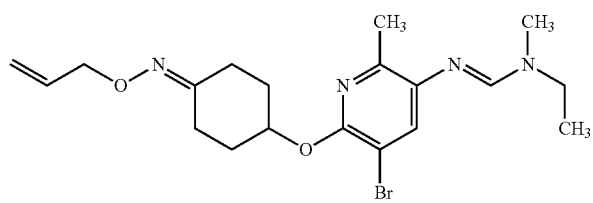 [SMILES: C=CCON=C1CCC(Oc2nc(C)c(/N=C/N(C)CC)cc2Br)CC1] |
| P.113 | 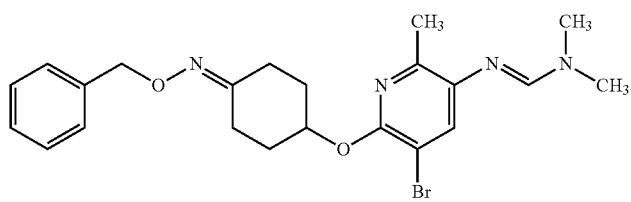 [SMILES: Cc1nc(OC2CCC(=NOCc3ccccc3)CC2)c(Br)cc1/N=C/N(C)C] |
| P.114 | 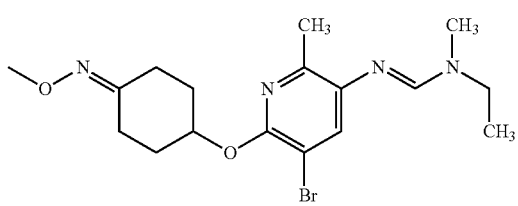 [SMILES: CCN(C)/C=N/c1cc(Br)c(OC2CCC(=NOC)CC2)nc1C] |
| P.115 | 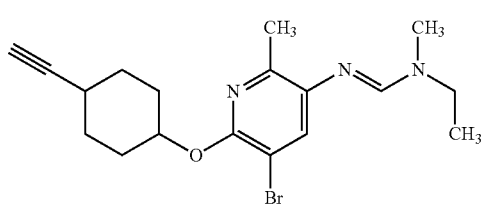 [SMILES: C#CC1CCC(Oc2nc(C)c(/N=C/N(C)CC)cc2Br)CC1] |

-continued
| Cpd No. | Structure |
|---|---|
| P.116 | 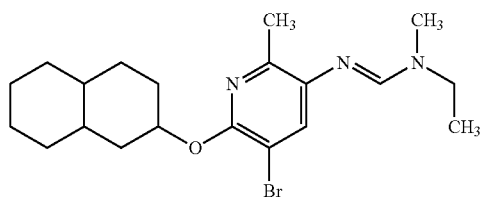 [SMILES: CCN(C)/C=N/c1cc(Br)c(OC2CCC3CCCCC3C2)nc1C] |
| P.117 | 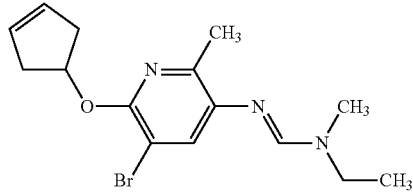 |
| P.118 | 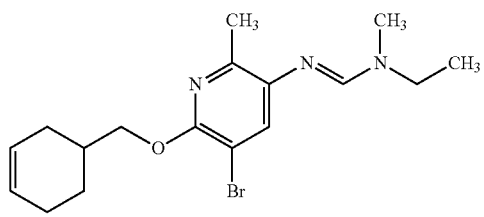 [SMILES: CCN(C)/C=N/c1cc(Br)c(OCC2CC=CCC2)nc1C] |
| P.119 | 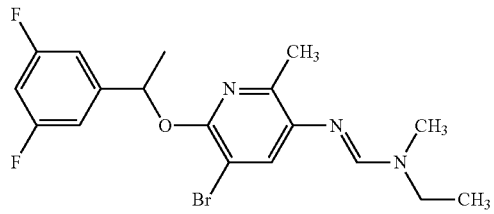 [SMILES: CCN(C)/C=N/c1cc(Br)c(OC(C)c2cc(F)cc(F)c2)nc1C] |
| P.120 | 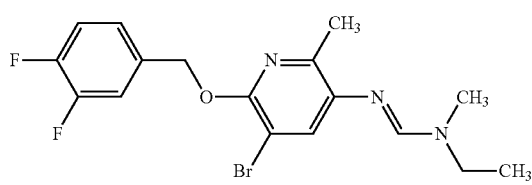 |
| P.121 | 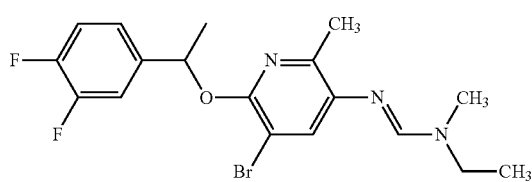 [SMILES: CCN(C)/C=N/c1cc(Br)c(OC(C)c2ccc(F)c(F)c2)nc1C] |
| P.122 | 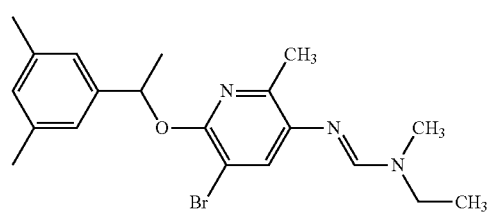 [SMILES: CCN(C)/C=N/c1cc(Br)c(OC(C)c2cc(C)cc(C)c2)nc1C] |

-continued
| Cpd No. | Structure |
|---|---|
| P.123 | 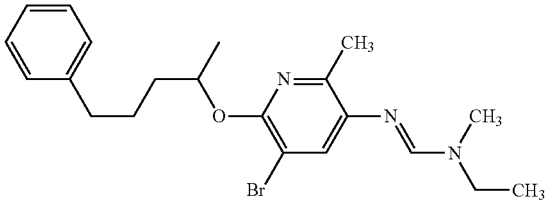 [SMILES: CCN(C)/C=N/c1cc(Br)c(OC(C)CCCc2ccccc2)nc1C] |
| P.124 | 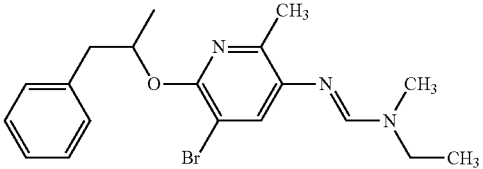 [SMILES: CCN(C)/C=N/c1cc(Br)c(OC(C)Cc2ccccc2)nc1C] |
| P.125 | 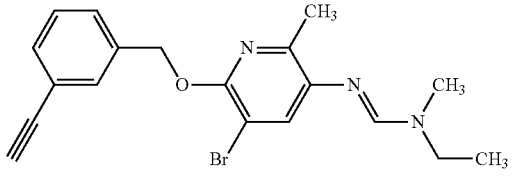 |
| P.126 | 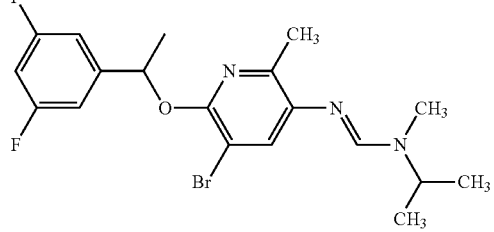 |
| P.127 | 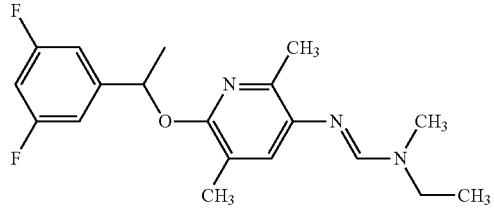 [SMILES: CCN(C)/C=N/c1cc(C)c(OC(C)c2cc(F)cc(F)c2)nc1C] |
| P.128 | 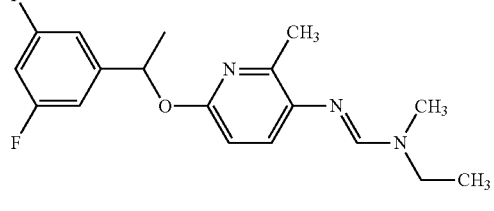 |
| P.129 | 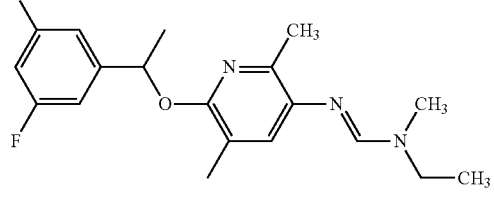 |

-continued
| Cpd No. | Structure |
|---|---|
| P.130 | 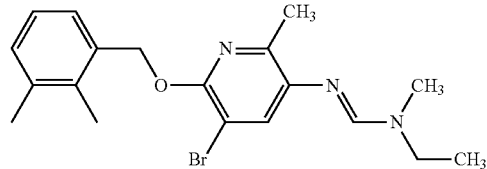 [SMILES: CCN(C)/C=N/c1cc(Br)c(OCc2cccc(C)c2C)nc1C] |
| P.131 | 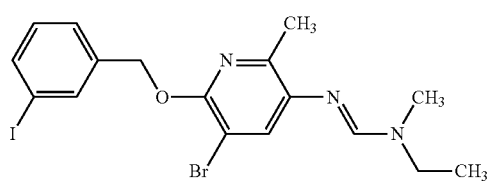 |
| P.132 | 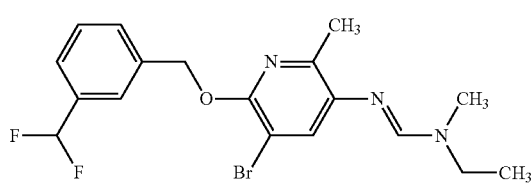 |
| P.133 | 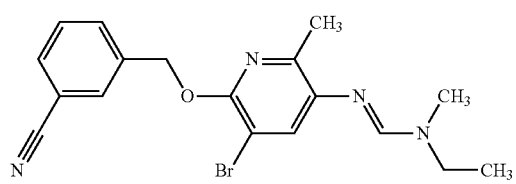 [SMILES: CCN(C)/C=N/c1cc(Br)c(OCc2cccc(C#N)c2)nc1C] |
| P.134 | 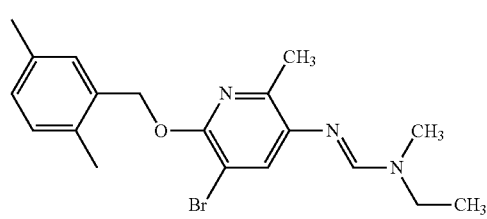 [SMILES: CCN(C)/C=N/c1cc(Br)c(OCc2cc(C)ccc2C)nc1C] |
| P.135 | 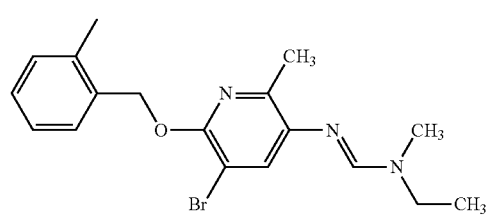 [SMILES: CCN(C)/C=N/c1cc(Br)c(OCc2ccccc2C)nc1C] |
| P.136 | 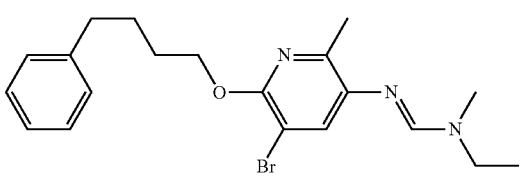 |

-continued

| Cpd No. | Structure |
|---|---|
| P.137 | 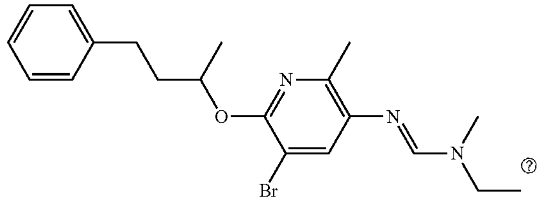 [SMILES: CCN(C)/C=N/c1cc(Br)c(OC(C)CCc2ccccc2)nc1C] |
| P.138 | 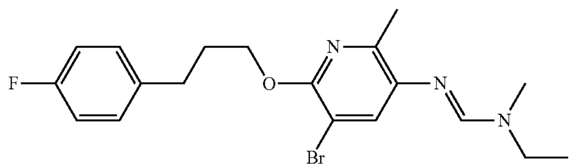 [SMILES: CCN(C)/C=N/c1cc(Br)c(OCCCc2ccc(F)cc2)nc1C] |
| P.139 | 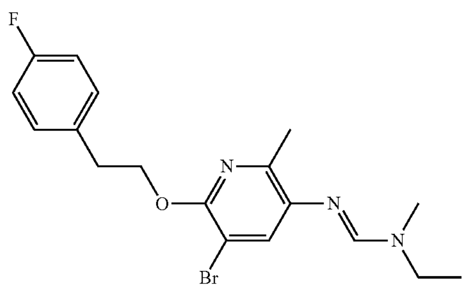 [SMILES: CCN(C)/C=N/c1cc(Br)c(OCCc2ccc(F)cc2)nc1C] |
| P.140 | 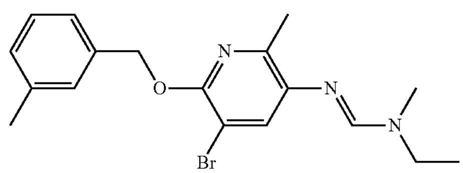 [SMILES: CCN(C)/C=N/c1cc(Br)c(OCc2cccc(C)c2)nc1C] |
| P.141 | 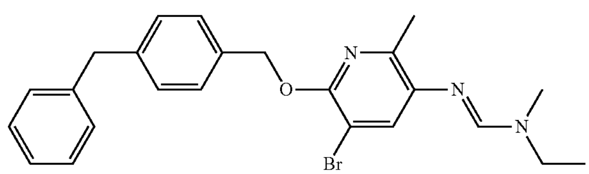 [SMILES: CCN(C)/C=N/c1cc(Br)c(OCc2ccc(Cc3ccccc3)cc2)nc1C] |
| P.142 | 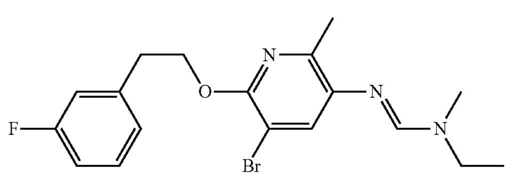 [SMILES: CCN(C)/C=N/c1cc(Br)c(OCCc2cccc(F)c2)nc1C] |
| P.143 | 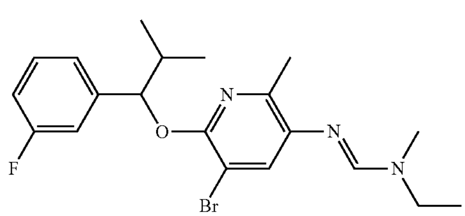 [SMILES: CCN(C)/C=N/c1cc(Br)c(OC(c2cccc(F)c2)C(C)C)nc1C] |

-continued

| Cpd No. | Structure |
|---|---|
| P.145 | *(structure image)* |
| P.146 | *(structure image)* |
| P.147 | *(structure image)* |
| P.148 | *(structure image)* |
| P.149 | *(structure image)* |
| P.150 | *(structure image)* |
| P.151 | *(structure image)* |
| P.152 | *(structure image)* |

-continued

| Cpd No. | Structure |
|---|---|
| P.153 | 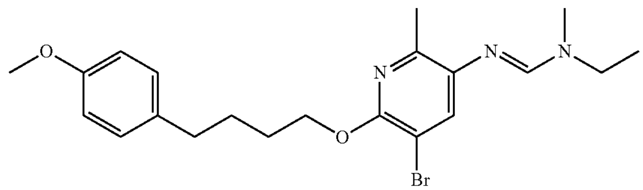 [SMILES: CCN(C)/C=N/c1cc(Br)c(OCCCCc2ccc(OC)cc2)nc1C] |
| P.154 | 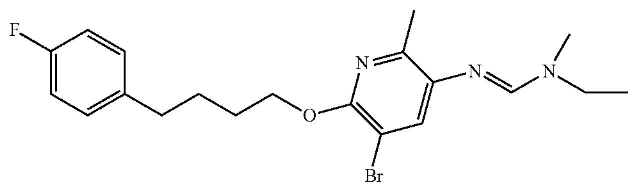 [SMILES: CCN(C)/C=N/c1cc(Br)c(OCCCCc2ccc(F)cc2)nc1C] |
| P.155 | 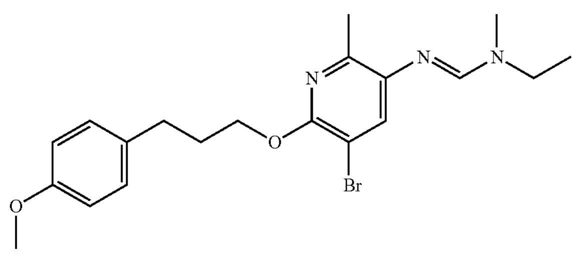 [SMILES: CCN(C)/C=N/c1cc(Br)c(OCCCc2ccc(OC)cc2)nc1C] |
| P.156 | 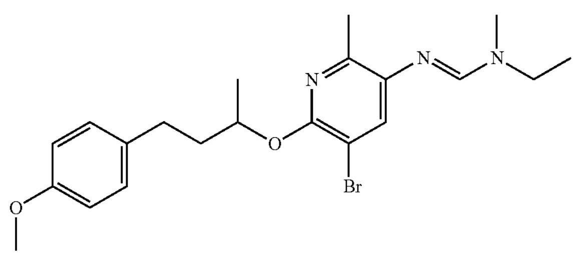 [SMILES: CCN(C)/C=N/c1cc(Br)c(OC(C)CCc2ccc(OC)cc2)nc1C] |
| P.157 | 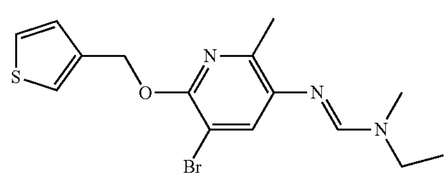 [SMILES: CCN(C)/C=N/c1cc(Br)c(OCc2ccsc2)nc1C] |
| P.158 | 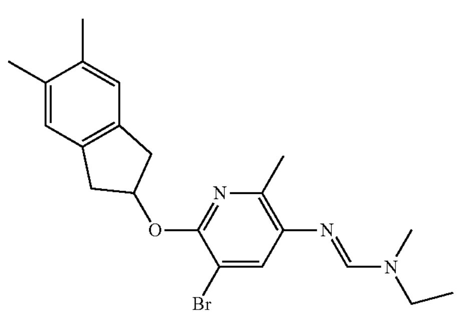 [SMILES: CCN(C)/C=N/c1cc(Br)c(OC2Cc3cc(C)c(C)cc3C2)nc1C] |

-continued
| Cpd No. | Structure |
|---|---|
| P.159 | 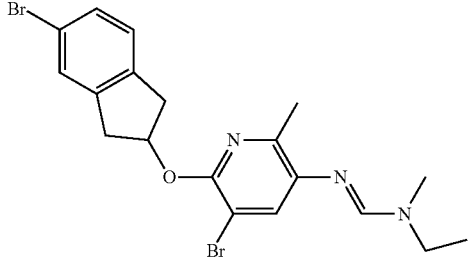 |
| P.160 | 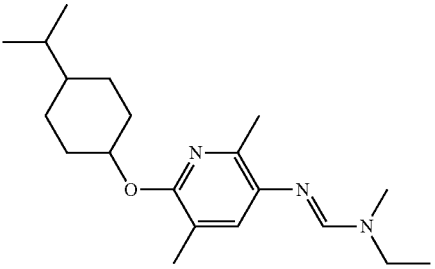 |
| P.161 | 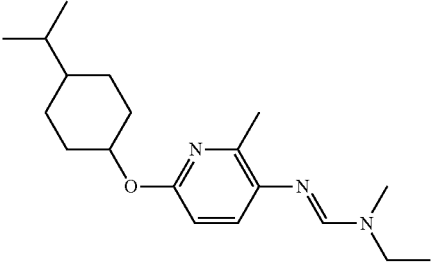 [SMILES: CCN(C)/C=N/c1ccc(OC2CCC(C(C)C)CC2)nc1C] |
| P.162 | 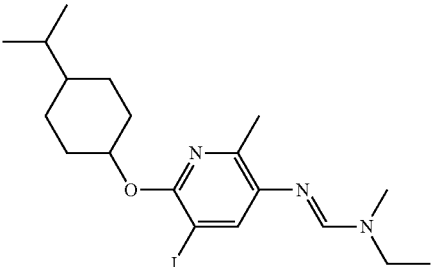 |
| P.163 | 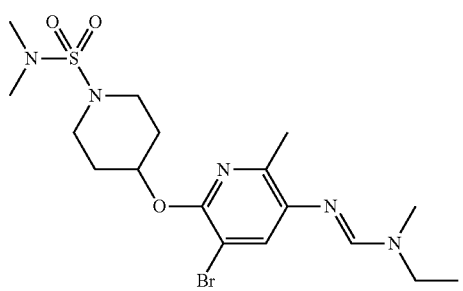 [SMILES: CCN(C)/C=N/c1cc(Br)c(OC2CCN(S(=O)(=O)N(C)C)CC2)nc1C] |

-continued
| Cpd No. | Structure |
|---|---|
| P.164 | 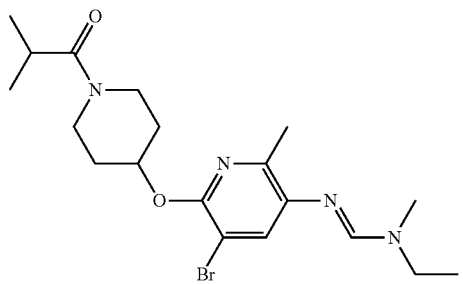 [SMILES: CCN(C)/C=N/c1cc(Br)c(OC2CCN(C(=O)C(C)C)CC2)nc1C] |
| P.165 | 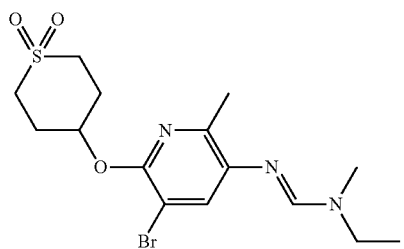 [SMILES: CCN(C)/C=N/c1cc(Br)c(OC2CCS(=O)(=O)CC2)nc1C] |
| P.166 | 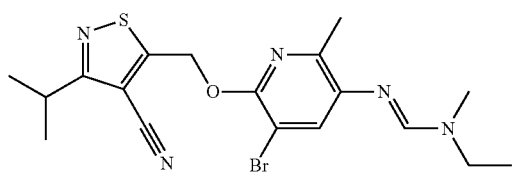 [SMILES: CCN(C)/C=N/c1cc(Br)c(OCc2snc(C(C)C)c2C#N)nc1C] |
| P.167 | 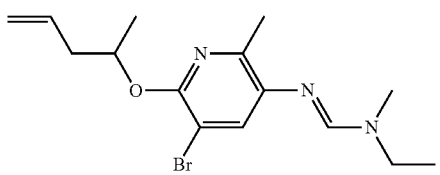 |
| P.168 | 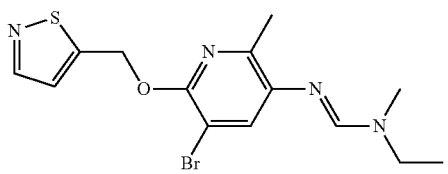 [SMILES: CCN(C)/C=N/c1cc(Br)c(OCc2ccns2)nc1C] |
| P.169 | 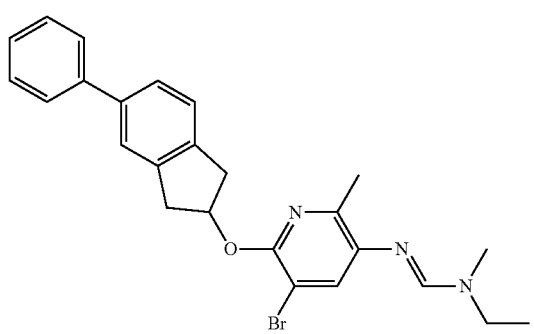 [SMILES: CCN(C)/C=N/c1cc(Br)c(OC2Cc3ccc(-c4ccccc4)cc3C2)nc1C] |

-continued
| Cpd No. | Structure |
|---|---|
| P.170 | 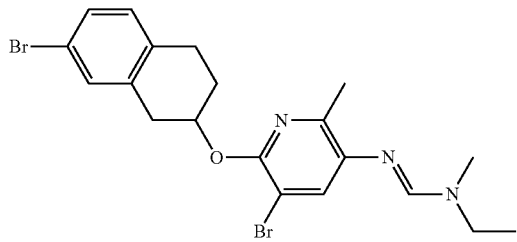 [SMILES: CCN(C)/C=N/c1cc(Br)c(OC2CCc3ccc(Br)cc3C2)nc1C] |
| P.171 | 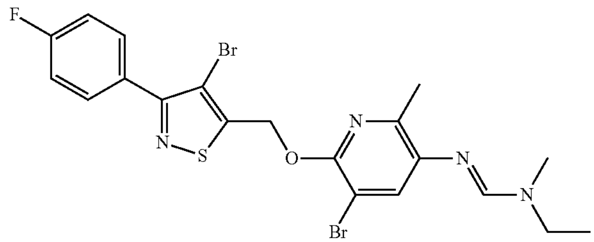 |
| P.172 | 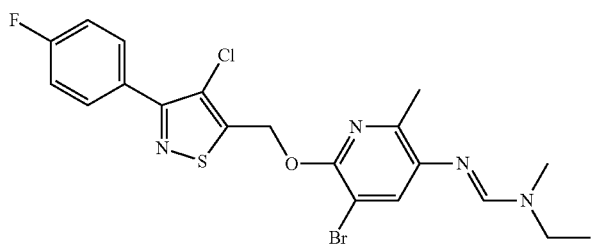 |
| P.173 | 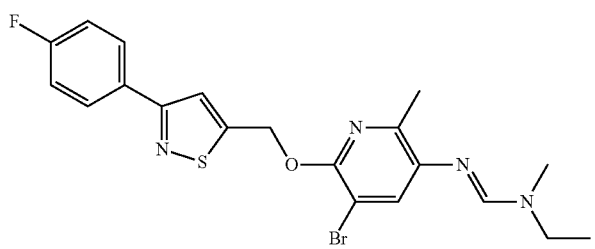 |
| P.174 | 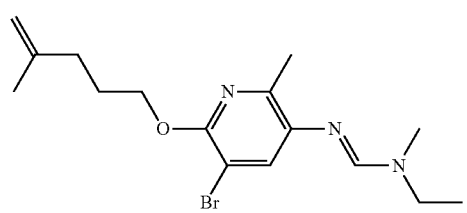 [SMILES: C=C(C)CCCOc1nc(C)c(/N=C/N(C)CC)cc1Br] |
| P.175 | 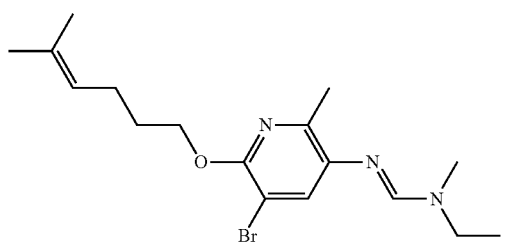 |

-continued

| Cpd No. | Structure |
|---|---|
| P.176 | 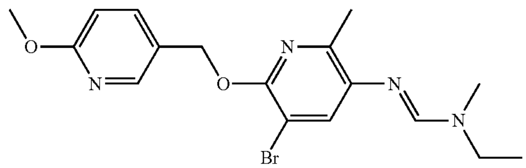 [SMILES: CCN(C)/C=N/c1cc(Br)c(OCc2ccc(OC)nc2)nc1C] |
| P.177 | 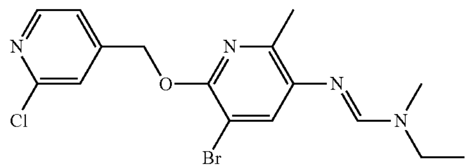 |
| P.178 | 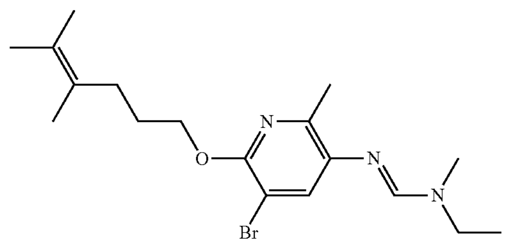 [SMILES: CCN(C)/C=N/c1cc(Br)c(OCCCC(C)=C(C)C)nc1C] |
| P.179 | 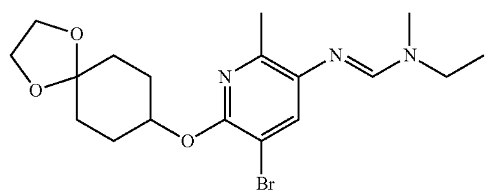 [SMILES: CCN(C)/C=N/c1cc(Br)c(OC2CCC3(CC2)OCCO3)nc1C] |
| P.180 | 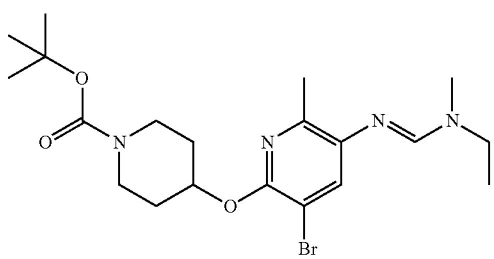 [SMILES: CCN(C)/C=N/c1cc(Br)c(OC2CCN(C(=O)OC(C)(C)C)CC2)nc1C] |
| P.181 | 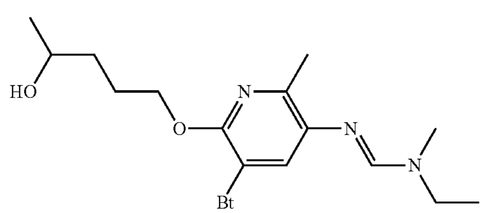 |
| P.182 | 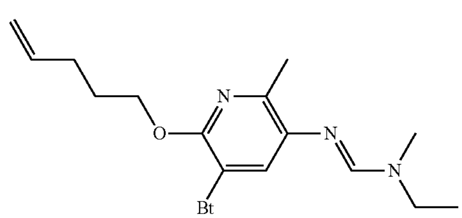 |

US 9,326,513 B2
157                                                                 158
-continued
| Cpd No. | Structure |
|---------|-----------|
| P.183 | 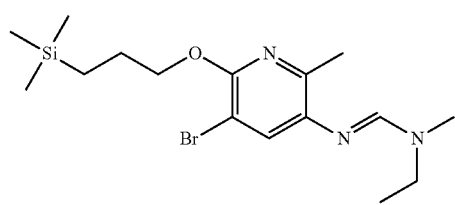 |
| P.184 | 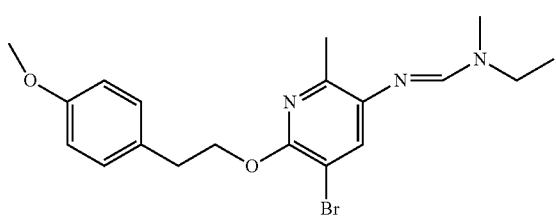 [SMILES: CCN(C)/C=N/c1cc(Br)c(OCCc2ccc(OC)cc2)nc1C] |
| P.185 | 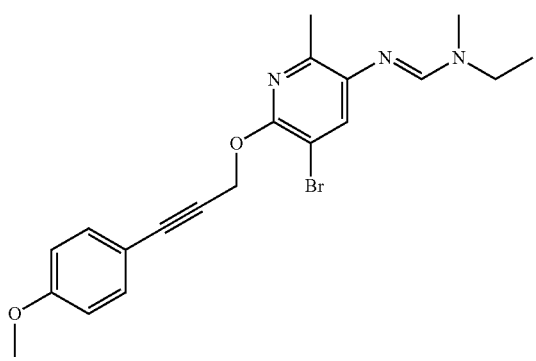 [SMILES: CCN(C)/C=N/c1cc(Br)c(OCC#Cc2ccc(OC)cc2)nc1C] |
| P.186 | 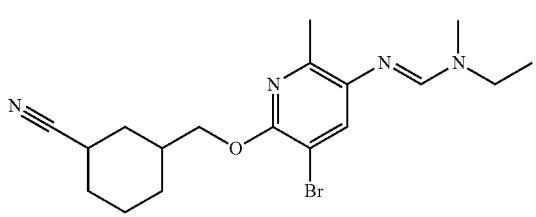 [SMILES: CCN(C)/C=N/c1cc(Br)c(OCC2CCCC(C#N)C2)nc1C] |
| P.187 | 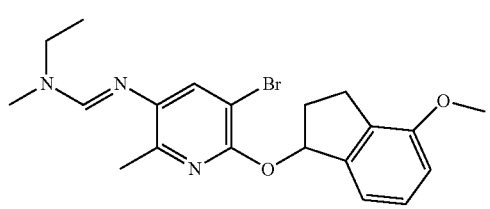 |
| P.188 | 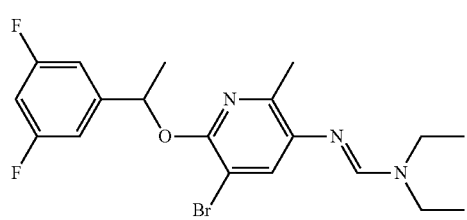 [SMILES: CCN(/C=N/c1cc(Br)c(OC(C)c2cc(F)cc(F)c2)nc1C)CC] |

-continued

| Cpd No. | Structure |
|---|---|
| P.189 | 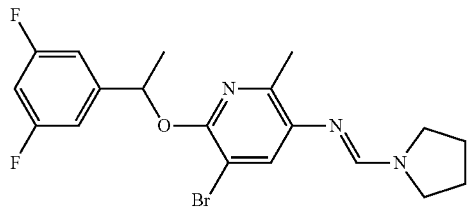 [SMILES: Cc1nc(OC(C)c2cc(F)cc(F)c2)c(Br)cc1/N=C/N1CCCC1] |
| P.190 | 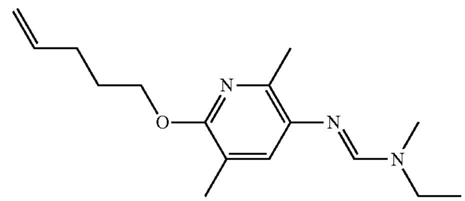 [SMILES: C=CCCCOc1nc(C)c(/N=C/N(C)CC)cc1C] |
| P.191 | 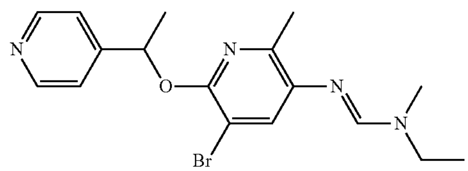 [SMILES: CCN(C)/C=N/c1cc(Br)c(OC(C)c2ccncc2)nc1C] |
| P.192 | 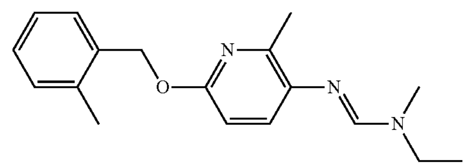 [SMILES: CCN(C)/C=N/c1ccc(OCc2ccccc2C)nc1C] |
| P.193 | 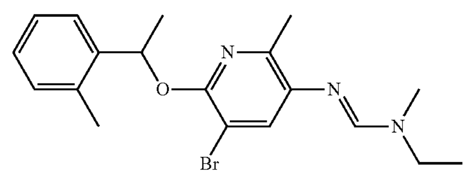 |
| P.194 | 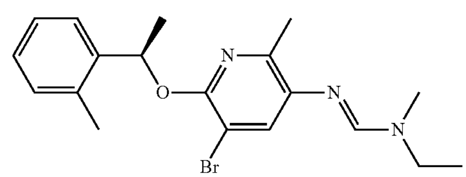 [SMILES: CCN(C)/C=N/c1cc(Br)c(O[C@H](C)c2ccccc2C)nc1C] |
| P.195 | 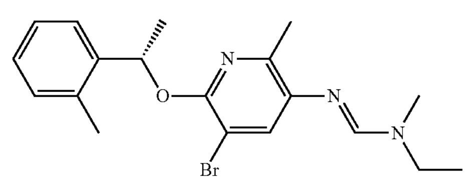 |
| P.196 | 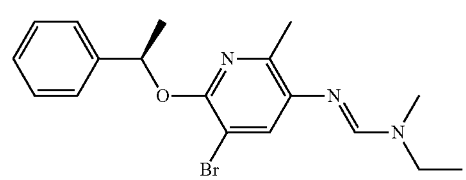 [SMILES: CCN(C)/C=N/c1cc(Br)c(O[C@H](C)c2ccccc2)nc1C] |

-continued
| Cpd No. | Structure |
|---|---|
| P.197 | 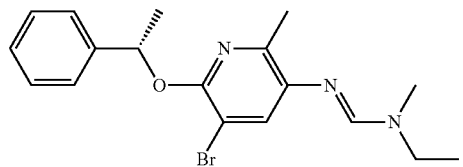 |
| P.198 | 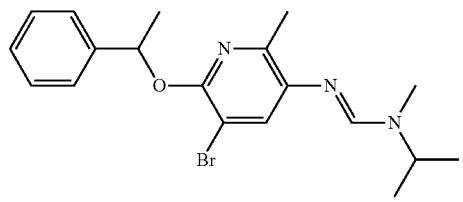 [SMILES: Cc1nc(OC(C)c2ccccc2)c(Br)cc1/N=C/N(C)C(C)C] |
| P.199 | 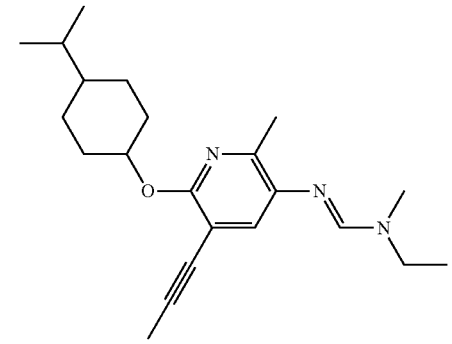 [SMILES: CC#Cc1cc(/N=C/N(C)CC)c(C)nc1OC1CCC(C(C)C)CC1] |
| P.200 | 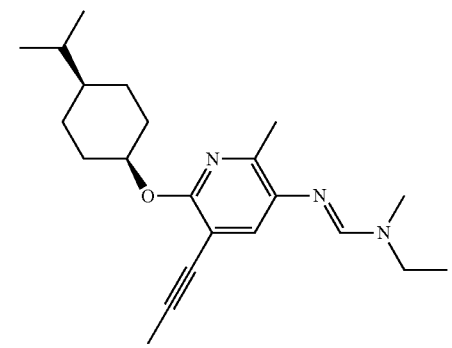 [SMILES: CC#Cc1cc(/N=C/N(C)CC)c(C)nc1O[C@H]1CC[C@@H](C(C)C)CC1] |
| P.201 | 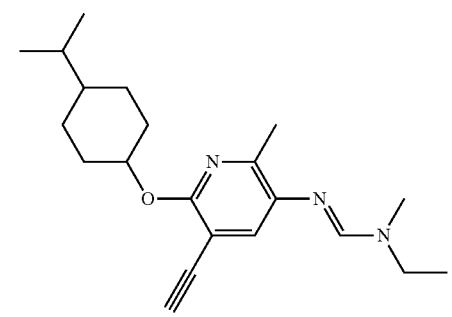 [SMILES: C#Cc1cc(/N=C/N(C)CC)c(C)nc1OC1CCC(C(C)C)CC1] |

-continued
| Cpd No. | Structure |
|---|---|
| P.202 | 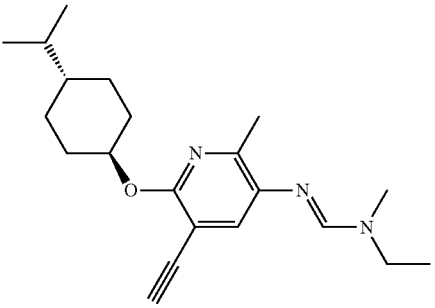 [SMILES: C#Cc1cc(/N=C/N(C)CC)c(C)nc1O[C@H]1CC[C@H](C(C)C)CC1] |
| P.203 | 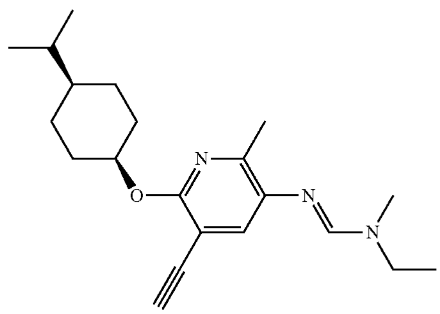 [SMILES: C#Cc1cc(/N=C/N(C)CC)c(C)nc1O[C@H]1CC[C@@H](C(C)C)CC1] |
| P.204 | 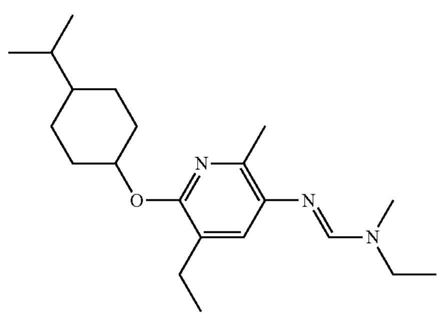 [SMILES: CCc1cc(/N=C/N(C)CC)c(C)nc1OC1CCC(C(C)C)CC1] |
| P.205 | 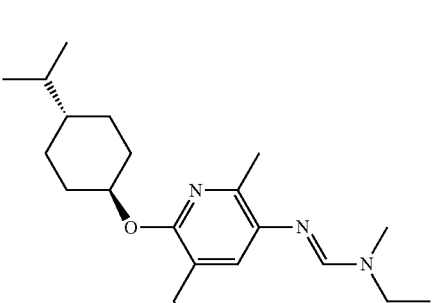 |

-continued
| Cpd No. | Structure |
|---|---|
| P.206 | 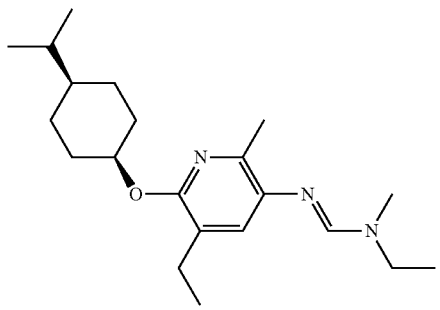 |
| P.207 | 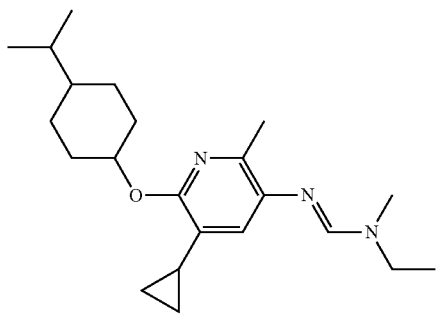 [SMILES: CCN(C)/C=N/c1cc(C2CC2)c(OC2CCC(C(C)C)CC2)nc1C] |
| P.208 | 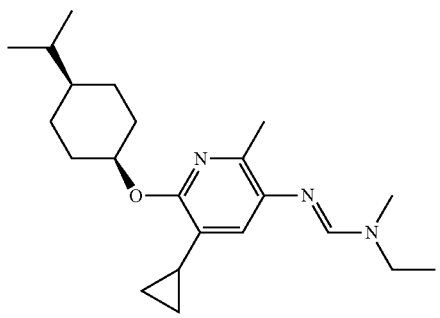 [SMILES: CCN(C)/C=N/c1cc(C2CC2)c(O[C@H]2CC[C@@H](C(C)C)CC2)nc1C] |
| P.209 | 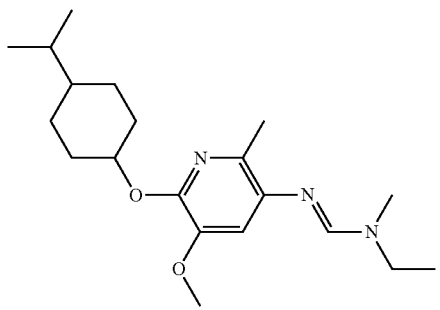 [SMILES: CCN(C)/C=N/c1cc(OC)c(OC2CCC(C(C)C)CC2)nc1C] |

-continued

| Cpd No. | Structure |
|---|---|
| P.210 | 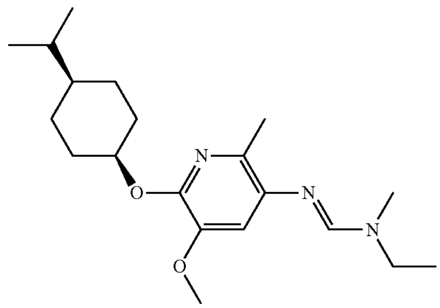 |
| P.211 | 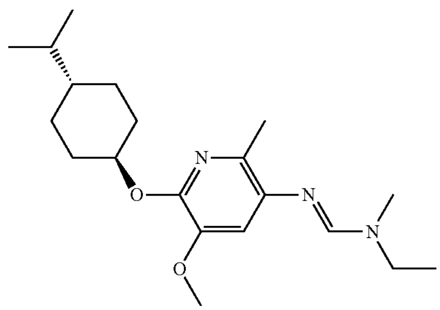 [SMILES: CCN(C)/C=N/c1cc(OC)c(O[C@H]2CC[C@H](C(C)C)CC2)nc1C] |
| P.212 | 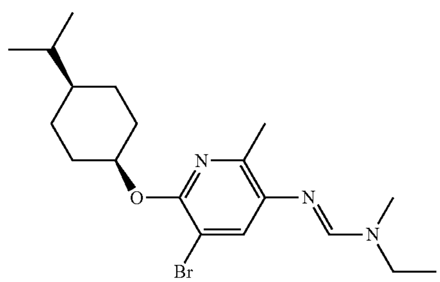 |
| P.213 | 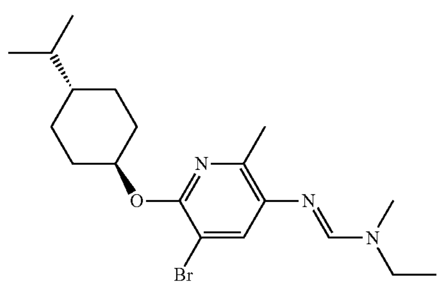 |
| P.214 | 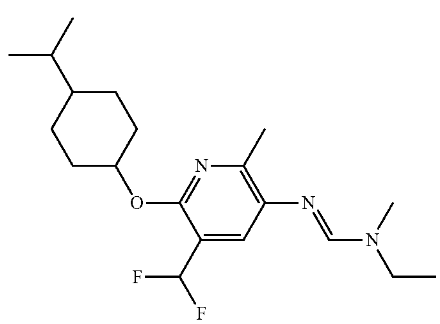 [SMILES: CCN(C)/C=N/c1cc(C(F)F)c(OC2CCC(C(C)C)CC2)nc1C] |

-continued
| Cpd No. | Structure |
|---|---|
| P.215 | 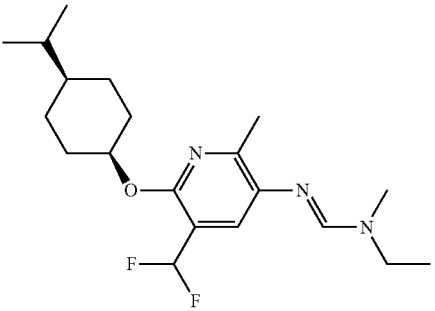 [SMILES: CCN(C)/C=N/c1cc(C(F)F)c(O[C@H]2CC[C@@H](C(C)C)CC2)nc1C] |
| P.216 | 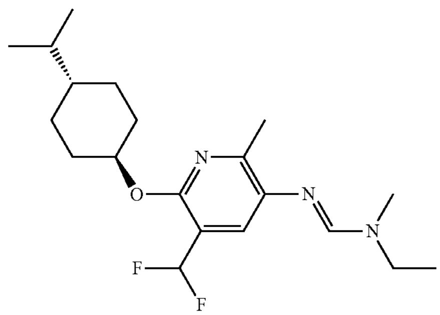 [SMILES: CCN(C)/C=N/c1cc(C(F)F)c(O[C@H]2CC[C@H](C(C)C)CC2)nc1C] |
| P.217 | 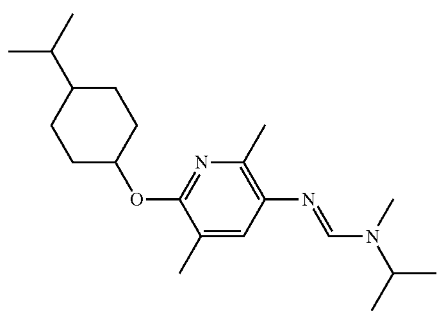 [SMILES: Cc1cc(/N=C/N(C)C(C)C)c(C)nc1OC1CCC(C(C)C)CC1] |
| P.218 | 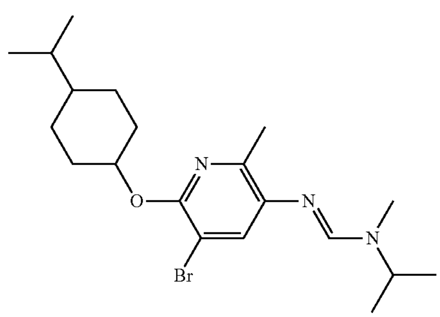 [SMILES: Cc1nc(OC2CCC(C(C)C)CC2)c(Br)cc1/N=C/N(C)C(C)C] |
| P.219 | 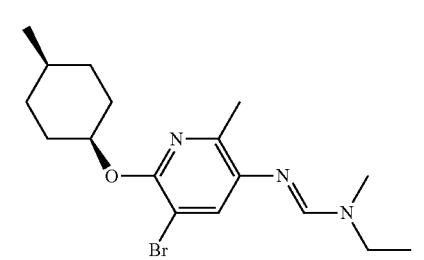 [SMILES: CCN(C)/C=N/c1cc(Br)c(O[C@H]2CC[C@@H](C)CC2)nc1C] |

-continued
| Cpd No. | Structure |
|---|---|
| P.220 | 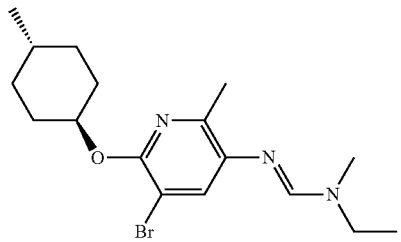 [SMILES: CCN(C)/C=N/c1cc(Br)c(O[C@H]2CC[C@H](C)CC2)nc1C] |
| P.221 | 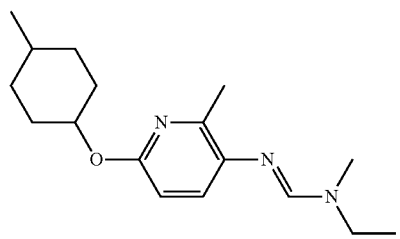 [SMILES: CCN(C)/C=N/c1ccc(OC2CCC(C)CC2)nc1C] |
| P.222 | 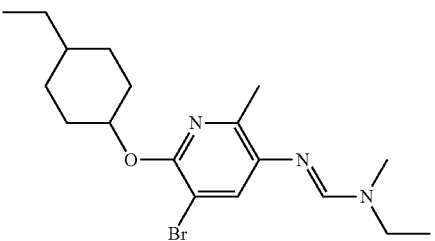 [SMILES: CCC1CCC(Oc2nc(C)c(/N=C/N(C)CC)cc2Br)CC1] |
| P.223 | 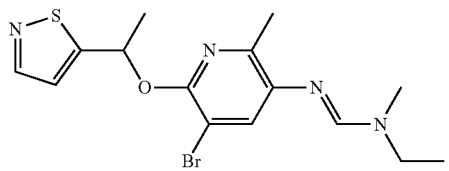 [SMILES: CCN(C)/C=N/c1cc(Br)c(OC(C)c2ccns2)nc1C] |
| P.224 | 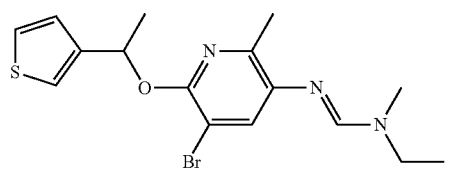 [SMILES: CCN(C)/C=N/c1cc(Br)c(OC(C)c2ccsc2)nc1C] |
| P.225 | 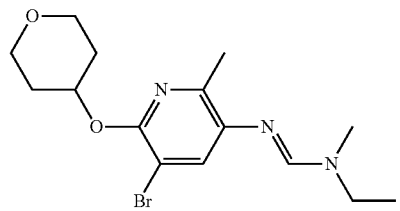 [SMILES: CCN(C)/C=N/c1cc(Br)c(OC2CCOCC2)nc1C] |

-continued
| Cpd No. | Structure |
|---|---|
| P.226 | 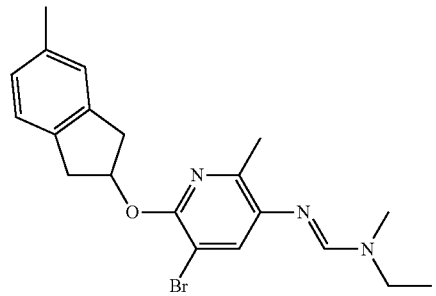 [SMILES: CCN(C)/C=N/c1cc(Br)c(OC2Cc3ccc(C)cc3C2)nc1C] |
| P.227 | 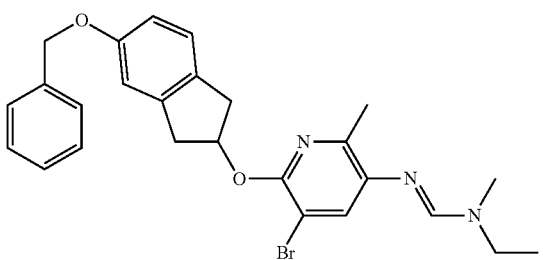 [SMILES: CCN(C)/C=N/c1cc(Br)c(OC2Cc3ccc(OCc4ccccc4)cc3C2)nc1C] |
| P.228 | 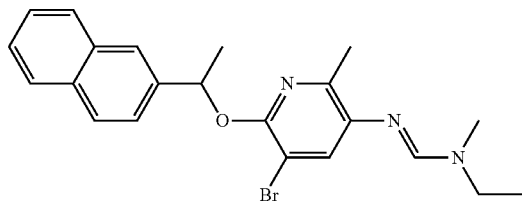 [SMILES: CCN(C)/C=N/c1cc(Br)c(OC(C)c2ccc3ccccc3c2)nc1C] |
| P.229 | 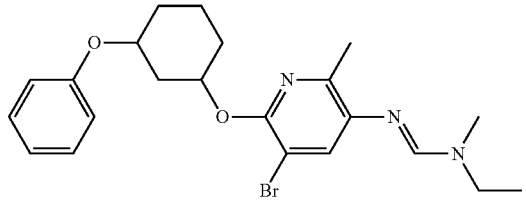 |
| P.230 | 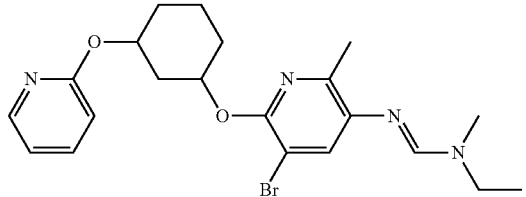 |
| P.231 | 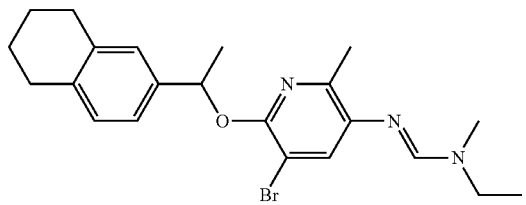 [SMILES: CCN(C)/C=N/c1cc(Br)c(OC(C)c2ccc3c(c2)CCCC3)nc1C] |

-continued
| Cpd No. | Structure |
|---|---|
| P.232 | 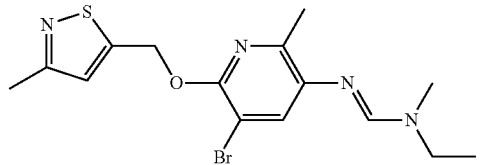 [SMILES: CCN(C)/C=N/c1cc(Br)c(OCc2cc(C)ns2)nc1C] |
| P.233 | 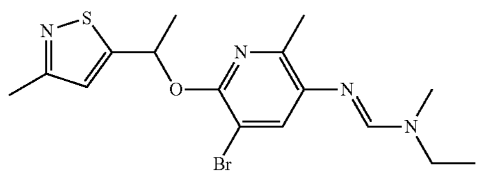 [SMILES: CCN(C)/C=N/c1cc(Br)c(OC(C)c2cc(C)ns2)nc1C] |
| P.234 | 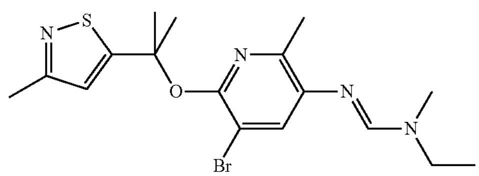 [SMILES: CCN(C)/C=N/c1cc(Br)c(OC(C)(C)c2cc(C)ns2)nc1C] |
| P.235 | 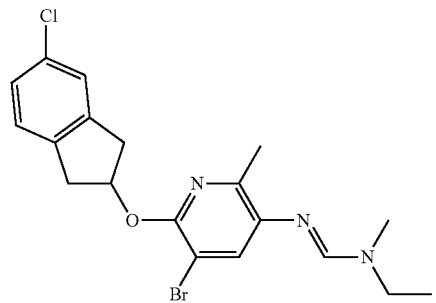 [SMILES: CCN(C)/C=N/c1cc(Br)c(OC2Cc3ccc(Cl)cc3C2)nc1C] |
| P.236 | 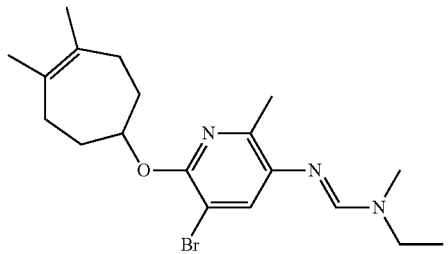 [SMILES: CCN(C)/C=N/c1cc(Br)c(OC2CCC(C)=C(C)CC2)nc1C] |
| P.237 | 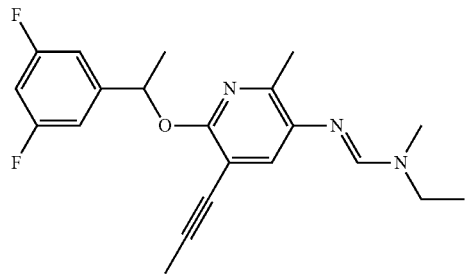 [SMILES: CC#Cc1cc(/N=C/N(C)CC)c(C)nc1OC(C)c1cc(F)cc(F)c1] |

| Cpd No. | Structure |
|---|---|
| P.238 | 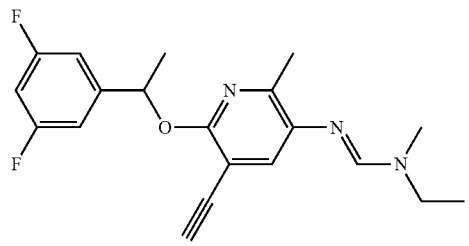 [SMILES: C#Cc1cc(/N=C/N(C)CC)c(C)nc1OC(C)c1cc(F)cc(F)c1] |
| P.239 | 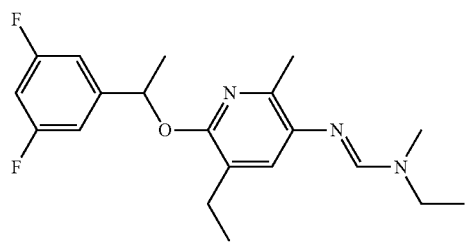 [SMILES: CCc1cc(/N=C/N(C)CC)c(C)nc1OC(C)c1cc(F)cc(F)c1] |
| P.240 | 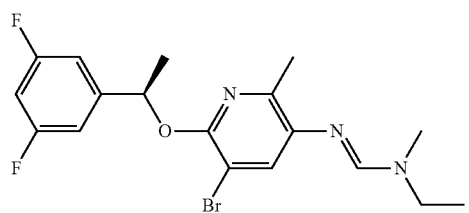 |
| P.241 | 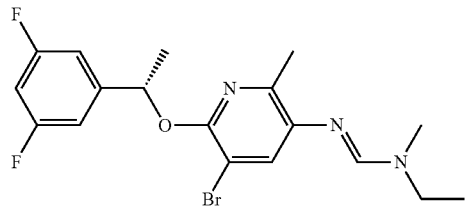 [SMILES: CCN(C)/C=N/c1cc(Br)c(O[C@@H](C)c2cc(F)cc(F)c2)nc1C] |
| P.242 | 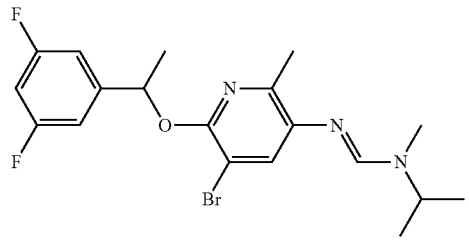 [SMILES: Cc1nc(OC(C)c2cc(F)cc(F)c2)c(Br)cc1/N=C/N(C)C(C)C] |
| P.243 | 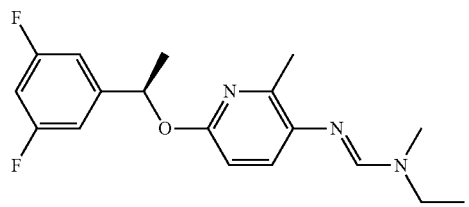 [SMILES: CCN(C)/C=N/c1ccc(O[C@H](C)c2cc(F)cc(F)c2)nc1C] |

| Cpd No. | Structure |
|---------|-----------|
| P.244 | 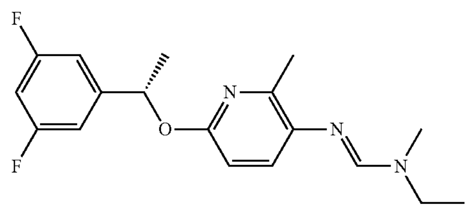 [SMILES: CCN(C)/C=N/c1ccc(O[C@@H](C)c2cc(F)cc(F)c2)nc1C] |
| P.245 | 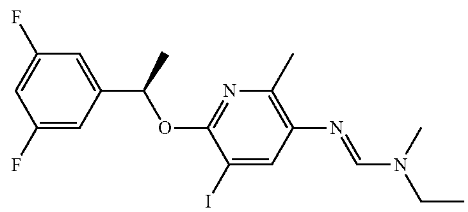 [SMILES: CCN(C)/C=N/c1cc(I)c(O[C@H](C)c2cc(F)cc(F)c2)nc1C] |
| P.246 | 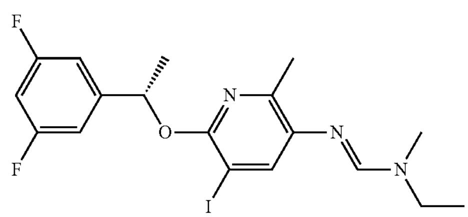 [SMILES: CCN(C)/C=N/c1cc(I)c(O[C@@H](C)c2cc(F)cc(F)c2)nc1C] |
| P.247 | 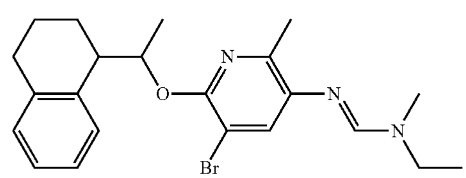 |
| P.248 | 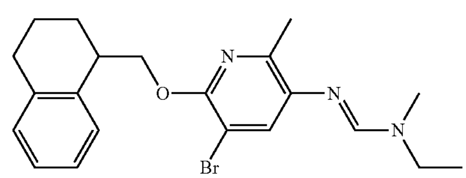 |
| P.249 | 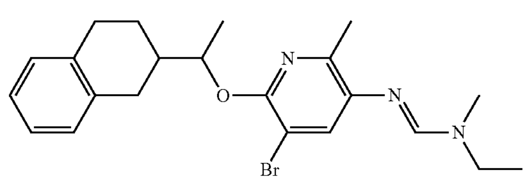 |
| P.250 | 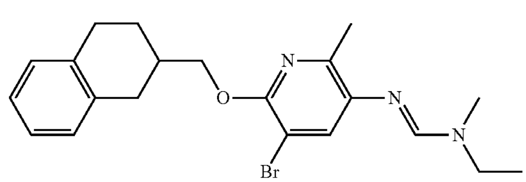 |

-continued
| Cpd No. | Structure |
|---|---|
| P.251 | 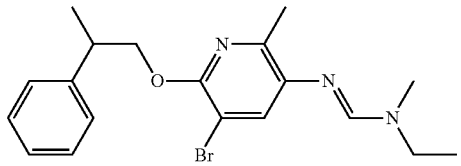 |
| P.252 | 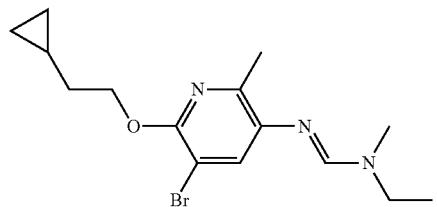 [SMILES: CCN(C)/C=N/c1cc(Br)c(OCCC2CC2)nc1C] |
| P.253 | 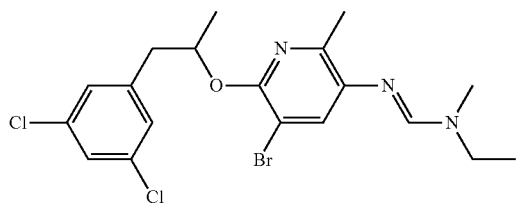 [SMILES: CCN(C)/C=N/c1cc(Br)c(OC(C)Cc2cc(Cl)cc(Cl)c2)nc1C] |
| P.254 | 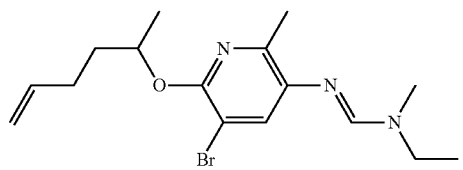 |
| P.255 | 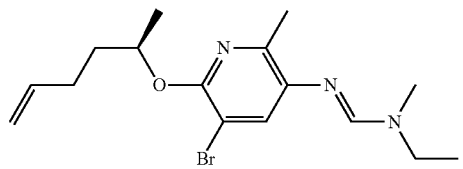 [SMILES: C=CCC[C@@H](C)Oc1nc(C)c(/N=C/N(C)CC)cc1Br] |
| P.256 | 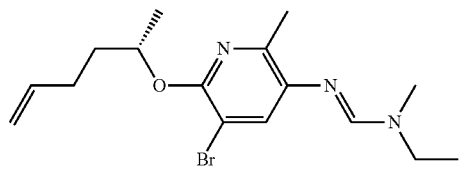 |
| P.257 | 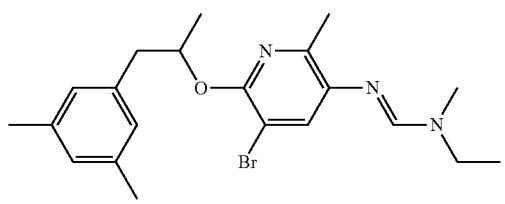 [SMILES: CCN(C)/C=N/c1cc(Br)c(OC(C)Cc2cc(C)cc(C)c2)nc1C] |

-continued
| Cpd No. | Structure |
|---|---|
| P.258 | 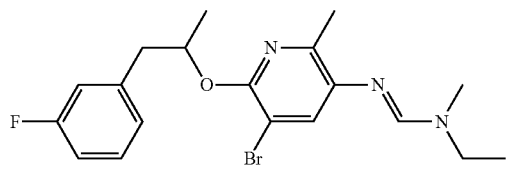 |
| P.259 | 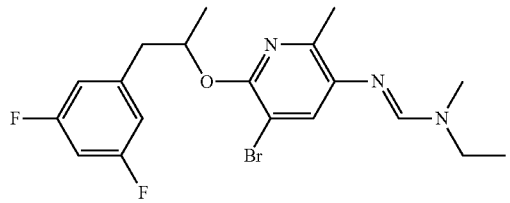 [SMILES: CCN(C)/C=N/c1cc(Br)c(OC(C)Cc2cc(F)cc(F)c2)nc1C] |
| P.260 | 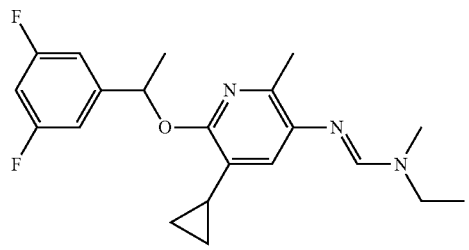 [SMILES: CCN(C)/C=N/c1cc(C2CC2)c(OC(C)c2cc(F)cc(F)c2)nc1C] |
| P.261 | 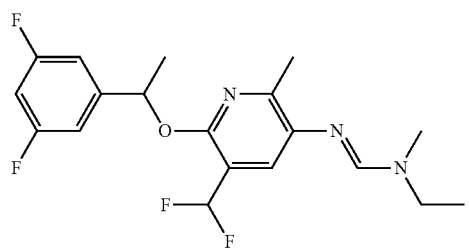 [SMILES: CCN(C)/C=N/c1cc(C(F)F)c(OC(C)c2cc(F)cc(F)c2)nc1C] |
| P.262 | 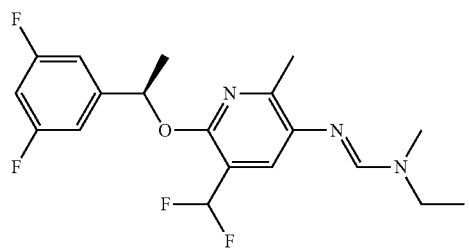 [SMILES: CCN(C)/C=N/c1cc(C(F)F)c(O[C@H](C)c2cc(F)cc(F)c2)nc1C] |
| P.263 | 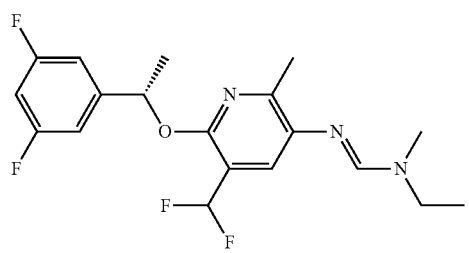 [SMILES: CCN(C)/C=N/c1cc(C(F)F)c(O[C@@H](C)c2cc(F)cc(F)c2)nc1C] |

-continued
| Cpd No. | Structure |
|---|---|
| P.264 | 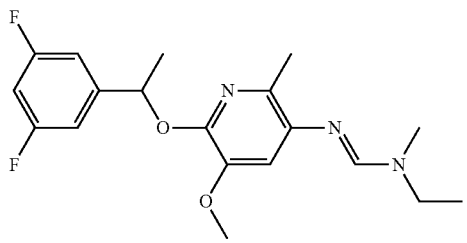 [SMILES: CCN(C)/C=N/c1cc(OC)c(OC(C)c2cc(F)cc(F)c2)nc1C] |
| P.265 | 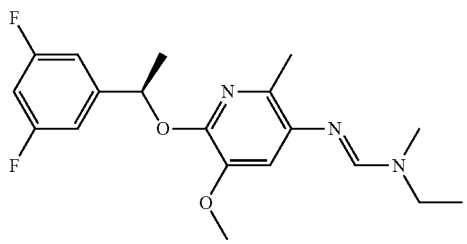 [SMILES: CCN(C)/C=N/c1cc(OC)c(O[C@H](C)c2cc(F)cc(F)c2)nc1C] |
| P.266 | 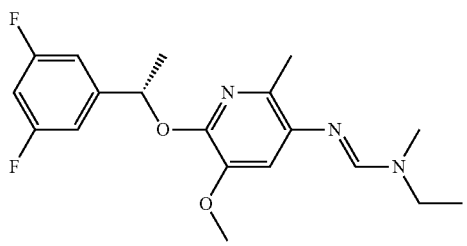 [SMILES: CCN(C)/C=N/c1cc(OC)c(O[C@@H](C)c2cc(F)cc(F)c2)nc1C] |
| P.267 | 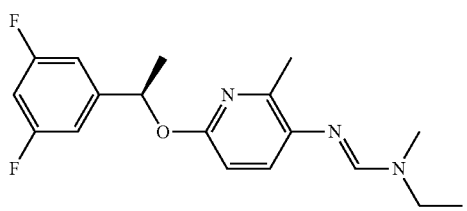 [SMILES: CCN(C)/C=N/c1ccc(O[C@H](C)c2cc(F)cc(F)c2)nc1C] |
| P.268 | 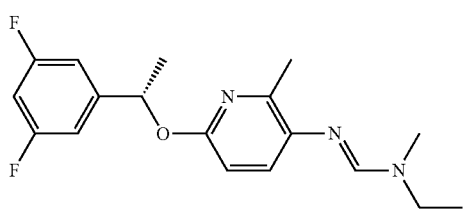 |
| P.269 | 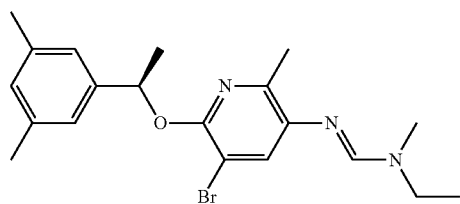 [SMILES: CCN(C)/C=N/c1cc(Br)c(O[C@H](C)c2cc(C)cc(C)c2)nc1C] |

| Cpd No. | Structure |
|---|---|
| P.270 | (3,5-dimethylphenyl)-CH(CH₃)-O-[3-Br-6-methylpyridin-2-yl]-N=CH-N(CH₃)(Et) |
| P.271 | PhCH₂-CH(CH₃)-O-[3-Br-6-methylpyridin-2-yl]-N=CH-N(CH₃)(Et) |
| P.272 | PhCH₂-CH(CH₃)-O-[3-Br-6-methylpyridin-2-yl]-N=CH-N(CH₃)(Et) |
| P.273 | isohexyl-O-[3-Br-6-methylpyridin-2-yl]-N=CH-N(Et)₂ |
| P.274 | isohexyl-O-[3-Br-6-methylpyridin-2-yl]-N=CH-NH(Et) |
| P.275 | isohexyl-O-[3,6-dimethylpyridin-2-yl]-N=CH-N(CH₃)(Et) |
| P.276 | (5,6-dibromoindan-2-yl)-O-[3-Br-6-methylpyridin-2-yl]-N=CH-N(CH₃)(Et) |

-continued
| Cpd No. | Structure |
|---|---|
| P.277 | 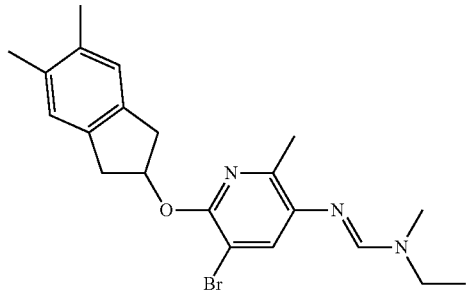 [SMILES: CCN(C)/C=N/c1cc(Br)c(OC2Cc3cc(C)c(C)cc3C2)nc1C] |
| P.278 | 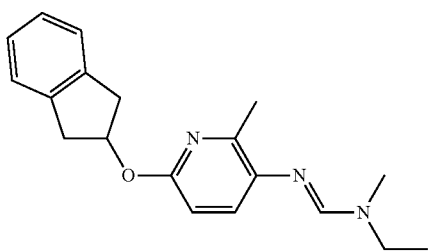 [SMILES: CCN(C)/C=N/c1ccc(OC2Cc3ccccc3C2)nc1C] |
| P.279 | 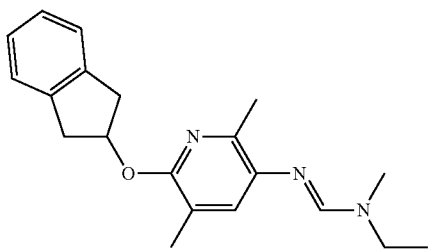 [SMILES: CCN(C)/C=N/c1cc(C)c(OC2Cc3ccccc3C2)nc1C] |
| P.280 | 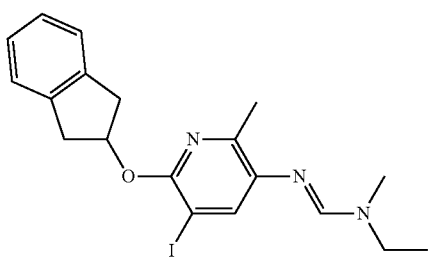 [SMILES: CCN(C)/C=N/c1cc(I)c(OC2Cc3ccccc3C2)nc1C] |
| P.281 | 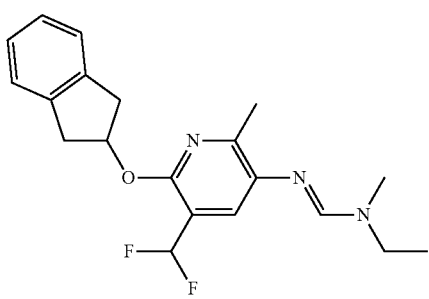 [SMILES: CCN(C)/C=N/c1cc(C(F)F)c(OC2Cc3ccccc3C2)nc1C] |

-continued
| Cpd No. | Structure |
|---|---|
| P.282 | 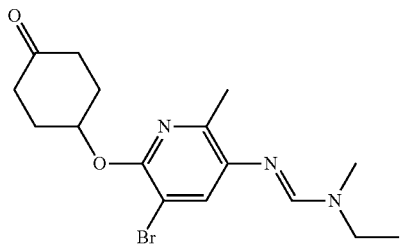 [SMILES: CCN(C)/C=N/c1cc(Br)c(OC2CCC(=O)CC2)nc1C] |
| P.283 | 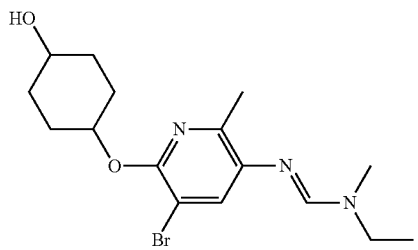 [SMILES: CCN(C)/C=N/c1cc(Br)c(OC2CCC(O)CC2)nc1C] |
| P.284 | 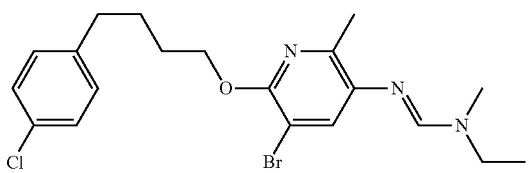 [SMILES: CCN(C)/C=N/c1cc(Br)c(OCCCCc2ccc(Cl)cc2)nc1C] |
| P.285 | 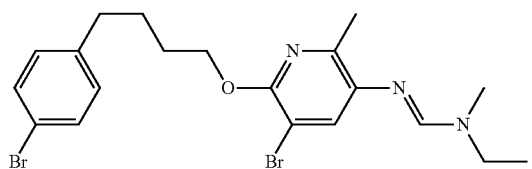 |
| P.286 | 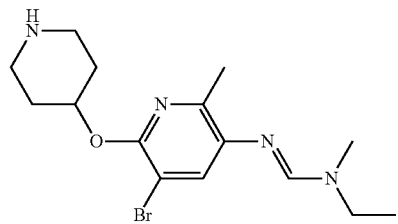 [SMILES: CCN(C)/C=N/c1cc(Br)c(OC2CCNCC2)nc1C] |
| P.287 | 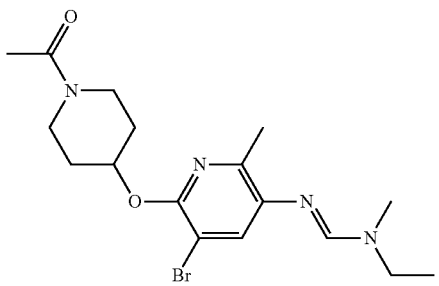 [SMILES: CCN(C)/C=N/c1cc(Br)c(OC2CCN(C(C)=O)CC2)nc1C] |

-continued
| Cpd No. | Structure |
|---|---|
| P.288 | 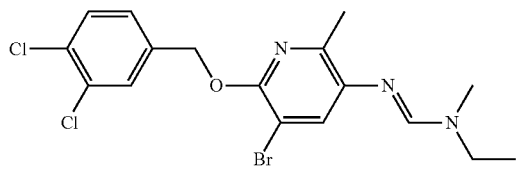 [SMILES: CCN(C)/C=N/c1cc(Br)c(OCc2ccc(Cl)c(Cl)c2)nc1C] |
| P.289 | 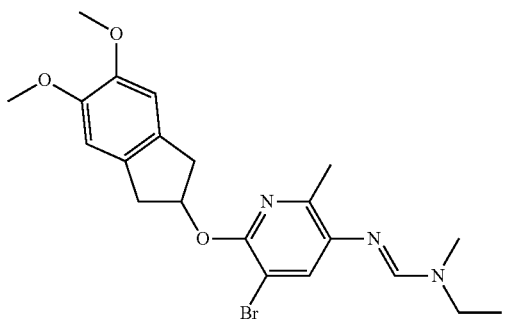 [SMILES: CCN(C)/C=N/c1cc(Br)c(OC2Cc3cc(OC)c(OC)cc3C2)nc1C] |
| P.290 | 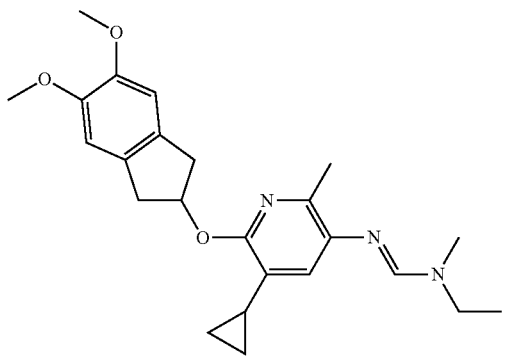 [SMILES: CCN(C)/C=N/c1cc(C2CC2)c(OC2Cc3cc(OC)c(OC)cc3C2)nc1C] |
| P.291 | 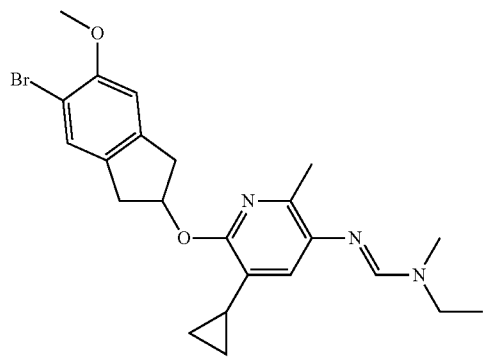 [SMILES: CCN(C)/C=N/c1cc(C2CC2)c(OC2Cc3cc(Br)c(OC)cc3C2)nc1C] |
| P.292 | 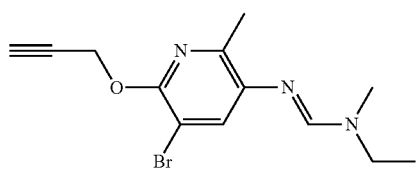 [SMILES: C#CCOc1nc(C)c(/N=C/N(C)CC)cc1Br] |

| Cpd No. | Structure |
|---|---|
| P.293 | 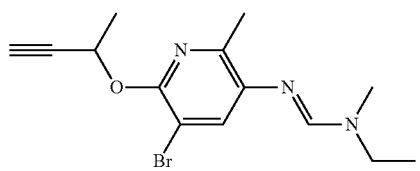 [SMILES: C#CC(C)Oc1nc(C)c(/N=C/N(C)CC)cc1Br] |
| P.294 | 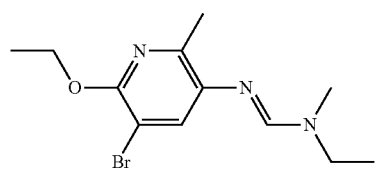 [SMILES: CCOc1nc(C)c(/N=C/N(C)CC)cc1Br] |
| P.295 | 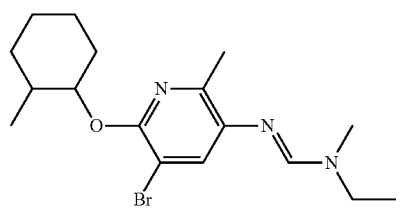 [SMILES: CCN(C)/C=N/c1cc(Br)c(OC2CCCCC2C)nc1C] |
| P.296 | 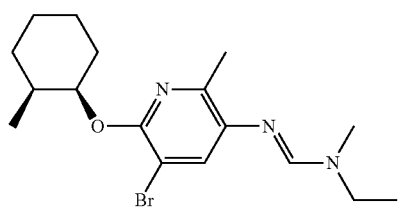 [SMILES: CCN(C)/C=N/c1cc(Br)c(O[C@@H]2CCCC[C@@H]2C)nc1C] |
| P.297 | 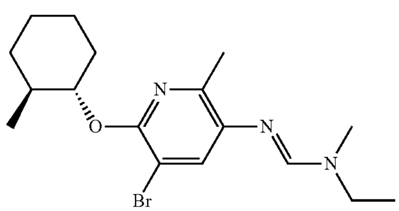 [SMILES: CCN(C)/C=N/c1cc(Br)c(O[C@H]2CCCC[C@@H]2C)nc1C] |
| P.298 | 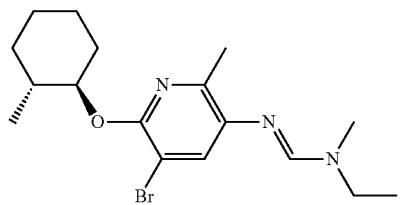 [SMILES: CCN(C)/C=N/c1cc(Br)c(O[C@@H]2CCCC[C@H]2C)nc1C] |
| P.299 | 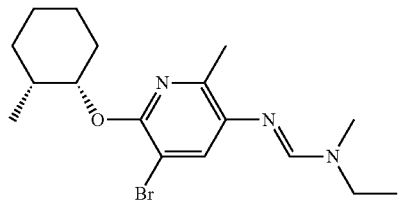 [SMILES: CCN(C)/C=N/c1cc(Br)c(O[C@H]2CCCC[C@H]2C)nc1C] |

-continued

| Cpd No. | Structure |
|---|---|
| P.300 | 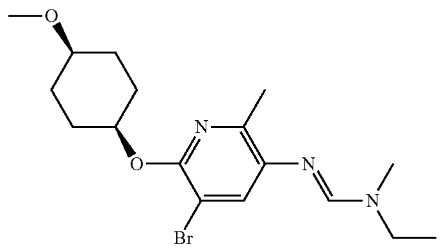 [SMILES: CCN(C)/C=N/c1cc(Br)c(O[C@H]2CC[C@@H](OC)CC2)nc1C] |
| P.301 | 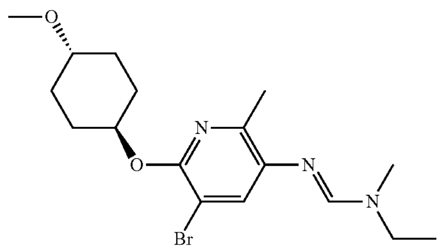 [SMILES: CCN(C)/C=N/c1cc(Br)c(O[C@H]2CC[C@H](OC)CC2)nc1C] |
| P.302 | 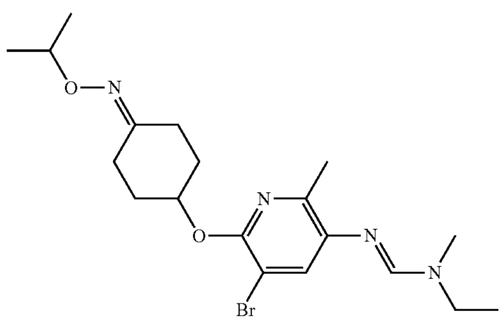 [SMILES: CCN(C)/C=N/c1cc(Br)c(OC2CCC(=NOC(C)C)CC2)nc1C] |
| P.303 | 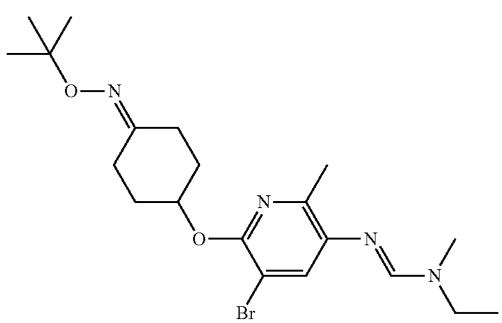 [SMILES: CCN(C)/C=N/c1cc(Br)c(OC2CCC(=NOC(C)(C)C)CC2)nc1C] |
| P.304 | 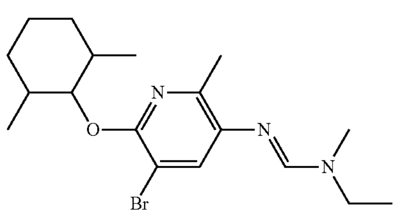 [SMILES: CCN(C)/C=N/c1cc(Br)c(OC2C(C)CCCC2C)nc1C] |
| P.305 | 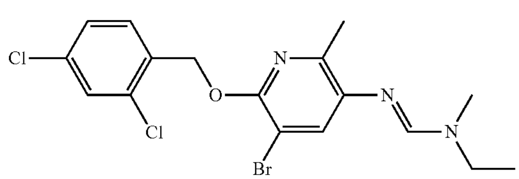 [SMILES: CCN(C)/C=N/c1cc(Br)c(OCc2ccc(Cl)cc2Cl)nc1C] |

-continued
| Cpd No. | Structure |
|---|---|
| P.306 | 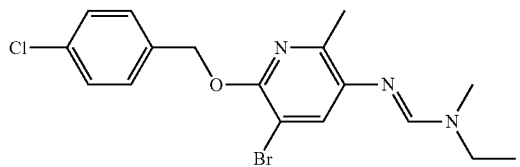 |
| P.307 | 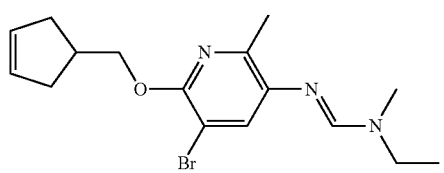 [SMILES: CCN(C)/C=N/c1cc(Br)c(OCC2CC=CC2)nc1C] |
| P.308 | 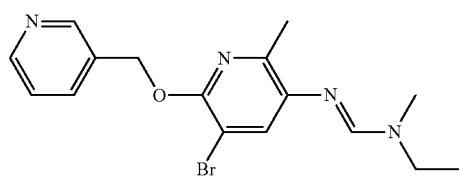 [SMILES: CCN(C)/C=N/c1cc(Br)c(OCc2cccnc2)nc1C] |
| P.309 | 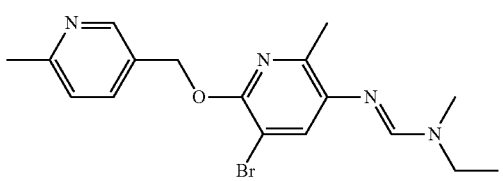 [SMILES: CCN(C)/C=N/c1cc(Br)c(OCc2ccc(C)nc2)nc1C] |
| P.310 | 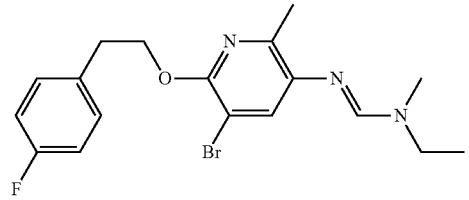 [SMILES: CCN(C)/C=N/c1cc(Br)c(OCCc2ccc(F)cc2)nc1C] |
| P.311 | 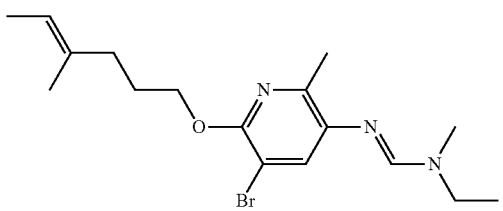 [SMILES: C/C=C(\C)CCCOc1nc(C)c(/N=C/N(C)CC)cc1Br] |
| P.312 | 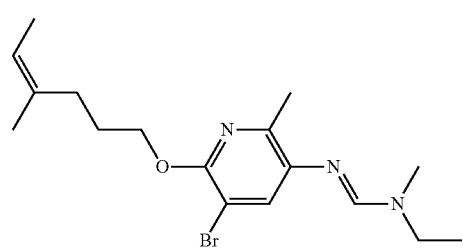 [SMILES: C/C=C(/C)CCCOc1nc(C)c(/N=C/N(C)CC)cc1Br] |

-continued
| Cpd No. | Structure |
|---|---|
| P.313 | 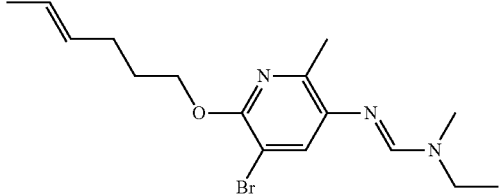 [SMILES: C/C=C/CCCOc1nc(C)c(/N=C/N(C)CC)cc1Br] |
| P.314 | 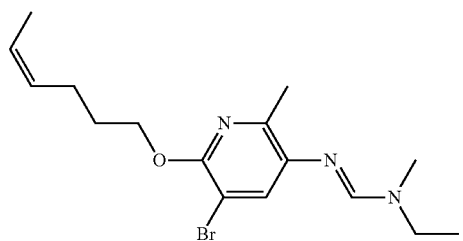 [SMILES: C/C=C\CCCOc1nc(C)c(/N=C/N(C)CC)cc1Br] |
| P.315 | 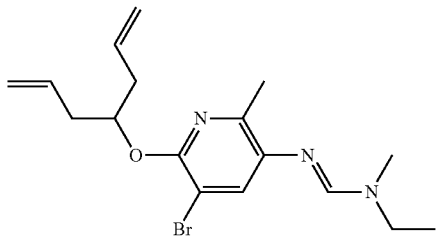 [SMILES: C=CCC(CC=C)Oc1nc(C)c(/N=C/N(C)CC)cc1Br] |
| P.316 | 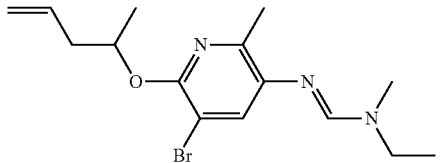 |
| P.317 | 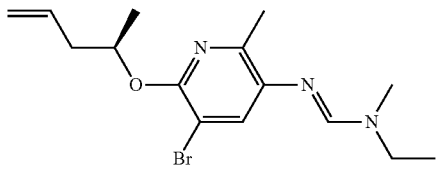 [SMILES: C=CC[C@@H](C)Oc1nc(C)c(/N=C/N(C)CC)cc1Br] |
| P.318 | 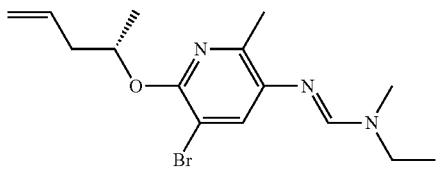 [SMILES: C=CC[C@H](C)Oc1nc(C)c(/N=C/N(C)CC)cc1Br] |
| P.319 | 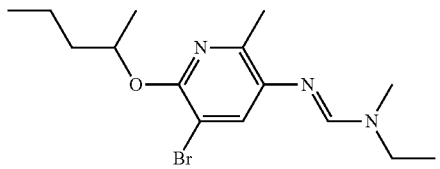 |

-continued
| Cpd No. | Structure |
|---|---|
| P.320 | 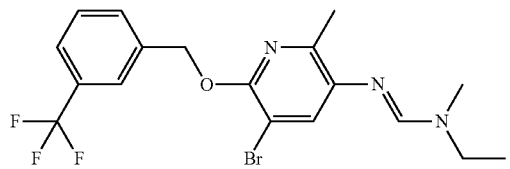 |
| P.321 | 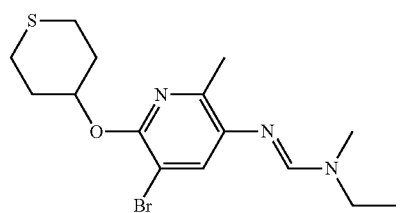 [SMILES: CCN(C)/C=N/c1cc(Br)c(OC2CCSCC2)nc1C] |
| P.322 | 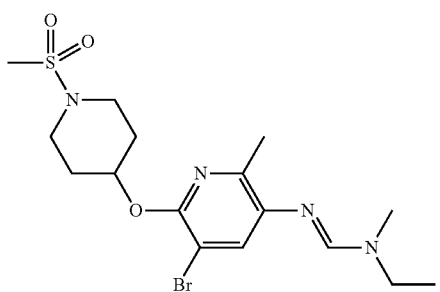 [SMILES: CCN(C)/C=N/c1cc(Br)c(OC2CCN(S(C)(=O)=O)CC2)nc1C] |
| P.323 | 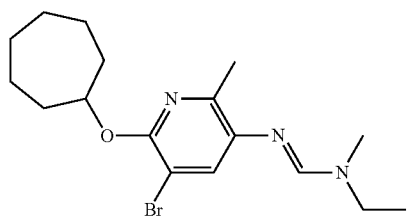 [SMILES: CCN(C)/C=N/c1cc(Br)c(OC2CCCCCC2)nc1C] |
| P.324 | 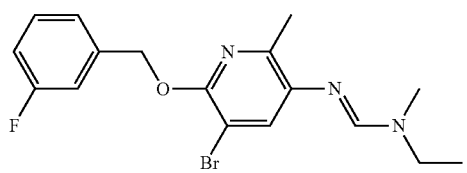 |
| P.325 | 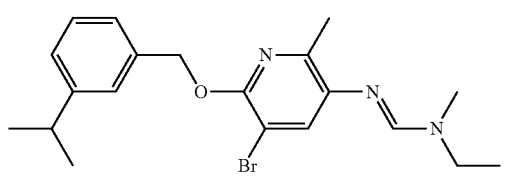 |

-continued
| Cpd No. | Structure |
|---|---|
| P.326 | 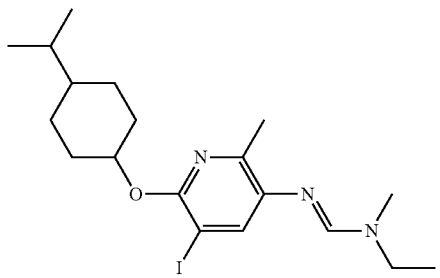 [SMILES: CCN(C)/C=N/c1cc(I)c(OC2CCC(C(C)C)CC2)nc1C] |
| P.327 | 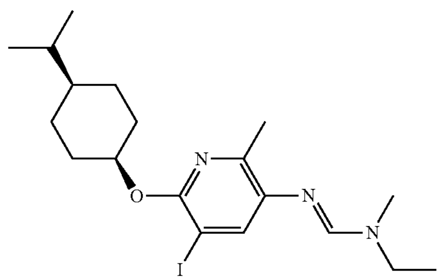 [SMILES: CCN(C)/C=N/c1cc(I)c(O[C@H]2CC[C@@H](C(C)C)CC2)nc1C] |
| P.328 | 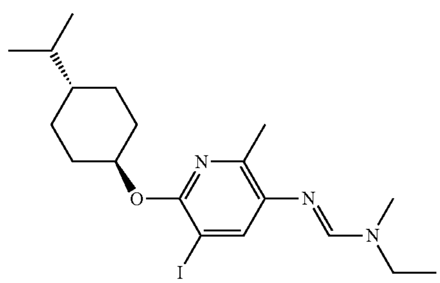 [SMILES: CCN(C)/C=N/c1cc(I)c(O[C@H]2CC[C@H](C(C)C)CC2)nc1C] |
| P.329 | 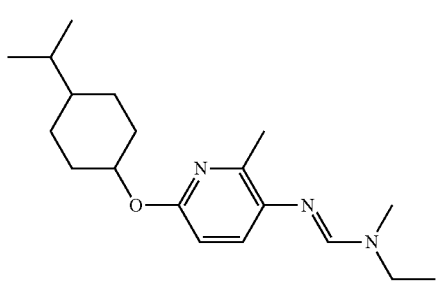 [SMILES: CCN(C)/C=N/c1ccc(OC2CCC(C(C)C)CC2)nc1C] |
| P.330 | 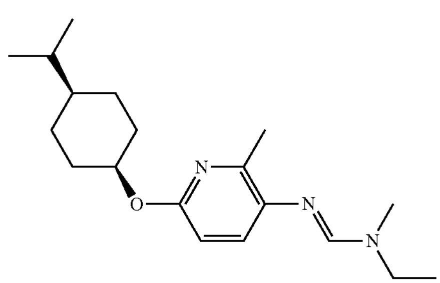 [SMILES: CCN(C)/C=N/c1ccc(O[C@H]2CC[C@@H](C(C)C)CC2)nc1C] |

-continued
| Cpd No. | Structure |
|---|---|
| P.331 | 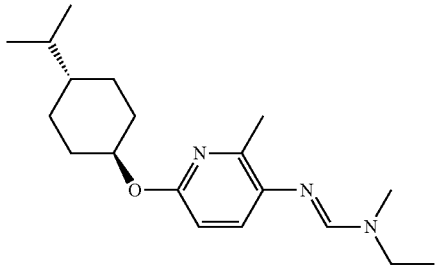 [SMILES: CCN(C)/C=N/c1ccc(O[C@H]2CC[C@H](C(C)C)CC2)nc1C] |
| P.332 | 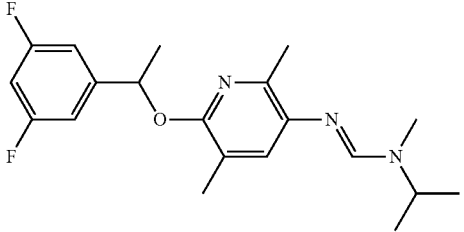 |
| P.333 | 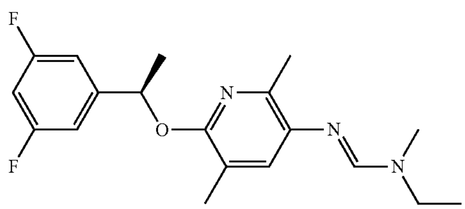 [SMILES: CCN(C)/C=N/c1cc(C)c(O[C@H](C)c2cc(F)cc(F)c2)nc1C] |
| P.334 | 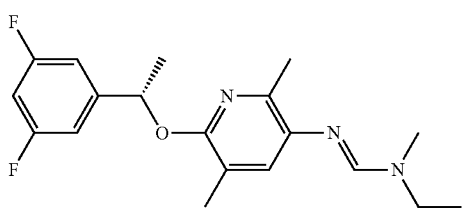 |
| P.335 | 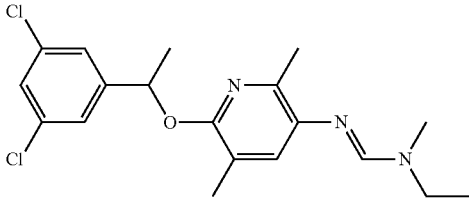 [SMILES: CCN(C)/C=N/c1cc(C)c(OC(C)c2cc(Cl)cc(Cl)c2)nc1C] |
| P.336 | 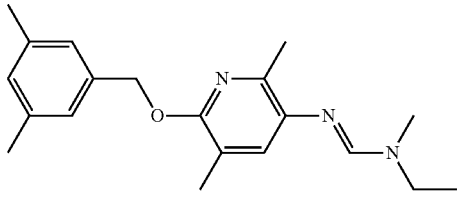 [SMILES: CCN(C)/C=N/c1cc(C)c(OCc2cc(C)cc(C)c2)nc1C] |

-continued
| Cpd No. | Structure |
|---|---|
| P.337 | 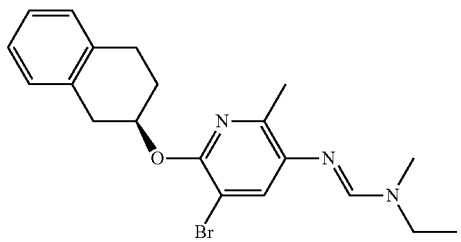 [SMILES: CCN(C)/C=N/c1cc(Br)c(O[C@@H]2CCc3ccccc3C2)nc1C] |
| P.338 | 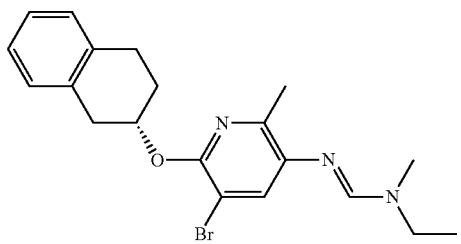 [SMILES: CCN(C)/C=N/c1cc(Br)c(O[C@H]2CCc3ccccc3C2)nc1C] |
| P.339 | 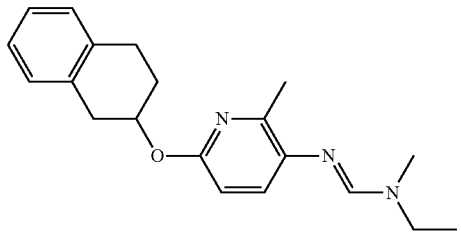 [SMILES: CCN(C)/C=N/c1ccc(OC2CCc3ccccc3C2)nc1C] |
| P.340 | 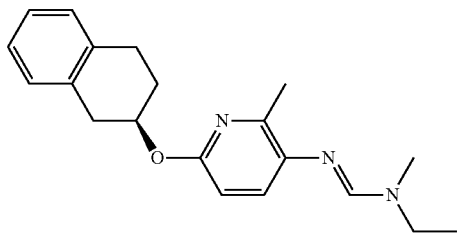 [SMILES: CCN(C)/C=N/c1ccc(O[C@@H]2CCc3ccccc3C2)nc1C] |
| P.341 | 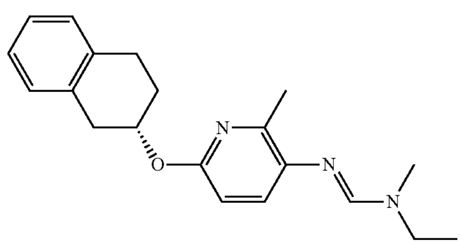 [SMILES: CCN(C)/C=N/c1ccc(O[C@H]2CCc3ccccc3C2)nc1C] |
| P.342 | 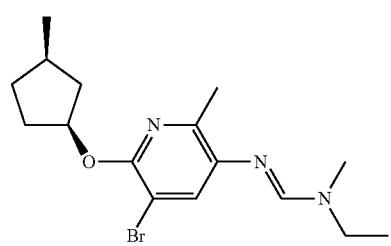 [SMILES: CCN(C)/C=N/c1cc(Br)c(O[C@H]2CC[C@@H](C)C2)nc1C] |

-continued
| Cpd No. | Structure |
|---|---|
| P.343 | 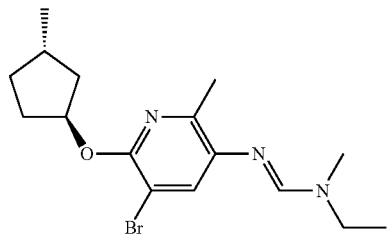 [SMILES: CCN(C)/C=N/c1cc(Br)c(O[C@H]2CC[C@H](C)C2)nc1C] |
| P.344 | 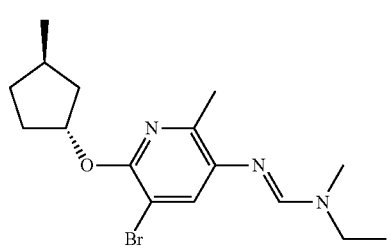 [SMILES: CCN(C)/C=N/c1cc(Br)c(O[C@@H]2CC[C@@H](C)C2)nc1C] |
| P.345 | 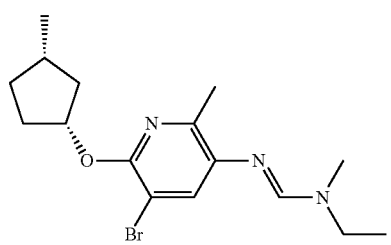 [SMILES: CCN(C)/C=N/c1cc(Br)c(O[C@@H]2CC[C@H](C)C2)nc1C] |
| P.346 | 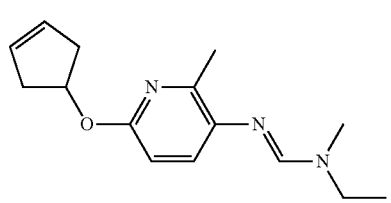 [SMILES: CCN(C)/C=N/c1ccc(OC2CC=CC2)nc1C] |
| P.347 | 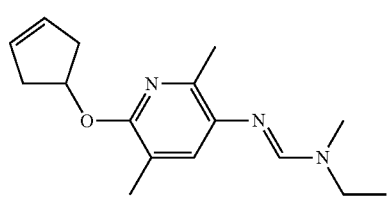 [SMILES: CCN(C)/C=N/c1cc(C)c(OC2CC=CC2)nc1C] |
| P.348 | 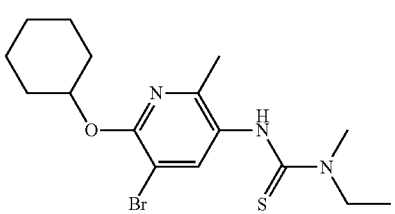 [SMILES: CCN(C)C(=S)Nc1cc(Br)c(OC2CCCCC2)nc1C] |

US 9,326,513 B2
213                                                                        214
-continued
| Cpd No. | Structure |
|---|---|
| P.349 | 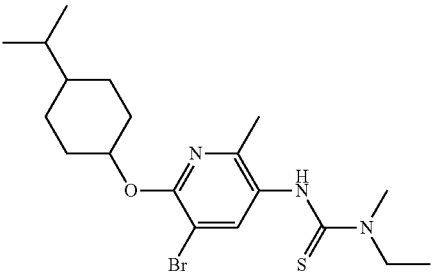 [SMILES: CCN(C)C(=S)Nc1cc(Br)c(OC2CCC(C(C)C)CC2)nc1C] |
| P.350 | 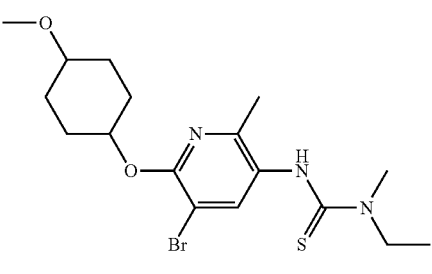 [SMILES: CCN(C)C(=S)Nc1cc(Br)c(OC2CCC(OC)CC2)nc1C] |
| P.351 | 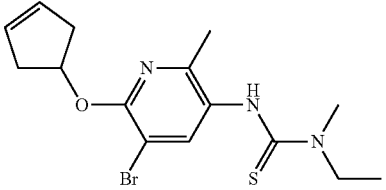 [SMILES: CCN(C)C(=S)Nc1cc(Br)c(OC2CC=CC2)nc1C] |
| P.352 | 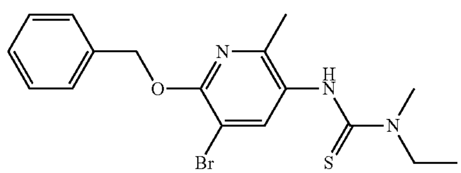 [SMILES: CCN(C)C(=S)Nc1cc(Br)c(OCc2ccccc2)nc1C] |
| P.353 | 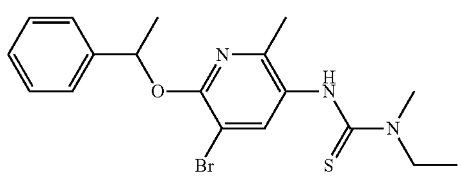 |
| P.354 | 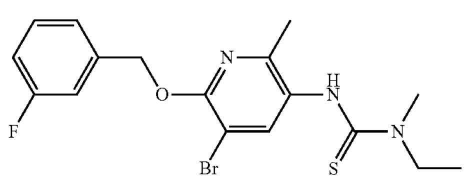 [SMILES: CCN(C)C(=S)Nc1cc(Br)c(OCc2cccc(F)c2)nc1C] |
| P.355 | 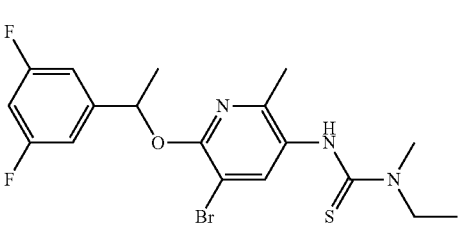 [SMILES: CCN(C)C(=S)Nc1cc(Br)c(OC(C)c2cc(F)cc(F)c2)nc1C] |

-continued
| Cpd No. | Structure |
|---|---|
| P.356 | 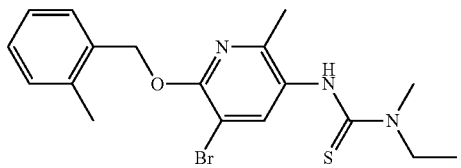 [SMILES: CCN(C)C(=S)Nc1cc(Br)c(OCc2ccccc2C)nc1C] |
| P.357 | 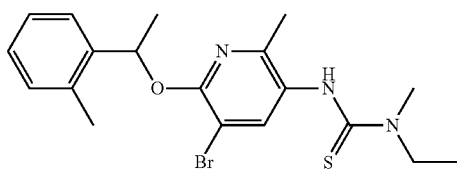 |
| P.358 | 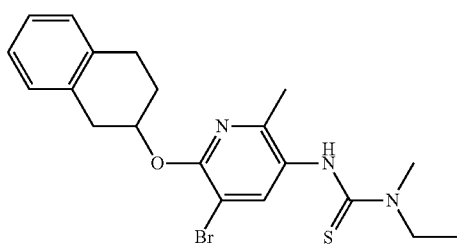 [SMILES: CCN(C)C(=S)Nc1cc(Br)c(OC2CCc3ccccc3C2)nc1C] |
| P.359 | 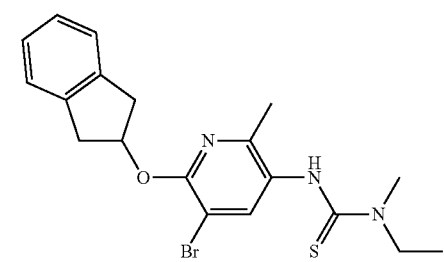 [SMILES: CCN(C)C(=S)Nc1cc(Br)c(OC2Cc3ccccc3C2)nc1C] |
| P.360 | 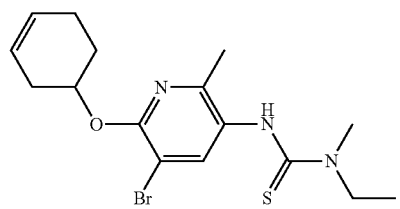 [SMILES: CCN(C)C(=S)Nc1cc(Br)c(OC2CC=CCC2)nc1C] |
| P.361 | 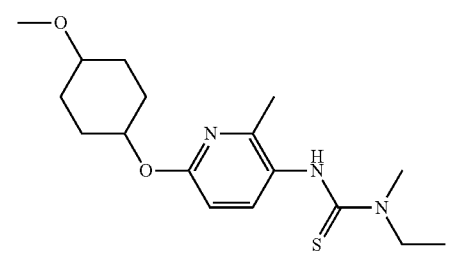 [SMILES: CCN(C)C(=S)Nc1ccc(OC2CCC(OC)CC2)nc1C] |

-continued

| Cpd No. | Structure |
|---|---|
| P.362 | 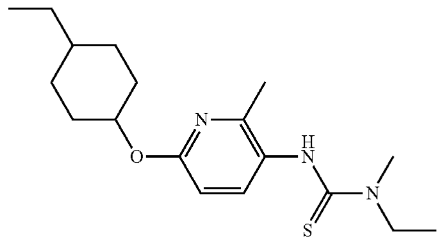 [SMILES: CCC1CCC(Oc2ccc(NC(=S)N(C)CC)c(C)n2)CC1] |
| P.363 | 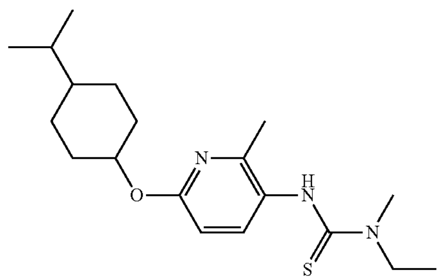 [SMILES: CCN(C)C(=S)Nc1ccc(OC2CCC(C(C)C)CC2)nc1C] |
| P.364 | 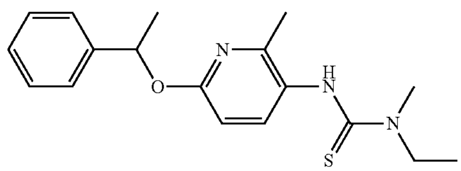 [SMILES: CCN(C)C(=S)Nc1ccc(OC(C)c2ccccc2)nc1C] |
| P.365 | 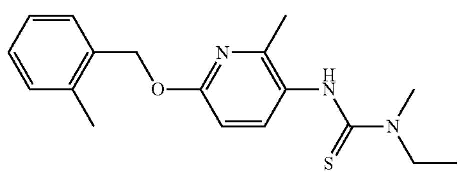 |
| P.366 | 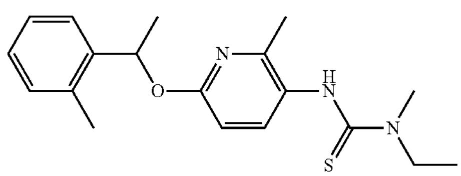 [SMILES: CCN(C)C(=S)Nc1ccc(OC(C)c2ccccc2C)nc1C] |
| P.367 | 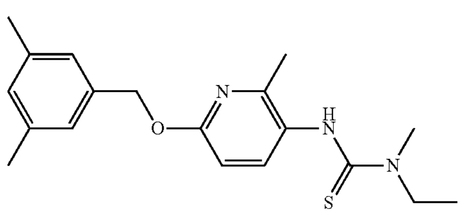 [SMILES: CCN(C)C(=S)Nc1ccc(OCc2cc(C)cc(C)c2)nc1C] |
| P.368 | 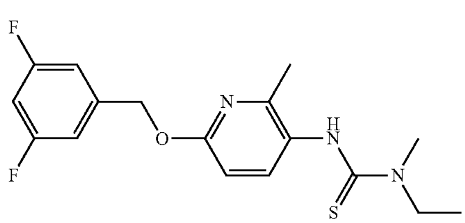 [SMILES: CCN(C)C(=S)Nc1ccc(OCc2cc(F)cc(F)c2)nc1C] |

| Cpd No. | Structure |
|---|---|
| P.369 | ![structure with 3,5-difluorophenyl-ethoxy-methylpyridine-thiourea-N-methyl-N-ethyl] |
| P.370 | ![structure with indanyloxy-methylpyridine-thiourea-N-methyl-N-ethyl] |
| P.371 | ![structure with cyclopentenyloxy-methylpyridine-thiourea-N-methyl-N-ethyl] |
| P.372 | ![structure with tetrahydronaphthalenyloxy-methylpyridine-thiourea-N-methyl-N-ethyl] |

Table A discloses 1201 sets of meanings of the variables $R_1$, $R_2$, $R_5$ and $R_6$ in a compound of formula I.

TABLE A

| | Meanings for $R_1$, $R_2$, $R_5$ and $R_6$: | | | |
|---|---|---|---|---|
| Line | $R_1$ | $R_2$ | $R_6$ | $R_5$ |
| A.1.1 | $CH_3$ | $CH_2CH_3$ | H | 2-chloro-5-methyl-(difluoromethyl)phenyl |
| A.1.2 | $CH_3$ | $CH_2CH_3$ | H | 3-chloro-4-methyl-(difluoromethyl)phenyl |

TABLE A-continued
Meanings for $R_1$, $R_2$, $R_5$ and $R_6$:
| | | | | |
|---|---|---|---|---|
| A.1.3 | $CH_3$ | $CH_2CH_3$ | H | 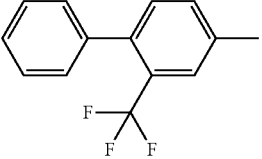 |
| A.1.4 | $CH_3$ | $CH_2CH_3$ | H | 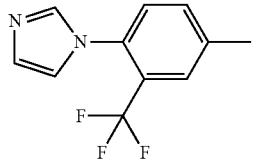 |
| A.1.5 | $CH_3$ | $CH_2CH_3$ | H | 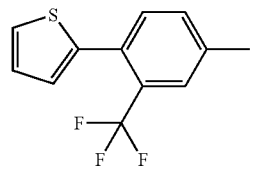 |
| A.1.6 | $CH_3$ | $CH_2CH_3$ | H | 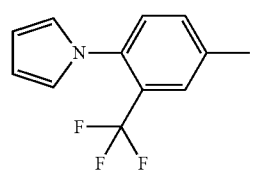 |
| A.1.7 | $CH_3$ | $CH_2CH_3$ | H | 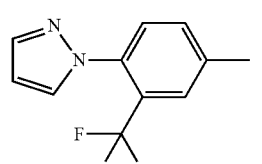 |
| A.1.8 | $CH_3$ | $CH_2CH_3$ | H | 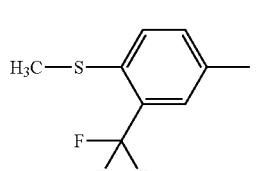 |
| A.1.9 | $CH_3$ | $CH_2CH_3$ | H | 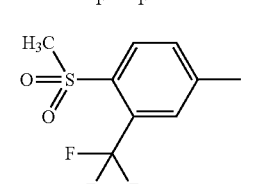 |
| A.1.10 | $CH_3$ | $CH_2CH_3$ | H | 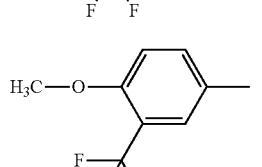 |
| A.1.11 | $CH_3$ | $CH_2CH_3$ | H | 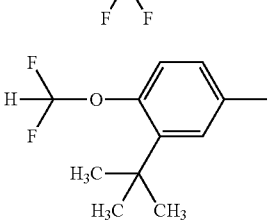 |

TABLE A-continued
| | Meanings for $R_1$, $R_2$, $R_5$ and $R_6$: | | | |
|---|---|---|---|---|
| A.1.12 | CH$_3$ | CH$_2$CH$_3$ | H | 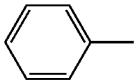 |
| A.1.13 | CH$_3$ | CH$_2$CH$_3$ | H | 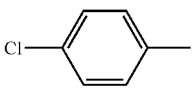 |
| A.1.14 | CH$_3$ | CH$_2$CH$_3$ | H | 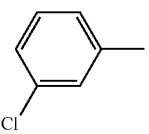 |
| A.1.15 | CH$_3$ | CH$_2$CH$_3$ | H | 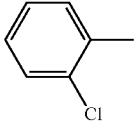 |
| A.1.16 | CH$_3$ | CH$_2$CH$_3$ | H | 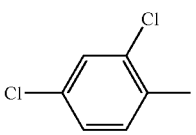 |
| A.1.17 | CH$_3$ | CH$_2$CH$_3$ | H | 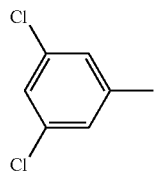 |
| A.1.18 | CH$_3$ | CH$_2$CH$_3$ | H | 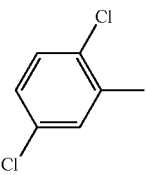 |
| A.1.19 | CH$_3$ | CH$_2$CH$_3$ | H | 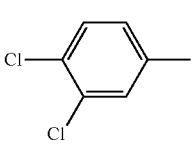 |
| A.1.20 | CH$_3$ | CH$_2$CH$_3$ | H | 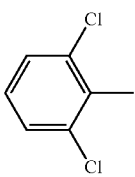 |
| A.1.21 | CH$_3$ | CH$_2$CH$_3$ | H | 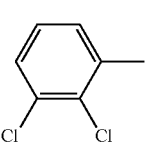 |

TABLE A-continued
| | Meanings for $R_1$, $R_2$, $R_5$ and $R_6$: | | | |
|---|---|---|---|---|
| A.1.22 | $CH_3$ | $CH_2CH_3$ | H | 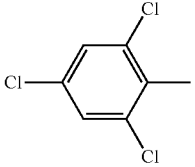 |
| A.1.23 | $CH_3$ | $CH_2CH_3$ | H | 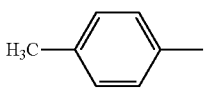 |
| A.1.24 | $CH_3$ | $CH_2CH_3$ | H | 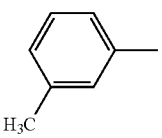 |
| A.1.25 | $CH_3$ | $CH_2CH_3$ | H | 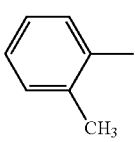 |
| A.1.26 | $CH_3$ | $CH_2CH_3$ | H | 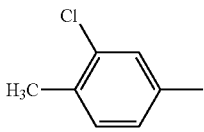 |
| A.1.27 | $CH_3$ | $CH_2CH_3$ | H | 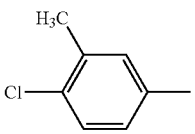 |
| A.1.28 | $CH_3$ | $CH_2CH_3$ | H | 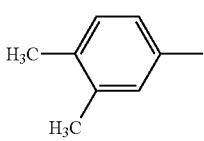 |
| A.1.29 | $CH_3$ | $CH_2CH_3$ | H | 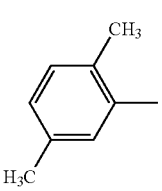 |
| A.1.30 | $CH_3$ | $CH_2CH_3$ | H | 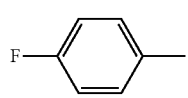 |
| A.1.31 | $CH_3$ | $CH_2CH_3$ | H | 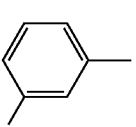 |
| A.1.32 | $CH_3$ | $CH_2CH_3$ | H | 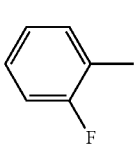 |

TABLE A-continued
Meanings for $R_1$, $R_2$, $R_5$ and $R_6$:
| A.1.33 | $CH_3$ | $CH_2CH_3$ | H | 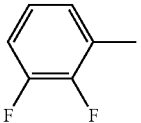 |
| A.1.34 | $CH_3$ | $CH_2CH_3$ | H | 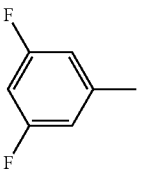 |
| A.1.35 | $CH_3$ | $CH_2CH_3$ | H | 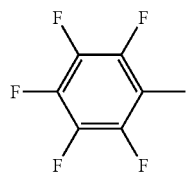 |
| A.1.36 | $CH_3$ | $CH_2CH_3$ | H | 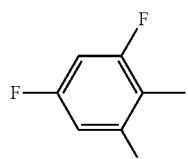 |
| A.1.37 | $CH_3$ | $CH_2CH_3$ | H | 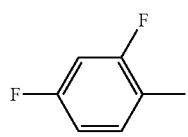 |
| A.1.38 | $CH_3$ | $CH_2CH_3$ | H | 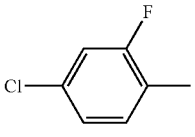 |
| A.1.39 | $CH_3$ | $CH_2CH_3$ | H | 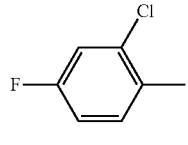 |
| A.1.40 | $CH_3$ | $CH_2CH_3$ | H | 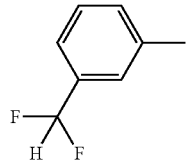 |
| A.1.41 | $CH_3$ | $CH_2CH_3$ | H | 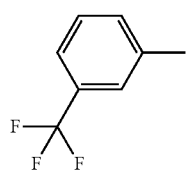 |

TABLE A-continued

| | | Meanings for $R_1$, $R_2$, $R_5$ and $R_6$: | | |
|---|---|---|---|---|
| A.1.42 | $CH_3$ | $CH_2CH_3$ | H | 3-(CCl$_3$)phenyl |
| A.1.43 | $CH_3$ | $CH_2CH_3$ | H | biphenyl-3-yl |
| A.1.44 | $CH_3$ | $CH_2CH_3$ | H | 3-(thiophen-2-yl)phenyl |
| A.1.45 | $CH_3$ | $CH_2CH_3$ | H | 3-(pentafluoroethyl)phenyl |
| A.1.46 | $CH_3$ | $CH_2CH_3$ | H | 3-methylphenyl |
| A.1.47 | $CH_3$ | $CH_2CH_3$ | H | 3-ethylphenyl |
| A.1.48 | $CH_3$ | $CH_2CH_3$ | H | 3-isopropylphenyl |
| A.1.49 | $CH_3$ | $CH_2CH_3$ | H | 3-tert-butylphenyl |

TABLE A-continued
Meanings for $R_1$, $R_2$, $R_5$ and $R_6$:
| | | | | |
|---|---|---|---|---|
| A.1.50 | $CH_3$ | $CH_2CH_3$ | H | 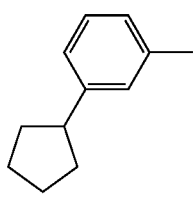 |
| A.1.51 | $CH_3$ | $CH_2CH_3$ | H | 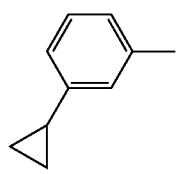 |
| A.1.52 | $CH_3$ | $CH_2CH_3$ | H | 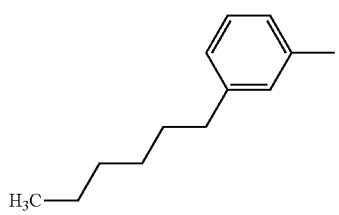 |
| A.1.53 | $CH_3$ | $CH_2CH_3$ | H | 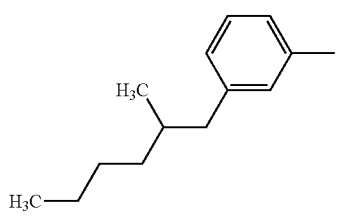 |
| A.1.54 | $CH_3$ | $CH_2CH_3$ | H | 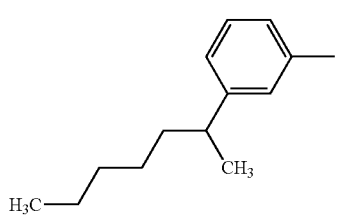 |
| A.1.55 | $CH_3$ | $CH_2CH_3$ | H | 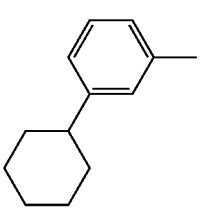 |
| A.1.56 | $CH_3$ | $CH_2CH_3$ | H | 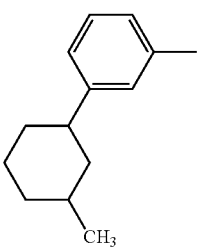 |

TABLE A-continued
| | | Meanings for $R_1$, $R_2$, $R_5$ and $R_6$: | | |
|---|---|---|---|---|
| A.1.57 | $CH_3$ | $CH_2CH_3$ | H | 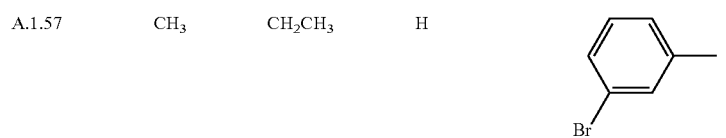 |
| A.1.58 | $CH_3$ | $CH_2CH_3$ | H | 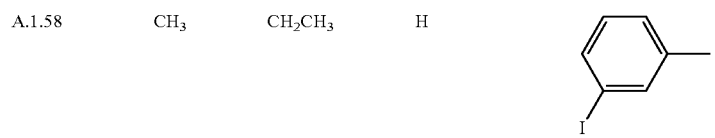 |
| A.1.59 | $CH_3$ | $CH_2CH_3$ | H | 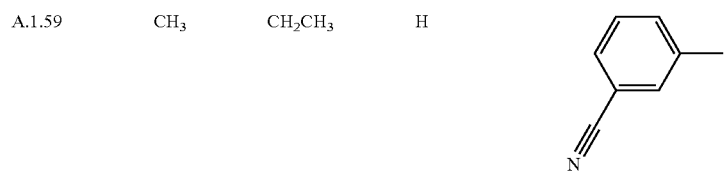 |
| A.1.60 | $CH_3$ | $CH_2CH_3$ | H | 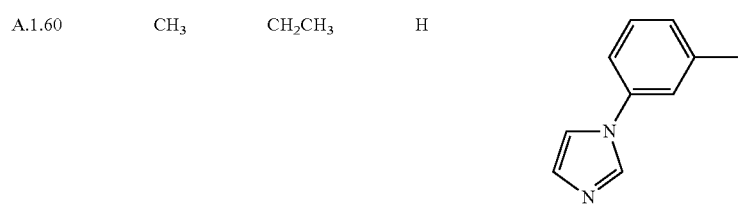 |
| A.1.61 | $CH_3$ | $CH_2CH_3$ | H | 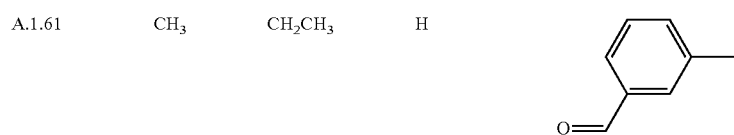 |
| A.1.62 | $CH_3$ | $CH_2CH_3$ | H | 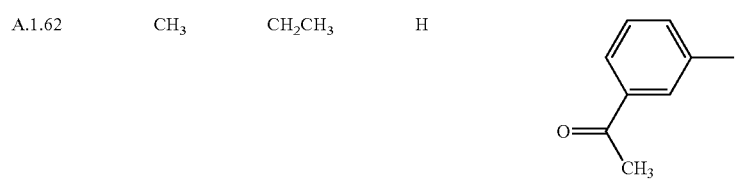 |
| A.1.63 | $CH_3$ | $CH_2CH_3$ | H | 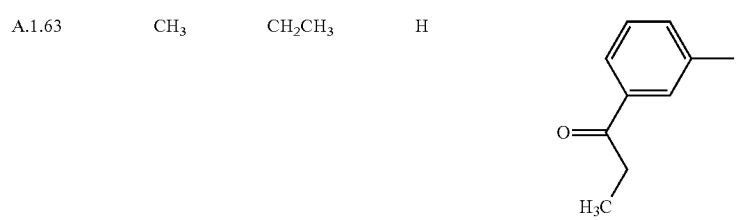 |
| A.1.64 | $CH_3$ | $CH_2CH_3$ | H | 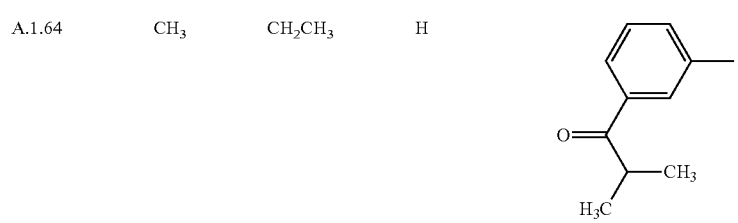 |

TABLE A-continued
Meanings for $R_1$, $R_2$, $R_5$ and $R_6$:
| A.1.65 | $CH_3$ | $CH_2CH_3$ | H | 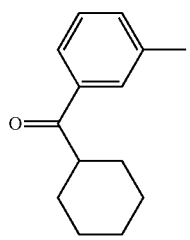 |
| A.1.66 | $CH_3$ | $CH_2CH_3$ | H | 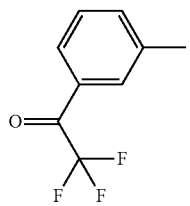 |
| A.1.67 | $CH_3$ | $CH_2CH_3$ | H | 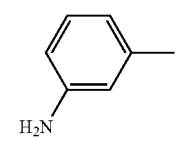 |
| A.1.68 | $CH_3$ | $CH_2CH_3$ | H | 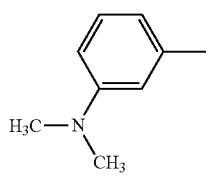 |
| A.1.69 | $CH_3$ | $CH_2CH_3$ | H | 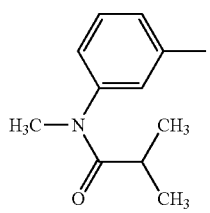 |
| A.1.70 | $CH_3$ | $CH_2CH_3$ | H | 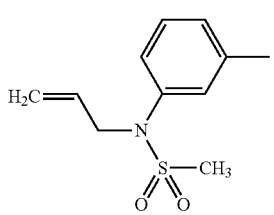 |
| A.1.71 | $CH_3$ | $CH_2CH_3$ | H | 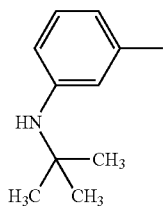 |
| A.1.72 | $CH_3$ | $CH_2CH_3$ | H | 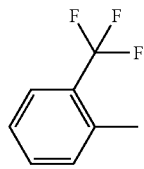 |

TABLE A-continued
Meanings for $R_1$, $R_2$, $R_5$ and $R_6$:
| A.1.73 | $CH_3$ | $CH_2CH_3$ | H | 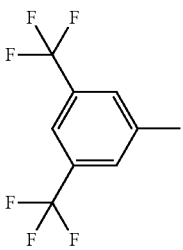 |
| A.1.74 | $CH_3$ | $CH_2CH_3$ | H | 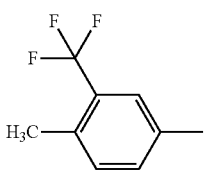 |
| A.1.75 | $CH_3$ | $CH_2CH_3$ | H | 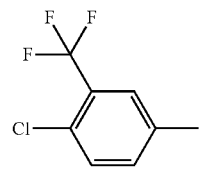 |
| A.1.76 | $CH_3$ | $CH_2CH_3$ | H | 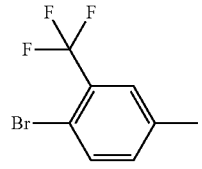 |
| A.1.77 | $CH_3$ | $CH_2CH_3$ | H | 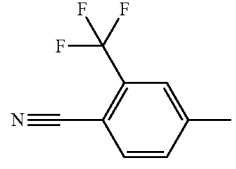 |
| A.1.78 | $CH_3$ | $CH_2CH_3$ | H | 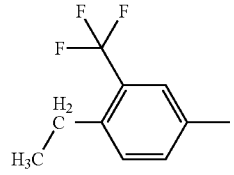 |
| A.1.79 | $CH_3$ | $CH_2CH_3$ | H | 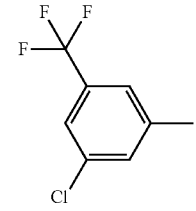 |
| A.1.80 | $CH_3$ | $CH_2CH_3$ | H | 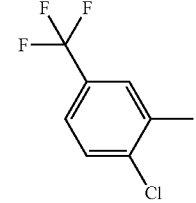 |

TABLE A-continued

Meanings for $R_1$, $R_2$, $R_5$ and $R_6$:

| | | | | |
|---|---|---|---|---|
| A.1.81 | $CH_3$ | $CH_2CH_3$ | H | 4-(trifluoromethyl)phenyl |
| A.1.82 | $CH_3$ | $CH_2CH_3$ | H | 3-tert-butylphenyl |
| A.1.83 | $CH_3$ | $CH_2CH_3$ | H | 4-tert-butylphenyl |
| A.1.84 | $CH_3$ | $CH_2CH_3$ | H | 3-isopropylphenyl |
| A.1.85 | $CH_3$ | $CH_2CH_3$ | H | 4-isopropylphenyl |
| A.1.86 | $CH_3$ | $CH_2CH_3$ | H | 2-ethyl-3-propyl-4-methylphenyl |
| A.1.87 | $CH_3$ | $CH_2CH_3$ | H | 2-tert-butyl-3-methylphenyl |
| A.1.88 | $CH_3$ | $CH_2CH_3$ | H | 2-tert-butyl-3-chlorophenyl |
| A.1.89 | $CH_3$ | $CH_2CH_3$ | H | 3-tert-butyl-5-chlorophenyl |
| A.1.90 | $CH_3$ | $CH_2CH_3$ | H | 2-(trifluoromethyl)-5-methylphenyl |

TABLE A-continued
Meanings for $R_1$, $R_2$, $R_5$ and $R_6$:
| | | | | |
|---|---|---|---|---|
| A.1.91 | CH$_3$ | CH$_2$CH$_3$ | H | 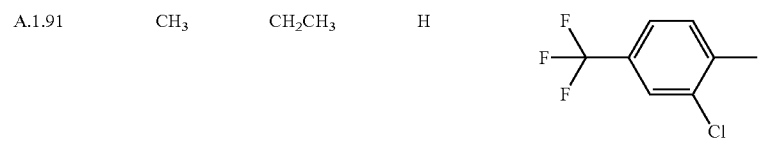 |
| A.1.92 | CH$_3$ | CH$_2$CH$_3$ | H | 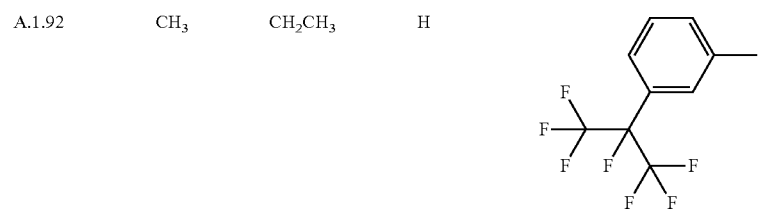 |
| A.1.93 | CH$_3$ | CH$_2$CH$_3$ | H | 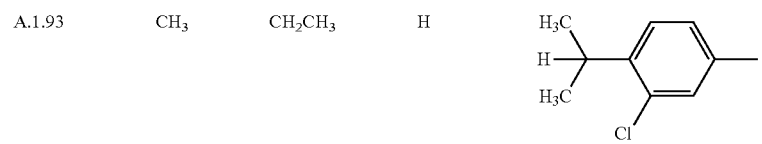 |
| A.1.94 | CH$_3$ | CH$_2$CH$_3$ | H | 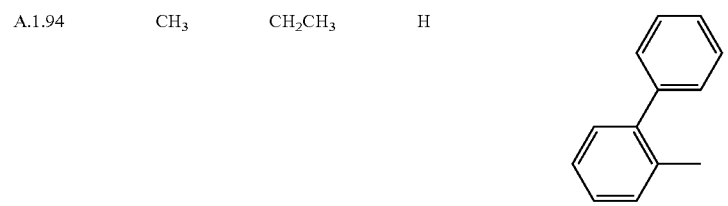 |
| A.1.95 | CH$_3$ | CH$_2$CH$_3$ | H | 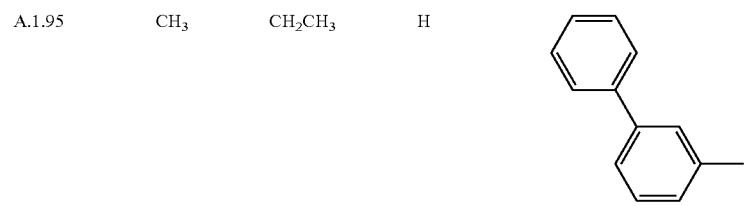 |
| A.1.96 | CH$_3$ | CH$_2$CH$_3$ | H | 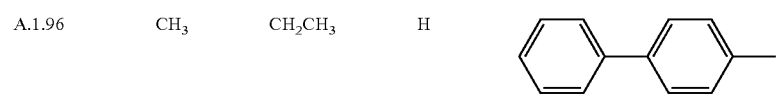 |
| A.1.97 | CH$_3$ | CH$_2$CH$_3$ | H | 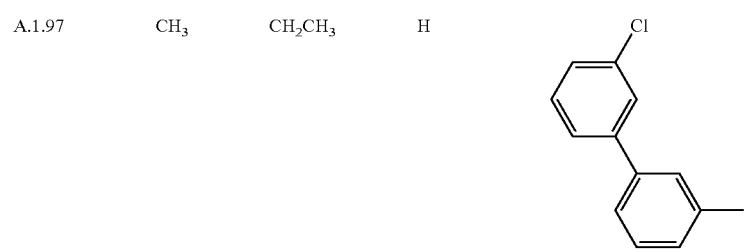 |
| A.1.98 | CH$_3$ | CH$_2$CH$_3$ | H | 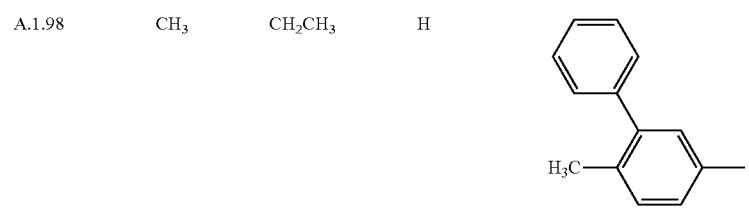 |

TABLE A-continued

Meanings for $R_1$, $R_2$, $R_5$ and $R_6$:

| | | | | |
|---|---|---|---|---|
| A.1.99 | $CH_3$ | $CH_2CH_3$ | H | 2-chloro-5-methyl biphenyl group |
| A.1.100 | $CH_3$ | $CH_2CH_3$ | H | 2-bromo-5-methyl biphenyl group |
| A.1.101 | $CH_3$ | $CH_2CH_3$ | H | 3-methylbenzoic acid group |
| A.1.102 | $CH_3$ | $CH_2CH_3$ | H | methyl 3-methylbenzoate group |
| A.1.103 | $CH_3$ | $CH_2CH_3$ | H | ethyl 3-methylbenzoate group |
| A.1.104 | $CH_3$ | $CH_2CH_3$ | H | pentyl 3-methylbenzoate group |
| A.1.105 | $CH_3$ | $CH_2CH_3$ | H | isopropyl 3-methylbenzoate group |
| A.1.106 | $CH_3$ | $CH_2CH_3$ | H | tert-butyl 3-methylbenzoate group |

TABLE A-continued

Meanings for $R_1$, $R_2$, $R_5$ and $R_6$:

| A.1.107 | $CH_3$ | $CH_2CH_3$ | H | 3-methylbenzoate of pentan-2-ol |
| A.1.108 | $CH_3$ | $CH_2CH_3$ | H | allyl 3-methylbenzoate |
| A.1.109 | $CH_3$ | $CH_2CH_3$ | H | but-3-en-2-yl 3-methylbenzoate |
| A.1.110 | $CH_3$ | $CH_2CH_3$ | H | prop-2-yn-1-yl 3-methylbenzoate |
| A.1.111 | $CH_3$ | $CH_2CH_3$ | H | but-3-yn-2-yl 3-methylbenzoate |
| A.1.112 | $CH_3$ | $CH_2CH_3$ | H | benzyl 3-methylbenzoate |

TABLE A-continued
Meanings for $R_1$, $R_2$, $R_5$ and $R_6$:
| | | | | |
|---|---|---|---|---|
| A.1.113 | CH$_3$ | CH$_2$CH$_3$ | H | 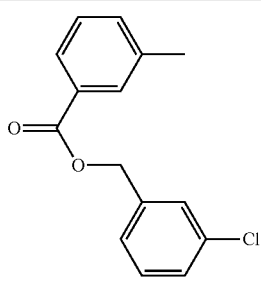 |
| A.1.114 | CH$_3$ | CH$_2$CH$_3$ | H | 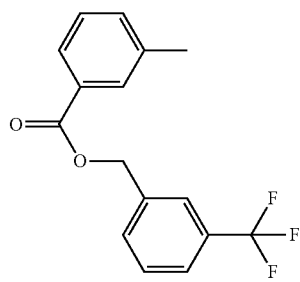 |
| A.1.115 | CH$_3$ | CH$_2$CH$_3$ | H | 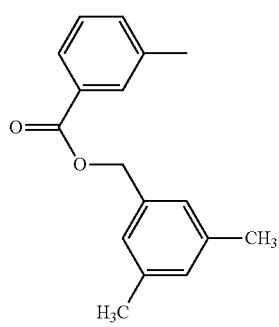 |
| A.1.116 | CH$_3$ | CH$_2$CH$_3$ | H | 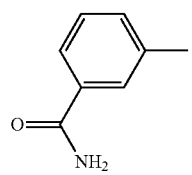 |
| A.1.117 | CH$_3$ | CH$_2$CH$_3$ | H | 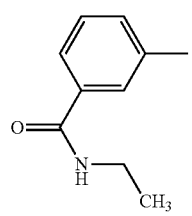 |
| A.1.118 | CH$_3$ | CH$_2$CH$_3$ | H | 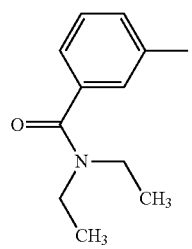 |

TABLE A-continued
Meanings for $R_1$, $R_2$, $R_5$ and $R_6$:
| | | | | |
|---|---|---|---|---|
| A.1.119 | $CH_3$ | $CH_2CH_3$ | H | 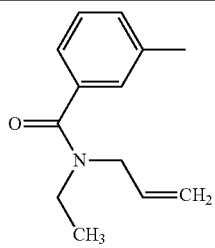 |
| A.1.120 | $CH_3$ | $CH_2CH_3$ | H | 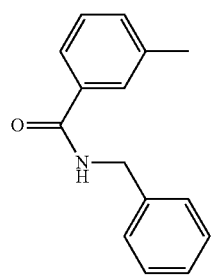 |
| A.1.121 | $CH_3$ | $CH_2CH_3$ | H | 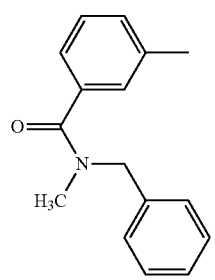 |
| A.1.122 | $CH_3$ | $CH_2CH_3$ | H | 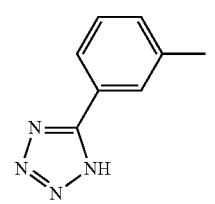 |
| A.1.123 | $CH_3$ | $CH_2CH_3$ | H | 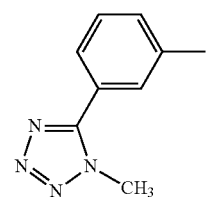 |
| A.1.124 | $CH_3$ | $CH_2CH_3$ | H | 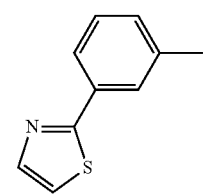 |
| A.1.125 | $CH_3$ | $CH_2CH_3$ | H | 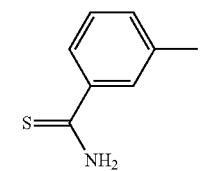 |

TABLE A-continued
Meanings for $R_1$, $R_2$, $R_5$ and $R_6$:
| | | | | |
|---|---|---|---|---|
| A.1.126 | CH$_3$ | CH$_2$CH$_3$ | H | 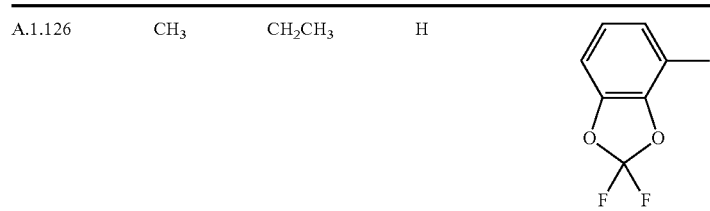 |
| A.1.127 | CH$_3$ | CH$_2$CH$_3$ | H | 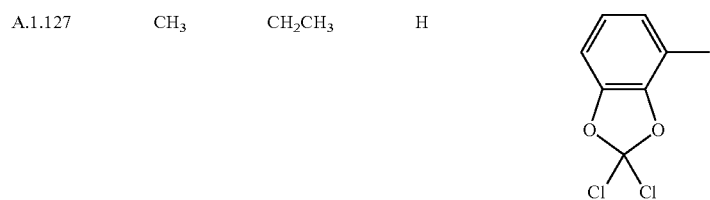 |
| A.1.128 | CH$_3$ | CH$_2$CH$_3$ | H | 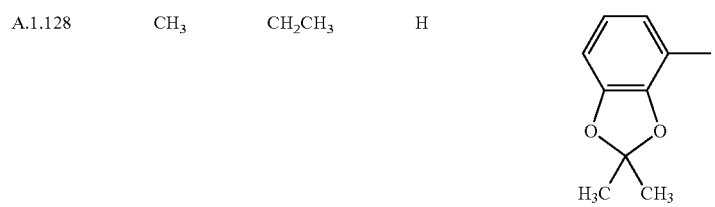 |
| A.1.129 | CH$_3$ | CH$_2$CH$_3$ | H | 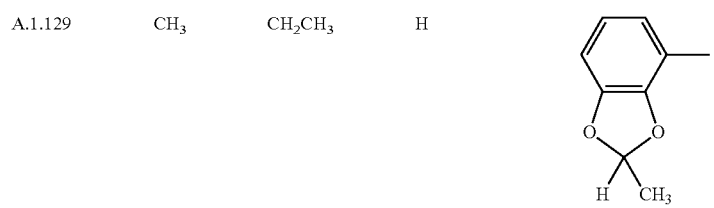 |
| A.1.130 | CH$_3$ | CH$_2$CH$_3$ | H | 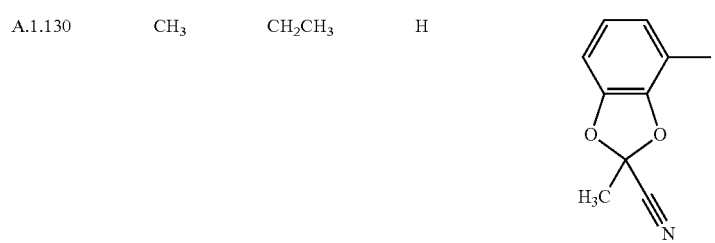 |
| A.1.131 | CH$_3$ | CH$_2$CH$_3$ | H | 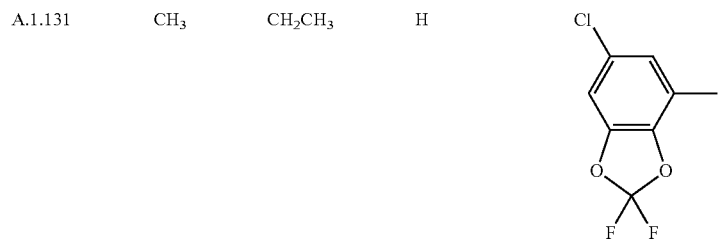 |
| A.1.132 | CH$_3$ | CH$_2$CH$_3$ | H | 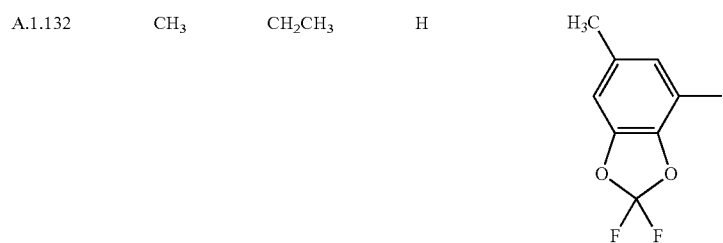 |

TABLE A-continued
| | | Meanings for $R_1$, $R_2$, $R_5$ and $R_6$: | | |
|---|---|---|---|---|
| A.1.133 | $CH_3$ | $CH_2CH_3$ | H | 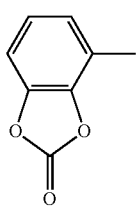 |
| A.1.134 | $CH_3$ | $CH_2CH_3$ | H | 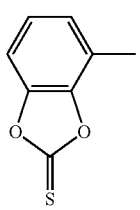 |
| A.1.135 | $CH_3$ | $CH_2CH_3$ | H | 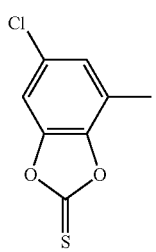 |
| A.1.136 | $CH_3$ | $CH_2CH_3$ | H | 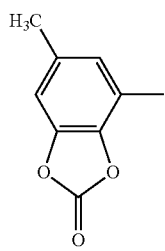 |
| A.1.137 | $CH_3$ | $CH_2CH_3$ | H | 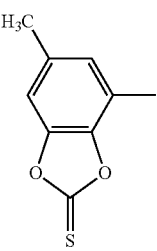 |
| A.1.138 | $CH_3$ | $CH_2CH_3$ | H | 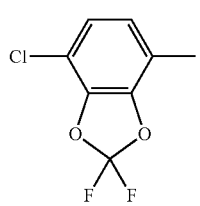 |

TABLE A-continued

| | | | | Meanings for $R_1$, $R_2$, $R_5$ and $R_6$: |
|---|---|---|---|---|
| A.1.139 | $CH_3$ | $CH_2CH_3$ | H | 4-chloro-5-methyl-2,2-difluoro-benzo[1,3]dioxole |
| A.1.140 | $CH_3$ | $CH_2CH_3$ | H | 5-methyl-benzo[1,3]dioxole |
| A.1.141 | $CH_3$ | $CH_2CH_3$ | H | 5-methyl-2,2-difluoro-benzo[1,3]dioxole |
| A.1.142 | $CH_3$ | $CH_2CH_3$ | H | 5-methyl-2,2-dichloro-benzo[1,3]dioxole |
| A.1.143 | $CH_3$ | $CH_2CH_3$ | H | 5-methyl-2,2-dimethyl-benzo[1,3]dioxole |
| A.1.144 | $CH_3$ | $CH_2CH_3$ | H | 5-methyl-2-methyl-benzo[1,3]dioxole |
| A.1.145 | $CH_3$ | $CH_2CH_3$ | H | 5-methyl-2-methyl-2-cyano-benzo[1,3]dioxole |
| A.1.146 | $CH_3$ | $CH_2CH_3$ | H | 5-methyl-benzo[1,3]dioxol-2-one |
| A.1.147 | $CH_3$ | $CH_2CH_3$ | H | 5-methyl-benzo[1,3]dioxole-2-thione |

TABLE A-continued
| | | Meanings for $R_1$, $R_2$, $R_5$ and $R_6$: | | |
|---|---|---|---|---|
| A.1.148 | CH$_3$ | CH$_2$CH$_3$ | H | 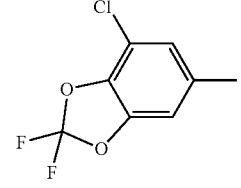 |
| A.1.149 | CH$_3$ | CH$_2$CH$_3$ | H | 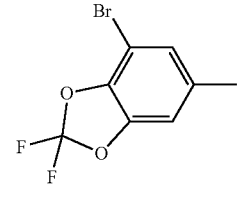 |
| A.1.150 | CH$_3$ | CH$_2$CH$_3$ | H | 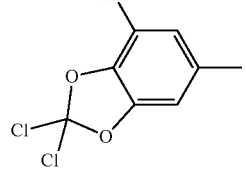 |
| A.1.151 | CH$_3$ | CH$_2$CH$_3$ | H | 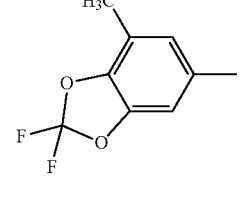 |
| A.1.152 | CH$_3$ | CH$_2$CH$_3$ | H | 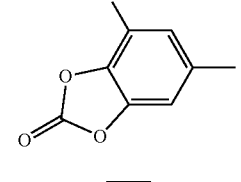 |
| A.1.153 | CH$_3$ | CH$_2$CH$_3$ | H | 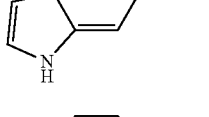 |
| A.1.154 | CH$_3$ | CH$_2$CH$_3$ | H | 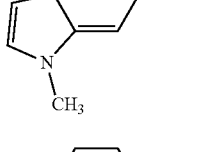 |
| A.1.155 | CH$_3$ | CH$_2$CH$_3$ | H | 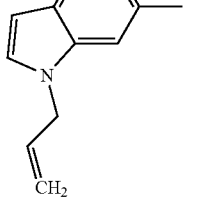 |

TABLE A-continued
| | | Meanings for $R_1$, $R_2$, $R_5$ and $R_6$: | | |
|---|---|---|---|---|
| A.1.156 | CH$_3$ | CH$_2$CH$_3$ | H | 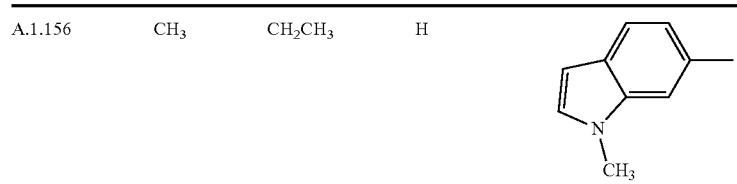 |
| A.1.157 | CH$_3$ | CH$_2$CH$_3$ | H | 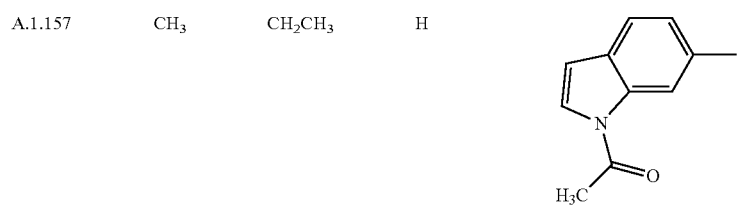 |
| A.1.158 | CH$_3$ | CH$_2$CH$_3$ | H | 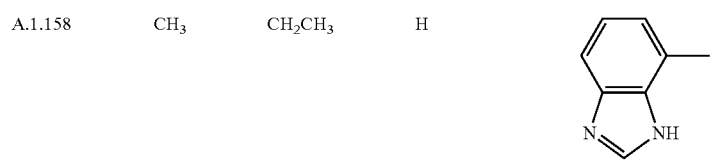 |
| A.1.159 | CH$_3$ | CH$_2$CH$_3$ | H | 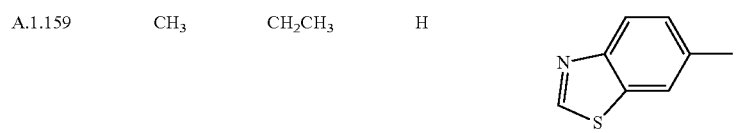 |
| A.1.160 | CH$_3$ | CH$_2$CH$_3$ | H | 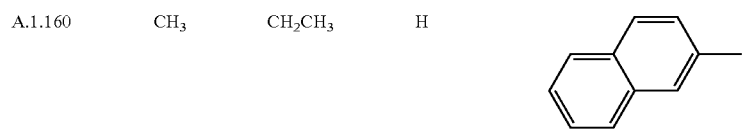 |
| A.1.161 | CH$_3$ | CH$_2$CH$_3$ | H | 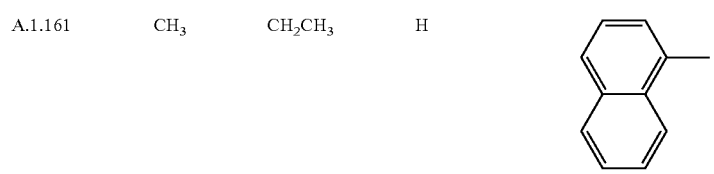 |
| A.1.162 | CH$_3$ | CH$_2$CH$_3$ | H | 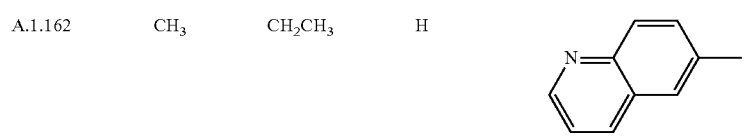 |
| A.1.163 | CH$_3$ | CH$_2$CH$_3$ | H | 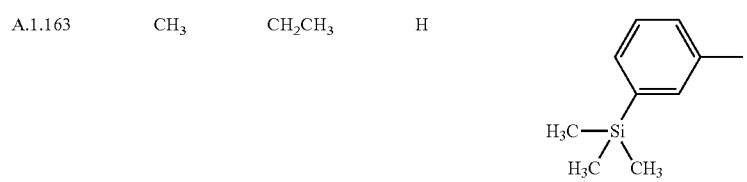 |
| A.1.164 | CH$_3$ | CH$_2$CH$_3$ | H | 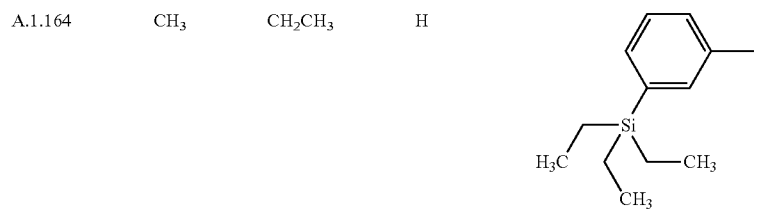 |

TABLE A-continued
Meanings for $R_1$, $R_2$, $R_5$ and $R_6$:
| | | | | |
|---|---|---|---|---|
| A.1.165 | $CH_3$ | $CH_2CH_3$ | H | 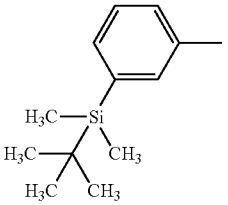 |
| A.1.166 | $CH_3$ | $CH_2CH_3$ | H | 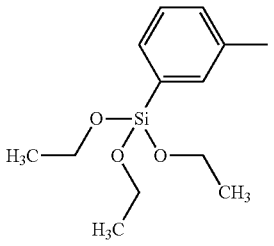 |
| A.1.167 | $CH_3$ | $CH_2CH_3$ | H | 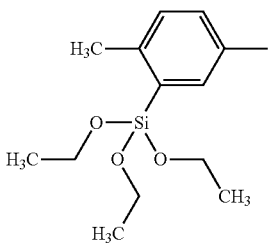 |
| A.1.168 | $CH_3$ | $CH_2CH_3$ | H | 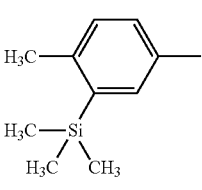 |
| A.1.169 | $CH_3$ | $CH_2CH_3$ | H | 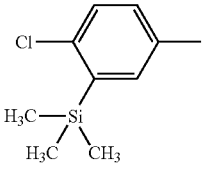 |
| A.1.170 | $CH_3$ | $CH_2CH_3$ | H | 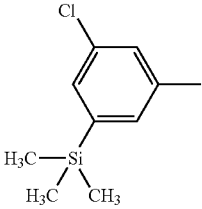 |
| A.1.171 | $CH_3$ | $CH_2CH_3$ | H | 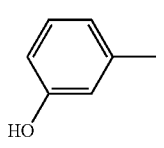 |
| A.1.172 | $CH_3$ | $CH_2CH_3$ | H | 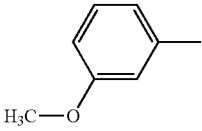 |

TABLE A-continued
Meanings for $R_1$, $R_2$, $R_5$ and $R_6$:
| A.1.173 | CH$_3$ | CH$_2$CH$_3$ | H | 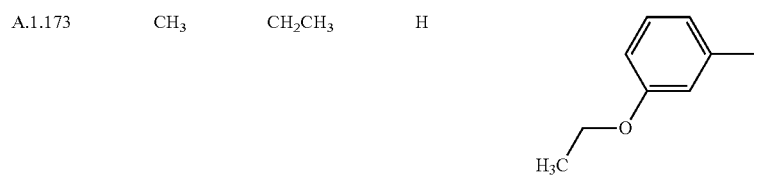 |
| A.1.174 | CH$_3$ | CH$_2$CH$_3$ | H | 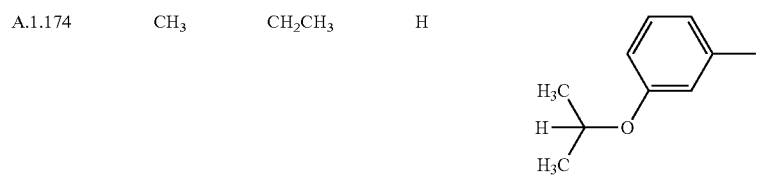 |
| A.1.175 | CH$_3$ | CH$_2$CH$_3$ | H | 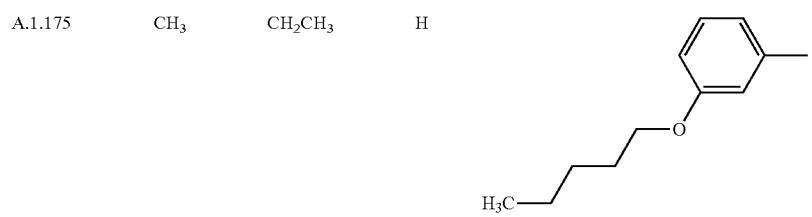 |
| A.1.176 | CH$_3$ | CH$_2$CH$_3$ | H | 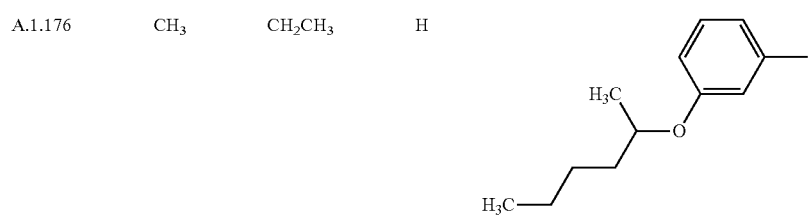 |
| A.1.177 | CH$_3$ | CH$_2$CH$_3$ | H | 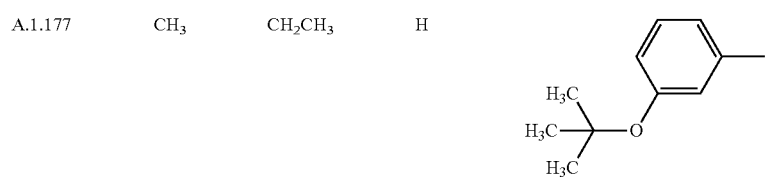 |
| A.1.178 | CH$_3$ | CH$_2$CH$_3$ | H | 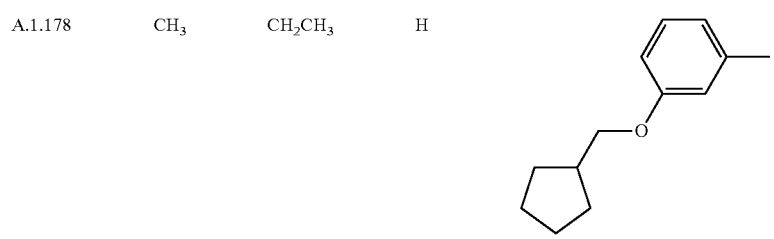 |
| A.1.179 | CH$_3$ | CH$_2$CH$_3$ | H | 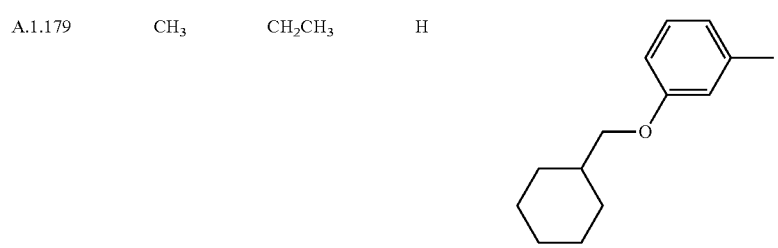 |

TABLE A-continued
| | | Meanings for $R_1$, $R_2$, $R_5$ and $R_6$: | | |
|---|---|---|---|---|
| A.1.180 | CH$_3$ | CH$_2$CH$_3$ | H | 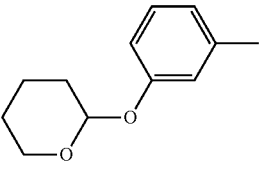 |
| A.1.181 | CH$_3$ | CH$_2$CH$_3$ | H | 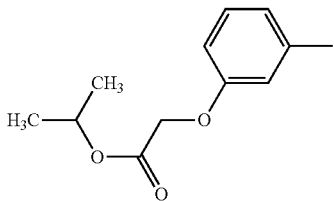 |
| A.1.182 | CH$_3$ | CH$_2$CH$_3$ | H | 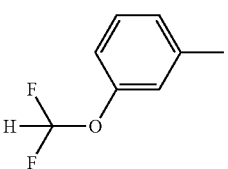 |
| A.1.183 | CH$_3$ | CH$_2$CH$_3$ | H | 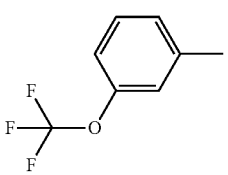 |
| A.1.184 | CH$_3$ | CH$_2$CH$_3$ | H | 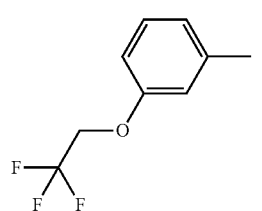 |
| A.1.185 | CH$_3$ | CH$_2$CH$_3$ | H | 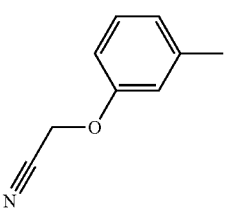 |
| A.1.186 | CH$_3$ | CH$_2$CH$_3$ | H | 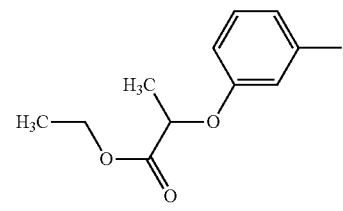 |
| A.1.187 | CH$_3$ | CH$_2$CH$_3$ | H | 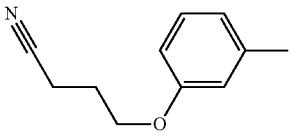 |

TABLE A-continued

| | | Meanings for $R_1$, $R_2$, $R_5$ and $R_6$: | | |
|---|---|---|---|---|
| A.1.188 | $CH_3$ | $CH_2CH_3$ | H | isopropyl 4-(3-methylphenoxy)butanoate group |
| A.1.189 | $CH_3$ | $CH_2CH_3$ | H | 2-(3-methylphenoxy)pyridine group |
| A.1.190 | $CH_3$ | $CH_2CH_3$ | H | 2-(3-methylphenoxy)pyrimidine group |
| A.1.191 | $CH_3$ | $CH_2CH_3$ | H | 3-phenoxy-methylphenyl group |
| A.1.192 | $CH_3$ | $CH_2CH_3$ | H | 3-(4-chlorophenoxy)-methylphenyl group |
| A.1.193 | $CH_3$ | $CH_2CH_3$ | H | 3-(3-trifluoromethylphenoxy)-methylphenyl group |
| A.1.194 | $CH_3$ | $CH_2CH_3$ | H | 3-(2,4-dichlorophenoxy)-methylphenyl group |
| A.1.195 | $CH_3$ | $CH_2CH_3$ | H | 3-(3-tert-butylphenoxy)-methylphenyl group |

TABLE A-continued

| | | Meanings for $R_1$, $R_2$, $R_5$ and $R_6$: | | |
|---|---|---|---|---|
| A.1.196 | $CH_3$ | $CH_2CH_3$ | H | 3-(3-methylphenoxy)phenyl |
| A.1.197 | $CH_3$ | $CH_2CH_3$ | H | 3-(3,5-difluorophenoxy)phenyl |
| A.1.198 | $CH_3$ | $CH_2CH_3$ | H | 3-(allyloxy)phenyl |
| A.1.199 | $CH_3$ | $CH_2CH_3$ | H | 3-(but-3-en-2-yloxy)phenyl |
| A.1.200 | $CH_3$ | $CH_2CH_3$ | H | 3-((E)-but-2-enyloxy)phenyl |
| A.1.201 | $CH_3$ | $CH_2CH_3$ | H | 3-(3-methylbut-2-enyloxy)phenyl |
| A.1.202 | $CH_3$ | $CH_2CH_3$ | H | 3-((Z)-but-2-enyloxy)phenyl |
| A.1.203 | $CH_3$ | $CH_2CH_3$ | H | 3-((E)-3-chloroallyloxy)phenyl |

TABLE A-continued
| | | Meanings for $R_1$, $R_2$, $R_5$ and $R_6$: | | |
|---|---|---|---|---|
| A.1.204 | $CH_3$ | $CH_2CH_3$ | H | 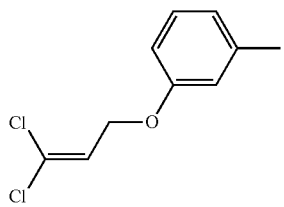 |
| A.1.205 | $CH_3$ | $CH_2CH_3$ | H | 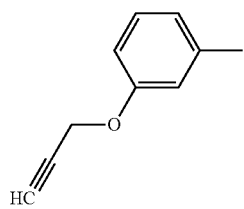 |
| A.1.206 | $CH_3$ | $CH_2CH_3$ | H | 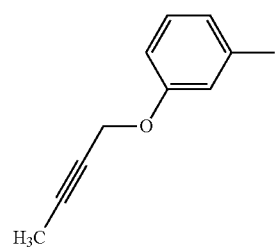 |
| A.1.207 | $CH_3$ | $CH_2CH_3$ | H | 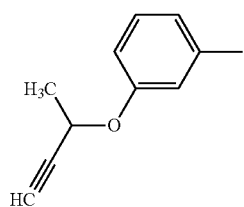 |
| A.1.208 | $CH_3$ | $CH_2CH_3$ | H | 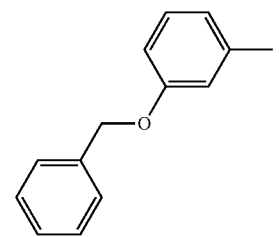 |
| A.1.209 | $CH_3$ | $CH_2CH_3$ | H | 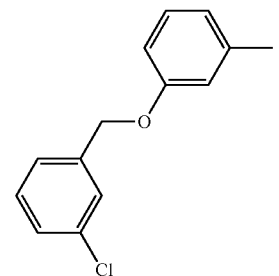 |

TABLE A-continued
Meanings for $R_1$, $R_2$, $R_5$ and $R_6$:
| | | | | |
|---|---|---|---|---|
| A.1.210 | $CH_3$ | $CH_2CH_3$ | H | 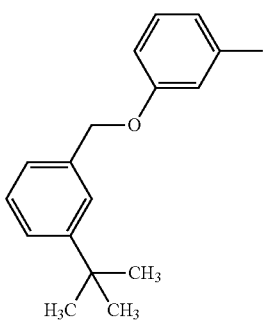 |
| A.1.211 | $CH_3$ | $CH_2CH_3$ | H | 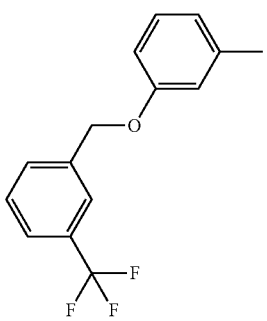 |
| A.1.212 | $CH_3$ | $CH_2CH_3$ | H | 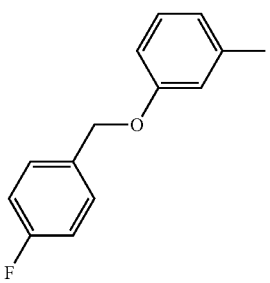 |
| A.1.213 | $CH_3$ | $CH_2CH_3$ | H | 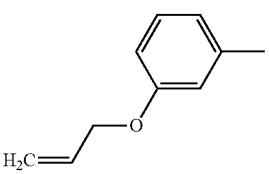 |
| A.1.214 | $CH_3$ | $CH_2CH_3$ | H | 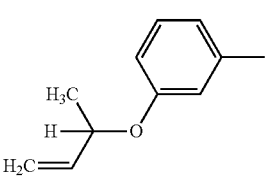 |
| A.1.215 | $CH_3$ | $CH_2CH_3$ | H | 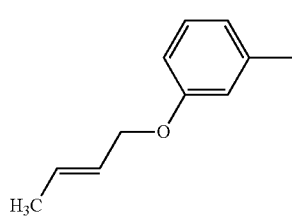 |

TABLE A-continued
Meanings for $R_1$, $R_2$, $R_5$ and $R_6$:
| | | | | |
|---|---|---|---|---|
| A.1.216 | $CH_3$ | $CH_2CH_3$ | H | 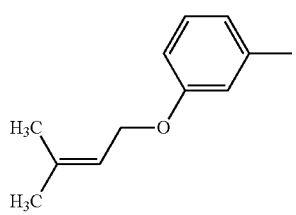 |
| A.1.217 | $CH_3$ | $CH_2CH_3$ | H | 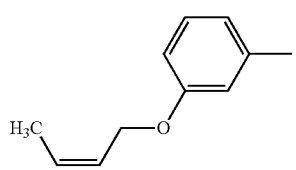 |
| A.1.218 | $CH_3$ | $CH_2CH_3$ | H | 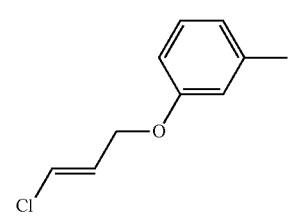 |
| A.1.219 | $CH_3$ | $CH_2CH_3$ | H | 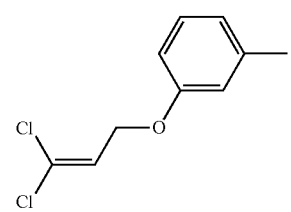 |
| A.1.220 | $CH_3$ | $CH_2CH_3$ | H | 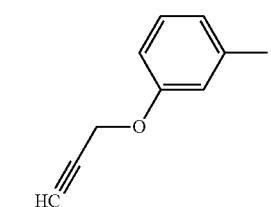 |
| A.1.221 | $CH_3$ | $CH_2CH_3$ | H | 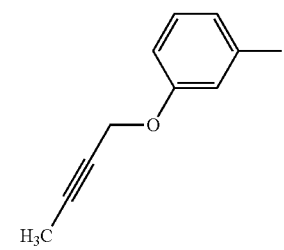 |
| A.1.222 | $CH_3$ | $CH_2CH_3$ | H | 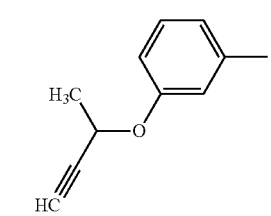 |

TABLE A-continued
| | Meanings for $R_1$, $R_2$, $R_5$ and $R_6$: | | | |
|---|---|---|---|---|
| A.1.223 | CH$_3$ | CH$_2$CH$_3$ | H | 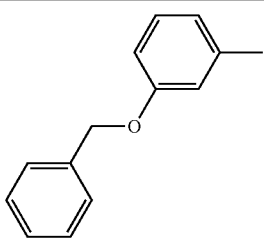 |
| A.1.224 | CH$_3$ | CH$_2$CH$_3$ | H | 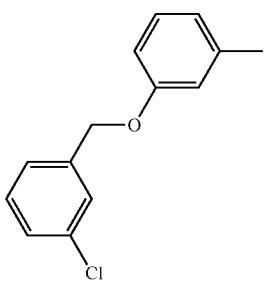 |
| A.1.225 | CH$_3$ | CH$_2$CH$_3$ | H | 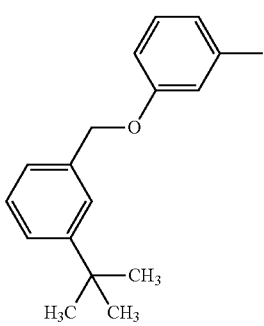 |
| A.1.226 | CH$_3$ | CH$_2$CH$_3$ | H | 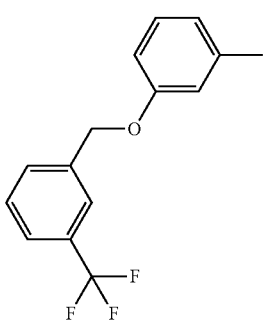 |
| A.1.227 | CH$_3$ | CH$_2$CH$_3$ | H | 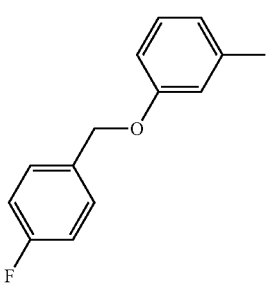 |
| A.1.228 | CH$_3$ | CH$_2$CH$_3$ | H | 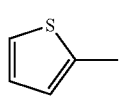 |

TABLE A-continued
Meanings for $R_1$, $R_2$, $R_5$ and $R_6$:
| | | | | |
|---|---|---|---|---|
| A.1.229 | $CH_3$ | $CH_2CH_3$ | H | 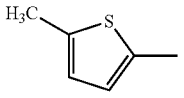 |
| A.1.230 | $CH_3$ | $CH_2CH_3$ | H | 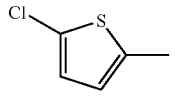 |
| A.1.231 | $CH_3$ | $CH_2CH_3$ | H | 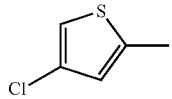 |
| A.1.232 | $CH_3$ | $CH_2CH_3$ | H | H— |
| A.1.233 | $CH_3$ | $CH_2CH_3$ | H | 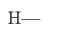 |
| A.1.234 | $CH_3$ | $CH_2CH_3$ | H | 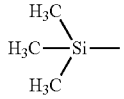 |
| A.1.235 | $CH_3$ | $CH_2CH_3$ | H | 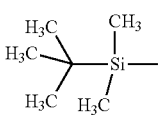 |
| A.1.236 | $CH_3$ | $CH_2CH_3$ | H |  |
| A.1.237 | $CH_3$ | $CH_2CH_3$ | H | 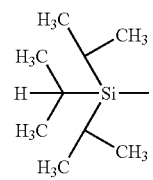 |
| A.1.238 | $CH_3$ | $CH_2CH_3$ | H | 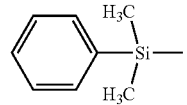 |
| A.1.239 | $CH_3$ | $CH_2CH_3$ | H | 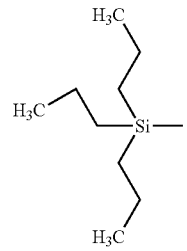 |
| A.1.240 | $CH_3$ | $CH_2CH_3$ | H | 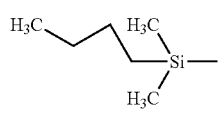 |

TABLE A-continued

| | | Meanings for $R_1$, $R_2$, $R_5$ and $R_6$: | | |
|---|---|---|---|---|
| A.1.241 | $CH_3$ | $CH_2CH_3$ | H | benzyldimethylsilyl |
| A.1.242 | $CH_3$ | $CH_2CH_3$ | H | (3-chlorophenyl)dimethylsilyl |
| A.1.243 | $CH_3$ | $CH_2CH_3$ | H | (3-trifluoromethylphenyl)dimethylsilyl |
| A.1.244 | $CH_3$ | $CH_2CH_3$ | H | triethoxysilyl |
| A.1.245 | $CH_3$ | $CH_2CH_3$ | H | $H_3C-$ |
| A.1.246 | $CH_3$ | $CH_2CH_3$ | H | ethyl |
| A.1.247 | $CH_3$ | $CH_2CH_3$ | H | propyl |
| A.1.248 | $CH_3$ | $CH_2CH_3$ | H | butyl |
| A.1.249 | $CH_3$ | $CH_2CH_3$ | H | hexyl |
| A.1.250 | $CH_3$ | $CH_2CH_3$ | H | decyl |
| A.1.251 | $CH_3$ | $CH_2CH_3$ | H | isobutyl (CHH) |
| A.1.252 | $CH_3$ | $CH_2CH_3$ | H | isobutyl |
| A.1.253 | $CH_3$ | $CH_2CH_3$ | H | 2,3-dimethylbutyl |
| A.1.254 | $CH_3$ | $CH_2CH_3$ | H | 3-methylpentyl |

TABLE A-continued

| | | | | Meanings for $R_1$, $R_2$, $R_5$ and $R_6$: | |
|---|---|---|---|---|---|
| A.1.255 | $CH_3$ | $CH_2CH_3$ | H | 2,2-dimethylbutyl | |
| A.1.256 | $CH_3$ | $CH_2CH_3$ | H | 2-methylpentyl | |
| A.1.257 | $CH_3$ | $CH_2CH_3$ | H | 2,2-dimethylpentyl | |
| A.1.258 | $CH_3$ | $CH_2CH_3$ | H | 3-methylhexyl | |
| A.1.259 | $CH_3$ | $CH_2CH_3$ | H | 2,4-dimethylpentyl | |
| A.1.260 | $CH_3$ | $CH_2CH_3$ | H | 3-chloropropyl | |
| A.1.261 | $CH_3$ | $CH_2CH_3$ | H | 4-chlorobutyl | |
| A.1.262 | $CH_3$ | $CH_2CH_3$ | H | 5-chloropentyl | |
| A.1.263 | $CH_3$ | $CH_2CH_3$ | H | 1,3-dichloropentyl | |
| A.1.264 | $CH_3$ | $CH_2CH_3$ | H | 1,1-dichloropentyl | |
| A.1.265 | $CH_3$ | $CH_2CH_3$ | H | 1,1,1-trichloropentyl | |
| A.1.266 | $CH_3$ | $CH_2CH_3$ | H | 1,2-dichloro-1-methylpentyl | |
| A.1.267 | $CH_3$ | $CH_2CH_3$ | H | 1-chloro-2-chloro-2-methylpentyl | |
| A.1.268 | $CH_3$ | $CH_2CH_3$ | H | 1-chloro-2-chloro-3-methylpentyl | |
| A.1.269 | $CH_3$ | $CH_2CH_3$ | H | 1,2-dichlorohexyl | |

TABLE A-continued
| | Meanings for $R_1$, $R_2$, $R_5$ and $R_6$: | | | |
|---|---|---|---|---|
| A.1.270 | $CH_3$ | $CH_2CH_3$ | H | 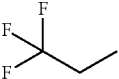 |
| A.1.271 | $CH_3$ | $CH_2CH_3$ | H | 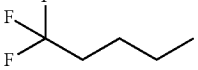 |
| A.1.272 | $CH_3$ | $CH_2CH_3$ | H | 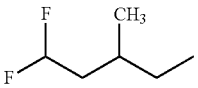 |
| A.1.273 | $CH_3$ | $CH_2CH_3$ | H |  |
| A.1.274 | $CH_3$ | $CH_2CH_3$ | H | 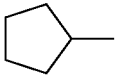 |
| A.1.275 | $CH_3$ | $CH_2CH_3$ | H | 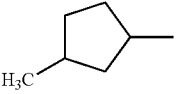 |
| A.1.276 | $CH_3$ | $CH_2CH_3$ | H | 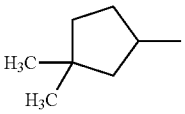 |
| A.1.277 | $CH_3$ | $CH_2CH_3$ | H | 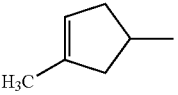 |
| A.1.278 | $CH_3$ | $CH_2CH_3$ | H | 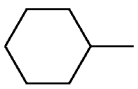 |
| A.1.279 | $CH_3$ | $CH_2CH_3$ | H | 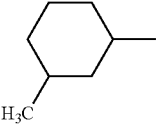 |
| A.1.280 | $CH_3$ | $CH_2CH_3$ | H | 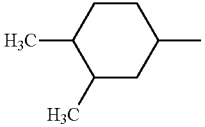 |
| A.1.281 | $CH_3$ | $CH_2CH_3$ | H |  |
| A.1.282 | $CH_3$ | $CH_2CH_3$ | H | 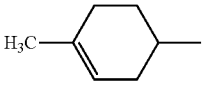 |
| A.1.283 | $CH_3$ | $CH_2CH_3$ | H | 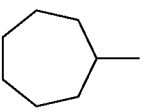 |

TABLE A-continued

| | | | | Meanings for $R_1$, $R_2$, $R_5$ and $R_6$: | |
|---|---|---|---|---|---|
| A.1.284 | $CH_3$ | $CH_2CH_3$ | H | cycloheptyl with CH₃ substituent and ethyl linker | |
| A.1.285 | $CH_3$ | $CH_2CH_3$ | H | cycloheptenyl with methyl linker | |
| A.1.286 | $CH_3$ | $CH_2CH_3$ | H | benzo[1,3]dioxole with methyl linker | |
| A.1.287 | $CH_3$ | $CH_2CH_3$ | H | cyclopropylethyl | |
| A.1.288 | $CH_3$ | $CH_2CH_3$ | H | cyclopentylethyl | |
| A.1.289 | $CH_3$ | $CH_2CH_3$ | H | methylcyclopentyl-ethyl | |
| A.1.290 | $CH_3$ | $CH_2CH_3$ | H | methylcyclopentenyl-ethyl | |
| A.1.291 | $CH_3$ | $CH_2CH_3$ | H | chlorocyclopentyl-ethyl | |
| A.1.292 | $CH_3$ | $CH_2CH_3$ | H | cyclohexylethyl | |
| A.1.293 | $CH_3$ | $CH_2CH_3$ | H | methylcyclohexyl-ethyl | |
| A.1.294 | $CH_3$ | $CH_2CH_3$ | H | methyltetrahydropyranyl-ethyl | |

TABLE A-continued

| | Meanings for $R_1$, $R_2$, $R_5$ and $R_6$: | | | |
|---|---|---|---|---|
| A.1.295 | $CH_3$ | $CH_2CH_3$ | H | 1-methyl-1-(H3C)-cyclohexyl-ethyl |
| A.1.296 | $CH_3$ | $CH_2CH_3$ | H | 3-chlorocyclopentyl-ethyl |
| A.1.297 | $CH_3$ | $CH_2CH_3$ | H | 2,3-dichlorocyclohexyl-ethyl |
| A.1.298 | $CH_3$ | $CH_2CH_3$ | H | chloro-methyl-benzodioxole |
| A.1.299 | $CH_3$ | $CH_2CH_3$ | H | chloro-methyl-benzodioxol-2-one |
| A.1.300 | $CH_3$ | $CH_2CH_3$ | H | trimethylsilyl-propyl |
| A.1.301 | $CH_3$ | $CH_2CH_3$ | H | tert-butyl-dimethylsilyl-propyl |
| A.1.302 | $CH_3$ | $CH_2CH_3$ | H | tert-butyl-methyl-silyl-ethyl |
| A.1.303 | $CH_3$ | $CH_2CH_3$ | H | phenyl-methyl-silyl-propyl |
| A.1.304 | $CH_3$ | $CH_2CH_3$ | H | silacyclohexyl-methyl-propyl |

TABLE A-continued

| | Meanings for $R_1$, $R_2$, $R_5$ and $R_6$: | | | |
|---|---|---|---|---|
| A.1.305 | $CH_3$ | $CH_2CH_3$ | H | cyclohexyl-Si(CH$_3$)$_2$-propyl |
| A.1.306 | $CH_3$ | $CH_2CH_3$ | H | triethyl-Si-propyl |
| A.1.307 | $CH_3$ | $CH_2CH_3$ | H | (CH$_3$)$_3$Si-CH(CH$_3$)CH$_2$CH$_3$ |
| A.1.308 | $CH_3$ | $CH_2CH_3$ | H | (CH$_3$)$_3$Si-butyl |
| A.1.309 | $CH_3$ | $CH_2CH_3$ | H | (CH$_3$)$_3$C-Si(CH$_3$)$_2$-butyl |
| A.1.310 | $CH_3$ | $CH_2CH_3$ | H | (CH$_3$)$_2$CH-Si(CH$_3$)(CH$_2$CH$_3$)-butyl |
| A.1.311 | $CH_3$ | $CH_2CH_3$ | H | phenyl-Si(CH$_3$)$_2$-butyl |
| A.1.312 | $CH_3$ | $CH_2CH_3$ | H | triethyl-Si-butyl |
| A.1.313 | $CH_3$ | $CH_2CH_3$ | H | triethyl-Si-CH$_2$CH(CH$_3$)CH$_2$CH$_3$ |
| A.1.314 | $CH_3$ | $CH_2CH_3$ | H | (CH$_3$)$_3$Si-CH$_2$CH$_2$CH(CH$_3$)$_2$ |

TABLE A-continued
Meanings for $R_1$, $R_2$, $R_5$ and $R_6$:
| | | | | |
|---|---|---|---|---|
| A.1.315 | $CH_3$ | $CH_2CH_3$ | H | 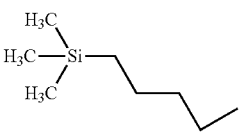 |
| A.1.316 | $CH_3$ | $CH_2CH_3$ | H | 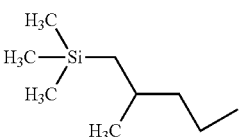 |
| A.1.317 | $CH_3$ | $CH_2CH_3$ | H | 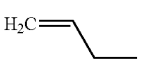 |
| A.1.318 | $CH_3$ | $CH_2CH_3$ | H | 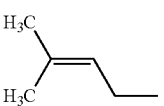 |
| A.1.319 | $CH_3$ | $CH_2CH_3$ | H | 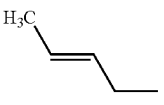 |
| A.1.320 | $CH_3$ | $CH_2CH_3$ | H | 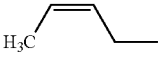 |
| A.1.321 | $CH_3$ | $CH_2CH_3$ | H | 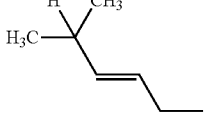 |
| A.1.322 | $CH_3$ | $CH_2CH_3$ | H | 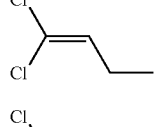 |
| A.1.323 | $CH_3$ | $CH_2CH_3$ | H | 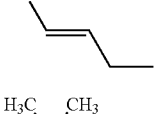 |
| A.1.324 | $CH_3$ | $CH_2CH_3$ | H | 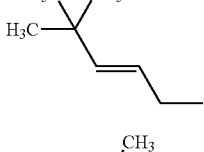 |
| A.1.325 | $CH_3$ | $CH_2CH_3$ | H | 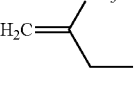 |
| A.1.326 | $CH_3$ | $CH_2CH_3$ | H | 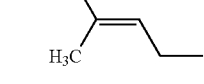 |
| A.1.327 | $CH_3$ | $CH_2CH_3$ | H | 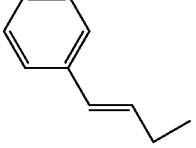 |

TABLE A-continued
Meanings for $R_1$, $R_2$, $R_5$ and $R_6$:
| | | | | |
|---|---|---|---|---|
| A.1.328 | CH$_3$ | CH$_2$CH$_3$ | H | 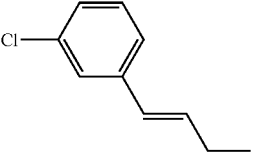 |
| A.1.329 | CH$_3$ | CH$_2$CH$_3$ | H | 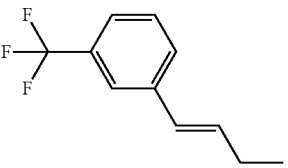 |
| A.1.330 | CH$_3$ | CH$_2$CH$_3$ | H | 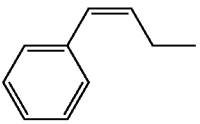 |
| A.1.331 | CH$_3$ | CH$_2$CH$_3$ | H | 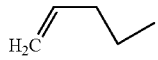 |
| A.1.332 | CH$_3$ | CH$_2$CH$_3$ | H | 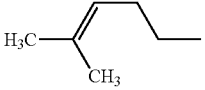 |
| A.1.333 | CH$_3$ | CH$_2$CH$_3$ | H |  |
| A.1.334 | CH$_3$ | CH$_2$CH$_3$ | H | 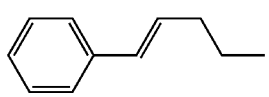 |
| A.1.335 | CH$_3$ | CH$_2$CH$_3$ | H | 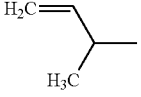 |
| A.1.336 | CH$_3$ | CH$_2$CH$_3$ | H | 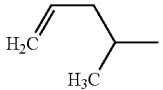 |
| A.1.337 | CH$_3$ | CH$_2$CH$_3$ | H | 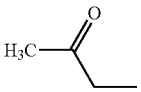 |
| A.1.338 | CH$_3$ | CH$_2$CH$_3$ | H | 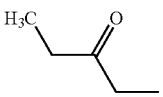 |
| A.1.339 | CH$_3$ | CH$_2$CH$_3$ | H | 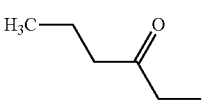 |
| A.1.340 | CH$_3$ | CH$_2$CH$_3$ | H | 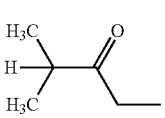 |

TABLE A-continued
Meanings for $R_1$, $R_2$, $R_5$ and $R_6$:
| A.1.341 | $CH_3$ | $CH_2CH_3$ | H | 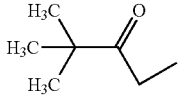 |
| A.1.342 | $CH_3$ | $CH_2CH_3$ | H | 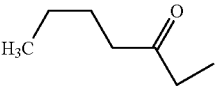 |
| A.1.343 | $CH_3$ | $CH_2CH_3$ | H | 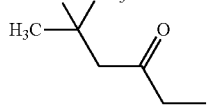 |
| A.1.344 | $CH_3$ | $CH_2CH_3$ | H | 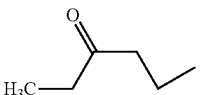 |
| A.1.345 | $CH_3$ | $CH_2CH_3$ | H | 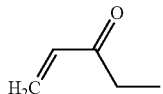 |
| A.1.346 | $CH_3$ | $CH_2CH_3$ | H | 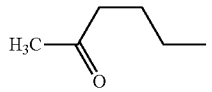 |
| A.1.347 | $CH_3$ | $CH_2CH_3$ | H | 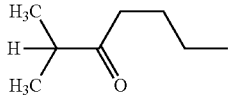 |
| A.1.348 | $CH_3$ | $CH_2CH_3$ | H | 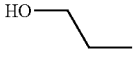 |
| A.1.349 | $CH_3$ | $CH_2CH_3$ | H | 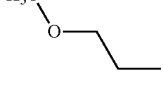 |
| A.1.350 | $CH_3$ | $CH_2CH_3$ | H | 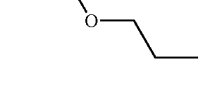 |
| A.1.351 | $CH_3$ | $CH_2CH_3$ | H | 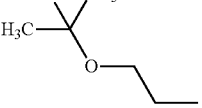 |
| A.1.352 | $CH_3$ | $CH_2CH_3$ | H | 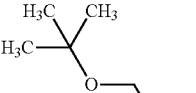 |
| A.1.353 | $CH_3$ | $CH_2CH_3$ | H | 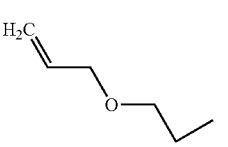 |

TABLE A-continued
Meanings for $R_1$, $R_2$, $R_5$ and $R_6$:
| | | | | |
|---|---|---|---|---|
| A.1.354 | $CH_3$ | $CH_2CH_3$ | H | 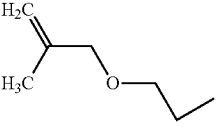 |
| A.1.355 | $CH_3$ | $CH_2CH_3$ | H | 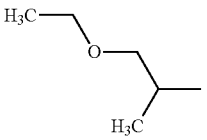 |
| A.1.356 | $CH_3$ | $CH_2CH_3$ | H | 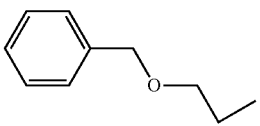 |
| A.1.357 | $CH_3$ | $CH_2CH_3$ | H | 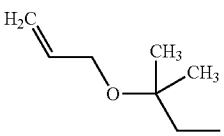 |
| A.1.358 | $CH_3$ | $CH_2CH_3$ | H | 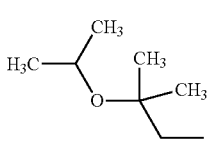 |
| A.1.359 | $CH_3$ | $CH_2CH_3$ | H | 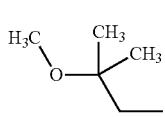 |
| A.1.360 | $CH_3$ | $CH_2CH_3$ | H | 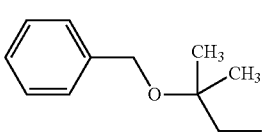 |
| A.1.361 | $CH_3$ | $CH_2CH_3$ | H | 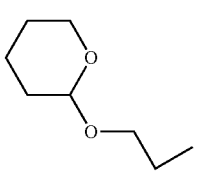 |
| A.1.362 | $CH_3$ | $CH_2CH_3$ | H | 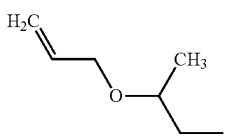 |
| A.1.363 | $CH_3$ | $CH_2CH_3$ | H | 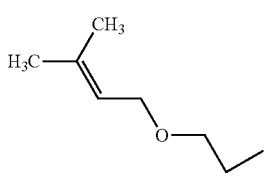 |
| A.1.364 | $CH_3$ | $CH_2CH_3$ | H | 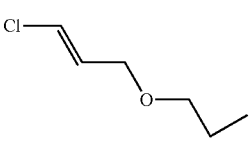 |

TABLE A-continued

| | | | | Meanings for $R_1$, $R_2$, $R_5$ and $R_6$: |
|---|---|---|---|---|
| A.1.365 | $CH_3$ | $CH_2CH_3$ | H | 1,1-dichloroprop-1-en-3-yloxy (CCl$_2$=CH-CH$_2$-O-CH$_2$CH$_2$CH$_2$-) |
| A.1.366 | $CH_3$ | $CH_2CH_3$ | H | phenoxypropyl |
| A.1.367 | $CH_3$ | $CH_2CH_3$ | H | 3-chlorophenoxypropyl |
| A.1.368 | $CH_3$ | $CH_2CH_3$ | H | 3-(trifluoromethyl)phenoxypropyl |
| A.1.369 | $CH_3$ | $CH_2CH_3$ | H | (pyridin-2-yloxy)ethyl |
| A.1.370 | $CH_3$ | $CH_2CH_3$ | H | (6-chloropyridin-2-yloxy)ethyl |
| A.1.371 | $CH_3$ | $CH_2CH_3$ | H | ethoxymethylpropyl |
| A.1.372 | $CH_3$ | $CH_2CH_3$ | H | 2-methyl-ethoxymethylbutyl |
| A.1.373 | $CH_3$ | $CH_2CH_3$ | H | isopropoxypropyl |

TABLE A-continued

| | Meanings for $R_1$, $R_2$, $R_5$ and $R_6$: | | | |
|---|---|---|---|---|
| A.1.374 | CH$_3$ | CH$_2$CH$_3$ | H | (CH$_3$)$_2$CH—O—CH(CH$_3$)CH$_2$CH$_3$ |
| A.1.375 | CH$_3$ | CH$_2$CH$_3$ | H | CH$_3$CH$_2$—O—C(CH$_3$)$_2$CH$_2$CH$_2$CH$_3$ |
| A.1.376 | CH$_3$ | CH$_2$CH$_3$ | H | CH$_2$=CHCH$_2$—O—C(CH$_3$)$_2$CH$_2$CH$_2$CH$_3$ |
| A.1.377 | CH$_3$ | CH$_2$CH$_3$ | H | PhCH(CH$_3$)—O—C(CH$_3$)$_2$CH$_2$CH$_2$CH$_3$ |
| A.1.378 | CH$_3$ | CH$_2$CH$_3$ | H | oxiranyl-CH$_2$CH$_3$ |
| A.1.379 | CH$_3$ | CH$_2$CH$_3$ | H | oxiranyl-CH$_2$CH$_2$CH$_3$ |
| A.1.380 | CH$_3$ | CH$_2$CH$_3$ | H | 3-methyloxiranyl-CH$_2$CH$_3$ |
| A.1.381 | CH$_3$ | CH$_2$CH$_3$ | H | 2-methyloxiranyl-CH$_2$CH$_2$CH$_3$ |
| A.1.382 | CH$_3$ | CH$_2$CH$_3$ | H | HS—CH$_2$CH$_2$CH$_3$ |
| A.1.383 | CH$_3$ | CH$_2$CH$_3$ | H | CH$_3$—S—CH$_2$CH$_2$CH$_3$ |
| A.1.384 | CH$_3$ | CH$_2$CH$_3$ | H | CH$_3$CH$_2$—S—CH$_2$CH$_2$CH$_3$ |
| A.1.385 | CH$_3$ | CH$_2$CH$_3$ | H | (CH$_3$)$_2$CH—S—CH$_2$CH$_2$CH$_3$ |
| A.1.386 | CH$_3$ | CH$_2$CH$_3$ | H | (CH$_3$)$_3$C—S—CH$_2$CH$_2$CH$_3$ |

TABLE A-continued
Meanings for $R_1$, $R_2$, $R_5$ and $R_6$:
| | | | | |
|---|---|---|---|---|
| A.1.387 | $CH_3$ | $CH_2CH_3$ | H | 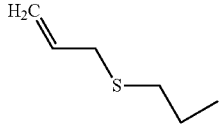 |
| A.1.388 | $CH_3$ | $CH_2CH_3$ | H | 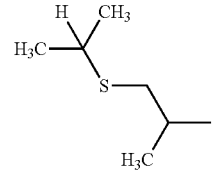 |
| A.1.389 | $CH_3$ | $CH_2CH_3$ | H | 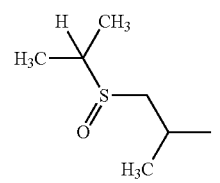 |
| A.1.390 | $CH_3$ | $CH_2CH_3$ | H | 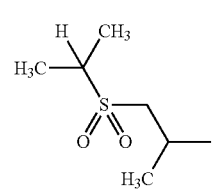 |
| A.1.391 | $CH_3$ | $CH_2CH_3$ | H | 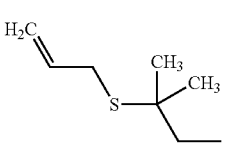 |
| A.1.392 | $CH_3$ | $CH_2CH_3$ | H | 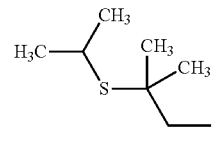 |
| A.1.393 | $CH_3$ | $CH_2CH_3$ | H | 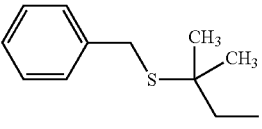 |
| A.1.394 | $CH_3$ | $CH_2CH_3$ | H | 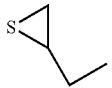 |
| A.1.395 | $CH_3$ | $CH_2CH_3$ | H | 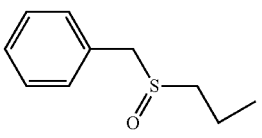 |
| A.1.396 | $CH_3$ | $CH_2CH_3$ | H | 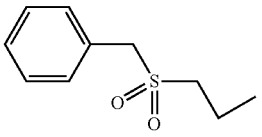 |

TABLE A-continued

| | | | | |
|---|---|---|---|---|
| | Meanings for $R_1$, $R_2$, $R_5$ and $R_6$: | | | |
| A.1.397 | $CH_3$ | $CH_2CH_3$ | H | tert-butyl-S(=O)-ethyl |
| A.1.398 | $CH_3$ | $CH_2CH_3$ | H | tert-butyl-S(=O)$_2$-ethyl |
| A.1.399 | $CH_3$ | $CH_2CH_3$ | H | phenyl-S-propyl |
| A.1.400 | $CH_3$ | $CH_2CH_3$ | H | 3-chlorophenyl-S-propyl |
| A.1.401 | $CH_3$ | $CH_2CH_3$ | H | 3-trifluoromethylphenyl-S-propyl |
| A.1.402 | $CH_3$ | $CH_2CH_3$ | H | pyridin-2-yl-S-ethyl |
| A.1.403 | $CH_3$ | $CH_2CH_3$ | H | 6-chloropyridin-2-yl-S-ethyl |
| A.1.404 | $CH_3$ | $CH_2CH_3$ | H | ethyl-S-butyl |
| A.1.405 | $CH_3$ | $CH_2CH_3$ | H | isopropyl-S-(2-methylbutyl) |

TABLE A-continued

| | | Meanings for $R_1$, $R_2$, $R_5$ and $R_6$: | | |
|---|---|---|---|---|
| A.1.406 | $CH_3$ | $CH_2CH_3$ | H | isopropyl-S-butyl |
| A.1.407 | $CH_3$ | $CH_2CH_3$ | H | isopropyl-S-(2-methylbutyl) |
| A.1.408 | $CH_3$ | $CH_2CH_3$ | H | 3-chlorophenyl-S(O)-propyl |
| A.1.409 | $CH_3$ | $CH_2CH_3$ | H | 3-chlorophenyl-S(O)$_2$-propyl |
| A.1.410 | $CH_3$ | $CH_2CH_3$ | H | isopropyl-S(O)-butyl |
| A.1.411 | $CH_3$ | $CH_2CH_3$ | H | isopropyl-S(O)$_2$-butyl |
| A.1.412 | $CH_3$ | $CH_2CH_3$ | H | $CH_3$-S-C($CH_3$)$_2$-propyl |
| A.1.413 | $CH_3$ | $CH_2CH_3$ | H | $CH_3$-S(O)-C($CH_3$)$_2$-propyl |
| A.1.414 | $CH_3$ | $CH_2CH_3$ | H | $CH_3$-S(O)$_2$-C($CH_3$)$_2$-propyl |
| A.1.415 | $CH_3$ | $CH_2CH_3$ | H | 2-propylthiirane |
| A.1.416 | $CH_3$ | $CH_2CH_3$ | H | but-1-ynyl |

TABLE A-continued

| | | | | Meanings for $R_1$, $R_2$, $R_5$ and $R_6$: |
|---|---|---|---|---|
| A.1.417 | $CH_3$ | $CH_2CH_3$ | H | 3-methyl-1-butyn-3-yl (HC≡C-CH(CH$_3$)-) |
| A.1.418 | $CH_3$ | $CH_2CH_3$ | H | 3,3-dimethyl-1-butynyl (HC≡C-C(CH$_3$)$_2$-) |
| A.1.419 | $CH_3$ | $CH_2CH_3$ | H | but-2-ynyl (CH$_3$-C≡C-CH$_2$-) |
| A.1.420 | $CH_3$ | $CH_2CH_3$ | H | 4-methylpent-2-ynyl ((CH$_3$)$_2$CH-C≡C-CH$_2$-) |
| A.1.421 | $CH_3$ | $CH_2CH_3$ | H | benzyl |
| A.1.422 | $CH_3$ | $CH_2CH_3$ | H | 3-methylbenzyl |
| A.1.423 | $CH_3$ | $CH_2CH_3$ | H | 3-chlorobenzyl |
| A.1.424 | $CH_3$ | $CH_2CH_3$ | H | 4-chlorobenzyl |
| A.1.425 | $CH_3$ | $CH_2CH_3$ | H | 2-chlorobenzyl |
| A.1.426 | $CH_3$ | $CH_2CH_3$ | H | 2,4-dichlorobenzyl |

TABLE A-continued
| | | | | Meanings for $R_1$, $R_2$, $R_5$ and $R_6$: |
|---|---|---|---|---|
| A.1.427 | $CH_3$ | $CH_2CH_3$ | H | 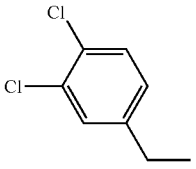 |
| A.1.428 | $CH_3$ | $CH_2CH_3$ | H | 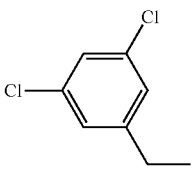 |
| A.1.429 | $CH_3$ | $CH_2CH_3$ | H | 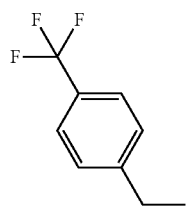 |
| A.1.430 | $CH_3$ | $CH_2CH_3$ | H | 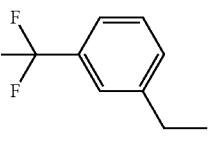 |
| A.1.431 | $CH_3$ | $CH_2CH_3$ | H | 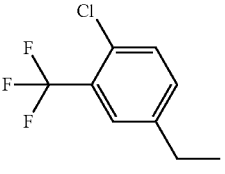 |
| A.1.432 | $CH_3$ | $CH_2CH_3$ | H | 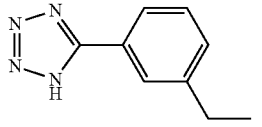 |
| A.1.433 | $CH_3$ | $CH_2CH_3$ | H | 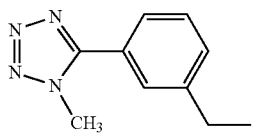 |
| A.1.434 | $CH_3$ | $CH_2CH_3$ | H | 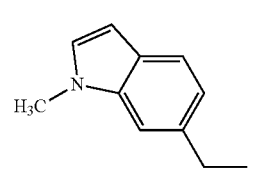 |
| A.1.435 | $CH_3$ | $CH_2CH_3$ | H | 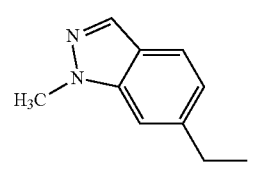 |

TABLE A-continued
Meanings for $R_1$, $R_2$, $R_5$ and $R_6$:
| Line | | | | |
|---|---|---|---|---|
| A.1.436 | CH$_3$ | CH$_2$CH$_3$ | H | 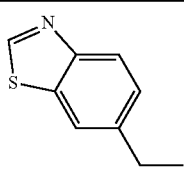 |
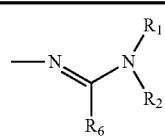
| Line | | $R_5$ |
|---|---|---|
| A.1.437 | 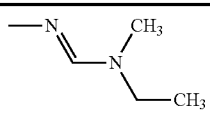 | 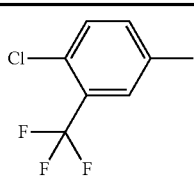 |
| A.1.438 | 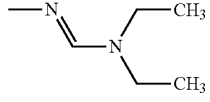 | 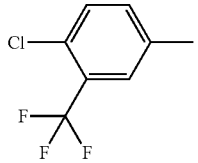 |
| A.1.439 | 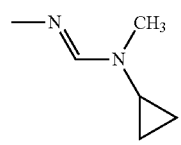 | 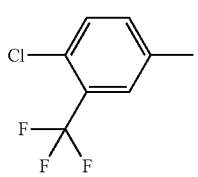 |
| A.1.440 | 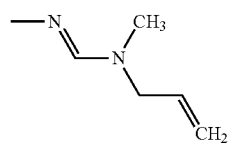 | 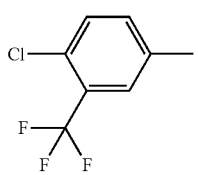 |
| A.1.441 | 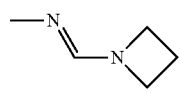 | 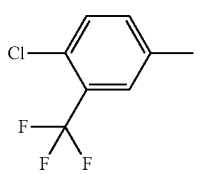 |
| A.1.442 | 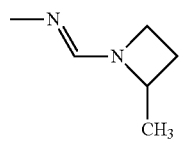 | 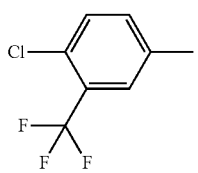 |
| A.1.443 | 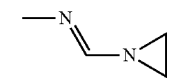 | 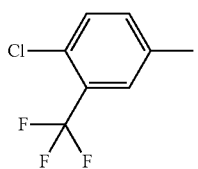 |

TABLE A-continued
| | Meanings for $R_1$, $R_2$, $R_5$ and $R_6$: | |
|---|---|---|
| A.1.444 | 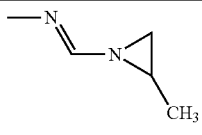 | 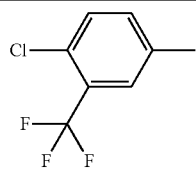 |
| A.1.445 | 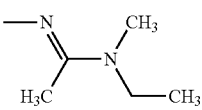 | 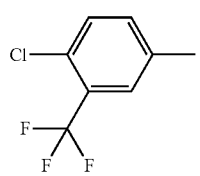 |
| A.1.446 | 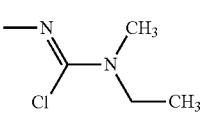 | 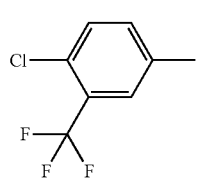 |
| A.1.447 | 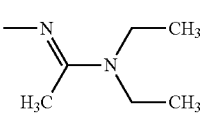 | 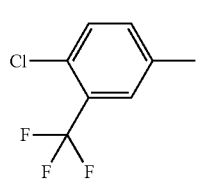 |
| A.1.448 | 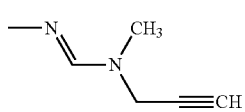 | 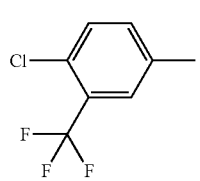 |
| A.1.449 | 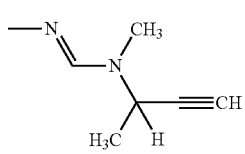 | 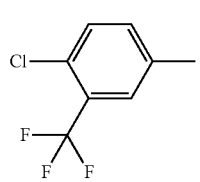 |
| A.1.450 | 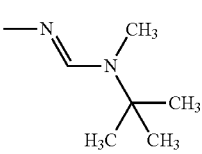 | 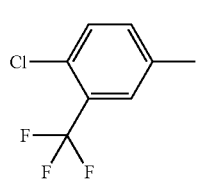 |
| A.1.451 | 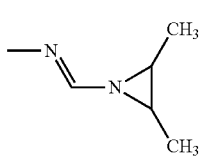 | 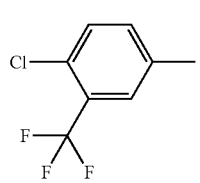 |
| A.1.452 | 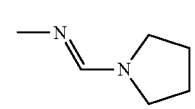 | 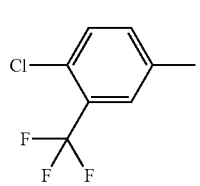 |

TABLE A-continued
Meanings for $R_1$, $R_2$, $R_5$ and $R_6$:
| | | |
|---|---|---|
| A.1.453 | 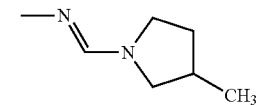 | 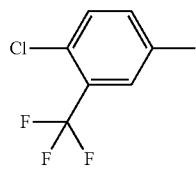 |
| A.1.454 | 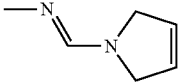 | 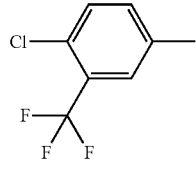 |
| A.1.455 | 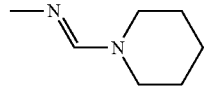 | 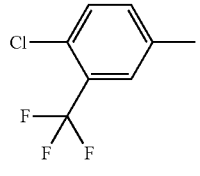 |
| A.1.456 | 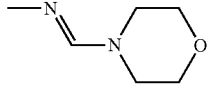 | 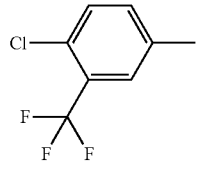 |
| A.1.457 | 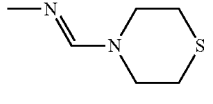 | 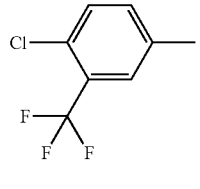 |
| A.1.458 | 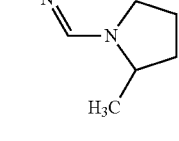 | 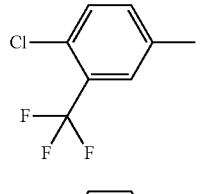 |
| A.1.459 | 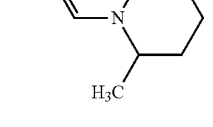 | 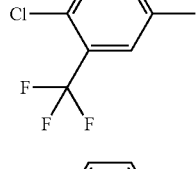 |
| A.1.460 | 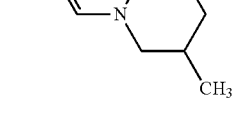 | 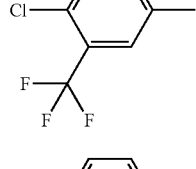 |
| A.1.461 | 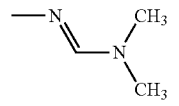 | 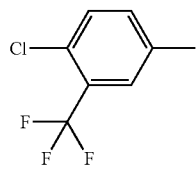 |

TABLE A-continued
Meanings for $R_1$, $R_2$, $R_5$ and $R_6$:
| | | |
|---|---|---|
| A.1.462 | 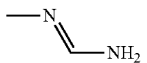 | 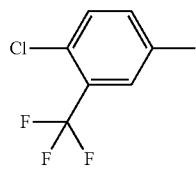 |
| A.1.463 | 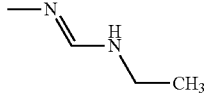 | 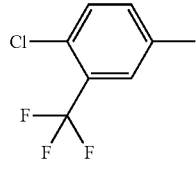 |
| A.1.464 | 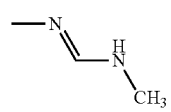 | 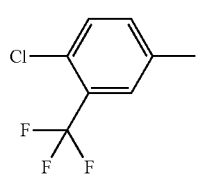 |
| A.1.465 | 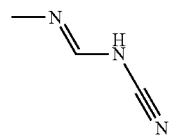 | 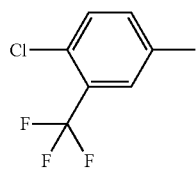 |
| A.1.466 | 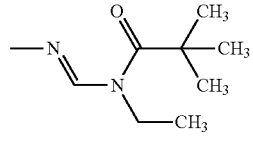 | 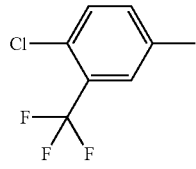 |
| A.1.467 | 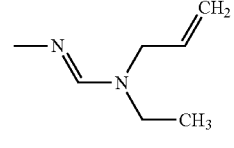 | 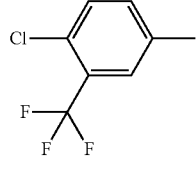 |
| A.1.468 | 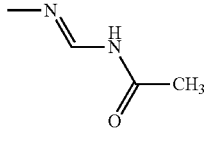 | 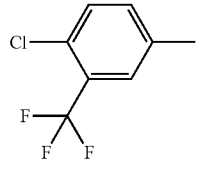 |
| A.1.469 | 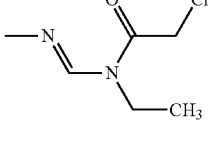 | 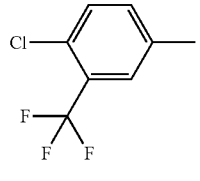 |
| A.1.470 | 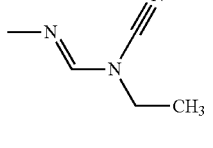 | 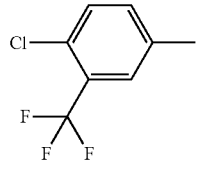 |

TABLE A-continued

Meanings for $R_1$, $R_2$, $R_5$ and $R_6$:

| | | |
|---|---|---|
| A.1.471 | —N=CH—N(SO$_2$CH$_3$)(CH$_2$CH$_3$) | 2-chloro-5-(trifluoromethyl)phenyl |
| A.1.472 | —N=CH—N(C(O)OCH$_2$CH=CH$_2$)(CH$_3$) | 2-chloro-5-(trifluoromethyl)phenyl |
| A.1.473 | —N=CH—N(NO$_2$)(CH$_2$CH$_3$) | 2-chloro-5-(trifluoromethyl)phenyl |
| A.1.474 | —N=CH—N(CH$_3$)(2-pyridyl) | 2-chloro-5-(trifluoromethyl)phenyl |
| A.1.475 | —N=CH—N(CH$_3$)(CH$_2$CH$_3$) | 2-methylhexyl |
| A.1.476 | —N=CH—N(CH$_2$CH$_3$)$_2$ | 2-methylhexyl |
| A.1.477 | —N=CH—N(CH$_3$)(cyclopropyl) | 2-methylhexyl |
| A.1.478 | —N=CH—N(CH$_3$)(CH$_2$CH=CH$_2$) | 2-methylhexyl |
| A.1.479 | —N=CH—N(azetidin-1-yl) | 2-methylhexyl |
| A.1.480 | —N=CH—N(2-methylazetidin-1-yl) | 2-methylhexyl |
| A.1.481 | —N=CH—N(aziridin-1-yl) | 2-methylhexyl |

TABLE A-continued
Meanings for $R_1$, $R_2$, $R_5$ and $R_6$:
| | | |
|---|---|---|
| A.1.482 | 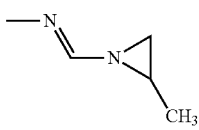 | 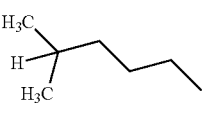 |
| A.1.483 | 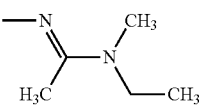 | 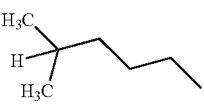 |
| A.1.484 | 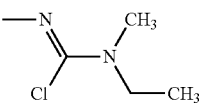 | 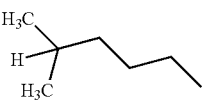 |
| A.1.485 | 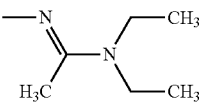 | 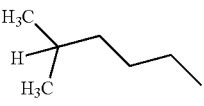 |
| A.1.486 | 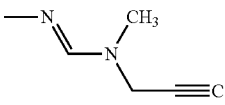 | 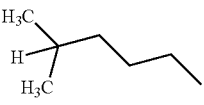 |
| A.1.487 | 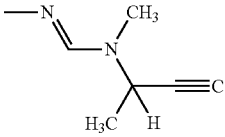 | 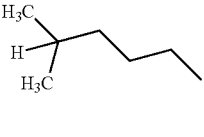 |
| A.1.488 | 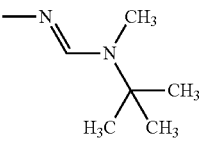 | 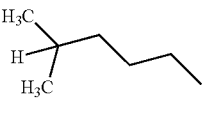 |
| A.1.489 | 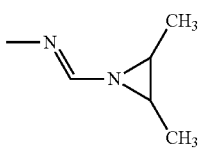 | 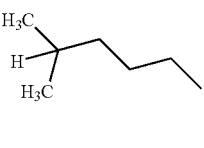 |
| A.1.490 | 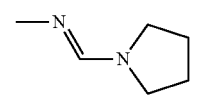 | 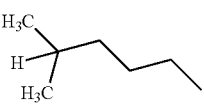 |
| A.1.491 | 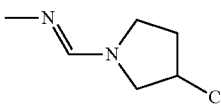 | 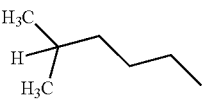 |
| A.1.492 | 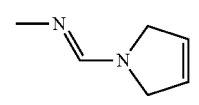 | 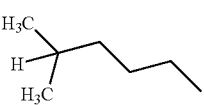 |
| A.1.493 | 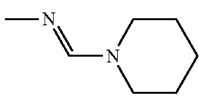 | 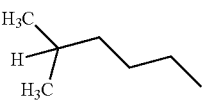 |

TABLE A-continued

Meanings for $R_1$, $R_2$, $R_5$ and $R_6$:

| | | |
|---|---|---|
| A.1.494 | —N=CH—N(morpholine) | (CH$_3$)$_2$CH-CH$_2$CH$_2$CH$_3$ |
| A.1.495 | —N=CH—N(thiomorpholine) | (CH$_3$)$_2$CH-CH$_2$CH$_2$CH$_3$ |
| A.1.496 | —N=CH—N(2-methylpyrrolidine) | (CH$_3$)$_2$CH-CH$_2$CH$_2$CH$_3$ |
| A.1.497 | —N=CH—N(2-methylpiperidine) | (CH$_3$)$_2$CH-CH$_2$CH$_2$CH$_3$ |
| A.1.498 | —N=CH—N(3-methylpiperidine) | (CH$_3$)$_2$CH-CH$_2$CH$_2$CH$_3$ |
| A.1.499 | —N=CH—N(CH$_3$)$_2$ | (CH$_3$)$_2$CH-CH$_2$CH$_2$CH$_3$ |
| A.1.500 | —N=CH—NH$_2$ | (CH$_3$)$_2$CH-CH$_2$CH$_2$CH$_3$ |
| A.1.501 | —N=CH—NH—CH$_2$CH$_3$ | (CH$_3$)$_2$CH-CH$_2$CH$_2$CH$_3$ |
| A.1.502 | —N=CH—NH—CH$_3$ | (CH$_3$)$_2$CH-CH$_2$CH$_2$CH$_3$ |
| A.1.503 | —N=CH—NH—C≡N | (CH$_3$)$_2$CH-CH$_2$CH$_2$CH$_3$ |
| A.1.504 | —N=CH—N(CH$_2$CH$_3$)—C(=O)—C(CH$_3$)$_3$ | (CH$_3$)$_2$CH-CH$_2$CH$_2$CH$_3$ |
| A.1.505 | —N=CH—N(CH$_2$CH$_3$)—CH$_2$—CH=CH$_2$ | (CH$_3$)$_2$CH-CH$_2$CH$_2$CH$_3$ |

TABLE A-continued
| | Meanings for $R_1$, $R_2$, $R_5$ and $R_6$: | |
|---|---|---|
| A.1.506 | 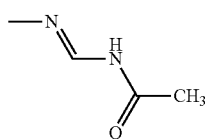 | 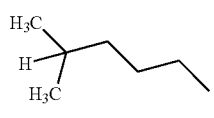 |
| A.1.507 | 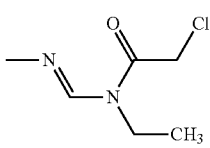 | 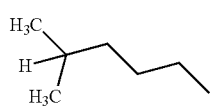 |
| A.1.508 | 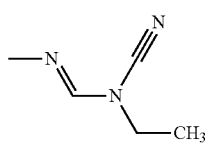 | 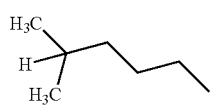 |
| A.1.509 | 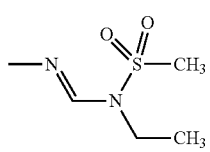 | 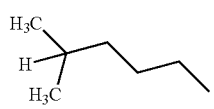 |
| A.1.510 | 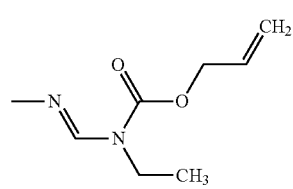 | 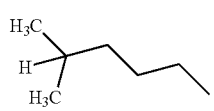 |
| A.1.511 | 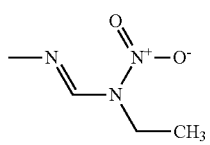 | 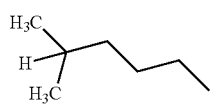 |
| A.1.512 | 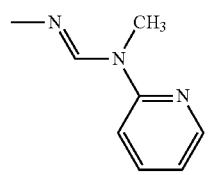 | 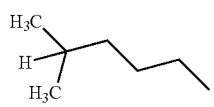 |
| A.1.513 | 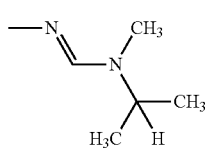 | 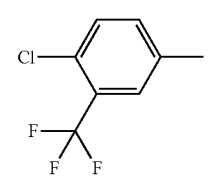 |
| A.1.514 | 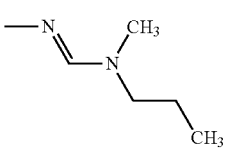 | 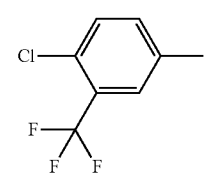 |

TABLE A-continued
Meanings for $R_1$, $R_2$, $R_5$ and $R_6$:
| | | |
|---|---|---|
| A.1.515 | 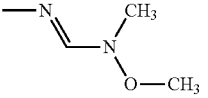 | 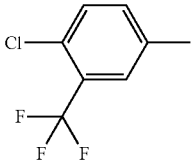 |
| A.1.516 | 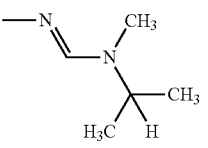 | 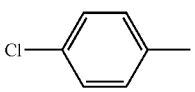 |
| A.1.517 | 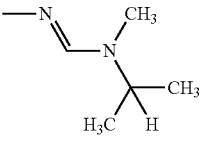 | 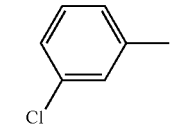 |
| A.1.518 | 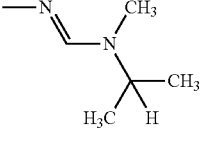 | 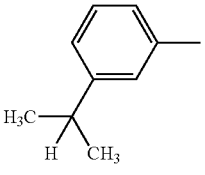 |
| A.1.519 | 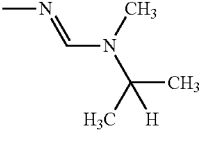 | 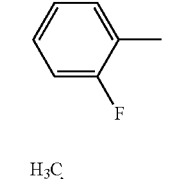 |
| A.1.520 | 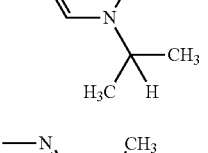 | 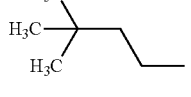 |
| A.1.521 | 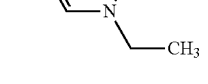 | 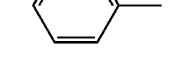 |
| A.1.522 | 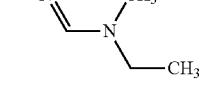 | 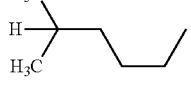 |
| A.1.523 | 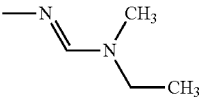 | 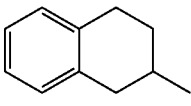 |
| A.1.524 | 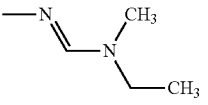 | 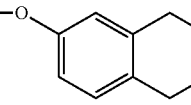 |
| A.1.525 | 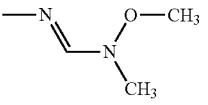 | 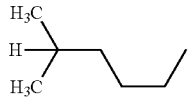 |

TABLE A-continued

Meanings for $R_1$, $R_2$, $R_5$ and $R_6$:

| | | |
|---|---|---|
| A.1.526 | —N=CH—N(CH$_2$CH$_3$)(CH$_2$CH$_3$) | (CH$_3$)$_2$CH-CH(CH$_3$)-CH$_2$-CH$_2$- (with H) |
| A.1.527 | —N=CH—N(CH$_3$)(CH$_2$CH$_3$) | 3,5-difluoro-isopropylphenyl |
| A.1.528 | —N=CH—N(CH$_3$)(CH$_2$CH$_3$) | 3,5-difluoro-ethylphenyl |
| A.1.529 | —N=CH—N(CH$_3$)(CH$_2$CH$_3$) | 3,5-dichloro-isopropylphenyl |
| A.1.530 | —N=CH—N(CH$_3$)(CH$_2$CH$_3$) | 3-fluoro-isopropylphenyl |
| A.1.531 | —N=CH—N(CH$_3$)(CH$_2$CH$_3$) | 3-methyl-isopropylphenyl |
| A.1.532 | —N=CH—N(CH$_3$)(CH$_2$CH$_3$) | tert-butylphenyl |
| A.1.533 | —N=CH—N(CH$_3$)(CH$_2$CH$_3$) | sec-butylphenyl |
| A.1.534 | —N=CH—N(CH$_3$)(CH$_2$CH$_3$) | methylcyclopentenyl |
| A.1.535 | —N=CH—N(CH$_3$)(CH$_2$CH$_3$) | 1,2-dimethyl-4-methyl-cyclopentenyl |
| A.1.536 | —N=CH—N(CH$_3$)(CH$_2$CH$_3$) | 1,2-dimethyl-4-methyl-cyclopentyl |

TABLE A-continued

| | Meanings for $R_1$, $R_2$, $R_5$ and $R_6$: | |
|---|---|---|
| A.1.537 | —N=CH—N(CH₃)(CH₂CH₃) | 1,2-dimethyl-cyclohept-1-enyl (methyl-substituted) |
| A.1.538 | —N=CH—N(CH₃)(CH₂CH₃) | 2,3-dimethylcycloheptyl |
| A.1.539 | —N=CH—N(CH₃)(CH₂CH₃) | 2-methylcyclohept-2-enyl |
| A.1.540 | —N=CH—N(CH₃)(CH₂CH₃) | 2-methylenehexyl |
| A.1.541 | —N=CH—N(CH₃)(CH₂CH₃) | hex-2-enyl |
| A.1.542 | —N=CH—N(CH₃)(CH₂CH₃) | 1-(3-fluorophenyl)ethyl |
| A.1.543 | —N=CH—N(CH₂CH₃)(CH₂CH₃) | cyclopent-3-enyl |
| A.1.544 | —N=CH—N(CH₃)(CH(CH₃)₂) | cyclopent-3-enyl |
| A.1.545 | —N=CH—N(CH₃)(CH(CH₃)C≡CH) | cyclopent-3-enyl |
| A.1.546 | —N=CH—N(CH₃)(CH₂CH₃) | 2-methylbenzyl (#) |
| A.1.547 | —N=CH—N(CH₃)(CH₂CH₃) | 4-methylbenzyl (#) |

TABLE A-continued

Meanings for $R_1$, $R_2$, $R_5$ and $R_6$:

| | | |
|---|---|---|
| A.1.548 | —N=CH—N(CH$_3$)CH$_2$CH$_3$ | 2-ethylbenzyl |
| A.1.549 | —N=CH—N(CH$_3$)CH$_2$CH$_3$ | 3-ethylbenzyl |
| A.1.550 | —N=CH—N(CH$_3$)CH$_2$CH$_3$ | 4-ethylbenzyl |
| A.1.551 | —N=CH—N(CH$_3$)CH$_2$CH$_3$ | 2,3-dimethylbenzyl |
| A.1.552 | —N=CH—N(CH$_3$)CH$_2$CH$_3$ | 2,4-dimethylbenzyl |
| A.1.553 | —N=CH—N(CH$_3$)CH$_2$CH$_3$ | 2,5-dimethylbenzyl |
| A.1.554 | —N=CH—N(CH$_3$)CH$_2$CH$_3$ | 2,6-dimethylbenzyl |
| A.1.555 | —N=CH—N(CH$_3$)CH$_2$CH$_3$ | 3,5-dimethylbenzyl |
| A.1.556 | —N=CH—N(CH$_3$)CH$_2$CH$_3$ | 3,4-dimethylbenzyl |

TABLE A-continued

Meanings for $R_1$, $R_2$, $R_5$ and $R_6$:

| | | |
|---|---|---|
| A.1.557 | —N=CH—N(CH$_3$)—CH$_2$CH$_3$ | 2-methylphenyl-CH(CH$_3$)-# |
| A.1.558 | —N=CH—N(CH$_3$)—CH$_2$CH$_3$ | 4-methylphenyl-CH(CH$_3$)-# |
| A.1.559 | —N=CH—N(CH$_3$)—CH$_2$CH$_3$ | 2-ethylphenyl-CH(CH$_3$)-# |
| A.1.560 | —N=CH—N(CH$_3$)—CH$_2$CH$_3$ | 3-ethylphenyl-CH(CH$_3$)-# |
| A.1.561 | —N=CH—N(CH$_3$)—CH$_2$CH$_3$ | 4-ethylphenyl-CH(CH$_3$)-# |
| A.1.562 | —N=CH—N(CH$_3$)—CH$_2$CH$_3$ | 2,3-dimethylphenyl-CH(CH$_3$)-# |
| A.1.563 | —N=CH—N(CH$_3$)—CH$_2$CH$_3$ | 2,4-dimethylphenyl-CH(CH$_3$)-# |
| A.1.564 | —N=CH—N(CH$_3$)—CH$_2$CH$_3$ | 2,5-dimethylphenyl-CH(CH$_3$)-# |

TABLE A-continued

Meanings for $R_1$, $R_2$, $R_5$ and $R_6$:

| | | |
|---|---|---|
| A.1.565 | —N=CH—N(CH₃)—CH₂CH₃ | 1-(2,6-dimethylphenyl)ethyl-# |
| A.1.566 | —N=CH—N(CH₃)—CH₂CH₃ | 1-(3,5-dimethylphenyl)ethyl-# |
| A.1.567 | —N=CH—N(CH₃)—CH₂CH₃ | 1-(3,4-dimethylphenyl)ethyl-# |
| A.1.568 | —N=CH—N(CH₃)—CH₂CH₃ | (2,4,6-trimethylphenyl)methyl-# |
| A.1.569 | —N=CH—N(CH₃)—CH₂CH₃ | 1-(2,4,6-trimethylphenyl)ethyl-# |
| A.1.570 | —N=CH—N(CH₃)—CH₂CH₃ | (5,6,7,8-tetrahydronaphthalen-2-yl)methyl-# |
| A.1.571 | —N=CH—N(CH₃)—CH₂CH₃ | 1-(5,6,7,8-tetrahydronaphthalen-2-yl)ethyl-# |
| A.1.572 | —N=CH—N(CH₃)—CH₂CH₃ | (5,6,7,8-tetrahydronaphthalen-1-yl)methyl-# |

TABLE A-continued

| | Meanings for $R_1$, $R_2$, $R_5$ and $R_6$: | |
|---|---|---|
| A.1.573 | —N=CH—N(CH₃)(CH₂CH₃) | 1-(1,2,3,4-tetrahydronaphthalen-1-yl)ethyl # |
| A.1.574 | —N=CH—N(CH₃)(CH₂CH₃) | 3-ethylbenzyl # |
| A.1.575 | —N=CH—N(CH₃)(CH₂CH₃) | 2,6-dichlorobenzyl # |
| A.1.576 | —N=CH—N(CH₃)(CH₂CH₃) | 1-(2-chlorophenyl)ethyl # |
| A.1.577 | —N=CH—N(CH₃)(CH₂CH₃) | 1-(3-chlorophenyl)ethyl # |
| A.1.578 | —N=CH—N(CH₃)(CH₂CH₃) | 1-(4-chlorophenyl)ethyl # |
| A.1.579 | —N=CH—N(CH₃)(CH₂CH₃) | 1-(2,3-dichlorophenyl)ethyl # |
| A.1.580 | —N=CH—N(CH₃)(CH₂CH₃) | 1-(2,4-dichlorophenyl)ethyl # |

TABLE A-continued
| | Meanings for $R_1$, $R_2$, $R_5$ and $R_6$: | |
|---|---|---|
| A.1.581 | 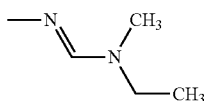 | 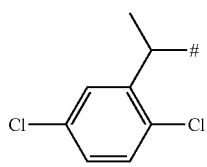 |
| A.1.582 | 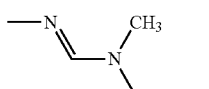 | 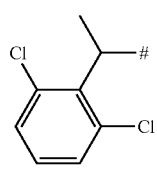 |
| A.1.583 | 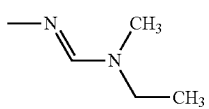 | 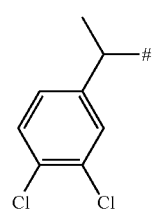 |
| A.1.584 | 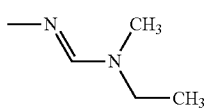 | 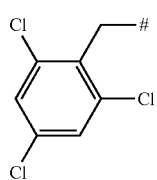 |
| A.1.585 | 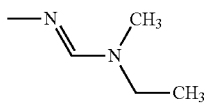 | 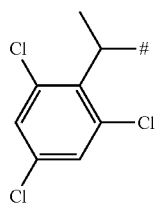 |
| A.1.586 | 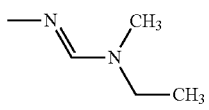 | 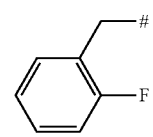 |
| A.1.587 | 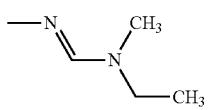 | 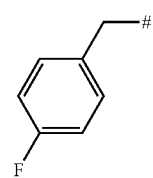 |
| A.1.588 | 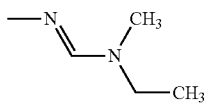 | 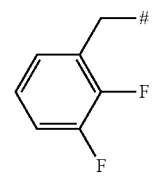 |

TABLE A-continued

Meanings for $R_1$, $R_2$, $R_5$ and $R_6$:

| | | |
|---|---|---|
| A.1.589 | —N=CH—N(CH$_3$)(CH$_2$CH$_3$) | 2,4-difluorobenzyl |
| A.1.590 | —N=CH—N(CH$_3$)(CH$_2$CH$_3$) | 2,5-difluorobenzyl |
| A.1.591 | —N=CH—N(CH$_3$)(CH$_2$CH$_3$) | 2,6-difluorobenzyl |
| A.1.592 | —N=CH—N(CH$_3$)(CH$_2$CH$_3$) | 3,4-difluorobenzyl |
| A.1.593 | —N=CH—N(CH$_3$)(CH$_2$CH$_3$) | 1-(2-fluorophenyl)ethyl |
| A.1.594 | —N=CH—N(CH$_3$)(CH$_2$CH$_3$) | 1-(4-fluorophenyl)ethyl |
| A.1.595 | —N=CH—N(CH$_3$)(CH$_2$CH$_3$) | 2-bromobenzyl |
| A.1.596 | —N=CH—N(CH$_3$)(CH$_2$CH$_3$) | 2-ethynylbenzyl |
| A.1.597 | —N=CH—N(CH$_3$)(CH$_2$CH$_3$) | 2-cyanobenzyl |
| A.1.598 | —N=CH—N(CH$_3$)(CH$_2$CH$_3$) | 2-phenylbenzyl |

TABLE A-continued

Meanings for $R_1$, $R_2$, $R_5$ and $R_6$:

| | | |
|---|---|---|
| A.1.599 | —N=CH—N(CH₃)(CH₂CH₃) | 1-(2-bromophenyl)ethyl-# |
| A.1.600 | —N=CH—N(CH₃)(CH₂CH₃) | 1-(2-ethynylphenyl)ethyl-# |
| A.1.601 | —N=CH—N(CH₃)(CH₂CH₃) | 1-(2-cyanophenyl)ethyl-# |
| A.1.602 | —N=CH—N(CH₃)(CH₂CH₃) | 1-(biphenyl-2-yl)ethyl-# |
| A.1.603 | —N=CH—N(CH₃)(CH₂CH₃) | 1-(2,3-difluorophenyl)ethyl-# |
| A.1.604 | —N=CH—N(CH₃)(CH₂CH₃) | 1-(2,4-difluorophenyl)ethyl-# |
| A.1.605 | —N=CH—N(CH₃)(CH₂CH₃) | 1-(2,5-difluorophenyl)ethyl-# |
| A.1.606 | —N=CH—N(CH₃)(CH₂CH₃) | 1-(2,6-difluorophenyl)ethyl-# |

TABLE A-continued

Meanings for $R_1$, $R_2$, $R_5$ and $R_6$:

| | | |
|---|---|---|
| A.1.607 | —N=CH—N(CH₃)(CH₃) | 1-(3,4-difluorophenyl)ethyl-# |
| A.1.608 | —N=CH—N(CH₃)(CH₃) | 2,4,6-trifluorobenzyl-# |
| A.1.609 | —N=CH—N(CH₃)(CH₃) | 3,4,5-trifluorobenzyl-# |
| A.1.610 | —N=CH—N(CH₃)(CH₃) | 1-(3,4,5-trifluorophenyl)ethyl-# |
| A.1.611 | —N=CH—N(CH₃)(CH₃) | 4-chloro-2-fluorobenzyl-# |
| A.1.612 | —N=CH—N(CH₃)(CH₃) | 2-chloro-4-fluorobenzyl-# |
| A.1.613 | —N=CH—N(CH₃)(CH₃) | 3-chloro-5-fluorobenzyl-# |
| A.1.614 | —N=CH—N(CH₃)(CH₃) | 1-(3-chloro-5-fluorophenyl)ethyl-# |

TABLE A-continued
| | Meanings for $R_1$, $R_2$, $R_5$ and $R_6$: | |
|---|---|---|
| A.1.615 | 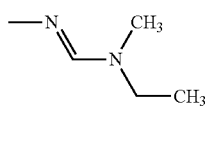 | 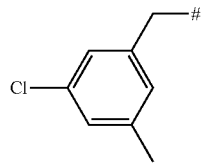 |
| A.1.616 | 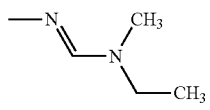 | 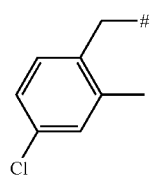 |
| A.1.617 | 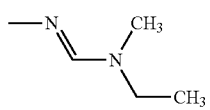 | 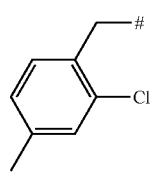 |
| A.1.618 | 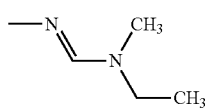 | 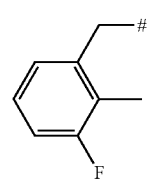 |
| A.1.619 | 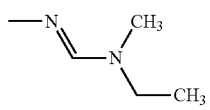 | 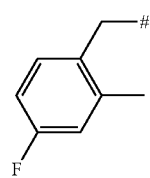 |
| A.1.620 | 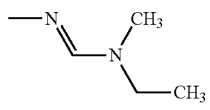 | 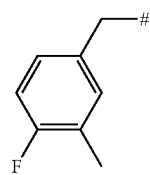 |
| A.1.621 | 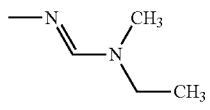 |  |
| A.1.622 | 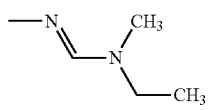 | 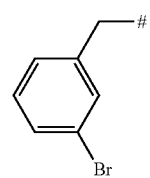 |

TABLE A-continued
Meanings for $R_1$, $R_2$, $R_5$ and $R_6$:
| | | |
|---|---|---|
| A.1.623 | 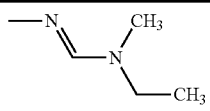 | 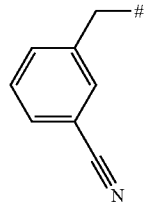 |
| A.1.624 | 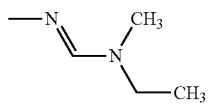 | 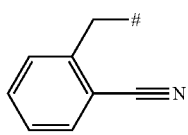 |
| A.1.625 | 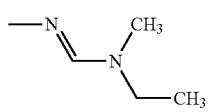 | 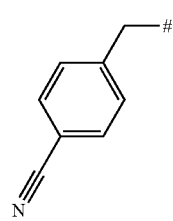 |
| A.1.626 | 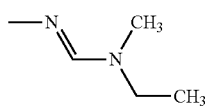 | 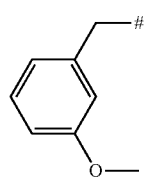 |
| A.1.627 | 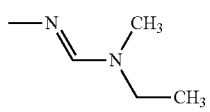 | 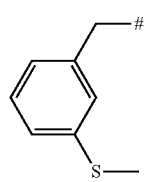 |
| A.1.628 | 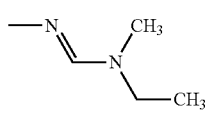 | 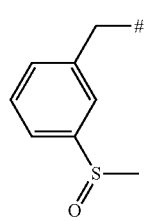 |
| A.1.629 | 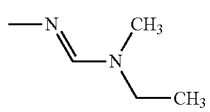 | 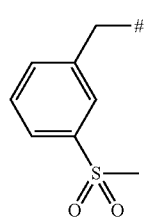 |
| A.1.630 | 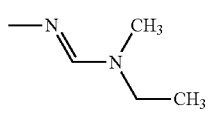 | 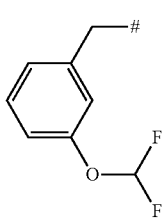 |

TABLE A-continued
Meanings for $R_1$, $R_2$, $R_5$ and $R_6$:
| | | |
|---|---|---|
| A.1.631 | 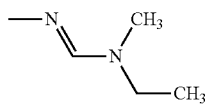 | 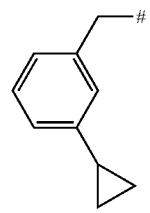 |
| A.1.632 | 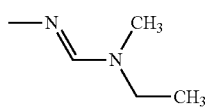 | 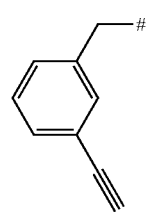 |
| A.1.633 | 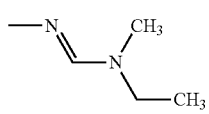 | 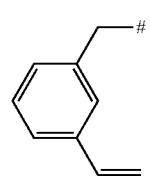 |
| A.1.634 | 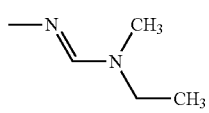 | 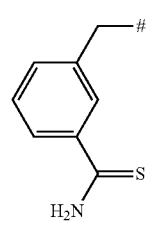 |
| A.1.635 | 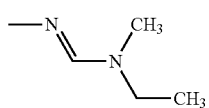 | 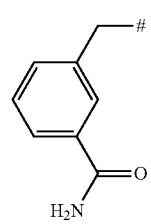 |
| A.1.636 | 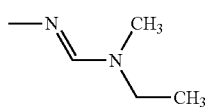 | 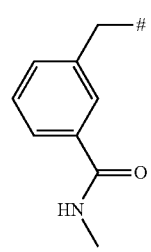 |
| A.1.637 | 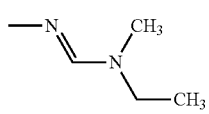 | 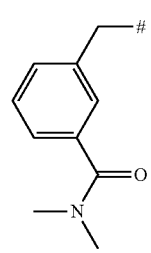 |

TABLE A-continued

| | Meanings for $R_1$, $R_2$, $R_5$ and $R_6$: | |
|---|---|---|
| A.1.638 | —N=CH—N(CH$_3$)—CH$_2$CH$_3$ | 3-(isopropoxycarbonyl)benzyl |
| A.1.639 | —N=CH—N(CH$_3$)—CH$_2$CH$_3$ | 2-methyl-3-cyanobenzyl |
| A.1.640 | —N=CH—N(CH$_3$)—CH$_2$CH$_3$ | 3-chloro-2-methylbenzyl |
| A.1.641 | —N=CH—N(CH$_3$)—CH$_2$CH$_3$ | 3-chloro-4-methoxybenzyl |
| A.1.642 | —N=CH—N(CH$_3$)—CH$_2$CH$_3$ | 1-(3-chloro-4-methoxyphenyl)ethyl |
| A.1.643 | —N=CH—N(CH$_3$)—CH$_2$CH$_3$ | 2-phenylethyl |
| A.1.644 | —N=CH—N(CH$_3$)—CH$_2$CH$_3$ | 2-methyl-2-phenylethyl |
| A.1.645 | —N=CH—N(CH$_3$)—CH$_2$CH$_3$ | 2-phenylpropyl |
| A.1.646 | —N=CH—N(CH$_3$)—CH$_2$CH$_3$ | 3-phenylbut-2-yl |

TABLE A-continued
Meanings for $R_1$, $R_2$, $R_5$ and $R_6$:
| | | |
|---|---|---|
| A.1.647 | 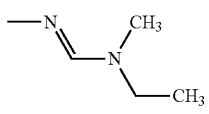 | 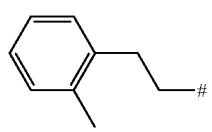 |
| A.1.648 | 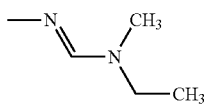 | 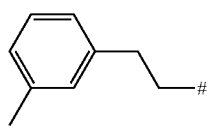 |
| A.1.649 | 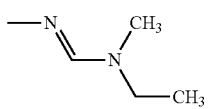 | 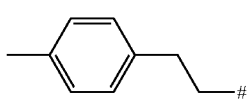 |
| A.1.650 | 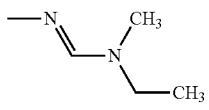 | 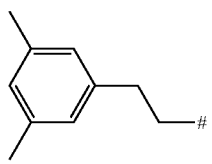 |
| A.1.651 | 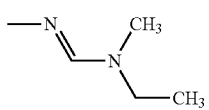 | 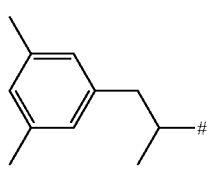 |
| A.1.652 | 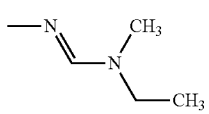 | 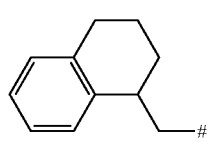 |
| A.1.653 | 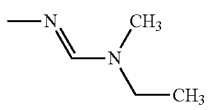 | 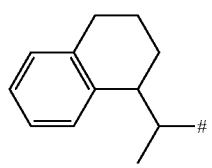 |
| A.1.654 | 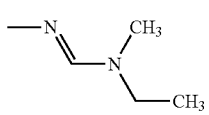 | 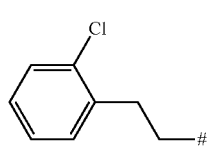 |
| A.1.655 | 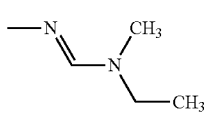 | 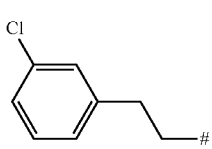 |
| A.1.656 | 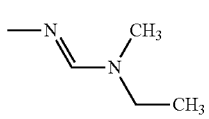 | 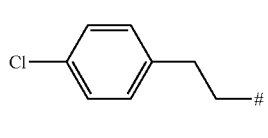 |
| A.1.657 | 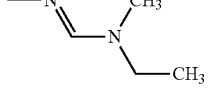 | 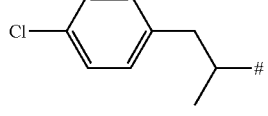 |

TABLE A-continued

| | Meanings for $R_1$, $R_2$, $R_5$ and $R_6$: | |
|---|---|---|
| A.1.658 | —N=CH—N(CH₃)(CH₂CH₃) | 4-methoxyphenethyl-# |
| A.1.659 | —N=CH—N(CH₃)(CH₂CH₃) | 3-methoxyphenethyl-# |
| A.1.660 | —N=CH—N(CH₃)(CH₂CH₃) | 2-(4-methoxyphenyl)propyl-# |
| A.1.661 | —N=CH—N(CH₃)(CH₂CH₃) | 2-fluorophenethyl-# |
| A.1.662 | —N=CH—N(CH₃)(CH₂CH₃) | 3-fluorophenethyl-# |
| A.1.663 | —N=CH—N(CH₃)(CH₂CH₃) | 4-fluorophenethyl-# |
| A.1.664 | —N=CH—N(CH₃)(CH₂CH₃) | 3,5-difluorophenethyl-# |
| A.1.665 | —N=CH—N(CH₃)(CH₂CH₃) | 3,5-dichlorophenethyl-# |
| A.1.666 | —N=CH—N(CH₃)(CH₂CH₃) | 2-(3,5-dichlorophenyl)propyl-# |
| A.1.667 | —N=CH—N(CH₃)(CH₂CH₃) | 3-cyanophenethyl-# |

TABLE A-continued

Meanings for $R_1$, $R_2$, $R_5$ and $R_6$:

| | | |
|---|---|---|
| A.1.668 | —N=CH–N(CH$_3$)(CH$_2$CH$_3$) | 4-cyanophenyl–CH$_2$CH$_2$–# |
| A.1.669 | —N=CH–N(CH$_3$)(CH$_2$CH$_3$) | phenyl–CH$_2$CH$_2$CH$_2$–# |
| A.1.670 | —N=CH–N(CH$_3$)(CH$_2$CH$_3$) | phenyl–CH$_2$CH(CH$_3$)–# |
| A.1.671 | —N=CH–N(CH$_3$)(CH$_2$CH$_3$) | tetrahydronaphthalen-2-ylmethyl–# |
| A.1.672 | —N=CH–N(CH$_3$)(CH$_2$CH$_3$) | 1-(tetrahydronaphthalen-2-yl)ethyl–# |
| A.1.673 | —N=CH–N(CH$_3$)(CH$_2$CH$_3$) | 2-methylphenyl–CH$_2$CH$_2$CH$_2$–# |
| A.1.674 | —N=CH–N(CH$_3$)(CH$_2$CH$_3$) | 3-methylphenyl–CH$_2$CH$_2$CH$_2$–# |
| A.1.675 | —N=CH–N(CH$_3$)(CH$_2$CH$_3$) | 4-methylphenyl–CH$_2$CH$_2$–# |
| A.1.676 | —N=CH–N(CH$_3$)(CH$_2$CH$_3$) | 3-chlorophenyl–CH$_2$CH$_2$–# |
| A.1.677 | —N=CH–N(CH$_3$)(CH$_2$CH$_3$) | 3-chlorophenyl–CH$_2$CH(CH$_3$)–# |

TABLE A-continued
Meanings for $R_1$, $R_2$, $R_5$ and $R_6$:
| | | |
|---|---|---|
| A.1.678 | 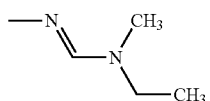 | 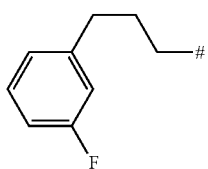 |
| A.1.679 | 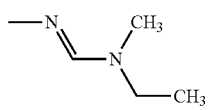 | 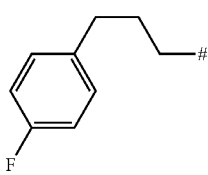 |
| A.1.680 | 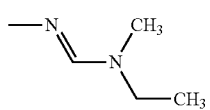 | 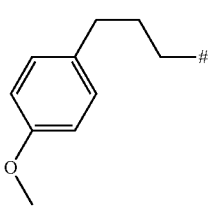 |
| A.1.681 | 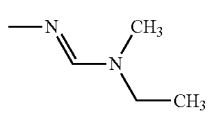 | 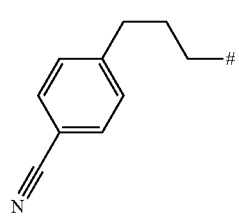 |
| A.1.682 | 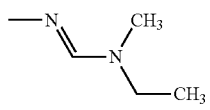 | 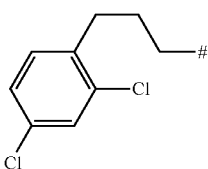 |
| A.1.683 | 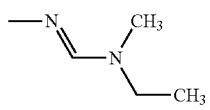 | 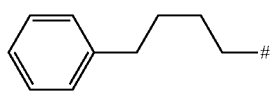 |
| A.1.684 | 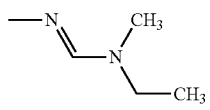 | 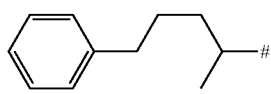 |
| A.1.685 | 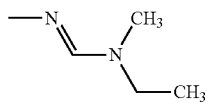 | 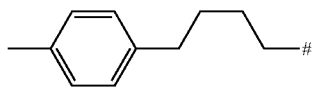 |
| A.1.686 | 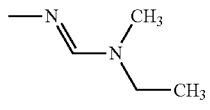 | 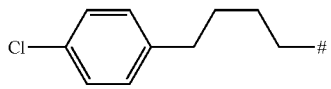 |
| A.1.687 | 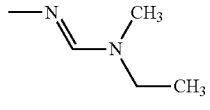 | 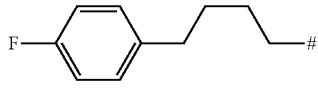 |

TABLE A-continued
Meanings for $R_1$, $R_2$, $R_5$ and $R_6$:
| | | |
|---|---|---|
| A.1.688 | 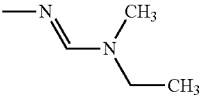 | 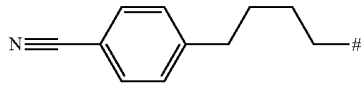 |
| A.1.689 | 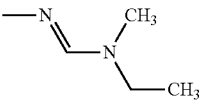 | 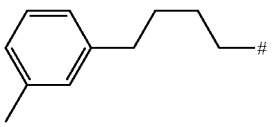 |
| A.1.690 | 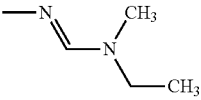 | 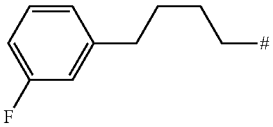 |
| A.1.691 | 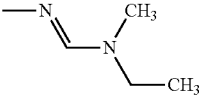 | 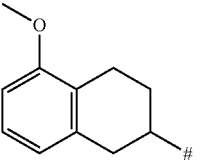 |
| A.1.692 | 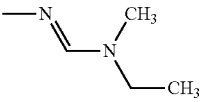 | 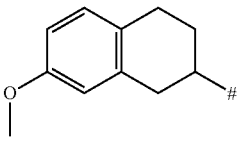 |
| A.1.693 | 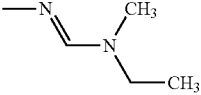 | 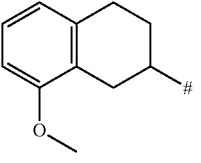 |
| A.1.694 | 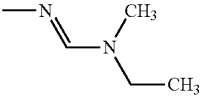 | 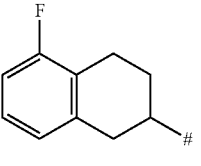 |
| A.1.695 | 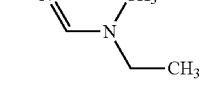 | 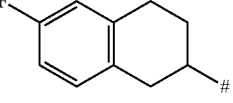 |
| A.1.696 | 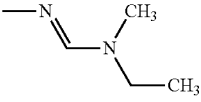 | 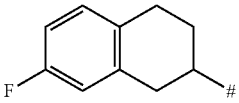 |
| A.1.697 | 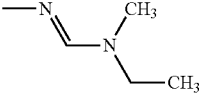 | 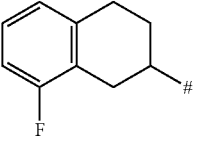 |
| A.1.698 | 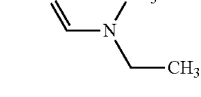 | 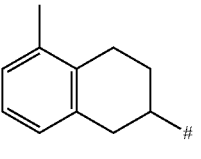 |

TABLE A-continued

Meanings for $R_1$, $R_2$, $R_5$ and $R_6$:

| | | |
|---|---|---|
| A.1.699 | —N=CH—N(CH₃)(CH₂CH₃) | 6-methyl-tetralin-2-yl (#) |
| A.1.700 | —N=CH—N(CH₃)(CH₂CH₃) | 7-methyl-tetralin-2-yl (#) |
| A.1.701 | —N=CH—N(CH₃)(CH₂CH₃) | 8-methyl-tetralin-2-yl (#) |
| A.1.702 | —N=CH—N(CH₃)(CH₂CH₃) | 5-Cl-tetralin-2-yl (#) |
| A.1.703 | —N=CH—N(CH₃)(CH₂CH₃) | 6-Cl-tetralin-2-yl (#) |
| A.1.704 | —N=CH—N(CH₃)(CH₂CH₃) | 7-Cl-tetralin-2-yl (#) |
| A.1.705 | —N=CH—N(CH₃)(CH₂CH₃) | 8-Cl-tetralin-2-yl (#) |
| A.1.706 | —N=CH—N(CH₃)(CH₂CH₃) | 7-Br-tetralin-2-yl (#) |
| A.1.707 | —N=CH—N(CH₃)(CH₂CH₃) | indan-2-yl (#) |
| A.1.708 | —N=CH—N(CH₃)(CH₂CH₃) | 4-methoxy-indan-2-yl (#) |
| A.1.709 | —N=CH—N(CH₃)(CH₂CH₃) | 5-methoxy-indan-2-yl (#) |
| A.1.710 | —N=CH—N(CH₃)(CH₂CH₃) | 5-hydroxy-indan-2-yl (#) |

TABLE A-continued

Meanings for $R_1$, $R_2$, $R_5$ and $R_6$:

| | | |
|---|---|---|
| A.1.711 | —N=CH—N(CH$_3$)(CH$_2$CH$_3$) | 4-hydroxyindan-2-yl (#), OH at position shown |
| A.1.712 | —N=CH—N(CH$_3$)(CH$_2$CH$_3$) | 4-chloroindan-2-yl |
| A.1.713 | —N=CH—N(CH$_3$)(CH$_2$CH$_3$) | 5-chloroindan-2-yl |
| A.1.714 | —N=CH—N(CH$_3$)(CH$_2$CH$_3$) | 6-chloroindan-2-yl |
| A.1.715 | —N=CH—N(CH$_3$)(CH$_2$CH$_3$) | 7-chloroindan-2-yl |
| A.1.716 | —N=CH—N(CH$_3$)(CH$_2$CH$_3$) | 4-fluoroindan-2-yl |
| A.1.717 | —N=CH—N(CH$_3$)(CH$_2$CH$_3$) | 5-fluoroindan-2-yl |
| A.1.718 | —N=CH—N(CH$_3$)(CH$_2$CH$_3$) | 6-fluoroindan-2-yl |
| A.1.719 | —N=CH—N(CH$_3$)(CH$_2$CH$_3$) | 7-fluoroindan-2-yl |
| A.1.720 | —N=CH—N(CH$_3$)(CH$_2$CH$_3$) | 4-methylindan-2-yl |
| A.1.721 | —N=CH—N(CH$_3$)(CH$_2$CH$_3$) | 5-methylindan-2-yl |

TABLE A-continued
Meanings for $R_1$, $R_2$, $R_5$ and $R_6$:
| | | |
|---|---|---|
| A.1.722 | 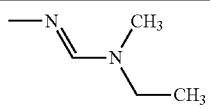 | 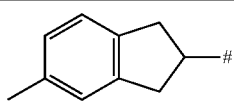 |
| A.1.723 | 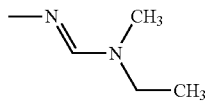 | 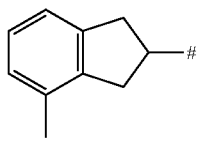 |
| A.1.724 | 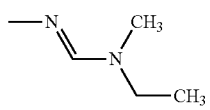 | 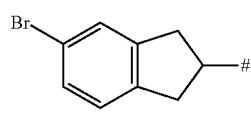 |
| A.1.725 | 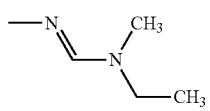 | 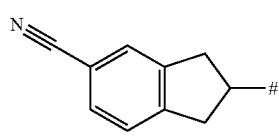 |
| A.1.726 | 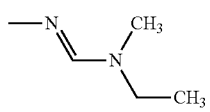 | 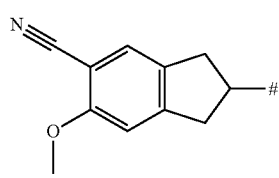 |
| A.1.727 | 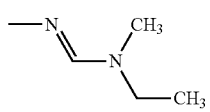 | 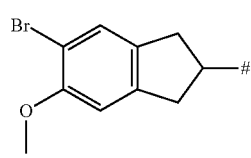 |
| A.1.728 | 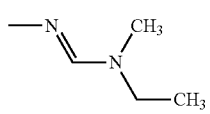 | 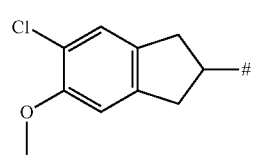 |
| A.1.729 | 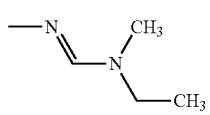 | 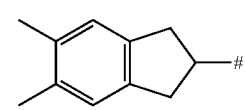 |
| A.1.730 | 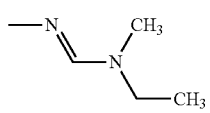 | 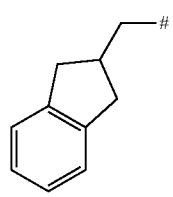 |
| A.1.731 | 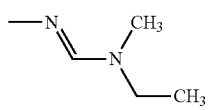 | 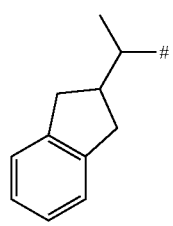 |

TABLE A-continued
| | Meanings for $R_1$, $R_2$, $R_5$ and $R_6$: | |
|---|---|---|
| A.1.732 | 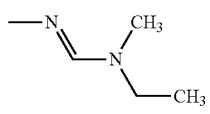 | 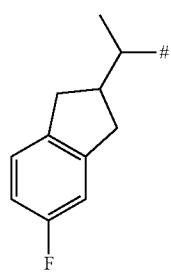 |
| A.1.733 | 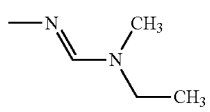 | 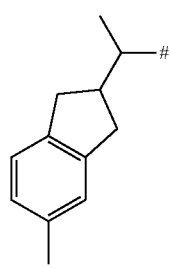 |
| A.1.734 | 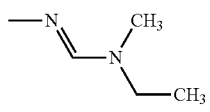 | 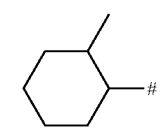 |
| A.1.735 | 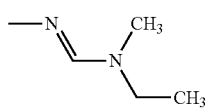 | 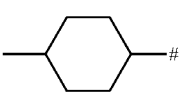 |
| A.1.736 | 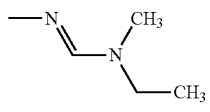 | 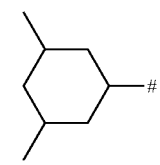 |
| A.1.737 | 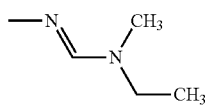 | 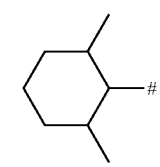 |
| A.1.738 | 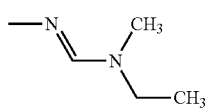 | 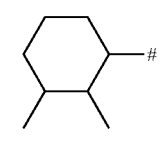 |
| A.1.739 | 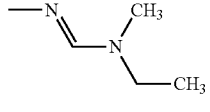 | 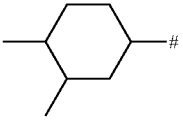 |
| A.1.740 | 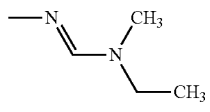 | 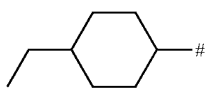 |

US 9,326,513 B2
TABLE A-continued
Meanings for $R_1$, $R_2$, $R_5$ and $R_6$:
| | | |
|---|---|---|
| A.1.741 | 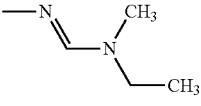 | 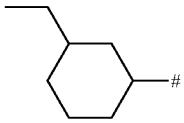 |
| A.1.742 | 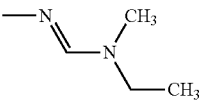 | 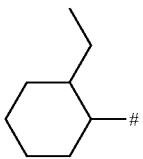 |
| A.1.743 | 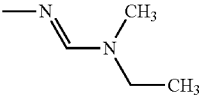 | 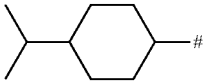 |
| A.1.744 | 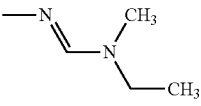 | 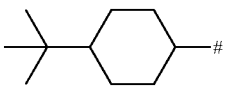 |
| A.1.745 | 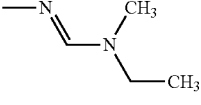 | 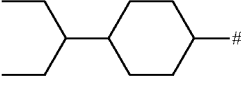 |
| A.1.746 | 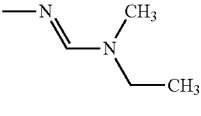 | 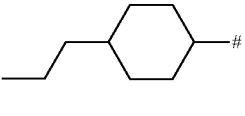 |
| A.1.747 | 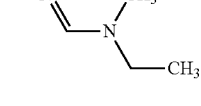 |  |
| A.1.748 | 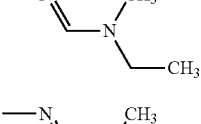 | 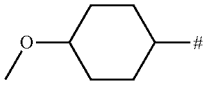 |
| A.1.749 | 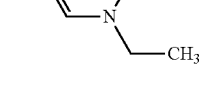 | 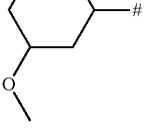 |
| A.1.750 | 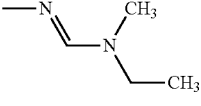 | 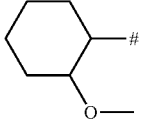 |
| A.1.751 | 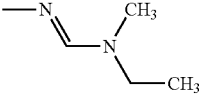 | 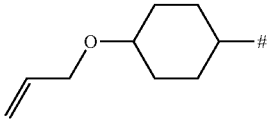 |
| A.1.752 | 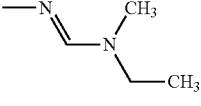 | 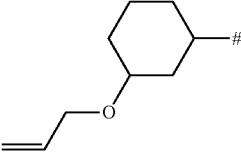 |

TABLE A-continued
Meanings for $R_1$, $R_2$, $R_5$ and $R_6$:
| | | |
|---|---|---|
| A.1.753 | 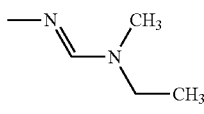 | 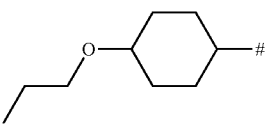 |
| A.1.754 | 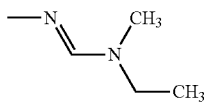 | 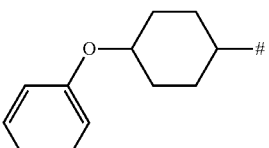 |
| A.1.755 | 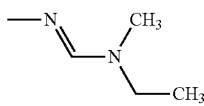 | 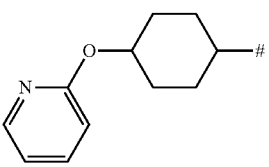 |
| A.1.756 | 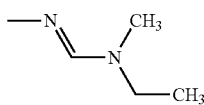 | 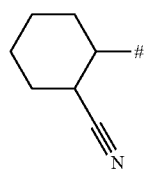 |
| A.1.757 | 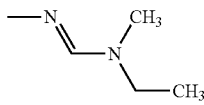 | 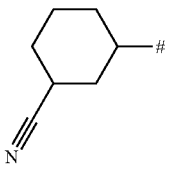 |
| A.1.758 | 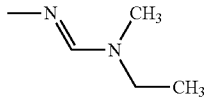 | 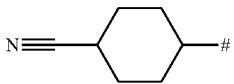 |
| A.1.759 | 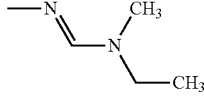 |  |
| A.1.760 | 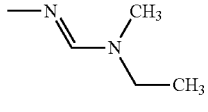 | 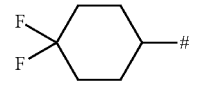 |
| A.1.761 | 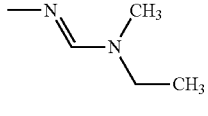 | 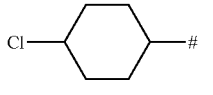 |
| A.1.762 | 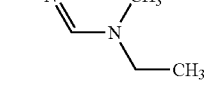 | 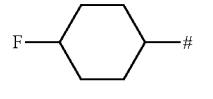 |
| A.1.763 | 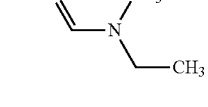 | 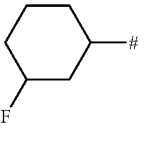 |

TABLE A-continued

| | Meanings for $R_1$, $R_2$, $R_5$ and $R_6$: | |
|---|---|---|
| A.1.764 | —N=CH—N(CH$_3$)(CH$_2$CH$_3$) | cyclohexyl with F substituent, # attachment |
| A.1.765 | —N=CH—N(CH$_3$)(CH$_2$CH$_3$) | 4-methylenecyclohexyl, # |
| A.1.766 | —N=CH—N(CH$_3$)(CH$_2$CH$_3$) | 4-ethylidenecyclohexyl, # |
| A.1.767 | —N=CH—N(CH$_3$)(CH$_2$CH$_3$) | 4-(propan-2-ylidene)cyclohexyl, # |
| A.1.768 | —N=CH—N(CH$_3$)(CH$_2$CH$_3$) | 4-(pentan-3-ylidene)cyclohexyl, # |
| A.1.769 | —N=CH—N(CH$_3$)(CH$_2$CH$_3$) | cyclohex-2-enyl, # |
| A.1.770 | —N=CH—N(CH$_3$)(CH$_2$CH$_3$) | 4-methylcyclohex-2-enyl, # |
| A.1.771 | —N=CH—N(CH$_3$)(CH$_2$CH$_3$) | 4-methylcyclohex-3-enyl, # |
| A.1.772 | —N=CH—N(CH$_3$)(CH$_2$CH$_3$) | 4-(difluoromethylene)cyclohexyl, # |
| A.1.773 | —N=CH—N(CH$_3$)(CH$_2$CH$_3$) | 4-(dichloromethylene)cyclohexyl, # |
| A.1.774 | —N=CH—N(CH$_3$)(CH$_2$CH$_3$) | tetrahydro-2H-pyran-4-yl, # |
| A.1.775 | —N=CH—N(CH$_3$)(CH$_2$CH$_3$) | tetrahydro-2H-thiopyran-4-yl, # |
| A.1.776 | —N=CH—N(CH$_3$)(CH$_2$CH$_3$) | 1-oxo-tetrahydro-2H-thiopyran-4-yl, # |

TABLE A-continued
Meanings for $R_1$, $R_2$, $R_5$ and $R_6$:
| | | |
|---|---|---|
| A.1.777 | 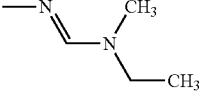 | 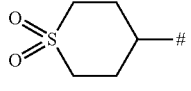 |
| A.1.778 | 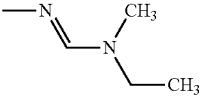 | 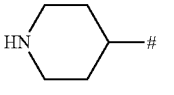 |
| A.1.779 | 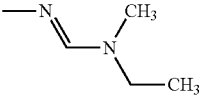 | 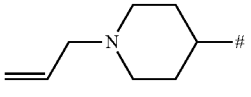 |
| A.1.780 | 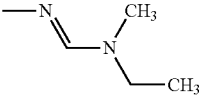 | 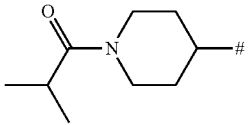 |
| A.1.781 | 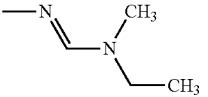 | 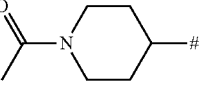 |
| A.1.782 | 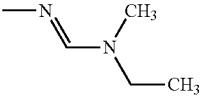 | 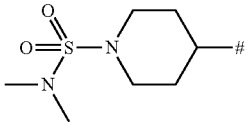 |
| A.1.783 | 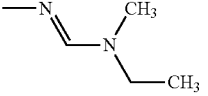 | 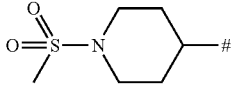 |
| A.1.784 | 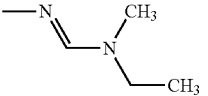 | 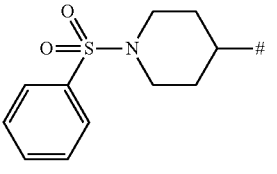 |
| A.1.785 | 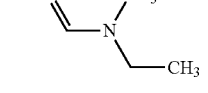 | 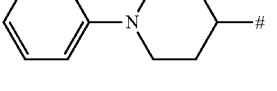 |
| A.1.786 | 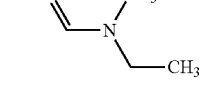 | 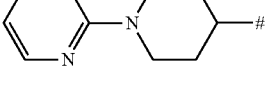 |
| A.1.787 | 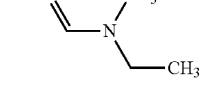 | 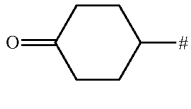 |
| A.1.788 | 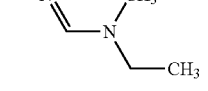 | 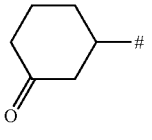 |

TABLE A-continued
Meanings for $R_1$, $R_2$, $R_5$ and $R_6$:
| | | |
|---|---|---|
| A.1.789 | 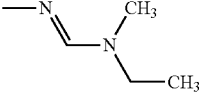 |  |
| A.1.790 | 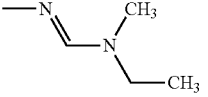 | 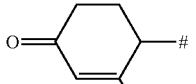 |
| A.1.791 | 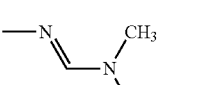 |  |
| A.1.792 | 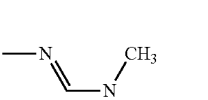 | 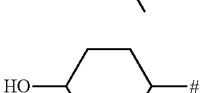 |
| A.1.793 | 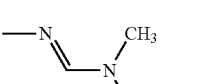 | 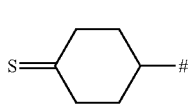 |
| A.1.794 | 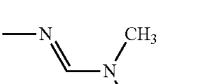 | 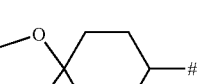 |
| A.1.795 | 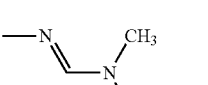 | 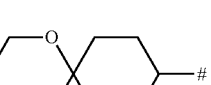 |
| A.1.796 | 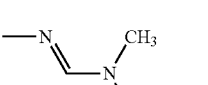 | 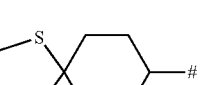 |
| A.1.797 | 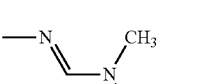 | 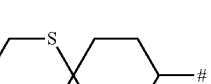 |
| A.1.798 | 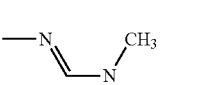 | 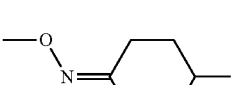 |
| A.1.799 | 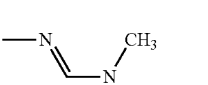 | 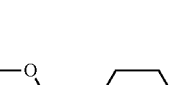 |
| A.1.800 | 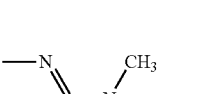 | 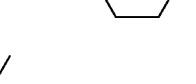 |

TABLE A-continued
Meanings for $R_1$, $R_2$, $R_5$ and $R_6$:
| A.1.801 | 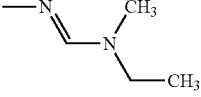 | 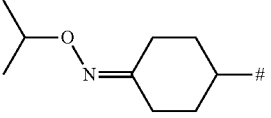 |
| A.1.802 | 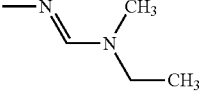 | 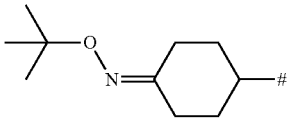 |
| A.1.803 | 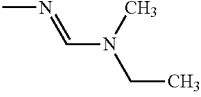 | 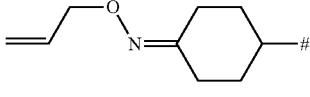 |
| A.1.804 | 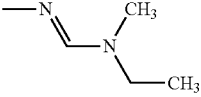 | 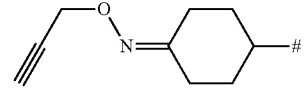 |
| A.1.805 | 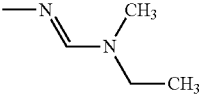 | 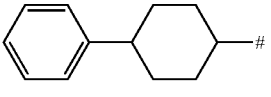 |
| A.1.806 | 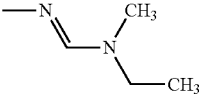 | 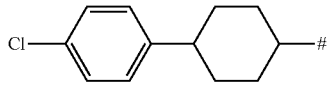 |
| A.1.807 | 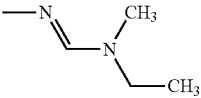 | 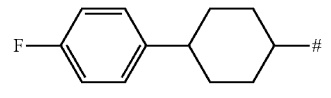 |
| A.1.808 | 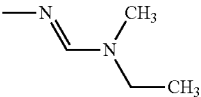 | 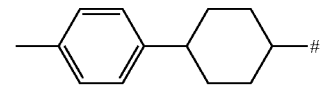 |
| A.1.809 | 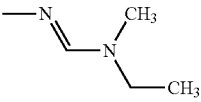 | 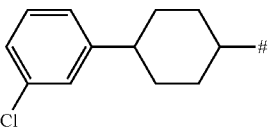 |
| A.1.810 | 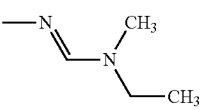 | 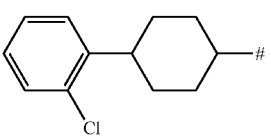 |
| A.1.811 | 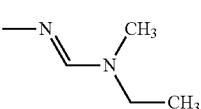 | 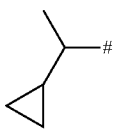 |
| A.1.812 | 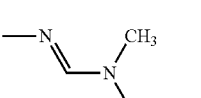 | 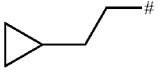 |

TABLE A-continued
| | Meanings for $R_1$, $R_2$, $R_5$ and $R_6$: | |
|---|---|---|
| A.1.813 | 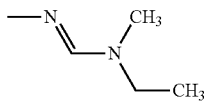 | 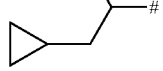 |
| A.1.814 | 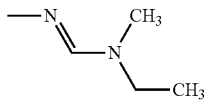 | 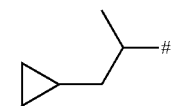 |
| A.1.815 | 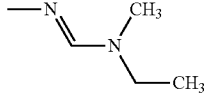 | 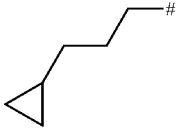 |
| A.1.816 | 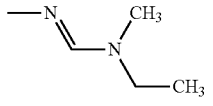 | 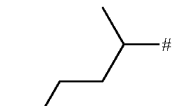 |
| A.1.817 | 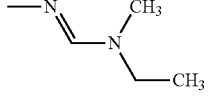 | 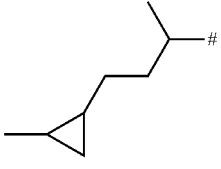 |
| A.1.818 | 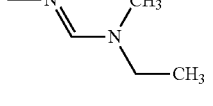 | 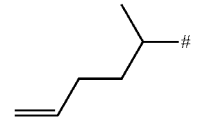 |
| A.1.819 | 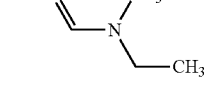 | 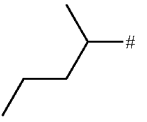 |
| A.1.820 | 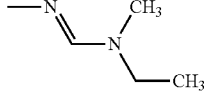 | 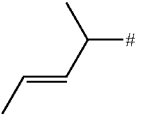 |
| A.1.821 | 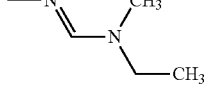 | 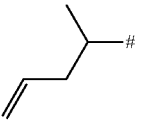 |
| A.1.822 | 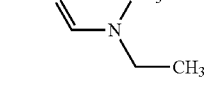 | 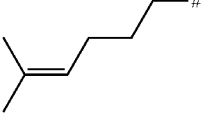 |
| A.1.823 | 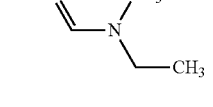 | 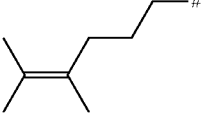 |

TABLE A-continued

Meanings for $R_1$, $R_2$, $R_5$ and $R_6$:

| | | |
|---|---|---|
| A.1.824 | —N=CH—N(CH$_3$)(CH$_2$CH$_3$) | CH$_2$=C(CH$_3$)CH$_2$CH$_2$—# |
| A.1.825 | —N=CH—N(CH$_3$)(CH$_2$CH$_3$) | CH$_3$CH=C(CH$_3$)CH$_2$CH$_2$—# |
| A.1.826 | —N=CH—N(CH$_3$)(CH$_2$CH$_3$) | CH$_3$CH=CH(CH$_2$)$_4$—# |
| A.1.827 | —N=CH—N(CH$_3$)(CH$_2$CH$_3$) | CH$_2$=CHCH$_2$CH(#)CH$_2$CH=CH$_2$ |
| A.1.828 | —N=CH—N(CH$_3$)(CH$_2$CH$_3$) | CH$_2$=C(CH$_3$)CH$_2$CH(#)CH$_2$C(CH$_3$)=CH$_2$ |
| A.1.829 | —N=CH—N(CH$_3$)(CH$_2$CH$_3$) | (CH$_3$)$_2$CHCH$_2$CH(#)CH(CH$_3$)$_2$ |
| A.1.830 | —N=CH—N(CH$_3$)(CH$_2$CH$_3$) | 2-furyl-CH$_2$—# |
| A.1.831 | —N=CH—N(CH$_3$)(CH$_2$CH$_3$) | 2-furyl-CH(CH$_3$)—# |
| A.1.832 | —N=CH—N(CH$_3$)(CH$_2$CH$_3$) | 3-furyl-CH$_2$—# |
| A.1.833 | —N=CH—N(CH$_3$)(CH$_2$CH$_3$) | 3-furyl-CH(CH$_3$)—# |

TABLE A-continued
Meanings for $R_1$, $R_2$, $R_5$ and $R_6$:
| | | |
|---|---|---|
| A.1.834 | 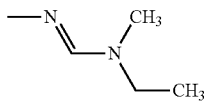 | 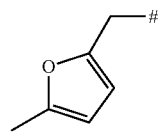 |
| A.1.835 | 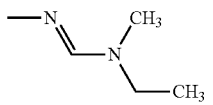 | 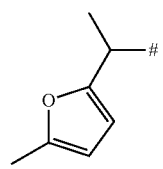 |
| A.1.836 | 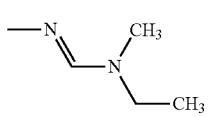 | 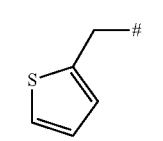 |
| A.1.837 | 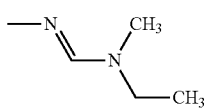 | 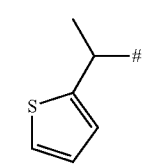 |
| A.1.838 | 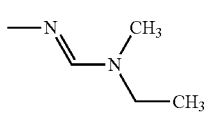 | 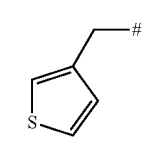 |
| A.1.839 | 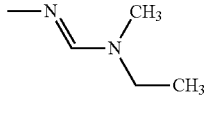 | 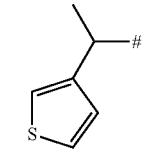 |
| A.1.840 | 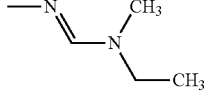 | 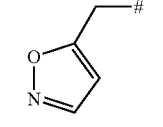 |
| A.1.841 | 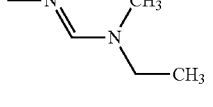 | 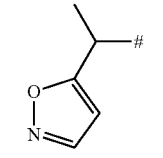 |
| A.1.842 | 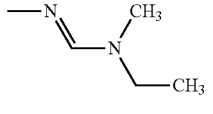 | 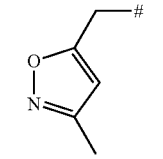 |
| A.1.843 | 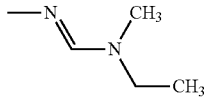 | 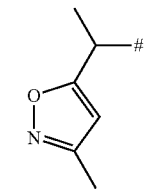 |

TABLE A-continued
Meanings for $R_1$, $R_2$, $R_5$ and $R_6$:
| | | |
|---|---|---|
| A.1.844 | 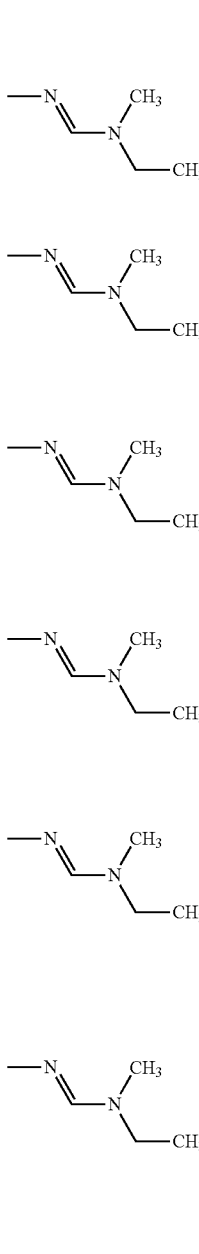 | 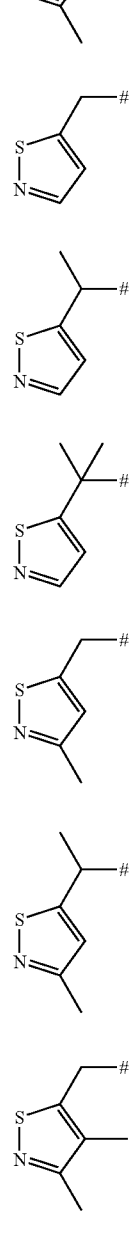 |
| A.1.845 | 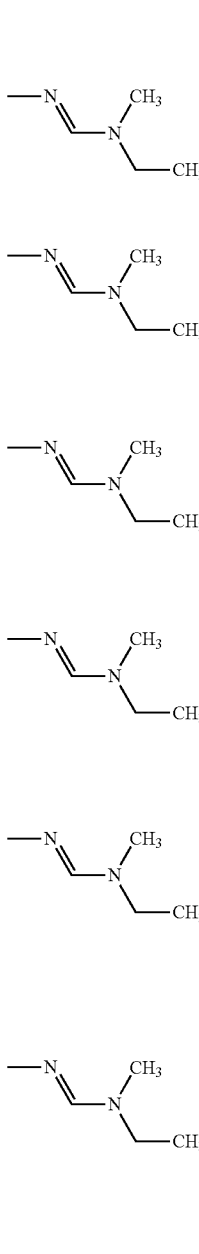 | 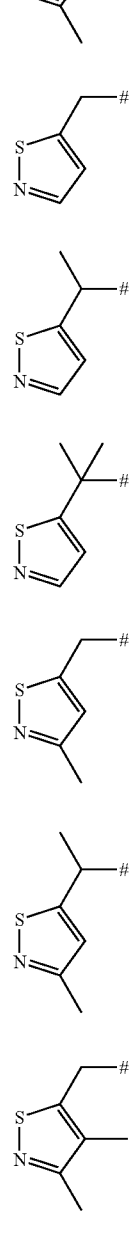 |
| A.1.846 | 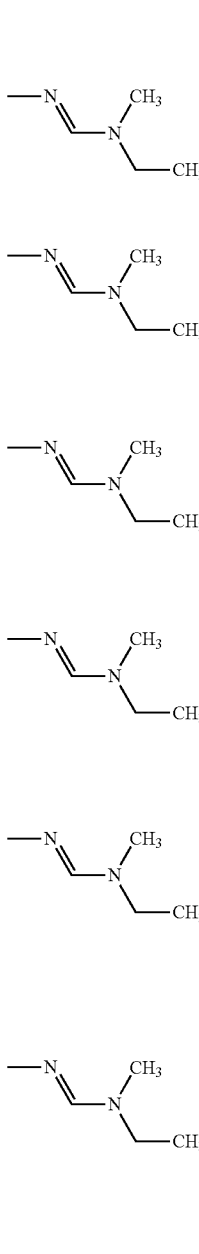 | 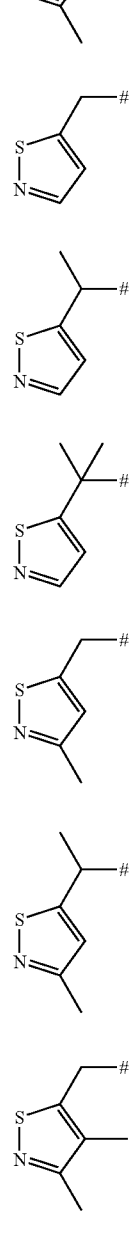 |
| A.1.847 | 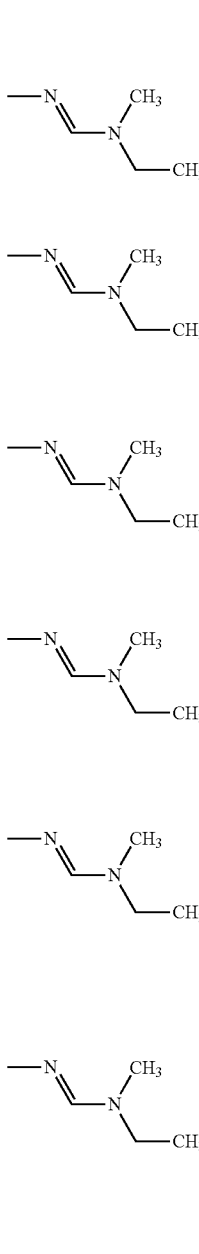 | 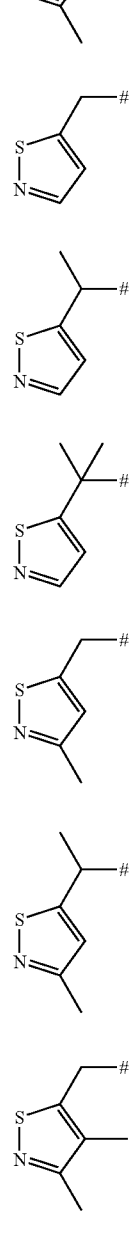 |
| A.1.848 | 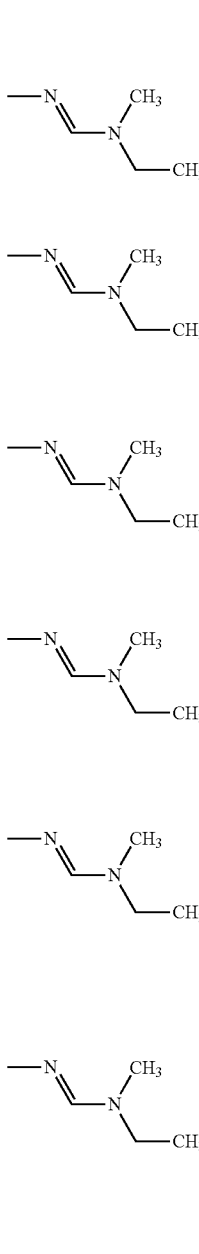 | 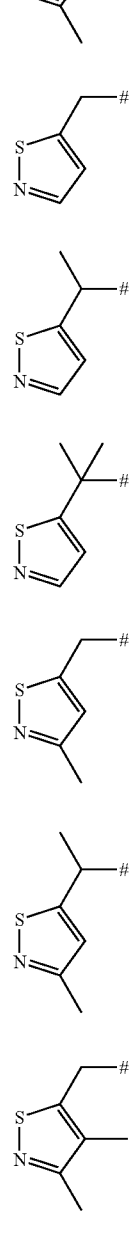 |
| A.1.849 | 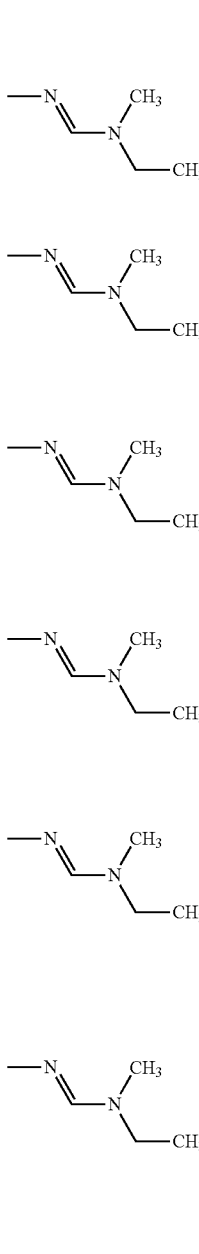 | 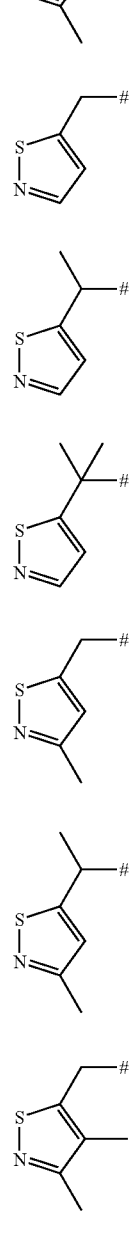 |
| A.1.850 | 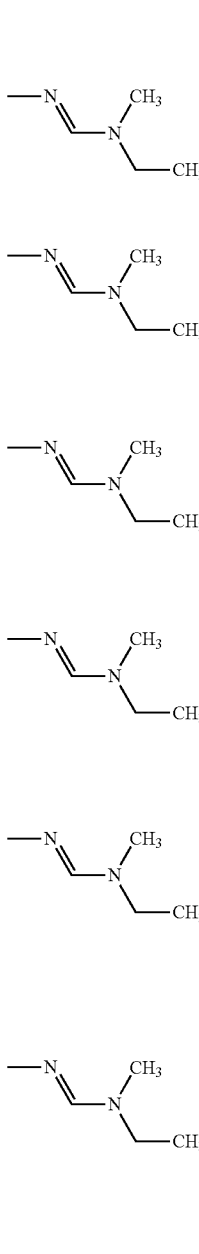 | 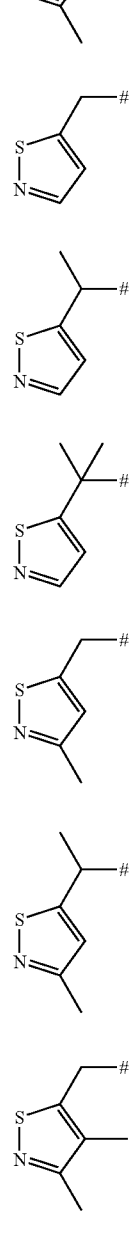 |
| A.1.851 | 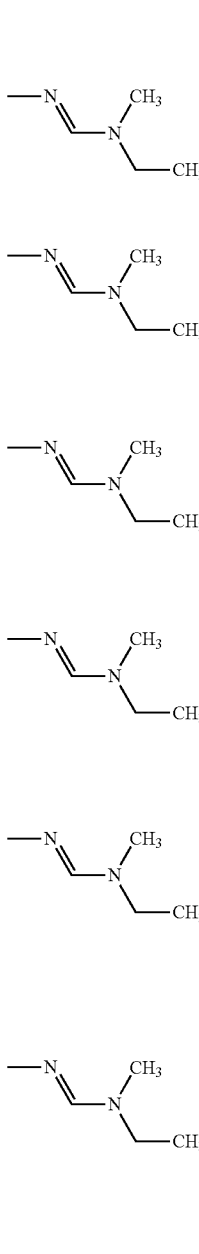 | 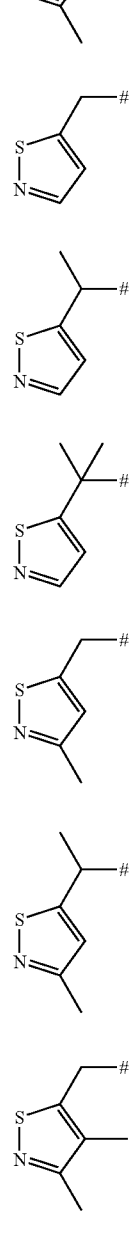 |

TABLE A-continued
Meanings for $R_1$, $R_2$, $R_5$ and $R_6$:
| | | |
|---|---|---|
| A.1.852 | 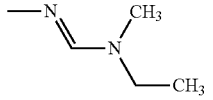 | 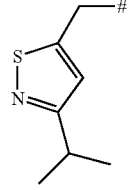 |
| A.1.853 | 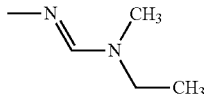 | 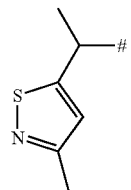 |
| A.1.854 | 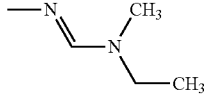 | 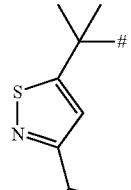 |
| A.1.855 | 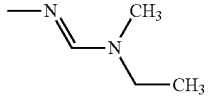 | 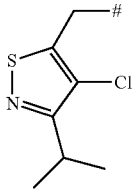 |
| A.1.856 | 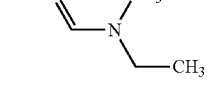 | 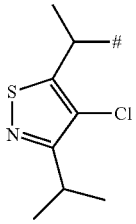 |
| A.1.857 | 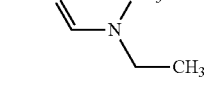 | 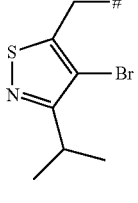 |
| A.1.858 | 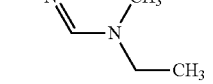 | 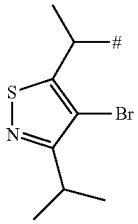 |

TABLE A-continued

Meanings for $R_1$, $R_2$, $R_5$ and $R_6$:

| | | |
|---|---|---|
| A.1.859 | —N=CH—N(CH$_3$)—CH$_2$CH$_3$ | 5-(#)methyl-3-isopropyl-4-cyanoisothiazole |
| A.1.860 | —N=CH—N(CH$_3$)—CH$_2$CH$_3$ | 5-(1-#-ethyl)-3-isopropyl-4-cyanoisothiazole |
| A.1.861 | —N=CH—N(CH$_3$)—CH$_2$CH$_3$ | (6-chloropyridin-3-yl)methyl-# |
| A.1.862 | —N=CH—N(CH$_3$)—CH$_2$CH$_3$ | 1-(6-chloropyridin-3-yl)ethyl-# |
| A.1.863 | —N=CH—N(CH$_3$)—CH$_2$CH$_3$ | (6-methoxypyridin-3-yl)methyl-# |
| A.1.864 | —N=CH—N(CH$_3$)—CH$_2$CH$_3$ | 1-(6-methoxypyridin-3-yl)ethyl-# |
| A.1.865 | —N=CH—N(CH$_3$)—CH$_2$CH$_3$ | (2-chloropyridin-4-yl)methyl-# |

TABLE A-continued

| | Meanings for $R_1$, $R_2$, $R_5$ and $R_6$: | |
|---|---|---|
| A.1.866 | —N=CH—N(CH₃)(CH₂CH₃) | 1-(2-chloropyridin-4-yl)ethyl-# |
| A.1.867 | —N=CH—N(CH₃)(CH₂CH₃) | (2-methoxypyridin-4-yl)methyl-# |
| A.1.868 | —N=CH—N(CH₃)(CH₂CH₃) | 1-(2-methoxypyridin-4-yl)ethyl-# |
| A.1.869 | —N=CH—N(CH₃)(CH₂CH₃) | (quinolin-7-yl)methyl-# |
| A.1.870 | —N=CH—N(CH₃)(CH₂CH₃) | 1-(quinolin-7-yl)ethyl-# |
| A.1.871 | —N=CH—N(CH₃)(CH₂CH₃) | (quinolin-6-yl)methyl-# |
| A.1.872 | —N=CH—N(CH₃)(CH₂CH₃) | 1-(quinolin-6-yl)ethyl-# |

TABLE A-continued
Meanings for $R_1$, $R_2$, $R_5$ and $R_6$:
| A.1.873 | 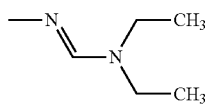 | 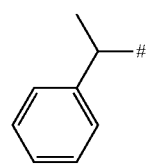 |
| A.1.874 | 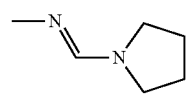 | 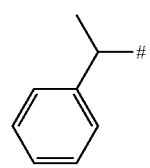 |
| A.1.875 | 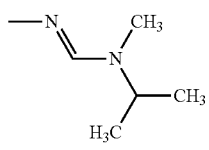 | 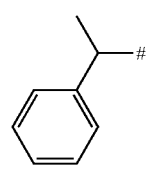 |
| A.1.876 | 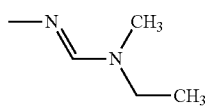 | 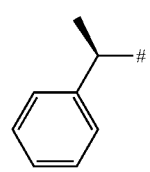 |
| A.1.877 | 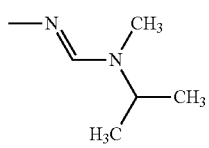 | 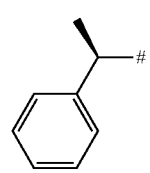 |
| A.1.878 | 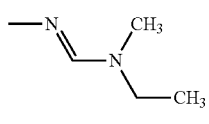 | 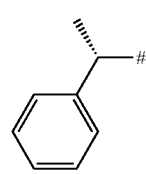 |
| A.1.879 | 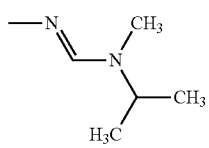 | 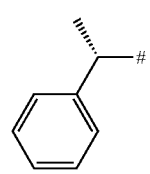 |
| A.1.880 | 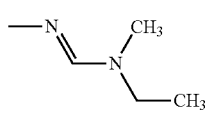 | 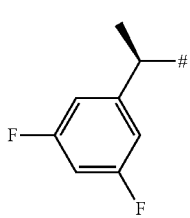 |

TABLE A-continued
| | Meanings for $R_1$, $R_2$, $R_5$ and $R_6$: | |
|---|---|---|
| A.1.881 | 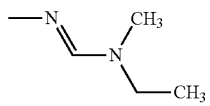 | 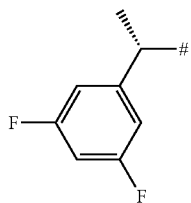 |
| A.1.882 | 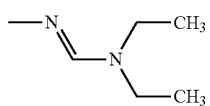 | 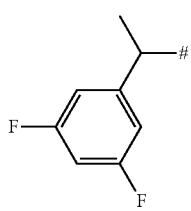 |
| A.1.883 | 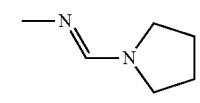 | 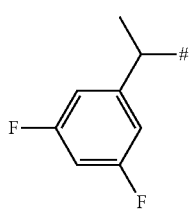 |
| A.1.884 | 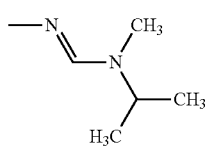 | 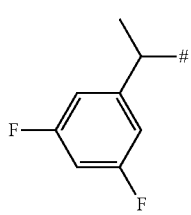 |
| A.1.885 | 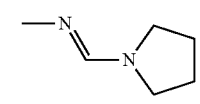 | 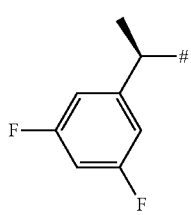 |
| A.1.886 | 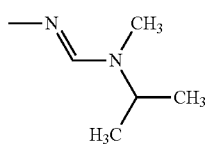 | 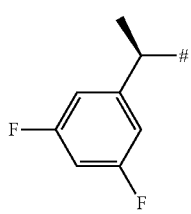 |
| A.1.887 | 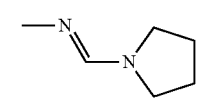 | 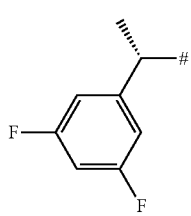 |

TABLE A-continued
| | Meanings for $R_1$, $R_2$, $R_5$ and $R_6$: | |
|---|---|---|
| A.1.888 | 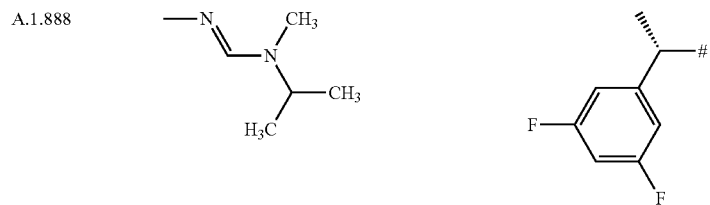 | |
| A.1.889 | 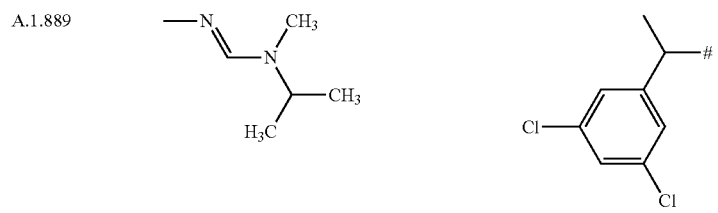 | |
| A.1.890 | 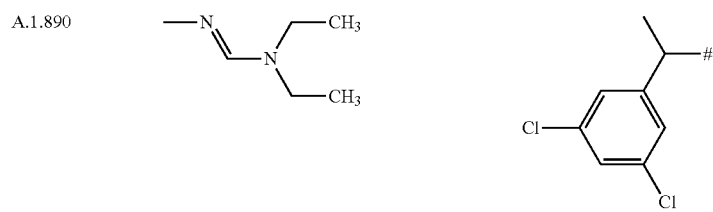 | |
| A.1.891 | 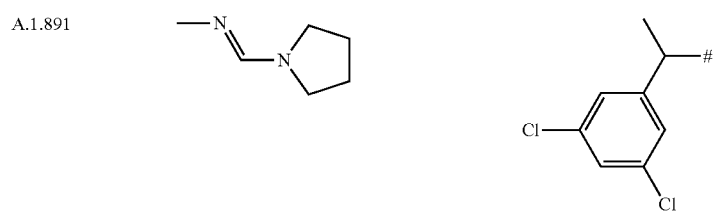 | |
| A.1.892 | 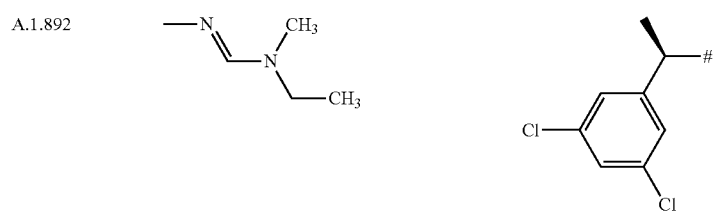 | |
| A.1.893 | 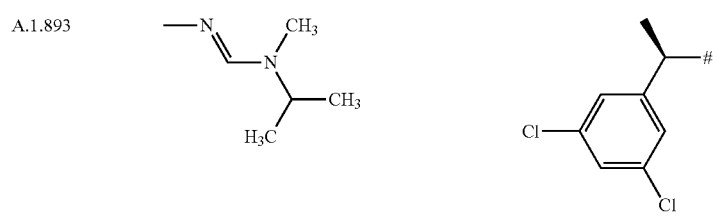 | |
| A.1.894 | 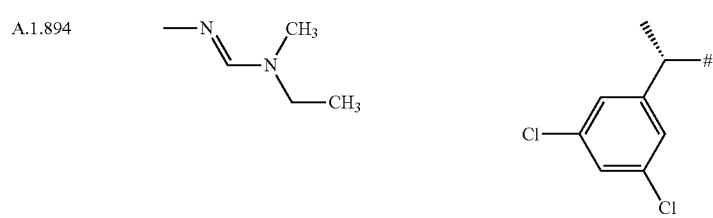 | |

TABLE A-continued
Meanings for $R_1$, $R_2$, $R_5$ and $R_6$:
| A.1.895 | 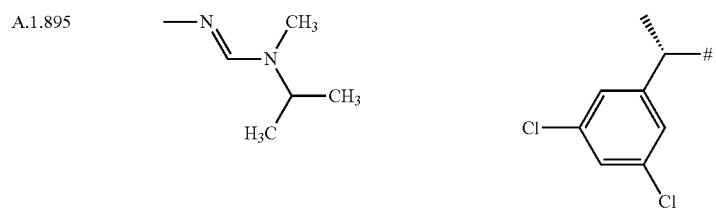 |
| A.1.896 | 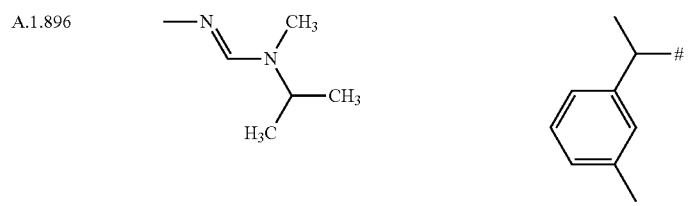 |
| A.1.897 | 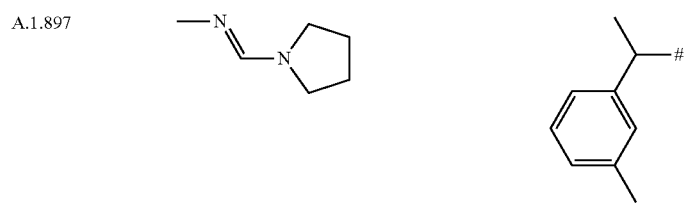 |
| A.1.898 | 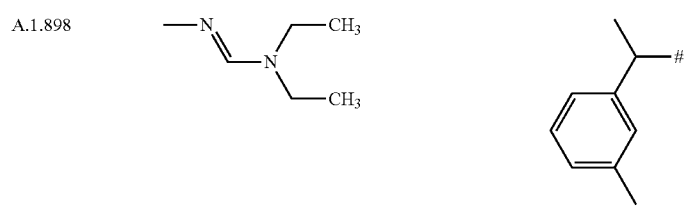 |
| A.1.899 | 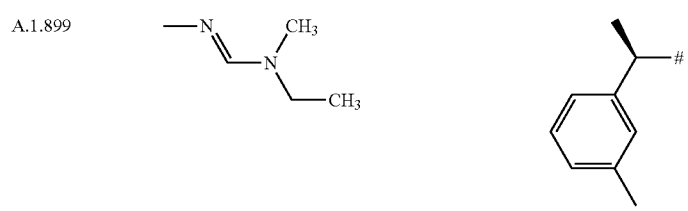 |
| A.1.900 | 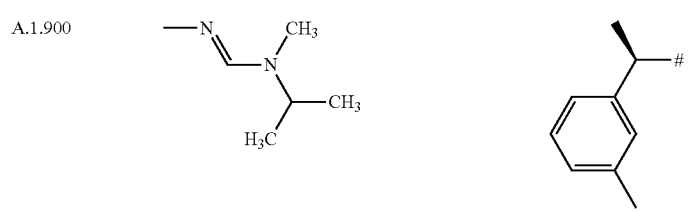 |
| A.1.901 | 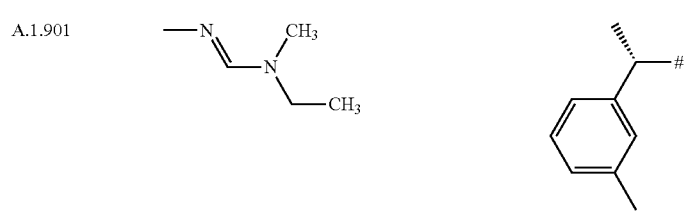 |

TABLE A-continued
| | Meanings for $R_1$, $R_2$, $R_5$ and $R_6$: | |
|---|---|---|
| A.1.902 | 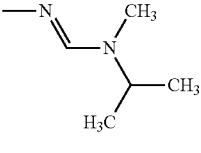 | 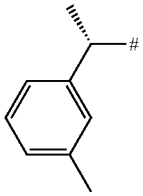 |
| A.1.903 | 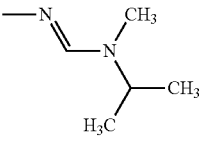 | 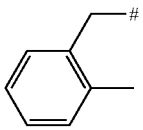 |
| A.1.904 | 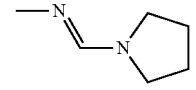 | 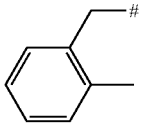 |
| A.1.905 | 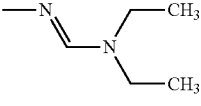 | 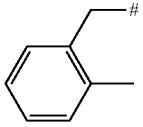 |
| A.1.906 | 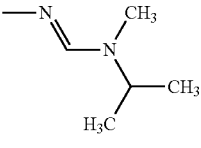 | 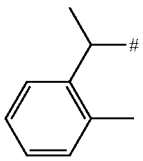 |
| A.1.907 | 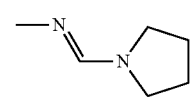 | 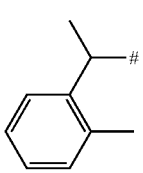 |
| A.1.908 | 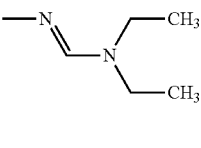 | 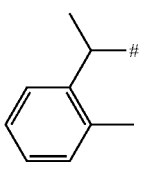 |
| A.1.909 | 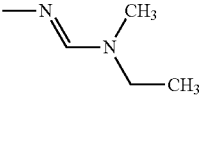 | 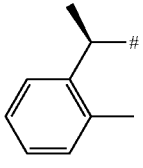 |
| A.1.910 | 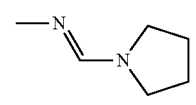 | 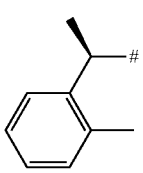 |

TABLE A-continued
| | Meanings for $R_1$, $R_2$, $R_5$ and $R_6$: | |
|---|---|---|
| A.1.911 | 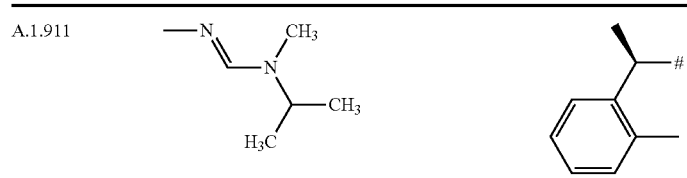 | 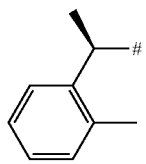 |
| A.1.912 | 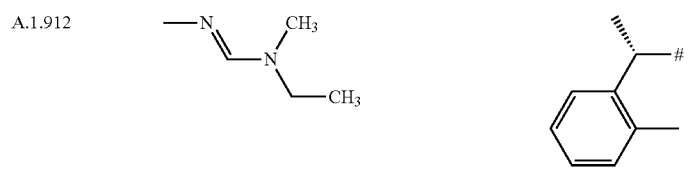 | 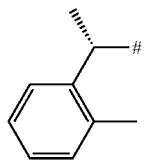 |
| A.1.913 | 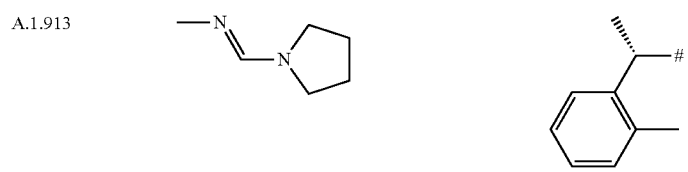 | 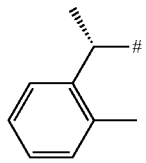 |
| A.1.914 | 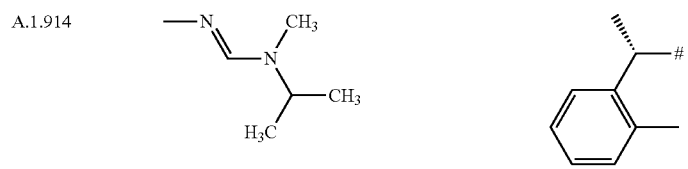 | 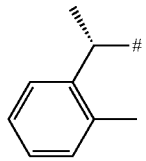 |
| A.1.915 | 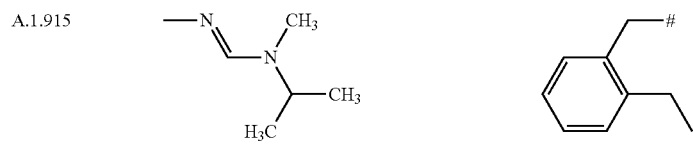 | 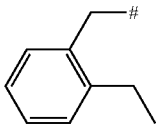 |
| A.1.916 | 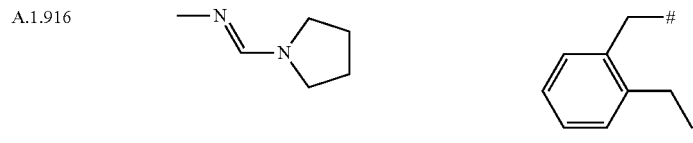 | 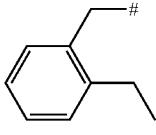 |
| A.1.917 | 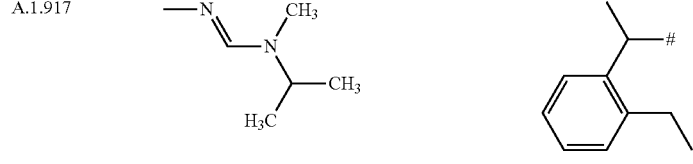 | 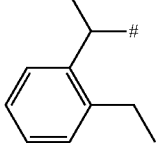 |
| A.1.918 | 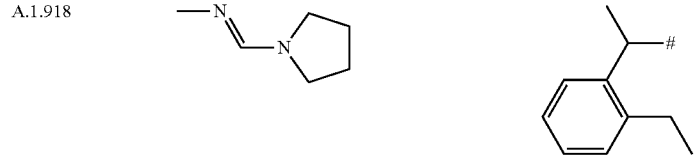 |  |
| A.1.919 | 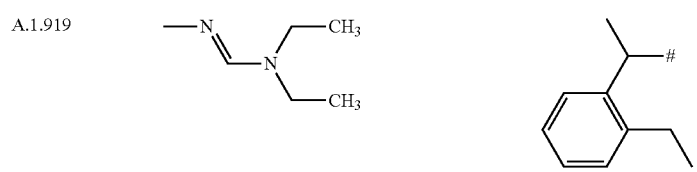 | 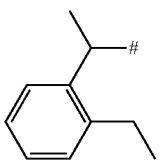 |

TABLE A-continued
Meanings for $R_1$, $R_2$, $R_5$ and $R_6$:
| | | |
|---|---|---|
| A.1.920 | 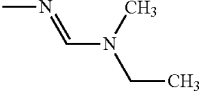 | 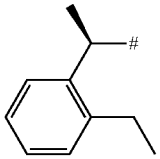 |
| A.1.921 | 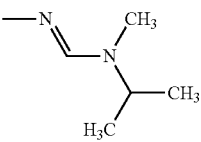 | 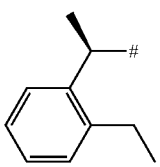 |
| A.1.922 | 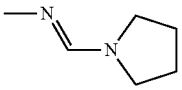 | 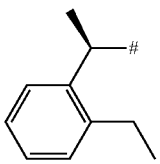 |
| A.1.923 | 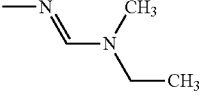 | 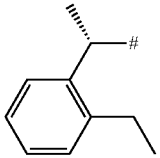 |
| A.1.924 | 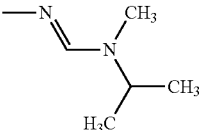 | 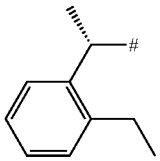 |
| A.1.925 | 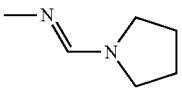 | 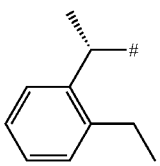 |
| A.1.926 | 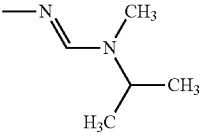 | 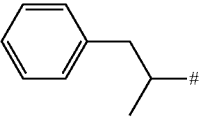 |
| A.1.927 | 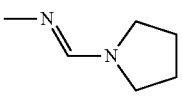 | 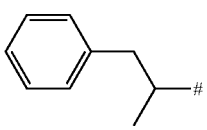 |
| A.1.928 | 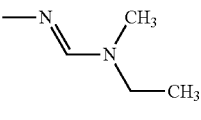 | 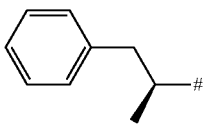 |
| A.1.929 | 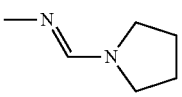 | 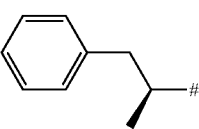 |

US 9,326,513 B2
TABLE A-continued
Meanings for R₁, R₂, R₅ and R₆:
| | | |
|---|---|---|
| A.1.930 | 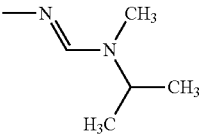 | 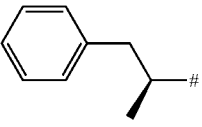 |
| A.1.931 | 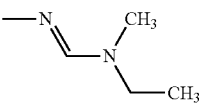 | 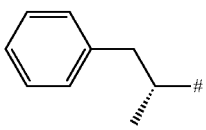 |
| A.1.932 | 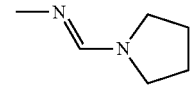 | 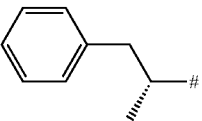 |
| A.1.933 | 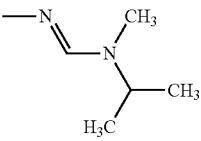 | 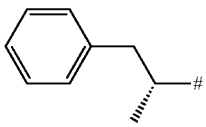 |
| A.1.934 | 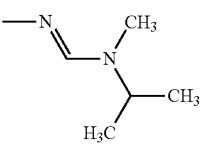 | 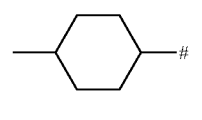 |
| A.1.935 | 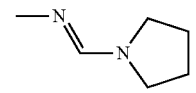 | 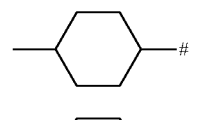 |
| A.1.936 | 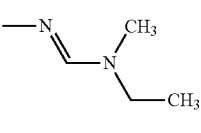 | 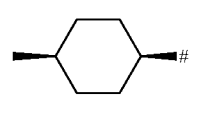 |
| A.1.937 | 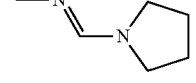 | 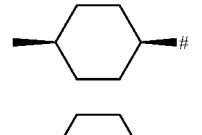 |
| A.1.938 | 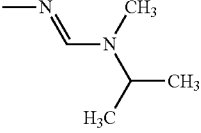 | 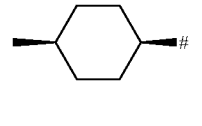 |
| A.1.939 | 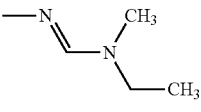 | 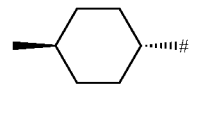 |
| A.1.940 | 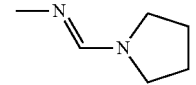 | 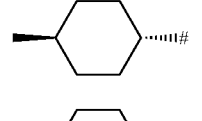 |
| A.1.941 | 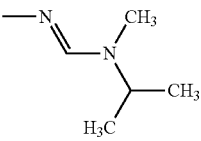 | 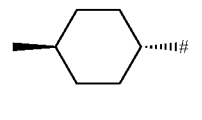 |

US 9,326,513 B2
TABLE A-continued
Meanings for $R_1$, $R_2$, $R_5$ and $R_6$:
| | | |
|---|---|---|
| A.1.942 | 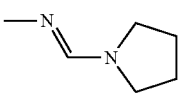 | 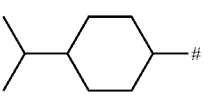 |
| A.1.943 | 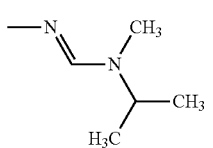 | 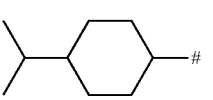 |
| A.1.944 | 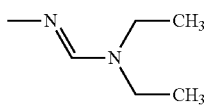 |  |
| A.1.945 | 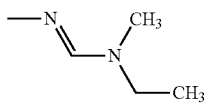 | 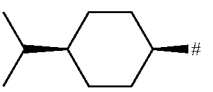 |
| A.1.946 | 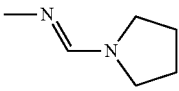 |  |
| A.1.947 | 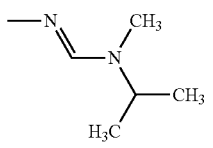 |  |
| A.1.948 | 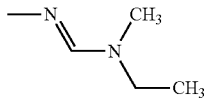 |  |
| A.1.949 | 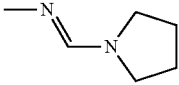 | 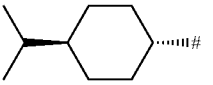 |
| A.1.950 | 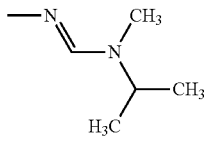 |  |
| A.1.951 | 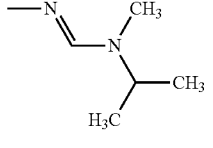 | 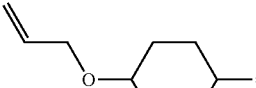 |
| A.1.952 | 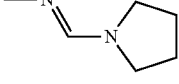 | 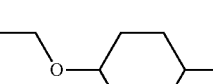 |
| A.1.953 | 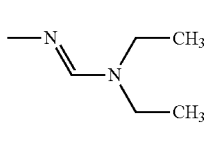 | 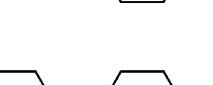 |

TABLE A-continued
| | Meanings for $R_1$, $R_2$, $R_5$ and $R_6$: | |
|---|---|---|
| A.1.954 | 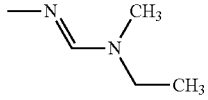 | 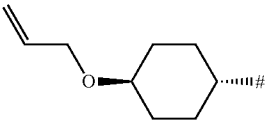 |
| A.1.955 | 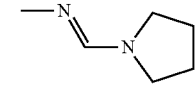 | 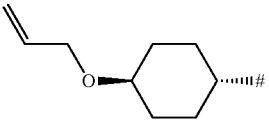 |
| A.1.956 | 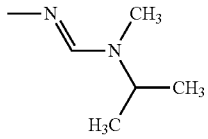 | 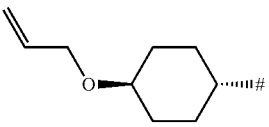 |
| A.1.957 | 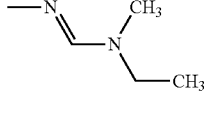 | 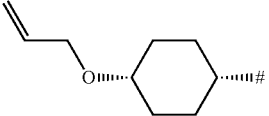 |
| A.1.958 | 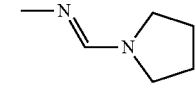 | 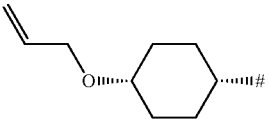 |
| A.1.959 | 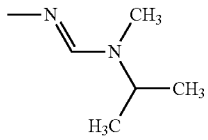 | 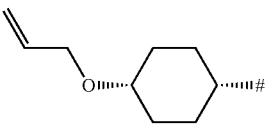 |
| A.1.960 | 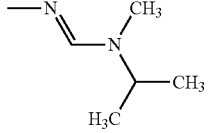 | 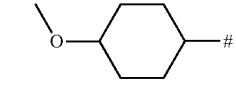 |
| A.1.961 | 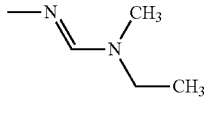 | 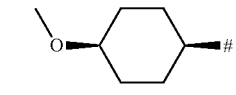 |
| A.1.962 | 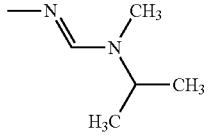 | 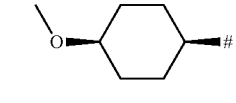 |
| A.1.963 | 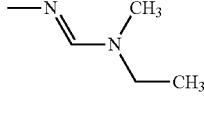 | 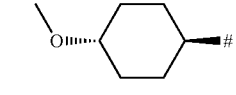 |
| A.1.964 | 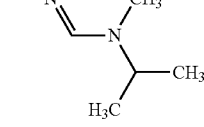 | 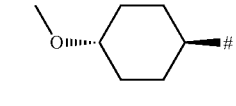 |

TABLE A-continued

| | Meanings for $R_1$, $R_2$, $R_5$ and $R_6$: | |
|---|---|---|
| A.1.965 | —N=CH—N(CH₃)(CH(CH₃)₂) | cyclopentyl-# |
| A.1.966 | —N=CH—N(CH₃)(CH₂CH₃) | 3-methylcyclopentyl-# |
| A.1.967 | —N=CH—N(CH₃)(CH₂CH₃) | (1S,3S)-3-methylcyclopentyl-# |
| A.1.968 | —N=CH—N(CH₃)(CH(CH₃)₂) | (1S,3S)-3-methylcyclopentyl-# |
| A.1.969 | —N=CH—N(CH₃)(CH₂CH₃) | (1R,3R)-3-methylcyclopentyl-# |
| A.1.970 | —N=CH—N(CH₃)(CH(CH₃)₂) | (1R,3R)-3-methylcyclopentyl-# |
| A.1.971 | —N=CH—N(CH₃)(CH₂CH₃) | (1S,3R)-3-methylcyclopentyl-# |
| A.1.972 | —N=CH—N(CH₃)(CH(CH₃)₂) | (1S,3R)-3-methylcyclopentyl-# |
| A.1.973 | —N=CH—N(CH₃)(CH(CH₃)₂) | (1R,3S)-3-methylcyclopentyl-# |
| A.1.974 | —N=CH—N(CH₃)(CH(CH₃)₂) | (1R,3S)-3-methylcyclopentyl-# |
| A.1.975 | —N=CH—pyrrolidin-1-yl | indan-2-yl-# |

TABLE A-continued
Meanings for $R_1$, $R_2$, $R_5$ and $R_6$:
| | | |
|---|---|---|
| A.1.976 | 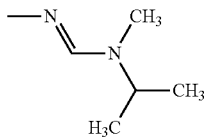 | 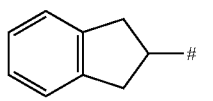 |
| A.1.977 | 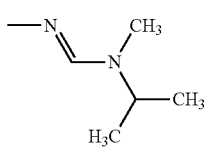 | 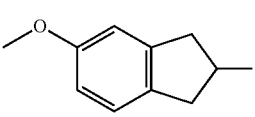 |
| A.1.978 | 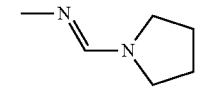 | 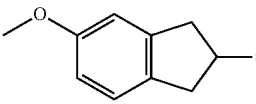 |
| A.1.979 | 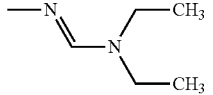 | 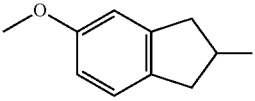 |
| A.1.980 | 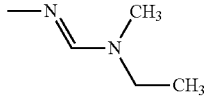 | 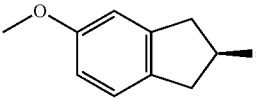 |
| A.1.981 | 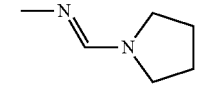 | 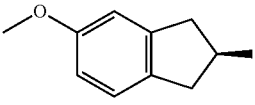 |
| A.1.982 | 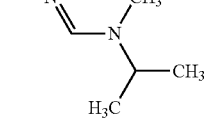 | 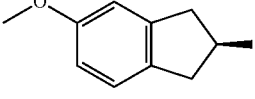 |
| A.1.983 | 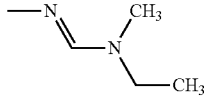 | 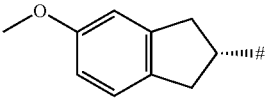 |
| A.1.984 | 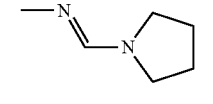 | 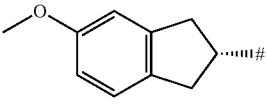 |
| A.1.985 | 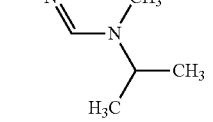 | 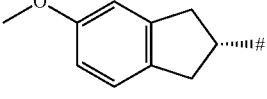 |
| A.1.986 | 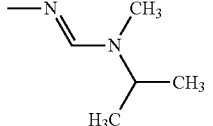 | 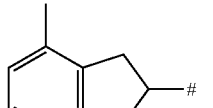 |
| A.1.987 | 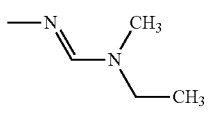 | 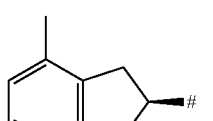 |

TABLE A-continued
Meanings for $R_1$, $R_2$, $R_5$ and $R_6$:
| | | |
|---|---|---|
| A.1.988 | 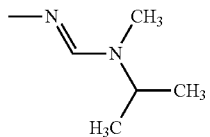 | 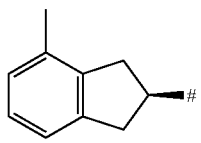 |
| A.1.989 | 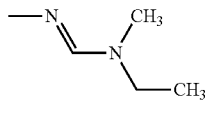 | 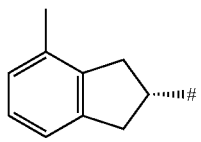 |
| A.1.990 | 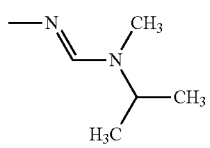 | 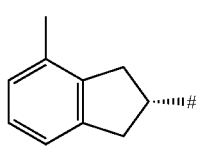 |
| A.1.991 | 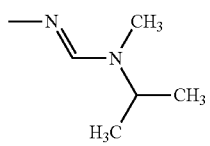 | 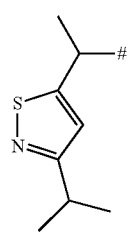 |
| A.1.992 | 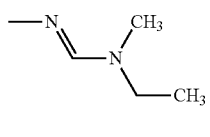 | 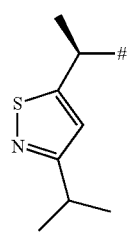 |
| A.1.993 | 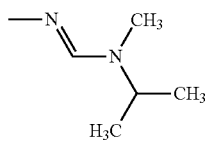 | 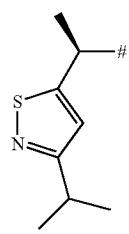 |
| A.1.994 | 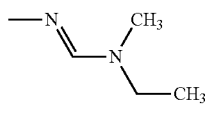 | 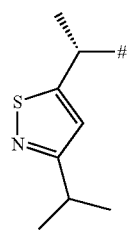 |

US 9,326,513 B2
TABLE A-continued
Meanings for $R_1$, $R_2$, $R_5$ and $R_6$:
| | | |
|---|---|---|
| A.1.995 | 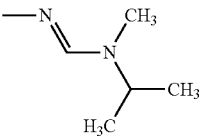 | 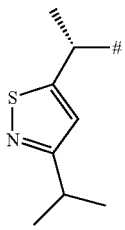 |
| A.1.996 | 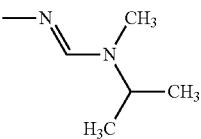 | 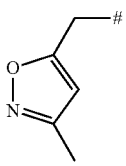 |
| A.1.997 | 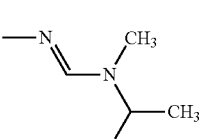 | 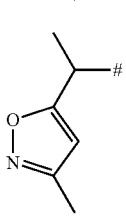 |
| A.1.998 | 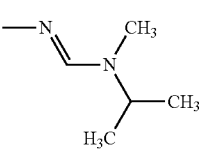 | 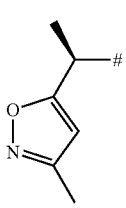 |
| A.1.999 | 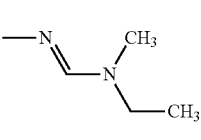 | 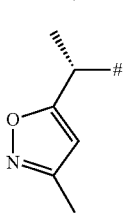 |
| A.1.1000 | 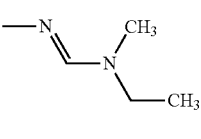 | 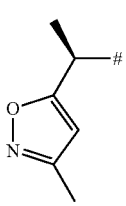 |
| A.1.1001 | 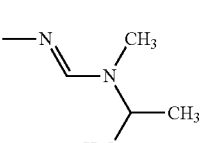 | 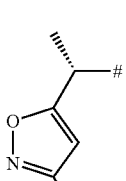 |
| A.1.1002 | 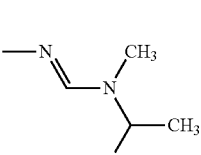 | 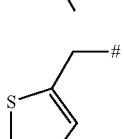 |

TABLE A-continued
Meanings for $R_1$, $R_2$, $R_5$ and $R_6$:
| | | |
|---|---|---|
| A.1.1003 | 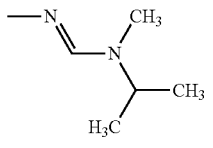 | 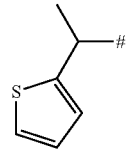 |
| A.1.1004 | 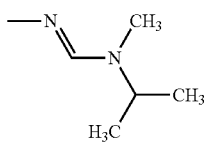 | 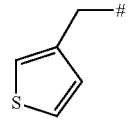 |
| A.1.1005 | 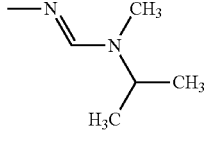 | 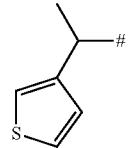 |
| A.1.1006 | 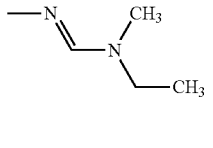 | 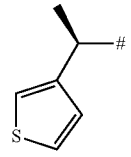 |
| A.1.1007 | 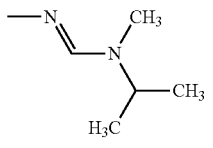 | 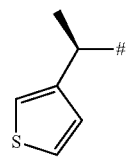 |
| A.1.1008 | 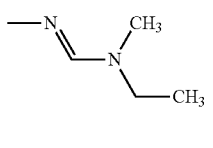 | 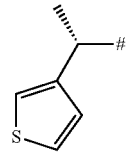 |
| A.1.1009 | 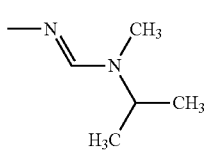 | 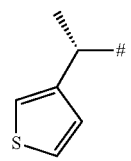 |
| A.1.1010 | 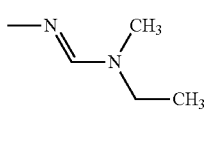 | 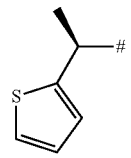 |
| A.1.1011 | 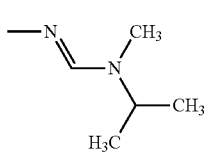 | 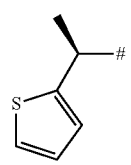 |

TABLE A-continued

Meanings for $R_1$, $R_2$, $R_5$ and $R_6$:

| | | |
|---|---|---|
| A.1.1012 | —N=CH—N(CH₃)(CH₂CH₃) | (R)-1-(thiophen-2-yl)ethyl-# |
| A.1.1013 | —N=CH—N(CH(CH₃)₂)(CH₃) | (R)-1-(thiophen-2-yl)ethyl-# |
| A.1.1014 | —N=CH—N(CH(CH₃)₂)(CH₃) | 1,2,3,4-tetrahydronaphthalen-2-yl-# |
| A.1.1015 | —N=CH—pyrrolidin-1-yl | 1,2,3,4-tetrahydronaphthalen-2-yl-# |
| A.1.1016 | —N=CH—N(CH₂CH₃)₂ | 1,2,3,4-tetrahydronaphthalen-2-yl-# |
| A.1.1017 | —N=CH—N(CH₃)(CH₂CH₃) | (R)-1,2,3,4-tetrahydronaphthalen-2-yl-# |
| A.1.1018 | —N=CH—N(CH(CH₃)₂)(CH₃) | (R)-1,2,3,4-tetrahydronaphthalen-2-yl-# |
| A.1.1019 | —N=CH—N(CH₃)(CH₂CH₃) | (S)-1,2,3,4-tetrahydronaphthalen-2-yl-# |
| A.1.1020 | —N=CH—N(CH(CH₃)₂)(CH₃) | (S)-1,2,3,4-tetrahydronaphthalen-2-yl-# |
| A.1.1021 | —N=CH—N(CH(CH₃)₂)(CH₃) | 6-methoxy-1,2,3,4-tetrahydronaphthalen-2-yl-# |
| A.1.1022 | —N=CH—N(CH₃)(CH₂CH₃) | (R)-6-methoxy-1,2,3,4-tetrahydronaphthalen-2-yl-# |

TABLE A-continued
| | Meanings for $R_1$, $R_2$, $R_5$ and $R_6$: | |
|---|---|---|
| A.1.1023 | 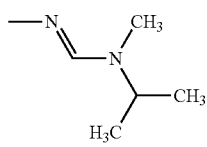 | 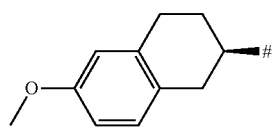 |
| A.1.1024 | 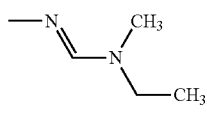 | 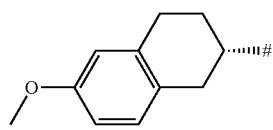 |
| A.1.1025 | 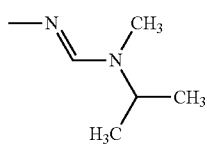 | 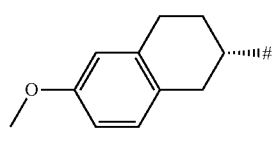 |
| A.1.1026 | 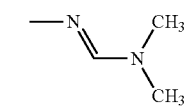 | H—# |
| A.1.1027 | 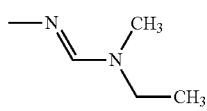 | H—# |
| A.1.1028 | 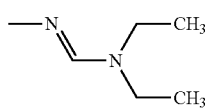 | H—# |
| A.1.1029 | 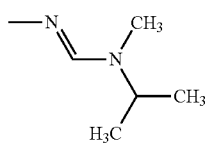 | H—# |
| A.1.1030 | 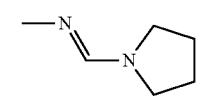 | H—# |
| A.1.1031 | 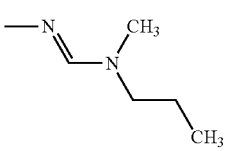 | H—# |
| A.1.1032 | 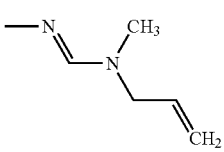 | H—# |
| A.1.1033 | 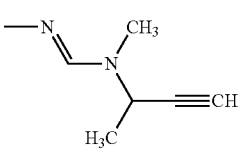 | H—# |

TABLE A-continued
Meanings for $R_1$, $R_2$, $R_5$ and $R_6$:
| A.1.1034 | 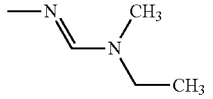 | 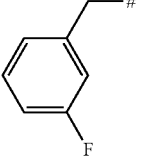 |
| A.1.1035 | 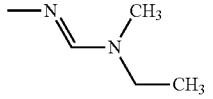 | 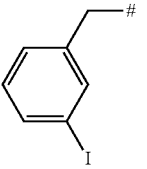 |
| A.1.1036 | 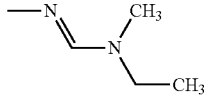 | 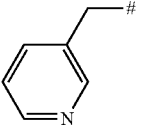 |
| A.1.1037 | 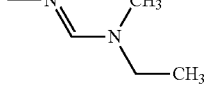 | 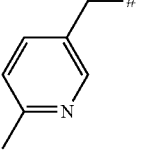 |
| A.1.1038 | 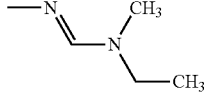 | 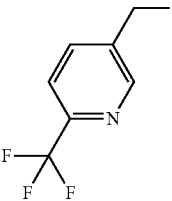 |
| A.1.1039 | 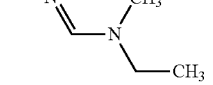 | 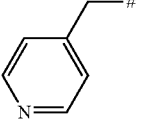 |
| A.1.1040 | 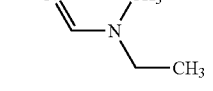 | 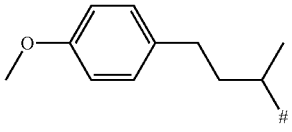 |
| A.1.1041 | 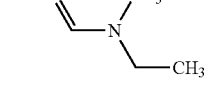 | 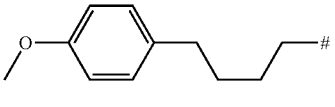 |
| A.1.1042 | 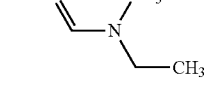 | 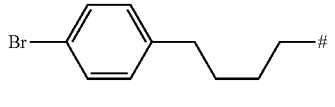 |
| A.1.1043 | 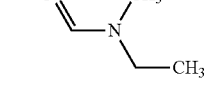 | 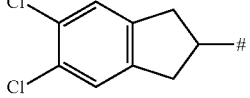 |

TABLE A-continued
Meanings for $R_1$, $R_2$, $R_5$ and $R_6$:
| | | |
|---|---|---|
| A.1.1044 | 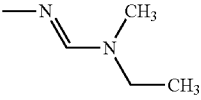 | 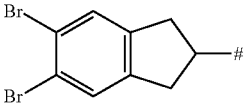 |
| A.1.1045 | 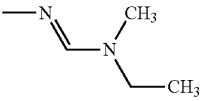 | 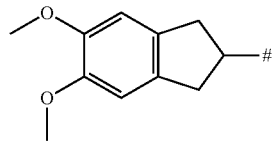 |
| A.1.1046 | 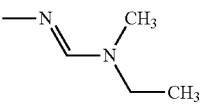 | 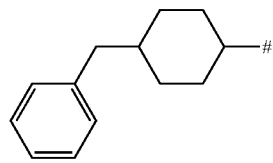 |
| A.1.1047 | 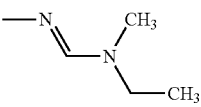 | 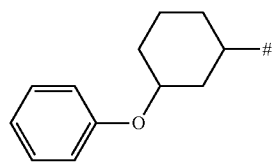 |
| A.1.1048 | 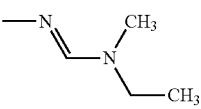 | 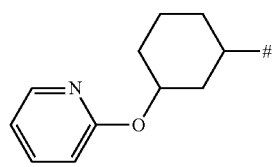 |
| A.1.1049 | 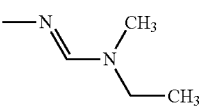 | 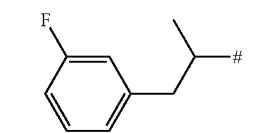 |
| A.1.1050 | 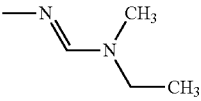 | 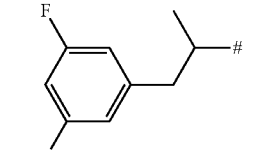 |
| A.1.1051 | 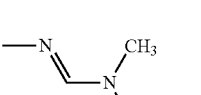 | 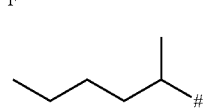 |
| A.1.1052 | 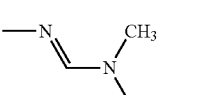 | 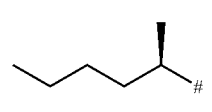 |
| A.1.1053 | 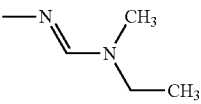 | 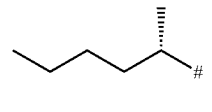 |
| A.1.1054 | 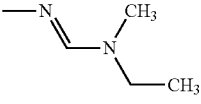 | 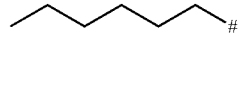 |

TABLE A-continued
Meanings for $R_1$, $R_2$, $R_5$ and $R_6$:
| A.1.1055 | 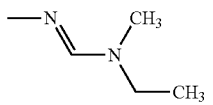 | 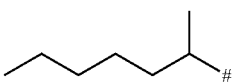 |
| A.1.1056 | 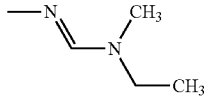 | 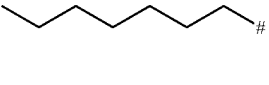 |
| A.1.1057 | 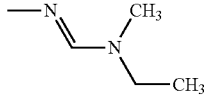 | 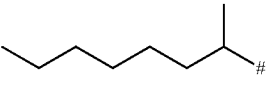 |
| A.1.1058 | 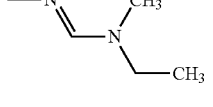 | 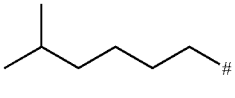 |
| A.1.1059 | 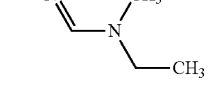 | 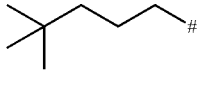 |
| A.1.1060 | 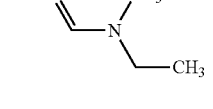 | 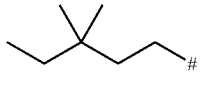 |
| A.1.1061 | 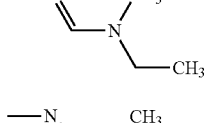 |  |
| A.1.1062 | 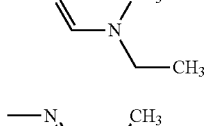 |  |
| A.1.1063 | 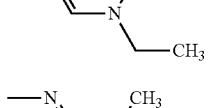 |  |
| A.1.1064 | 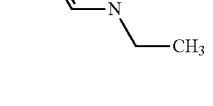 | 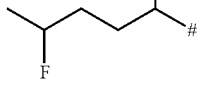 |
| A.1.1065 | 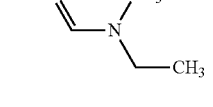 | 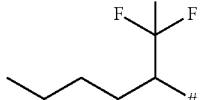 |
| A.1.1066 | 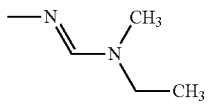 | 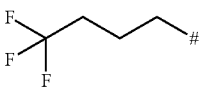 |
| A.1.1067 | 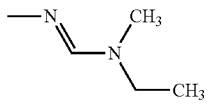 | 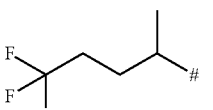 |

TABLE A-continued
| | Meanings for $R_1$, $R_2$, $R_5$ and $R_6$: | |
|---|---|---|
| A.1.1068 | 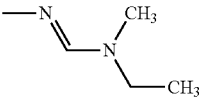 | 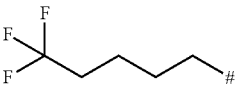 |
| A.1.1069 | 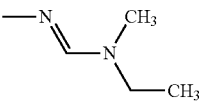 | 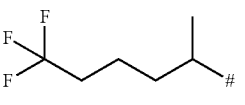 |
| A.1.1070 | 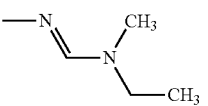 | 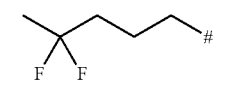 |
| A.1.1071 | 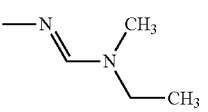 | 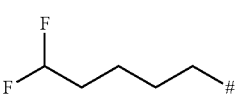 |
| A.1.1072 | 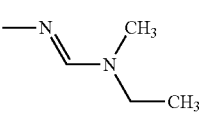 | 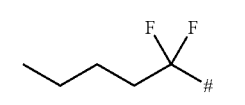 |
| A.1.1073 | 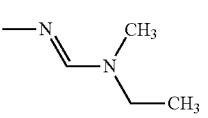 | 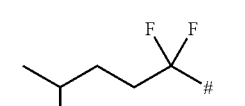 |
| A.1.1074 | 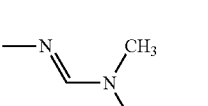 | 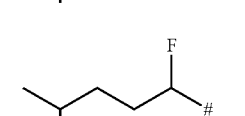 |
| A.1.1075 | 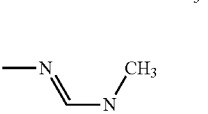 |  |
| A.1.1076 | 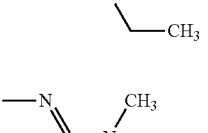 | 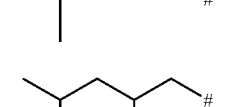 |
| A.1.1077 | 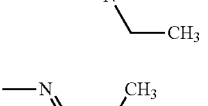 | 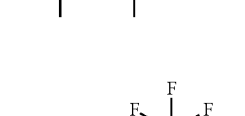 |
| A.1.1078 | 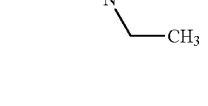 | 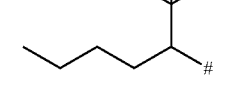 |
| A.1.1079 | 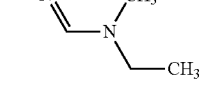 | 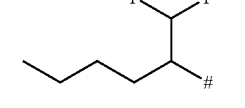 |

TABLE A-continued
Meanings for $R_1$, $R_2$, $R_5$ and $R_6$:
| | | |
|---|---|---|
| A.1.1080 | 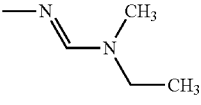 | 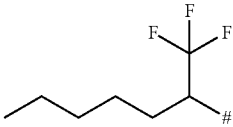 |
| A.1.1081 | 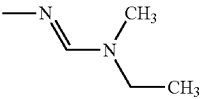 | 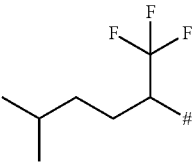 |
| A.1.1082 | 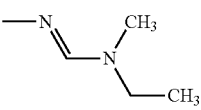 | 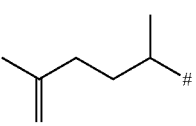 |
| A.1.1083 | 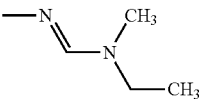 | 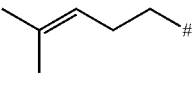 |
| A.1.1084 | 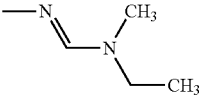 | 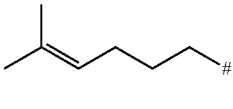 |
| A.1.1085 | 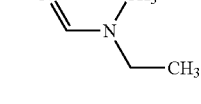 | 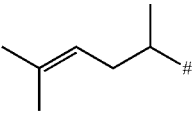 |
| A.1.1086 | 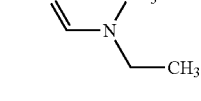 | 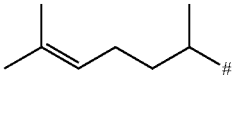 |
| A.1.1087 | 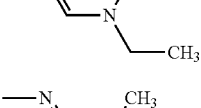 |  |
| A.1.1088 | 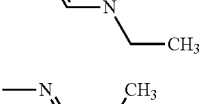 | 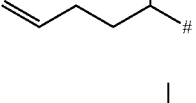 |
| A.1.1089 | 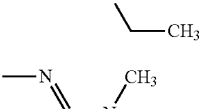 | 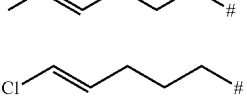 |
| A.1.1090 | 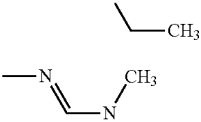 |  |
| A.1.1091 | 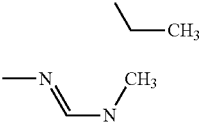 | 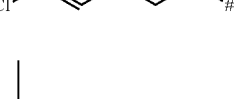 |
| A.1.1092 | 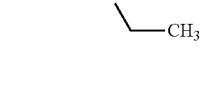 | 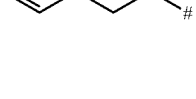 |

US 9,326,513 B2
TABLE A-continued
Meanings for $R_1$, $R_2$, $R_5$ and $R_6$:
| | | |
|---|---|---|
| A.1.1093 | 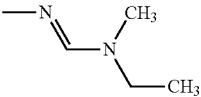 | 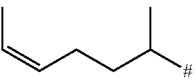 |
| A.1.1094 | 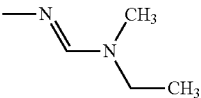 | 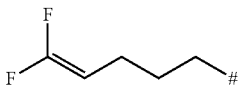 |
| A.1.1095 | 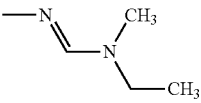 | 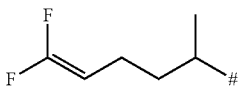 |
| A.1.1096 | 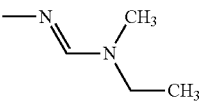 | 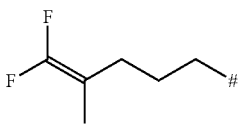 |
| A.1.1097 | 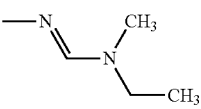 | 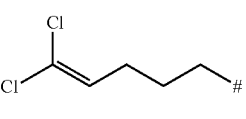 |
| A.1.1098 | 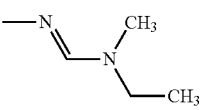 | 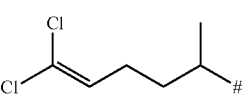 |
| A.1.1099 | 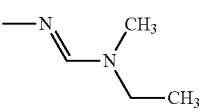 | 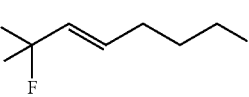 |
| A.1.1100 | 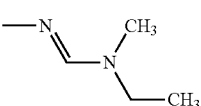 | 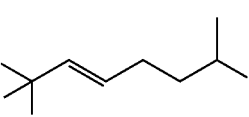 |
| A.1.1101 | 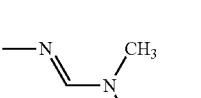 | 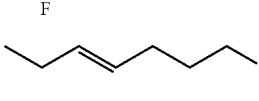 |
| A.1.1102 | 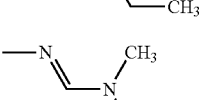 | 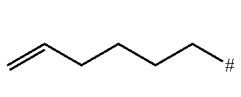 |
| A.1.1103 | 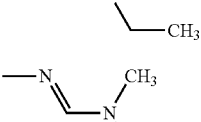 | 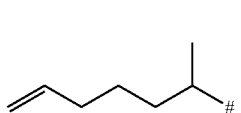 |
| A.1.1104 | 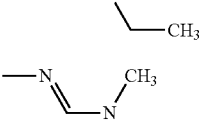 | 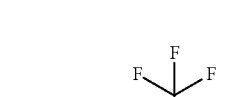 |
| A.1.1105 | 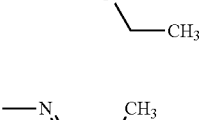 | 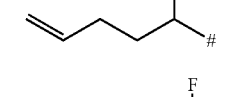 |

TABLE A-continued
Meanings for $R_1$, $R_2$, $R_5$ and $R_6$:
| | | |
|---|---|---|
| A.1.1106 | 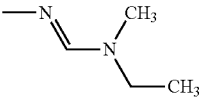 | 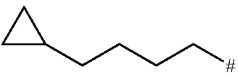 |
| A.1.1107 | 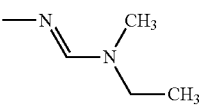 | 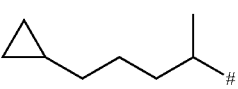 |
| A.1.1108 | 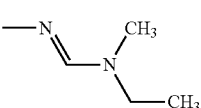 | 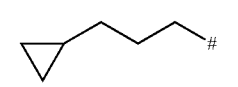 |
| A.1.1109 | 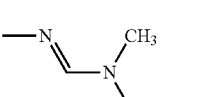 | 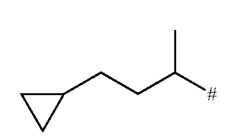 |
| A.1.1110 | 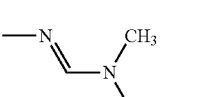 | 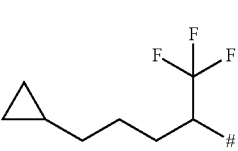 |
| A.1.1111 | 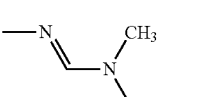 | 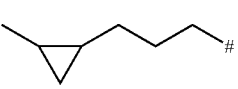 |
| A.1.1112 | 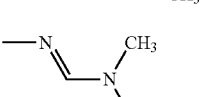 | 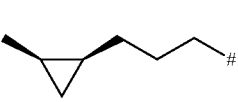 |
| A.1.1113 | 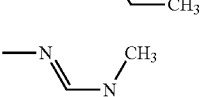 | 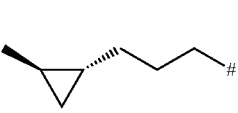 |
| A.1.1114 | 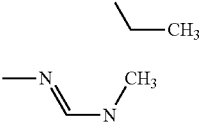 | 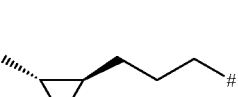 |
| A.1.1115 | 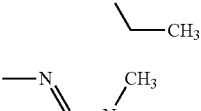 | 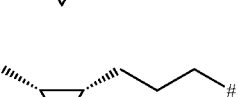 |
| A.1.1116 | 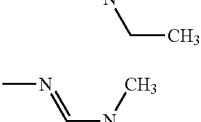 | 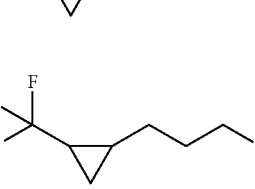 |
| A.1.1117 | 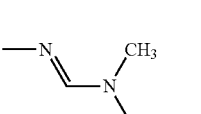 |  |
| A.1.1118 | 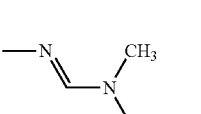 | 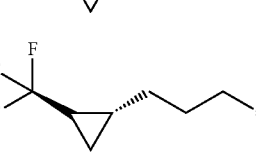 |

TABLE A-continued

Meanings for $R_1$, $R_2$, $R_5$ and $R_6$:

| | | |
|---|---|---|
| A.1.1119 | —N=CH—N(CH$_3$)(CH$_2$CH$_3$) | (cis-2-(trifluoromethyl)cyclopropyl)propyl-# |
| A.1.1120 | —N=CH—N(CH$_3$)(CH$_2$CH$_3$) | (trans-2-(trifluoromethyl)cyclopropyl)propyl-# |
| A.1.1121 | —N=CH—N(CH$_3$)(CH$_2$CH$_3$) | 2-(trifluoromethyl)cyclopropyl)-3-methylbutyl-# |
| A.1.1122 | —N=CH—N(CH$_3$)(CH$_2$CH$_3$) | 2-(trifluoromethyl)cyclopropyl)-4,4,4-trifluoro-3-fluorobutyl-# |
| A.1.1123 | —N=CH—N(CH$_3$)(CH$_2$CH$_3$) | 3-isopropylcyclopentyl-# |
| A.1.1124 | —N=CH—N(CH$_3$)(CH$_2$CH$_3$) | trans-3-isopropylcyclopentyl-# |
| A.1.1125 | —N=CH—N(CH$_3$)(CH$_2$CH$_3$) | cis-3-isopropylcyclopentyl-# |
| A.1.1126 | —N=CH—N(CH$_3$)(CH$_2$CH$_3$) | cis-3-isopropylcyclopentyl-# |
| A.1.1127 | —N=CH—N(CH$_3$)(CH$_2$CH$_3$) | trans-3-isopropylcyclopentyl-# |
| A.1.1128 | —N=CH—N(CH$_3$)(CH$_2$CH$_3$) | 3-vinylcyclopentyl-# |

TABLE A-continued
Meanings for $R_1$, $R_2$, $R_5$ and $R_6$:
| | | |
|---|---|---|
| A.1.1129 | 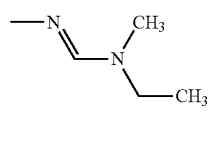 | 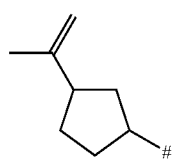 |
| A.1.1130 | 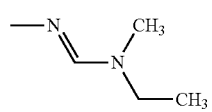 | 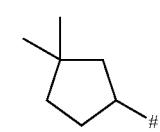 |
| A.1.1131 | 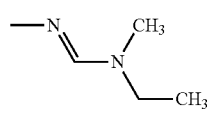 | 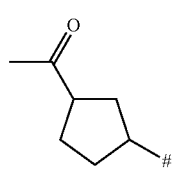 |
| A.1.1132 | 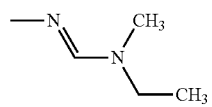 | 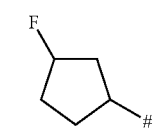 |
| A.1.1133 | 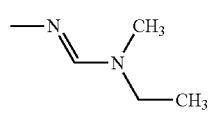 | 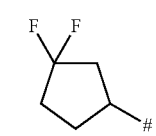 |
| A.1.1134 | 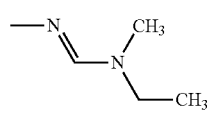 | 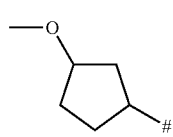 |
| A.1.1135 | 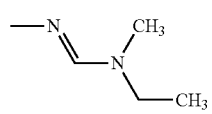 | 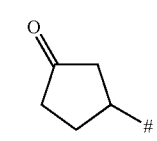 |
| A.1.1136 | 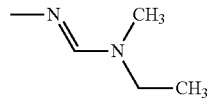 | 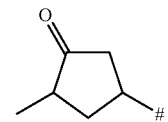 |
| A.1.1137 | 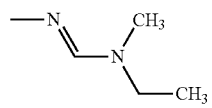 | 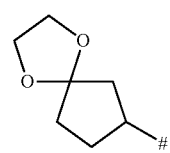 |
| A.1.1138 | 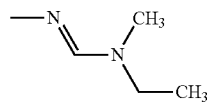 | 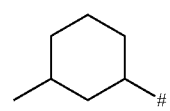 |
| A.1.1139 | 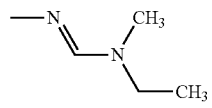 | 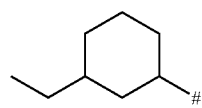 |

TABLE A-continued
| | Meanings for $R_1$, $R_2$, $R_5$ and $R_6$: | |
|---|---|---|
| A.1.1140 | 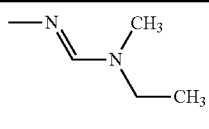 | 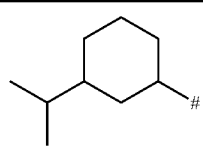 |
| A.1.1141 | 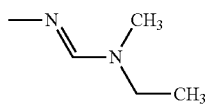 | 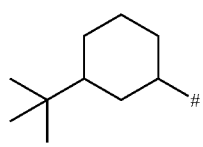 |
| A.1.1142 | 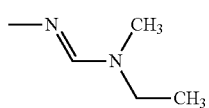 | 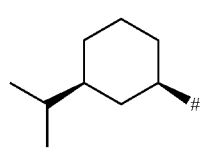 |
| A.1.1143 | 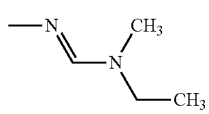 | 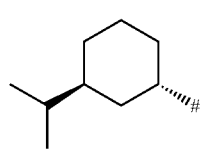 |
| A.1.1144 | 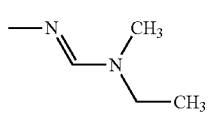 | 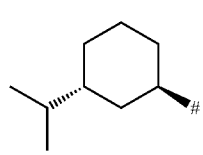 |
| A.1.1145 | 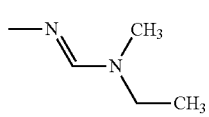 | 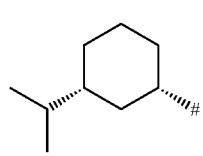 |
| A.1.1146 | 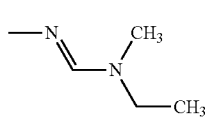 | 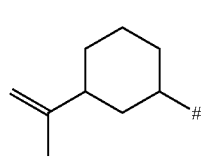 |
| A.1.1147 | 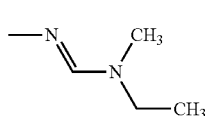 | 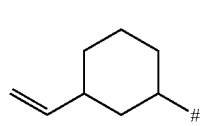 |
| A.1.1148 | 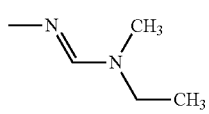 | 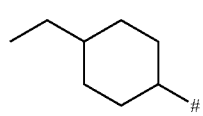 |
| A.1.1149 | 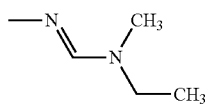 | 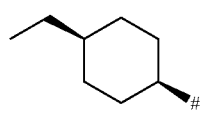 |
| A.1.1150 | 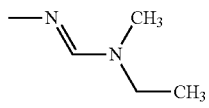 | 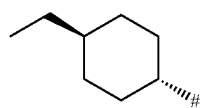 |

TABLE A-continued
| | Meanings for $R_1$, $R_2$, $R_5$ and $R_6$: | |
|---|---|---|
| A.1.1151 | 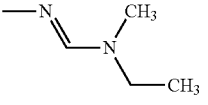 | 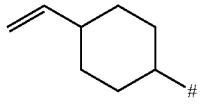 |
| A.1.1152 | 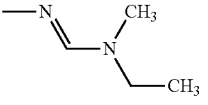 | 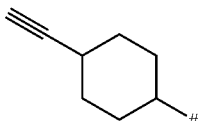 |
| A.1.1153 | 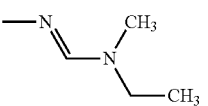 | 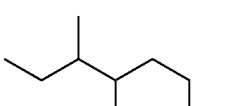 |
| A.1.1154 | 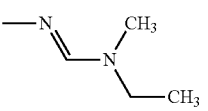 | 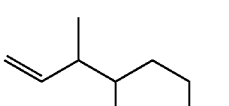 |
| A.1.1155 | 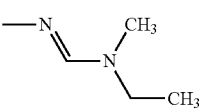 | 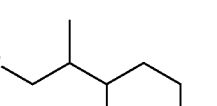 |
| A.1.1156 | 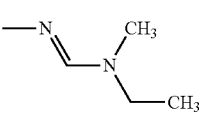 | 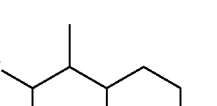 |
| A.1.1157 | 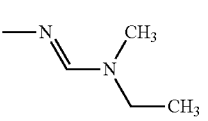 | 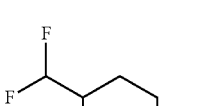 |
| A.1.1158 | 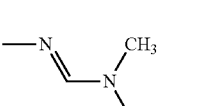 | 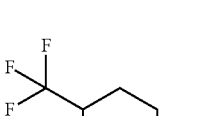 |
| A.1.1159 | 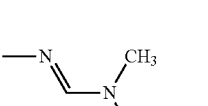 | 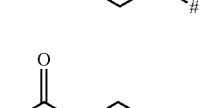 |
| A.1.1160 | 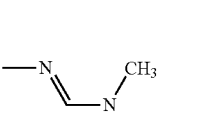 | 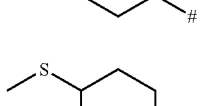 |

TABLE A-continued
| | Meanings for $R_1$, $R_2$, $R_5$ and $R_6$: | |
|---|---|---|
| A.1.1161 | 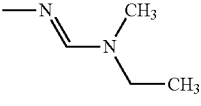 | 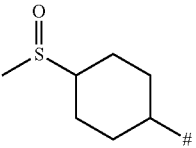 |
| A.1.1162 | 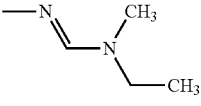 | 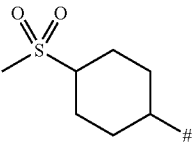 |
| A.1.1163 | 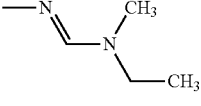 | 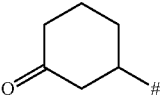 |
| A.1.1164 | 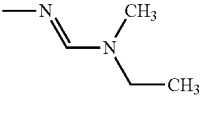 | 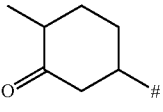 |
| A.1.1165 | 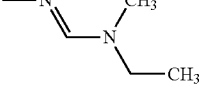 | 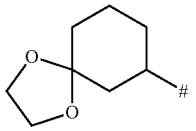 |
| A.1.1166 | 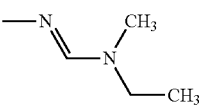 | 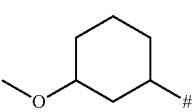 |
| A.1.1167 | 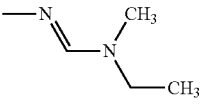 | 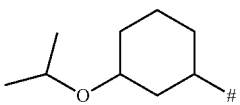 |
| A.1.1168 | 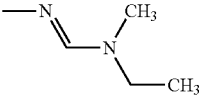 | 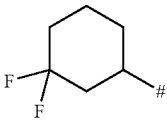 |
| A.1.1169 | 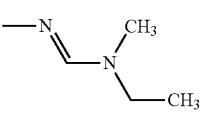 | 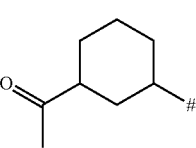 |
| A.1.1170 | 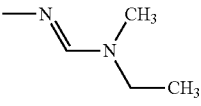 | 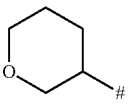 |
| A.1.1171 | 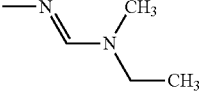 | 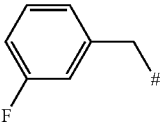 |
| A.1.1172 | 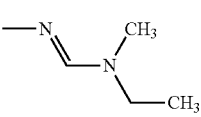 | 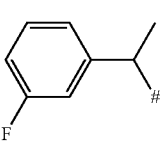 |

TABLE A-continued
| | Meanings for $R_1$, $R_2$, $R_5$ and $R_6$: | |
|---|---|---|
| A.1.1173 | 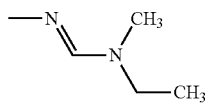 | 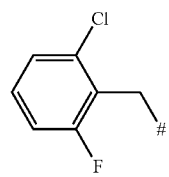 |
| A.1.1174 | 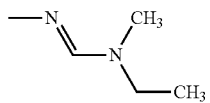 | 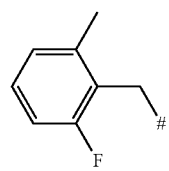 |
| A.1.1175 | 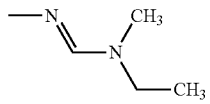 | 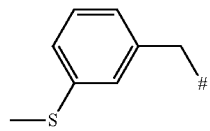 |
| A.1.1176 | 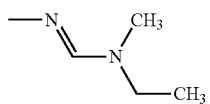 | 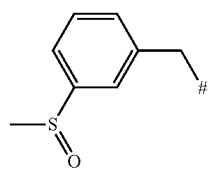 |
| A.1.1177 | 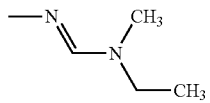 | 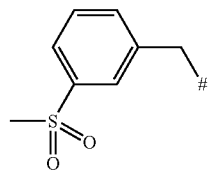 |
| A.1.1178 | 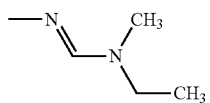 | 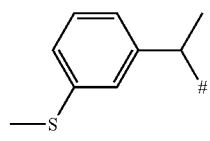 |
| A.1.1179 | 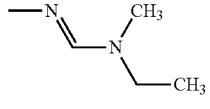 | 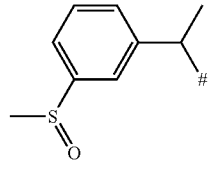 |
| A.1.1180 | 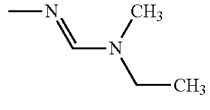 | 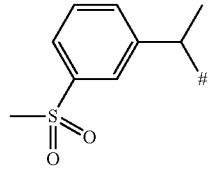 |
| A.1.1181 | 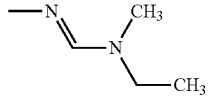 | 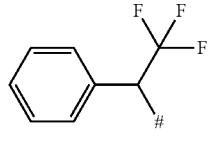 |

TABLE A-continued
| | Meanings for $R_1$, $R_2$, $R_5$ and $R_6$: | |
|---|---|---|
| A.1.1182 | 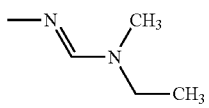 | 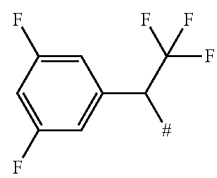 |
| A.1.1183 | 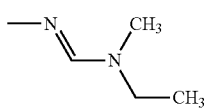 | 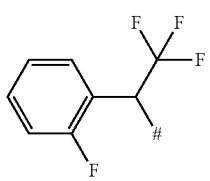 |
| A.1.1184 | 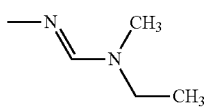 | 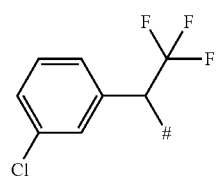 |
| A.1.1185 | 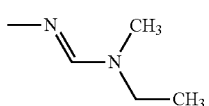 | 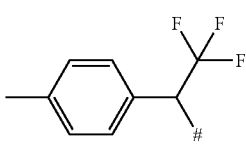 |
| A.1.1186 | 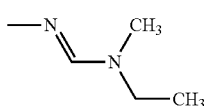 | 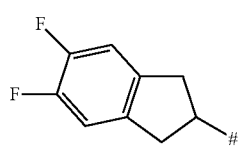 |
| A.1.1187 | 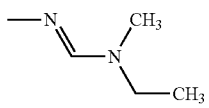 | 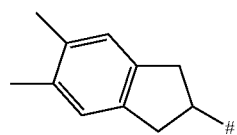 |
| A.1.1188 | 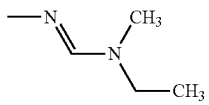 | 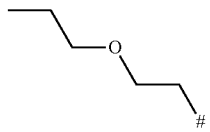 |
| A.1.1189 | 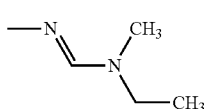 | 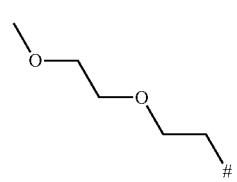 |
| A.1.1190 | 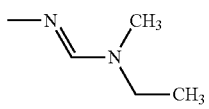 | 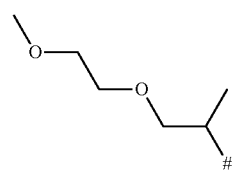 |

TABLE A-continued
| | Meanings for $R_1$, $R_2$, $R_5$ and $R_6$: | |
|---|---|---|
| A.1.1191 | 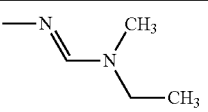 | 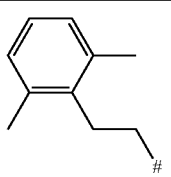 |
| A.1.1192 | 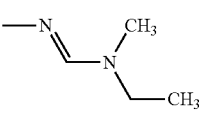 | 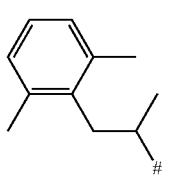 |
| A.1.1193 | 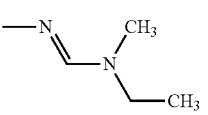 | 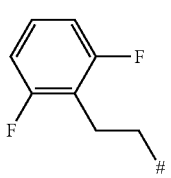 |
| A.1.1194 | 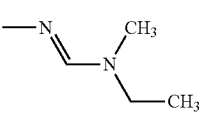 | 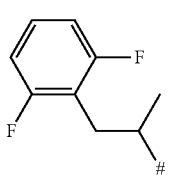 |
| A.1.1195 | 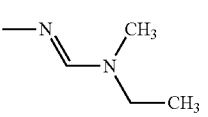 | 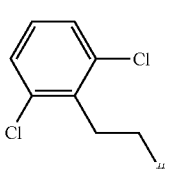 |
| A.1.1196 | 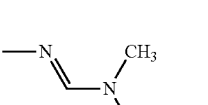 | 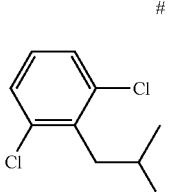 |
| A.1.1197 | 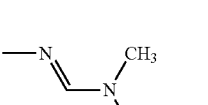 | 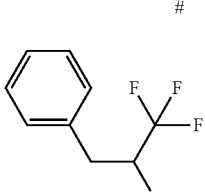 |
| A.1.1198 | 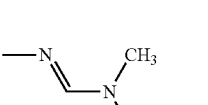 | 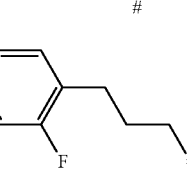 |
| A.1.1199 | 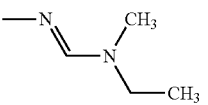 | 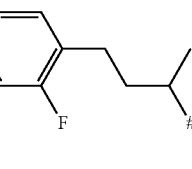 |

TABLE A-continued

Meanings for $R_1$, $R_2$, $R_5$ and $R_6$:

| A.1.1200 | | |
|---|---|---|

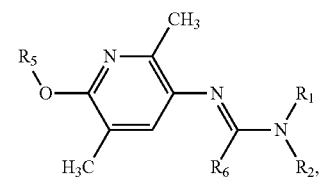

| A.1.1201 | | |
|---|---|---|

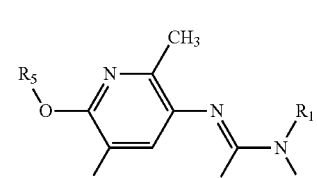

The following tables T1 to T151 disclose preferred compounds of formula I for inclusion as component A in compositions of the invention.

TABLE 1

This table discloses the 1201 compounds T1.1.1 to T1.1.1201 of the formula (T1)

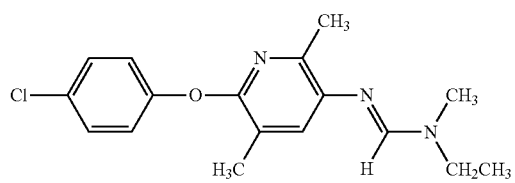

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A. For example, the specific compound T1.1.13 is the compound of the formula T1, in which each of the variables $R_1$, $R_2$, $R_5$ and $R_6$ has the specific meaning given in the line A.1.13 of Table A:

(T1.1.13)

According to the same system, also all of the other 1201 specific compounds disclosed in the Table 1 as well as all of the specific compounds disclosed in the Tables 2 to T151 are specified analogously.

TABLE 2

This table discloses the 1201 compounds T2.1.1 to T2.1.1201 of the formula (T2)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 3

This table discloses the 1201 compounds T3.1.1 to T3.1.1201 of the formula (T3)

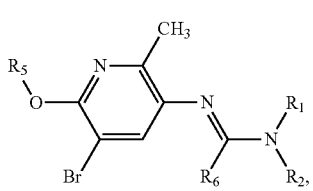

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 4

This table discloses the 1201 compounds T4.1.1 to T4.1.1201 of the formula (T4)

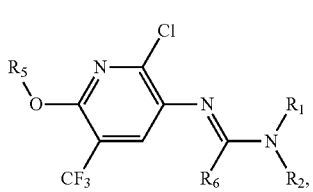

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 5

This table discloses the 1201 compounds T5.1.1 to T5.1.1201 of the formula

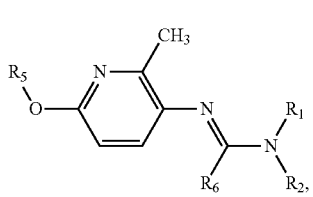
(T5)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 6

This table discloses the 1201 compounds T6.1.1 to T6.1.1201 of the formula

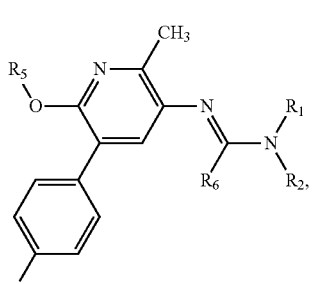
(T6)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 7

This table discloses the 1201 compounds T7.1.1 to T7.1.1201 of the formula

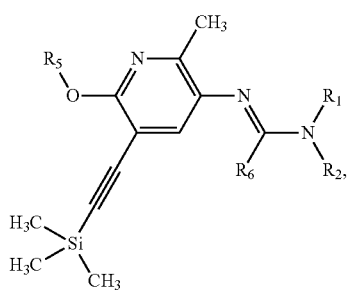
(T7)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 8

This table discloses the 1201 compounds T8.1.1 to T8.1.1201 of the formula

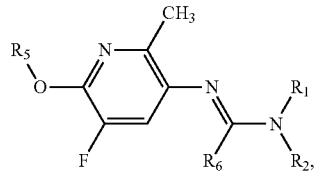
(T8)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 9

This table discloses the 1201 compounds T9.1.1 to T9.1.1201 of the formula

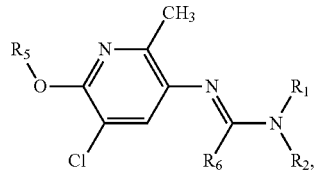
(T9)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 10

This table discloses the 1201 compounds T10.1.1 to T10.1.1201 of the formula

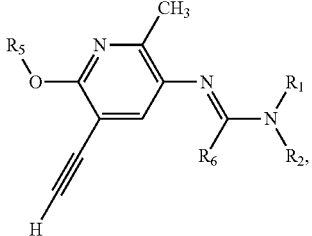
(T10)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 11

This table discloses the 1201 compounds T11.1.1 to T11.1.1201 of the formula

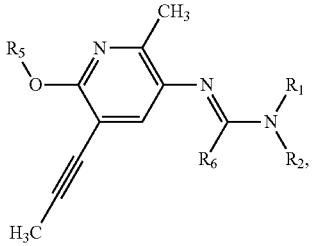
(T11)

TABLE 12

This table discloses the 1201 compounds T12.1.1 to T12.1.1201 of the formula

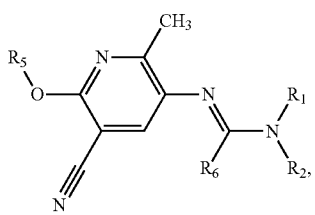
(T12)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 13

This table discloses the 1201 compounds T13.1.1 to T13.1.1201 of the formula

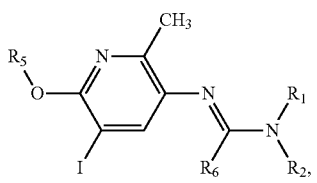
(T13)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 14

This table discloses the 1201 compounds T14.1.1 to T14.1.1201 of the formula

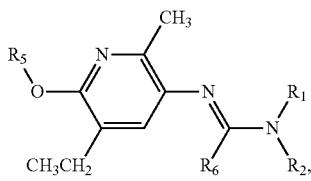
(T14)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 15

This table discloses the 1201 compounds T15.1.1 to T15.1.1201 of the formula

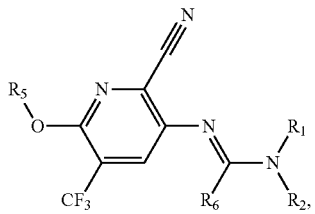
(T15)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 16

This table discloses the 1201 compounds T16.1.1 to T16.1.1201 of the formula

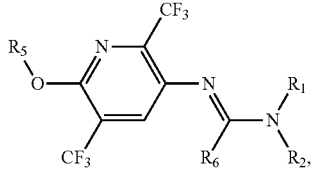
(T16)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 17

This table discloses the 1201 compounds T17.1.1 to T17.1.1201 of the formula

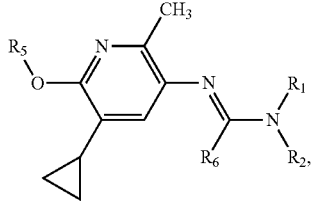
(T17)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 18

This table discloses the 1201 compounds T18.1.1 to T18.1.1201 of the formula

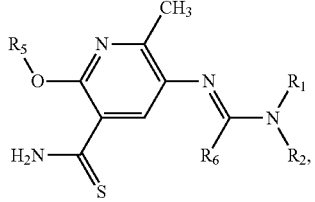
(T18)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 19

This table discloses the 1201 compounds T19.1.1 to T19.1.1201 of the formula

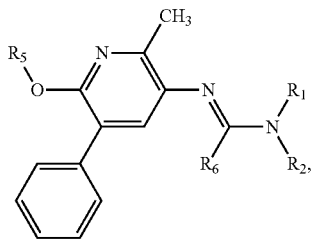
(T19)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 20

This table discloses the 1201 compounds T20.1.1 to T20.1.1201 of the formula

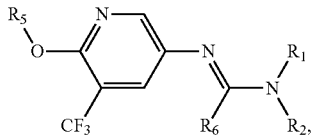
(T20)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 21

This table discloses the 1201 compounds T21.1.1 to T21.1.1201 of the formula

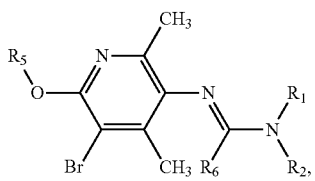
(T21)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 22

This table discloses the 1201 compounds T22.1.1 to T22.1.1201 of the formula

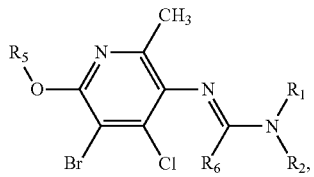
(T22)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 23

This table discloses the 1201 compounds T23.1.1 to T23.1.1201 of the formula

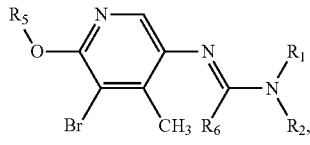
(T23)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 24

This table discloses the 1201 compounds T24.1.1 to T24.1.1201 of the formula

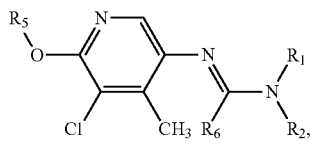
(T24)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 25

This table discloses the 1201 compounds T25.1.1 to T25.1.1201 of the formula

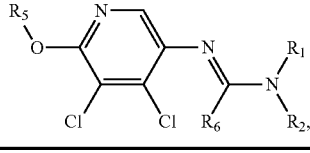
(T25)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 26

This table discloses the 1201 compounds
T26.1.1 to T26.1.1201 of the formula

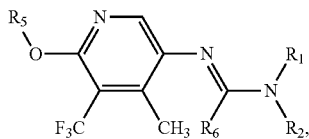
(T26)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 27

This table discloses the 1201 compounds
T27.1.1 to T27.1.1201 of the formula

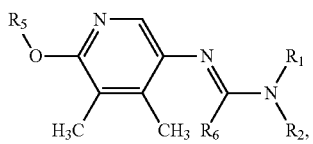
(T27)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 28

This table discloses the 1201 compounds
T28.1.1 to T28.1.1201 of the formula

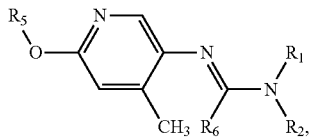
(T28)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 29

This table discloses the 1201 compounds
T29.1.1 to T29.1.1201 of the formula

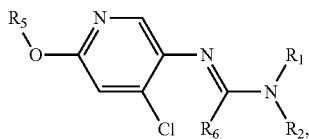
(T29)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 30

This table discloses the 1201 compounds
T30.1.1 to T30.1.1201 of the formula

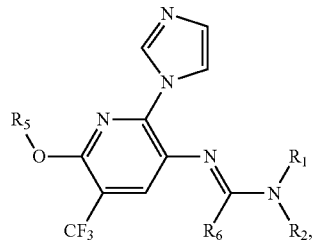
(T30)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 31

This table discloses the 1201 compounds
T31.1.1 to T31.1.1201 of the formula

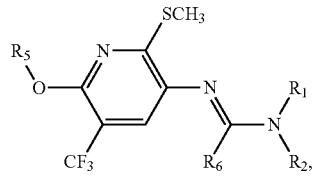
(T31)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 32

This table discloses the 1201 compounds
T32.1.1 to T32.1.1201 of the formula

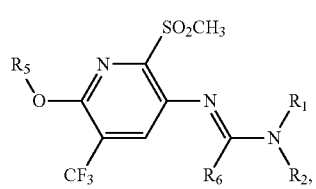
(T32)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 33

This table discloses the 1201 compounds
T33.1.1 to T33.1.1201 of the formula

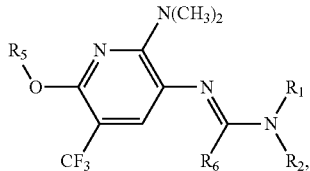
(T33)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 34

This table discloses the 1201 compounds
T34.1.1 to T34.1.1201 of the formula

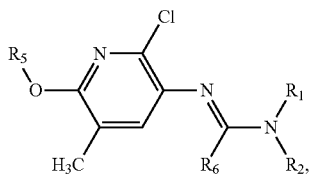
(T34)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 35

This table discloses the 1201 compounds
T35.1.1 to T35.1.1201 of the formula

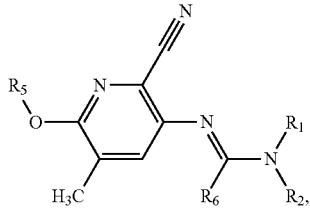
(T35)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 36

This table discloses the 1201 compounds
T36.1.1 to T36.1.1201 of the formula

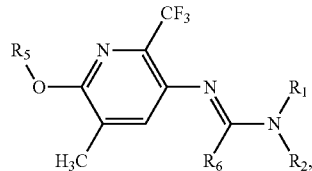
(T36)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 37

This table discloses the 1201 compounds
T37.1.1 to T37.1.1201 of the formula

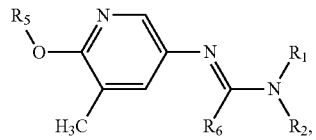
(T37)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 38

This table discloses the 1201 compounds
T38.1.1 to T38.1.1201 of the formula

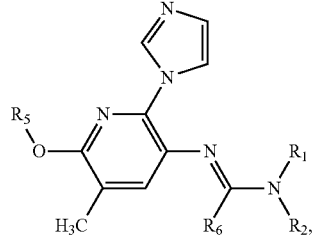
(T38)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 39

This table discloses the 1201 compounds
T39.1.1 to T39.1.1201 of the formula

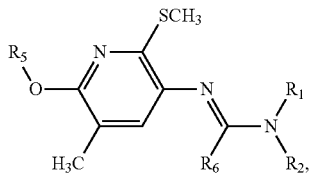
(T39)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 40

This table discloses the 1201 compounds
T40.1.1 to T40.1.1201 of the formula

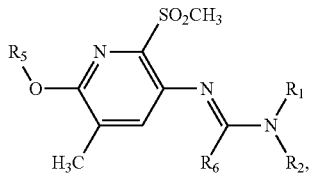
(T40)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 41

This table discloses the 1201 compounds
T41.1.1 to T41.1.1201 of the formula

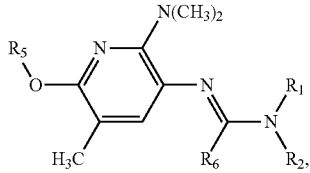
(T41)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 42

This table discloses the 1201 compounds
T42.1.1 to T42.1.1201 of the formula

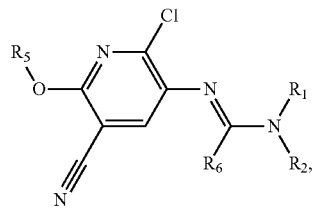
(T42)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 43

This table discloses the 1201 compounds
T43.1.1 to T43.1.1201 of the formula

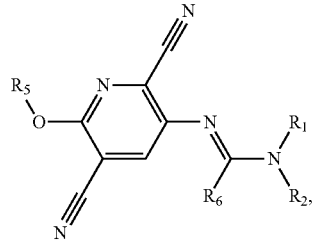
(T43)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 44

This table discloses the 1201 compounds
T44.1.1 to T44.1.1201 of the formula

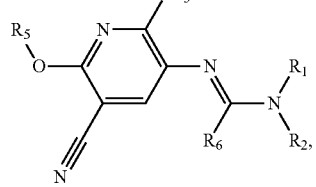
(T44)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 45

This table discloses the 1201 compounds
T45.1.1 to T45.1.1201 of the formula

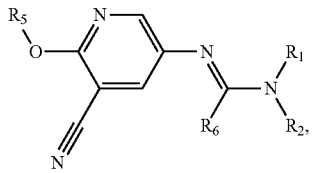
(T45)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 46

This table discloses the 1201 compounds
T46.1.1 to T46.1.1201 of the formula

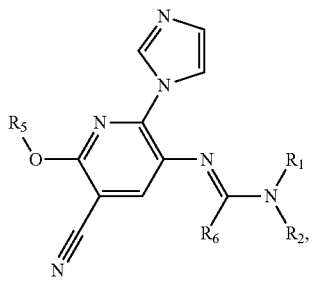
(T46)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 47

This table discloses the 1201 compounds
T47.1.1 to T47.1.1201 of the formula

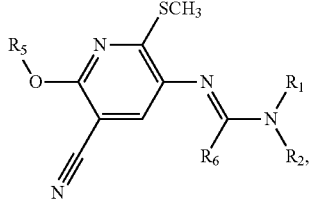
(T47)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 48

This table discloses the 1201 compounds
T48.1.1 to T48.1.1201 of the formula

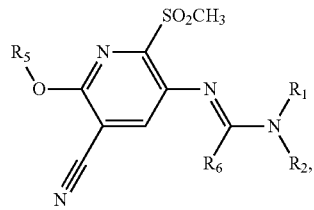
(T48)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 49

This table discloses the 1201 compounds
T49.1.1 to T49.1.1201 of the formula

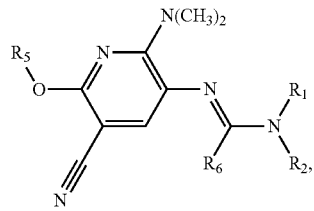
(T49)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 50

This table discloses the 1201 compounds
T50.1.1 to T50.1.1201 of the formula

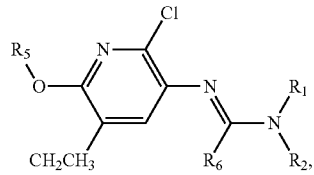
(T50)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 51

This table discloses the 1201 compounds
T51.1.1 to T51.1.1201 of the formula

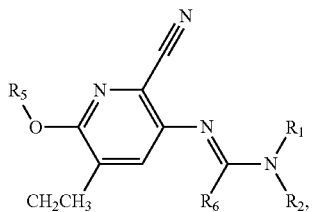

(T51)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 52

This table discloses the 1201 compounds
T52.1.1 to T52.1.1201 of the formula

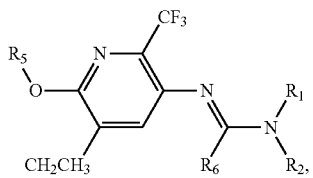

(T52)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 53

This table discloses the 1201 compounds
T53.1.1 to T53.1.1201 of the formula

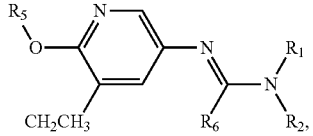

(T53)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 54

This table discloses the 1201 compounds
T54.1.1 to T54.1.1201 of the formula

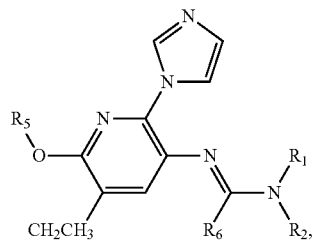

(T54)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 55

This table discloses the 1201 compounds
T55.1.1 to T55.1.1201 of the formula

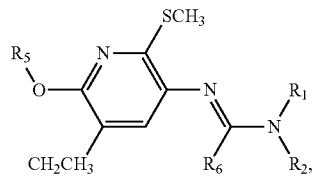

(T55)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 56

This table discloses the 1201 compounds
T56.1.1 to T56.1.1201 of the formula

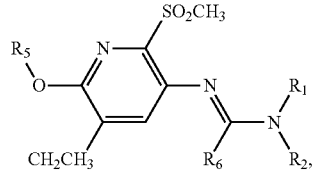

(T56)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 57

This table discloses the 1201 compounds
T57.1.1 to T57.1.1201 of the formula

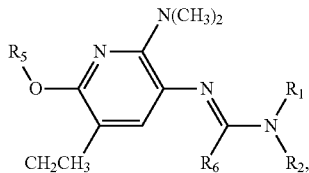

(T57)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 58

This table discloses the 1201 compounds
T58.1.1 to T58.1.1201 of the formula

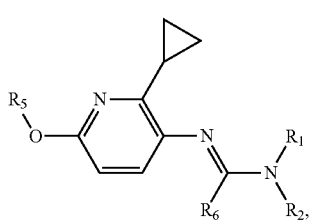

(T58)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 59

This table discloses the 1201 compounds
T59.1.1 to T59.1.1201 of the formula

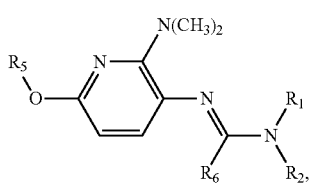

(T59)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 60

This table discloses the 1201 compounds
T60.1.1 to T60.1.1201 of the formula

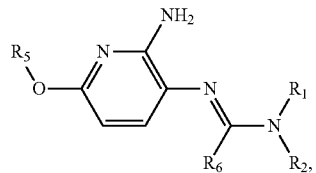

(T60)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 61

This table discloses the 1201 compounds
T61.1.1 to T61.1.1201 of the formula

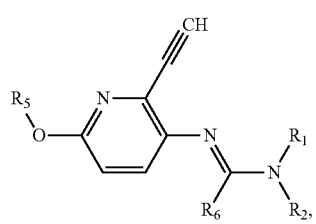

(T61)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 62

This table discloses the 1201 compounds
T62.1.1 to T62.1.1201 of the formula

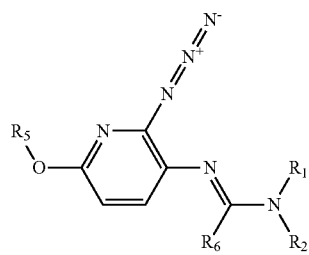

(T62)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 63

This table discloses the 1201 compounds
T63.1.1 to T63.1.1201 of the formula

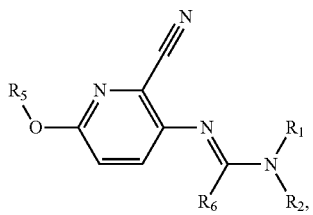

(T63)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 64

This table discloses the 1201 compounds
T64.1.1 to T64.1.1201 of the formula

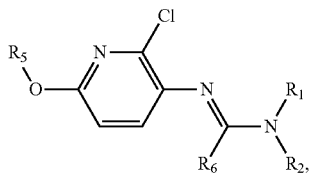

(T64)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 65

This table discloses the 1201 compounds
T65.1.1 to T65.1.1201 of the formula

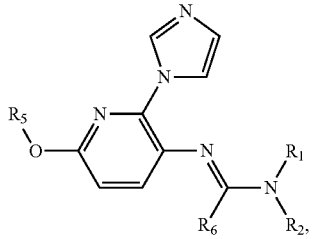

(T65)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 66

This table discloses the 1201 compounds
T66.1.1 to T66.1.1201 of the formula

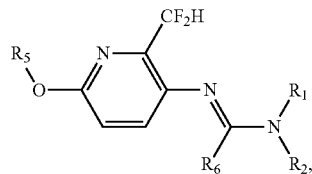

(T66)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 67

This table discloses the 1201 compounds
T67.1.1 to T67.1.1201 of the formula

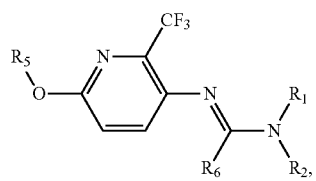

(T67)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 68

This table discloses the 1201 compounds
T68.1.1 to T68.1.1201 of the formula

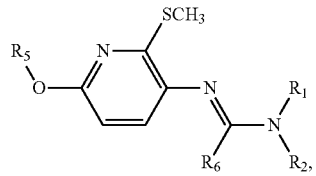

(T68)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 69

This table discloses the 1201 compounds
T69.1.1 to T69.1.1201 of the formula

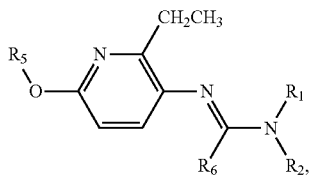
(T69)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 70

This table discloses the 1201 compounds
T70.1.1 to T70.1.1201 of the formula

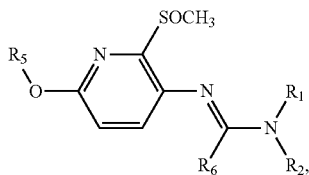
(T70)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 71

This table discloses the 1201 compounds
T71.1.1 to T71.1.1201 of the formula

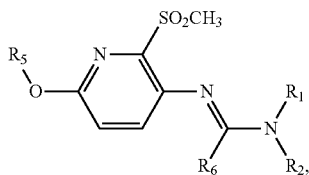
(T71)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 72

This table discloses the 1201 compounds
T72.1.1 to T72.1.1201 of the formula

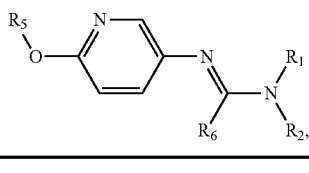
(T72)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 73

This table discloses the 1201 compounds
T73.1.1 to T73.1.1201 of the formula

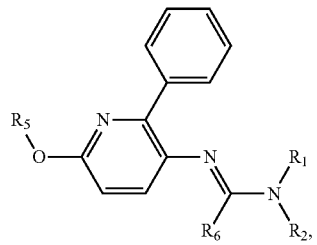
(T73)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 74

This table discloses the 1201 compounds
T74.1.1 to T74.1.1201 of the formula

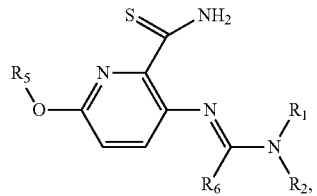
(T74)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 75

This table discloses the 1201 compounds
T75.1.1 to T75.1.1201 of the formula

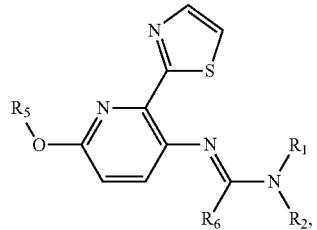
(T75)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 76

This table discloses the 1201 compounds T76.1.1 to T76.1.1201 of the formula

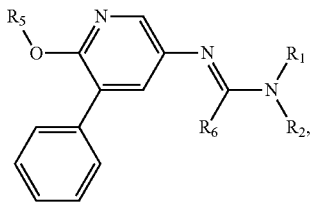
(T76)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 77

This table discloses the 1201 compounds T77.1.1 to T77.1.1201 of the formula

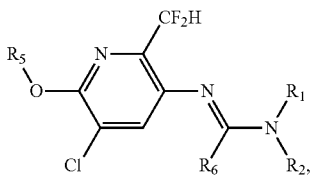
(T77)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 78

This table discloses the 1201 compounds T78.1.1 to T78.1.1201 of the formula

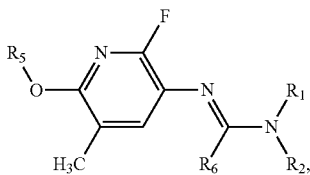
(T78)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 79

This table discloses the 1201 compounds T79.1.1 to T79.1.1201 of the formula

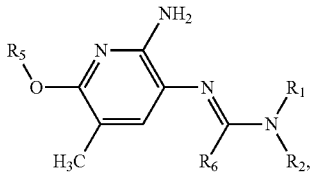
(T79)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 80

This table discloses the 1201 compounds T80.1.1 to T80.1.1201 of the formula

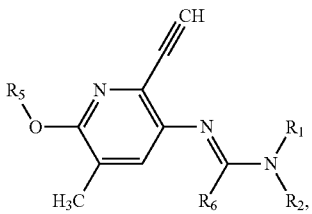
(T80)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 81

This table discloses the 1201 compounds T81.1.1 to T81.1.1201 of the formula

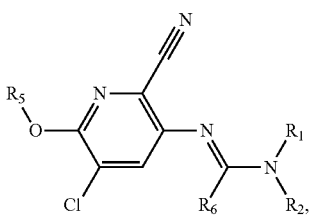
(T81)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 82

This table discloses the 1201 compounds T82.1.1 to T82.1.1201 of the formula

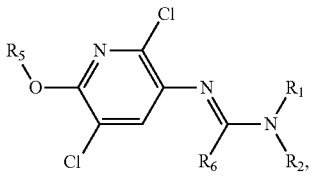
(T82)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 83

This table discloses the 1201 compounds T83.1.1 to T83.1.1201 of the formula

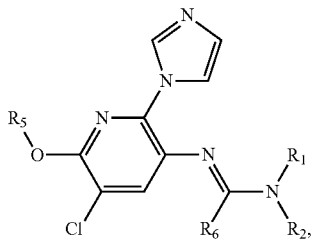
(T83)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 84

This table discloses the 1201 compounds T84.1.1 to T84.1.1201 of the formula

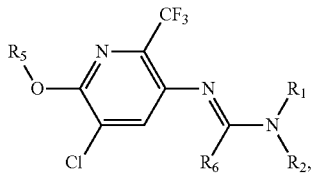
(T84)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 85

This table discloses the 1201 compounds T85.1.1 to T85.1.1201 of the formula

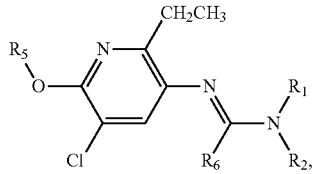
(T85)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 86

This table discloses the 1201 compounds T86.1.1 to T86.1.1201 of the formula

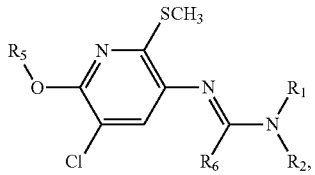
(T86)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 87

This table discloses the 1201 compounds T87.1.1 to T87.1.1201 of the formula

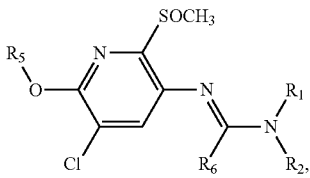
(T87)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 88

This table discloses the 1201 compounds T88.1.1 to T88.1.1201 of the formula

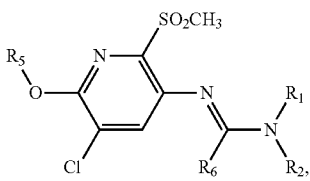
(T88)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 89

This table discloses the 1201 compounds T89.1.1 to T89.1.1201 of the formula

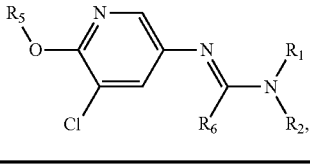
(T89)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 90

This table discloses the 1201 compounds T90.1.1 to T90.1.1201 of the formula

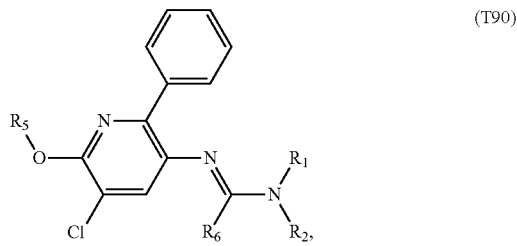
(T90)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 91

This table discloses the 1201 compounds T91.1.1 to T91.1.1201 of the formula

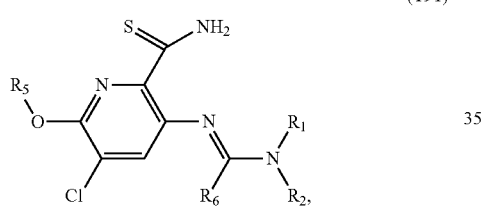
(T91)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 92

This table discloses the 1201 compounds T92.1.1 to T92.1.1201 of the formula

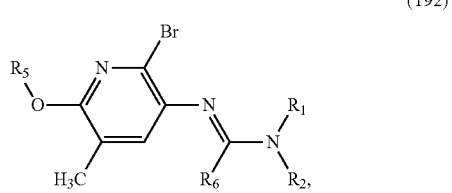
(T92)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 93

This table discloses the 1201 compounds T93.1.1 to T93.1.1201 of the formula

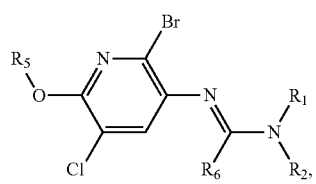
(T93)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 94

This table discloses the 1201 compounds T94.1.1 to T94.1.1201 of the formula

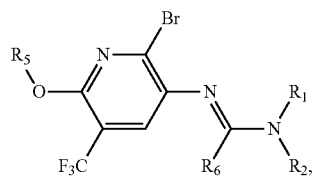
(T94)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 95

This table discloses the 1201 compounds T95.1.1 to T95.1.1201 of the formula

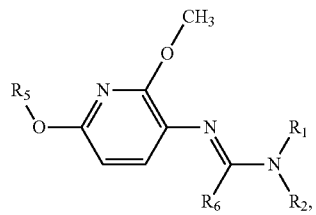
(T95)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 96

This table discloses the 1201 compounds T96.1.1 to T96.1.1201 of the formula

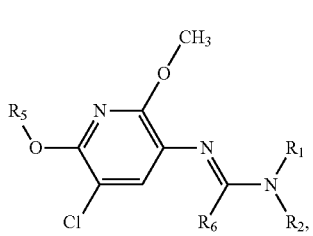
(T96)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 97

This table discloses the 1201 compounds T97.1.1 to T97.1.1201 of the formula

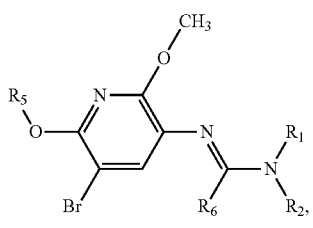
(T97)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 98

This table discloses the 1201 compounds T98.1.1 to T98.1.1201 of the formula

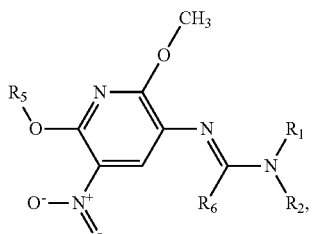
(T98)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 99

This table discloses the 1201 compounds T99.1.1 to T99.1.1201 of the formula

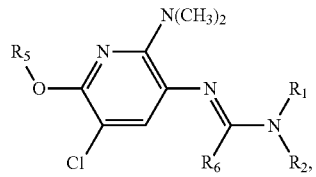
(T99)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 100

This table discloses the 1201 compounds T100.1.1 to T100.1.1201 of the formula

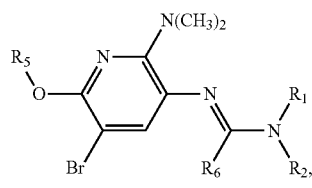
(T100)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 101

This table discloses the 1201 compounds T101.1.1 to T101.1.1201 of the formula

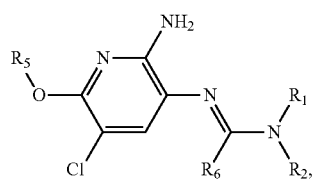
(T101)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 102

This table discloses the 1201 compounds T102.1.1 to T102.1.1201 of the formula

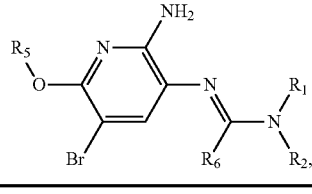
(T102)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 103

This table discloses the 1201 compounds
T103.1.1 to T103.1.1201 of the formula

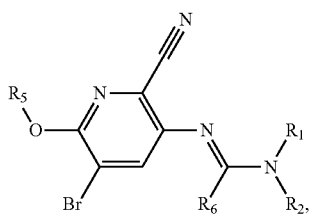

(T103)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 104

This table discloses the 1201 compounds
T104.1.1 to T104.1.1201 of the formula

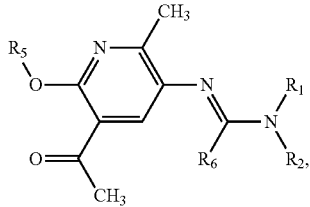

(T104)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 105

This table discloses the 1201 compounds
T105.1.1 to T105.1.1201 of the formula

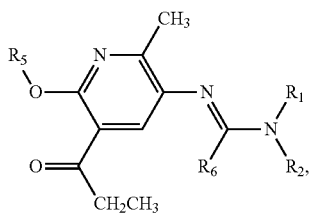

(T105)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 106

This table discloses the 1201 compounds
T106.1.1 to T106.1.1201 of the formula

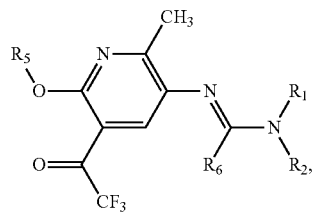

(T106)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 107

This table discloses the 1201 compounds
T107.1.1 to T107.1.1201 of the formula (T107)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 108

This table discloses the 1201 compounds
T108.1.1 to T108.1.1201 of the formula (T108)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 109

This table discloses the 1201 compounds
T109.1.1 to T109.1.1201 of the formula

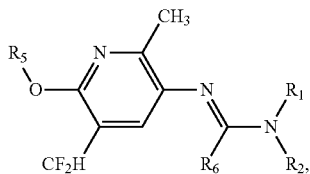
(T109)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 110

This table discloses the 1201 compounds
T110.1.1 to T110.1.1201 of the formula

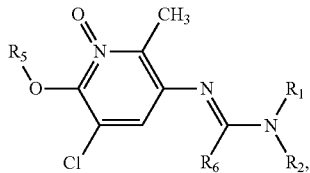
(T110)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 111

This table discloses the 1201 compounds
T111.1.1 to T111.1.1201 of the formula

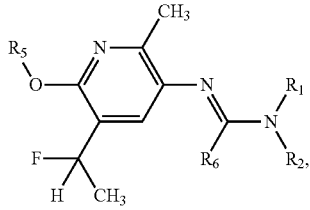
(T111)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 112

This table discloses the 1201 compounds
T112.1.1 to T112.1.1201 of the formula

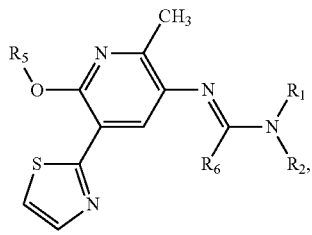
(T112)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 113

This table discloses the 1201 compounds
T113.1.1 to T113.1.1201 of the formula (T113)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 114

This table discloses the 1201 compounds
T114.1.1 to T114.1.1201 of the formula

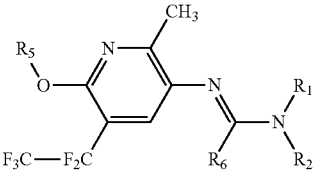
(T114)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 115

This table discloses the 1201 compounds
T115.1.1 to T115.1.1201 of the formula

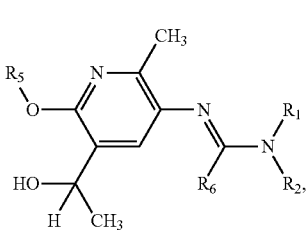

(T115)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 116

This table discloses the 1201 compounds
T116.1.1 to T116.1.1201 of the formula

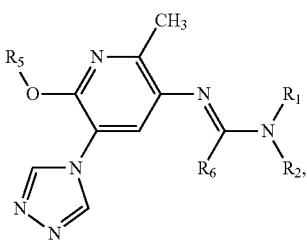

(T116)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 117

This table discloses the 1201 compounds
T117.1.1 to T117.1.1201 of the formula

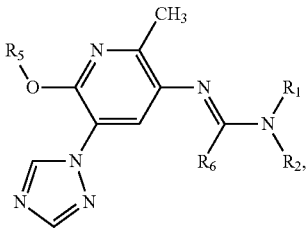

(T117)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 118

This table discloses the 1201 compounds
T118.1.1 to T118.1.1201 of the formula

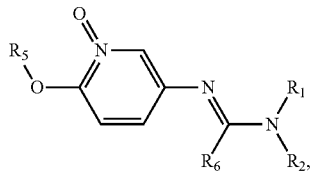

(T118)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 119

This table discloses the 1201 compounds
T119.1.1 to T119.1.1201 of the formula

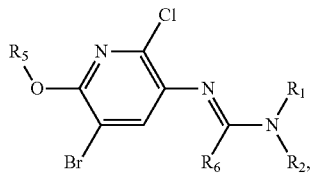

(T119)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 120

This table discloses the 1201 compounds
T120.1.1 to T120.1.1201 of the formula

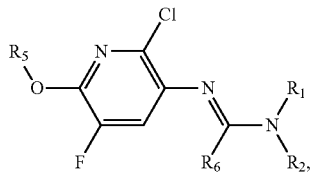

(T120)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 121

This table discloses the 1201 compounds
T121.1.1 to T121.1.1201 of the formula

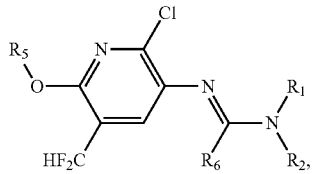

(T121)

TABLE 122

This table discloses the 1201 compounds
T122.1.1 to T122.1.1201 of the formula

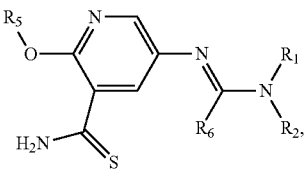

(T122)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 123

This table discloses the 1201 compounds
T123.1.1 to T123.1.1201 of the formula

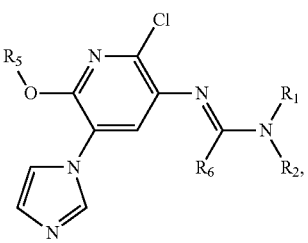

(T123)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 124

This table discloses the 1201 compounds
T124.1.1 to T124.1.1201 of the formula

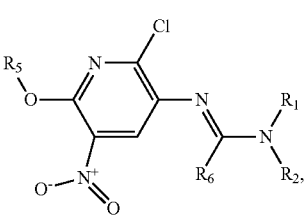

(T124)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 125

This table discloses the 1201 compounds
T125.1.1 to T125.1.1201 of the formula

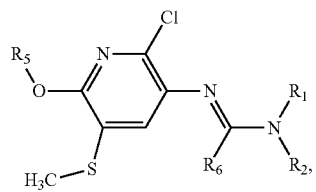

(T125)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 126

This table discloses the 1201 compounds
T126.1.1 to T126.1.1201 of the formula

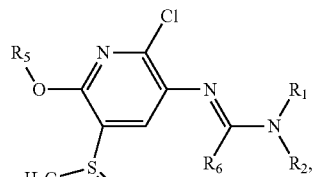

(T126)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 127

This table discloses the 1201 compounds
T127.1.1 to T127.1.1201 of the formula

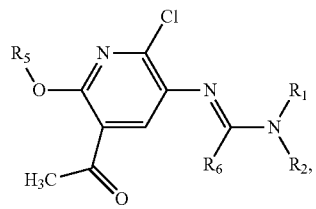

(T127)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 128

This table discloses the 1201 compounds
T128.1.1 to T128.1.1201 of the formula (T128)

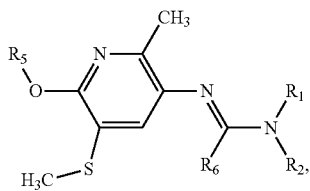

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 129

This table discloses the 1201 compounds
T129.1.1 to T129.1.1201 of the formula (T129)

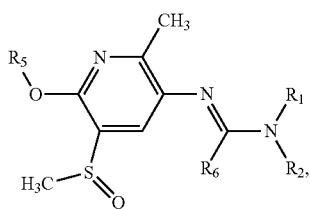

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 130

This table discloses the 1201 compounds
T130.1.1 to T130.1.1201 of the formula (T130)

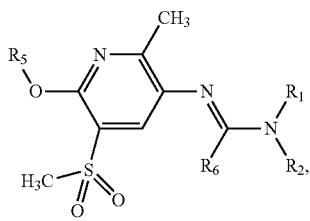

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 131

This table discloses the 1201 compounds
T131.1.1 to T131.1.1201 of the formula (T131)

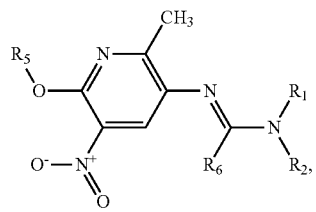

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 132

This table discloses the 1201 compounds
T132.1.1 to T132.1.1201 of the formula (T132)

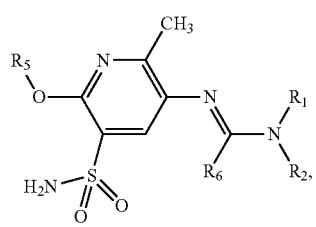

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 133

This table discloses the 1201 compounds
T133.1.1 to T133.1.1201 of the formula (T133)

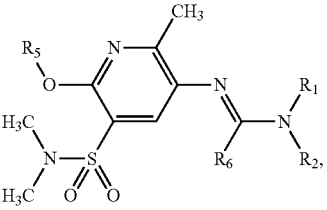

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 134

This table discloses the 1201 compounds
T134.1.1 to T134.1.1201 of the formula

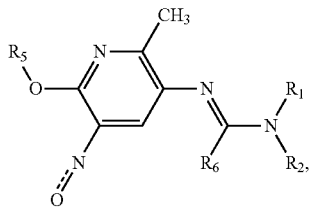
(T134)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 135

This table discloses the 1201 compounds
T135.1.1 to T135.1.1201 of the formula

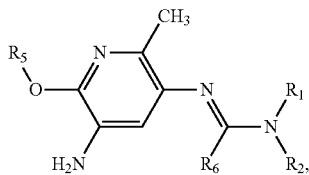
(T135)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 136

This table discloses the 1201 compounds
T136.1.1 to T136.1.1201 of the formula

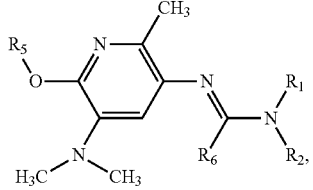
(T136)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 137

This table discloses the 1201 compounds
T137.1.1 to T137.1.1201 of the formula

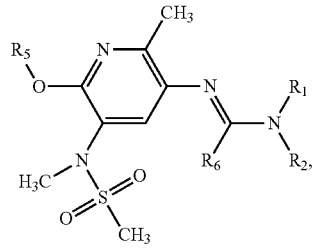
(T137)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 138

This table discloses the 1201 compounds
T138.1.1 to T138.1.1201 of the formula

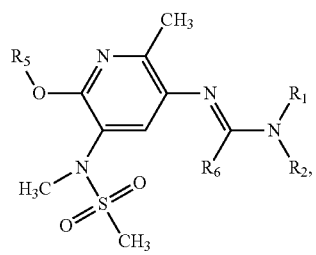
(T138)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 139

This table discloses the 1201 compounds
T139.1.1 to T139.1.1201 of the formula

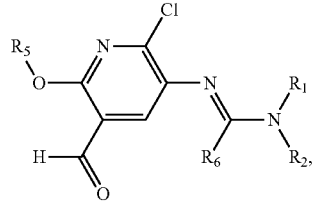
(T139)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 140

This table discloses the 1201 compounds
T140.1.1 to T140.1.1201 of the formula

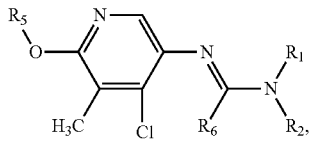
(T140)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 141

This table discloses the 1201 compounds
T141.1.1 to T141.1.1201 of the formula

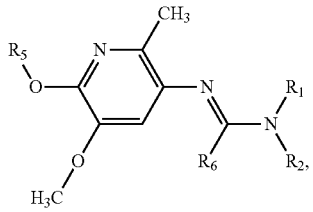
(T141)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 142

This table discloses the 1201 compounds
T142.1.1 to T142.1.1201 of the formula

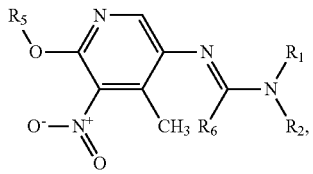
(T142)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 143

This table discloses the 1201 compounds
T143.1.1 to T143.1.1201 of the formula

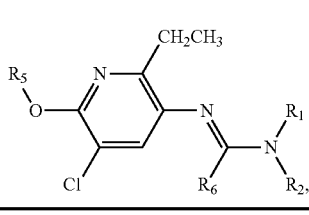
(T143)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 144

This table discloses the 1201 compounds
T144.1.1 to T144.1.1201 of the formula

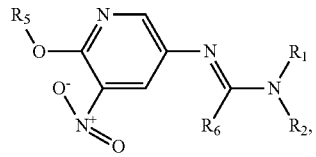
(T144)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 145

This table discloses the 1201 compounds
T145.1.1 to T145.1.1201 of the formula

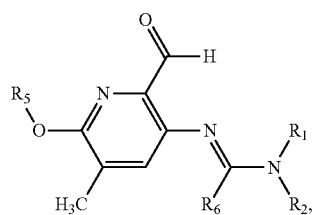
(T145)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 146

This table discloses the 1201 compounds
T146.1.1 to T146.1.1201 of the formula

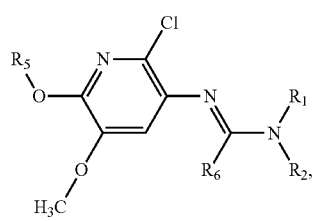
(T146)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 147

This table discloses the 1201 compounds
T147.1.1 to T147.1.1201 of the formula

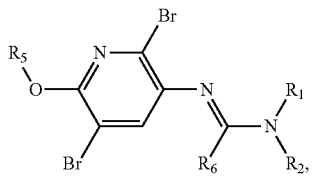

(T147)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 148

This table discloses the 1201 compounds
T148.1.1 to T148.1.1201 of the formula

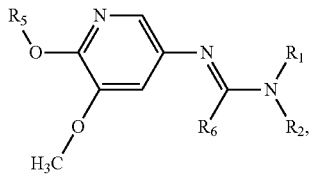

(T148)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 149

This table discloses the 1201 compounds
T149.1.1 to T149.1.1201 of the formula

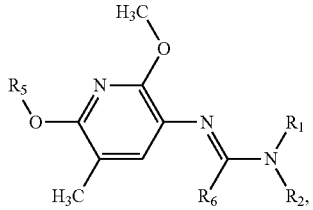

(T149)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 150

This table discloses the 1201 compounds
T150.1.1 to T150.1.1201 of the formula

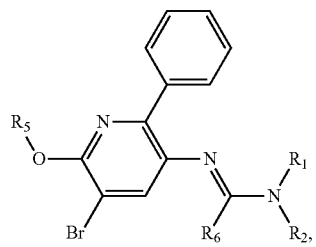

(T150)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 151

This table discloses the 1201 compounds
T151.1.1 to T151.1.1201 of the formula

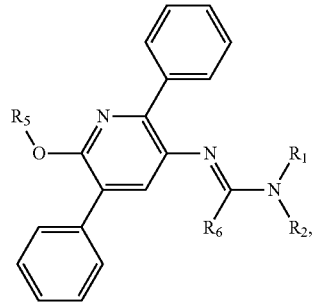

(T151)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 152

This table discloses the 1201 compounds
T152.1.1 to T152.1.1201 of the formula

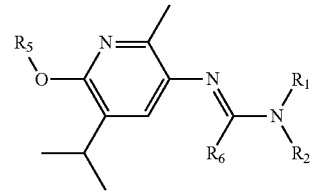

(T152)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 153

This table discloses the 1201 compounds
T153.1.1 to T153.1.1201 of the formula

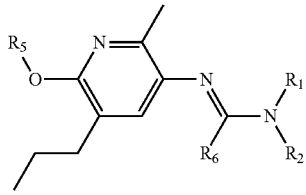

(T153)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 154

This table discloses the 1201 compounds
T154.1.1 to T154.1.1201 of the formula

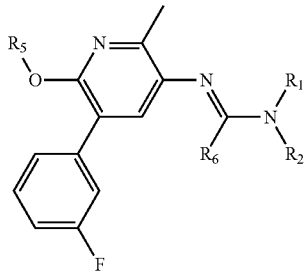

(T154)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 155

This table discloses the 1201 compounds
T155.1.1 to T155.1.1201 of the formula

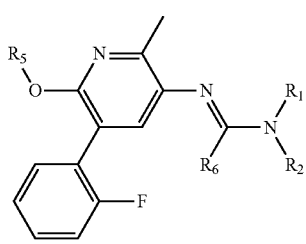

(T155)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 156

This table discloses the 1201 compounds
T156.1.1 to T156.1.1201 of the formula

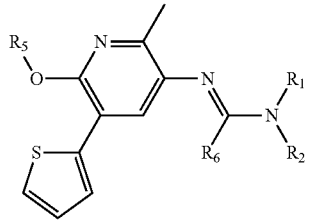

(T156)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 157

This table discloses the 1201 compounds
T157.1.1 to T157.1.1201 of the formula

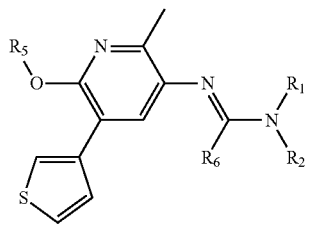

(T157)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 158

This table discloses the 1201 compounds
T158.1.1 to T158.1.1201 of the formula

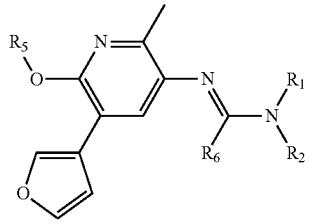

(T158)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 159

This table discloses the 1201 compounds
T159.1.1 to T159.1.1201 of the formula

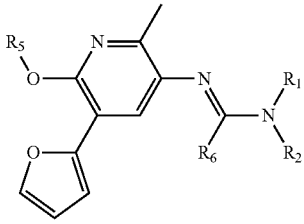

(T159)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 160

This table discloses the 1201 compounds
T160.1.1 to T160.1.1201 of the formula

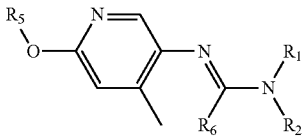

(T160)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 161

This table discloses the 1201 compounds
T161.1.1 to T161.1.1201 of the formula

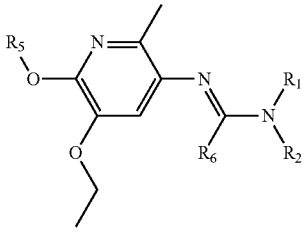

(T161)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 162

This table discloses the 1201 compounds
T162.1.1 to T162.1.1201 of the formula

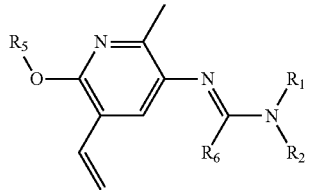

(T162)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 163

This table discloses the 1201 compounds
T163.1.1 to T163.1.1201 of the formula

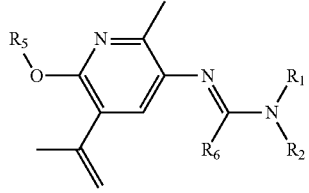

(T163)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

TABLE 164

This table discloses the 1201 compounds
T164.1.1 to T164.1.1201 of the formula

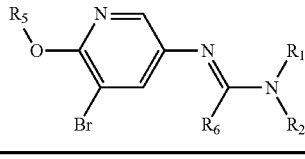

(T164)

in which, for each of these 1201 specific compounds, each of the variables $R_1$, $R_2$, $R_5$ and $R_6$ has the specific meaning given in the corresponding line, appropriately selected from the 1201 lines A.1.1 to A.1.1201 of Table A.

In further embodiments the invention provides novel intermediates to provide compounds according to formula (I) are compounds of formula (IV)

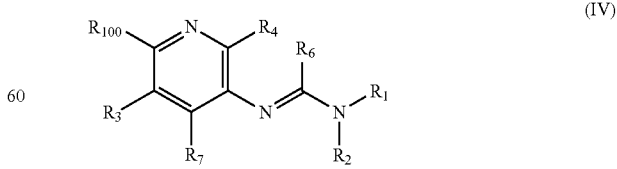

(IV)

wherein $R_{100}$ is wherein $R_{100}$ is halogen, SH, $C_1$-$C_4$-alkylthio, $C_1$-$C_4$-alkylsulfinyl, $C_1$-$C_4$-alkylsulfonyl and $R_1$, $R_2$, $R_3$, $R_4$, $R_6$ and $R_7$ are as described herein for compounds of formula (I).

The Following Table Provides a Selection of Compounds of Formula (IV)
R.01 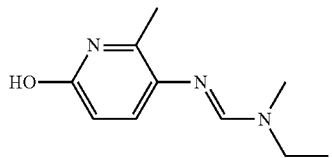
R.02 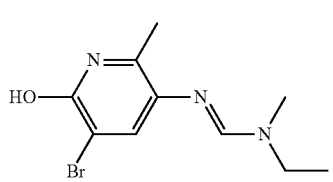 Mp: 168-170° C.
R.03 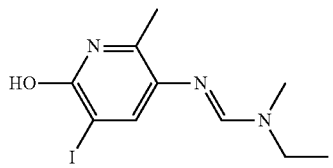
R.04 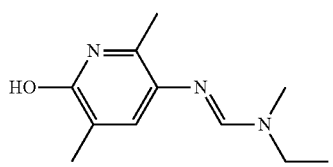
R.05 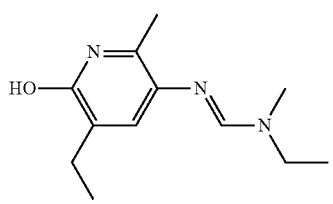 [SMILES: CCc1cc(/N=C/N(C)CC)c(C)nc1O]
R.06 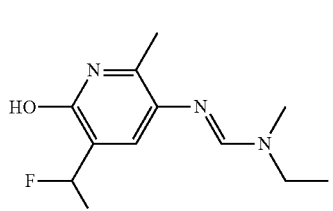
R.07 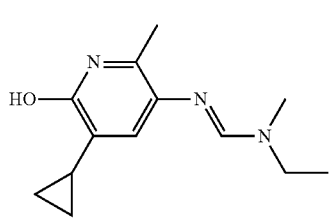 [SMILES: CCN(C)/C=N/c1cc(C2CC2)c(O)nc1C]
R.08 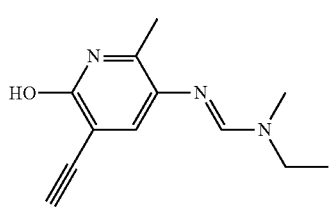 [SMILES: C#Cc1cc(/N=C/N(C)CC)c(C)nc1O]
R.09 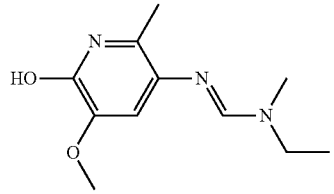 [SMILES: CCN(C)/C=N/c1cc(OC)c(O)nc1C]
R.10 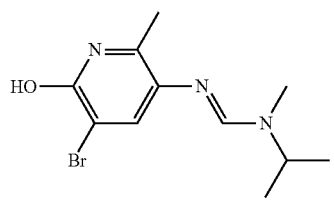 [SMILES: Cc1nc(O)c(Br)cc1/N=C/N(C)C(C)C]
R.11 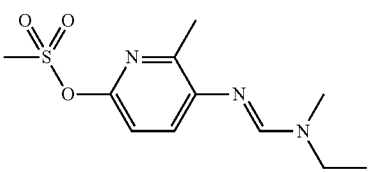 [SMILES: CCN(C)/C=N/c1ccc(OS(C)(=O)=O)nc1C]
R.12 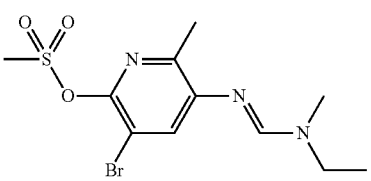 [SMILES: CCN(C)/C=N/c1cc(Br)c(OS(C)(=O)=O)nc1C] Mp: 85-87° C.
R.13 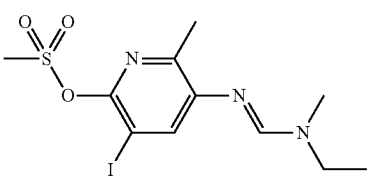
R.14 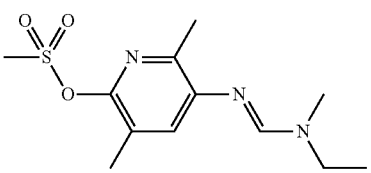 [SMILES: CCN(C)/C=N/c1cc(C)c(OS(C)(=O)=O)nc1C]
R.15 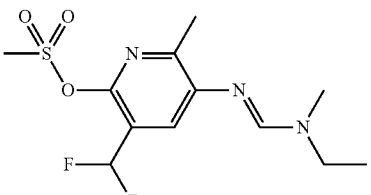
R.16 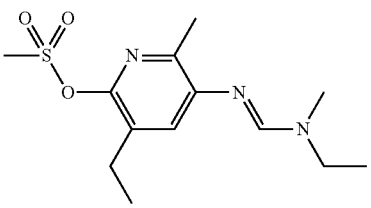

| | | |
|---|---|---|
| R.17 | 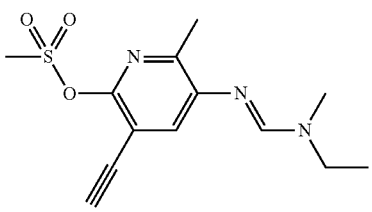 | |
| R.18 | 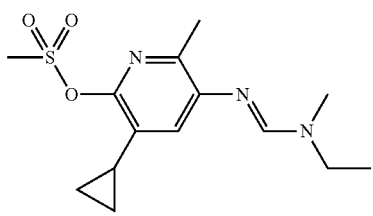 | |
| R.19 | 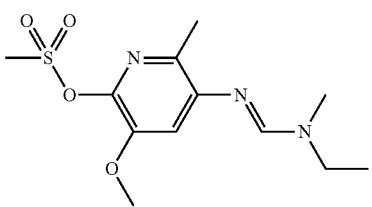 | |
| R.20 | 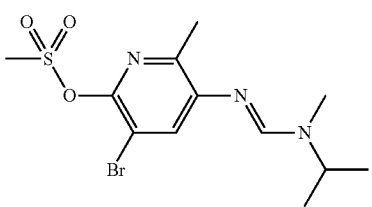 | |
| R.21 | 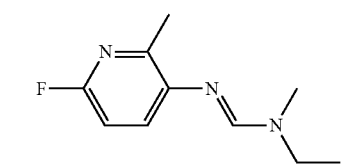 | |
| R.22 | 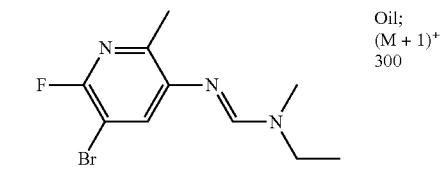 | Oil; $(M+1)^+$ 300 |
| R.23 | 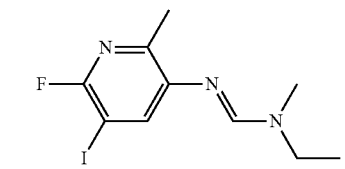 | |
| R.24 | 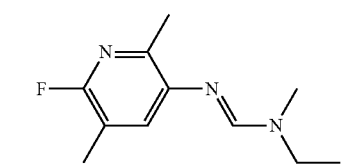 | |
| | | |
|---|---|---|
| R.25 | 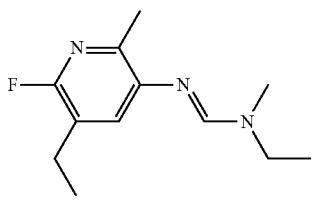 | |
| R.26 | 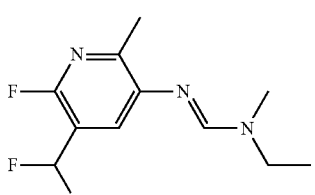 | |
| R.27 | 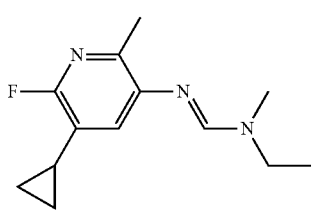 | |
| R.28 | 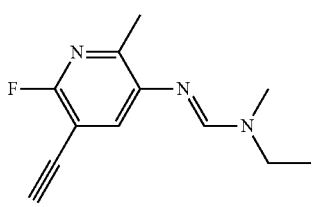 | |
| R.29 | 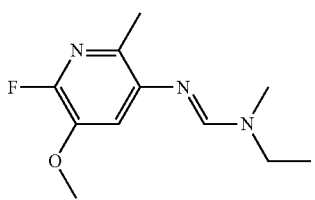 | |
| R.30 | 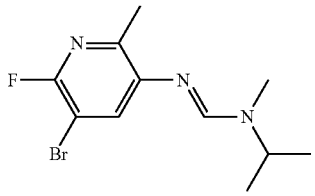 | |
| R.31 | 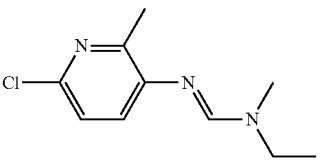 | |
| R.32 | 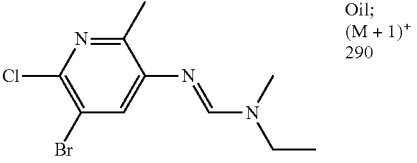 | Oil; $(M+1)^+$ 290 |

| | | | |
|---|---|---|---|
| R.33 | 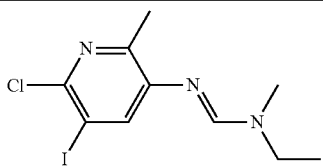 | R.41 | 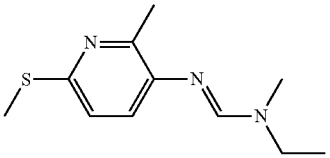 |
| R.34 | 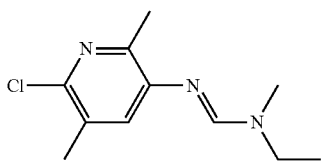 | R.42 | 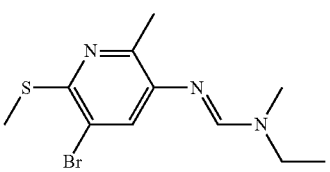 |
| R.35 | 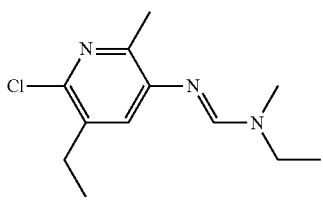 | R.43 | 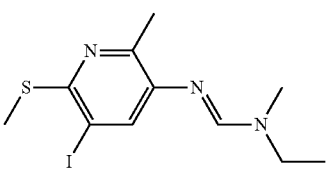 |
| R.36 | 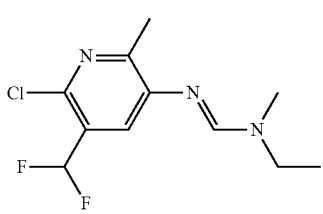 | R.44 | 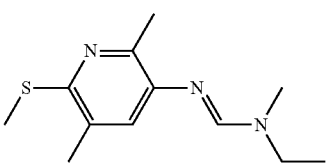 |
| R.37 | 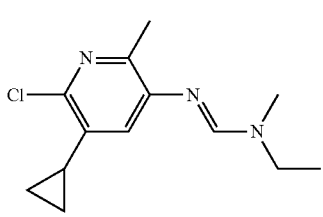 | R.45 | 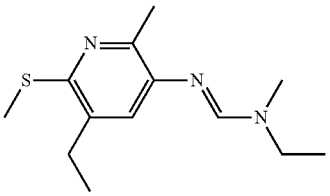 |
| R.38 | 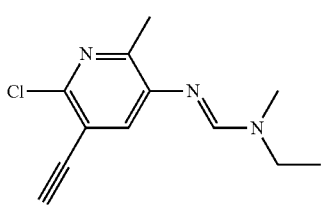 | R.46 | 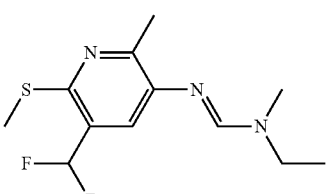 |
| R.39 | 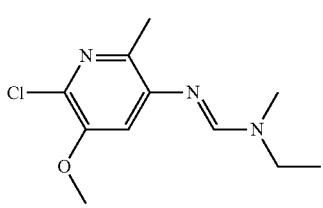 | R.47 | 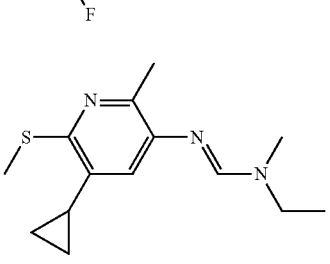 |
| R.40 | 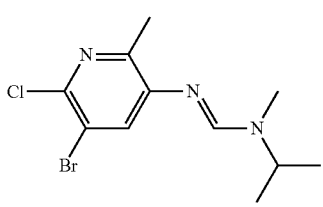 | R.48 | 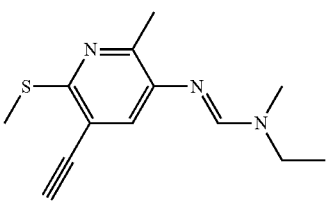 |

R.49 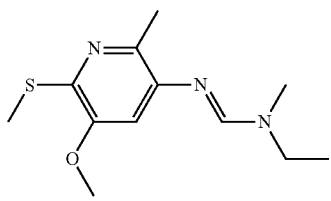 [SMILES: CCN(C)/C=N/c1cc(OC)c(SC)nc1C]

R.50 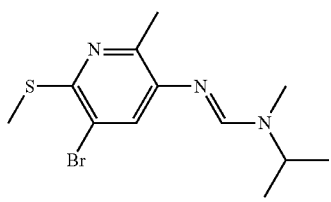 [SMILES: CSc1nc(C)c(/N=C/N(C)C(C)C)cc1Br]

R.51 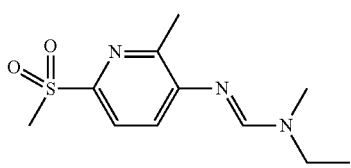 [SMILES: CCN(C)/C=N/c1ccc(S(C)(=O)=O)nc1C]

R.52 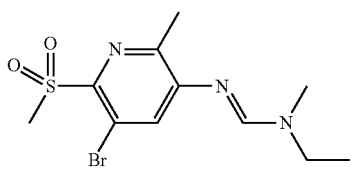 [SMILES: CCN(C)/C=N/c1cc(Br)c(S(C)(=O)=O)nc1C]

R.53 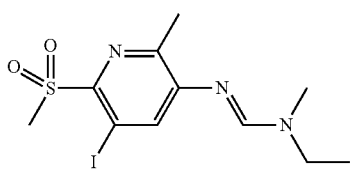 [SMILES: CCN(C)/C=N/c1cc(I)c(S(C)(=O)=O)nc1C]

R.54 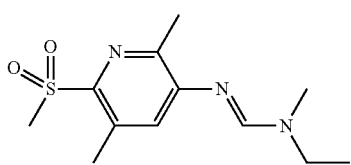 [SMILES: CCN(C)/C=N/c1cc(C)c(S(C)(=O)=O)nc1C]

R.55 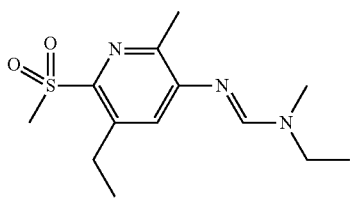 [SMILES: CCc1cc(/N=C/N(C)CC)c(C)nc1S(C)(=O)=O]

R.56 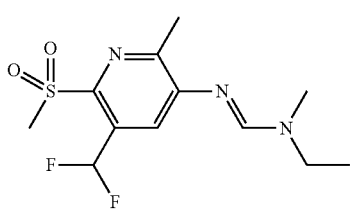 [SMILES: CCN(C)/C=N/c1cc(C(F)F)c(S(C)(=O)=O)nc1C]

R.57 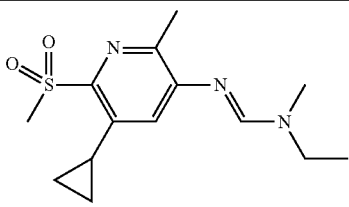

R.58 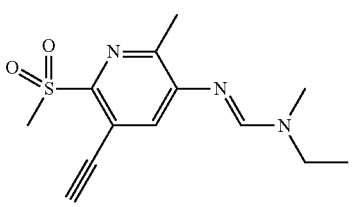 [SMILES: C#Cc1cc(/N=C/N(C)CC)c(C)nc1S(C)(=O)=O]

R.59 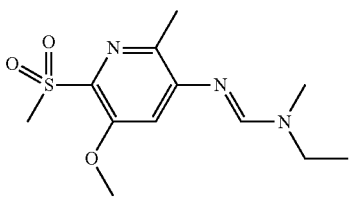 [SMILES: CCN(C)/C=N/c1cc(OC)c(S(C)(=O)=O)nc1C]

R.60 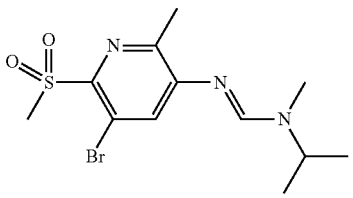 [SMILES: Cc1nc(S(C)(=O)=O)c(Br)cc1/N=C/N(C)C(C)C]

The active compounds of component B are known e.g. from the Pesticide Manual (British Crop Protection Council). N-[9-(dichloromethylene)-1,2,3,4-tetrahydro-1,4-methanonaphthalen-5-yl]-3-(difluoromethyl)-1-methyl-1H-pyrazole-4-carboxamide has the Chemical Abstracts Registry Number [1072957-71-1]. The compound of formula (II) has the Chemical Abstracts Registry Number [173662-97-0]. The compounds (S)-[3-(4-Chloro-2-fluoro-phenyl)-5-(2,4-difluoro-phenyl)isoxazol-4-yl]pyridin-3-yl-methanol, 3-(4-Chloro-2-fluoro-phenyl)-5-(2,4-difluoro-phenyl)isoxazol-4-yl]pyridin-3-yl-methanol are found in WO2010069881.

The active ingredient mixture of the compounds of formula I selected from tables T1 to T164 or a specific compound selected from P.1 to P.372 with active ingredients described above comprises a compound selected from tables T1 to T164 and an active ingredient as described above preferably in a mixing ratio of from 100:1 to 1:6000, especially from 50:1 to 1:500, more especially in a ratio of from 20:1 to 1:200, even more especially from 10:1 to 1:100, very especially from 5:1 and 1:50, special preference being given to a ratio of from 3:1 to 1:10, and a ratio of from 3:1 to 1:5 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures comprising a compound of formula I e.g. selected from tables T1 to T164 or a specific compound selected from P.1 to P.372 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I e.g. those selected from tables T1 to T164 and the active ingredients as described above is not essential for working the present invention.

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient. According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of $\geq 1.2$ indicates significant improvement over the purely complementary addition of activities (expected activity), while an SF of $\leq 0.9$ in the practical application routine signals a loss of activity compared to the expected activity.

EXAMPLES

Preparation of 1-(3,5-difluorophenyl)ethanol

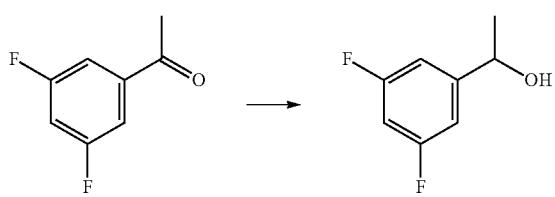

To a colorless stirred solution of 3',5'-difluoroacetophenone (50.00 g, 320.24 mmol) in methanol (320 mL), sodium borohydride (3.41 g, 86.47 mmol, 0.27 eq) was added portion wise over 20 minutes at room temperature under inert atmosphere (Ar). Then the reaction mixture was stirred for 45 min at room temperature and then quenched carefully by the addition of a saturated aqueous ammonium chloride solution (150 mL). The extraction was carried out with ethyl acetate (2×200 mL). The combined organic layers were washed with brine (200 mL), dried over anhydrous $Na_2SO_4$ and filtered. The solvent was removed in vacuo to give the title compound (50.29 g, 99%) as a colorless oil. The alcohol was used as such in the subsequent step.

TLC: Plates: Merck TLC-Plates, silica gel $F_{254}$, saturated atmosphere in developing tank, UV detection, eluent: heptanes/ethyl acetate 4:1 (v/v); $R_f$ of the title compound=0.27.

Preparation of (−)-(S)-1-(3,5-difluorophenyl)ethanol

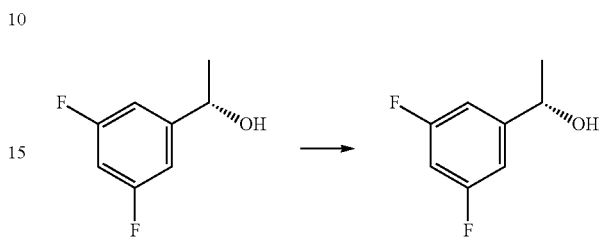

To a stirred solution of (−)-DIP-Cl ((−)-diisopinocampheylboron chloride) (2.67 g, 8.33 mmol, 1.3 eq) in THF (20 mL) kept under inert atmosphere (Ar) and cooled to −27° C. to −25° C., 3',5'-difluoroacetophenone (1.00 g, 6.40 mmol) was added drop wise over 2 min. The reaction was maintained at this temperature for 17 h. The reaction mixture was then treated with acetaldehyde (0.44 mL, 7.69 mmol, 1.2 eq). Thereafter, the temperature was allowed to reach room temperature and the reaction mixture was stirred at for 7 h. The solvent was then removed in vacuo and the resulting residue was partitioned between water (10 mL) and TBME (tert-butyl-methyl ether) (20 mL). The aqueous phase was extracted again with TBME (20 mL). The organic layer was washed with an aqueous 2 N NaOH solution (20 mL), brine (20 mL), dried over anhydrous $Na_2SO_4$ and filtered. The solvent was removed in vacuo to give a residue, which was purified by two subsequent column chromatographic steps: First by normal phase chromatography (silica gel, heptane/ethyl acetate, v/v=1/0-9/1) followed by a reversed phase chromatography (90 $C_{18}$-silica gel, acetonitrile for the second one). This gave the title compound (0.40 g, 40%) as a colorless oil with a specific rotation of $[\alpha]^{25}_D = -26.66$ (c=1.054 g/100 mL, $CH_2Cl_2$, 589 nm).

Preparation of cis and trans 4-isopropylcyclohexanol

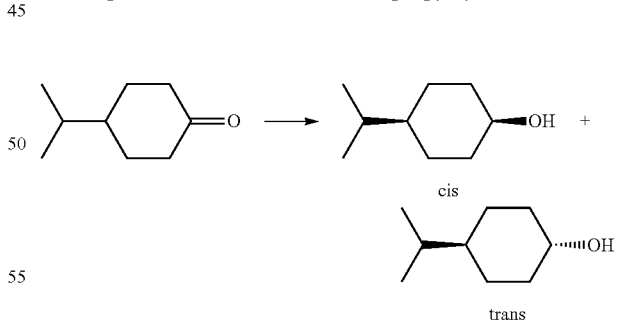

To a stirred solution of 4-isopropylcyclohexanone (10.00 g, 68.46 mmol) in tert-butyl methyl ether (136 mL) cooled to 7° C. (cooling bath with a cyclohexane/liquid nitrogen slurry), a 1.00 M solution of lithium aluminium hydride in THF (23 mL, 22.59 mmol, 0.33 eq) was added drop wise over 35 minutes while keeping the temperature in the range of 7 to 10° C. Stirring was continued under these conditions. The reaction mixture was then allowed to reach room temperature and stirred at this temperature for an additional 40 minutes. It was then carefully quenched by the slow addition of water (20 mL), followed by a one molar aqueous sulfuric acid solution (60 mL). The extraction was carried out with tert-butyl methyl ether (2×50 mL). The organic layer was washed with a saturated aqueous Na$_2$CO$_3$ solution (80 mL), brine (80 mL), dried over anhydrous Na$_2$SO$_4$ and filtered. The solvent was removed in vacuo to give a residue, which was purified by column chromatography (silica gel, heptane/ethyl acetate, v/v=1/0–9/1). Fractions containing the pure compounds were collected and concentrated in vacuo to give pure trans (6.91 g, 71%) and the pure cis isomer (0.68 g, 5%) of 4-isopropyl-cyclohexanol both as colourless oils.

TLC: Plates: Merck TLC-Plates, silica gel F$_{254}$, saturated atmosphere in developing tank, detection by spraying with Mo—Ce reagent, eluent: heptanes/ethyl acetate 4:1 (v/v); R$_f$ of cis 4-isopropylcyclohexanol=0.20); R$_f$ of trans 4-isopropylcyclohexanol=0.15.

Preparation of 3-bromo-2-(cis-4-isopropylcyclohexoxy)-6-methyl-5-nitro-pyridine

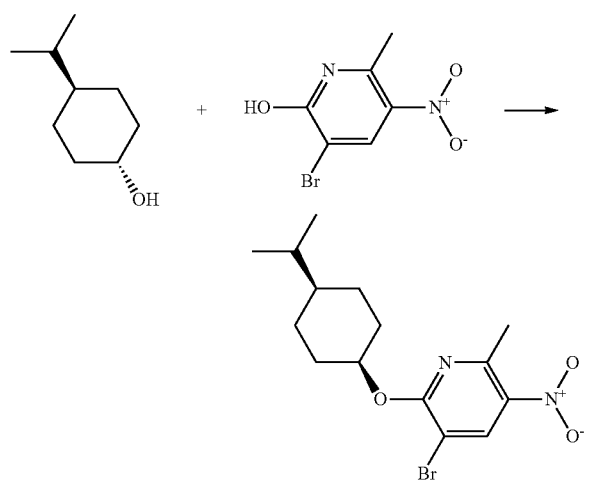

To a stirred suspension of 3-bromo-6-methyl-5-nitro-pyridin-2-ol (23.65 g, 101.5 mmol) in THF (180 mL), trans isopropylcyclohexanol (14.44 g, 101.5 mmol, 1.0 eq) and triphenylphosphine (32.27 g, 121.8 mmol, 1.2 eq) were added at room temperature under inert atmosphere (Ar). To this mixture, DIAD (diisopropyl diazodicarboxylate) (25.51 mL, 121.8 mmol, 1.2 eq) was added drop wise over 45 min while keeping the temperature below 45° C. Then, the reaction mixture was stirred for 5 h under heating to reflux. TLC indicated that the starting material was consumed. The reaction mixture was therefore allowed to reach room temperature and it was quenched by the addition of water (250 mL). The extraction was carried out with ethyl acetate (3×200 mL). The organic layer was washed with brine (300 mL), dried over anhydrous Na$_2$SO$_4$ and filtered. The solvent was removed in vacuo to give a residue, which was purified by column chromatography (silica gel, heptane/ethyl acetate, v/v=1/0-98/2). Fractions containing the pure compound were collected and concentrated in vacuo to give title compound (22.59 g, 62%) in the form of an oil.

TLC: Plates: Merck TLC-Plates, silica gel F$_{254}$, saturated atmosphere in developing tank, UV detection, eluent: heptanes/ethyl acetate 4:1 (v/v); R$_f$ of the title compound=0.64.

Preparation of 5-bromo-6-(cis-4-isopropylcyclohexoxy)-2-methyl-pyridin-3-amine

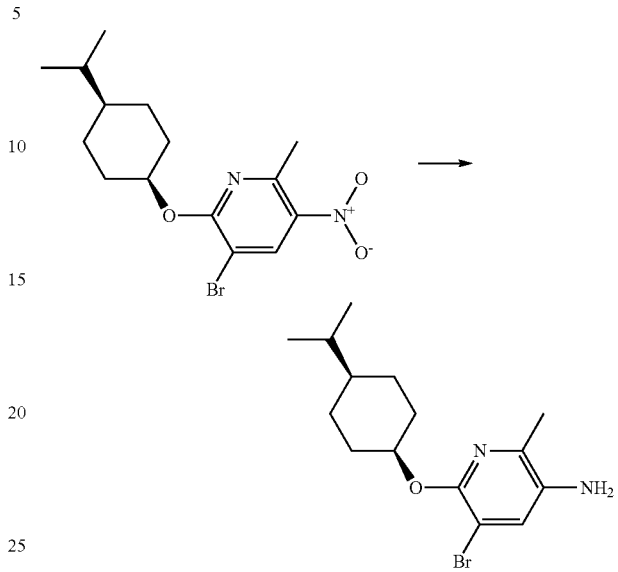

To a stirred solution of 3-bromo-2-(cis-4-isopropylcyclohexoxy)-6-methyl-5-nitro-pyridine (22.59 g, 63.24 mmol) in EtOH/H$_2$O (600 mL/150 mL, 4/1 v/v), ammonium chloride (3.45 g, 63.24 mmol, 1.0 eq) and iron powder (14.27 g, 253.0 mmol, 4 eq) were added at room temperature under inert atmosphere (Ar). The reaction mixture was stirred for 3 h under heating to reflux. As TLC indicated that the starting material was consumed at this point in time, the reaction mixture was cooled to room temperature and filtered through a pad of celite. The resulting filtrate was concentrated in vacuo and the residue partitioned between a 2 molar aqueous NaOH solution (100 mL) and ethyl acetate (150 mL). After phase separation, the aqueous phase was extracted once more with ethyl acetate (2×100 mL). The organic layer was washed with brine (400 mL), dried over anhydrous Na$_2$SO$_4$ and filtered. The solvent was removed in vacuo to afford the title compound (21.01 g, 101%) in the form of an oil.

TLC: Plates: Merck TLC-Plates, silica gel F$_{254}$, saturated atmosphere in developing tank, UV detection, eluent: heptanes/ethyl acetate 4:1 (v/v); R$_f$ of the title compound=0.19.

Preparation of N'-[5-bromo-6-(cis-4-isopropylcyclohexoxy)-2-methyl-3-pyridyl]-N-ethyl-N-methyl formamidine

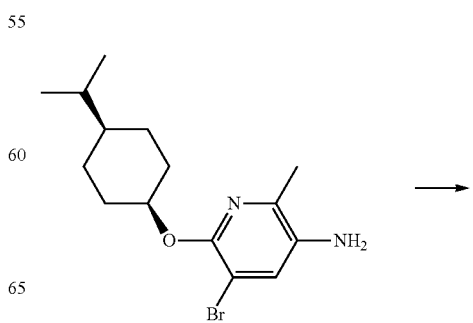

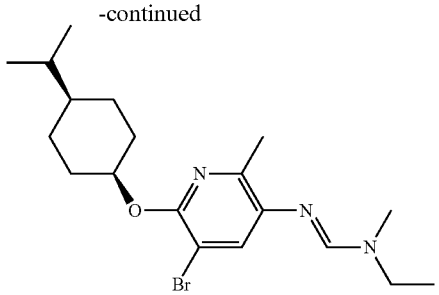

The Vilsmeier reagent was freshly prepared by the slow addition of phosphorus oxychloride (7.09 mL, 75.89 mmol, 1.2 eq) to a solution of N,N-ethylmethylformamide (6.61 g, 75.89 mmol, 1.2 eq) in dichloromethane (75 mL) at room temperature. After the addition was complete, the reaction mixture was stirred at room temperature for 1 h. The Vilsmeier reagent was then added drop wise over 40 min to a solution of 5-bromo-6-(cis-4-isopropylcyclohexoxy)-2-methyl-pyridin-3-amine (20.70 g, 63.24 mmol) in dichloromethane (225 mL) at room temperature under inert atmosphere (Ar). Stirring was continued for 1.5 h at room temperature. The reaction mixture was then quenched by the addition of water (100 mL) and the pH was adjusted to 14 by the addition of a 2.0 molar aqueous NaOH solution (80 mL). The phases were separated and the aqueous phase extracted with dichloromethane (2×100 mL). The organic layer was washed with brine (250 mL), dried over anhydrous $Na_2SO_4$ and filtered. The solvent was removed in vacuo to give a residue, which was purified by column chromatography (silica gel, heptane/ethyl acetate, v/v=1/0-4/1). Fractions containing the pure compound were collected and concentrated in vacuo to give the title compound (20.23 g, 81%) as a yellow oil.

TLC: Plates: Merck TLC-Plates, silica gel $F_{254}$, saturated atmosphere in developing tank, UV detection, eluent: heptanes/ethyl acetate 4:1 (v/v); $R_f$ of the title compound=0.29.

$^1$H NMR (400 MHz, $CDCl_3$): δ (ppm)=7.45-7.30 (broad s, 1H), 7.23 (s, 1H), 5.32-5.28 (m, 1H), 3.55-3.24 (broad s, 2H), 2.98 (s, 3H), 2.35 (s, 3H), 2.04-2.01 (m, 2H), 1.63-1.46 (m, 7H), 1.20 (t, 3H), 1.18-1.10 (m, 1H), 0.91-0.89 (d, 6H).

Preparation of 3-bromo-2-(trans-4-isopropylcyclohexoxy)-6-methyl-5-nitro-pyridine

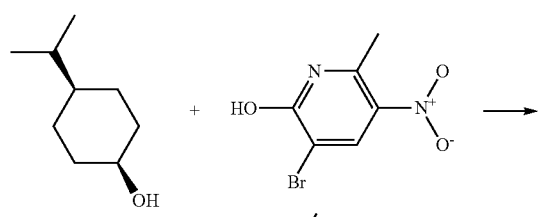

To a stirred suspension of 3-bromo-6-methyl-5-nitro-pyridin-2-ol (2.00 g, 8.58 mmol) in THF (8.6 mL), cis isopropylcyclohexanol (1.44 g, 8.58 mmol, 1.0 eq) and triphenylphosphine (2.73 g, 10.30 mmol, 1.2 eq) were added at room temperature under inert atmosphere (Ar). To this mixture, DIAD (diisopropyl diazodicarboxylate) (2.16 mL, 10.30 mmol, 1.2 eq) was added drop wise over 10 minutes while keeping the temperature below 40° C. The reaction mixture was stirred for 1.5 h under heating to. After this point in time, TLC indicted consumption of the starting material and the reaction mixture was allowed to reach room temperature and was quenched by adding water (20 mL). The water phase was extracted with ethyl acetate (3×20 mL). The organic layer was washed with brine (35 mL), dried over anhydrous $Na_2SO_4$ and filtered. The solvent was removed in vacuo to give a residue, which was purified by column chromatography (silica gel, heptane/ethyl acetate, v/v=1/0-9/1). Fractions containing the pure compound were collected and concentrated in vacuo to give the title compound (0.94 g, 30%) as an oil.

TLC: Plates: Merck TLC-Plates, silica gel $F_{254}$, saturated atmosphere in developing tank, UV detection, eluent: heptanes/ethyl acetate 4:1 (v/v); $R_f$ of the title compound=0.65.

Preparation of 5-bromo-6-(trans-4-isopropylcyclohexoxy)-2-methyl-pyridin-3-amine

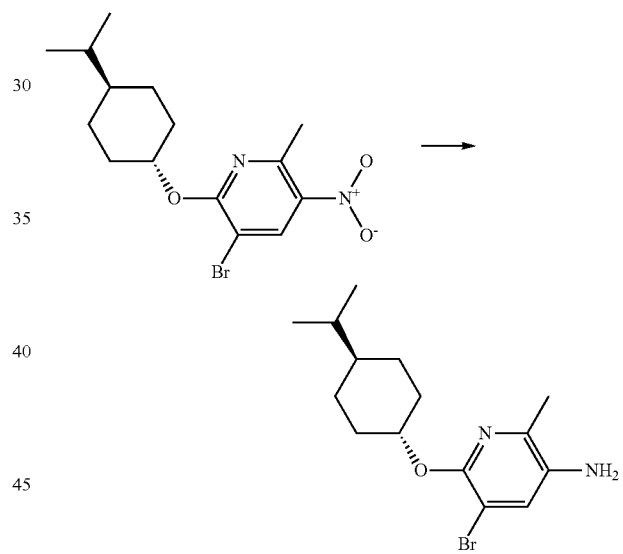

To a stirred solution of 3-bromo-2-(trans-4-isopropylcyclohexoxy)-6-methyl-5-nitro-pyridine (0.917 g, 2.00 mmol) in $EtOH/H_2O$ (24 mL/6 mL, 4/1 v/v), ammonium chloride (0.109 g, 2.00 mmol, 1.0 eq) and iron powder (0.452 g, 8.00 mmol, 4 eq) were added at room temperature under inert atmosphere (Ar). The reaction mixture was stirred under heating to reflux for 3 h. At this point in time, TLC indicated that the starting material was consumed. Therefore, the reaction mixture was allowed to reach room temperature and was filtered through a pad of celite. The filtrate was concentrated under reduced pressure and the residue partitioned between a 2 molar aqueous NaOH solution (20 mL) and ethyl acetate (30 mL). The phases were separated and the aqueous phase extracted with ethyl acetate (2×20 mL). The organic layer was washed with brine (40 mL), dried over anhydrous $Na_2SO_4$ and filtered. The solvent was removed in vacuo to afford the title compound (0.658 g, 100%) as an oil.

TLC: Plates: Merck TLC-Plates, silica gel $F_{254}$, saturated atmosphere in developing tank, UV detection, eluent: heptanes/ethyl acetate 4:1 (v/v); $R_f$ of the title compound=0.19.

Preparation of 5-bromo-6-(trans-4-isopropylcyclohexoxy)-2-methyl-pyridin-3-amine

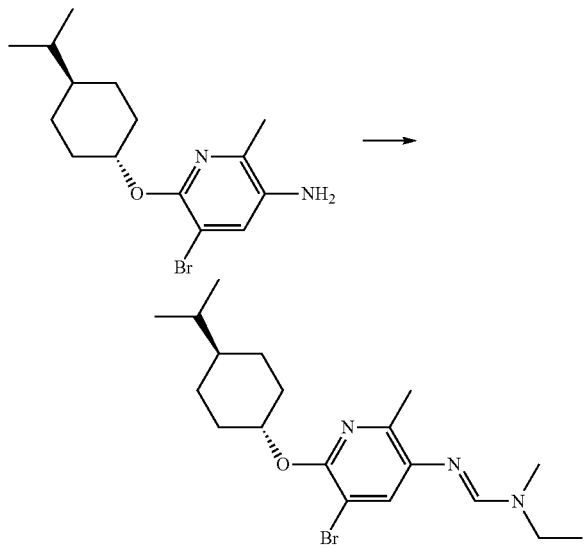

The Vilsmeier reagent was freshly prepared by the slow addition of phosphorus oxychloride (0.101 mL, 1.08 mmol, 1.2 eq) to a solution of N,N-ethylmethylformamide (0.094 g, 1.08 mmol, 1.2 eq) in dichloromethane (0.5 mL) at room temperature. After the addition was complete, the reaction mixture was stirred at room temperature for 1 h. Then the Vilsmeier reagent thus obtained was added drop wise to a solution of 5-bromo-6-(trans-4-isopropylcyclohexoxy)-2-methyl-pyridin-3-amine (0.295 g, 0.90 mmol) in dichloromethane (1.0 mL) at room temperature under inert atmosphere (Ar). Stirring was continued was for 1.5 h at room temperature. The reaction was then quenched by the addition of a 2 molar aqueous NaOH solution (5 mL). The phases were separated and the aqueous phase extracted with dichloromethane (2×10 mL). The organic layer was washed with brine (10 mL), dried over anhydrous $Na_2SO_4$ and filtered. The solvent was removed in vacuo to give a residue, which was purified by column chromatography (silica gel, heptane/ethyl acetate, v/v=1/0-4/1). Fractions containing the pure compound were collected and concentrated in vacuo to give the title compound (0.191 g, 54%) as a light yellow oil.

TLC: Plates: Merck TLC-Plates, silica gel $F_{254}$, saturated atmosphere in developing tank, UV detection, eluent: heptanes/ethyl acetate 4:1 (v/v); $R_f$ of the title compound=0.29.

$^1$H NMR (400 MHz, $CDCl_3$): δ (ppm)=7.45-7.30 (broad s, 1H), 7.22 (s, 1H), 4.93-4.85 (m, 1H), 3.55-3.22 (broad s, 2H), 2.98 (s, 3H), 2.35 (s, 3H), 2.19-2.15 (m, 2H), 1.80-1.77 (m, 2H), 1.50-1.09 (m, 5H), 1.28 (t, 3H), 0.88-0.86 (d, 6H).

Preparation of N-Ethyl-N-methyl-formamide

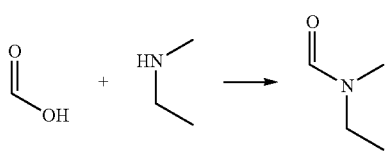

113 g (1.912 mol) of ethylmethylamine was dissolved in 500 mL of dry toluene. 75.86 mL of formic acid (92.2 g, 2.01 mol) was added drop-wise over 20 minutes. Hereby, an exothermic reaction was observed. The temperature was kept below 35° C. by cooling with an ice-water cooling bath. The turbid solution was stirred under heating to reflux (bath temperature of 175° C.) and the water removed using a Dean and Stark separator. 46 mL of water phase was thus separated. This water phase was extracted with 50 mL of ethyl acetate. And this ethyl acetate solution was added to the reaction mixture, after this one was allowed to reach room temperature. After evaporation of the solvent, the resulting liquid was subjected to a fractionating column distillation (Widmer column) at 80 mbar. 138 g of a colourless liquid of bp=95-96° C. was collected. As this material was contaminated with formic acid, the liquid was taken up in 1.0 L of ethyl acetate and kept over $K_2CO_3$ (occasional stirring, 24 h overall). The solution was then filtered and washed with water and the organic phase was again subjected to the distillation procedure mentioned before. This gave 130.4 g of the title compound as a liquid (bp=95-96° C., 80 mbar).

Preparation of methoxyethylmethyl-methanaminium methyl sulfate

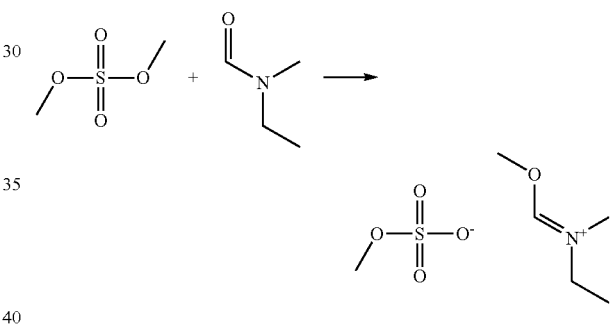

128 g of N-ethyl-N-methyl-formamide was added slowly to 139 mL (185 g, 1.469 mol) of dimethyl sulfate (the dimethyl sulfate used was freshly distilled in vacuo after having been tried over $K_2CO_3$). The colourless solution was warmed under stirring to 50° C. whereupon an exothermic reaction was starting up. The heating bath was removed and the reaction mixture reached a temperature of 86° C. After the exothermicity came to an end, the reaction mixture was stirred at a temperature of 80° C. for an additional 3 hours. Thereafter, the reaction mixture was allowed to reach room temperature. The resulting liquid was then shaken in a separatory funnel first with 100 mL of toluene and, after phase separation, with 100 mL of diethyl ether. Traces of solvents were removed in vacuo (rotovapor) to give 294 g of the title compound in the form of a colourless liquid. The compound was used as such in the subsequent step.

Preparation of 5-Bromo-2-methyl-3-nitro-6-[2,2,2-trifluoro-1-(4-fluorophenyl)ethoxy]pyridine

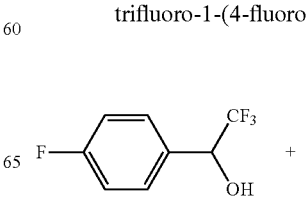

-continued

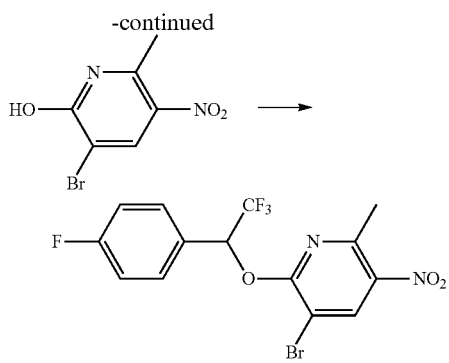

To a stirred suspension of 3-bromo-6-methyl-5-nitro-pyridin-2-ol (0.10 g, 0.43 mmol) in THF (3 mL), 2,2,2-trifluoro-1-(4-fluorophenyl)ethanol (0.13 g, 0.64 mmol, 1.5 equiv) and triphenylphosphine (0.17 g, 0.64 mmol, 1.5 eq) were added at room temperature under inert atmosphere (Ar). To this mixture, DIAD (diisopropyl diazodicarboxylate) (0.13 mL, 0.64 mmol, 1.5 eq) was added dropwise over 10 minutes while keeping the temperature below 40° C. The reaction mixture was stirred for 6 h under heating at 60° C. After this time, TLC indicted that the starting material had been consumed and the reaction mixture was allowed to reach room temperature before quenching with water (10 mL). The water phase was extracted with ethyl acetate (3×15 mL). The organic layer was washed with brine (20 mL), dried over anhydrous $Na_2SO_4$ and filtered. The solvent was removed in vacuo to give a brown residue, which was purified by combiflash column chromatography (silica gel, heptane/ethyl acetate, v/v=95/5). Fractions containing the pure compound were collected and concentrated in vacuo to give the title compound (0.11 g, 62% yield) as a yellow oil.

TLC: Plates: Merck TLC-Plates, silica gel $F_{254}$, saturated atmosphere in developing tank, UV detection, eluent: heptanes/ethyl acetate 4:1 (v/v); $R_f$ of the title compound=0.65.

Preparation of 2,2,2-Trifluoro-1-[4-(trifluoromethyl)phenyl]ethanol

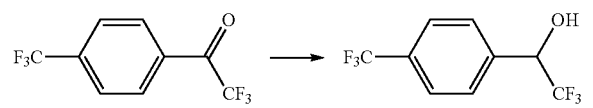

In a 50 mL two-neck flask, 2,2,2-trifluoro-1-[4-(trifluoromethyl)phenyl]ethanone (2.0 g, 8.3 mmol) was dissolved in methanol (8 mL) and sodium borohydride (0.31 g, 8.3 mmol) was added carefully in portions with ice-bath cooling. The resultant colourless solution was stirred at RT for 2 hours and monitored by TLC. Upon the disappearance of all starting material, 5 mL of an aqueous saturated $NH_4Cl$ solution was slowly added to the reaction mixture with additional stirring for 10 min. The later was extracted 3 times with 20 mL of EtOAc and the organic fractions were combined and washed with 10 mL of brine, dried over $Na_2SO_4$, and filtered. The solvent was removed under reduced pressure to give 2,2,2-trifluoro-1-[4-(trifluoromethyl)phenyl]ethanol (2.13 g, quantitative) as a colourless oil which was used with no further purification.

TLC: Plates: Merck TLC-Plates, silica gel $F_{254}$, saturated atmosphere in developing tank, UV detection, eluent: heptanes/ethyl acetate 2:1 (v/v); $R_f$ of the title compound=0.50.

Preparation of 5-Bromo-2-methyl-3-nitro-6-[2,2,2-trifluoro-1-[4-(trifluoromethyl)phenyl]ethoxy]pyridine

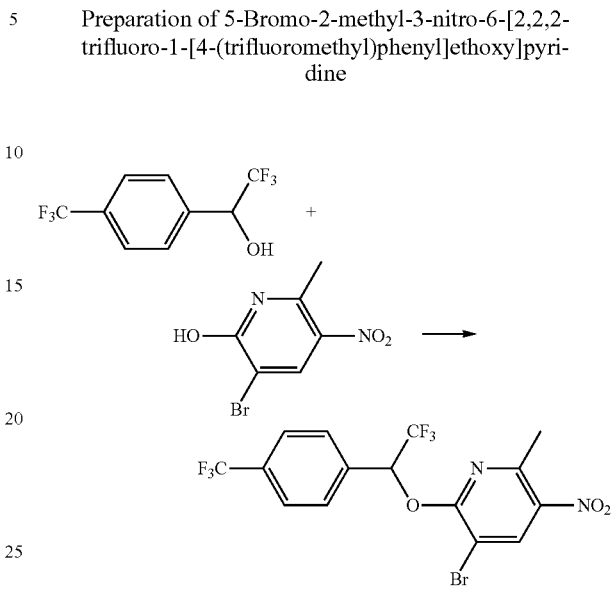

To a stirring suspension of 3-bromo-6-methyl-5-nitro-pyridin-2-ol (0.25 g, 1.07 mmol) in THF (7 mL), 2,2,2-trifluoro-1-[4-(trifluoromethyl)phenyl]ethanol (0.39 g, 1.61 mmol, 1.5 equiv) and triphenylphosphine (0.42 g, 1.61 mmol, 1.5 eq) were added at room temperature under inert atmosphere (Ar). To this mixture, DIAD (diisopropyl diazodicarboxylate) (0.33 mL, 1.61 mmol, 1.5 eq) was added dropwise over 10 minutes while keeping the temperature below 40° C. The reaction mixture was stirred for 6 h under heating at 60° C. After this time, TLC indicted that the starting material was consumed and the reaction mixture was allowed to reach room temperature before quenching with water (10 mL). The water phase was extracted with ethyl acetate (2×50 mL). The organic layer was washed with brine (20 mL), dried over anhydrous $Na_2SO_4$ and filtered. The solvent was removed in vacuo to give a brown residue, which was purified by combiflash column chromatography (silica gel, heptane/ethyl acetate, v/v=95/5). Fractions containing the pure compound were collected and concentrated in vacuo to give the title compound (0.18 g, 41% yield) as a yellow oil.

TLC: Plates: Merck TLC-Plates, silica gel $F_{254}$, saturated atmosphere in developing tank, UV detection, eluent: heptanes/ethyl acetate 2:1 (v/v); $R_f$ of the title compound=0.74.

Preparation of 1,1,1-Trifluorohept-6-en-2-ol

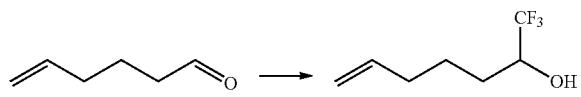

To a ice-bath cooled solution of hex-5-enal (500 mg, 4.331 mmol) and trimethyl(trifluoromethyl)silane (0.74 g, 5.13 mmol, 1.2 equiv.) in THF (10 mL) was added tetrabutylammonium hydrofluoride (10 mg, 0.04 mmol). The ice bath was removed and the reaction progress was monitored via GCMS and 1H NMR. Upon complete transformation of the starting material the reaction mixture was treated with 2M HCl and stirred for an additional 2 h. Then, 50 mL of Et$_2$O was introduced and the layers were separated. The aqueous fraction was additionally extracted with Et$_2$O and the combined organic phases were washed sequentially with a saturated aqueous NaHCO$_3$ solution, water, and brine. After drying with MgSO$_4$ and filtration the solvent was removed under reduced pressure and the resultant crude residue was purified by column chromatography (silica gel, pentane/Et$_2$O, v/v=8/2). Fractions containing the pure compound were collected and concentrated in vacuo to give 1,1,1-trifluorohept-6-en-2-ol (225 mg, 31% yield) as a yellow oil.

Using techniques analogous to those above and further techniques known to the person skilled in the art, for example as found in WO 08/101,682, the compounds found in Table Q were prepared.

TABLE Q

| | | LC-Method: R$_t$ (min); MS-ESI (m/z; (M + H)$^+$) |
|---|---|---|
| Q.001 | 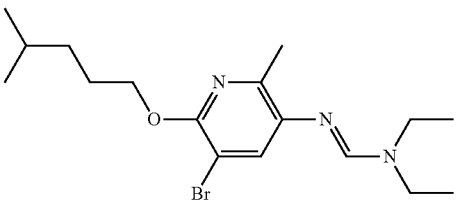 [SMILES: CCN(/C=N/c1cc(Br)c(OCCCC(C)C)nc1C)CC] | Method 4: 1.42 min; 370 |
| Q.002 | 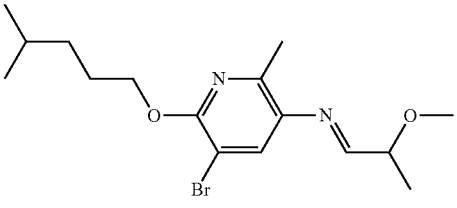 [SMILES: COC(C)/C=N/c1cc(Br)c(OCCCC(C)C)nc1C] | Method 4: 1.46 min; 358 |
| Q.003 | 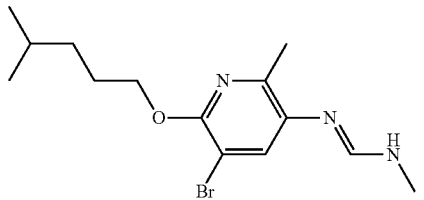 [SMILES: CN/C=N/c1cc(Br)c(OCCCC(C)C)nc1C] | Method 4: 1.30 min; 328 |
| Q.004 | 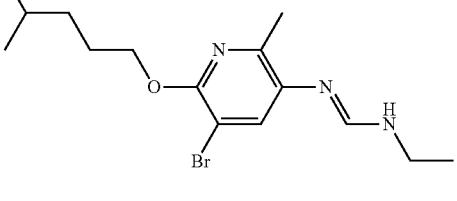 | Method 4: 1.33 min; 342 |
| Q.005 | 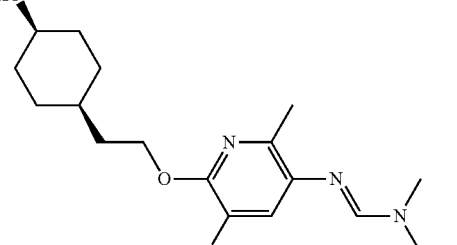 | Method 4: 1.17 min; 398 |

TABLE Q-continued

| | | LC-Method: R$_t$ (min); MS-ESI (m/z; (M + H)$^+$) |
|---|---|---|
| Q.006 | [structure] | Gum |
| Q.007 | [structure] | Method 4: 1.32 min; 292 |
| Q.008 | [structure] | Method 4: 1.39 min; 356 |
| Q.009 | [structure] | Mp 72-73° C. |
| Q.010 | [structure] | Method 4: 1.42 min; 356 |
| Q.011 | [structure] | Gum |

TABLE Q-continued
| | | LC-Method:<br>$R_t$ (min);<br>MS-ESI<br>(m/z; (M + H)$^+$) |
|---|---|---|
| Q.012 | 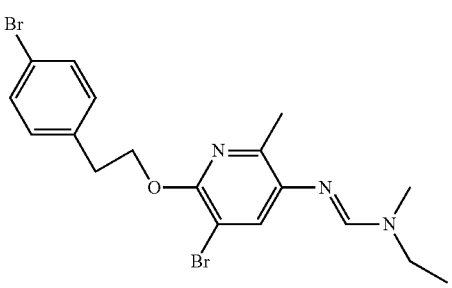 [SMILES: CCN(C)/C=N/c1cc(Br)c(OCCc2ccc(Br)cc2)nc1C] | Gum |
| Q.013 | 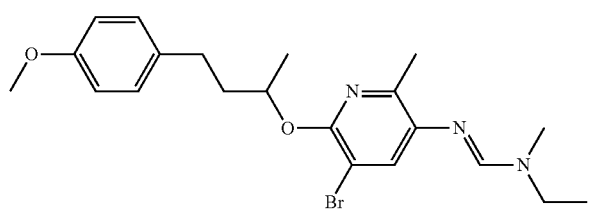 [SMILES: CCN(C)/C=N/c1cc(Br)c(OC(C)CCc2ccc(OC)cc2)nc1C] | Gum |
| Q.014 | 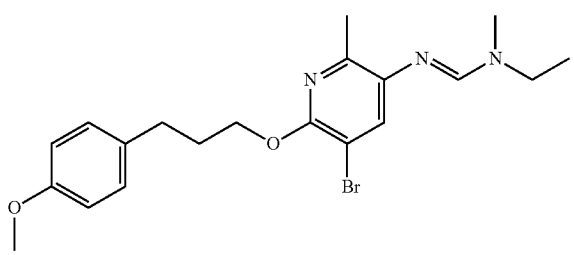 [SMILES: CCN(C)/C=N/c1cc(Br)c(OCCCc2ccc(OC)cc2)nc1C] | Gum |
| Q.015 | 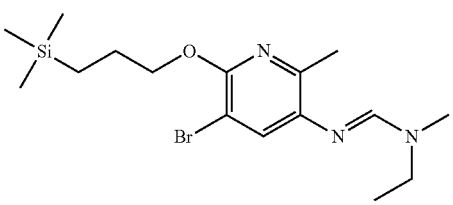 | Gum |
| Q.016 | 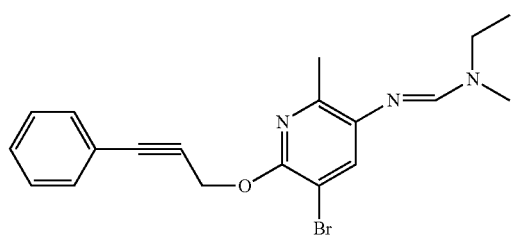 [SMILES: CCN(C)/C=N/c1cc(Br)c(OCC#Cc2ccccc2)nc1C] | Gum |
| Q.017 | 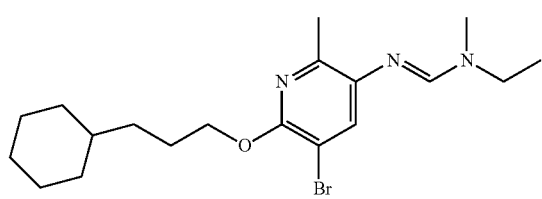 [SMILES: CCN(C)/C=N/c1cc(Br)c(OCCCC2CCCCC2)nc1C] | Gum |

TABLE Q-continued
| | | LC-Method: $R_t$ (min); MS-ESI (m/z; (M + H)$^+$) |
|---|---|---|
| Q.018 | 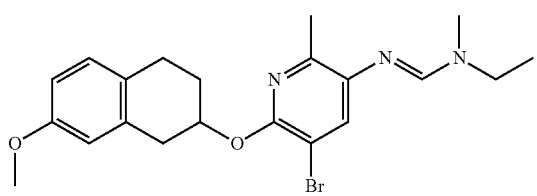 [SMILES: CCN(C)/C=N/c1cc(Br)c(OC2CCc3ccc(OC)cc3C2)nc1C] | Gum |
| Q.019 | 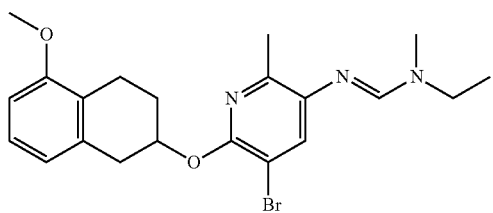 [SMILES: CCN(C)/C=N/c1cc(Br)c(OC2CCc3c(cccc3OC)C2)nc1C] | Gum |
| Q.020 | 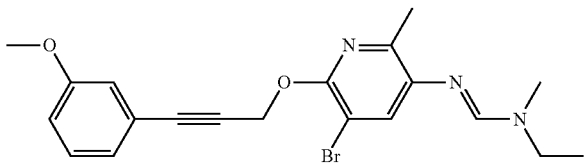 [SMILES: CCN(C)/C=N/c1cc(Br)c(OCC#Cc2cccc(OC)c2)nc1C] | Gum |
| Q.021 | 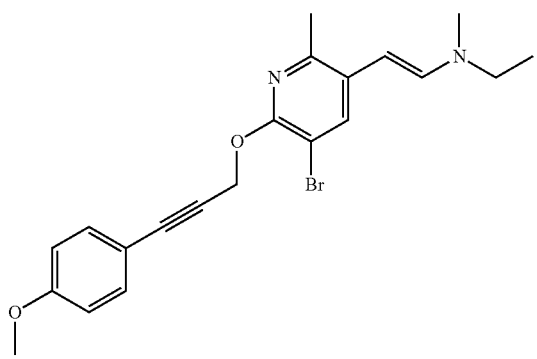 [SMILES: CCN(C)/C=C/c1cc(Br)c(OCC#Cc2ccc(OC)cc2)nc1C] | Gum |
| Q.022 | 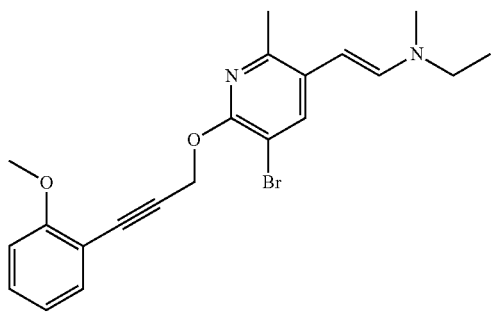 [SMILES: CCN(C)/C=C/c1cc(Br)c(OCC#Cc2ccccc2OC)nc1C] | Gum |
| Q.023 | 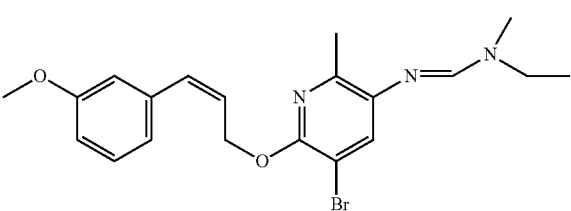 [SMILES: CCN(C)/C=N/c1cc(Br)c(OC/C=C\c2cccc(OC)c2)nc1C] | Gum |

TABLE Q-continued

| | | LC-Method: R$_t$ (min); MS-ESI (m/z; (M + H)$^+$) |
|---|---|---|
| Q.024 | | Gum |
| Q.025 | | Gum |
| Q.026 | | Gum |
| Q.027 | | Gum |
| Q.028 | | Method 4: 1.32 min; 418 |
| Q.029 | | Liquid |
| Q.030 | | Method 4: 1.53 min; 544 |

TABLE Q-continued

| | | LC-Method:<br>R$_t$ (min);<br>MS-ESI<br>(m/z; (M + H)$^+$) |
|---|---|---|
| Q.031 | | Gum |
| Q.032 | | Liquid |
| Q.033 | | Method 4:<br>1.31 min;<br>444 |
| Q.034 | | Method 4:<br>1.22 min;<br>340 |
| Q.035 | | Method 4:<br>0.99 min;<br>358 |
| Q.036 | | Method 4:<br>0.98 min;<br>388 |
| Q.037 | | Solid |

TABLE Q-continued
| | | LC-Method: $R_t$ (min); MS-ESI (m/z; (M + H)$^+$) |
|---|---|---|
| Q.038 | 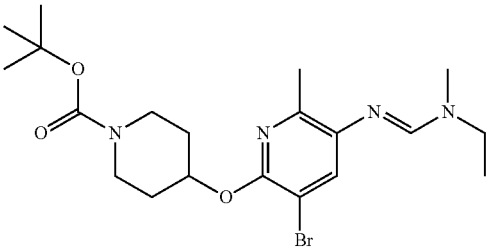 [SMILES: CCN(C)/C=N/c1cc(Br)c(OC2CCN(C(=O)OC(C)(C)C)CC2)nc1C] | Liquid |
| Q.039 | 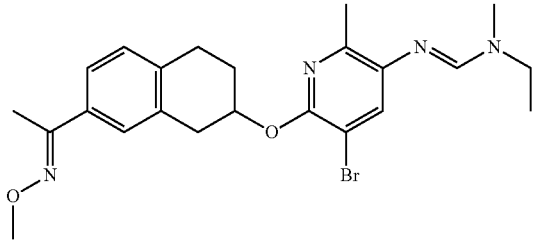 [SMILES: CCN(C)/C=N/c1cc(Br)c(OC2CCc3ccc(/C(C)=N/OC)cc3C2)nc1C] | Method 4: 1.48 min; 473 |
| Q.040 | 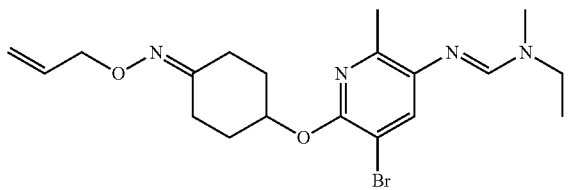 [SMILES: C=CCON=C1CCC(Oc2nc(C)c(/N=C/N(C)CC)cc2Br)CC1] | Liquid |
| Q.041 | 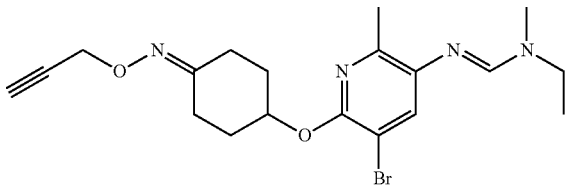 [SMILES: C#CCON=C1CCC(Oc2nc(C)c(/N=C/N(C)CC)cc2Br)CC1] | Liquid |
| Q.042 | 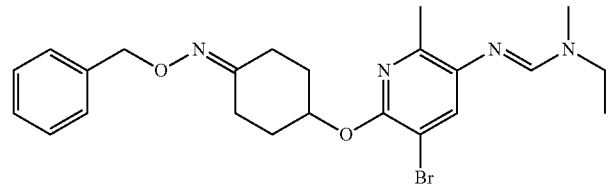 [SMILES: CCN(C)/C=N/c1cc(Br)c(OC2CCC(=NOCc3ccccc3)CC2)nc1C] | Liquid |
| Q.043 | 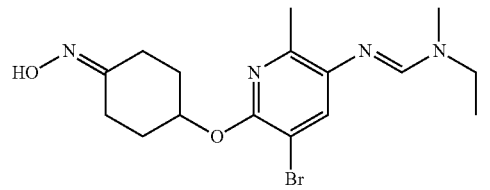 [SMILES: CCN(C)/C=N/c1cc(Br)c(OC2CCC(=NO)CC2)nc1C] | Liquid |
| Q.044 | 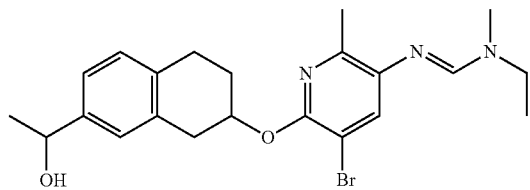 [SMILES: CCN(C)/C=N/c1cc(Br)c(OC2CCc3ccc(C(C)O)cc3C2)nc1C] | Method 4: 1.28 min; 446 |

| | | LC-Method: R$_t$ (min); MS-ESI (m/z; (M + H)$^+$) |
|---|---|---|
| Q.045 | 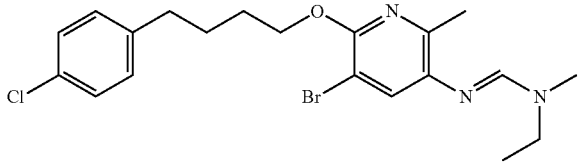 [SMILES: CCN(C)/C=N/c1cc(Br)c(OCCCCc2ccc(Cl)cc2)nc1C] | Gum |
| Q.046 | 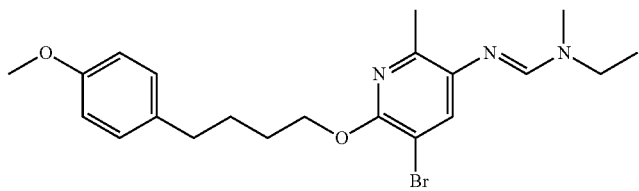 [SMILES: CCN(C)/C=N/c1cc(Br)c(OCCCCc2ccc(OC)cc2)nc1C] | Gum |
| Q.047 | 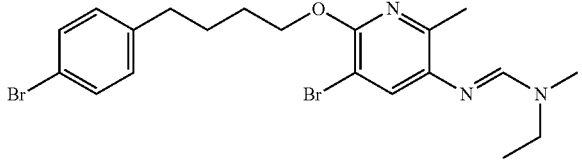 [SMILES: CCN(C)/C=N/c1cc(Br)c(OCCCCc2ccc(Br)cc2)nc1C] | Gum |
| Q.048 | 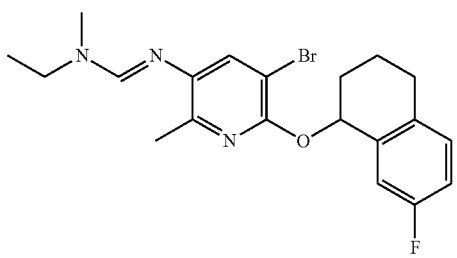 [SMILES: CCN(C)/C=N/c1cc(Br)c(OC2CCCc3ccc(F)cc32)nc1C] | Gum |
| Q.049 | 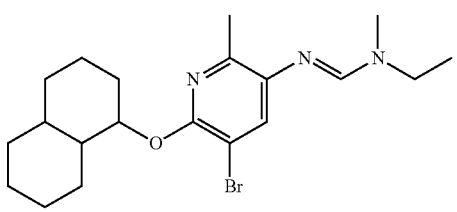 [SMILES: CCN(C)/C=N/c1cc(Br)c(OC2CCCC3CCCCC32)nc1C] | Gum |
| Q.050 | 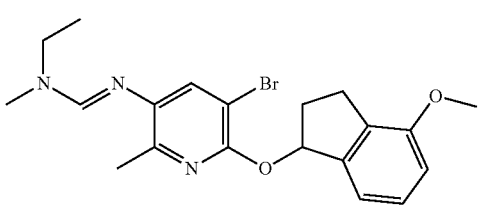 | Gum |
| Q.051 | 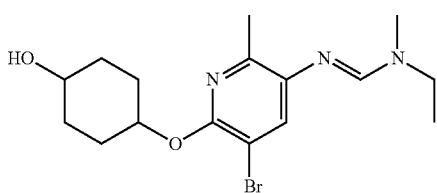 [SMILES: CCN(C)/C=N/c1cc(Br)c(OC2CCC(O)CC2)nc1C] | Liquid |

TABLE Q-continued
| | | LC-Method:<br>R$_t$ (min);<br>MS-ESI<br>(m/z; (M + H)$^+$) |
|---|---|---|
| Q.052 | 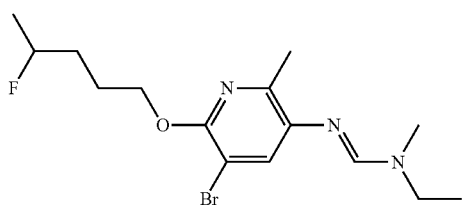 [SMILES: CCN(C)/C=N/c1cc(Br)c(OCCCC(C)F)nc1C] | Method 4:<br>1.18 min;<br>360 |
| Q.053 | 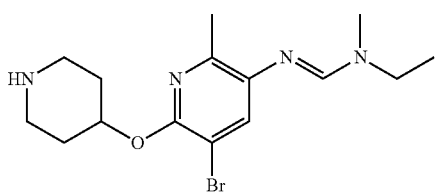 [SMILES: CCN(C)/C=N/c1cc(Br)c(OC2CCNCC2)nc1C] | Liquid |
| Q.054 | 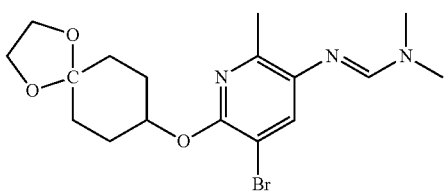 [SMILES: Cc1nc(OC2CCC3(CC2)OCCO3)c(Br)cc1/N=C/N(C)C] | Liquid |
| Q.055 | 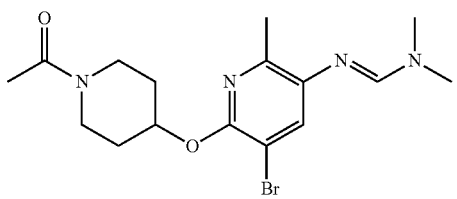 [SMILES: CC(=O)N1CCC(Oc2nc(C)c(/N=C/N(C)C)cc2Br)CC1] | Liquid |
| Q.056 | 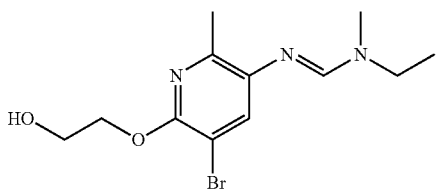 [SMILES: CCN(C)/C=N/c1cc(Br)c(OCCO)nc1C] | Solid |
| Q.057 | 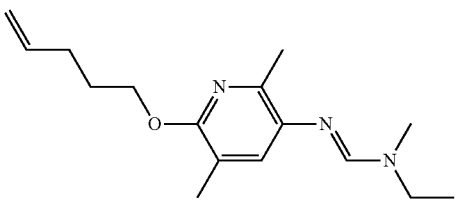 [SMILES: C=CCCCOc1nc(C)c(/N=C/N(C)CC)cc1C] | Method 4:<br>1.19 min;<br>276 |
| Q.058 | 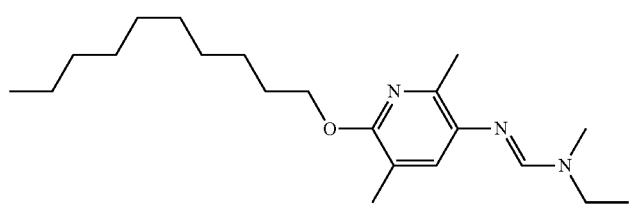 [SMILES: CCCCCCCCCCOc1nc(C)c(/N=C/N(C)CC)cc1C] | Method 4:<br>1.64 min;<br>348 |

TABLE Q-continued
| | | LC-Method: $R_t$ (min); MS-ESI (m/z; (M + H)$^+$) |
|---|---|---|
| Q.059 | 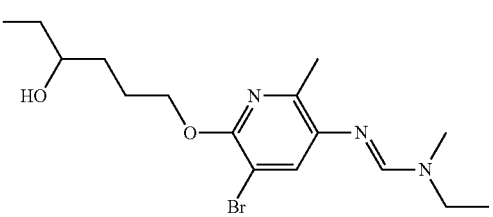 | Method 4: 1.00 min; 392 |
| Q.060 | 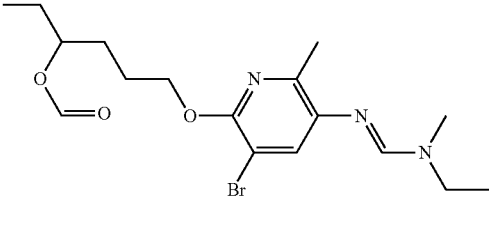 | Method 4: 1.16 min; 420 |
| Q.061 | 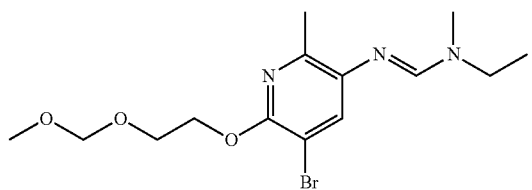 [SMILES: CCN(C)/C=N/c1cc(Br)c(OCCOCOC)nc1C] | Liquid |
| Q.062 | 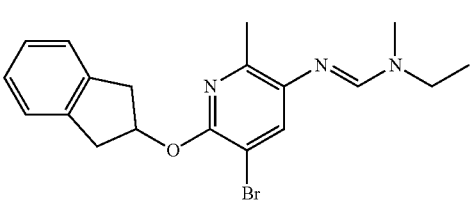 [SMILES: CCN(C)/C=N/c1cc(Br)c(OC2Cc3ccccc3C2)nc1C] | Method 4: 1.34 min; 388 |
| Q.063 | 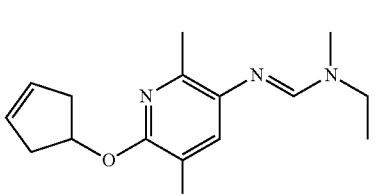 | Method 4: 1.16 min; 338 |
| Q.064 | 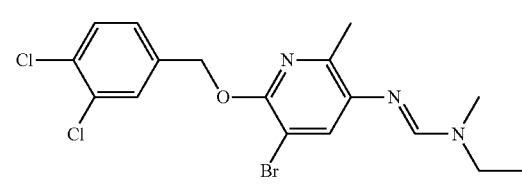 [SMILES: CCN(C)/C=N/c1cc(Br)c(OCc2ccc(Cl)c(Cl)c2)nc1C] | Mp 77-78° C. |
| Q.065 | 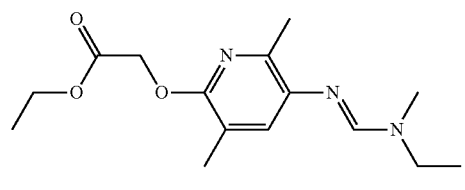 [SMILES: CCOC(=O)COc1nc(C)c(/N=C/N(C)CC)cc1C] | Liquid |

TABLE Q-continued
| | | LC-Method: $R_t$ (min); MS-ESI (m/z; (M + H)$^+$) |
|---|---|---|
| Q.066 | 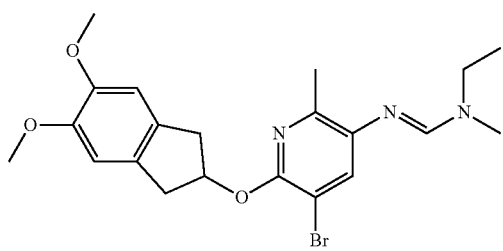 [SMILES: CCN(C)/C=N/c1cc(Br)c(OC2Cc3cc(OC)c(OC)cc3C2)nc1C] | Liquid |
| Q.067 | 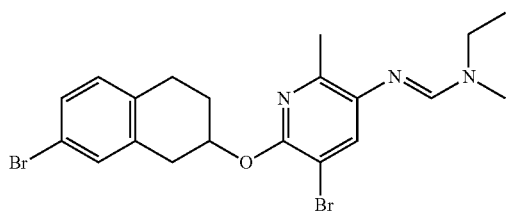 [SMILES: CCN(C)/C=N/c1cc(Br)c(OC2CCc3ccc(Br)cc3C2)nc1C] | Liquid |
| Q.068 | 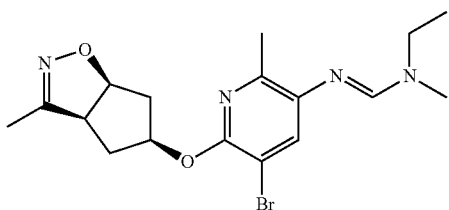 [SMILES: CCN(C)/C=N/c1cc(Br)c(O[C@@H]2C[C@@H]3ON=C(C)[C@@H]3C2)nc1C] | Solid |
| Q.069 | 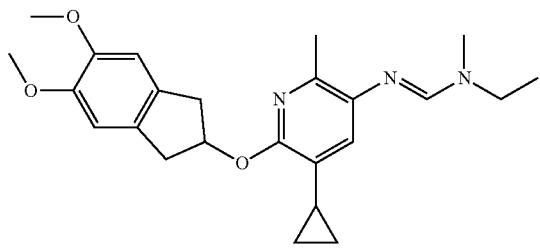 [SMILES: CCN(C)/C=N/c1cc(C2CC2)c(OC2Cc3cc(OC)c(OC)cc3C2)nc1C] | Method 4: 1.30 min; 410 |
| Q.070 | 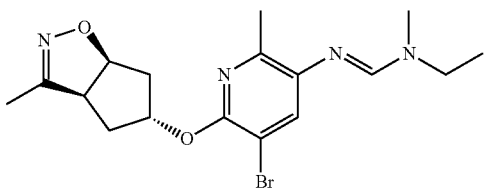 [SMILES: CCN(C)/C=N/c1cc(Br)c(O[C@H]2C[C@@H]3ON=C(C)[C@@H]3C2)nc1C] | Liquid |
| Q.071 | 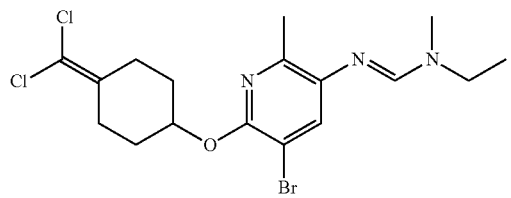 [SMILES: CCN(C)/C=N/c1cc(Br)c(OC2CCC(=C(Cl)Cl)CC2)nc1C] | Gum |

TABLE Q-continued

| | | LC-Method: R$_t$ (min); MS-ESI (m/z; (M + H)$^+$) |
|---|---|---|
| Q.072 | (structure) | Solid |
| Q.073 | (structure) | Solid |
| Q.074 | (structure) | Liquid |
| Q.075 | (structure) | Liquid |
| Q.076 | (structure) | Liquid |
| Q.077 | (structure) | Liquid |
| Q.078 | (structure) | Liquid |

TABLE Q-continued
| | | LC-Method: R$_t$ (min); MS-ESI (m/z; (M + H)$^+$) |
|---|---|---|
| Q.079 | 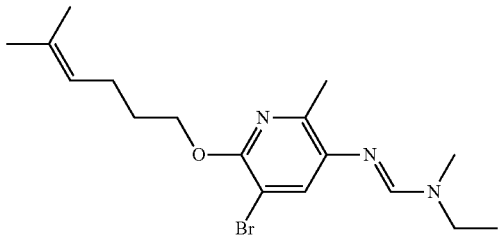 | Method 4: 1.39 min; 368 |
| Q.080 | 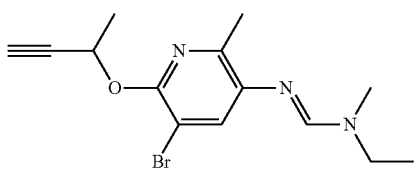 | Liquid |
| Q.081 | 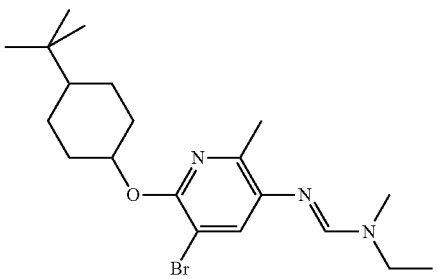 | Liquid |
| Q.082 | 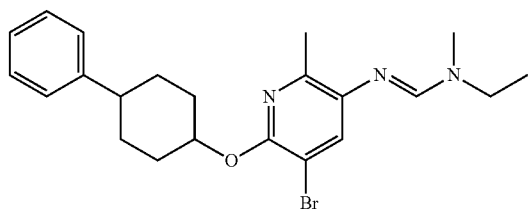 [SMILES: CCN(C)/C=N/c1cc(Br)c(OC2CCC(c3ccccc3)CC2)nc1C] | Liquid |
| Q.083 | 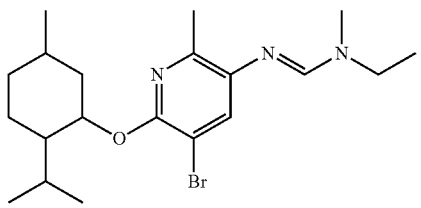 [SMILES: CCN(C)/C=N/c1cc(Br)c(OC2CC(C)CCC2C(C)C)nc1C] | Liquid |
| Q.84 | 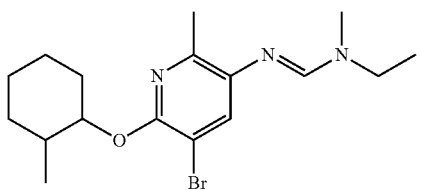 [SMILES: CCN(C)/C=N/c1cc(Br)c(OC2CCCCC2C)nc1C] | Liquid |
| Q.085 | 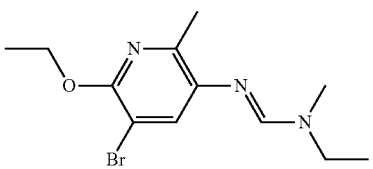 | Gum |

TABLE Q-continued
| | | LC-Method: R$_t$ (min); MS-ESI (m/z; (M + H)$^+$) |
|---|---|---|
| Q.086 | 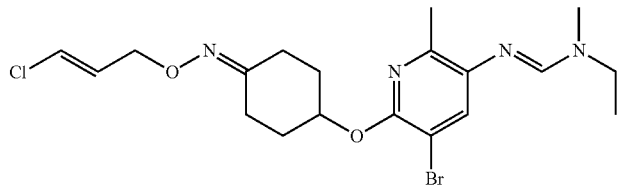 [SMILES: CCN(C)/C=N/c1cc(Br)c(OC2CCC(=NOC/C=C/Cl)CC2)nc1C] | Liquid |
| Q.087 | 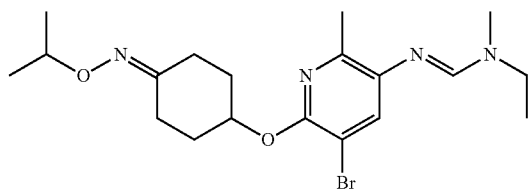 [SMILES: CCN(C)/C=N/c1cc(Br)c(OC2CCC(=NOC(C)C)CC2)nc1C] | Liquid |
| Q.088 | 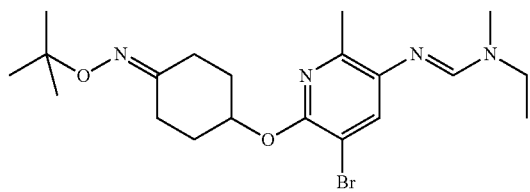 [SMILES: CCN(C)/C=N/c1cc(Br)c(OC2CCC(=NOC(C)(C)C)CC2)nc1C] | Liquid |
| Q.089 | 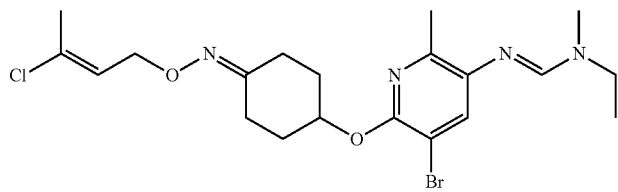 [SMILES: CCN(C)/C=N/c1cc(Br)c(OC2CCC(=NOC/C=C(\C)Cl)CC2)nc1C] | Liquid |
| Q.090 | 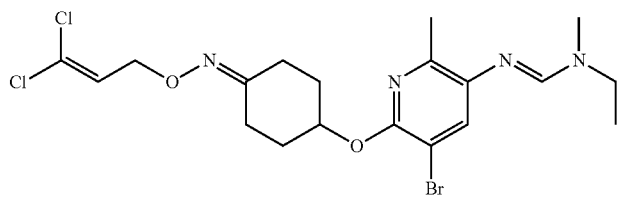 [SMILES: CCN(C)/C=N/c1cc(Br)c(OC2CCC(=NOCC=C(Cl)Cl)CC2)nc1C] | Liquid |
| Q.091 | 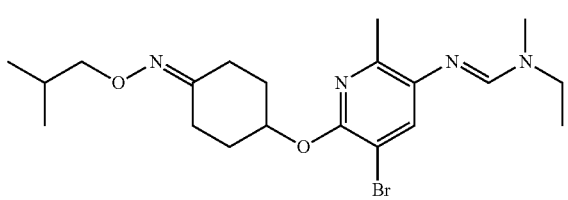 [SMILES: CCN(C)/C=N/c1cc(Br)c(OC2CCC(=NOCC(C)C)CC2)nc1C] | Liquid |
| Q.092 | 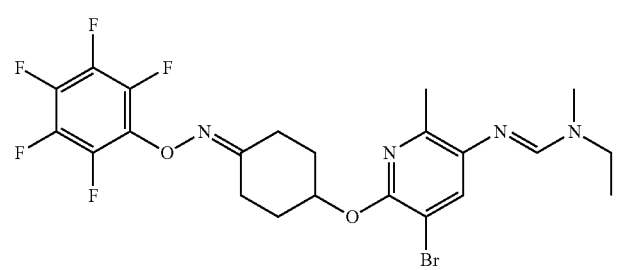 [SMILES: CCN(C)/C=N/c1cc(Br)c(OC2CCC(=NOc3c(F)c(F)c(F)c(F)c3F)CC2)nc1C] | Liquid |

TABLE Q-continued

| | | LC-Method: R_t (min); MS-ESI (m/z; (M + H)+) |
|---|---|---|
| Q.093 | [structure: 2,4-dichlorophenyl-O-N=cyclohexyl-O-pyridine(Br,Me)-N=CH-N(Me)Et] | Gum |
| Q.094 | [structure: 2,6-dimethylcyclohexyl-O-pyridine(Br,Me)-N=CH-N(Me)Et] | Liquid |
| Q.095 | [structure: benzyl-O-pyridine(Br,Me)-N=CH-N(Me)Et] | Method 1: 13.577 min; 362 |
| Q.096 | [structure: 2,4-dichlorobenzyl-O-pyridine(Br,Me)-N=CH-N(Me)Et] | Mp 81-82° C. |
| Q.097 | [structure: 4-chlorobenzyl-O-pyridine(Br,Me)-N=CH-N(Me)Et] | Method 2: 11.956 min; 398 |
| Q.098 | [structure: cyclopentenylmethyl-O-pyridine(Br,Me)-N=CH-N(Me)Et] | Method 1: 11.773 min; 352 |
| Q.099 | [structure: phenethyl-O-pyridine(Br,Me)-N=CH-N(Me)Et] | Method 1: 11.755 min; 376 |
| Q.100 | [structure: 3-phenylpropyl-O-pyridine(Br,Me)-N=CH-N(Me)Et] | Method 1: 12.320 min; 390 |

TABLE Q-continued
| | | LC-Method: $R_t$ (min); MS-ESI (m/z; (M + H)$^+$) |
|---|---|---|
| Q.101 | 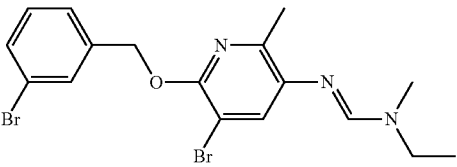 [SMILES: CCN(C)/C=N/c1cc(Br)c(OCc2cccc(Br)c2)nc1C] | Method 1: 12.207 min; 440 |
| Q.102 | 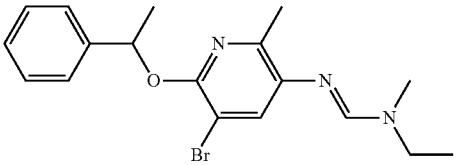 | Method 1: 11.873 min; 376 |
| Q.103 | 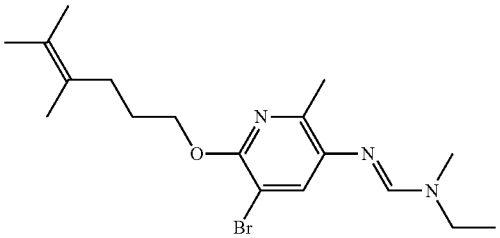 [SMILES: CCN(C)/C=N/c1cc(Br)c(OCCCC(C)=C(C)C)nc1C] | Method 1: 13.153 min; 382 |
| Q.104 | 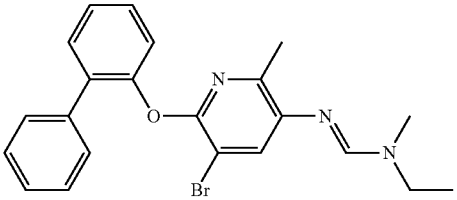 [SMILES: CCN(C)/C=N/c1cc(Br)c(Oc2ccccc2-c2ccccc2)nc1C] | Method 1: 6.418 min; 438 |
| Q.105 | 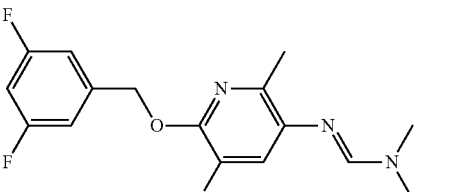 | Method 1: 11.571 min; 400 |
| Q.106 | 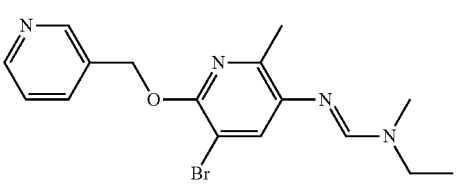 [SMILES: CCN(C)/C=N/c1cc(Br)c(OCc2cccnc2)nc1C] | Method 1: 12.115 min; 365 |
| Q.107 | 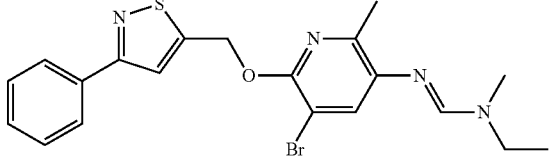 | Mp 107-108° C. |

TABLE Q-continued
| | | LC-Method: $R_t$ (min); MS-ESI (m/z; (M + H)$^+$) |
|---|---|---|
| Q.108 | 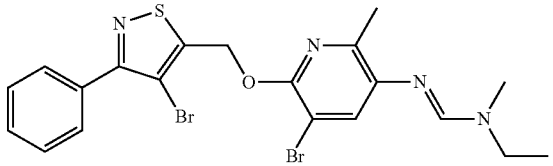 [SMILES: CCN(C)/C=N/c1cc(Br)c(OCc2snc(-c3ccccc3)c2Br)nc1C] | Method 2: 12.713 min; 523 |
| Q.109 | 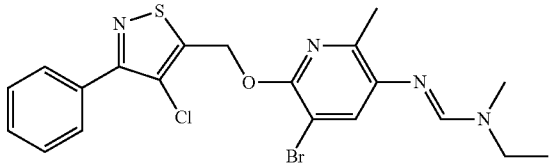 [SMILES: CCN(C)/C=N/c1cc(Br)c(OCc2snc(-c3ccccc3)c2Cl)nc1C] | Method 1: 12.881 min; 479 |
| Q.110 | 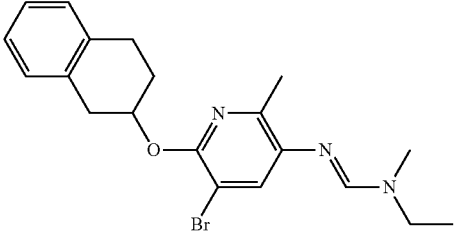 [SMILES: CCN(C)/C=N/c1cc(Br)c(OC2CCc3ccccc3C2)nc1C] | Method 2: 12.214 min; 402 |
| Q.111 | 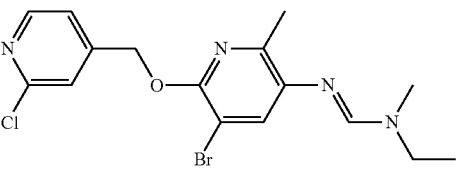 | Mp 57-59° C. |
| Q.112 | 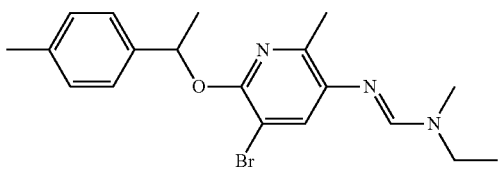 [SMILES: CCN(C)/C=N/c1cc(Br)c(OC(C)c2ccc(C)cc2)nc1C] | Method 2: 12.236 min; 390 |
| Q.113 | 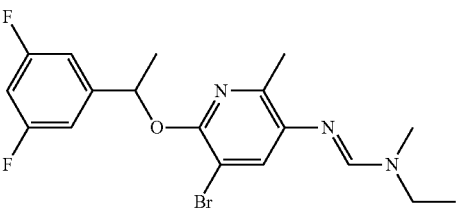 | Method 1: 12.030 min; 412 |
| Q.114 | 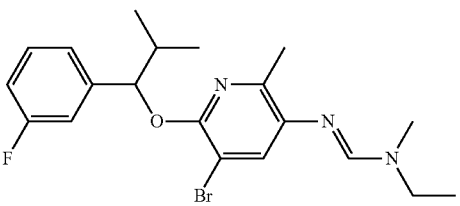 [SMILES: CCN(C)/C=N/c1cc(Br)c(OC(c2cccc(F)c2)C(C)C)nc1C] | Method 2: 13.002 min; 404 |

TABLE Q-continued
| | | LC-Method: R$_t$ (min); MS-ESI (m/z; (M + H)$^+$) |
|---|---|---|
| Q.115 | 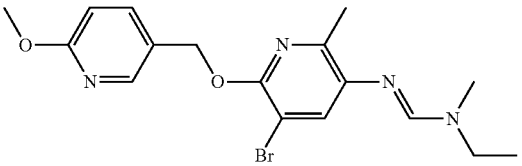 [SMILES: CCN(C)/C=N/c1cc(Br)c(OCc2ccc(OC)nc2)nc1C] | Method 1: 9.589 min; 393 |
| Q.116 | 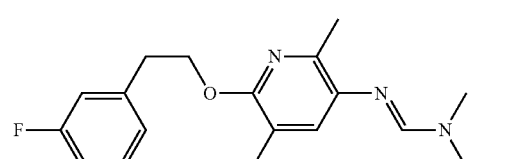 | Method 2: 11.625 min; 394 |
| Q.117 | 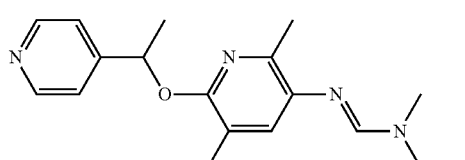 | Method 2: 6.956 min; 377 |
| Q.118 | 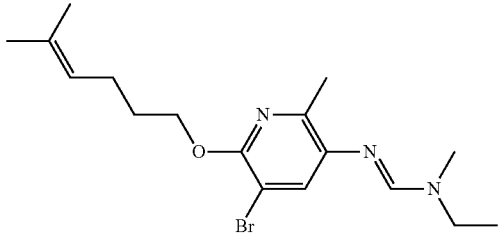 [SMILES: CCN(C)/C=N/c1cc(Br)c(OCCCC=C(C)C)nc1C] | Method 2: 12.577 min; 368 |
| Q.119 | 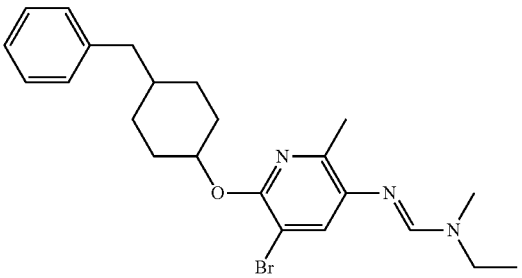 [SMILES: CCN(C)/C=N/c1cc(Br)c(OC2CCC(Cc3ccccc3)CC2)nc1C] | Method 1: 13.850 min; 444 |
| Q.120 | 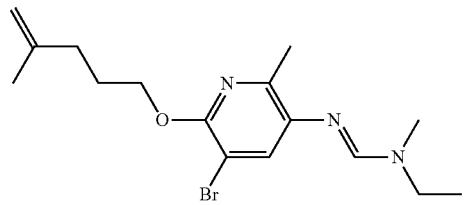 [SMILES: C=C(C)CCCOc1nc(C)c(/N=C/N(C)CC)cc1Br] | Method 2: 11.861 min; 354 |
| Q.121 | 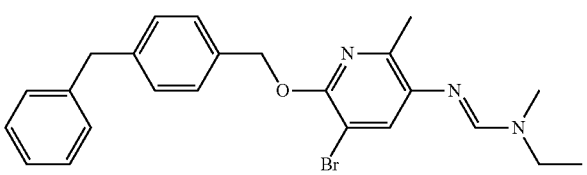 | Method 2: 12.977 min; 451 |

TABLE Q-continued

| | | LC-Method: R$_t$ (min); MS-ESI (m/z; (M + H)$^+$) |
|---|---|---|
| Q.122 | | Method 2 13.353 min; 394 |
| Q.123 | | Mp 120-121° C. |
| Q.124 | | Mp 98-99° C. |
| Q.125 | | Mp 101-102° C. |
| Q.126 | | Method 1: 13.029 min; 480 |
| Q.127 | | Method 2: 13.168 min; 481 |

TABLE Q-continued

| | | LC-Method:<br>R$_t$ (min);<br>MS-ESI<br>(m/z; (M + H)$^+$) |
|---|---|---|
| Q.128 | | Mp 60-62° C. |
| Q.129 | | Mp 46-48° C. |
| Q.130 | | Method 2:<br>3.41 min;<br>377 |
| Q.131 | | Method 2:<br>12.242 min;<br>408 |
| Q.132 | | Method 1:<br>12.688 min;<br>368 |
| Q.133 | | Method 1:<br>12.522 min;<br>368 |
| Q.134 | | Method 2:<br>12.979 min;<br>380 |

TABLE Q-continued
| | | LC-Method: $R_t$ (min); MS-ESI (m/z; (M + H)$^+$) |
|---|---|---|
| Q.135 | 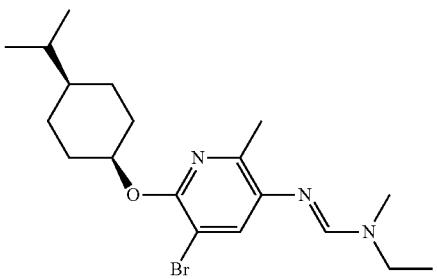 [SMILES: CCN(C)/C=N/c1cc(Br)c(O[C@H]2CC[C@@H](C(C)C)CC2)nc1C] | Method 3: 1.49 min; 396: Cis |
| Q.136 | 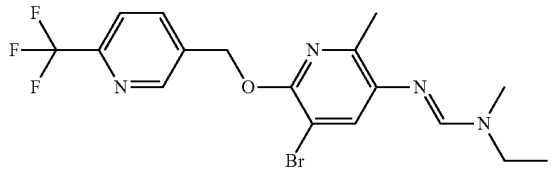 [SMILES: CCN(C)/C=N/c1cc(Br)c(OCc2ccc(C(F)(F)F)nc2)nc1C] | Method 1: 10.914 min; 431 |
| Q.137 | 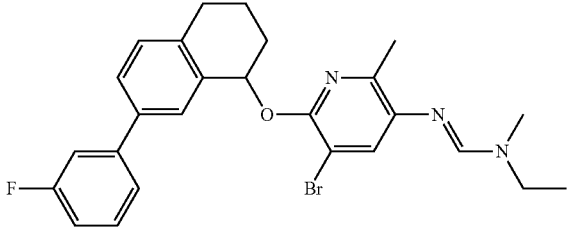 [SMILES: CCN(C)/C=N/c1cc(Br)c(OC2CCCc3ccc(-c4cccc(F)c4)cc32)nc1C] | Mp 43-45° C. |
| Q.138 | 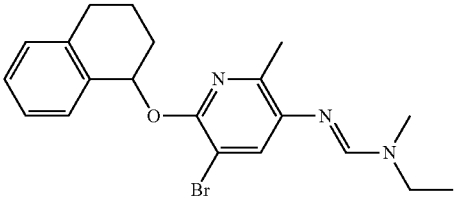 [SMILES: CCN(C)/C=N/c1cc(Br)c(OC2CCCc3ccccc32)nc1C] | Method 1: 13.065 min; 402 |
| Q.139 | 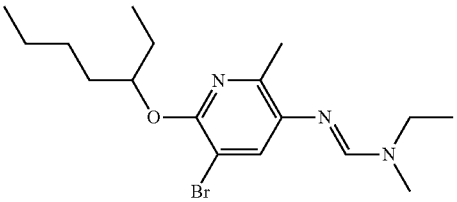 | Method 1: 13.387 min; 370 |
| Q.140 | 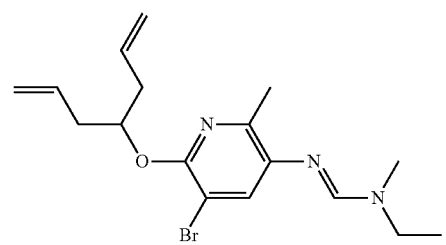 [SMILES: C=CCC(CC=C)Oc1nc(C)c(/N=C/N(C)CC)cc1Br] | Method 2: 12.176 min; 366 |

TABLE Q-continued
| | | LC-Method:<br>$R_t$ (min);<br>MS-ESI<br>(m/z; (M + H)$^+$) |
|---|---|---|
| Q.141 | 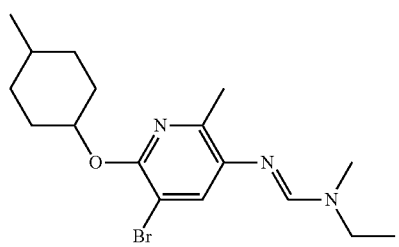 [SMILES: CCN(C)/C=N/c1cc(Br)c(OC2CCC(C)CC2)nc1C] | Method 1:<br>12.712 min;<br>368 |
| Q.142 | 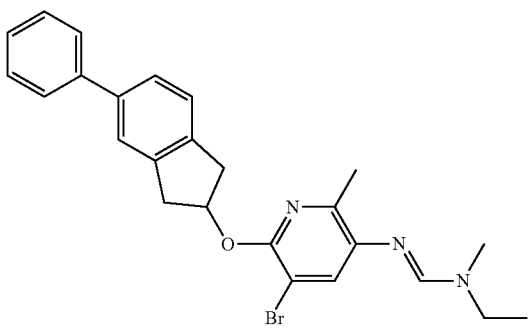 [SMILES: CCN(C)/C=N/c1cc(Br)c(OC2Cc3ccc(-c4ccccc4)cc3C2)nc1C] | Method 1:<br>13.557 min;<br>466 |
| Q.143 | 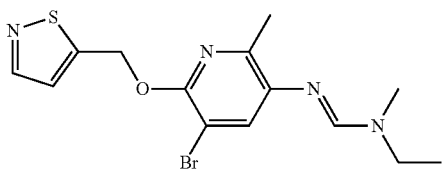 [SMILES: CCN(C)/C=N/c1cc(Br)c(OCc2ccns2)nc1C] | Mp 71-73° C. |
| Q.144 | 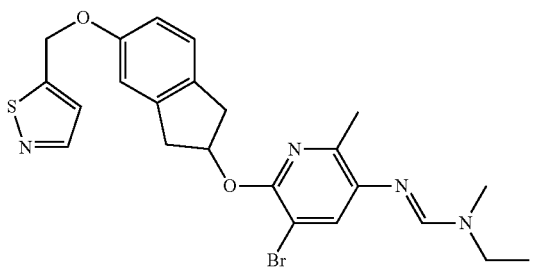 [SMILES: CCN(C)/C=N/c1cc(Br)c(OC2Cc3ccc(OCc4ccns4)cc3C2)nc1C] | Method 1:<br>11.879 min;<br>503 |
| Q.145 | 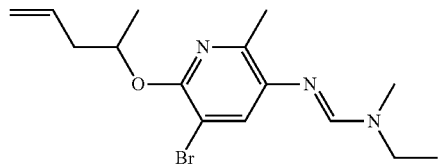 | Mp 106-107° C. |
| Q.146 | 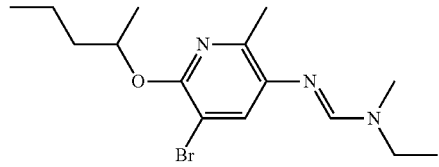 | Method 1:<br>11.862 min;<br>344 |

TABLE Q-continued
| | | LC-Method: $R_t$ (min); MS-ESI (m/z; (M + H)$^+$) |
|---|---|---|
| Q.147 | 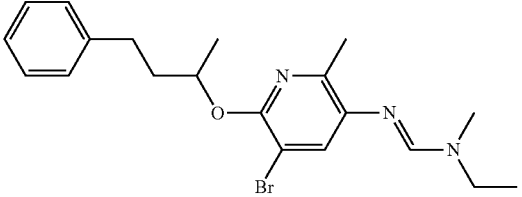 [SMILES: CCN(C)/C=N/c1cc(Br)c(OC(C)CCc2ccccc2)nc1C] | Method 1: 12.605 min; 404 |
| Q.148 | 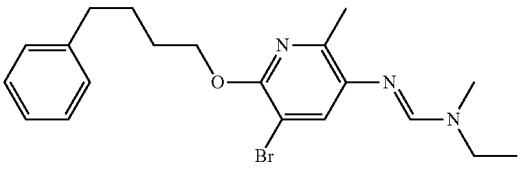 [SMILES: CCN(C)/C=N/c1cc(Br)c(OCCCCc2ccccc2)nc1C] | Method 1: 12.704 min; 405 |
| Q.149 | 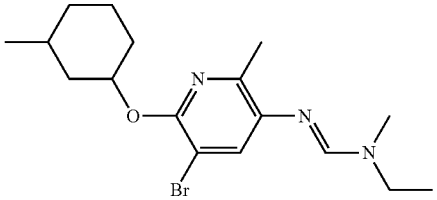 [SMILES: CCN(C)/C=N/c1cc(Br)c(OC2CCCC(C)C2)nc1C] | Method 1: 12.642 min; 370 |
| Q.150 | 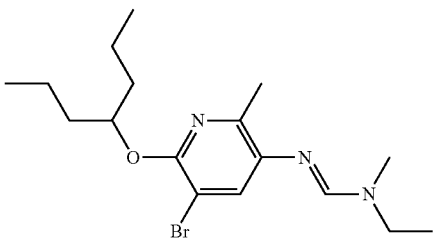 [SMILES: CCCC(CCC)Oc1nc(C)c(/N=C/N(C)CC)cc1Br] | Method 1: 13.317 min; 372 |
| Q.151 | 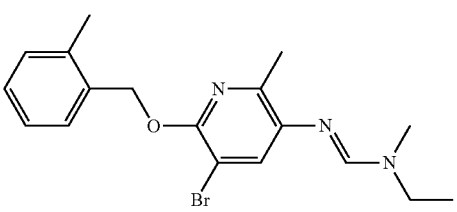 [SMILES: CCN(C)/C=N/c1cc(Br)c(OCc2ccccc2C)nc1C] | Liquid |
| Q.152 | 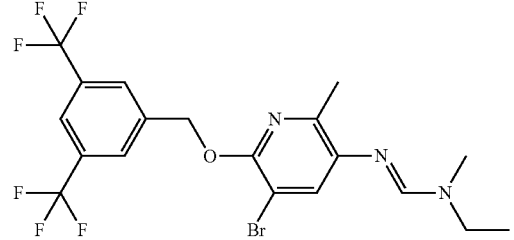 [SMILES: CCN(C)/C=N/c1cc(Br)c(OCc2cc(C(F)(F)F)cc(C(F)(F)F)c2)nc1C] | Mp 100-101° C. |

TABLE Q-continued

| | LC-Method: R$_t$ (min); MS-ESI (m/z; (M + H)$^+$) |
|---|---|
| Q.153 | Mp 43-44° C. |
| Q.154 | Mp 53-57° C. |
| Q.155 | Mp 75-78° C. |
| Q.156 | Mp 90-91° C. |
| Q.157 | Mp 125-127° C. |
| Q.158 | Liquid |
| Q.159 | Liquid |

TABLE Q-continued
| | | LC-Method: $R_t$ (min); MS-ESI (m/z; (M + H)$^+$) |
|---|---|---|
| Q.160 | 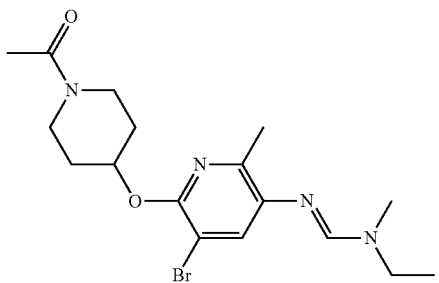 [SMILES: CCN(C)/C=N/c1cc(Br)c(OC2CCN(C(C)=O)CC2)nc1C] | Liquid |
| Q.161 | 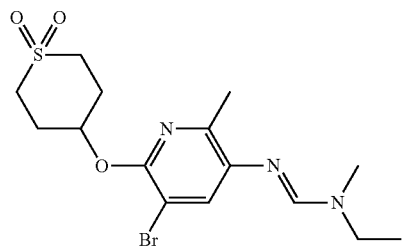 [SMILES: CCN(C)/C=N/c1cc(Br)c(OC2CCS(=O)(=O)CC2)nc1C] | Liquid |
| Q.162 | 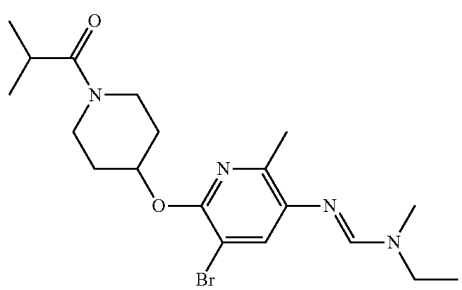 [SMILES: CCN(C)/C=N/c1cc(Br)c(OC2CCN(C(=O)C(C)C)CC2)nc1C] | Liquid |
| Q.163 | 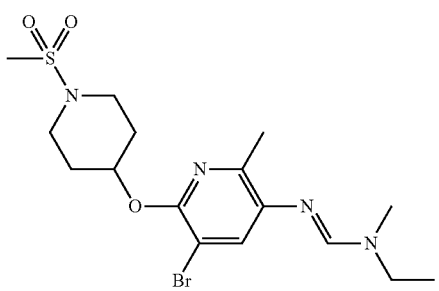 [SMILES: CCN(C)/C=N/c1cc(Br)c(OC2CCN(S(C)(=O)=O)CC2)nc1C] | Mp 90-95° C. |
| Q.164 | 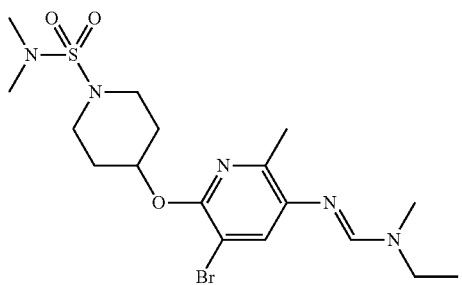 [SMILES: CCN(C)/C=N/c1cc(Br)c(OC2CCN(S(=O)(=O)N(C)C)CC2)nc1C] | Mp 88-90° C. |

TABLE Q-continued

| | | LC-Method:<br>R$_t$ (min);<br>MS-ESI<br>(m/z; (M + H)$^+$) |
|---|---|---|
| Q.165 | | Liquid |
| Q.166 | | Liquid |
| Q.167 | | Liquid |
| Q.168 | | Liquid |
| Q.169 | | Liquid |
| Q.170 | | Liquid |

TABLE Q-continued
| | | LC-Method: $R_t$ (min); MS-ESI (m/z; (M + H)$^+$) |
|---|---|---|
| Q.171 | 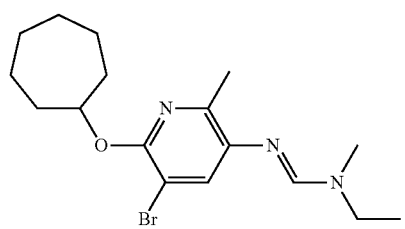 [SMILES: CCN(C)/C=N/c1cc(Br)c(OC2CCCCCC2)nc1C] | Liquid |
| Q.172 | 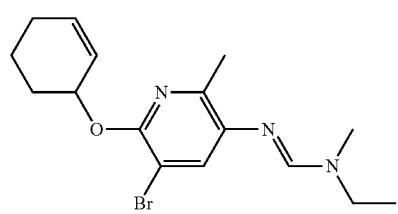 [SMILES: CCN(C)/C=N/c1cc(Br)c(OC2C=CCCC2)nc1C] | Mp 72-76° C. |
| Q.173 | 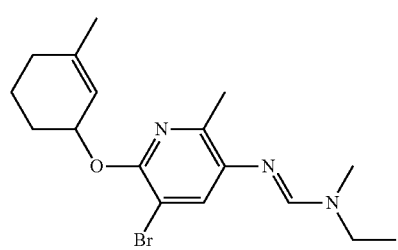 [SMILES: CCN(C)/C=N/c1cc(Br)c(OC2C=C(C)CCC2)nc1C] | Liquid |
| Q.174 | 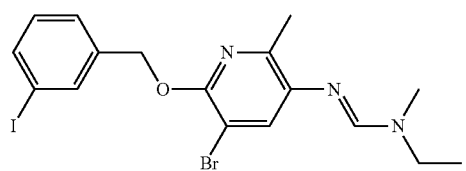 [SMILES: CCN(C)/C=N/c1cc(Br)c(OCc2cccc(I)c2)nc1C] | Liquid |
| Q.175 | 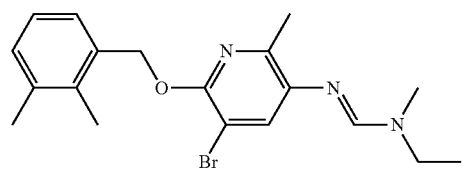 [SMILES: CCN(C)/C=N/c1cc(Br)c(OCc2cccc(C)c2C)nc1C] | Liquid |
| Q.176 | 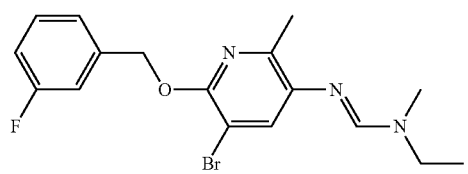 | Liquid |
| Q.177 | 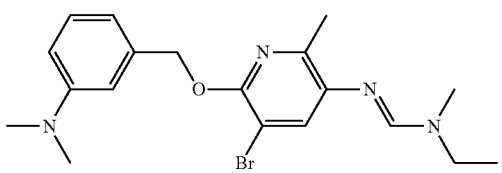 [SMILES: CCN(C)/C=N/c1cc(Br)c(OCc2cccc(N(C)C)c2)nc1C] | Liquid |

TABLE Q-continued

| | | LC-Method: R$_t$ (min); MS-ESI (m/z; (M + H)$^+$) |
|---|---|---|
| Q.178 | [structure] | Method 2: 12.011 min; 460 |
| Q.179 | [structure] | Method 1: 13.777 min; 444; Trans |
| Q.180 | [structure] | Method 1: 13.653 min; 444; Cis |
| Q.181 | [structure] | Method 2: 11.260 min; 334 |
| Q.182 | [structure] | Method 1: 13.163 min; 318; Trans |
| Q.183 | [structure] | Method 1: 14.926 min; 318; Cis |

TABLE Q-continued
| | | LC-Method: R_t (min); MS-ESI (m/z; (M + H)+) |
|---|---|---|
| Q.184 | 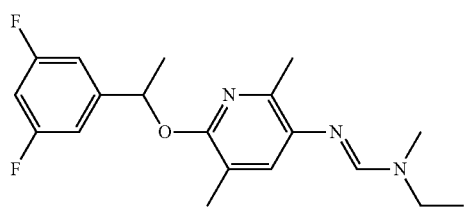 [SMILES: CCN(C)/C=N/c1cc(C)c(OC(C)c2cc(F)cc(F)c2)nc1C] | Method 2: 12.116 min; 348 |
| Q.185 | 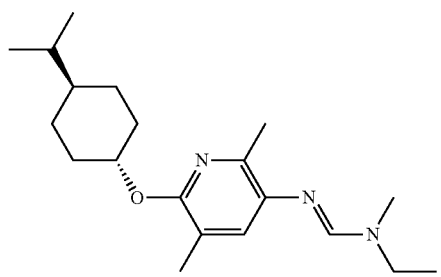 [SMILES: CCN(C)/C=N/c1cc(C)c(O[C@H]2CC[C@H](C(C)C)CC2)nc1C] | Method 1: 14.254 min; 332; Trans |
| Q.186 | 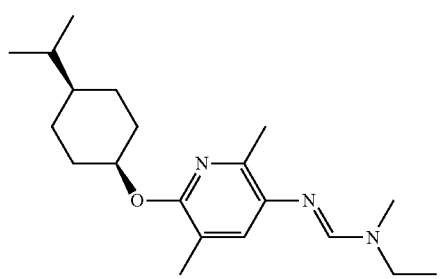 [SMILES: CCN(C)/C=N/c1cc(C)c(O[C@H]2CC[C@@H](C(C)C)CC2)nc1C] | Method 1: 15.845 min; 332; Cis |
| Q.187 | 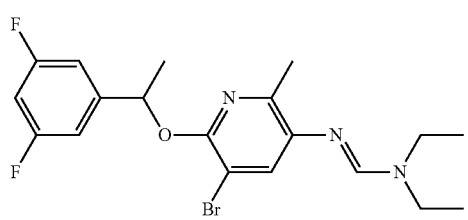 [SMILES: CCN(/C=N/c1cc(Br)c(OC(C)c2cc(F)cc(F)c2)nc1C)CC] | Method 2: 12.707 min; 426 |
| Q.188 | 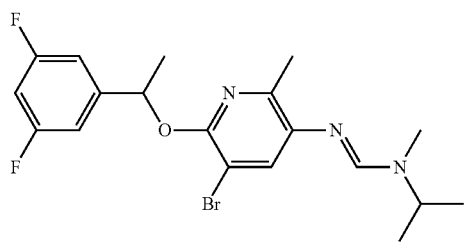 [SMILES: Cc1nc(OC(C)c2cc(F)cc(F)c2)c(Br)cc1/N=C/N(C)C(C)C] | Method 2: 12.145 min; 426 |
| Q.189 | 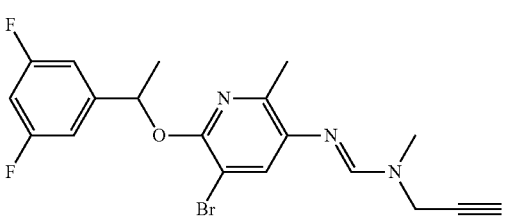 [SMILES: C#CCN(C)/C=N/c1cc(Br)c(OC(C)c2cc(F)cc(F)c2)nc1C] | Method 2: 11.943 min; 422 |

TABLE Q-continued
| | | LC-Method:<br>R$_t$ (min);<br>MS-ESI<br>(m/z; (M + H)$^+$) |
|---|---|---|
| Q.190 | 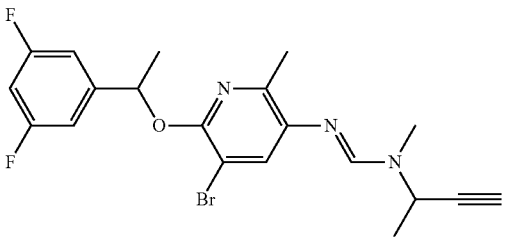 [SMILES: C#CC(C)N(C)/C=N/c1cc(Br)c(OC(C)c2cc(F)cc(F)c2)nc1C] | Method 1:<br>12.216 min;<br>436 |
| Q.191 | 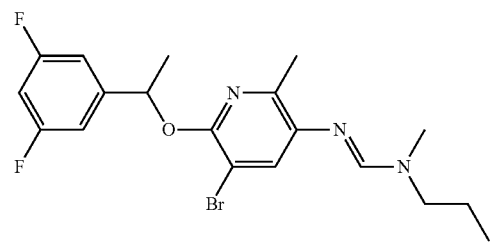 [SMILES: CCCN(C)/C=N/c1cc(Br)c(OC(C)c2cc(F)cc(F)c2)nc1C] | Method 2:<br>12.769 min;<br>426 |
| Q.192 | 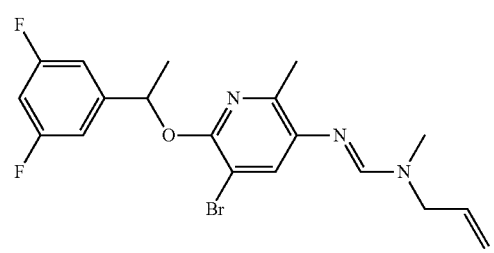 [SMILES: C=CCN(C)/C=N/c1cc(Br)c(OC(C)c2cc(F)cc(F)c2)nc1C] | Method 2:<br>12.121 min;<br>424 |
| Q.193 | 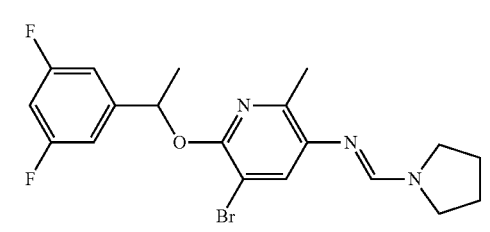 [SMILES: Cc1nc(OC(C)c2cc(F)cc(F)c2)c(Br)cc1/N=C/N1CCCC1] | Method 2:<br>11.891 min;<br>424 |
| Q.194 | 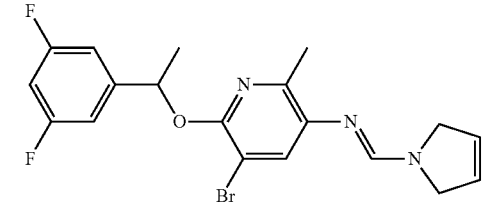 [SMILES: Cc1nc(OC(C)c2cc(F)cc(F)c2)c(Br)cc1/N=C/N1CC=CC1] | Method 2:<br>11.881 min;<br>422 |
| Q.195 | 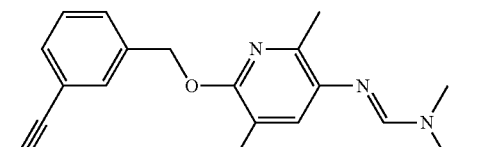 | Mp 52-54° C. |

TABLE Q-continued
| | | LC-Method: $R_t$ (min); MS-ESI (m/z; (M + H)$^+$) |
|---|---|---|
| Q.196 | 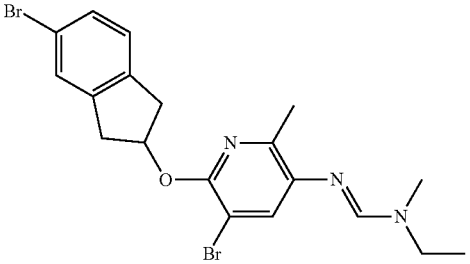 | Method 1: 12.439 min; 466 |
| Q.197 | 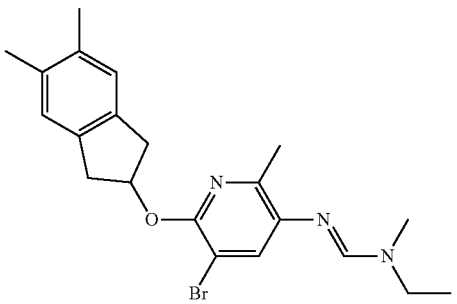 [SMILES: CCN(C)/C=N/c1cc(Br)c(OC2Cc3cc(C)c(C)cc3C2)nc1C] | Method 1: 11.886 min; 416 |
| Q.198 | 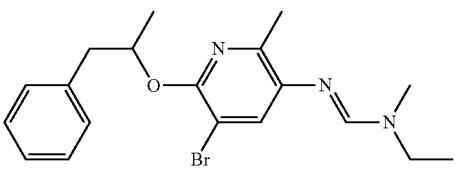 | Method 1: 11.886 min; 390 |
| Q.199 | 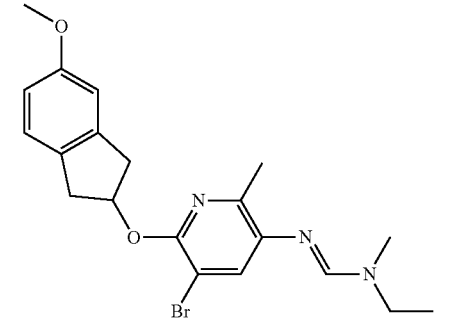 [SMILES: CCN(C)/C=N/c1cc(Br)c(OC2Cc3ccc(OC)cc3C2)nc1C] | Method 1: 11.955 min; 418 |
| Q.200 | 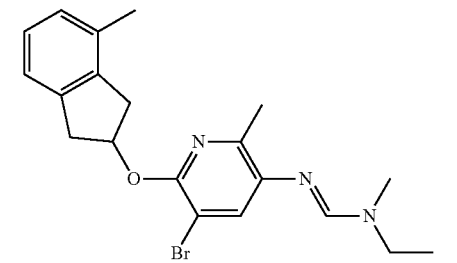 [SMILES: CCN(C)/C=N/c1cc(Br)c(OC2Cc3cccc(C)c3C2)nc1C] | Method 1: 12.096 min; 402 |

TABLE Q-continued
| | | LC-Method: R$_t$ (min); MS-ESI (m/z; (M + H)$^+$) |
|---|---|---|
| Q.201 | 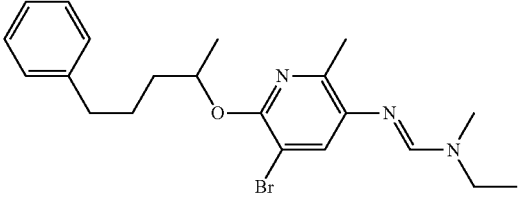 [SMILES: CCN(C)/C=N/c1cc(Br)c(OC(C)CCCc2ccccc2)nc1C] | Method 1: 12.796 min; 418 |
| Q.202 | 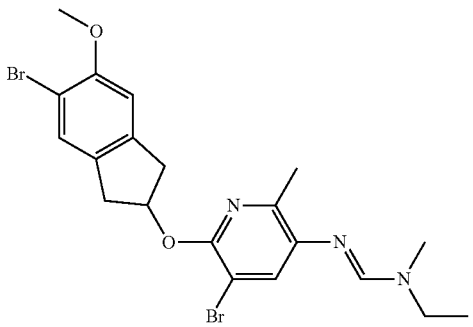 [SMILES: CCN(C)/C=N/c1cc(Br)c(OC2Cc3cc(Br)c(OC)cc3C2)nc1C] | Method 1: 12.154 min; 496 |
| Q.203 | 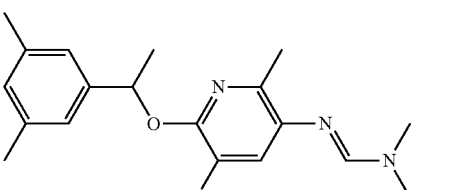 | Method 2: 13.148 min; 404 |
| Q.204 | 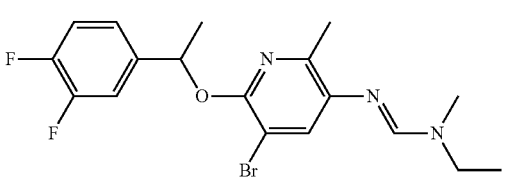 | Method 2: 11.780 min; 412 |
| Q.205 | 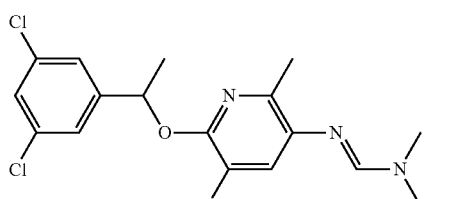 | Method 1: 6.785 min; 444 |
| Q.206 | 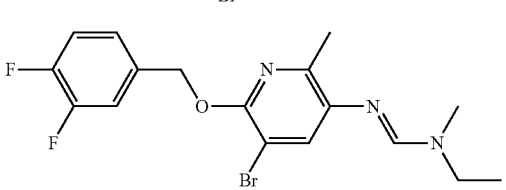 | Mp 75-78° C. |
| Q.207 | 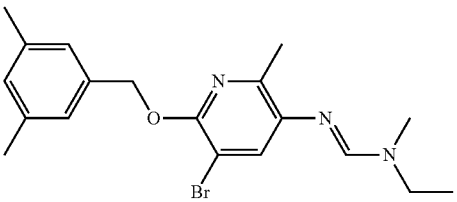 [SMILES: CCN(C)/C=N/c1cc(Br)c(OC(C)c2cc(C)cc(C)c2)nc1C] | Mp 57-58° C. |

TABLE Q-continued

| | | LC-Method: R$_t$ (min); MS-ESI (m/z; (M + H)$^+$) |
|---|---|---|
| Q.208 | | Method 1: 10.753 min; 368 |
| Q.209 | | Method 1: 7.472 min; 413 |
| Q.210 | | Mp 134-135° C. |
| Q.211 | | Method 1: 11.913 min; 440 |
| Q.212 | | Method 1: 11.392 min; 410 |
| Q.213 | | Method 1: 8.301 min; 370 |

TABLE Q-continued

| | | LC-Method:<br>R$_t$ (min);<br>MS-ESI<br>(m/z; (M + H)$^+$) |
|---|---|---|
| Q.214 | | Method 1:<br>11.318 min;<br>364 |
| Q.215 | | Method 1:<br>12.017 min;<br>384 |
| Q.216 | | Method 2:<br>12.660 min;<br>374 |
| Q.217 | | Method 1:<br>12.015 min;<br>426 |
| Q.218 | | Method 2:<br>12.403 min;<br>408 |
| Q.219 | | Method 2:<br>13.469 min;<br>418 |
| Q.220 | | Method 1:<br>11.837 min;<br>354 |

TABLE Q-continued
| | | LC-Method: $R_t$ (min); MS-ESI (m/z; (M + H)$^+$) |
|---|---|---|
| Q.221 | 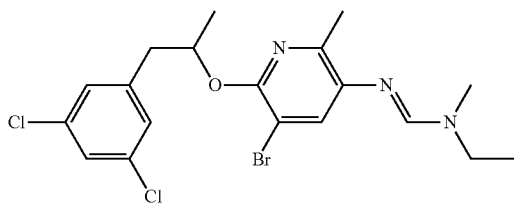 [SMILES: CCN(C)/C=N/c1cc(Br)c(OC(C)Cc2cc(Cl)cc(Cl)c2)nc1C] | Method 1: 13.221 min; 458 |
| Q.222 | 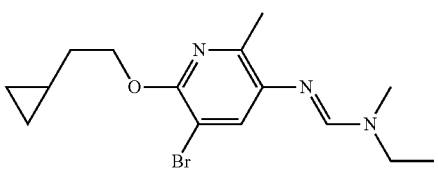 [SMILES: CCN(C)/C=N/c1cc(Br)c(OCCC2CC2)nc1C] | Method 2: 11.427 min; 340 |
| Q.223 | 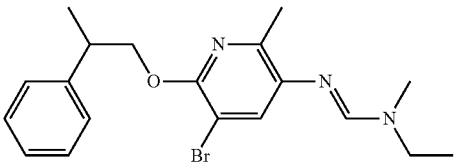 [SMILES: CCN(C)/C=N/c1cc(Br)c(OCC(C)c2ccccc2)nc1C] | Method 1: 12.006 min; 390 |
| Q.224 | 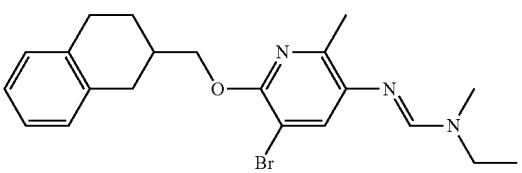 [SMILES: CCN(C)/C=N/c1cc(Br)c(OCC2CCc3ccccc3C2)nc1C] | Method 2: 12.567 min; 416 |
| Q.225 | 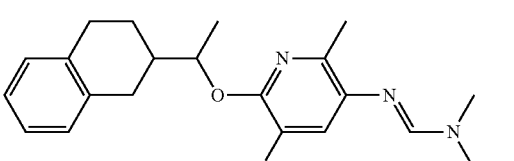 | Method 2: 13.408 min; 430 |
| Q.226 | 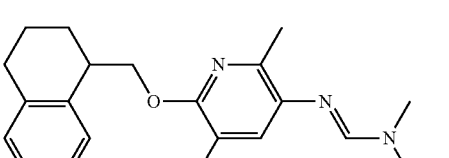 | Method 1: 12.686 min; 416 |
| Q.227 | 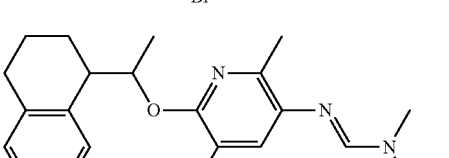 | Method 2: 13.431 min; 430 |
| Q.228 | 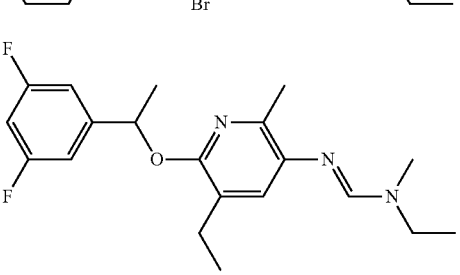 | Method 2: 12.346 min; 362 |

TABLE Q-continued
| | | LC-Method: $R_t$ (min); MS-ESI (m/z; (M + H)$^+$) |
|---|---|---|
| Q.229 | 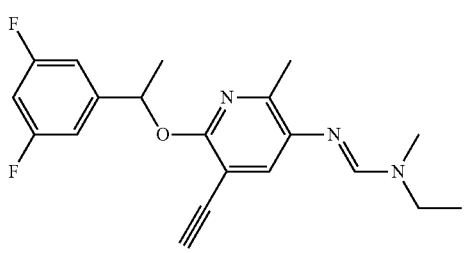 [SMILES: C#Cc1cc(/N=C/N(C)CC)c(C)nc1OC(C)c1cc(F)cc(F)c1] | Method 2: 11.570 min; 358 |
| Q.230 | 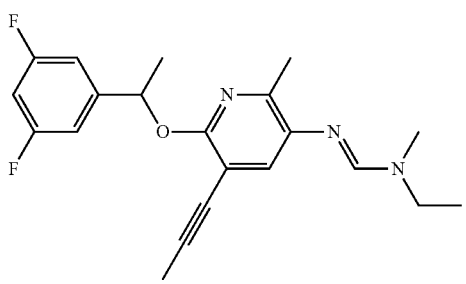 [SMILES: CC#Cc1cc(/N=C/N(C)CC)c(C)nc1OC(C)c1cc(F)cc(F)c1] | Method 1: 12.261 min; 372 |
| Q.231 | 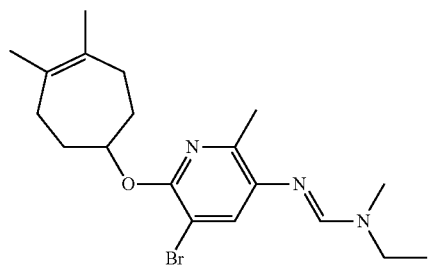 [SMILES: CCN(C)/C=N/c1cc(Br)c(OC2CCC(C)=C(C)CC2)nc1C] | Method 1: 13.535 min; 394 |
| Q.232 | 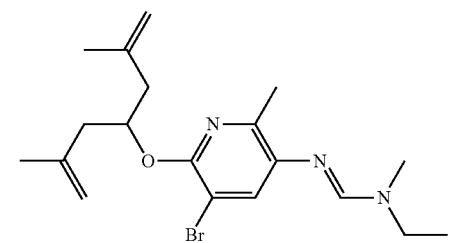 [SMILES: C=C(C)CC(CC(=C)C)Oc1nc(C)c(/N=C/N(C)CC)cc1Br] | Method 1: 13.295 min; 394 |
| Q.233 | 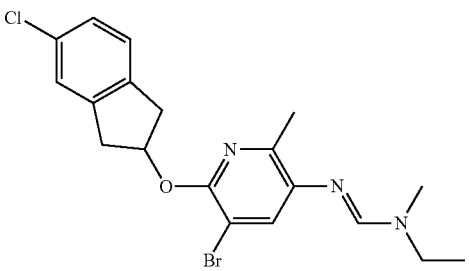 [SMILES: CCN(C)/C=N/c1cc(Br)c(OC2Cc3ccc(Cl)cc3C2)nc1C] | Method 2: 11.937 min; 422 |

TABLE Q-continued

| | | LC-Method:<br>R_t (min);<br>MS-ESI<br>(m/z; (M + H)+) |
|---|---|---|
| Q.234 | | Method 1:<br>14.173 min;<br>398 |
| Q.235 | | Mp 55-57° C. |
| Q.236 | | Mp 40-42° C. |
| Q.237 | | Method 1:<br>8.524 min;<br>382 |
| Q.238 | | Method 1:<br>19.177 min;<br>430 |
| Q.239 | | Method 1:<br>18.583 min;<br>416 |
| Q.240 | | Method 1:<br>10.070 min;<br>447 |

TABLE Q-continued
| | | LC-Method: $R_t$ (min); MS-ESI (m/z; (M + H)$^+$) |
|---|---|---|
| Q.241 | 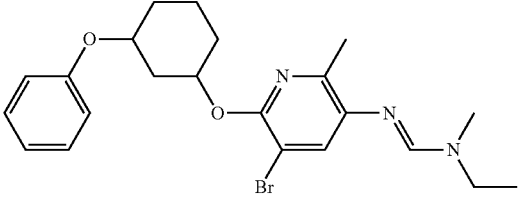 [SMILES: CCN(C)/C=N/c1cc(Br)c(OC2CCCC(Oc3ccccc3)C2)nc1C] | Method 1: 12.850 min; 446 |
| Q.242 | 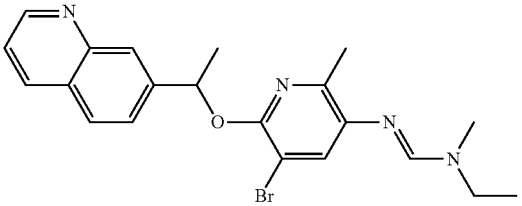 [SMILES: CCN(C)/C=N/c1cc(Br)c(OC(C)c2ccc3cccnc3c2)nc1C] | Method 1: 8.079 min; 427 |
| Q.243 | 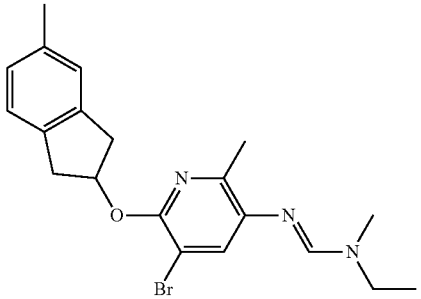 [SMILES: CCN(C)/C=N/c1cc(Br)c(OC2Cc3ccc(C)cc3C2)nc1C] | Method 1: 12.200 min; 402 |
| Q.244 | 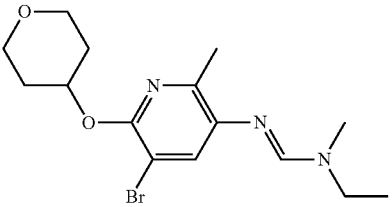 | Method 1: 9.090 min; 356 |
| Q.245 | 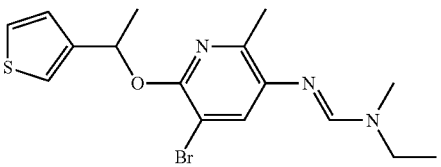 | Method 1: 8.672 min; 382 |
| Q.246 | 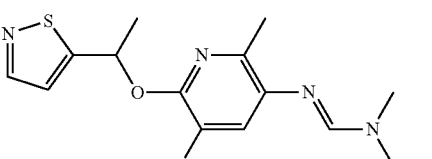 | Method 1: 11.718 min; 383 |

TABLE Q-continued
| | | LC-Method:<br>R$_t$ (min);<br>MS-ESI<br>(m/z; (M + H)$^+$) |
|---|---|---|
| Q.247 | 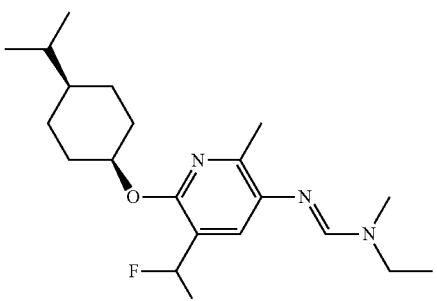 | Method 1:<br>13.430 min;<br>368; Cis |
| Q.248 | 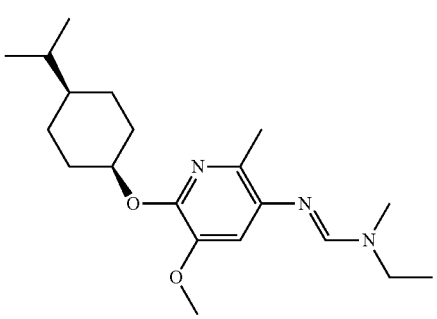 [SMILES: CCN(C)/C=N/c1cc(OC)c(O[C@H]2CC[C@@H](C(C)C)CC2)nc1C] | Method 1:<br>13.051 min;<br>348; Cis |
| Q.249 | 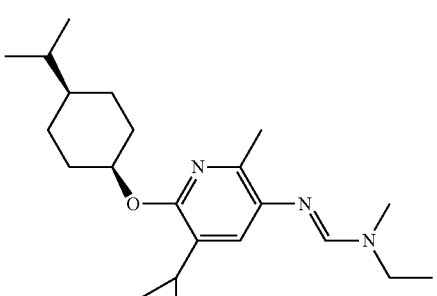 | Method 1:<br>14.416 min;<br>358; Cis |
| Q.250 | 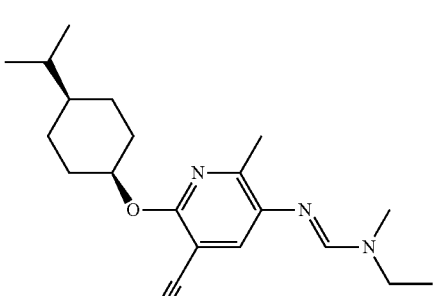 | Method 1:<br>13.413 min;<br>342; Cis |

TABLE Q-continued
| | | LC-Method: $R_t$ (min); MS-ESI (m/z; (M + H)$^+$) |
|---|---|---|
| Q.251 | 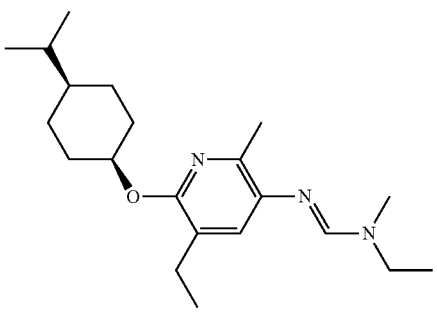 [SMILES: CCc1cc(/N=C/N(C)CC)c(C)nc1O[C@H]1CC[C@@H](C(C)C)CC1] | Method 1; 14.420 min; 346; Cis |
| Q.252 | 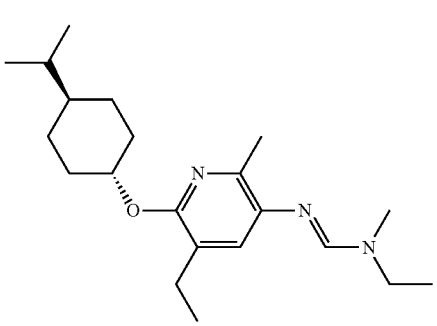 [SMILES: CCc1cc(/N=C/N(C)CC)c(C)nc1O[C@H]1CC[C@H](C(C)C)CC1] | Method 1: 13.397 min; 346; Trans |
| Q.253 | 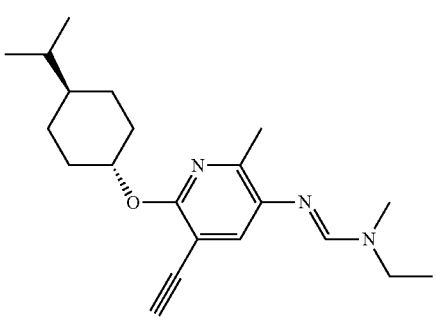 [SMILES: C#Cc1cc(/N=C/N(C)CC)c(C)nc1O[C@H]1CC[C@H](C(C)C)CC1] | Method 2: 13.397 min; 342; Trans |
| Q.254 | 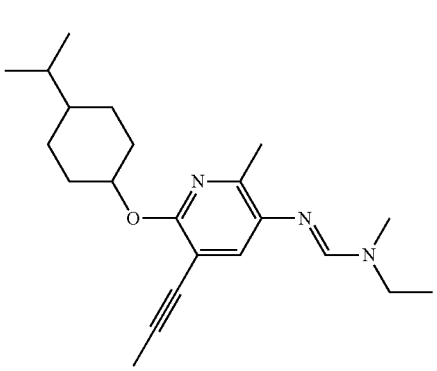 [SMILES: CC#Cc1cc(/N=C/N(C)CC)c(C)nc1OC1CCC(C(C)C)CC1] | Method 1: 13.900 min; 356 |
| Q.255 | 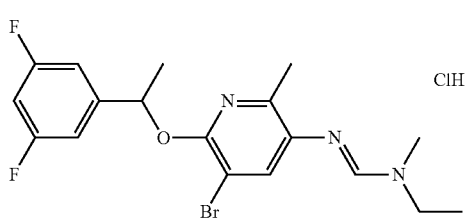 [SMILES: CCN(C)/C=N/c1cc(Br)c(OC(C)c2cc(F)cc(F)c2)nc1C ; Cl] | Mp 178-180° C. |

TABLE Q-continued

| | | LC-Method: $R_t$ (min); MS-ESI (m/z; (M + H)$^+$) |
|---|---|---|
| Q.256 | | Mp 165-168° C. |
| Q.257 | | Method 3: 1.42 min; 370 |
| Q.258 | | Method 3: 1.55 min; 412 |
| Q.259 | | Method 3: 1.68 min; 454 |
| Q.260 | | Method 3: 1.34 min; 412; (S) |
| Q.261 | | Method 3: 1.34 min; 412; (R) |

TABLE Q-continued

| | | LC-Method: R$_t$ (min); MS-ESI (m/z; (M + H)$^+$) |
|---|---|---|
| Q.262 | | Ionic liquid |
| Q.263 | | Method 3: 1.41 min; 410 |
| Q.264 | | Method 3: 1.42 min; 428 |
| Q.265 | | Method 3 1.40 min; 416 |
| Q.266 | | Method 3: 1.21 min; 411 |

TABLE Q-continued

| | | LC-Method: $R_t$ (min); MS-ESI (m/z; (M + H)$^+$) |
|---|---|---|
| Q.267 | | Method 3: 1.55 min: 452 |
| Q.268 | | Method 3: 1.52 min; 396; Trans |
| Q.269 | | Method 3: 1.43 min: 430; Cis |
| Q.270 | | Mp 111-113° C.; Trans |
| Q.271 | | Method 1: 13.010 min; 372 |

TABLE Q-continued
| | | LC-Method:<br>R$_t$ (min);<br>MS-ESI<br>(m/z; (M + H)$^+$) |
|---|---|---|
| Q.272 | 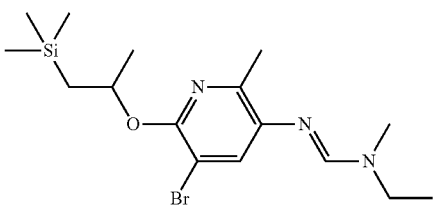 [SMILES: CCN(C)/C=N/c1cc(Br)c(OC(C)C[Si](C)(C)C)nc1C] | Method 1:<br>11.512 min;<br>386 |
| Q.273 | 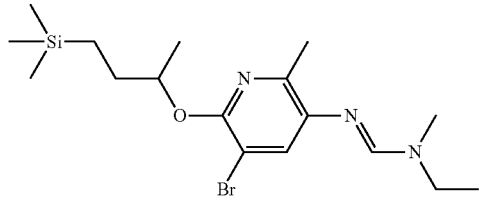 [SMILES: CCN(C)/C=N/c1cc(Br)c(OC(C)CC[Si](C)(C)C)nc1C] | Method 1:<br>14.147 min;<br>400 |
| Q.274 | 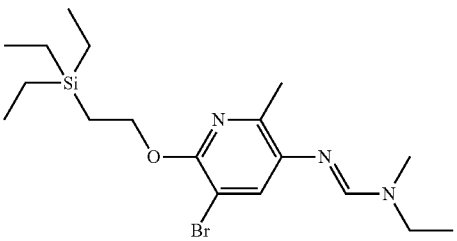 [SMILES: CCN(C)/C=N/c1cc(Br)c(OCC[Si](CC)(CC)CC)nc1C] | Method 1:<br>14.704 min;<br>414 |
| Q.275 | 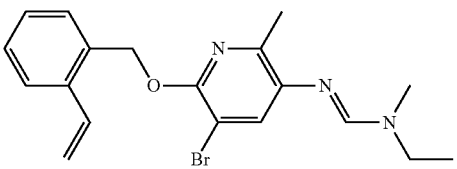 | Method 1:<br>12.441 min;<br>388 |
| Q.276 | 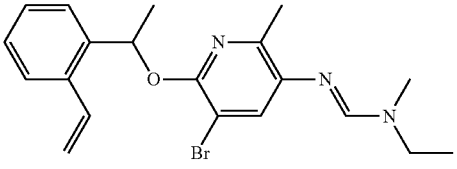 [SMILES: C=Cc1ccccc1C(C)Oc1nc(C)c(/N=C/N(C)CC)cc1Br] | Method 1:<br>12.949 min;<br>402 |
| Q.277 | 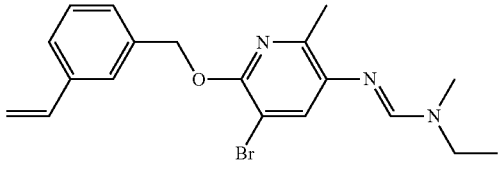 [SMILES: C=Cc1cccc(COc2nc(C)c(/N=C/N(C)CC)cc2Br)c1] | Method 1:<br>12.412 min;<br>388 |
| Q.278 | 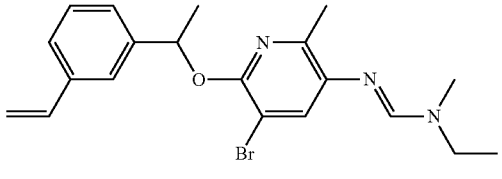 | Method 1:<br>12.930 min;<br>402 |
| Q.279 | 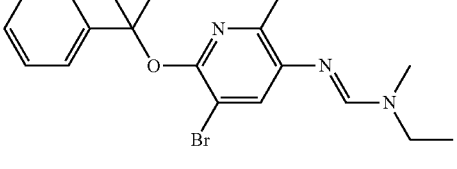 | Method 1:<br>11.765 min;<br>390 |

TABLE Q-continued
| | | LC-Method: R$_t$ (min); MS-ESI (m/z; (M + H)$^+$) |
|---|---|---|
| Q.280 | 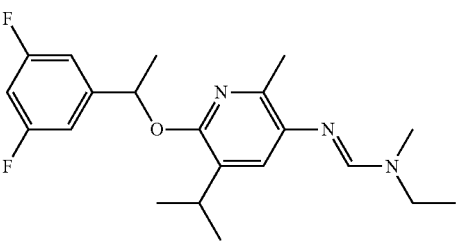 [SMILES: CCN(C)/C=N/c1cc(C(C)C)c(OC(C)c2cc(F)cc(F)c2)nc1C] | Method 1: 13.223 min; 376 |
| Q.281 | 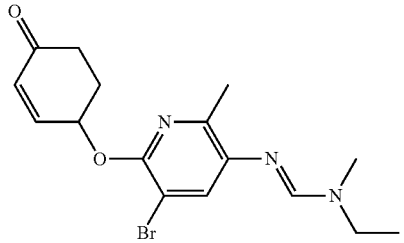 | Method 1: 9.144 min; 366 |
| Q.282 | 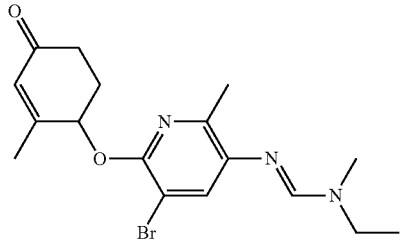 [SMILES: CCN(C)/C=N/c1cc(Br)c(OC2CCC(=O)C=C2C)nc1C] | Method 1: 9.411 min; 380 |
| Q.283 | 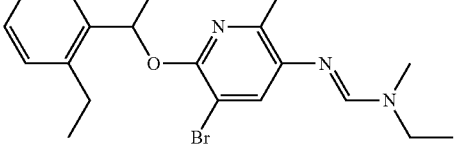 | Method 1: 13.076 min; 404 |
| Q.284 | 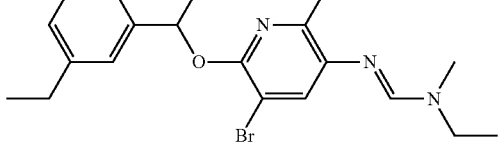 | Method 1: 13.397 min; 404 |
| Q.285 | 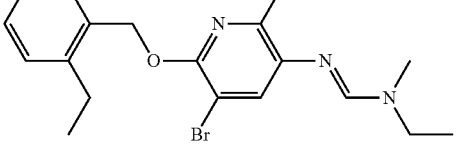 | Method 1: 12.345 min; 390 |
| Q.286 | 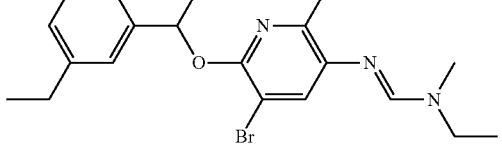 | Method 1: 12.464 min; 390 |

TABLE Q-continued

| | | LC-Method: $R_t$ (min); MS-ESI (m/z; (M + H)$^+$) |
|---|---|---|
| Q.287 | | Method 1: 13.376 min; 418 |
| Q.288 | | Method 2: 12.056 min; 354 |
| Q.289 | | Method 1: 11.736 min; 412 |
| Q.290 | | Mp 81-85° C. |
| Q.291 | | Method 1: 11.782 min; 408 |
| Q.292 | | Method 1: 12.318 min; 422 |
| Q.293 | | Method 1: 12.503 min; 366 |

TABLE Q-continued
| | | LC-Method:<br>R<sub>t</sub> (min);<br>MS-ESI<br>(m/z; (M + H)<sup>+</sup>) |
|---|---|---|
| Q.294 | 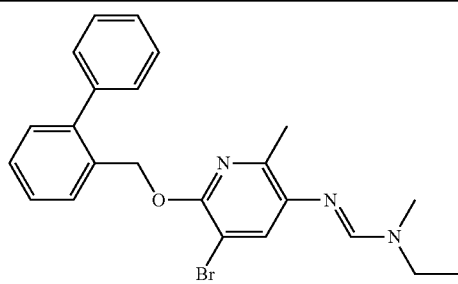 | Method 1:<br>13.526 min;<br>438 |
| Q.295 | 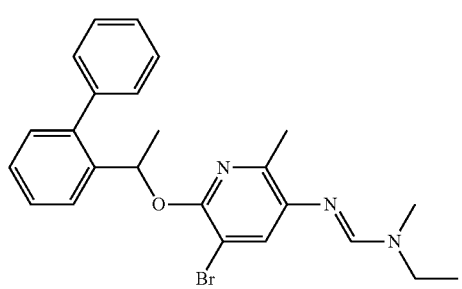 [SMILES: CCN(C)/C=N/c1cc(Br)c(OC(C)c2ccccc2-c2ccccc2)nc1C] | Mp 59-62° C. |
| Q.296 | 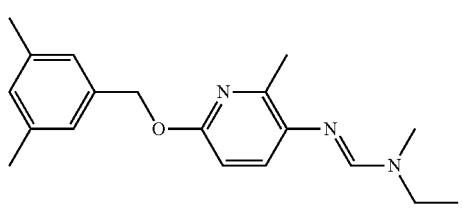 [SMILES: CCN(C)/C=N/c1ccc(OCc2cc(C)cc(C)c2)nc1C] | Method 1:<br>11.641 min;<br>312 |
| Q.297 | 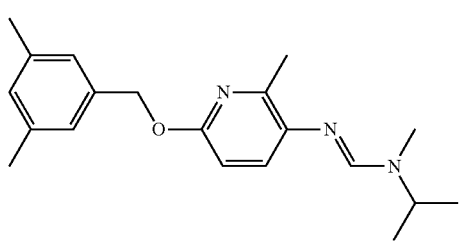 [SMILES: Cc1cc(C)cc(COc2ccc(/N=C/N(C)C(C)C)c(C)n2)c1] | Method 1:<br>11.974 min;<br>326 |
| Q.298 | 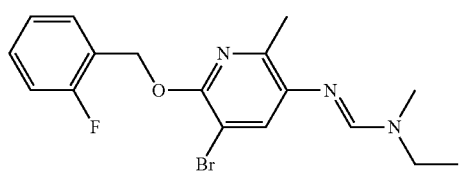 | Mp 57-61° C. |
| Q.299 | 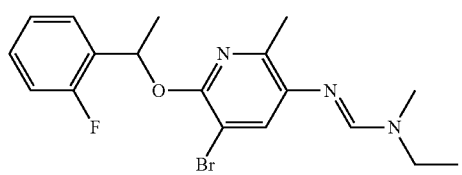 | Method 1:<br>12.313 min;<br>394 |
| Q.300 | 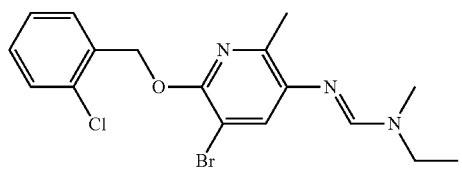 | Mp 53-56° C. |

TABLE Q-continued
| | | LC-Method:<br>$R_t$ (min);<br>MS-ESI<br>(m/z; (M + H)+) |
|---|---|---|
| Q.301 | 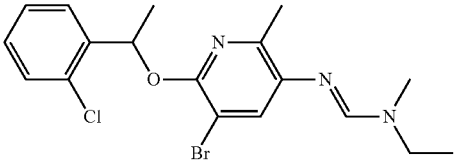 | Method 1:<br>12.908 min;<br>410 |
| Q.302 | 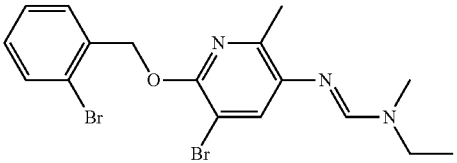 [SMILES: CCN(C)/C=N/c1cc(Br)c(OCc2ccccc2Br)nc1C] | Method 1:<br>12.267 min;<br>440 |
| Q.303 | 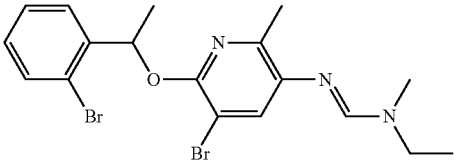 | Method 1:<br>12.897 min;<br>454 |
| Q.304 | 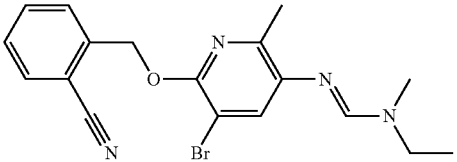 [SMILES: CCN(C)/C=N/c1cc(Br)c(OCc2ccccc2C#N)nc1C] | Mp 82-86° C. |
| Q.305 | 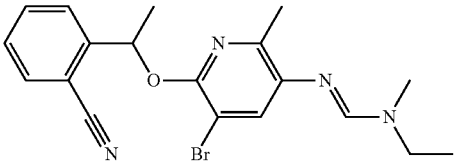 | Mp 77-81° C. |
| Q.306 | 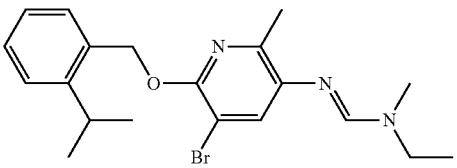 [SMILES: CCN(C)/C=N/c1cc(Br)c(OCc2ccccc2C(C)C)nc1C] | Method 1:<br>12.789 min;<br>404 |
| Q.307 | 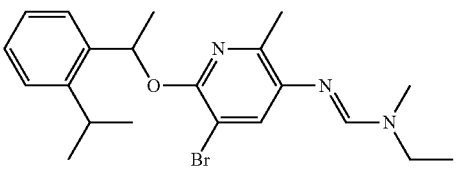 | Method 1:<br>13.266 min;<br>418 |
| Q.308 | 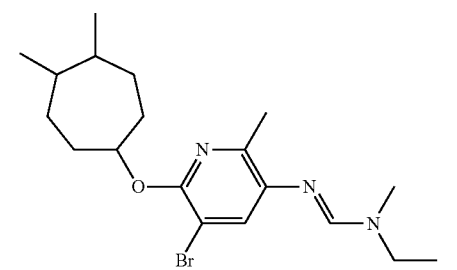 [SMILES: CCN(C)/C=N/c1cc(Br)c(OC2CCC(C)C(C)CC2)nc1C] | Method 1:<br>13.998 min;<br>396 |

TABLE Q-continued

| | | LC-Method: R_t (min); MS-ESI (m/z; (M + H)+) |
|---|---|---|
| Q.309 | | Method 1: 13.324 min; 466 |
| Q.310 | | Method 1: 13.568 min; 462 |
| Q.311 | | Method 1: 13.806 min; 462 |
| Q.312 | | Method 1: 14.266 min; 476 |
| Q.313 | | Method 1: 14.120 min; 476 |

TABLE Q-continued
| | LC-Method: $R_t$ (min); MS-ESI (m/z; (M + H)$^+$) |
|---|---|
| Q.314 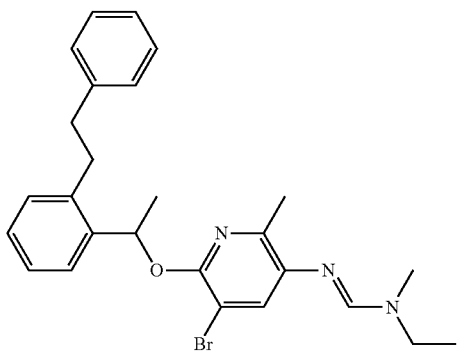 | Method 1: 14.042 min; 480 |
| Q.315 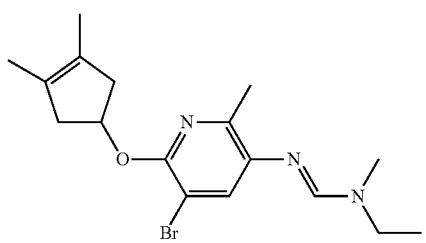 | Method 1: 12.395 min; 366 |
| Q.316 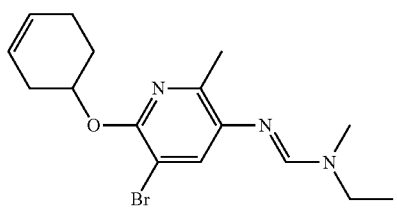 | Method 1: 7.382 min; 352 |
| Q.317 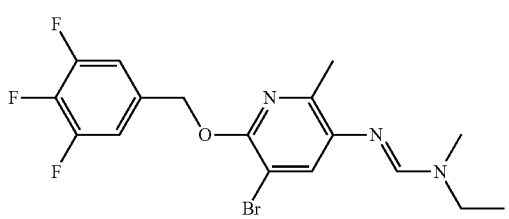 | Mp 78-81° C. |
| Q.318 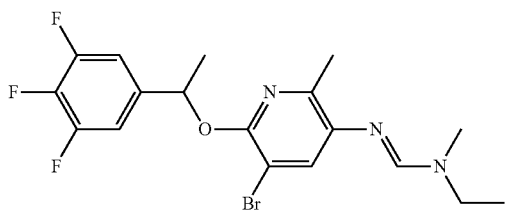 | Method 1: 12.537 min; 430 |
| Q.319 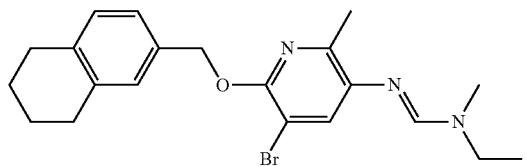 | Method 1: 13.594 min; 416 |

TABLE Q-continued

| | | LC-Method: R$_t$ (min); MS-ESI (m/z; (M + H)$^+$) |
|---|---|---|
| Q.320 | | Mp 27-30° C. |
| Q.321 | | Method 1: 12.591 min; 390 |
| Q.322 | | Mp 67-68° C. |
| Q.323 | | Mp 83-84° C. |
| Q.324 | | Method 1: 12.813 min; 390 |
| Q.325 | | Mp 56-57° C. |
| Q.326 | | Mp 61-62° C. |
| Q.327 | | Method 1: 13.121 min; 426 |

TABLE Q-continued
| | | LC-Method: $R_t$ (min); MS-ESI (m/z; (M + H)$^+$) |
|---|---|---|
| Q.328 | 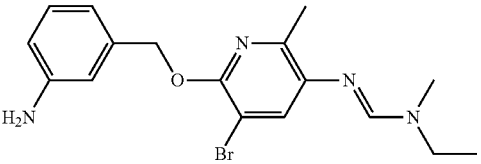 [SMILES: CCN(C)/C=N/c1cc(Br)c(OCc2cccc(N)c2)nc1C] | Liquid |
| Q.329 | 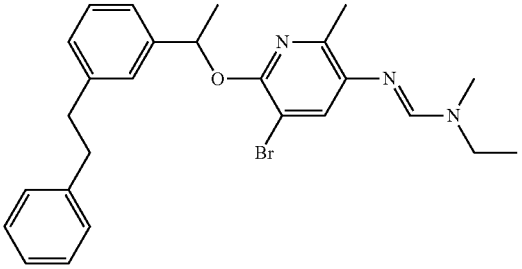 [SMILES: CCN(C)/C=N/c1cc(Br)c(OC(C)c2cccc(CCc3ccccc3)c2)nc1C] | Method 1: 14.077 min; 480 |
| Q.330 | 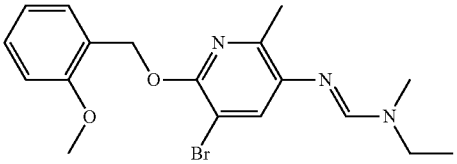 [SMILES: CCN(C)/C=N/c1cc(Br)c(OCc2ccccc2OC)nc1C] | Method 1: 11.439 min; 392 |
| Q.331 | 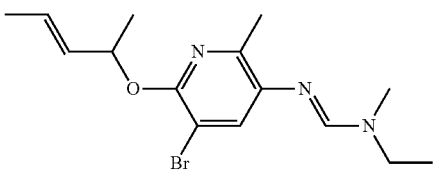 | Method 1: 11.711 min; 340 |
| Q.332 | 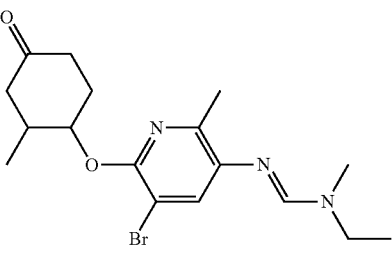 [SMILES: CCN(C)/C=N/c1cc(Br)c(OC2CCC(=O)CC2C)nc1C] | Method 1: 9.781 min; 382; Isomer 1 |
| Q.333 | 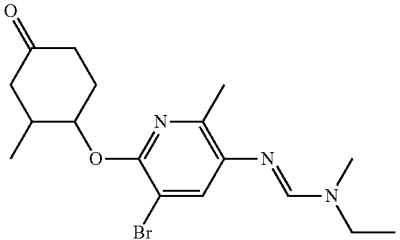 | Method 1: 9.758 min; 382 Isomer 2 |

TABLE Q-continued

| | | LC-Method: $R_t$ (min); MS-ESI (m/z; (M + H)$^+$) |
|---|---|---|
| Q.334 | | Method 6: 0.92 min; 396 |
| Q.335 | | Method 1: 11.804 min; 408 |
| Q.336 | | Method 1: 8.965 min; 424 |
| Q.337 | | Mp 104-108° C. |
| Q.338 | | Method 1: 10.918 min; 331 |
| Q.339 | | Method 1: 11.312 min; 344 |
| Q.340 | | Method 1: 12.292 min; 366 |

TABLE Q-continued

| | | LC-Method: R$_t$ (min); MS-ESI (m/z; (M + H)$^+$) |
|---|---|---|
| Q.341 | | Method 1: 11.200 min; 290 |
| Q.342 | | Method 1: 11.930 min; 304 |
| Q.343 | | Method 1: 14.959 min; 360 |
| Q.344 | | Method 1: 13.527 min; 418 |
| Q.345 | | Method 1: 12.808 min; 404 |
| Q.346 | | Method 1: 13.160 min; 404 |
| Q.347 | | Method 1: 11.431 min; 312 |

TABLE Q-continued
| | | LC-Method: R$_t$ (min); MS-ESI (m/z; (M + H)$^+$) |
|---|---|---|
| Q.348 | 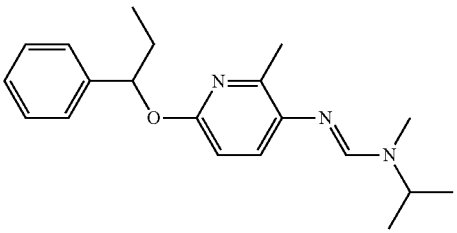 [SMILES: CCC(Oc1ccc(/N=C/N(C)C(C)C)c(C)n1)c1ccccc1] | Method 1: 11.698 min; 326 |
| Q.349 | 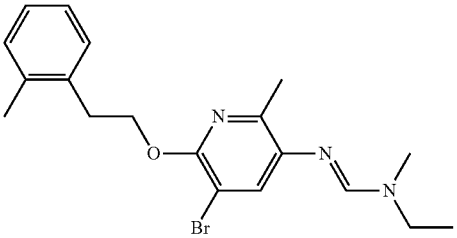 [SMILES: CCN(C)/C=N/c1cc(Br)c(OCCc2ccccc2C)nc1C] | Method 1: 12.595 min; 390 |
| Q.350 | 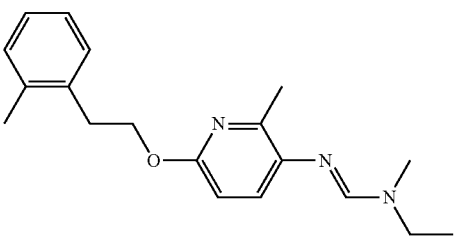 [SMILES: CCN(C)/C=N/c1ccc(OCCc2ccccc2C)nc1C] | Method 1: 11.248 min; 312 |
| Q.351 | 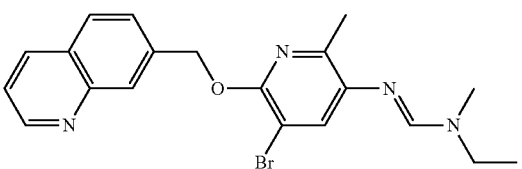 [SMILES: CCN(C)/C=N/c1cc(Br)c(OCc2ccc3cccnc3c2)nc1C] | Mp 110-114° C. |
| Q.352 | 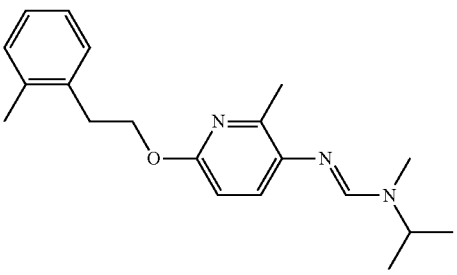 [SMILES: Cc1ccccc1CCOc1ccc(/N=C/N(C)C(C)C)c(C)n1] | Method 1: 11.715 min; 326 |
| Q.353 | 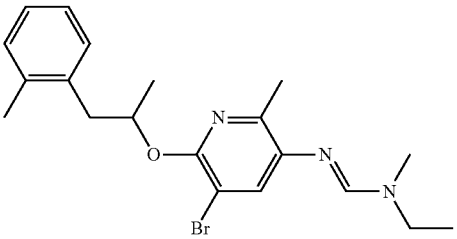 [SMILES: CCN(C)/C=N/c1cc(Br)c(OC(C)Cc2ccccc2C)nc1C] | Method 1: 12.754 min; 404 |

TABLE Q-continued
| | | LC-Method:<br>R$_t$ (min);<br>MS-ESI<br>(m/z; (M + H)$^+$) |
|---|---|---|
| Q.354 | 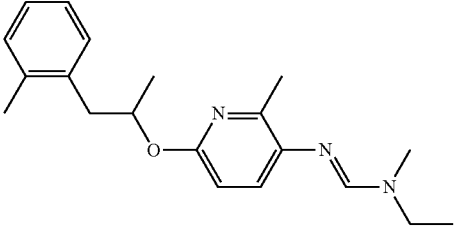 [SMILES: CCN(C)/C=N/c1ccc(OC(C)Cc2ccccc2C)nc1C] | Method 1:<br>11.787 min;<br>326 |
| Q.355 | 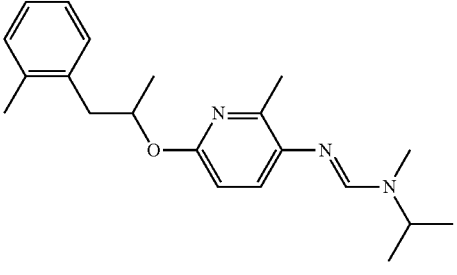 [SMILES: Cc1ccccc1CC(C)Oc1ccc(/N=C/N(C)C(C)C)c(C)n1] | Method 1:<br>12.370 min;<br>340 |
| Q.356 | 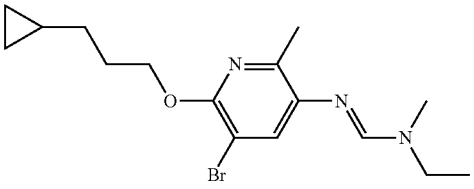 [SMILES: CCN(C)/C=N/c1cc(Br)c(OCCCC2CC2)nc1C] | Method 1:<br>12.096 min;<br>354 |
| Q.357 | 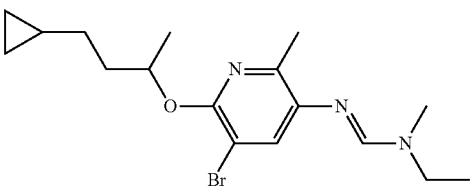 [SMILES: CCN(C)/C=N/c1cc(Br)c(OC(C)CCC2CC2)nc1C] | Method 1:<br>12.656 min;<br>368 |
| Q.358 | 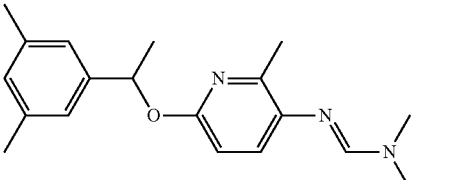 | Method 1:<br>11.887 min;<br>326 |
| Q.359 | 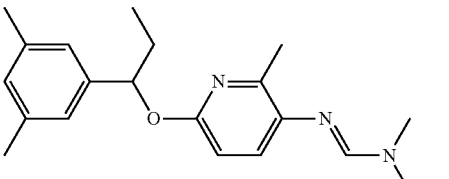 | Method 1:<br>12.700 min;<br>340 |

TABLE Q-continued
| | | LC-Method: $R_t$ (min); MS-ESI (m/z; (M + H)$^+$) |
|---|---|---|
| Q.360 | 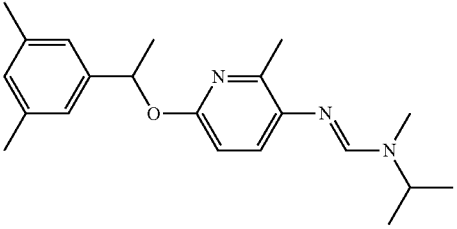 [SMILES: Cc1cc(C)cc(C(C)Oc2ccc(/N=C/N(C)C(C)C)c(C)n2)c1] | Method 1: 12.328 min; 340 |
| Q.361 | 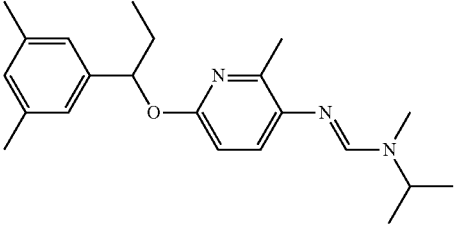 [SMILES: CCC(Oc1ccc(/N=C/N(C)C(C)C)c(C)n1)c1cc(C)cc(C)c1] | Method 1: 12.882 min; 354 |
| Q.362 | 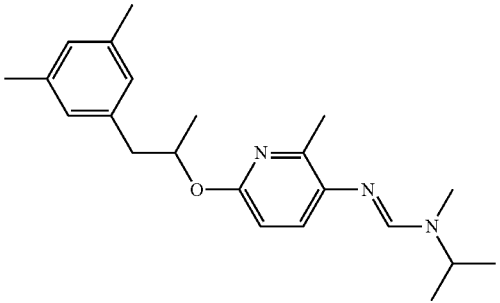 [SMILES: Cc1cc(C)cc(CC(C)Oc2ccc(/N=C/N(C)C(C)C)c(C)n2)c1] | Method 1: 15.320 min; 354 |
| Q.363 | 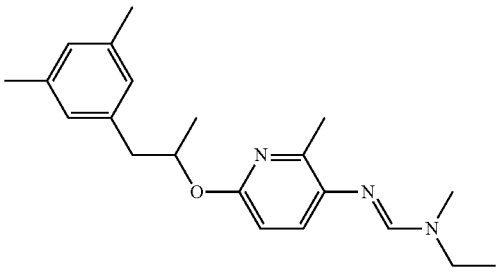 [SMILES: CCN(C)/C=N/c1ccc(OC(C)Cc2cc(C)cc(C)c2)nc1C] | Method 1: 12.506 min; 341 |
| Q.364 | 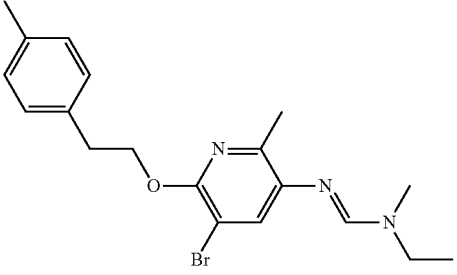 [SMILES: CCN(C)/C=N/c1cc(Br)c(OCCc2ccc(C)cc2)nc1C] | Method 1: 12.385 min; 390 |

TABLE Q-continued
| | | LC-Method: R$_t$ (min); MS-ESI (m/z; (M + H)$^+$) |
|---|---|---|
| Q.365 | 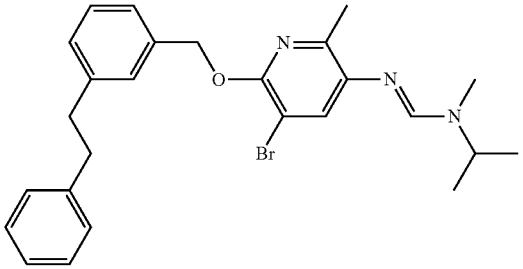 [SMILES: Cc1nc(OCc2cccc(CCc3ccccc3)c2)c(Br)cc1/N=C/N(C)C(C)C] | Method 1: 13.743 min; 466 |
| Q.366 | 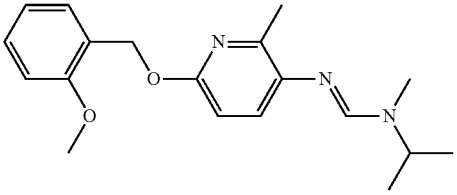 [SMILES: COc1ccccc1COc1ccc(/N=C/N(C)C(C)C)c(C)n1] | Method 1: 10.775 min; 328 |
| Q.367 | 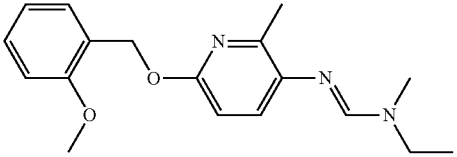 | Method 1: 10.377 min; 314 |
| Q.368 | 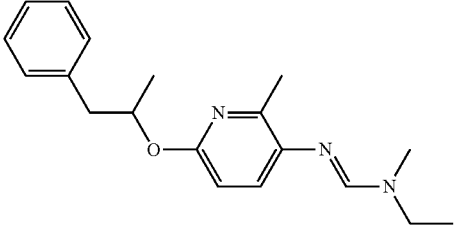 [SMILES: CCN(C)/C=N/c1ccc(OC(C)Cc2ccccc2)nc1C] | Method 1: 11.191 min; 312 |
| Q.369 | 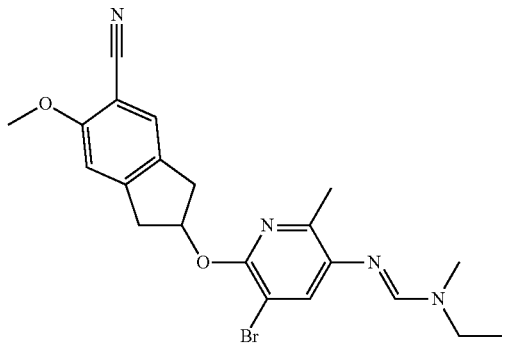 [SMILES: CCN(C)/C=N/c1cc(Br)c(OC2Cc3cc(C#N)c(OC)cc3C2)nc1C] | Mp 120-121° C. |
| Q.370 | 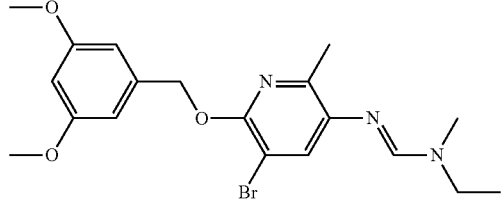 [SMILES: CCN(C)/C=N/c1cc(Br)c(OCc2cc(OC)cc(OC)c2)nc1C] | Method 1: 11.282 min; 423 |

TABLE Q-continued

| | | LC-Method: R$_t$ (min); MS-ESI (m/z; (M + H)$^+$) |
|---|---|---|
| Q.371 | | Method 1: 11.875 min; 272 |
| Q.372 | | Method 1: 10.334 min; 344 |
| Q.373 | | Method 1: 10.676 min; 358 |
| Q.374 | | Method 1: 11.096 min; 372 |
| Q.375 | | Method 1: 11.418 min; 390 |
| Q.376 | | Method 1: 11.717 min; 413 |

TABLE Q-continued
| | | LC-Method: R_t (min); MS-ESI (m/z; (M + H)+) |
|---|---|---|
| Q.377 | 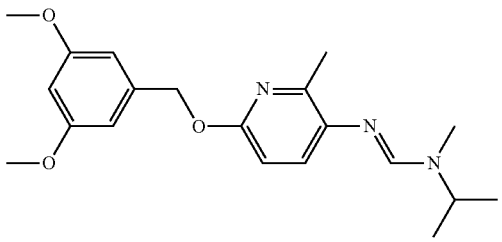 [SMILES: COc1cc(COc2ccc(/N=C/N(C)C(C)C)c(C)n2)cc(OC)c1] | Method 1: 10.791 min; 358 |
| Q.378 | 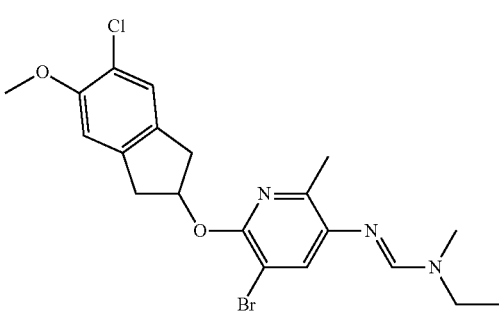 [SMILES: CCN(C)/C=N/c1cc(Br)c(OC2Cc3cc(Cl)c(OC)cc3C2)nc1C] | Method 1: 12.258 min; 452 |
| Q.379 | 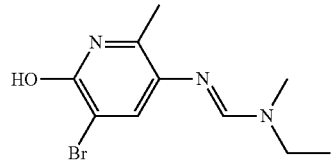 | Mp 168-170° C. |
| Q.380 | 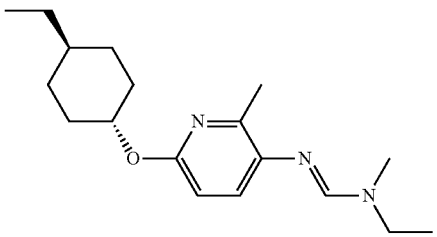 [SMILES: CCN(C)/C=N/c1ccc(O[C@H]2CC[C@H](CC)CC2)nc1C] | Method 1: 12.229 min; 304; Trans |
| Q.381 | 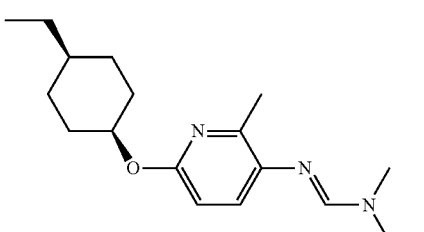 | Method 1: 12.388 min; 305; Cis |
| Q.382 | 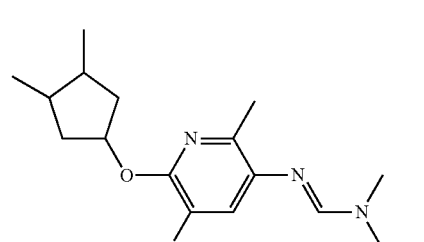 | Method 1: 12.998 min; 368 |

TABLE Q-continued
| | | LC-Method: $R_t$ (min); MS-ESI (m/z; (M + H)⁺) |
|---|---|---|
| Q.383 | 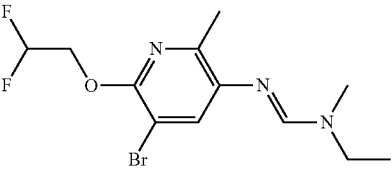 | Method 6: 0.61 min; 336 |
| Q.384 | 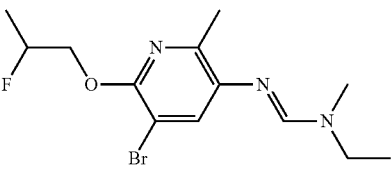 [SMILES: CCN(C)/C=N/c1cc(Br)c(OCC(C)F)nc1C] | Method 6: 0.67 min; 332 |
| Q.385 | 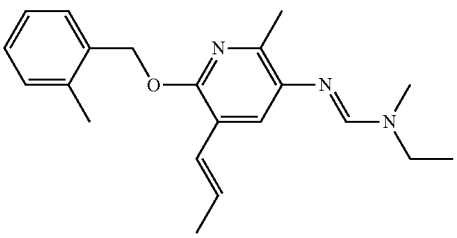 [SMILES: C/C=C/c1cc(/N=C/N(C)CC)c(C)nc1OCc1ccccc1C] | Method 3: 1.34 min; 338 |
| Q.386 | 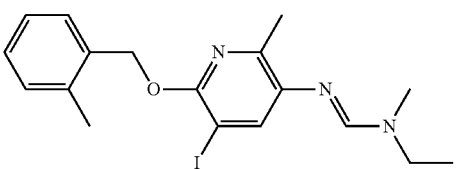 [SMILES: CCN(C)/C=N/c1cc(I)c(OCc2ccccc2C)nc1C] | Method 3: 1.34 min; 424 |
| Q.387 | 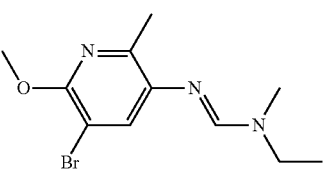 [SMILES: CCN(C)/C=N/c1cc(Br)c(OC)nc1C] | Method 6: 0.55 min; 286 |
| Q.388 | 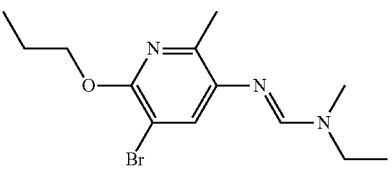 [SMILES: CCCOc1nc(C)c(/N=C/N(C)CC)cc1Br] | Method 6: 0.73 min; 314 |
| Q.389 | 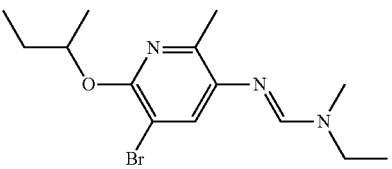 | Method 6: 0.79 min; 328 |
| Q.390 | 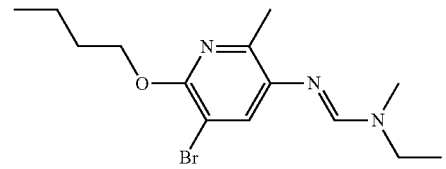 | Method 6: 0.79 min; 328 |

TABLE Q-continued
| | | LC-Method: $R_t$ (min); MS-ESI (m/z; (M + H)$^+$) |
|---|---|---|
| Q.391 | 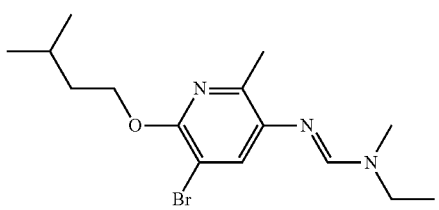 | Method 6: 0.83 min; 342 |
| Q.392 | 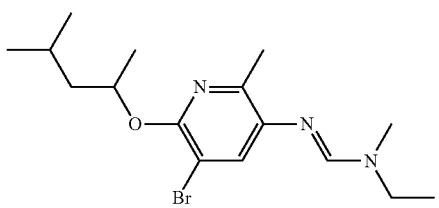 [SMILES: CCN(C)/C=N/c1cc(Br)c(OC(C)CC(C)C)nc1C] | Method 6: 0.88 min; 356 |
| Q.393 | 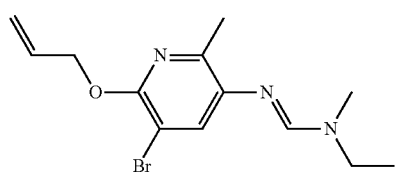 [SMILES: C=CCOc1nc(C)c(/N=C/N(C)CC)cc1Br] | Method 6: 0.69 min; 312 |
| Q.394 | 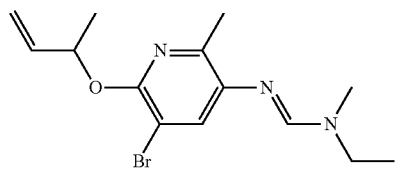 [SMILES: C=CC(C)Oc1nc(C)c(/N=C/N(C)CC)cc1Br] | Method 6: 0.76 min; 326 |
| Q.395 | 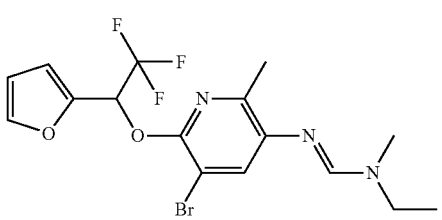 [SMILES: CCN(C)/C=N/c1cc(Br)c(OC(c2ccco2)C(F)(F)F)nc1C] | Method 6: 0.79 min; 420 |
| Q.396 | 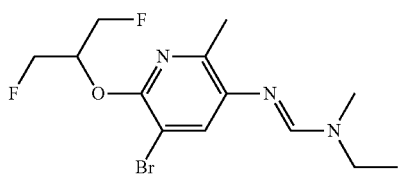 [SMILES: CCN(C)/C=N/c1cc(Br)c(OC(CF)CF)nc1C] | Method 6: 0.60 min; 350 |
| Q.397 | 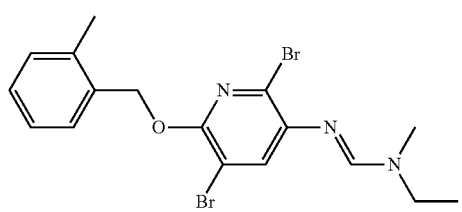 [SMILES: CCN(C)/C=N/c1cc(Br)c(OCc2ccccc2C)nc1Br] | Method 6: 0.93 min; 442 |

TABLE Q-continued
| | | LC-Method: $R_t$ (min); MS-ESI (m/z; (M + H)$^+$) |
|---|---|---|
| Q.398 | 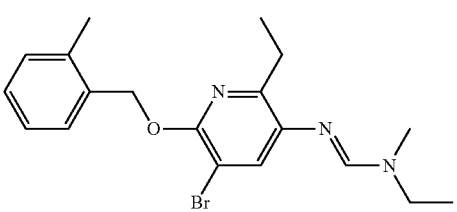 | Method 6: 0.86 min; 392 |
| Q.399 | 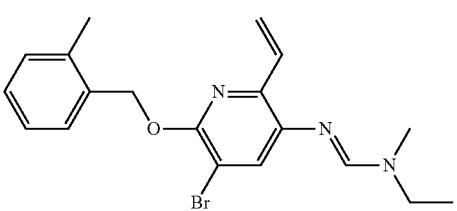 [SMILES: C=Cc1nc(OCc2ccccc2C)c(Br)cc1/N=C/N(C)CC] | Method 6: 0.89 min; 390 |
| Q.400 | 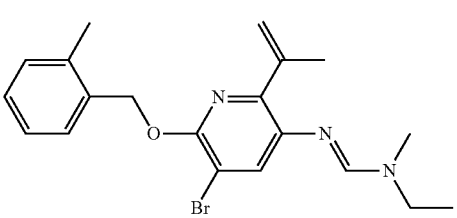 [SMILES: C=C(C)c1nc(OCc2ccccc2C)c(Br)cc1/N=C/N(C)CC] | Method 6: 0.83 min; 404 |
| Q.401 | 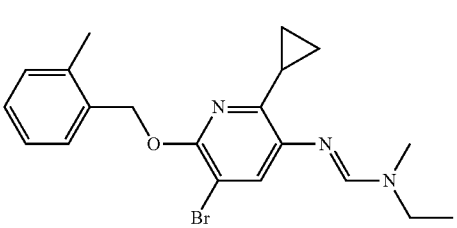 [SMILES: CCN(C)/C=N/c1cc(Br)c(OCc2ccccc2C)nc1C1CC1] | Method 6: 0.89 min; 404 |
| Q.402 | 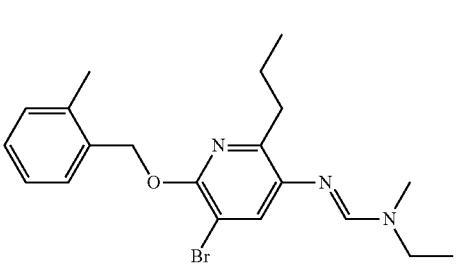 [SMILES: CCCc1nc(OCc2ccccc2C)c(Br)cc1/N=C/N(C)CC] | Method 6: 0.88 min; 406 |
| Q.403 | 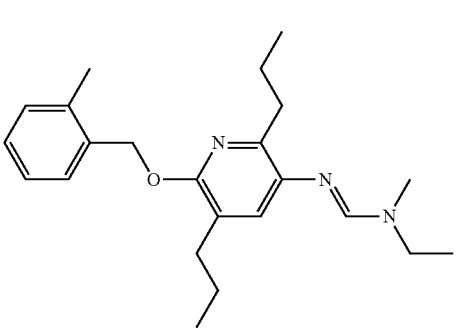 [SMILES: CCCc1cc(/N=C/N(C)CC)c(CCC)nc1OCc1ccccc1C] | Method 6: 0.99 min; 369 |

TABLE Q-continued

| | | LC-Method: R$_t$ (min); MS-ESI (m/z; (M + H)$^+$) |
|---|---|---|
| Q.404 | [structure] | Method 6: 0.92 min; 406 |
| Q.405 | [structure] | Method 6: 0.54 min; 334 |
| Q.406 | [structure] | Method 1: 8.584 min; 396 |
| Q.407 | [structure] | Method 1: 12.363 min; 392 |
| Q.408 | [structure] | Method 1: 12.632 min; 319; Trans |
| Q.409 | [structure] | Method 1: 12.533 min; 319; Cis |

TABLE Q-continued
| | | LC-Method:<br>R_t (min);<br>MS-ESI<br>(m/z; (M + H)+) |
|---|---|---|
| Q.410 | 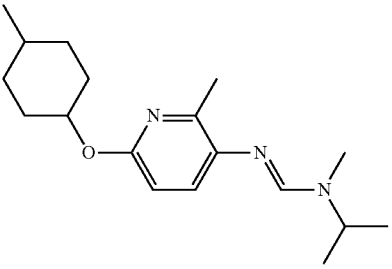 [SMILES: Cc1nc(OC2CCC(C)CC2)ccc1/N=C/N(C)C(C)C] | Method 1:<br>11.796 min;<br>304 |
| Q.411 | 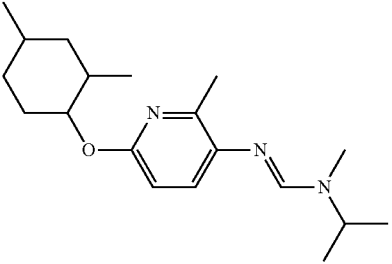 [SMILES: Cc1nc(OC2CCC(C)CC2C)ccc1/N=C/N(C)C(C)C] | Method 1:<br>12.661 min;<br>318 |
| Q.412 | 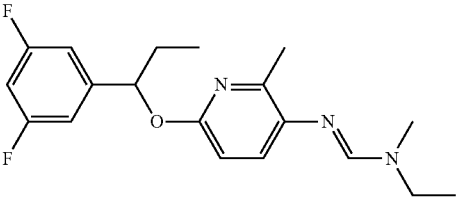 [SMILES: CCC(Oc1ccc(/N=C/N(C)CC)c(C)n1)c1cc(F)cc(F)c1] | Method 1:<br>14.132 min;<br>348 |
| Q.413 | 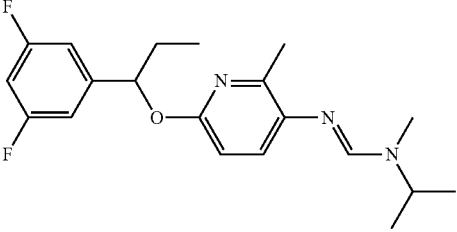 [SMILES: CCC(Oc1ccc(/N=C/N(C)C(C)C)c(C)n1)c1cc(F)cc(F)c1] | Method 1:<br>14.531 min;<br>362 |
| Q.414 | 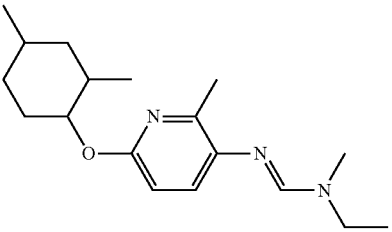 [SMILES: CCN(C)/C=N/c1ccc(OC2CCC(C)CC2C)nc1C] | Method 1:<br>12.019 min;<br>304 |
| Q.415 | 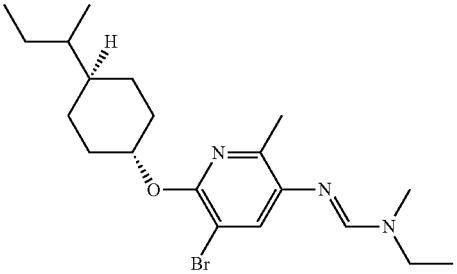 [SMILES: CCC(C)[C@H]1CC[C@H](Oc2nc(C)c(/N=C/N(C)CC)cc2Br)CC1] | Mp 81-83° C. |

TABLE Q-continued

| | | LC-Method:<br>R$_t$ (min);<br>MS-ESI<br>(m/z; (M + H)$^+$) |
|---|---|---|
| Q.416 | | Method 1:<br>14.621 min;<br>410 |
| Q.417 | | Method 1:<br>15.162 min;<br>404 |
| Q.418 | | Method 1:<br>14.413 min;<br>340 |
| Q.419 | | Method 1:<br>13.860 min;<br>326 |
| Q.420 | | Method 1:<br>13.191 min;<br>418 |
| Q.421 | | Method 1:<br>12.542 min;<br>354 |

TABLE Q-continued
| | | LC-Method: $R_t$ (min); MS-ESI (m/z; (M + H)$^+$) |
|---|---|---|
| Q.422 | 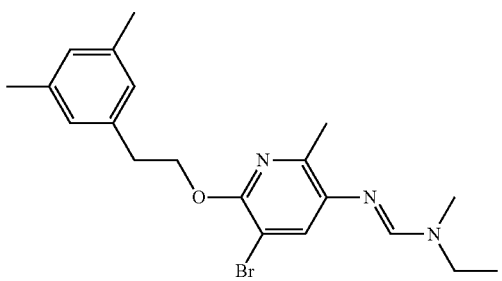 [SMILES: CCN(C)/C=N/c1cc(Br)c(OCCc2cc(C)cc(C)c2)nc1C] | Mp 61-63° C. |
| Q.423 | 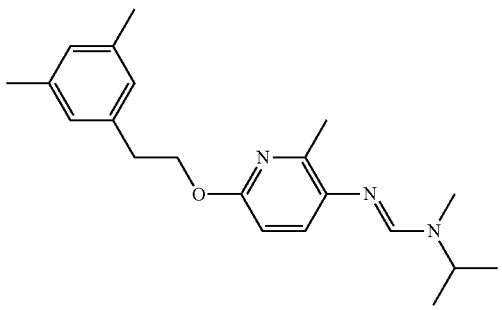 [SMILES: Cc1cc(C)cc(CCOc2ccc(/N=C/N(C)C(C)C)c(C)n2)c1] | Method 1: 12.785 min; 340 |
| Q.424 | 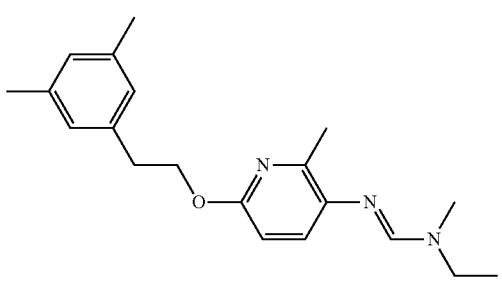 [SMILES: CCN(C)/C=N/c1ccc(OCCc2cc(C)cc(C)c2)nc1C] | Method 1: 12.041 min; 326 |
| Q.425 | 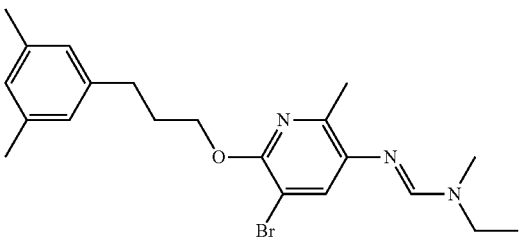 [SMILES: CCN(C)/C=N/c1cc(Br)c(OCCCc2cc(C)cc(C)c2)nc1C] | Method 1: 13.378 min; 418 |
| Q.426 | 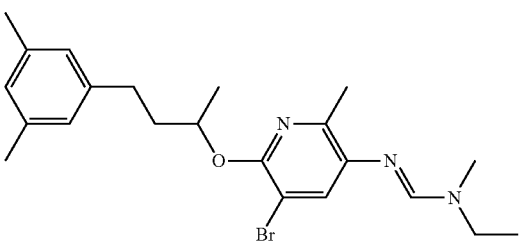 [SMILES: CCN(C)/C=N/c1cc(Br)c(OC(C)CCc2cc(C)cc(C)c2)nc1C] | Method 1: 13.958 min; 432 |

TABLE Q-continued
| | | LC-Method: $R_t$ (min); MS-ESI (m/z; (M + H)$^+$) |
|---|---|---|
| Q.427 | 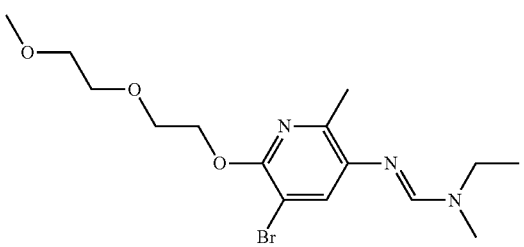 [SMILES: CCN(C)/C=N/c1cc(Br)c(OCCOCCOC)nc1C] | Method 1: 8.845 min; 374 |
| Q.428 | 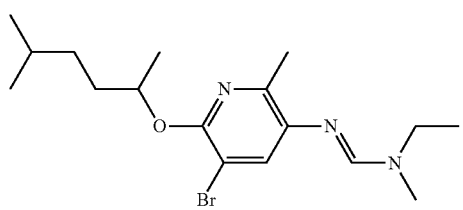 [SMILES: CCN(C)/C=N/c1cc(Br)c(OC(C)CCC(C)C)nc1C] | Method 1: 13.142 min; 370 |
| Q.429 | 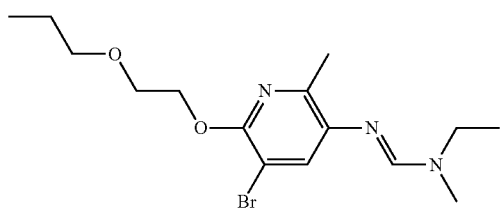 [SMILES: CCCOCCOc1nc(C)c(/N=C/N(C)CC)cc1Br] | Method 1: 10.416 min; 358 |
| Q.430 | 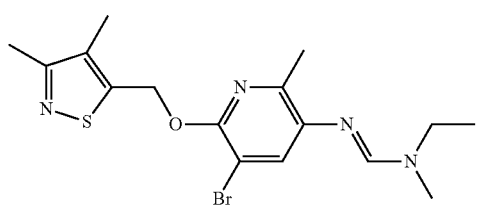 [SMILES: CCN(C)/C=N/c1cc(Br)c(OCc2snc(C)c2C)nc1C] | Mp 122-124° C. |
| Q.431 | 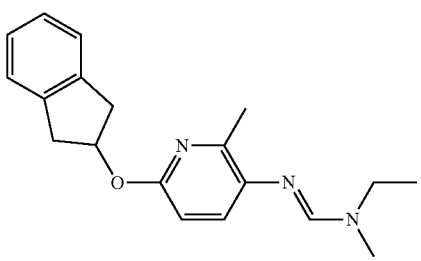 [SMILES: CCN(C)/C=N/c1ccc(OC2Cc3ccccc3C2)nc1C] | Method 1: 10.943 min; 310 |
| Q.432 | 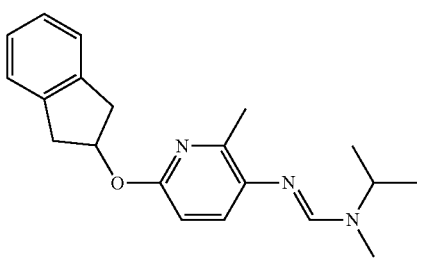 [SMILES: Cc1nc(OC2Cc3ccccc3C2)ccc1/N=C/N(C)C(C)C] | Method 1: 11.341 min; 324 |

TABLE Q-continued

| | | LC-Method: R_t (min); MS-ESI (m/z; (M + H)+) |
|---|---|---|
| Q.433 | | Method 1: 12.746 min; 356 |
| Q.434 | | Method 1: 10.964 min; 278 |
| Q.435 | | Method 1: 10.497 min; 264 |
| Q.436 | | Method 1: 12.277 min; 390 |
| Q.437 | | Method 1: 12.606 min; 368 |
| Q.438 | | Method 1: 9.727 min; 370 |
| Q.439 | | Method 1: 12.860 min; 404 |

TABLE Q-continued
| | | LC-Method: $R_t$ (min); MS-ESI (m/z; (M + H)$^+$) |
|---|---|---|
| Q.440 | 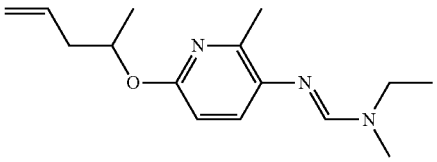 | Method 1: 10.054 min; 262 |
| Q.441 | 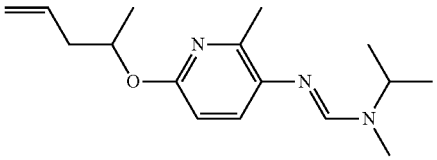 [SMILES: C=CCC(C)Oc1ccc(/N=C/N(C)C(C)C)c(C)n1] | Method 1: 12.781 min; 276 |
| Q.442 | 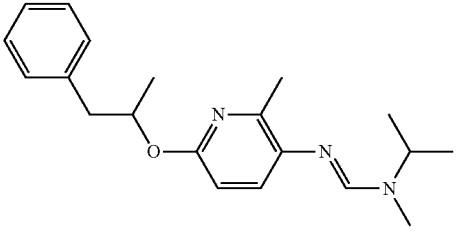 [SMILES: Cc1nc(OC(C)Cc2ccccc2)ccc1/N=C/N(C)C(C)C] | Method 1: 13.922 min; 326 |
| Q.443 | 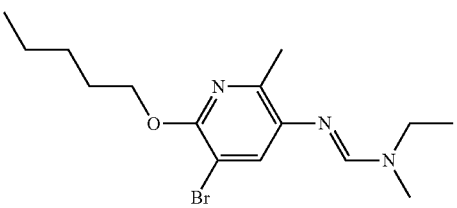 [SMILES: CCCCCOc1nc(C)c(/N=C/N(C)CC)cc1Br] | Method 1: 12.141 min; 342 |
| Q.444 | 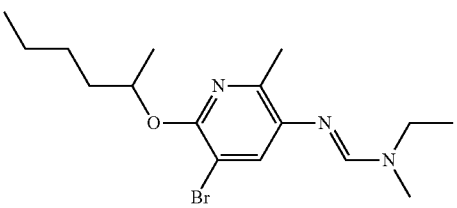 [SMILES: CCCCC(C)Oc1nc(C)c(/N=C/N(C)CC)cc1Br] | Method 1: 12.715 min; 356 |
| Q.445 | 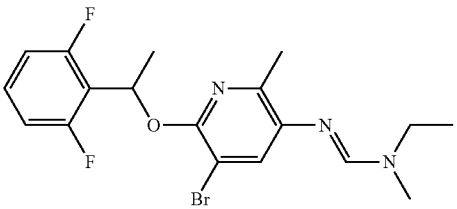 [SMILES: CCN(C)/C=N/c1cc(Br)c(OC(C)c2c(F)cccc2F)nc1C] | Method 1: 11.909 min; 412 |
| Q.446 | 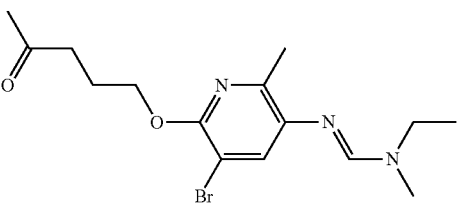 [SMILES: CCN(C)/C=N/c1cc(Br)c(OCCCC(C)=O)nc1C] | Method 1: 9.174 min; 356 |

TABLE Q-continued
| | | LC-Method:<br>R$_t$ (min);<br>MS-ESI<br>(m/z; (M + H)$^+$) |
|---|---|---|
| Q.447 | 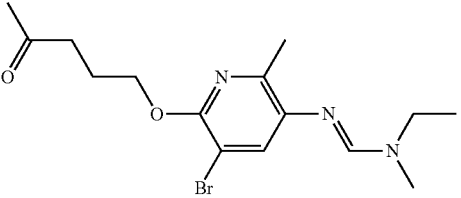 [SMILES: CCN(C)/C=N/c1cc(Br)c(OCCCC(C)=O)nc1C] | Method 1:<br>9.174 min;<br>356 |
| Q.448 | 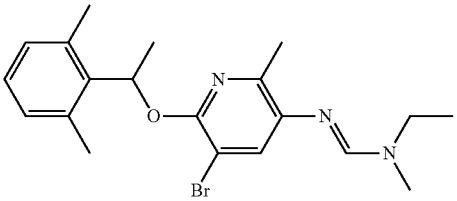 [SMILES: CCN(C)/C=N/c1cc(Br)c(OC(C)c2c(C)cccc2C)nc1C] | Mp 106-107° C. |
| Q.449 | 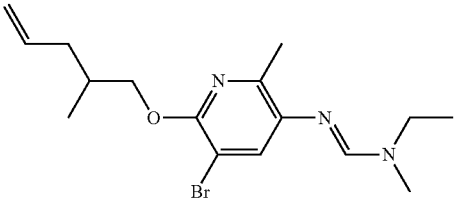 [SMILES: C=CCC(C)COc1nc(C)c(/N=C/N(C)CC)cc1Br] | Method 1:<br>12.070 min;<br>354 |
| Q.450 | 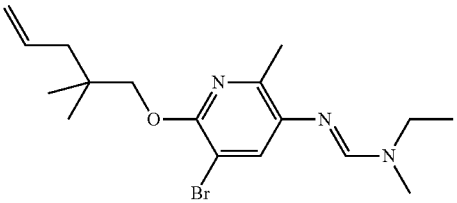 [SMILES: C=CCC(C)(C)COc1nc(C)c(/N=C/N(C)CC)cc1Br] | Method 1:<br>12.652 min;<br>368 |
| Q.451 | 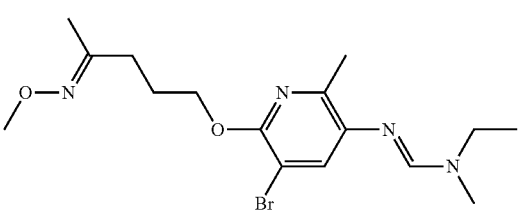 [SMILES: CCN(C)/C=N/c1cc(Br)c(OCCC/C(C)=N/OC)nc1C] | Method 1:<br>10.212 min;<br>385 |
| Q.452 | 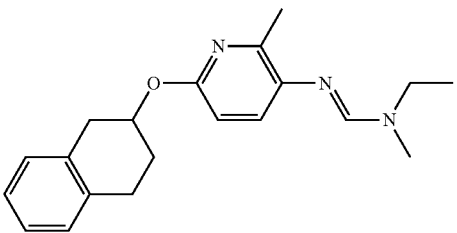 [SMILES: CCN(C)/C=N/c1ccc(OC2CCc3ccccc3C2)nc1C] | Method 1:<br>11.435 min;<br>324 |
| Q.453 | 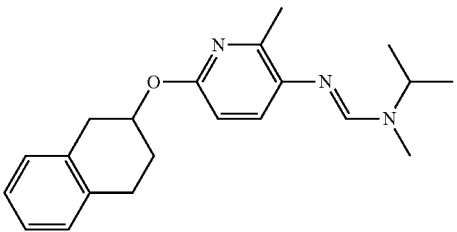 [SMILES: Cc1nc(OC2CCc3ccccc3C2)ccc1/N=C/N(C)C(C)C] | Method 1:<br>11.704 min;<br>338 |

TABLE Q-continued

| | | LC-Method:<br>$R_t$ (min);<br>MS-ESI<br>(m/z; (M + H)$^+$) |
|---|---|---|
| Q.454 | [structure: methylsulfonyloxy pyridine with Br, methyl, and N=CH-N(methyl)(ethyl) substituents] | Mp 85-87° C. |

Biological Examples

*Blumeria graminis* f. sp. *tritici* (*Erysiphe graminis* f. sp. *tritici*)/Wheat/Leaf Disc Preventative (Powdery Mildew on Wheat)

Wheat leaf segments cv. Kanzler were placed on agar in a multiwell plate (24-well format) and sprayed with the formulated test compound diluted in water. The leaf disks were inoculated by shaking powdery mildew infected plants above the test plates 1 day after application. The inoculated leaf disks were incubated at 20° C. and 60% rh under a light regime of 24 h darkness followed by 12 h light/12 h darkness in a climate chamber and the activity of a compound was assessed as percent disease control compared to untreated when an appropriate level of disease damage appears on untreated check leaf segments (6-8 days after application).

The following compounds gave at 200 ppm give at least 50% disease control in this test when compared to untreated control leaf disks under the same conditions, which show extensive disease development:

Q.001, Q.004, Q.005, Q.006, Q.007, Q.010, Q.011, Q.012, Q.013, Q.014, Q.015, Q.016, Q.017, Q.018, Q.019, Q.020, Q.021, Q.022, Q.023, Q.024, Q.025, Q.026, Q.027, Q.028, Q.029, Q.030, Q.031, Q.032, Q.033, Q.034, Q.035, Q.036, Q.037, Q.038, Q.039, Q.040, Q.041, Q.042, Q.043, Q.044, Q.045, Q.046, Q.047, Q.048, Q.049, Q.050, Q.051, Q.052, Q.053, Q.054, Q.055, Q.057, Q.058, Q.059, Q.060, Q.062, Q.063, Q.064, Q.065, Q.066, Q.067, Q.068, Q.069, Q.070, Q.071, Q.072, Q.073, Q.074, Q.075, Q.076, Q.077, Q.078, Q.079, Q.080, Q.081, Q.082, Q.084, Q.085, Q.086, Q.087, Q.088, Q.089, Q.090, Q.091, Q.092, Q.093, Q.094, Q.095, Q.097, Q.098, Q.099, Q.100, Q.101, Q.102, Q.103, Q.104, Q.105, Q.106, Q.108, Q.109, Q.110, Q.111, Q.112, Q.113, Q.114, Q.115, Q.116, Q.117, Q.118, Q.119, Q.120, Q.121, Q.122, Q.123, Q.124, Q.125, Q.126, Q.127, Q.128, Q.129, Q.130, Q.131, Q.132, Q.133, Q.134, Q.135, Q.136, Q.140, Q.141, Q.142, Q.143, Q.144, Q.145, Q.146, Q.147, Q.148, Q.149, Q.151, Q.152, Q.153, Q.154, Q.155, Q.156, Q.158, Q.160, Q.161, Q.162, Q.163, Q.164, Q.165, Q.166, Q.167, Q.168, Q.170, Q.171, Q.172, Q.174, Q.175, Q.176, Q.177, Q.178, Q.179, Q.180, Q.181, Q.183, Q.184, Q.185, Q.186, Q.187, Q.188, Q.191, Q.192, Q.193, Q.195, Q.196, Q.197, Q.198, Q.199, Q.200, Q.201, Q.202, Q.203, Q.204, Q.205, Q.206, Q.207, Q.208, Q.209, Q.211, Q.212, Q.213, Q.214, Q.215, Q.216, Q.217, Q.218, Q.219, Q.220, Q.221, Q.222, Q.223, Q.224, Q.225, Q.226, Q.227, Q.228, Q.229, Q.230, Q.231, Q.233, Q.235, Q.238, Q.239, Q.240, Q.241, Q.242, Q.243, Q.244, Q.245, Q.246, Q.247, Q.248, Q.249, Q.250, Q.251, Q.255, Q.256, Q.260, Q.261, Q.262, Q.263, Q.265, Q.267, Q.269, Q.270, Q.271, Q.272, Q.273, Q.274, Q.275, Q.276, Q.277, Q.278, Q.280, Q.281, Q.282, Q.283, Q.284, Q.285, Q.286, Q.287, Q.288, Q.289, Q.290, Q.291, Q.292, Q.293, Q.294, Q.296, Q.297, Q.298, Q.299, Q.300, Q.301, Q.302, Q.303, Q.304, Q.305, Q.306, Q.307, Q.308, Q.309, Q.310, Q.312, Q.315, Q.316, Q.317, Q.318, Q.319, Q.320, Q.321, Q.322, Q.323, Q.324, Q.325, Q.326, Q.327, Q.329, Q.330, Q.331, Q.332, Q.333, Q.334, Q.335, Q.336, Q.337, Q.338, Q.339, Q.340, Q.341, Q.342, Q.343, Q.344, Q.345, Q.346, Q.347, Q.349, Q.350, Q.351, Q.352, Q.353, Q.354, Q.355, Q.356, Q.357, Q.358, Q.359, Q.360, Q.361, Q.364, Q.365, Q.367, Q.368, Q.369, Q.370, Q.371, Q.373, Q.374, Q.375, Q.376, Q.378, Q.380, Q.381, Q.382, Q.383, Q.384, Q.385, Q.386, Q.388, Q.389, Q.390, Q.391, Q.392, Q.393, Q.394, Q.397, Q.398, Q.400, Q.401

*Puccinia recondita* f. sp. *tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (7-9 days after application).

The following compounds gave at 200 ppm gave at least 50% disease control in this test when compared to untreated control leaf disks under the same conditions, which show extensive disease development:

Q.001, Q.002, Q.003, Q.004, Q.005, Q.006, Q.007, Q.008, Q.009, Q.010, Q.011, Q.012, Q.013, Q.014, Q.015, Q.016, Q.017, Q.018, Q.019, Q.020, Q.021, Q.022, Q.023, Q.024, Q.025, Q.026, Q.027, Q.028, Q.029, Q.030, Q.031, Q.032, Q.033, Q.034, Q.035, Q.036, Q.037, Q.038, Q.039, Q.040, Q.041, Q.042, Q.043, Q.044, Q.045, Q.046, Q.047, Q.048, Q.049, Q.050, Q.051, Q.052, Q.053, Q.054, Q.055, Q.056, Q.057, Q.058, Q.059, Q.060, Q.061, Q.062, Q.063, Q.064, Q.065, Q.066, Q.067, Q.068, Q.069, Q.070, Q.071, Q.072, Q.073, Q.074, Q.075, Q.076, Q.077, Q.078, Q.079, Q.080, Q.081, Q.082, Q.083, Q.084, Q.085, Q.086, Q.087, Q.088, Q.089, Q.090, Q.091, Q.092, Q.093, Q.094, Q.095, Q.096, Q.097, Q.098, Q.099, Q.100, Q.101, Q.102, Q.103, Q.104, Q.105, Q.106, Q.107, Q.108, Q.109, Q.110, Q.111, Q.112, Q.113, Q.114, Q.115, Q.116, Q.117, Q.118, Q.119, Q.120, Q.121, Q.122, Q.123, Q.124, Q.125, Q.126, Q.127, Q.128, Q.129, Q.130, Q.131, Q.132, Q.133, Q.134, Q.135, Q.136, Q.137, Q.138, Q.140, Q.141, Q.142, Q.143, Q.144, Q.145, Q.146, Q.147, Q.148, Q.149, Q.150, Q.151, Q.152, Q.153, Q.154, Q.155, Q.156, Q.157, Q.158, Q.159, Q.160, Q.161,

Q.162, Q.163, Q.164, Q.165, Q.166, Q.167, Q.168, Q.169, Q.170, Q.171, Q.172, Q.173, Q.174, Q.175, Q.176, Q.177, Q.178, Q.179, Q.180, Q.181, Q.182, Q.183, Q.184, Q.185, Q.186, Q.187, Q.188, Q.189, Q.190, Q.191, Q.192, Q.193, Q.194, Q.195, Q.196, Q.197, Q.198, Q.199, Q.200, Q.201, Q.202, Q.203, Q.204, Q.205, Q.206, Q.207, Q.208, Q.209, Q.210, Q.211, Q.212, Q.213, Q.214, Q.215, Q.216, Q.217, Q.218, Q.219, Q.220, Q.221, Q.222, Q.223, Q.224, Q.225, Q.226, Q.227, Q.228, Q.229, Q.230, Q.231, Q.232, Q.233, Q.234, Q.235, Q.236, Q.237, Q.238, Q.239, Q.240, Q.241, Q.242, Q.243, Q.244, Q.245, Q.246, Q.247, Q.248, Q.249, Q.250, Q.251, Q.252, Q.253, Q.254, Q.255, Q.256, Q.257, Q.258, Q.259, Q.260, Q.261, Q.262, Q.263, Q.264, Q.265, Q.266, Q.267, Q.268, Q.269, Q.270, Q.271, Q.272, Q.273, Q.274, Q.275, Q.276, Q.277, Q.278, Q.279, Q.280, Q.281, Q.282, Q.283, Q.284, Q.285, Q.286, Q.287, Q.288, Q.289, Q.290, Q.291, Q.292, Q.293, Q.294, Q.295, Q.296, Q.297, Q.298, Q.299, Q.300, Q.301, Q.302, Q.303, Q.304, Q.305, Q.306, Q.307, Q.308, Q.309, Q.310, Q.311, Q.312, Q.313, Q.314, Q.315, Q.316, Q.317, Q.318, Q.319, Q.320, Q.321, Q.322, Q.323, Q.324, Q.325, Q.326, Q.327, Q.328, Q.329, Q.330, Q.331, Q.332, Q.333, Q.334, Q.335, Q.336, Q.337, Q.338, Q.339, Q.340, Q.341, Q.342, Q.343, Q.344, Q.345, Q.346, Q.347, Q.348, Q.349, Q.350, Q.351, Q.352, Q.353, Q.354, Q.355, Q.356, Q.357, Q.358, Q.359, Q.360, Q.361, Q.362, Q.363, Q.364, Q.365, Q.366, Q.367, Q.368, Q.369, Q.370, Q.371, Q.372, Q.373, Q.374, Q.375, Q.376, Q.377, Q.378, Q.379, Q.380, Q.381, Q.382, Q.383, Q.384, Q.385, Q.386, Q.387, Q.388, Q.389, Q.390, Q.391, Q.392, Q.393, Q.394, Q.397, Q.398, Q.400, Q.401

*Puccinia recondita* f. sp. *tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates were stored in darkness at 19° C. and 75% rh. The formulated test compound diluted in water was applied 1 day after inoculation. The leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (6-8 days after application).

The following compounds gave at 200 ppm gaive at least 50% disease control in this test when compared to untreated control leaf disks under the same conditions, which show extensive disease development:

Q.001, Q.004, Q.005, Q.006, Q.007, Q.010, Q.011, Q.012, Q.013, Q.014, Q.015, Q.016, Q.018, Q.019, Q.020, Q.021, Q.022, Q.023, Q.024, Q.025, Q.026, Q.027, Q.028, Q.029, Q.030, Q.031, Q.032, Q.033, Q.034, Q.035, Q.036, Q.037, Q.038, Q.039, Q.040, Q.041, Q.042, Q.043, Q.044, Q.045, Q.046, Q.047, Q.048, Q.049, Q.050, Q.051, Q.052, Q.053, Q.054, Q.055, Q.057, Q.058, Q.059, Q.060, Q.062, Q.063, Q.064, Q.065, Q.066, Q.067, Q.068, Q.069, Q.070, Q.071, Q.072, Q.073, Q.074, Q.075, Q.076, Q.077, Q.078, Q.079, Q.080, Q.081, Q.082, Q.084, Q.085, Q.086, Q.087, Q.088, Q.089, Q.090, Q.091, Q.092, Q.093, Q.094, Q.095, Q.096, Q.097, Q.098, Q.099, Q.100, Q.101, Q.102, Q.103, Q.104, Q.105, Q.106, Q.109, Q.110, Q.111, Q.112, Q.113, Q.114, Q.115, Q.116, Q.117, Q.118, Q.119, Q.120, Q.121, Q.122, Q.123, Q.124, Q.126, Q.127, Q.128, Q.129, Q.130, Q.131, Q.132, Q.133, Q.134, Q.135, Q.136, Q.140, Q.141, Q.143, Q.144, Q.145, Q.146, Q.147, Q.148, Q.149, Q.151, Q.152, Q.153, Q.154, Q.155, Q.156, Q.158, Q.159, Q.160, Q.161, Q.162, Q.163, Q.164, Q.165, Q.166, Q.167, Q.168, Q.169, Q.170, Q.171, Q.172, Q.174, Q.175, Q.176, Q.177, Q.178, Q.179, Q.180, Q.181, Q.182, Q.183, Q.184, Q.185, Q.186, Q.188, Q.191, Q.192, Q.193, Q.194, Q.195, Q.196, Q.197, Q.198, Q.199, Q.200, Q.201, Q.203, Q.204, Q.205, Q.206, Q.207, Q.208, Q.209, Q.211, Q.212, Q.213, Q.214, Q.215, Q.216, Q.217, Q.218, Q.219, Q.220, Q.221, Q.222, Q.223, Q.224, Q.225, Q.226, Q.227, Q.228, Q.229, Q.230, Q.231, Q.232, Q.233, Q.235, Q.236, Q.238, Q.239, Q.240, Q.241, Q.242, Q.243, Q.244, Q.246, Q.247, Q.248, Q.249, Q.250, Q.251, Q.253, Q.254, Q.255, Q.256, Q.257, Q.258, Q.260, Q.261, Q.262, Q.263, Q.265, Q.269, Q.270, Q.271, Q.273, Q.274, Q.275, Q.276, Q.277, Q.278, Q.279, Q.280, Q.281, Q.282, Q.283, Q.284, Q.285, Q.286, Q.287, Q.288, Q.289, Q.290, Q.291, Q.292, Q.293, Q.294, Q.296, Q.297, Q.298, Q.299, Q.300, Q.301, Q.302, Q.303, Q.304, Q.305, Q.306, Q.307, Q.308, Q.309, Q.310, Q.311, Q.315, Q.316, Q.317, Q.318, Q.319, Q.320, Q.321, Q.322, Q.323, Q.324, Q.325, Q.326, Q.327, Q.329, Q.330, Q.331, Q.332, Q.333, Q.334, Q.335, Q.336, Q.337, Q.338, Q.339, Q.340, Q.341, Q.342, Q.344, Q.345, Q.346, Q.347, Q.348, Q.349, Q.350, Q.351, Q.352, Q.353, Q.354, Q.355, Q.356, Q.357, Q.358, Q.359, Q.360, Q.361, Q.362, Q.363, Q.364, Q.365, Q.366, Q.367, Q.368, Q.369, Q.370, Q.371, Q.372, Q.373, Q.374, Q.375, Q.376, Q.377, Q.378, Q.380, Q.381, Q.382, Q.383, Q.384, Q.385, Q.386, Q.388, Q.389, Q.390, Q.391, Q.392, Q.393, Q.394, Q.397, Q.398, Q.400, Q.401

*Pyrenophora teres*/Barley/Leaf Disc Preventative (Net Blotch)

Barley leaf segments cv. Hasso were placed on agar in a multiwell plate (24-well format) and sprayed with the formulated test compound diluted in water. The leaf segments were inoculated with a spore suspension of the fungus 2 days after application. The inoculated leaf segments were incubated at 20° C. and 65% rh under a light regime of 12 h light/12 h darkness in a climate cabinet and the activity of a compound was assessed as disease control compared to untreated when an appropriate level of disease damage appears in untreated check leaf segments (5-7 days after application).

The following compounds gave at 200 ppm give at least 50% disease control in this test when compared to untreated control leaf disks under the same conditions, which show extensive disease development:

Q.001, Q.004, Q.005, Q.007, Q.011, Q.012, Q.013, Q.014, Q.015, Q.016, Q.018, Q.019, Q.020, Q.021, Q.022, Q.023, Q.024, Q.025, Q.026, Q.027, Q.028, Q.029, Q.032, Q.033, Q.034, Q.035, Q.038, Q.039, Q.041, Q.042, Q.043, Q.044, Q.046, Q.047, Q.052, Q.053, Q.054, Q.055, Q.057, Q.059, Q.062, Q.063, Q.066, Q.067, Q.069, Q.070, Q.071, Q.074, Q.075, Q.076, Q.079, Q.082, Q.086, Q.087, Q.088, Q.089, Q.090, Q.091, Q.093, Q.095, Q.097, Q.099, Q.100, Q.101, Q.102, Q.103, Q.105, Q.106, Q.110, Q.111, Q.113, Q.115, Q.116, Q.117, Q.118, Q.119, Q.120, Q.121, Q.122, Q.124, Q.125, Q.127, Q.128, Q.129, Q.131, Q.133, Q.136, Q.141, Q.143, Q.144, Q.146, Q.148, Q.153, Q.154, Q.155, Q.158, Q.160, Q.161, Q.162, Q.163, Q.164, Q.166, Q.167, Q.168, Q.169, Q.170, Q.174, Q.175, Q.176, Q.178, Q.180, Q.183, Q.184, Q.186, Q.191, Q.193, Q.195, Q.196, Q.197, Q.198, Q.199, Q.200, Q.201, Q.202, Q.203, Q.204, Q.206, Q.207, Q.208, Q.209, Q.211, Q.212, Q.214, Q.215, Q.216, Q.217, Q.218, Q.219, Q.220, Q.221, Q.222, Q.223, Q.224, Q.225, Q.226, Q.227, Q.228, Q.229, Q.231, Q.232, Q.233, Q.235, Q.236, Q.237, Q.238, Q.240, Q.241, Q.242, Q.243, Q.244, Q.245, Q.246, Q.247, Q.248, Q.249, Q.250, Q.251, Q.252, Q.253, Q.255, Q.256, Q.260, Q.261, Q.262, Q.269, Q.275, Q.277, Q.278, Q.280, Q.282, Q.284, Q.285, Q.286, Q.289, Q.291, Q.292, Q.293, Q.298, Q.299, Q.301, Q.302, Q.304, Q.308, Q.311, Q.315, Q.316, Q.320, Q.322, Q.324, Q.326, Q.329, Q.334, Q.335, Q.336, Q.337, Q.340, Q.344, Q.346, Q.349, Q.352, Q.353, Q.354, Q.355, Q.357, Q.358, Q.361,

Q.363, Q.364, Q.366, Q.370, Q.371, Q.375, Q.376, Q.377, Q.378, Q.380, Q.382, Q.386, Q.389, Q.390, Q.391, Q.392, Q.393, Q.394, Q.398, Q.400

In the following Tables 'Activity (%)' means the assessed experimental activity (% disease control in this test when compared to untreated control leaf disks under the same conditions, which show extensive disease development) and "P" is the expected value calculated (expected) activity according to the COLBY formula (see above). The column headed 'S?' indicates whether or not synergy was observed, with 'y' meaning that synergy was observed.

In the following tables, compound (V) is N-[9-(dichloromethylene)-1,2,3,4-tetrahydro-1,4-methanonaphthalen-5-yl]-3-(difluoromethyl)-1-methyl-1H-pyrazole-4-carboxamide, compound (VI) is 3-(difluoromethyl)-N-methoxy-1-methyl-N-[1-methyl-2-(2,4,6-trichlorophenyl)ethyl]-1H-pyrazole-4-carboxamide, compound (VII) is [3-(4-chloro-2-fluoro-phenyl)-5-(2,4-difluoro-phenyl)-isoxazol-4-yl]-pyridin-3-yl-methanol.

*Monographella nivalis* (syn. *Microdochium nivale, Fusarium nivale*), snow mould, foot rot of cereals Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and activity was determined visually after 72 hrs

| Q.135 rate ppm | Compound (V) rate ppm | Activity (%) | P | S? |
|---|---|---|---|---|
| 0.0625 | | 20 | | |
| 0.03125 | | 0 | | |
| 0.015625 | | 0 | | |
| 0.0078125 | | 0 | | |
| | 0.0625 | 50 | | |
| | 0.03125 | 0 | | |
| 0.0625 | 0.03125 | 50 | 20 | y |
| 0.03125 | 0.03125 | 50 | 0 | y |
| 0.03125 | 0.0625 | 70 | 50 | y |
| 0.015625 | 0.03125 | 20 | 0 | y |
| 0.015625 | 0.0625 | 70 | 50 | y |
| 0.0078125 | 0.03125 | 70 | 0 | y |

| Q.135 rate ppm | Metconazole rate ppm | Activity (%) | P | S? |
|---|---|---|---|---|
| 0.0625 | | 70 | | |
| 0.03125 | | 0 | | |
| | 0.25 | 0 | | |
| | 0.125 | 0 | | |
| | 0.0625 | 0 | | |
| | 0.03125 | 0 | | |
| | 0.015625 | 0 | | |
| 0.0625 | 0.25 | 100 | 70 | y |
| 0.0625 | 0.125 | 100 | 70 | y |
| 0.0625 | 0.0625 | 100 | 70 | y |
| 0.0625 | 0.03125 | 100 | 70 | y |
| 0.0625 | 0.015625 | 100 | 70 | y |
| 0.03125 | 0.125 | 100 | 0 | y |
| 0.03125 | 0.0625 | 70 | 0 | y |
| 0.03125 | 0.03125 | 50 | 0 | y |
| 0.03125 | 0.015625 | 20 | 0 | y |

| Q.135 rate ppm | cis-Jasmone rate ppm | Activity (%) | P | S? |
|---|---|---|---|---|
| 0.0625 | | 50 | | |
| 0.03125 | | 0 | | |
| | 1.25 | 0 | | |
| | 0.625 | 0 | | |
| | 0.3125 | 0 | | |
| | 0.15625 | 0 | | |
| 0.0625 | 1.25 | 100 | 50 | y |
| 0.0625 | 0.625 | 90 | 50 | y |
| 0.0625 | 0.3125 | 100 | 50 | y |
| 0.0625 | 0.15625 | 100 | 50 | y |
| 0.03125 | 1.25 | 100 | 0 | y |
| 0.03125 | 0.625 | 50 | 0 | y |
| 0.03125 | 0.3125 | 20 | 0 | y |

| Q.135 rate ppm | 2,4-D rate ppm | Activity (%) | P | S? |
|---|---|---|---|---|
| 0.625 | | 50 | | |
| 0.3125 | | 0 | | |
| | 2.5 | 0 | | |
| | 1.25 | 0 | | |
| | 0.625 | 0 | | |
| | 0.3125 | 0 | | |
| 0.625 | 2.5 | 100 | 50 | y |
| 0.625 | 1.25 | 90 | 50 | y |
| 0.625 | 0.625 | 90 | 50 | y |
| 0.625 | 0.3125 | 90 | 50 | y |
| 0.625 | 0.15625 | 100 | 50 | y |
| 0.3125 | 1.25 | 20 | 0 | y |

| Q.135 rate ppm | Azoxystrobin rate ppm | Activity (%) | P | S? |
|---|---|---|---|---|
| 0.125 | | 70 | | |
| 0.0625 | | 0 | | |
| | 0.00625 | 70 | | |
| | 0.003125 | 20 | | |
| | 0.0015625 | 0 | | |
| 0.125 | 0.003125 | 90 | 70 | y |
| 0.0625 | 0.00625 | 100 | 70 | y |
| 0.0625 | 0.0015625 | 20 | 0 | y |

| Q.135 rate ppm | Fenpropimorph rate ppm | Activity (%) | P | S? |
|---|---|---|---|---|
| 0.03125 | | 20 | | |
| | 0.125 | 0 | | |
| | 0.0625 | 0 | | |
| | 0.03125 | 0 | | |
| | 0.015625 | 0 | | |
| | 0.0078125 | 0 | | |
| 0.03125 | 0.125 | 100 | 20 | y |
| 0.03125 | 0.0625 | 90 | 20 | y |
| 0.03125 | 0.03125 | 90 | 20 | y |
| 0.03125 | 0.015625 | 70 | 20 | y |
| 0.03125 | 0.0078125 | 90 | 20 | y |

| Q.135 rate ppm | Bicyclopyrone rate ppm | Activity (%) | P | S? |
|---|---|---|---|---|
| 0.0625 | | 20 | | |
| 0.03125 | | 0 | | |
| | 0.3125 | 0 | | |
| | 0.15625 | 0 | | |
| | 0.078125 | 0 | | |
| 0.0625 | 0.15625 | 90 | 20 | y |
| 0.03125 | 0.078125 | 20 | 0 | y |
| 0.0625 | 0.3125 | 70 | 20 | y |

| Q.135 rate ppm | Abamectin rate ppm | Activity (%) | P | S? |
|---|---|---|---|---|
| 0.0625 | | 20 | | |
| | 2.5 | 0 | | |
| | 1.25 | 0 | | |
| | 0.625 | 0 | | |
| | 0.3125 | 0 | | |
| | 0.15625 | 0 | | |
| 0.0625 | 0.15625 | 70 | 20 | y |
| 0.0625 | 0.3125 | 50 | 20 | y |
| 0.0625 | 0.625 | 20 | 20 | y |
| 0.0625 | 1.25 | 50 | 20 | y |
| 0.0625 | 2.5 | 100 | 20 | y |

| Q.135 rate ppm | Thiamethoxam rate ppm | Activity (%) | P | S? |
|---|---|---|---|---|
| 0.125 | | 70 | | |
| 0.0625 | | 20 | | |
| | 5 | 0 | | |
| | 2.5 | 0 | | |
| | 0.625 | 0 | | |
| | 0.3125 | 0 | | |
| 0.125 | 0.3125 | 100 | 70 | y |
| 0.125 | 0.625 | 90 | 70 | y |
| 0.0625 | 0.3125 | 50 | 20 | y |
| 0.125 | 0.25 | 90 | 70 | y |
| 0.125 | 0.5 | 100 | 70 | y |
| 0.0625 | 0.25 | 70 | 20 | y |

| Q.135 rate ppm | Propiconazole rate ppm | Activity (%) | P | S? |
|---|---|---|---|---|
| 0.0625 | | 70 | | |
| 0.03125 | | 0 | | |
| | 0.25 | 0 | | |
| | 0.125 | 0 | | |
| | 0.0625 | 0 | | |
| | 0.03125 | 0 | | |
| | 0.015625 | 0 | | |
| 0.0625 | 0.015625 | 90 | 70 | y |
| 0.0625 | 0.03125 | 100 | 70 | y |
| 0.0625 | 0.0625 | 100 | 70 | y |
| 0.03125 | 0.015625 | 50 | 0 | y |
| 0.03125 | 0.03125 | 20 | 0 | y |
| 0.0625 | 0.125 | 100 | 70 | y |
| 0.03125 | 0.0625 | 50 | 0 | y |
| 0.0625 | 0.25 | 100 | 70 | y |
| 0.03125 | 0.125 | 70 | 0 | y |

| Q.135 rate ppm | Glufosinate rate ppm | Activity (%) | P | S? |
|---|---|---|---|---|
| 0.0625 | | 70 | | |
| 0.03125 | | 0 | | |
| | 2.5 | 0 | | |
| | 1.25 | 0 | | |
| | 0.625 | 0 | | |
| | 0.3125 | 0 | | |
| 0.0625 | 0.3125 | 90 | 70 | y |
| 0.0625 | 0.625 | 70 | 70 | |
| 0.0625 | 1.25 | 90 | 70 | y |
| 0.03125 | 0.625 | 20 | 0 | y |
| 0.0625 | 2.5 | 90 | 70 | y |
| 0.03125 | 1.25 | 20 | 0 | y |

| Q.135 rate ppm | Flutriafol rate ppm | Activity (%) | P | S? |
|---|---|---|---|---|
| 0.0625 | | 70 | | |
| | 0.25 | 0 | | |
| | 0.125 | 0 | | |
| | 0.0625 | 0 | | |
| | 0.03125 | 0 | | |
| 0.0625 | 0.25 | 100 | 70 | y |
| 0.0625 | 0.125 | 90 | 70 | y |
| 0.0625 | 0.0625 | 90 | 70 | y |
| 0.0625 | 0.03125 | 90 | 70 | y |

| Q.135 rate ppm | Trinexapacethyl rate ppm | Activity (%) | P | S? |
|---|---|---|---|---|
| 0.0625 | | 50 | | |
| 0.03125 | | 0 | | |
| | 2.5 | 0 | | |
| | 1.25 | 0 | | |
| | 0.625 | 0 | | |
| | 0.3125 | 0 | | |
| | 0.12625 | 0 | | |
| 0.0625 | 2.5 | 100 | 50 | y |
| 0.0625 | 1.25 | 90 | 50 | y |
| 0.0625 | 0.625 | 70 | 50 | y |
| 0.0625 | 0.3125 | 90 | 50 | y |
| 0.0625 | 0.15625 | 90 | 50 | y |
| 0.03125 | 1.25 | 20 | 0 | y |

| Q.135 rate ppm | Paclobutrazol rate ppm | Activity (%) | P | S? |
|---|---|---|---|---|
| 0.0625 | | 70 | | |
| 0.03125 | | 0 | | |
| 0.015625 | | 0 | | |
| | 1.25 | 0 | | |
| | 0.625 | 0 | | |
| | 0.3125 | 0 | | |
| | 0.15625 | 0 | | |
| 0.0625 | 1.25 | 100 | 70 | y |
| 0.0625 | 0.625 | 100 | 70 | y |
| 0.0625 | 0.3125 | 100 | 70 | y |
| 0.0625 | 0.15625 | 100 | 70 | y |
| 0.03125 | 1.25 | 100 | 0 | y |
| 0.03125 | 0.625 | 100 | 0 | y |
| 0.03125 | 0.3125 | 50 | 0 | y |
| 0.03125 | 0.15625 | 20 | 0 | y |
| 0.015625 | 0.625 | 20 | 0 | y |

| Q.135 rate ppm | Pyraclostrobin rate ppm | Activity (%) | P | S? |
|---|---|---|---|---|
| 0.125 | | 70 | | |
| 0.0625 | | 0 | | |
| | 0.003125 | 0 | | |
| | 0.0015625 | 0 | | |
| 0.125 | 0.003125 | 90 | 70 | y |
| 0.0625 | 0.003125 | 20 | 0 | y |
| 0.0625 | 0.0015625 | 20 | 0 | y |

| Q.135 rate ppm | Mandipropamid rate ppm | Activity (%) | P | S? |
|---|---|---|---|---|
| 0.125 | | 70 | | |
| 0.0625 | | 20 | | |
| 0.03125 | | 0 | | |
| | 0.0625 | 0 | | |
| | 0.03125 | 0 | | |
| 0.125 | 0.0625 | 90 | 70 | y |
| 0.125 | 0.03125 | 90 | 70 | y |
| 0.0625 | 0.0625 | 20 | 20 | |
| 0.03125 | 0.0625 | 50 | 0 | y |

| Q.135 rate ppm | Carbendazim rate ppm | Activity (%) | P | S? |
|---|---|---|---|---|
| 0.125 | | 70 | | |
| 0.0625 | | 20 | | |
| | 0.0625 | 0 | | |
| | 0.03125 | 0 | | |
| | 0.015625 | 0 | | |
| 0.125 | 0.0625 | 90 | 70 | y |
| 0.0625 | 0.03125 | 50 | 20 | y |
| 0.0625 | 0.015625 | 50 | 20 | y |

| Q.135 rate ppm | Copper hydroxide rate ppm | Activity (%) | P | S? |
|---|---|---|---|---|
| 0.125 | | 70 | | |
| 0.0625 | | 20 | | |
| | 5 | 0 | | |
| | 2.5 | 0 | | |
| | 1.25 | 0 | | |
| | 0.625 | 0 | | |
| | 0.3125 | 0 | | |
| | 0.15625 | 0 | | |
| 0.125 | 0.3125 | 100 | 70 | y |
| 0.125 | 0.625 | 100 | 70 | y |
| 0.125 | 1.25 | 100 | 70 | y |
| 0.0625 | 0.15625 | 70 | 20 | y |
| 0.0625 | 0.3125 | 70 | 20 | y |
| 0.125 | 2.5 | 100 | 70 | y |
| 0.125 | 5 | 100 | 70 | y |

-continued

| Q.135 rate ppm | Manganese oxide rate ppm | Activity (%) | P | S? |
|---|---|---|---|---|
| 0.0625 | | 20 | | |
| | 2.5 | 0 | | |
| | 1.25 | 0 | | |
| | 0.625 | 0 | | |
| | 0.3125 | 0 | | |
| | 0.15625 | 0 | | |
| 0.0625 | 0.15625 | 70 | 20 | y |
| 0.0625 | 0.3125 | 50 | 20 | y |
| 0.0625 | 0.625 | 20 | 20 | |
| 0.0625 | 1.25 | 70 | 20 | y |
| 0.0625 | 2.5 | 90 | 20 | y |

| Q.135 rate ppm | Mesotrione rate ppm | Activity (%) | P | S? |
|---|---|---|---|---|
| 0.0625 | | 20 | | |
| 0.03125 | | 0 | | |
| | 2.5 | 0 | | |
| | 1.25 | 0 | | |
| | 0.625 | 0 | | |
| | 0.3125 | 0 | | |
| | 0.15625 | 0 | | |
| | 0.078125 | 0 | | |
| 0.0625 | 0.15625 | 70 | 20 | y |
| 0.0625 | 0.3125 | 70 | 20 | y |
| 0.0625 | 0.625 | 50 | 20 | y |
| 0.03125 | 0.078125 | 20 | 0 | y |
| 0.03125 | 0.15625 | 20 | 0 | y |
| 0.03125 | 0.3125 | 0 | 0 | y |
| 0.0625 | 1.25 | 70 | 20 | y |
| 0.03125 | 0.625 | 20 | 0 | y |
| 0.0625 | 2.5 | 90 | 20 | y |
| 0.03125 | 1.25 | 20 | 0 | y |

| Q.135 rate ppm | Prothioconazole rate ppm | Activity (%) | P | S? |
|---|---|---|---|---|
| 0.0625 | | 70 | | |
| 0.03125 | | 0 | | |
| | 0.0125 | 0 | | |
| | 0.00625 | 0 | | |
| | 0.003125 | 0 | | |
| | 0.0015625 | 0 | | |
| 0.0625 | 0.0015625 | 100 | 70 | y |
| 0.0625 | 0.003125 | 100 | 70 | y |
| 0.0625 | 0.00625 | 100 | 70 | y |
| 0.03125 | 0.0015625 | 20 | 0 | y |
| 0.03125 | 0.003125 | 20 | 0 | y |
| 0.0625 | 0.0125 | 100 | 70 | y |
| 0.03125 | 0.00625 | 100 | 0 | y |
| 0.03125 | 0.0125 | 100 | 0 | y |

| Q.113 rate ppm | Flutriafol rate ppm | Activity (%) | P | S? |
|---|---|---|---|---|
| 2 | | 70 | | |
| 1 | | 20 | | |
| 0.5 | | 20 | | |
| 0.25 | | 0 | | |
| | 2 | 0 | | |
| | 1 | 0 | | |
| | 0.5 | 0 | | |
| | 0.25 | 0 | | |
| 2 | 2 | 100 | 70 | y |
| 2 | 1 | 100 | 70 | y |
| 2 | 0.5 | 90 | 70 | y |
| 1 | 2 | 90 | 20 | y |
| 1 | 1 | 70 | 20 | y |
| 1 | 0.5 | 70 | 20 | y |
| 1 | 0.25 | 50 | 20 | y |
| 0.5 | 2 | 50 | 20 | y |
| 0.25 | 1 | 20 | 0 | y |

-continued

| Q.113 rate ppm | Metconazole rate ppm | Activity (%) | P | S? |
|---|---|---|---|---|
| 1 | | 50 | | |
| 0.5 | | 20 | | |
| 0.25 | | 0 | | |
| 0.125 | | 0 | | |
| | 1 | 20 | | |
| | 0.5 | 0 | | |
| | 0.25 | 0 | | |
| | 0.125 | 0 | | |
| 1 | 1 | 100 | 60 | y |
| 1 | 0.5 | 100 | 50 | y |
| 1 | 0.25 | 100 | 50 | y |
| 0.5 | 1 | 100 | 36 | y |
| 0.5 | 0.5 | 100 | 20 | y |
| 0.5 | 0.25 | 90 | 20 | y |
| 0.5 | 0.125 | 50 | 20 | y |
| 0.25 | 1 | 100 | 20 | y |
| 0.25 | 0.5 | 70 | 0 | y |
| 0.25 | 0.25 | 50 | 0 | y |
| 0.25 | 0.125 | 20 | 0 | y |
| 0.125 | 0.5 | 50 | 0 | y |
| 0.125 | 0.25 | 20 | 0 | y |
| 0.125 | 0.125 | 20 | 0 | y |

| Q.113 rate ppm | Penflufen rate ppm | Activity (%) | P | S? |
|---|---|---|---|---|
| 1 | | 20 | | |
| 0.5 | | 2 | | |
| 0.25 | | 2 | | |
| 0.125 | | 2 | | |
| | 1 | 20 | | |
| | 0.5 | 0 | | |
| 1 | 1 | 50 | 36 | y |
| 0.5 | 1 | 50 | 20 | y |
| 0.5 | 0.5 | 20 | 0 | y |
| 0.25 | 1 | 50 | 20 | y |
| 0.25 | 0.5 | 20 | 0 | y |
| 0.125 | 0.5 | 20 | 0 | y |

| Q.113 rate ppm | Bixafen rate ppm | Activity (%) | P | S? |
|---|---|---|---|---|
| 0.25 | | 0 | | |
| 0.125 | | 0 | | |
| 0.0625 | | 0 | | |
| | 0.25 | 20 | | |
| 0.25 | 0.25 | 50 | 20 | y |
| 0.125 | 0.25 | 50 | 20 | y |
| 0.0625 | 0.25 | 50 | 20 | y |

| Q.113 rate ppm | Fenpropimorph rate ppm | Activity (%) | P | S? |
|---|---|---|---|---|
| 0.5 | | 20 | | |
| 0.25 | | 0 | | |
| | 1 | 20 | | |
| | 0.5 | 0 | | |
| | 0.25 | 0 | | |
| | 0.125 | 0 | | |
| | 0.0625 | 0 | | |
| 0.5 | 1 | 700 | 36 | y |
| 0.5 | 0.5 | 100 | 20 | y |
| 0.5 | 0.25 | 100 | 20 | y |
| 0.5 | 0.125 | 100 | 20 | y |
| 0.25 | 1 | 100 | 20 | y |
| 0.25 | 0.5 | 90 | 0 | y |
| 0.25 | 0.25 | 70 | 0 | y |
| 0.25 | 0.125 | 20 | 0 | y |
| 0.25 | 0.0625 | 20 | 0 | y |

| Q.113 rate ppm | Prothioconazole rate ppm | Activity (%) | P | S? |
|---|---|---|---|---|
| 0.5 | | 0 | | |
| 0.25 | | 0 | | |

| Q.113 rate ppm | Propiconazole rate ppm | Activity (%) | P | S? |
|---|---|---|---|---|
| 0.125 | | 0 | | |
| | 0.0125 | 0 | | |
| 0.5 | 0.0125 | 90 | 0 | y |
| 0.25 | 0.0125 | 50 | 0 | y |
| 0.125 | 0.0125 | 20 | 0 | y |

| Q.113 rate ppm | Propiconazole rate ppm | Activity (%) | P | S? |
|---|---|---|---|---|
| 2 | | 70 | | |
| 1 | | 20 | | |
| 0.5 | | 0 | | |
| 0.25 | | 0 | | |
| | 1 | 20 | | |
| | 0.5 | 0 | | |
| | 0.25 | 0 | | |
| | 0.125 | 0 | | |
| 2 | 0.5 | 100 | 70 | y |
| 2 | 1 | 100 | 76 | y |
| 1 | 0.25 | 90 | 20 | y |
| 1 | 0.5 | 100 | 20 | y |
| 1 | 1 | 100 | 36 | y |
| 0.5 | 0.125 | 20 | 0 | y |
| 0.5 | 0.25 | 50 | 0 | y |
| 0.5 | 0.5 | 90 | 0 | y |
| 0.25 | 0.125 | 20 | 0 | y |
| 0.25 | 0.25 | 20 | 0 | y |
| 0.5 | 1 | 100 | 20 | y |
| 0.25 | 0.5 | 50 | 0 | y |
| 0.25 | 1 | 90 | 20 | y |

| Q.113 rate ppm | Paclobutrazol rate ppm | Activity (%) | P | S? |
|---|---|---|---|---|
| 1 | | 50 | | |
| 0.5 | | 20 | | |
| 0.25 | | 0 | | |
| 0.125 | | 0 | | |
| | 10 | 0 | | |
| | 5 | 0 | | |
| | 2.5 | 0 | | |
| | 1.25 | 0 | | |
| 1 | 10 | 100 | 50 | y |
| 1 | 5 | 100 | 50 | y |
| 1 | 2.5 | 90 | 50 | y |
| 0.5 | 10 | 70 | 20 | y |
| 0.5 | 5 | 70 | 20 | y |
| 0.5 | 2.5 | 50 | 20 | y |
| 0.5 | 1.25 | 50 | 20 | y |
| 0.25 | 10 | 50 | 0 | y |
| 0.25 | 5 | 50 | 0 | y |
| 0.25 | 2.5 | 50 | 0 | y |
| 0.25 | 1.25 | 20 | 0 | y |
| 0.125 | 5 | 20 | 0 | y |
| 0.125 | 2.5 | 20 | 0 | y |

| Q.113 rate ppm | Azoxystrobin rate ppm | Activity (%) | P | S? |
|---|---|---|---|---|
| 0.25 | | 0 | | |
| 0.125 | | 0 | | |
| 0.0625 | | 0 | | |
| 0.03125 | | 0 | | |
| | 0.00625 | 50 | | |
| 0.25 | 0.00625 | 70 | 50 | y |
| 0.125 | 0.00625 | 70 | 50 | y |
| 0.0625 | 0.00625 | 50 | 50 | |
| 0.03125 | 0.00625 | 100 | 50 | y |

| Q.113 rate ppm | Cyprodinil rate ppm | Activity (%) | P | S? |
|---|---|---|---|---|
| 0.015625 | | 0 | | |
| 0.0078125 | | 0 | | |
| 0.00390625 | | 0 | | |
| | 0.003125 | 20 | | |
| | 0.0015625 | 0 | | |
| 0.015625 | 0.003125 | 50 | 20 | y |
| 0.0078125 | 0.0015625 | 20 | 0 | y |
| 0.0078125 | 0.003125 | 50 | 20 | y |
| 0.00390625 | 0.0015625 | 20 | 0 | y |

| Q.113 rate ppm | Abamectin rate ppm | Activity (%) | P | S? |
|---|---|---|---|---|
| 2 | | 70 | | |
| 1 | | 20 | | |
| 0.5 | | 0 | | |
| | 20 | 50 | | |
| | 10 | 0 | | |
| | 5 | 0 | | |
| 2 | 10 | 100 | 70 | y |
| 1 | 5 | 50 | 20 | y |
| 2 | 20 | 100 | 85 | y |
| 1 | 10 | 50 | 20 | y |
| 1 | 20 | 100 | 60 | y |
| 0.5 | 10 | 20 | 0 | y |
| 0.5 | 20 | 70 | 50 | y |

| Q.113 rate ppm | Mesotrione rate ppm | Activity (%) | P | S? |
|---|---|---|---|---|
| 1 | | 20 | | |
| 0.5 | | 0 | | |
| | 5 | 0 | | |
| | 2.5 | 0 | | |
| 1 | 2.5 | 50 | 20 | y |
| 1 | 5 | 50 | 20 | y |
| 0.5 | 2.5 | 20 | 0 | y |

| Q.062 rate ppm | Compound (V) rate ppm | Activity (%) | P | S? |
|---|---|---|---|---|
| 0.0625 | | 0 | | |
| 0.03125 | | 0 | | |
| 0.015625 | | 0 | | |
| | 0.125 | 70 | | |
| | 0.0625 | 50 | | |
| | 0.03125 | 0 | | |
| 0.0625 | 0.125 | 100 | 70 | y |
| 0.03125 | 0.0625 | 70 | 50 | y |
| 0.015625 | 0.03125 | 20 | 0 | y |
| 0.03125 | 0.125 | 90 | 70 | y |
| 0.015625 | 0.0625 | 70 | 50 | y |

| Q.062 rate ppm | Compound (VI) rate ppm | Activity (%) | P | S? |
|---|---|---|---|---|
| 0.03125 | | 0 | | |
| 0.015625 | | 0 | | |
| | 0.125 | 50 | | |
| | 0.0625 | 0 | | |
| 0.03125 | 0.125 | 70 | 50 | y |
| 0.03125 | 0.0625 | 20 | 0 | y |
| 0.015625 | 0.0625 | 20 | 0 | y |

| Q.062 rate ppm | Chlorothalonil rate ppm | Activity (%) | P | S? |
|---|---|---|---|---|
| 0.5 | | 50 | | |
| 0.25 | | 20 | | |
| 0.125 | | 0 | | |
| | 0.125 | 70 | | |
| | 0.0625 | 20 | | |
| | 0.03125 | 0 | | |
| 0.25 | 0.0625 | 50 | 36 | y |
| 0.5 | 0.125 | 100 | 85 | y |
| 0.125 | 0.0625 | 50 | 20 | y |
| 0.125 | 0.03125 | 20 | 0 | y |

| Q.062 rate ppm | Flutriafol rate ppm | Activity (%) | P | S? |
|---|---|---|---|---|
| 0.5 | | 50 | | |
| 0.25 | | 20 | | |

693 -continued

| Q.062 rate ppm | | Activity (%) | P | S? |
|---|---|---|---|---|
| | 0.125 | 0 | | |
| | 0.5 | 0 | | |
| | 0.25 | 0 | | |
| | 0.125 | 0 | | |
| | 0.0625 | 0 | | |
| 0.5 | 0.5 | 90 | 50 | y |
| 0.5 | 0.25 | 90 | 50 | y |
| 0.5 | 0.125 | 90 | 50 | y |
| 0.25 | 0.5 | 50 | 20 | y |
| 0.25 | 0.25 | 50 | 20 | y |
| 0.25 | 0.125 | 50 | 20 | y |
| 0.25 | 0.0625 | 50 | 20 | y |
| 0.125 | 0.5 | 20 | 0 | y |
| 0.125 | 0.25 | 20 | 0 | y |
| 0.125 | 0.125 | 20 | 0 | y |
| 0.125 | 0.0625 | 20 | 0 | y |

| Q.062 rate ppm | Paclobutrazol rate ppm | Activity (%) | P | S? |
|---|---|---|---|---|
| 0.5 | | 70 | | |
| 0.25 | | 20 | | |
| 0.125 | | 0 | | |
| | 10 | 0 | | |
| | 5 | 0 | | |
| | 2.5 | 0 | | |
| | 1.25 | 0 | | |
| | 0.625 | 0 | | |
| 0.5 | 10 | 100 | 70 | y |
| 0.5 | 5 | 100 | 70 | y |
| 0.5 | 2.5 | 100 | 70 | y |
| 0.5 | 1.25 | 100 | 70 | y |
| 0.25 | 10 | 100 | 20 | y |
| 0.25 | 5 | 100 | 20 | y |
| 0.25 | 2.5 | 90 | 20 | y |
| 0.25 | 1.25 | 70 | 20 | y |
| 0.25 | 0.625 | 70 | 20 | y |
| 0.125 | 5 | 70 | 0 | y |
| 0.125 | 2.5 | 70 | 0 | y |
| 0.125 | 1.25 | 50 | 0 | y |
| 0.125 | 0.625 | 20 | 0 | y |

| Q.062 rate ppm | cis-Jasmone rate ppm | Activity (%) | P | S? |
|---|---|---|---|---|
| 0.25 | | 20 | | |
| 0.125 | | 0 | | |
| | 5 | 0 | | |
| | 2.5 | 0 | | |
| | 1.25 | 0 | | |
| | 0.625 | 0 | | |
| 0.25 | 5 | 50 | 20 | y |
| 0.25 | 2.5 | 50 | 20 | y |
| 0.25 | 1.25 | 50 | 20 | y |
| 0.25 | 0.625 | 50 | 20 | y |
| 0.125 | 5 | 50 | 0 | y |
| 0.125 | 2.5 | 50 | 0 | y |
| 0.125 | 1.25 | 50 | 0 | y |

| Q.062 rate ppm | Penflufen rate ppm | Activity (%) | P | S? |
|---|---|---|---|---|
| 2 | | 20 | | |
| 1 | | 0 | | |
| 0.5 | | 0 | | |
| 0.25 | | 0 | | |
| | 1 | 20 | | |
| | 0.5 | 0 | | |
| 2 | 1 | 50 | 36 | y |
| 1 | 0.5 | 20 | 0 | y |
| 0.5 | 1 | 50 | 20 | y |
| 0.25 | 0.5 | 20 | 0 | y |

694 -continued

| Q.062 rate ppm | Fenpropimorph rate ppm | Activity (%) | P | S? |
|---|---|---|---|---|
| 2 | | 20 | | |
| 1 | | 0 | | |
| | 2 | 20 | | |
| | 1 | 0 | | |
| | 0.5 | 0 | | |
| | 0.25 | 0 | | |
| 2 | 2 | 100 | 36 | y |
| 2 | 1 | 90 | 20 | y |
| 2 | 0.5 | 70 | 20 | y |
| 1 | 2 | 70 | 20 | y |
| 1 | 1 | 50 | 0 | y |
| 1 | 0.5 | 20 | 0 | y |
| 1 | 0.25 | 20 | 0 | y |

| Q.062 rate ppm | Abamectin rate ppm | Activity (%) | P | S? |
|---|---|---|---|---|
| 1 | | 70 | | |
| 0.5 | | 50 | | |
| | 20 | 50 | | |
| | 10 | 0 | | |
| | 5 | 0 | | |
| 1 | 5 | 90 | 70 | y |
| 1 | 10 | 100 | 70 | y |
| 1 | 20 | 100 | 85 | y |
| 0.5 | 10 | 70 | 50 | y |
| 0.5 | 20 | 100 | 75 | y |

| Q.062 rate ppm | Propiconazole rate ppm | Activity (%) | P | S? |
|---|---|---|---|---|
| 0.5 | | 50 | | |
| 0.25 | | 20 | | |
| 0.125 | | 0 | | |
| 0.0625 | | 0 | | |
| | 1 | 20 | | |
| | 0.5 | 0 | | |
| | 0.25 | 0 | | |
| | 0.125 | 0 | | |
| | 0.0625 | 0 | | |
| 0.5 | 0.125 | 70 | 50 | y |
| 0.5 | 0.25 | 100 | 50 | y |
| 0.5 | 0.5 | 100 | 50 | y |
| 0.25 | 0.125 | 50 | 20 | y |
| 0.25 | 0.25 | 70 | 20 | y |
| 0.5 | 1 | 100 | 60 | y |
| 0.125 | 0.0625 | 20 | 0 | y |
| 0.125 | 0.125 | 20 | 0 | y |
| 0.25 | 0.5 | 100 | 20 | y |
| 0.125 | 0.25 | 50 | 0 | y |
| 0.0625 | 0.125 | 20 | 0 | y |
| 0.25 | 1 | 100 | 36 | y |
| 0.125 | 0.5 | 70 | 0 | y |
| 0.0625 | 0.25 | 20 | 0 | y |

| Q.062 rate ppm | Metconazole rate ppm | Activity (%) | P | S? |
|---|---|---|---|---|
| 0.5 | | 50 | | |
| 0.25 | | 20 | | |
| 0.125 | | 0 | | |
| 0.0625 | | 0 | | |
| | 1 | 20 | | |
| | 0.5 | 0 | | |
| | 0.25 | 0 | | |
| | 0.125 | 0 | | |
| | 0.0625 | 0 | | |
| 0.5 | 1 | 100 | 60 | y |
| 0.5 | 0.5 | 100 | 50 | y |
| 0.5 | 0.25 | 70 | 50 | y |
| 0.5 | 0.125 | 100 | 50 | y |
| 0.25 | 1 | 100 | 36 | y |
| 0.25 | 0.5 | 100 | 20 | y |
| 0.25 | 0.25 | 90 | 20 | y |
| 0.25 | 0.125 | 20 | 20 | y |
| 0.25 | 0.0625 | 50 | 20 | y |

| Q.062 rate ppm | Trinexapacethyl rate ppm | Activity (%) | P | S? |
|---|---|---|---|---|
| 0.125 | 0.5 | 90 | 0 | y |
| 0.125 | 0.25 | 50 | 0 | y |
| 0.125 | 0.125 | 20 | 0 | y |
| 0.0625 | 0.25 | 20 | 0 | y |

| Q.062 rate ppm | Trinexapacethyl rate ppm | Activity (%) | P | S? |
|---|---|---|---|---|
| 0.5 | | 70 | | |
| 0.25 | | 20 | | |
| 0.125 | | 0 | | |
| | 5 | 0 | | |
| | 2.5 | 0 | | |
| | 1.25 | 0 | | |
| | 0.625 | 0 | | |
| 0.5 | 5 | 90 | 70 | y |
| 0.5 | 2.5 | 90 | 70 | y |
| 0.5 | 1.25 | 90 | 70 | y |
| 0.25 | 5 | 50 | 20 | y |
| 0.25 | 1.25 | 50 | 20 | y |
| 0.25 | 0.625 | 50 | 20 | y |
| 0.125 | 5 | 20 | 0 | y |
| 0.125 | 2.5 | 20 | 0 | y |

| Q.062 rate ppm | 2,4-D rate ppm | Activity (%) | P | S? |
|---|---|---|---|---|
| 0.5 | | 70 | | |
| 0.25 | | 20 | | |
| 0.125 | | 0 | | |
| | 10 | 0 | | |
| | 5 | 0 | | |
| | 2.5 | 0 | | |
| | 1.25 | 0 | | |
| | 0.625 | 0 | | |
| 0.5 | 10 | 90 | 70 | y |
| 0.5 | 5 | 90 | 70 | y |
| 0.5 | 2.5 | 90 | 70 | y |
| 0.5 | 1.25 | 90 | 70 | y |
| 0.25 | 10 | 50 | 20 | y |
| 0.25 | 5 | 50 | 20 | y |
| 0.25 | 2.5 | 50 | 20 | y |
| 0.25 | 1.25 | 50 | 20 | y |
| 0.25 | 0.625 | 50 | 20 | y |
| 0.125 | 5 | 20 | 0 | y |
| 0.125 | 2.5 | 20 | 0 | y |
| 0.125 | 1.25 | 20 | 0 | y |

| Q.062 rate ppm | Pyraclostrobin rate ppm | Activity (%) | P | S? |
|---|---|---|---|---|
| 0.0625 | | 0 | | |
| 0.03125 | | 0 | | |
| 0.015625 | | 0 | | |
| | 0.0125 | 50 | | |
| | 0.00625 | 0 | | |
| 0.0625 | 0.0125 | 70 | 50 | y |
| 0.03125 | 0.0125 | 70 | 50 | y |
| 0.03125 | 0.00625 | 20 | 0 | y |
| 0.015625 | 0.00625 | 20 | 0 | y |

| Q.062 rate ppm | Mesotrione rate ppm | Activity (%) | P | S? |
|---|---|---|---|---|
| 1 | | 70 | | |
| | 20 | 0 | | |
| | 10 | 0 | | |
| | 5 | 0 | | |
| 1 | 5 | 90 | 70 | y |
| 1 | 10 | 90 | 70 | y |
| 1 | 20 | 90 | 70 | y |

| Q.062 rate ppm | Prothioconazole rate ppm | Activity (%) | P | S? |
|---|---|---|---|---|
| 0.5 | | 50 | | |
| 0.25 | | 20 | | |
| 0.125 | | 0 | | |
| 0.0625 | | 0 | | |
| | 0.0125 | 0 | | |
| 0.5 | 0.0125 | 100 | 50 | y |
| 0.25 | 0.0125 | 100 | 20 | y |
| 0.125 | 0.0125 | 50 | 0 | y |
| 0.0625 | 0.0125 | 20 | 0 | y |

| Q.062 rate ppm | Glufosinate rate ppm | Activity (%) | P | S? |
|---|---|---|---|---|
| 0.125 | | 0 | | |
| | 5 | 0 | | |
| | 2.5 | 0 | | |
| | 1.25 | 0 | | |
| 0.125 | 1.25 | 20 | 0 | y |
| 0.125 | 2.5 | 20 | 0 | y |
| 0.125 | 5 | 20 | 0 | y |

*Botrytis cinerea* (Gray mould)

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the activity was determined visually after 72 hrs.

| Q.135 rate ppm | Fluxapyroxad rate ppm | Activity (%) | P | S? |
|---|---|---|---|---|
| 0.03125 | | 0 | | |
| 0.015625 | | 0 | | |
| 0.0078125 | | 0 | | |
| 0.00390625 | | 0 | | |
| | 0.0625 | 50 | | |
| | 0.03125 | 20 | | |
| | 0.015625 | 20 | | |
| | 0.0078125 | 0 | | |
| 0.03125 | 0.0625 | 70 | 50 | y |
| 0.015625 | 0.03125 | 50 | 20 | y |
| 0.0078125 | 0.015625 | 50 | 20 | y |
| 0.00390625 | 0.0078125 | 20 | 0 | y |
| 0.015625 | 0.0625 | 70 | 50 | y |
| 0.0078125 | 0.03125 | 50 | 20 | y |
| 0.00390625 | 0.015625 | 50 | 20 | y |

| Q.135 rate ppm | Compound (V) rate ppm | Activity (%) | P | S? |
|---|---|---|---|---|
| 0.03125 | | 0 | | |
| 0.015625 | | 0 | | |
| 0.0078125 | | 0 | | |
| | 0.125 | 70 | | |
| | 0.0625 | 70 | | |
| | 0.03125 | 50 | | |
| | 0.015625 | 20 | | |
| 0.015625 | 0.03125 | 70 | 50 | y |
| 0.0078125 | 0.015625 | 50 | 20 | y |
| 0.03125 | 0.125 | 90 | 70 | y |
| 0.015625 | 0.0625 | 70 | 70 | y |
| 0.0078125 | 0.03125 | 70 | 50 | y |

| Q.135 rate ppm | Flutriafol rate ppm | Activity (%) | P | S? |
|---|---|---|---|---|
| 1 | | 50 | | |
| 0.5 | | 20 | | |
| 0.25 | | 0 | | |
| 0.125 | | 0 | | |
| | 1 | 0 | | |
| | 0.5 | 0 | | |
| | 0.25 | 0 | | |
| | 0.125 | 0 | | |
| 1 | 1 | 100 | 50 | y |
| 1 | 0.5 | 100 | 50 | y |

-continued

| Q.135 rate ppm | rate ppm | Activity (%) | P | S? |
|---|---|---|---|---|
| 1 | 0.25 | 100 | 50 | y |
| 0.5 | 1 | 90 | 20 | y |
| 0.5 | 0.5 | 90 | 20 | y |
| 0.5 | 0.25 | 90 | 20 | y |
| 0.5 | 0.125 | 70 | 20 | y |
| 0.25 | 1 | 70 | 0 | y |
| 0.25 | 0.5 | 50 | 0 | y |
| 0.25 | 0.25 | 50 | 0 | y |
| 0.25 | 0.125 | 50 | 0 | y |
| 0.125 | 0.5 | 20 | 0 | y |

| Q.135 rate ppm | Metconazole rate ppm | Activity (%) | P | S? |
|---|---|---|---|---|
| 0.125 | | 0 | | |
| 0.0625 | | 0 | | |
| 0.03125 | | 0 | | |
| | 0.03125 | 0 | | |
| | 0.015625 | 0 | | |
| 0.125 | 0.03125 | 70 | 0 | y |
| 0.0625 | 0.03125 | 50 | 0 | y |
| 0.0625 | 0.015625 | 20 | 0 | y |
| 0.03125 | 0.03125 | 50 | 0 | y |

| Q.135 rate ppm | cis-Jasmone rate ppm | Activity (%) | P | S? |
|---|---|---|---|---|
| 1 | | 50 | | |
| 0.5 | | 20 | | |
| 0.25 | | 0 | | |
| | 5 | 0 | | |
| | 2.5 | 0 | | |
| | 1.25 | 0 | | |
| | 0.625 | 0 | | |
| 1 | 5 | 90 | 50 | y |
| 1 | 2.5 | 90 | 50 | y |
| 0.5 | 2.5 | 50 | 20 | y |
| 0.5 | 1.25 | 50 | 20 | y |
| 0.25 | 1.25 | 20 | 0 | y |
| 0.25 | 0.625 | 20 | 0 | y |

| Q.135 rate ppm | 2,4-D rate ppm | Activity (%) | P | S? |
|---|---|---|---|---|
| 1 | | 50 | | |
| 0.5 | | 20 | | |
| | 10 | 0 | | |
| | 5 | 0 | | |
| | 2.5 | 0 | | |
| 1 | 10 | 90 | 50 | y |
| 1 | 5 | 100 | 50 | y |
| 1 | 2.5 | 90 | 50 | y |
| 0.5 | 10 | 50 | 20 | y |
| 0.5 | 5 | 50 | 20 | y |
| 0.5 | 2.5 | 50 | 20 | y |
| 0.5 | 1.25 | 50 | 20 | y |

| Q.135 rate ppm | Pyraclostrobin rate ppm | Activity (%) | P | S? |
|---|---|---|---|---|
| 1 | | 20 | | |
| 0.5 | | 0 | | |
| 0.25 | | 0 | | |
| | 0.2 | 20 | | |
| | 0.1 | 0 | | |
| | 0.05 | 0 | | |
| | 0.025 | 0 | | |
| 1 | 0.2 | 70 | 36 | y |
| 1 | 0.1 | 50 | 20 | y |
| 1 | 0.05 | 50 | 20 | y |
| 1 | 0.025 | 50 | 20 | y |
| 0.5 | 0.2 | 50 | 20 | y |
| 0.5 | 0.1 | 50 | 0 | y |
| 0.5 | 0.05 | 20 | 0 | y |
| 0.5 | 0.025 | 20 | 0 | y |
| 0.25 | 0.1 | 20 | 0 | y |
| 0.25 | 0.05 | 20 | 0 | y |

-continued

| Q.135 rate ppm | Picoxystrobin rate ppm | Activity (%) | P | S? |
|---|---|---|---|---|
| 1 | | 20 | | |
| 0.5 | | 0 | | |
| 0.25 | | 0 | | |
| 0.125 | | 0 | | |
| | 2 | 50 | | |
| | 1 | 50 | | |
| | 0.5 | 50 | | |
| | 0.25 | 50 | | |
| 1 | 2 | 90 | 60 | y |
| 1 | 1 | 90 | 60 | y |
| 1 | 0.5 | 90 | 60 | y |
| 0.5 | 2 | 90 | 50 | y |
| 0.5 | 1 | 70 | 50 | y |
| 0.5 | 0.5 | 70 | 50 | y |
| 0.5 | 0.25 | 70 | 50 | y |
| 0.25 | 1 | 70 | 50 | y |
| 0.25 | 0.58 | 70 | 50 | y |
| 0.25 | 0.25 | 70 | 50 | y |
| 0.25 | 0.5 | 70 | 50 | y |
| 0.125 | 0.25 | 70 | 50 | y |

| Q.135 rate ppm | Fenpropimorph rate ppm | Activity (%) | P | S? |
|---|---|---|---|---|
| 1 | | 50 | | |
| 0.5 | | 20 | | |
| 0.25 | | 0 | | |
| 0.125 | | 0 | | |
| 0.0625 | | 0 | | |
| | 0.25 | 0 | | |
| | 0.125 | 0 | | |
| | 0.0625 | 0 | | |
| 1 | 0.25 | 100 | 50 | y |
| 0.5 | 0.25 | 100 | 20 | y |
| 0.5 | 0.125 | 100 | 20 | y |
| 0.25 | 0.25 | 100 | 0 | y |
| 0.25 | 0.125 | 100 | 0 | y |
| 0.25 | 0.0625 | 90 | 0 | y |
| 0.125 | 0.25 | 100 | 0 | y |
| 0.125 | 0.125 | 100 | 0 | y |
| 0.125 | 0.0625 | 70 | 0 | y |
| 0.0625 | 0.25 | 90 | 0 | y |
| 0.0625 | 0.125 | 70 | 0 | y |
| 0.0625 | 0.0625 | 20 | 0 | y |

| Q.135 rate ppm | Bicyclopyrone rate ppm | Activity (%) | P | S? |
|---|---|---|---|---|
| 1 | | 50 | | |
| 0.5 | | 20 | | |
| | 5 | 0 | | |
| | 2.5 | 0 | | |
| | 1.25 | 0 | | |
| 1 | 2.5 | 70 | 50 | y |
| 1 | 5 | 70 | 50 | y |
| 0.5 | 1.25 | 50 | 20 | y |
| 0.5 | 2.5 | 50 | 20 | y |

| Q.135 rate ppm | Thiamethoxam rate ppm | Activity (%) | P | S? |
|---|---|---|---|---|
| 1 | | 50 | | |
| 0.5 | | 20 | | |
| 0.25 | | 0 | | |
| | 2.5 | 0 | | |
| | 1.25 | 0 | | |
| | 0.625 | 0 | | |
| 1 | 2.5 | 70 | 50 | y |
| 0.5 | 1.25 | 50 | 20 | y |
| 0.25 | 0.625 | 20 | 0 | y |

| Q.135 rate ppm | Mesotrione rate ppm | Activity (%) | P | S? |
|---|---|---|---|---|
| 1 | | 50 | | |
| 0.5 | | 20 | | |

| Q.135 rate ppm | Propiconazole rate ppm | Activity (%) | P | S? |
|---|---|---|---|---|
| 0.25 | | 0 | | |
| | 10 | 0 | | |
| | 5 | 0 | | |
| | 2.5 | 0 | | |
| | 1.25 | 0 | | |
| | 0.625 | 0 | | |
| 1 | 2.5 | 70 | 50 | y |
| 1 | 5 | 70 | 50 | y |
| 0.5 | 1.25 | 50 | 20 | y |
| 0.5 | 2.5 | 50 | 20 | y |
| 0.25 | 0.625 | 20 | 0 | y |
| 0.25 | 1.25 | 20 | 0 | y |
| 0.5 | 10 | 50 | 20 | y |

| Q.135 rate ppm | Propiconazole rate ppm | Activity (%) | P | S? |
|---|---|---|---|---|
| 2 | | 70 | | |
| 1 | | 50 | | |
| 0.5 | | 20 | | |
| 0.25 | | 0 | | |
| 0.125 | | 0 | | |
| | 0.5 | 50 | | |
| | 0.25 | 0 | | |
| | 0.125 | 0 | | |
| | 0.0625 | 0 | | |
| 2 | 0.5 | 100 | 85 | y |
| 1 | 0.25 | 100 | 20 | y |
| 1 | 0.5 | 100 | 60 | y |
| 0.5 | 0.125 | 70 | 20 | y |
| 0.5 | 0.25 | 90 | 20 | y |
| 0.5 | 0.5 | 100 | 60 | y |
| 0.25 | 0.0625 | 50 | 0 | y |
| 0.25 | 0.125 | 70 | 0 | y |
| 0.25 | 0.25 | 70 | 0 | y |
| 0.125 | 0.0625 | 20 | 0 | y |
| 0.125 | 0.125 | 20 | 0 | y |
| 0.25 | 0.5 | 90 | 50 | y |
| 0.125 | 0.25 | 50 | 0 | y |
| 0.125 | 0.5 | 70 | 50 | y |

| Q.135 rate ppm | Mandipropamid rate ppm | Activity (%) | P | S? |
|---|---|---|---|---|
| 2 | | 70 | | |
| 1 | | 20 | | |
| 0.5 | | 0 | | |
| | 20 | 0 | | |
| | 10 | 0 | | |
| | 5 | 0 | | |
| 2 | 10 | 90 | 70 | y |
| 2 | 20 | 90 | 70 | y |
| 1 | 5 | 50 | 20 | y |
| 1 | 10 | 50 | 20 | y |
| 0.5 | 5 | 20 | 0 | y |
| 1 | 20 | 50 | 20 | y |
| 0.5 | 10 | 20 | 0 | y |
| 0.5 | 20 | 20 | 0 | y |

| Q.135 rate ppm | Chlorotalonil rate ppm | Activity (%) | P | S? |
|---|---|---|---|---|
| 0.5 | | 20 | | |
| 0.25 | | 0 | | |
| 0.125 | | 0 | | |
| 0.0625 | | 0 | | |
| | 0.25 | 20 | | |
| | 0.125 | 0 | | |
| | 0.0625 | 0 | | |
| 0.5 | 0.25 | 90 | 36 | y |
| 0.5 | 0.125 | 50 | 20 | y |
| 0.25 | 0.25 | 90 | 20 | y |
| 0.25 | 0.125 | 50 | 0 | y |
| 0.25 | 0.0625 | 20 | 0 | y |
| 0.125 | 0.25 | 50 | 20 | y |
| 0.125 | 0.125 | 50 | 0 | y |
| 0.125 | 0.0625 | 20 | 0 | y |
| 0.0625 | 0.25 | 50 | 20 | y |

| Q.135 rate ppm | Chlorotalonil rate ppm | Activity (%) | P | S? |
|---|---|---|---|---|
| 0.0625 | 0.125 | 20 | 0 | y |
| 0.0625 | 0.0625 | 20 | 0 | y |

| Q.135 rate ppm | Trinexapacethyl rate ppm | Activity (%) | P | S? |
|---|---|---|---|---|
| 1 | | 50 | | |
| 0.5 | | 20 | | |
| 0.25 | | 0 | | |
| | 20 | 0 | | |
| | 10 | 0 | | |
| | 5 | 0 | | |
| | 2.5 | 0 | | |
| | 1.25 | 0 | | |
| 1 | 20 | 90 | 50 | y |
| 1 | 10 | 90 | 50 | y |
| 1 | 5 | 90 | 50 | y |
| 1 | 2.5 | 90 | 50 | y |
| 0.5 | 20 | 70 | 20 | y |
| 0.5 | 10 | 50 | 20 | y |
| 0 | 5 | 50 | 20 | y |
| 0.5 | 2.5 | 50 | 20 | y |
| 0.5 | 1.25 | 50 | 20 | y |
| 0.25 | 10 | 20 | 0 | y |
| 0.25 | 5 | 20 | 0 | y |
| 0.25 | 1.25 | 20 | 0 | y |

| Q.135 rate ppm | Paclobutrazol rate ppm | Activity (%) | P | S? |
|---|---|---|---|---|
| 0.5 | | 20 | | |
| 0.25 | | 0 | | |
| 0.125 | | 0 | | |
| 0.0625 | | 0 | | |
| | 2.5 | 0 | | |
| | 1.25 | 0 | | |
| | 0.625 | 0 | | |
| 0.5 | 2.5 | 100 | 20 | y |
| 0.5 | 1.25 | 100 | 20 | y |
| 0.25 | 2.5 | 100 | 0 | y |
| 0.25 | 1.25 | 90 | 0 | y |
| 0.25 | 0.625 | 70 | 0 | y |
| 0.125 | 2.5 | 100 | 0 | y |
| 0.125 | 1.25 | 70 | 0 | y |
| 0.125 | 0.625 | 50 | 0 | y |
| 0.0625 | 2.5 | 100 | 0 | y |
| 0.0625 | 1.25 | 50 | 0 | y |

| Q.135 rate ppm | Azoxystrobin rate ppm | Activity (%) | P | S? |
|---|---|---|---|---|
| 2 | | 50 | | |
| 1 | | 20 | | |
| 0.5 | | 0 | | |
| 0.25 | | 0 | | |
| | 0.2 | 20 | | |
| | 0.1 | 0 | | |
| | 0.05 | 0 | | |
| | 0.025 | 0 | | |
| 2 | 0.1 | 90 | 50 | y |
| 2 | 0.05 | 70 | 50 | y |
| 1 | 0.2 | 70 | 36 | y |
| 1 | 0.1 | 50 | 20 | y |
| 1 | 0.05 | 50 | 20 | y |
| 1 | 0.025 | 50 | 20 | y |
| 0.5 | 0.2 | 50 | 20 | y |
| 0.5 | 0.1 | 50 | 0 | y |
| 0.5 | 0.05 | 20 | 0 | y |
| 0.5 | 0.025 | 20 | 0 | y |
| 0.25 | 0.1 | 50 | 0 | y |
| 0.25 | 0.05 | 20 | 0 | y |
| 0.25 | 0.025 | 20 | 0 | y |

| Q.135 rate ppm | Trifloxystrobin rate ppm | Activity (%) | P | S? |
|---|---|---|---|---|
| 0.5 | | 20 | | |
| 0.25 | | 0 | | |
| | 0.1 | 50 | | |
| | 0.05 | 50 | | |
| | 0.025 | 20 | | |
| | 0.0125 | 0 | | |
| 0.5 | 0.025 | 50 | 36 | y |
| 0.5 | 0.0125 | 50 | 20 | y |
| 0.25 | 0.1 | 70 | 50 | y |
| 0.25 | 0.05 | 50 | 50 | y |
| 0.25 | 0.025 | 50 | 20 | y |
| 0.25 | 0.0125 | 20 | 0 | y |

| Q.135 rate ppm | Fludioxonil rate ppm | Activity (%) | P | S? |
|---|---|---|---|---|
| 0.25 | | 0 | | |
| 0.125 | | 0 | | |
| 0.0625 | | 0 | | |
| 0.03125 | | 0 | | |
| | 0.0625 | 70 | | |
| | 0.03125 | 0 | | |
| 0.25 | 0.0625 | 100 | 70 | y |
| 0.125 | 0.0625 | 100 | 70 | y |
| 0.125 | 0.03125 | 50 | 0 | y |
| 0.0625 | 0.0625 | 100 | 70 | y |
| 0.0625 | 0.03125 | 50 | 0 | y |
| 0.03125 | 0.0625 | 100 | 70 | y |
| 0.03125 | 0.03125 | 50 | 0 | y |

| Q.135 rate ppm | Copper hydroxide rate ppm | Activity (%) | P | S? |
|---|---|---|---|---|
| 1 | | 50 | | |
| 0.5 | | 20 | | |
| | 5 | 0 | | |
| | 2.5 | 0 | | |
| | 1.25 | 0 | | |
| 1 | 2.5 | 70 | 50 | y |
| 1 | 5 | 70 | 50 | y |
| 0.5 | 1.25 | 50 | 20 | y |
| 0.5 | 2.5 | 50 | 20 | y |

| Q.135 rate ppm | Abamectin rate ppm | Activity (%) | P | S? |
|---|---|---|---|---|
| 1 | | 50 | | |
| 0.5 | | 20 | | |
| 0.25 | | 0 | | |
| | 20 | 0 | | |
| | 10 | 0 | | |
| | 5 | 0 | | |
| | 2.5 | 0 | | |
| | 1.25 | 0 | | |
| 1 | 2.5 | 90 | 50 | y |
| 1 | 5 | 90 | 50 | y |
| 1 | 10 | 70 | 50 | y |
| 0.5 | 1.25 | 50 | 20 | y |
| 0.5 | 2.5 | 70 | 20 | y |
| 0.5 | 5 | 50 | 20 | y |
| 1 | 20 | 70 | 50 | y |
| 0.25 | 1.25 | 20 | 0 | y |
| 0.25 | 2.5 | 20 | 0 | y |
| 0.5 | 10 | 50 | 20 | y |
| 0.25 | 5 | 50 | 0 | y |
| 0.5 | 20 | 50 | 20 | y |
| 0.25 | 10 | 50 | 0 | y |

| Q.135 rate ppm | Prothioconazole rate ppm | Activity (%) | P | S? |
|---|---|---|---|---|
| 0.5 | | 20 | | |
| 0.25 | | 0 | | |
| 0.125 | | 0 | | |
| | 0.05 | 50 | | |
| | 0.025 | 0 | | |
| | 0.0125 | 0 | | |
| | 0.00625 | 0 | | |
| 2 | 0.05 | 100 | 85 | y |
| 1 | 0.025 | 100 | 20 | y |
| 1 | 0.05 | 100 | 60 | y |
| 0.5 | 0.0125 | 90 | 20 | y |
| 0.5 | 0.025 | 100 | 20 | y |
| 0.5 | 0.05 | 100 | 60 | y |
| 0.25 | 0.00625 | 50 | 0 | y |
| 0.25 | 0.0125 | 70 | 0 | y |
| 0.25 | 0.025 | 90 | 0 | y |
| 0.125 | 0.00625 | 20 | 0 | y |
| 0.125 | 0.0125 | 50 | 0 | y |
| 0.125 | 0.05 | 100 | 50 | y |
| 0.125 | 0.025 | 70 | 0 | y |
| 0.125 | 0.05 | 100 | 50 | y |

| Q.135 rate ppm | Glufosinate rate ppm | Activity (%) | P | S? |
|---|---|---|---|---|
| 1 | | 20 | | |
| 0.5 | | 0 | | |
| 0.25 | | 0 | | |
| | 20 | 0 | | |
| | 10 | 0 | | |
| | 5 | 0 | | |
| | 2.5 | 0 | | |
| 1 | 2.5 | 50 | 20 | y |
| 1 | 5 | 50 | 20 | y |
| 0.5 | 2.5 | 20 | 0 | y |
| 1 | 20 | 50 | 20 | y |
| 0.5 | 10 | 20 | 0 | y |
| 0.5 | 20 | 20 | 0 | y |
| 0.5 | 10 | 20 | 0 | y |

| Q.135 rate ppm | Procymidone rate ppm | Activity (%) | P | S? |
|---|---|---|---|---|
| 1 | | 20 | | |
| 0.5 | | 0 | | |
| 0.25 | | 0 | | |
| | 2.5 | 50 | | |
| | 1.25 | 0 | | |
| 1 | 2.5 | 100 | 60 | y |
| 0.5 | 1.25 | 50 | 0 | y |
| 0.25 | 2.5 | 90 | 50 | y |

| Q.113 rate ppm | Fluxapyroxad rate ppm | Activity (%) | P | S? |
|---|---|---|---|---|
| 0.03125 | | 0 | | |
| 0.015625 | | 0 | | |
| 0.0078125 | | 0 | | |
| 0.00390625 | | 0 | | |
| | 0.0625 | 50 | | |
| | 0.03125 | 50 | | |
| | 0.015625 | 20 | | |
| | 0.0078125 | 20 | | |
| 0.03125 | 0.0625 | 70 | 50 | y |
| 0.015625 | 0.03125 | 70 | 50 | y |
| 0.0078125 | 0.015625 | 50 | 20 | y |
| 0.00390625 | 0.0078125 | 20 | 20 | y |
| 0.015625 | 0.0625 | 70 | 50 | y |
| 0.0078125 | 0.03125 | 70 | 50 | y |
| 0.00390625 | 0.015625 | 50 | 20 | y |

| Q.113 rate ppm | Pyraclostrobin rate ppm | Activity (%) | P | S? |
|---|---|---|---|---|
| 2 | | 0 | | |
| 1 | | 0 | | |
| 0.5 | | 0 | | |
| | 2 | 70 | | |
| | 0.25 | 50 | | |
| 2 | 2 | 90 | 70 | y |
| 1 | 2 | 90 | 70 | y |

| Q.113 rate ppm | Chlorotalonil rate ppm | Activity (%) | P | S? |
|---|---|---|---|---|
| 1 | 0.25 | 70 | 50 | y |
| 0.5 | 2 | 90 | 70 | y |

| Q.113 rate ppm | Chlorotalonil rate ppm | Activity (%) | P | S? |
|---|---|---|---|---|
| 1 | | 0 | | |
| 0.5 | | 0 | | |
| 0.25 | | 0 | | |
| | 0.25 | 20 | | |
| 1 | 0.25 | 50 | 20 | y |
| 0.5 | 0.25 | 70 | 20 | y |
| 0.25 | 0.25 | 70 | 20 | y |

| Q.113 rate ppm | Flutriafol rate ppm | Activity (%) | P | S? |
|---|---|---|---|---|
| 2 | | 0 | | |
| 1 | | 0 | | |
| | 2 | 0 | | |
| | 1 | 0 | | |
| 2 | 2 | 50 | 0 | y |
| 2 | 1 | 20 | 0 | y |
| 1 | 2 | 20 | 0 | y |

| Q.113 rate ppm | Fludioxonil rate ppm | Activity (%) | P | S? |
|---|---|---|---|---|
| 0.25 | | 0 | | |
| 0.125 | | 0 | | |
| 0.0625 | | 0 | | |
| 0.03125 | | 0 | | |
| | 0.0625 | 70 | | |
| | 0.03125 | 0 | | |
| 0.25 | 0.03125 | 70 | 70 | |
| 0.125 | 0.0625 | 20 | 0 | y |
| 0.125 | 0.03125 | 90 | 70 | y |
| 0.0625 | 0.0625 | 90 | 70 | y |
| 0.0625 | 0.03125 | 20 | 0 | y |
| 0.03125 | 0.0625 | 20 | 0 | y |

| Q.113 rate ppm | Fenpropimorph rate ppm | Activity (%) | P | S? |
|---|---|---|---|---|
| 2 | | 0 | | |
| 1 | | 0 | | |
| 0.5 | | 0 | | |
| 0.25 | | 0 | | |
| 0.125 | | 0 | | |
| | 0.5 | 70 | | |
| | 0.25 | 0 | | |
| | 0.125 | 0 | | |
| 2 | 0.5 | 100 | 70 | y |
| 1 | 0.5 | 100 | 70 | y |
| 1 | 0.25 | 100 | 0 | y |
| 0.5 | 0.5 | 100 | 70 | y |
| 0.5 | 0.25 | 70 | 0 | y |
| 0.5 | 0.125 | 20 | 0 | y |
| 0.25 | 0.5 | 100 | 70 | y |
| 0.25 | 0.25 | 70 | 0 | y |
| 0.125 | 0.5 | 90 | 70 | y |
| 0.125 | 0.25 | 20 | 0 | y |

| Q.113 rate ppm | Compound (VI) rate ppm | Activity (%) | P | S? |
|---|---|---|---|---|
| 0.25 | | 0 | | |
| 0.125 | | 0 | | |
| 0.0625 | | 0 | | |
| 0.03125 | | 0 | | |
| 0.015625 | | 0 | | |
| 0.0078125 | | 0 | | |
| | 0.0625 | 70 | | |
| | 0.03125 | 70 | | |
| | 0.015625 | 50 | | |
| | 0.0078125 | 20 | | |
| 0.25 | 0.0625 | 90 | 70 | y |
| 0.125 | 0.0625 | 90 | 70 | y |
| 0.0625 | 0.0625 | 90 | 70 | y |
| 0.03125 | 0.0625 | 90 | 70 | y |
| 0.015625 | 0.0625 | 90 | 70 | y |
| 0.015625 | 0.015625 | 70 | 50 | y |
| 0.015625 | 0.03125 | 70 | 70 | |
| 0.0078125 | 0.0078125 | 50 | 20 | y |
| 0.0078125 | 0.015625 | 70 | 50 | y |

| Q.113 rate ppm | Azoxystrobin rate ppm | Activity (%) | P | S? |
|---|---|---|---|---|
| 0.5 | | 0 | | |
| 0.25 | | 0 | | |
| 0.125 | | 0 | | |
| 0.0625 | | 0 | | |
| 0.03125 | | 0 | | |
| | 0.25 | 20 | | |
| | 0.125 | 0 | | |
| 0.5 | 0.125 | 20 | 0 | y |
| 0.25 | 0.125 | 20 | 0 | y |
| 0.125 | 0.125 | 20 | 0 | y |
| 0.125 | 0.25 | 50 | 20 | y |
| 0.0625 | 0.125 | 20 | 0 | y |
| 0.0625 | 0.25 | 50 | 20 | y |
| 0.03125 | 0.125 | 20 | 0 | y |

| Q.113 rate ppm | Picoxystrobin rate ppm | Activity (%) | P | S? |
|---|---|---|---|---|
| 2 | | 0 | | |
| 1 | | 0 | | |
| 0.5 | | 0 | | |
| | 2 | 50 | | |
| | 1 | 50 | | |
| | 0.5 | 50 | | |
| 2 | 2 | 70 | 50 | y |
| 2 | 1 | 70 | 50 | y |
| 2 | 0.5 | 70 | 50 | y |
| 1 | 2 | 70 | 50 | y |
| 1 | 1 | 70 | 50 | y |
| 0.5 | 2 | 70 | 50 | y |

| Q.113 rate ppm | Trifloxystrobin rate ppm | Activity (%) | P | S? |
|---|---|---|---|---|
| 2 | | 0 | | |
| 1 | | 0 | | |
| 0.5 | | 0 | | |
| | 2 | 50 | | |
| | 1 | 50 | | |
| | 0.5 | 50 | | |
| 2 | 2 | 70 | 50 | y |
| 2 | 1 | 70 | 50 | y |
| 2 | 0.5 | 70 | 50 | y |
| 1 | 2 | 70 | 50 | y |
| 1 | 1 | 70 | 50 | y |
| 0.5 | 2 | 70 | 50 | y |

| Q.113 rate ppm | Prothioconazole rate ppm | Activity (%) | P | S? |
|---|---|---|---|---|
| 2 | | 0 | | |
| 1 | | 0 | | |
| 0.5 | | 0 | | |
| 0.25 | | 0 | | |
| 0.125 | | 0 | | |
| | 0.05 | 70 | | |
| | 0.025 | 0 | | |
| 2 | 0.05 | 90 | 70 | y |
| 1 | 0.025 | 50 | 0 | y |
| 1 | 0.05 | 90 | 70 | y |
| 0.5 | 0.025 | 20 | 0 | y |
| 0.5 | 0.05 | 90 | 70 | y |
| 0.25 | 0.025 | 0 | 0 | |
| 0.25 | 0.05 | 100 | 70 | y |
| 0.125 | 0.025 | 20 | 0 | y |
| 0.125 | 0.05 | 90 | 70 | y |

| Q.113 rate ppm | Propiconazole rate ppm | Activity (%) | P | S? |
|---|---|---|---|---|
| 2 | | 0 | | |
| 1 | | 0 | | |
| 0.5 | | 0 | | |
| 0.25 | | 0 | | |
| 0.125 | | 0 | | |
| | 0.5 | 50 | | |
| | 0.25 | 0 | | |
| 2 | 0.5 | 70 | 50 | y |
| 1 | 0.25 | 20 | 0 | y |
| 1 | 0.5 | 70 | 50 | y |
| 0.5 | 0.25 | 20 | 0 | y |
| 0.5 | 0.5 | 70 | 50 | y |
| 0.25 | 0.25 | 0 | 0 | |
| 0.25 | 0.5 | 70 | 50 | y |
| 0.125 | 0.25 | 20 | 0 | y |

| Q.062 rate ppm | Fluxapyroxad rate ppm | Activity (%) | P | S? |
|---|---|---|---|---|
| 0.03125 | | 0 | | |
| 0.015625 | | 0 | | |
| 0.0078125 | | 0 | | |
| 0.00390625 | | 0 | | |
| | 0.125 | 70 | | |
| | 0.0625 | 50 | | |
| | 0.03125 | 50 | | |
| | 0.015625 | 20 | | |
| 0.03125 | 0.0625 | 70 | 50 | y |
| 0.03125 | 0.125 | 90 | 70 | y |
| 0.015625 | 0.0625 | 70 | 50 | y |
| 0.0078125 | 0.03125 | 70 | 50 | y |
| 0.00390625 | 0.015625 | 50 | 20 | y |
| 0.0078125 | 0.015625 | 50 | 20 | y |

| Q.062 rate ppm | Pyraclostrobin rate ppm | Activity (%) | P | S? |
|---|---|---|---|---|
| 2 | | 0 | | |
| 1 | | 0 | | |
| 0.5 | | 0 | | |
| | 2 | 70 | | |
| 2 | 2 | 90 | 70 | y |
| 1 | 2 | 90 | 70 | y |
| 0.5 | 2 | 90 | 70 | y |

| Q.062 rate ppm | Chlorotalonil rate ppm | Activity (%) | P | S? |
|---|---|---|---|---|
| 1 | | 0 | | |
| 0.5 | | 0 | | |
| 0.25 | | 0 | | |
| | 0.25 | 20 | | |
| 1 | 0.25 | 50 | 20 | y |
| 0.5 | 0.25 | 50 | 20 | y |
| 0.25 | 0.25 | 50 | 20 | y |

| Q.062 rate ppm | Picoxystrobin rate ppm | Activity (%) | P | S? |
|---|---|---|---|---|
| 2 | | 0 | | |
| 1 | | 0 | | |
| 0.5 | | 0 | | |
| | 2 | 50 | | |
| | 1 | 50 | | |
| | 0.5 | 50 | | |
| 2 | 2 | 70 | 50 | y |
| 2 | 1 | 70 | 50 | y |
| 2 | 0.5 | 70 | 50 | y |
| 1 | 2 | 70 | 50 | y |
| 1 | 1 | 70 | 50 | y |
| 1 | 0.5 | 70 | 50 | y |
| 0.5 | 2 | 70 | 50 | y |
| 0.5 | 1 | 70 | 50 | y |

| Q.062 rate ppm | Fludioxonil rate ppm | Activity (%) | P | S? |
|---|---|---|---|---|
| 0.25 | | 0 | | |
| 0.1258 | | 0 | | |
| 0.0625 | | 0 | | |
| 0.03125 | | 0 | | |
| | 0.0625 | 50 | | |
| | 0.03125 | 0 | | |
| 0.25 | 0.03125 | 90 | 50 | y |
| 0.125 | 0.0625 | 20 | 0 | y |
| 0.125 | 0.03125 | 90 | 50 | y |
| 0.0625 | 0.0625 | 100 | 50 | y |
| 0.0625 | 0.03125 | 20 | 0 | y |
| 0.03125 | 0.0625 | 20 | 0 | y |

| .062 rate ppm | Prothioconazole rate ppm | Activity (%) | P | S? |
|---|---|---|---|---|
| 2 | | 0 | | |
| 1 | | 0 | | |
| 0.5 | | 0 | | |
| 0.25 | | 0 | | |
| 0.125 | | 0 | | |
| | 0.05 | 50 | | |
| | 0.025 | 0 | | |
| 2 | 0.05 | 100 | 50 | y |
| 1 | 0.025 | 50 | 0 | y |
| 1 | 0.05 | 100 | 50 | y |
| 0.5 | 0.025 | 50 | 0 | y |
| 0.5 | 0.05 | 90 | 50 | y |
| 0.25 | 0.025 | 20 | 0 | y |
| 0.25 | 0.05 | 90 | 50 | y |
| 0.125 | 0.025 | 20 | 0 | y |
| 0.125 | 0.05 | 90 | 50 | y |

| Q.062 rate ppm | Flutriafol rate ppm | Activity (%) | P | S? |
|---|---|---|---|---|
| 2 | | 0 | | |
| 1 | | 0 | | |
| 0.5 | | 0 | | |
| | 2 | 0 | | |
| | 1 | 0 | | |
| | 0.5 | 0 | | |
| 2 | 2 | 50 | 0 | y |
| 2 | 1 | 20 | 0 | y |
| 2 | 0.5 | 20 | 0 | y |
| 1 | 2 | 20 | 0 | y |
| 0.5 | 2 | 20 | 0 | y |

| Q.062 rate ppm | Paclobutrazol rate ppm | Activity (%) | P | S? |
|---|---|---|---|---|
| 1 | | 0 | | |
| 0.5 | | 0 | | |
| 0.25 | | 0 | | |
| 0.125 | | 0 | | |
| | 5 | 70 | | |
| | 2.5 | 0 | | |
| | 1.25 | 0 | | |
| 1 | 5 | 100 | 70 | y |
| 1 | 2.5 | 70 | 0 | y |
| 0.5 | 5 | 100 | 70 | y |
| 0.5 | 2.5 | 20 | 0 | y |
| 0.5 | 1.25 | 20 | 0 | y |
| 0.25 | 5 | 100 | 70 | y |
| 0.125 | 5 | 100 | 70 | y |
| 0.125 | 2.5 | 100 | 0 | y |

| Q.062 rate ppm | Fenpropimorph rate ppm | Activity (%) | P | S? |
|---|---|---|---|---|
| 2 | | 0 | | |
| 1 | | 0 | | |
| 0.5 | | 0 | | |
| 0.25 | | 0 | | |

707

| | | | | |
|---|---|---|---|---|
| 0.125 | | 0 | | |
| | 0.5 | 70 | | |
| | 0.25 | 0 | | |
| | 0.125 | 0 | | |
| 2 | 0.5 | 100 | 70 | y |
| 1 | 0.5 | 100 | 70 | y |
| 1 | 0.25 | 100 | 0 | y |
| 0.5 | 0.5 | 100 | 70 | y |
| 0.5 | 0.25 | 70 | 0 | y |
| 0.5 | 0.125 | 20 | 0 | y |
| 0.25 | 0.5 | 100 | 70 | y |
| 0.25 | 0.25 | 70 | 0 | y |
| 0.125 | 0.5 | 90 | 70 | y |
| 0.125 | 0.25 | 20 | 0 | y |

| Q.062 rate ppm | Procymidone rate ppm | Activity (%) | P | S? |
|---|---|---|---|---|
| 0.125 | | 0 | | |
| 0.0625 | | 0 | | |
| 0.03125 | | 0 | | |
| 0.015625 | | 0 | | |
| | 1.25 | 0 | | |
| | 0.625 | 0 | | |
| | 0.3125 | 0 | | |
| 0.125 | 1.25 | 70 | 0 | y |
| 0.0625 | 1.25 | 100 | 0 | y |
| 0.03125 | 1.25 | 90 | 0 | y |
| 0.015625 | 0.625 | 70 | 0 | y |
| 0.015625 | 0.3125 | 50 | 0 | y |

| Q.062 rate ppm | Propiconazole rate ppm | Activity (%) | P | S? |
|---|---|---|---|---|
| 2 | | 0 | | |
| 1 | | 0 | | |
| 0.5 | | 0 | | |
| 0.25 | | 0 | | |
| 0.125 | | 0 | | |
| | 0.5 | 50 | | |
| | 0.25 | 0 | | |
| 2 | 0.5 | 90 | 50 | y |
| 1 | 0.25 | 50 | 0 | y |
| 1 | 0.5 | 70 | 50 | y |
| 0.5 | 0.25 | 20 | 0 | y |
| 0.5 | 0.5 | 70 | 50 | y |
| 0.25 | 0.25 | 0 | 0 | |
| 0.25 | 0.5 | 70 | 50 | y |
| 0.125 | 0.25 | 20 | 0 | y |

*Septoria tritici* (Leaf Blotch)

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the activity was determined visually after 72 hrs.

| Q.135 rate ppm | Fluxapyroxad rate ppm | Activity (%) | P | S? |
|---|---|---|---|---|
| 0.03125 | | 0 | | |
| 0.015625 | | 0 | | |
| 0.0078125 | | 0 | | |
| 0.00390625 | | 0 | | |
| | 0.0625 | 20 | | |
| | 0.03125 | 0 | | |
| | 0.015625 | 0 | | |
| 0.03125 | 0.0625 | 70 | 20 | y |
| 0.015625 | 0.03125 | 20 | 0 | y |
| 0.015625 | 0.0625 | 90 | 20 | y |
| 0.0078125 | 0.03125 | 50 | 0 | y |
| 0.00390625 | 0.015625 | 20 | 0 | y |

708

| Q.135 rate ppm | Metconazole rate ppm | % Activity | P | S? |
|---|---|---|---|---|
| 0.25 | | 0 | | |
| 0.125 | | 0 | | |
| 0.0625 | | 0 | | |
| 0.03125 | | 0 | | |
| | 0.0625 | 70 | | |
| | 0.03125 | 0 | | |
| 0.25 | 0.0625 | 90 | 70 | y |
| 0.125 | 0.0625 | 90 | 70 | y |
| 0.125 | 0.03125 | 50 | 0 | y |
| 0.0625 | 0.0625 | 100 | 70 | y |
| 0.0625 | 0.03125 | 20 | 0 | y |
| 0.03125 | 0.03125 | 20 | 0 | y |

| Q.135 rate ppm | Paclobutrazol rate ppm | Activity (%) | P | S? |
|---|---|---|---|---|
| 1 | | 0 | | |
| 0.5 | | 0 | | |
| 0.25 | | 0 | | |
| 0.125 | | 0 | | |
| | 5 | 50 | | |
| | 2.5 | 0 | | |
| | 1.25 | 0 | | |
| | 0.625 | 0 | | |
| 1 | 2.5 | 50 | 0 | y |
| 1 | 5 | 70 | 50 | y |
| 0.5 | 5 | 90 | 50 | y |
| 0.5 | 2.5 | 50 | 0 | y |
| 0.5 | 1.25 | 20 | 0 | y |
| 0.25 | 5 | 70 | 50 | y |
| 0.25 | 2.5 | 50 | 0 | y |
| 0.25 | 1.25 | 20 | 0 | y |
| 0.25 | 0.625 | 20 | 0 | y |
| 0.125 | 5 | 70 | 50 | y |
| 0.125 | 2.5 | 50 | 0 | y |
| 0.125 | 1.25 | 20 | 0 | y |
| 0.125 | 0.625 | 20 | 0 | y |

| Q.135 rate ppm | Fluopyram rate ppm | Activity (%) | P | S? |
|---|---|---|---|---|
| 1 | | 0 | | |
| 0.5 | | 0 | | |
| 0.25 | | 0 | | |
| | 0.25 | 50 | | |
| 1 | 0.25 | 90 | 50 | y |
| 0.5 | 0.25 | 70 | 50 | y |
| 0.25 | 0.25 | 70 | 50 | y |

| Q.135 rate ppm | Prothioconazole rate ppm | Activity (%) | P | S? |
|---|---|---|---|---|
| 0.5 | | 0 | | |
| 0.25 | | 0 | | |
| 0.125 | | 0 | | |
| 0.0625 | | 0 | | |
| 0.03125 | | 0 | | |
| | 0.0125 | 70 | | |
| 0.5 | 0.0125 | 90 | 70 | y |
| 0.25 | 0.0125 | 90 | 70 | y |
| 0.125 | 0.0125 | 90 | 70 | y |
| 0.0625 | 0.0125 | 90 | 70 | y |
| 0.03125 | 0.0125 | 90 | 70 | y |

| Q.135 rate ppm | Propiconazole rate ppm | Activity (%) | P | S? |
|---|---|---|---|---|
| 0.5 | | 0 | | |
| 0.25 | | 0 | | |
| 0.125 | | 0 | | |
| 0.0625 | | 0 | | |
| 0.03125 | | 0 | | |
| | 0.125 | 50 | | |
| 0.5 | 0.125 | 90 | 50 | y |
| 0.25 | 0.125 | 90 | 50 | y |
| 0.125 | 0.125 | 90 | 50 | y |

| Q.135 rate ppm | Flutriafol rate ppm | Activity (%) | P | S? |
|---|---|---|---|---|
| 0.0625 | 0.125 | 90 | 50 | y |
| 0.03125 | 0.125 | 90 | 50 | y |

| Q.135 rate ppm | Flutriafol rate ppm | Activity (%) | P | S? |
|---|---|---|---|---|
| 2 | | 0 | | |
| 1 | | 0 | | |
| 0.5 | | 0 | | |
| | 1 | 0 | | |
| | 0.5 | 0 | | |
| 2 | 1 | 90 | 0 | y |
| 2 | 0.5 | 50 | 0 | y |
| 1 | 1 | 70 | 0 | y |
| 1 | 0.5 | 20 | 0 | y |
| 0.5 | 1 | 50 | 0 | y |
| 0.5 | 0.5 | 20 | 0 | y |

| Q.135 rate ppm | Mandipropamid rate ppm | % Activity | P | S? |
|---|---|---|---|---|
| | 2 | 0 | | |
| 1 | | 0 | | |
| 0.5 | | 0 | | |
| 0.25 | | 0 | | |
| | 0.5 | 70 | | |
| 2 | 0.5 | 700 | 70 | y |
| 1 | 0.5 | 90 | 70 | y |
| 0.5 | 0.5 | 70 | 70 | y |
| 0.25 | 0.5 | 90 | 70 | y |

| Q.135 rate ppm | Penflufen rate ppm | Activity (%) | P | S? |
|---|---|---|---|---|
| 2 | | 0 | | |
| 1 | | 0 | | |
| 0.5 | | 0 | | |
| | 0.5 | 70 | | |
| | 0.25 | 20 | | |
| | 0.125 | 0 | | |
| 2 | 0.5 | 100 | 70 | y |
| 1 | 0.5 | 90 | 70 | y |
| 1 | 0.25 | 70 | 20 | y |
| 0.5 | 0.25 | 50 | 20 | y |
| 0.5 | 0.125 | 20 | 0 | y |

| Q.135 rate ppm | Fluazinam rate ppm | Activity (%) | P | S? |
|---|---|---|---|---|
| 0.015625 | | 0 | | |
| 0.0078125 | | 0 | | |
| 0.00390625 | | 0 | | |
| | 0.03125 | 20 | | |
| | 0.015625 | 0 | | |
| 0.015625 | 0.03125 | 50 | 20 | y |
| 0.0078125 | 0.03125 | 50 | 20 | y |
| 0.0078125 | 0.015625 | 20 | 0 | y |
| 0.00390625 | 0.015625 | 20 | 0 | y |

| Q.113 rate ppm | Fluxapyroxad rate ppm | Activity (%) | P | S? |
|---|---|---|---|---|
| 0.03125 | | 0 | | |
| 0.015625 | | 0 | | |
| 0.0078125 | | 0 | | |
| 0.00390625 | | 0 | | |
| | 0.0625 | 20 | | |
| | 0.03125 | 0 | | |
| | 0.015625 | 0 | | |
| 0.03125 | 0.0625 | 70 | 20 | y |
| 0.015625 | 0.03125 | 20 | 0 | y |
| 0.015625 | 0.0625 | 90 | 20 | y |
| 0.0078125 | 0.03125 | 50 | 0 | y |
| 0.00390625 | 0.015625 | 20 | 0 | y |

| Q.113 rate ppm | Flutriafol rate ppm | Activity (%) | P | S? |
|---|---|---|---|---|
| 2 | | 0 | | |
| 1 | | 0 | | |
| 0.5 | | 0 | | |
| | 1 | 0 | | |
| | 0.5 | 0 | | |
| 2 | 1 | 70 | 0 | y |
| 2 | 0.5 | 20 | 0 | y |
| 1 | 1 | 70 | 0 | y |
| 1 | 0.5 | 20 | 0 | y |
| 0.5 | 1 | 70 | 0 | y |
| 0.5 | 0.5 | 20 | 0 | y |

| Q.113 rate ppm | Paclobutrazol rate ppm | Activity (%) | P | S? |
|---|---|---|---|---|
| 0.5 | | 0 | | |
| 0.125 | | 0 | | |
| 0.0625 | | 0 | | |
| 0.03125 | | 0 | | |
| 0.015625 | | 0 | | |
| | 2.5 | 50 | | |
| | 0.625 | 0 | | |
| | 0.3125 | 20 | | |
| | 0.15625 | 0 | | |
| 0.5 | 2.5 | 90 | 50 | y |
| 0.125 | 2.5 | 70 | 0 | y |
| 0.0625 | 0.625 | 70 | 50 | y |
| 0.03125 | 0.15625 | 20 | 0 | y |
| 0.015625 | 0.3125 | 70 | 20 | y |

| Q.113 rate ppm | Picoxystrobin rate ppm | Activity (%) | P | S? |
|---|---|---|---|---|
| 0.0078125 | | 0 | | |
| 0.00390625 | | 0 | | |
| | 0.03125 | 90 | | |
| | 0.015625 | 70 | | |
| | 0.0078125 | 50 | | |
| 0.0078125 | 0.03125 | 90 | 70 | y |
| 0.0078125 | 0.015625 | 90 | 70 | y |
| 0.00390625 | 0.0078125 | 70 | 50 | y |

| Q.113 rate ppm | Fluazinam rate ppm | Activity (%) | P | S? |
|---|---|---|---|---|
| 0.015625 | | 0 | | |
| 0.0078125 | | 0 | | |
| 0.00390625 | | 0 | | |
| | 0.03125 | 20 | | |
| | 0.015625 | 0 | | |
| 0.015625 | 0.03125 | 50 | 20 | y |
| 0.0078125 | 0.03125 | 50 | 20 | y |
| 0.0078125 | 0.015625 | 20 | 0 | y |
| 0.00390625 | 0.015625 | 20 | 0 | y |

| Q.113 rate ppm | Fludioxonil rate ppm | Activity (%) | P | S? |
|---|---|---|---|---|
| 1 | | 0 | | |
| 0.5 | | 0 | | |
| 0.25 | | 0 | | |
| | 0.25 | 70 | | |
| 1 | 0.25 | 90 | 70 | y |
| 0.5 | 0.25 | 90 | 70 | y |
| 0.25 | 0.25 | 90 | 70 | y |

| Q.113 rate ppm | Prothioconazole rate ppm | Activity (%) | P | S? |
|---|---|---|---|---|
| 0.5 | | 0 | | |
| 0.25 | | 0 | | |
| 0.125 | | 0 | | |
| 0.0625 | | 0 | | |
| 0.03125 | | 0 | | |
| | 0.0125 | 70 | | |
| 0.5 | 0.0125 | 90 | 70 | y |

711 -continued

| Q rate ppm | rate ppm | Activity (%) | P | S? |
|---|---|---|---|---|
| 0.25 | 0.0125 | 90 | 70 | y |
| 0.125 | 0.0125 | 90 | 70 | y |
| 0.0625 | 0.0125 | 90 | 70 | y |
| 0.03125 | 0.0125 | 90 | 70 | y |

| Q.113 rate ppm | Propiconazole rate ppm | Activity (%) | P | S? |
|---|---|---|---|---|
| 0.5 | | 0 | | |
| 0.25 | | 0 | | |
| 0.125 | | 0 | | |
| 0.0625 | | 0 | | |
| 0.03125 | | 0 | | |
| | 0.125 | 50 | | |
| 0.5 | 0.125 | 90 | 50 | y |
| 0.25 | 0.125 | 70 | 50 | y |
| 0.125 | 0.125 | 70 | 50 | y |
| 0.0625 | 0.125 | 70 | 50 | y |
| 0.03125 | 0.125 | 70 | 50 | y |

| Q.062 rate ppm | Isopyrazam rate ppm | Activity (%) | P | S? |
|---|---|---|---|---|
| 0.0078125 | | 0 | | |
| 0.00390625 | | 0 | | |
| | 0.03125 | 20 | | |
| | 0.015625 | 0 | | |
| 0.0078125 | 0.03125 | 70 | 20 | y |
| 0.00390625 | 0.015625 | 70 | 0 | y |

| Q.062 rate ppm | Fluxapyroxad rate ppm | Activity (%) | P | S? |
|---|---|---|---|---|
| 0.03125 | | 0 | | |
| 0.015625 | | 0 | | |
| 0.0078125 | | 0 | | |
| 0.00390625 | | 0 | | |
| | 0.0625 | 20 | | |
| | 0.03125 | 0 | | |
| | 0.015625 | 0 | | |
| 0.03125 | 0.0625 | 70 | 20 | y |
| 0.015625 | 0.03125 | 20 | 0 | y |
| 0.015625 | 0.0625 | 90 | 20 | y |
| 0.0078125 | 0.03125 | 70 | 0 | y |
| 0.00390625 | 0.015625 | 20 | 0 | y |

| Q.062 rate ppm | Flutriafol rate ppm | Activity (%) | P | S? |
|---|---|---|---|---|
| 2 | | 0 | | |
| 1 | | 0 | | |
| 0.5 | | 0 | | |
| | 1 | 0 | | |
| | 0.5 | 0 | | |
| 2 | 1 | 70 | 0 | y |
| 2 | 0.5 | 20 | 0 | y |
| 1 | 1 | 70 | 0 | y |
| 1 | 0.5 | 20 | 0 | y |
| 0.5 | 1 | 70 | 0 | y |

| Q.062 rate ppm | Picoxystrobin rate ppm | Activity (%) | P | S? |
|---|---|---|---|---|
| 0.03125 | | 0 | | |
| 0.015625 | | 0 | | |
| 0.0078125 | | 0 | | |
| 0.00390625 | | 0 | | |
| | 0.015625 | 70 | | |
| | 0.0078125 | 20 | | |
| 0.03125 | 0.0078125 | 50 | 20 | y |
| 0.015625 | 0.0078125 | 20 | 20 | |
| 0.0078125 | 0.0078125 | 70 | 20 | y |
| 0.0078125 | 0.0015625 | 100 | 70 | y |
| 0.00390625 | 0.0078125 | 90 | 20 | y |

712 -continued

| Q.062 rate ppm | Fluazinam rate ppm | Activity (%) | P | S? |
|---|---|---|---|---|
| 0.03125 | | 0 | | |
| 0.015625 | | 0 | | |
| 0.0078125 | | 0 | | |
| 0.00390625 | | 0 | | |
| | 0.0625 | 70 | | |
| | 0.03125 | 20 | | |
| | 0.015625 | 0 | | |
| 0.03125 | 0.0625 | 90 | 70 | y |
| 0.015625 | 0.0625 | 90 | 70 | y |
| 0.015625 | 0.03125 | 50 | 20 | y |
| 0.0078125 | 0.03125 | 50 | 20 | y |
| 0.0078125 | 0.015625 | 20 | 0 | y |
| 0.00390625 | 0.015625 | 20 | 0 | y |

| Q.062 rate ppm | Metconazole rate ppm | Activity (%) | P | S? |
|---|---|---|---|---|
| 0.25 | | 0 | | |
| 0.125 | | 0 | | |
| 0.0625 | | 0 | | |
| 0.03125 | | 0 | | |
| | 0.0625 | 50 | | |
| 0.25 | 0.0625 | 70 | 50 | y |
| 0.125 | 0.0625 | 70 | 50 | y |
| 0.0625 | 0.0625 | 70 | 50 | y |
| 0.03125 | 0.0625 | 70 | 50 | y |

| Q.062 rate ppm | Paclobutrazol rate ppm | Activity (%) | P | S? |
|---|---|---|---|---|
| 1 | | 0 | | |
| 0.5 | | 0 | | |
| 0.25 | | 0 | | |
| | 10 | 70 | | |
| | 5 | 70 | | |
| | 2.5 | 20 | | |
| | 1.25 | 0 | | |
| | 0.625 | 0 | | |
| 1 | 2.5 | 50 | 20 | y |
| 0.5 | 10 | 100 | 70 | y |
| 0.5 | 2.5 | 70 | 20 | y |
| 0.5 | 1.25 | 20 | 0 | y |
| 0.25 | 10 | 100 | 70 | y |
| 0.25 | 5 | 100 | 70 | y |
| 0.25 | 2.5 | 70 | 20 | y |
| 0.25 | 0.625 | 90 | 0 | y |

| Q.062 rate ppm | Fluopyram rate ppm | Activity (%) | P | S? |
|---|---|---|---|---|
| 0.125 | | 0 | | |
| 0.0625 | | 0 | | |
| 0.03125 | | 0 | | |
| | 0.25 | 50 | | |
| | 0.125 | 0 | | |
| 0.125 | 0.25 | 70 | 50 | y |
| 0.0625 | 0.25 | 70 | 50 | y |
| 0.0625 | 0.125 | 20 | 0 | y |
| 0.03125 | 0.125 | 20 | 0 | y |

| Q.062 rate ppm | Prothioconazole rate ppm | Activity (%) | P | S? |
|---|---|---|---|---|
| 0.5 | | 0 | | |
| 0.25 | | 0 | | |
| 0.125 | | 0 | | |
| 0.0625 | | 0 | | |
| 0.03125 | | 0 | | |
| | 0.0125 | 70 | | |
| 0.5 | 0.0125 | 90 | 70 | y |
| 0.25 | 0.0125 | 90 | 70 | y |
| 0.125 | 0.0125 | 90 | 70 | y |
| 0.0625 | 0.0125 | 90 | 70 | y |
| 0.03125 | 0.0125 | 90 | 70 | y |

-continued

| Q.062 rate ppm | Propiconazole rate ppm | Activity (%) | P | S? |
|---|---|---|---|---|
| 0.5 | | 0 | | |
| 0.25 | | 0 | | |
| 0.125 | | 0 | | |
| 0.0625 | | 0 | | |
| 0.03125 | | 0 | | |
| | 0.125 | 50 | | |
| 0.5 | 0.125 | 90 | 50 | y |
| 0.25 | 0.125 | 90 | 50 | y |
| 0.125 | 0.125 | 90 | 50 | y |
| 0.0625 | 0.125 | 70 | 50 | y |
| 0.03125 | 0.125 | 70 | 50 | y |

*Gaeumannomvces graminis* (Take-all of Cereals)

Mycelial fragments of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the activity was determined visually after 48 hrs

| | Compound (V) rate ppm | Activity (%) | P | S? |
|---|---|---|---|---|
| Q.113 rate ppm | | | | |
| 0.25 | | 0 | | |
| 0.125 | | 0 | | |
| 0.0625 | | 0 | | |
| 0.03125 | | 0 | | |
| 0.015625 | | 0 | | |
| | 0.0625 | 70 | | |
| | 0.03125 | 20 | | |
| | 0.015625 | 0 | | |
| 0.25 | 0.0625 | 90 | 70 | y |
| 0.125 | 0.03125 | 50 | 20 | y |
| 0.0625 | 0.015625 | 20 | 0 | y |
| 0.0625 | 0.03125 | 50 | 20 | y |
| 0.03125 | 0.0625 | 90 | 70 | y |
| 0.015625 | 0.03125 | 50 | 20 | y |
| Q.062 rate ppm | | | | |
| 0.015625 | | 0 | | |
| 0.0078125 | | 0 | | |
| 0.00390625 | | 0 | | |
| | 0.0625 | 70 | | |
| | 0.03125 | 20 | | |
| | 0.015625 | 0 | | |
| 0.015625 | 0.03125 | 50 | 20 | y |
| 0.0078125 | 0.015625 | 20 | 0 | y |
| 0.015625 | 0.0625 | 100 | 70 | y |
| 0.0078125 | 0.03125 | 70 | 20 | y |
| 0.00390625 | 0.015625 | 20 | 0 | y |

*Pythium ultimum* (Damping Off):

Mycelial fragments of the fungus, prepared from a fresh liquid culture, were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the activity was determined visually after 48 hrs

| Q.135 rate ppm | Mefenoxam rate ppm | Activity (%) | P | S? |
|---|---|---|---|---|
| 0.0625 | | 0 | | |
| 0.03125 | | 0 | | |
| 0.015625 | | 0 | | |
| 0.0078125 | | 0 | | |
| | 0.03125 | 50 | | |
| 0.0625 | 0.03125 | 70 | 50 | y |
| 0.03125 | 0.03125 | 50 | 50 | |
| 0.015625 | 0.03125 | 70 | 50 | y |
| 0.0078125 | 0.03125 | 70 | 50 | y |

*Mycosphaerella arachidis* (y. *Cercospora arachidicola*),

Brown leaf spot of groundnut (peanut): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and activity was determined visually after 5-6 days.

| Q.135 rate ppm | Sedaxan rate ppm | Activity (%) | P | S? |
|---|---|---|---|---|
| 0.0625 | | 50 | | |
| 0.03125 | | 50 | | |
| 0.015625 | | 20 | | |
| 0.0078125 | | 0 | | |
| | 0.03125 | 0 | | |
| | 0.015625 | 0 | | |
| | 0.00390625 | 0 | | |
| 0.0625 | 0.03125 | 70 | 50 | y |
| 0.0625 | 0.015625 | 70 | 50 | y |
| 0.03125 | 0.031215 | 50 | 50 | |
| 0.015625 | 0.00390625 | 50 | 20 | y |
| 0.0078125 | 0.00390625 | 20 | 0 | y |

| Q.135 rate ppm | Fluazinam rate ppm | Activity (%) | P | S? |
|---|---|---|---|---|
| 0.0625 | | 50 | | |
| 0.03125 | | 50 | | |
| 0.15625 | | 0 | | |
| 0.0078125 | | 0 | | |
| | 0.03125 | 0 | | |
| | 0.015625 | 0 | | |
| | 0.0078125 | 0 | | |
| | 0.00390625 | 0 | | |
| 0.0625 | 0.015625 | 70 | 50 | y |
| 0.03125 | 0.015625 | 50 | 50 | y |
| 0.015625 | 0.03125 | 20 | 0 | y |
| 0.015625 | 0.015625 | 20 | 0 | y |
| 0.015625 | 0.0078125 | 50 | 0 | y |
| 0.015625 | 0.00390625 | 50 | 0 | y |
| 0.0078125 | 0.03125 | 20 | 0 | y |
| 0.0078125 | 0.00390625 | 20 | 0 | y |

| Q.135 rate ppm | Cyprodinil rate ppm | % Activity | P | S? |
|---|---|---|---|---|
| 0.03125 | | 50 | | |
| 0.015625 | | 20 | | |
| | 0.00125 | 0 | | |
| | 0.0625 | 0 | | |
| | 0.003125 | 0 | | |
| | 0.0015625 | 0 | | |
| | 0.00078125 | 0 | | |
| 0.03125 | 0.00078125 | 90 | 50 | y |
| 0.03125 | 0.0015625 | 70 | 50 | y |
| 0.03125 | 0.003125 | 70 | 50 | y |
| 0.03125 | 0.00625 | 70 | 50 | y |
| 0.03125 | 0.0125 | 70 | 50 | y |
| 0.015625 | 0.00078125 | 50 | 20 | y |

715
-continued

| Q.135 rate ppm | Fludioxonil rate ppm | Activity (%) | P | S? |
|---|---|---|---|---|
| 0.03125 | | 50 | | |
| 0.015625 | | 20 | | |
| | 0.0625 | 0 | | |
| | 0.03125 | 0 | | |
| | 0.015625 | 0 | | |
| | 0.0078125 | 0 | | |
| | 0.00390625 | 0 | | |
| 0.03125 | 0.015625 | 70 | 50 | y |
| 0.015625 | 0.0625 | 50 | 20 | y |
| 0.015625 | 0.03125 | 50 | 20 | y |
| 0.015625 | 0.015625 | 50 | 20 | y |
| 0.015625 | 0.0078125 | 50 | 20 | y |
| 0.015625 | 0.00390625 | 50 | 20 | y |

| Q.135 rate ppm | Fenpropimorph rate ppm | Activity (%) | P | S? |
|---|---|---|---|---|
| 0.0625 | | 70 | | |
| 0.03125 | | 70 | | |
| 0.015625 | | 70 | | |
| 0.0078125 | | 20 | | |
| 0.00390625 | | 0 | | |
| | 0.03125 | 70 | | |
| | 0.015625 | 50 | | |
| | 0.0078125 | 20 | | |
| | 0.00390625 | 20 | | |
| 0.0625 | 0.015625 | 100 | 85 | y |
| 0.03125 | 0.015625 | 100 | 85 | y |
| 0.015625 | 0.0078125 | 90 | 76 | y |
| 0.015625 | 0.00390625 | 90 | 76 | y |
| 0.0078125 | 0.03125 | 100 | 76 | y |
| 0.0078125 | 0.0078125 | 50 | 36 | y |
| 0.0078125 | 0.00390625 | 50 | 36 | y |
| 0.00390625 | 0.015625 | 70 | 50 | y |
| 0.00390625 | 0.0078125 | 50 | 20 | y |

| Q.113 rate ppm | Sedaxan rate ppm | Activity (%) | P | S? |
|---|---|---|---|---|
| 0.125 | | 20 | | |
| 0.0625 | | 0 | | |
| | 0.125 | 0 | | |
| | 0.0625 | 0 | | |
| | 0.03125 | 0 | | |
| | 0.015625 | 0 | | |
| 0.125 | 0.125 | 50 | 20 | y |
| 0.0625 | 0.125 | 20 | 0 | y |
| 0.0625 | 0.0625 | 20 | 0 | y |
| 0.0625 | 0.03125 | 20 | 0 | y |
| 0.0625 | 0.015625 | 20 | 0 | y |

| Q.113 rate ppm | Fluazinam rate ppm | Activity (%) | P | S? |
|---|---|---|---|---|
| 0.03125 | | 0 | | |
| 0.015625 | | 0 | | |
| 0.0078125 | | 0 | | |
| | 0.0625 | 20 | | |
| | 0.03125 | 0 | | |
| 0.03125 | 0.0625 | 50 | 20 | y |
| 0.015625 | 0.0625 | 50 | 20 | y |
| 0.0078125 | 0.03125 | 20 | 0 | y |

| Q.113 rate ppm | Fludioxonil rate ppm | Activity (%) | P | S? |
|---|---|---|---|---|
| 0.5 | | 70 | | |
| 0.25 | | 70 | | |
| 0.125 | | 50 | | |
| 0.0625 | | 20 | | |
| 0.03125 | | 0 | | |
| | 0.5 | 70 | | |
| | 0.25 | 0 | | |
| | 0.125 | 0 | | |
| 0.5 | 0.25 | 100 | 70 | y |
| 0.25 | 0.25 | 90 | 70 | y |

716
-continued

| | | | | |
|---|---|---|---|---|
| 0.125 | 0.5 | 100 | 85 | y |
| 0.125 | 0.25 | 70 | 50 | y |
| 0.0625 | 0.25 | 50 | 20 | y |
| 0.03125 | 0.125 | 20 | 0 | y |

| Q.113 rate ppm | Fenpropimorph rate ppm | Activity (%) | P | S? |
|---|---|---|---|---|
| 0.125 | | 50 | | |
| 0.0625 | | 50 | | |
| 0.03125 | | 20 | | |
| 0.015625 | | 0 | | |
| | 0.0625 | 70 | | |
| | 0.03125 | 50 | | |
| 0.125 | 0.0625 | 100 | 85 | y |
| 0.125 | 0.03125 | 100 | 75 | y |
| 0.0625 | 0.03125 | 90 | 75 | y |
| 0.03125 | 0.0625 | 100 | 76 | y |
| 0.015625 | 0.03125 | 70 | 50 | y |

| Q.062 rate ppm | Bixafen rate ppm | Activity (%) | P | S? |
|---|---|---|---|---|
| 0.0625 | | 0 | | |
| 0.03125 | | 0 | | |
| 0.015625 | | 0 | | |
| | 0.0625 | 70 | | |
| | 0.03125 | 50 | | |
| 0.0625 | 0.0625 | 90 | 70 | y |
| 0.03125 | 0.0625 | 90 | 70 | y |
| 0.015625 | 0.0625 | 100 | 70 | y |
| 0.015625 | 0.03125 | 70 | 50 | y |

| Q.062 rate ppm | Fludioxonil rate ppm | Activity (%) | P | S? |
|---|---|---|---|---|
| 2 | | 70 | | |
| 1 | | 70 | | |
| 0.5 | | 0 | | |
| 0.25 | | 0 | | |
| 0.125 | | 0 | | |
| | 0.5 | 50 | | |
| | 0.25 | 0 | | |
| | 0.125 | 0 | | |
| 2 | 0.5 | 100 | 85 | y |
| 1 | 0.5 | 100 | 85 | y |
| 0.5 | 0.5 | 100 | 50 | y |
| 0.5 | 0.25 | 50 | 0 | y |
| 0.5 | 0.125 | 20 | 0 | y |
| 0.25 | 0.5 | 70 | 50 | y |
| 0.25 | 0.25 | 20 | 0 | y |
| 0.125 | 0.25 | 20 | 0 | y |

| Q.062 rate ppm | Cyprodinil rate ppm | Activity (%) | P | S? |
|---|---|---|---|---|
| 1 | | 70 | | |
| | 0.2 | 0 | | |
| | 0.1 | 0 | | |
| | 0.05 | 0 | | |
| | 0.025 | 0 | | |
| 1 | 0.025 | 90 | 70 | y |
| 1 | 0.1 | 90 | 70 | y |
| 1 | 0.2 | 90 | 70 | y |

*Septoria tritici* (Leaf Blotch):

After placing solutions of the test compounds (containing 0.2% DMSO) into a microtiter plate (96-well format), an equal amount of the nutrient broth (YBG) was added to each of the well. Finally the fungal spore solution was added. The test plates were incubated at 20° C. The inhibition of growth was determined photometrically after 6 days and the activity calculated in relation to untreated control.

| Q.135 rate ppm | Tebuconazole rate ppm | Activity (%) | P | S? |
|---|---|---|---|---|
| 1.25 | | 24 | | |
| 0.625 | | 25 | | |
| 0.3125 | | 35 | | |
| | 1.25 | 0 | | |
| 1.25 | 1.25 | 59 | 24 | y |
| 0.625 | 1.25 | 51 | 25 | y |
| 0.3125 | 1.25 | 54 | 35 | y |

| Q.135 rate ppm | Epoxiconazole rate ppm | % Activity | P | S? |
|---|---|---|---|---|
| 1.25 | | 22 | | |
| 0.625 | | 32 | | |
| 0.3125 | | 34 | | |
| 0.15625 | | 29 | | |
| | 0.3125 | 78 | | |
| | 0.15625 | 65 | | |
| 1.25 | 0.3125 | 95 | 83 | y |
| 0.625 | 0.3125 | 98 | 85 | y |
| 0.625 | 0.15625 | 94 | 76 | y |
| 0.3125 | 0.3125 | 100 | 86 | y |
| 0.15625 | 0.3125 | 100 | 85 | y |
| 0.15625 | 0.15625 | 98 | 75 | y |

| Q.113 rate ppm | Cyproconazole rate ppm | Activity (%) | P | S? |
|---|---|---|---|---|
| 10 | | 63 | | |
| | 1 | 84 | | |
| | 0.5 | 64 | | |
| | 0.25 | 0 | | |
| 10 | 1 | 100 | 94 | y |
| 10 | 0.5 | 100 | 87 | y |
| 10 | 0.25 | 86 | 63 | y |

| Q.113 rate ppm | Prothioconazole rate ppm | Activity (%) | P | S? |
|---|---|---|---|---|
| 0.15625 | | 42 | | |
| 0.078125 | | 31 | | |
| 0.0390625 | | 28 | | |
| 0.01953125 | | 15 | | |
| | 0.0390625 | 63 | | |
| | 0.01953125 | 69 | | |
| 0.15625 | 0.0390625 | 96 | 78 | y |
| 0.078125 | 0.0390625 | 100 | 74 | y |
| 0.078125 | 0.01953125 | 100 | 79 | y |
| 0.0390625 | 0.0390625 | 99 | 73 | y |
| 0.01953125 | 0.0390625 | 100 | 68 | y |
| 0.01953125 | 0.01953125 | 93 | 74 | y |

| Q.113 rate ppm | Epoxiconazole rate ppm | Activity (%) | P | S? |
|---|---|---|---|---|
| 1.25 | | 42 | | |
| 0.625 | | 39 | | |
| 0.3125 | | 34 | | |
| 0.15625 | | 34 | | |
| 0.078125 | | 33 | | |
| | 0.3125 | 50 | | |
| 1.25 | 0.3125 | 97 | 71 | y |
| 0.625 | 0.3125 | 100 | 70 | y |
| 0.3125 | 0.3125 | 99 | 67 | y |
| 0.15625 | 0.3125 | 99 | 67 | y |
| 0.078125 | 0.3125 | 98 | 67 | y |

| Q.062 rate ppm | Cyproconazole rate ppm | Activity (%) | P | S? |
|---|---|---|---|---|
| 5 | | 64 | | |
| 2.5 | | 49 | | |
| 1.25 | | 48 | | |
| | 2.5 | 76 | | |
| | 1.25 | 39 | | |
| 5 | 1.25 | 96 | 78 | y |
| 2.5 | 2.5 | 100 | 88 | y |
| 2.5 | 1.25 | 86 | 69 | y |
| 1.25 | 2.5 | 98 | 88 | y |
| 1.25 | 1.25 | 87 | 69 | y |

| Q.062 rate ppm | Prothioconazole rate ppm | Activity (%) | P | S? |
|---|---|---|---|---|
| 0.3125 | | 33 | | |
| 0.15625 | | 38 | | |
| 0.0078125 | | 31 | | |
| | 0.0625 | 63 | | |
| | 0.03125 | 9 | | |
| 0.3125 | 0.0625 | 88 | 75 | y |
| 0.15625 | 0.0625 | 98 | 77 | y |
| 0.078125 | 0.03125 | 63 | 37 | y |

| Q.062 rate ppm | Tebuconazole rate ppm | Activity (%) | P | S? |
|---|---|---|---|---|
| 5 | | 57 | | |
| 2.5 | | 41 | | |
| 1.25 | | 51 | | |
| | 5 | 73 | | |
| | 2.5 | 47 | | |
| 5 | 5 | 100 | 89 | y |
| 5 | 2.5 | 96 | 77 | y |
| 2.5 | 5 | 100 | 84 | y |
| 2.5 | 2.5 | 81 | 69 | y |
| 1.25 | 5 | 99 | 87 | y |

| Q.062 rate ppm | Prochloraz rate ppm | Activity (%) | P | S? |
|---|---|---|---|---|
| 0.625 | | 35 | | |
| 0.3125 | | 37 | | |
| | 0.03125 | 80 | | |
| | 0.015625 | 48 | | |
| 0.625 | 0.03125 | 98 | 87 | y |
| 0.625 | 0.015625 | 79 | 66 | y |
| 0.3125 | 0.03125 | 97 | 87 | y |

| Q.062 rate ppm | Epoxiconazole rate ppm | Activity (%) | P | S? |
|---|---|---|---|---|
| 2.5 | | 48 | | |
| 1.25 | | 51 | | |
| 0.625 | | 48 | | |
| 0.3125 | | 42 | | |
| | 0.625 | 71 | | |
| | 0.3125 | 33 | | |
| 2.5 | 0.625 | 98 | 85 | y |
| 1.25 | 0.3125 | 77 | 67 | y |
| 0.625 | 0.3125 | 79 | 65 | y |
| 0.3125 | 0.3125 | 71 | 61 | y |

| Q.062 rate ppm | Difenoconazole rate ppm | Activity (%) | P | S? |
|---|---|---|---|---|
| 0.625 | | 40 | | |
| 0.3125 | | 36 | | |
| 0.15625 | | 39 | | |
| 0.078125 | | 29 | | |
| 0.00390625 | | 32 | | |
| | 0.15625 | 48 | | |
| 0.625 | 0.15625 | 89 | 69 | y |
| 0.3125 | 0.15625 | 81 | 67 | y |
| 0.15625 | 0.15625 | 77 | 68 | y |
| 0.078125 | 0.15625 | 81 | 63 | y |
| 0.00390625 | 0.15625 | 84 | 64 | y |

| Q.062 rate ppm | Compound (S)-(VII) rate ppm | Activity (%) | P | S? |
|---|---|---|---|---|
| 0.625 | | 26 | | |
| 0.3125 | | 22 | | |
| | 0.125 | 62 | | |
| | 0.0625 | 44 | | |
| | 0.03125 | 0 | | |

*Sclerotinia sclerotiorum* on Oilseed Rape, Preventive Treatment

The compound activity was tested under 1 day preventive conditions. Oilseed rape plants with 3 unfolded leafs were sprayed with a track sprayer and 200 I/ha spray volume with the test compounds, either solo or in tankmix as shown in the table below.

1 day after application the plants were infested with a solution of *Sclerotinia sclerotiorum* mycelium. The plants were placed under plastic hoods and high humidity conditions in a climate chamber at 14 h day/10 h night cycle and 15° C. Disease infestation was evaluated visually 11 days after application and average activity calculated in relation to disease severity on untreated check.

|  | Boscalid rate g a.i./ha | Activity (%) | P | S? |
|---|---|---|---|---|
| Q.135 rate ppm |  |  |  |  |
| 100 |  | 15 |  |  |
| 50 |  | 0 |  |  |
| 25 |  | 0 |  |  |
|  | 100 | 25 |  |  |
|  | 50 | 8 |  |  |
| 100 | 100 | 59 | 36 | y |
| 50 | 50 | 49 | 8 | y |
| 25 | 100 | 76 | 25 | y |
| 100 | 50 | 62 | 21 | y |
| 50 | 50 | 92 | 10 | y |
| 25 | 100 | 83 | 25 | y |
| 100 | 50 | 93 | 32 | y |
| Q.113 rate ppm |  |  |  |  |
| 100 |  | 39 |  |  |
| 50 |  | 2 |  |  |
| 25 |  | 2 |  |  |
|  | 100 | 25 |  |  |
|  | 50 | 8 |  |  |
| 100 | 100 | 83 | 54 | y |
| 50 | 50 | 89 | 10 | y |
| 25 | 100 | 83 | 26 | y |
| 100 | 50 | 86 | 44 | y |
| Q.062 rate ppm |  |  |  |  |
| 100 |  | 26 |  |  |
| 50 |  | 2 |  |  |
| 25 |  | 0 |  |  |
|  | 100 | 25 |  |  |
|  | 50 | 8 |  |  |
| 100 | 100 | 91 | 44 | y |
| 50 | 50 | 92 | 10 | y |
| 25 | 100 | 83 | 25 | y |
| 100 | 50 | 93 | 32 | y |

*Sphaerotheca fuliqinea* (Powdery Mildew) on Cucumber, Preventive Treatment

The compound activity was tested under 2 days preventive conditions. Cucumber plants with unfolded cotyledons were sprayed with a roomsprayer and 40 ml/4 plants spray volume with the test compounds, either solo or in tankmix as shown in the table below.

2 days after application the plants were infested with spores of *Sphaerotheca fuliginea*. The plants were placed in a climate chamber under 70% rel. humidity, 22° C. and 14 h day/10 h night cycle. Disease infestation was evaluated visually 10 days after application and average activity calculated in relation to disease severity on untreated check.

|  | Acibenzolar-s-methyl rate ppm | Activity (%) | P | S? |
|---|---|---|---|---|
| Q.135 rate ppm |  |  |  |  |
| 2 |  | 0 |  |  |
| 0.6 |  | 0 |  |  |
| 0.2 |  | 0 |  |  |
|  | 20 | 4 |  |  |
|  | 6 | 0 |  |  |
|  | 2 | 0 |  |  |
|  | 0.6 | 0 |  |  |
| 2 | 20 | 49 | 4 | y |
| 2 | 6 | 16 | 0 | y |
| 0.6 | 6 | 15 | 0 | y |
| 0.6 | 2 | 4 | 0 |  |
| 0.2 | 2 | 3 | 0 |  |
| Q.113 rate ppm |  |  |  |  |
| 2 |  | 0 |  |  |
| 0.6 |  | 0 |  |  |
| 0.2 |  | 0 |  |  |
|  | 20 | 4 |  |  |
|  | 6 | 0 |  |  |
|  | 2 | 0 |  |  |
|  | 0.6 | 0 |  |  |
| 2 | 20 | 18 | 4 | y |
| 2 | 6 | 12 | 0 | y |
| 0.6 | 6 | 5 | 0 |  |
| 0.6 | 2 | 7 | 0 |  |
| 0.2 | 2 | 9 | 0 | y |
| Q.062 rate ppm |  |  |  |  |
| 2 |  | 7 |  |  |
| 0.6 |  | 0 |  |  |
| 0.2 |  | 0 |  |  |
|  | 20 | 4 |  |  |
|  | 6 | 0 |  |  |
|  | 2 | 0 |  |  |
|  | 0.6 | 0 |  |  |
| 2 | 20 | 11 | 11 |  |
| 2 | 6 | 4 | 7 |  |
| 0.6 | 6 | 9 | 0 | y |
| 0.6 | 2 | 5 | 0 |  |
| 0.2 | 2 | 9 | 0 | y |

*Fusarium* spp. on Wheat, Preventive Treatment

The compound activity was tested under 1 day preventive condition. Flowering wheat plants were sprayed with a track sprayer and 220 I/ha spray volume with the test compounds, either solo or in tankmix as shown in the table below. The compounds were formulated as standard EC100 and diluted into water to the given spray-dosis.

1 day after application the flowering ears were infested with a mix of spores of *Fusarium graminearum* and *Fusarium culmorum*. The plants were placed in a climate chamber under 60% rel. humidity, and 14 h day/10 h night cycle with 23/21° C. Disease infestation was evaluated visually 9 days after application and average activity calculated in relation to disease severity on untreated check.

| Compound | g a.i./ha | Activity (%) | P | S? |
|---|---|---|---|---|
| Prothioconazole (PTZ) | 50 | 55 |  |  |
| Q.062 | 200 | 17 |  |  |
| Q.135 | 200 | 28 |  |  |
| Q.113 | 200 | 23 |  |  |
| Q.151 | 200 | 3 |  |  |
| PTZ + Q.062 | 200 + 50 | 83 | 63 | y |
| PTZ + Q.135 | 200 + 50 | 86 | 68 | y |

-continued

| Compound | g a.i./ha | Activity (%) | P | S? |
|---|---|---|---|---|
| PTZ + Q.113 | 200 + 50 | 85 | 65 | y |
| PTZ + Q.151 | 200 + 50 | 88 | 56 | y |

*Phakopsora pachyrhizi* on Soybean, Preventive Treatment

The compound activity was tested under 1 day preventive conditions. Soybean plants with a fully enfolded first trifoliate leaf were sprayed with a track sprayer and 50 I/ha spray volume with the test compounds, either solo or in tankmix as shown in the table below. 1 day after application leaf discs were cutted from the first trifoliate leaf and placed in multiwell plates on water-agar. 5 leaf discs per treatment where infested with spores of a triazole tolerant soybeanrust strain. The multiwell plates where sealed and placed in an incubator 48 h in darkness and 12 h light/dark cycle afterwards. Rust infestation on leaf discs was evaluated visually 11 days after application and average activity calculated in relation to disease severity on untreated check leaf discs.

| Compound | Rate (g ai/ha) | Activity (%) | P | S? |
|---|---|---|---|---|
| Cyproconazole | 2 | 53 | N/A | N/A |
| Cyproconazole | 0.5 | 38 | N/A | N/A |
| Q.062 | 2 | 13 | N/A | N/A |
| Q.062 | 0.5 | 0 | N/A | N/A |
| Q.063 | 2 | 0 | N/A | N/A |
| Q.063 | 0.5 | 0 | N/A | N/A |
| Q.113 | 2 | 25 | N/A | N/A |
| Q.113 | 0.5 | 1 | N/A | N/A |
| Q.135 | 2 | 41 | N/A | N/A |
| Q.135 | 0.5 | 13 | N/A | N/A |
| Q.062 + Cyproconazole | 2 + 2 | 99 | 59 | Yes |
| Q.062 + Cyproconazole | 2 + 0.5 | 78 | 46 | Yes |
| Q.062 + Cyproconazole | 0.5 + 2 | 96 | 53 | Yes |
| Q.063 + Cyproconazole | 2 + 2 | 100 | 53 | Yes |
| Q.063 + Cyproconazole | 2 + 0.5 | 98 | 38 | Yes |
| Q.063 + Cyproconazole | 0.5 + 2 | 98 | 53 | Yes |
| Q.113 + Cyproconazole | 2 + 2 | 100 | 65 | Yes |
| Q.113 + Cyproconazole | 2 + 0.5 | 94 | 54 | Yes |
| Q.113 + Cyproconazole | 0.5 + 2 | 96 | 54 | Yes |
| Q.135 + Cyproconazole | 2 + 2 | 95 | 72 | Yes |
| Q.135 + Cyproconazole | 2 + 0.5 | 98 | 72 | Yes |
| Q.135 + Cyproconazole | 0.5 + 2 | 97 | 46 | Yes |

*Septoria tritici* on Wheat, Preventive Treatment

Four pots per treatment with 4 plants of the wheat variety Riband in each of 6.5 cm pots have been treated 14 days after sowing with the compounds given in the results table. The compounds were formulated as standard EC100 and diluted into water to the given spray-dosis. One day after application of the compounds solo and in mixture, the plants were infested with spores of *Septoria tritici*. To enable a good infestation, the plants were covered with a plexiglas hood for 48 h after inoculation. The plants grew in a controlled environment for 14 h at 21° C. during day and 10 h at 19° C. during night. 18 days after application the infestation of the $2^{nd}$ leaf of each of the plants and of the untreated, infested check was evaluated visually. The activity data in the table then derived from a calculation of the infestation of the means of the 4 plants of 4 repetitions of each of the solo or mixture treatments with the mean of the of the 4 plants of 4 repetitions of the untreated infested check.

| | ga/ha | Activity (%) | P | S? |
|---|---|---|---|---|
| compound (VII) | 27 | 96 | N/A | N/A |
| | 9 | 20 | | |
| | 3 | 0 | | |
| Q.062 | 27 | 71 | N/A | N/A |
| | 9 | 8 | | |
| | 3 | 6 | | |
| Q.135 | 27 | 82 | N/A | N/A |
| | 9 | 33 | | |
| | 3 | 0 | | |
| Q.113 | 27 | 16 | N/A | N/A |
| | 9 | 0 | | |
| | 3 | 0 | | |
| Q.151 | 27 | 0 | N/A | N/A |
| | 9 | 0 | | |
| | 3 | 0 | | |
| compound (VII) + Q.062 | 9 + 27 | 98 | 77 | Y |
| | 3 + 9 | 36 | 8 | Y |
| compound (VII) + Q.062 | 27 + 27 | 99 | 99 | |
| | 9 + 9 | 93 | 26 | Y |
| compound (VII) + Q.062 | 27 + 9 | 97 | 97 | |
| | 9 + 3 | 58 | 25 | Y |
| compound (VII) + Q.135 | 9 + 27 | 98 | 47 | Y |
| | 3 + 9 | 47 | 0 | Y |
| compound (VII) + Q.135 | 27 + 27 | 100 | 99 | |
| | 9 + 9 | 92 | 47 | Y |
| compound (VII) + Q.135 | 27 + 9 | 100 | 98 | |
| | 9 + 3 | 91 | 20 | Y |
| compound (VII) + Q.113 | 9 + 27 | 97 | 33 | Y |
| | 3 + 9 | 38 | 0 | Y |
| compound (VII) + Q.113 | 27 + 27 | 100 | 97 | |
| | 9 + 9 | 76 | 20 | Y |
| compound (VII) + Q.113 | 27 + 9 | 99 | 96 | |
| | 9 + 3 | 70 | 20 | Y |
| compound (VII) + Q.151 | 9 + 27 | 97 | 20 | Y |
| | 3 + 9 | 69 | 0 | Y |
| compound (VII) + Q.151 | 27 + 27 | 99 | 96 | |
| | 9 + 9 | 96 | 20 | Y |
| compound (VII) + Q.151 | 27 + 9 | 99 | 96 | |
| | 9 + 3 | 71 | 20 | Yes |

| Compound | g a.i./ha | Activity (%) | P | S? |
|---|---|---|---|---|
| Difenoconazole (DFZ) | 27 | 5 | | |
| | 9 | 3 | | |
| | 3 | 0 | | |
| | 1 | 0 | | |
| | 0.33 | 0 | | |
| Q.062 | 81 | 61 | | |
| | 27 | 50 | | |
| | 9 | 26 | | |
| | 3 | 8 | | |
| | 1 | 2 | | |
| Q.135 | 81 | 70 | | |
| | 27 | 52 | | |
| | 9 | 43 | | |
| | 3 | 9 | | |
| | 1 | 0 | | |
| Q.113 | 81 | 53 | | |
| | 27 | 61 | | |
| | 9 | 29 | | |
| | 3 | 0 | | |
| | 1 | 1 | | |
| Q.151 | 81 | 43 | | |
| | 27 | 13 | | |
| | 9 | 0 | | |
| | 3 | 4 | | |
| | 1 | 0 | | |

-continued

| | | | | |
|---|---|---|---|---|
| DFZ + Q.062 | 27 + 81 | 97 | 63 | Y |
| | 9 + 27 | 49 | 51 | |
| | 27 + 27 | 85 | 52 | Y |
| | 9 + 9 | 21 | 28 | |
| | 27 + 9 | 61 | 30 | Y |
| | 9 + 3 | 0 | 10 | |
| DFZ + Q.135 | 27 + 81 | 100 | 71 | Y |
| | 9 + 27 | 92 | 54 | Y |
| | 27 + 27 | 90 | 55 | Y |
| | 9 + 9 | 42 | 45 | |
| | 27 + 9 | 68 | 46 | Y |
| | 9 + 3 | 41 | 12 | Y |
| DFZ + Q.113 | 27 + 81 | 98 | 56 | Y |
| | 9 + 27 | 94 | 62 | Y |
| | 27 + 27 | 95 | 63 | Y |
| | 9 + 9 | 69 | 31 | Y |
| | 27 + 9 | 91 | 32 | Y |
| | 9 + 3 | 50 | 3 | Y |
| DFZ + Q.151 | 27 + 81 | 94 | 46 | Y |
| | 9 + 27 | 68 | 15 | Y |
| | 27 + 27 | 97 | 17 | Y |
| | 9 + 9 | 64 | 3 | Y |
| | 27 + 9 | 85 | 5 | Y |
| | 9 + 3 | 28 | 7 | Y |

What is claimed is:

1. A fungicidal composition, comprising a combination of components A) and B), wherein component A) is a compound of formula (I)

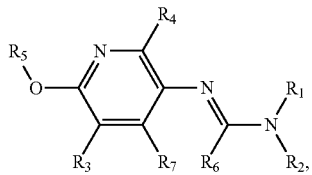

(I)

wherein $R_1$ and $R_2$ are each independently selected from hydrogen, $C_1$-$C_4$ alkyl, $C_3$-$C_4$ alkenyl, $C_3$-$C_4$ alkynyl, $(R_{10})$carbonyl and $(R_{10})$oxycarbonyl;

or $R_1$ and $R_2$ together with the nitrogen atom to which they are attached form a 5- or 6 membered cyclic group which may be saturated or unsaturated and may contain a further heteroatom selected from S or O;

$R_3$ represents hydrogen, halogen, cyano, nitro, mercapto, hydroxy, —C(=S)NH$_2$, —SF$_5$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ cycloalkyl, amino, $C_1$-$C_2$ alkylamino, di($C_1$-$C_6$alkyl)amino, a 5-membered heterocycle containing 1-4 nitrogen atoms, piperidino, morpholino, thiomorpholino, formyl, hydroxycarbonyl, $C_2$-$C_7$ alkoxycarbonyl, $C_2$-$C_7$ haloalkoxycarbonyl, $C_4$-$C_7$ alkenyloxycarbonyl, $C_4$-$C_7$ haloalkenyloxycarbonyl, $C_2$-$C_7$ alkylcarbonyl, $C_2$-$C_7$ haloalkylcarbonyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ hydroxyalkyl, phenyl or benzyl wherein the phenyl and benzyl are optionally substituted by one or more groups independently selected from the group consisting of halogen, cyano, hydroxy, mercapto, amino, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl;

$R_4$ represents hydrogen, halogen, cyano, amino, $C_1$-$C_4$ alkyl, $C_1$-$C_4$ haloalkyl, $C_3$-$C_6$ cycloalkyl, $C_2$-$C_4$ alkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, methylamino or dimethylamino;

$R_5$ is hydrogen, $C_1$-$C_{12}$alkyl, $C_3$-$C_{12}$alkenyl, $C_3$-$C_{12}$alkynyl, $C_1$-$C_{12}$alkylsulfonyl, $C_2$-$C_{12}$alkenylsulfonyl, phenylsulfonyl or benzylsulfonyl, or is $C_1$-$C_{12}$alkyl, $C_2$-$C_{12}$alkenyl, $C_2$-$C_{12}$alkynyl, $C_1$-$C_{12}$alkylsulfonyl, $C_2$-$C_{12}$alkenylsulfonyl, phenylsulfonyl or benzylsulfonyl mono- to polysubstituted by substituents independently selected from the group consisting of halogen, cyano, nitro, hydroxy, mercapto, azido, formyl, $C_2$-$C_7$alkylcarbonyl, $C_2$-$C_7$haloalkylcarbonyl, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or $R_5$ is formyl, $C_2$-$C_{12}$ alkylcarbonyl, $C_3$-$C_{12}$ alkenylcarbonyl, $C_3$-$C_{12}$ alkynylcarbonyl, $C_4$-$C_{12}$ cycloalkylcarbonyl, benzylcarbonyl, phenylcarbonyl, $C_2$-$C_{12}$ alkoxycarbonyl, $C_4$-$C_{12}$ alkenyloxycarbonyl, $C_4$-$C_{12}$ alkynyloxycarbonyl, $C_4$-$C_{12}$ cycloalkoxycarbonyl, benzyloxycarbonyl or phenoxycarbonyl, or is $C_2$-$C_{12}$ alkylcarbonyl, $C_3$-$C_{12}$ alkenylcarbonyl, $C_3$-$C_{12}$ alkynylcarbonyl, $C_4$-$C_{12}$ cycloalkylcarbonyl, benzylcarbonyl, phenylcarbonyl, $C_2$-$C_{12}$ alkoxycarbonyl, $C_4$-$C_{12}$ alkenyloxycarbonyl, $C_4$-$C_{12}$ alkynyloxycarbonyl, $C_4$-$C_{12}$ cycloalkoxycarbonyl, benzyloxycarbonyl or phenoxycarbonyl mono- to polysubstituted by substituents independently selected from the group consisting of halogen, cyano, $C_1$-$C_6$ alkyl, $C_1$-$C_6$ haloalkyl and $C_1$-$C_6$ alkoxy; or $R_5$ is $(R_{51})(R_{52})(R_{53})$Si—, $(R_{51})(R_{52})(R_{53})$Si—($C_1$-$C_{12}$alkyl)-, $(R_{51})(R_{52})(R_{53})$Si—($C_3$-$C_8$cycloalkyl)-, $(R_{54}O)(R_{55}O)(R_{56}O)$Si—, $(R_{54}O)(R_{55}O)(R_{56}O)$Si—($C_1$-$C_{12}$ alkyl)- or $(R_{54}O)(R_{55}O)(R_{56}O)$Si—($C_3$-$C_8$ cycloalkyl)-; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl- or phenyl-B—$C_3$-$C_{12}$cycloalkyl-, wherein the group B is selected from —C(=O)—, —C(=S)—, —C(=NOR$_{59}$)—, —C(R$_{60}$)=NO—, —ON=C(R$_{60}$)—, —O—C(=O)—, —C(=O)—O—, —O—, —S—, —S(=O)—, —S(=O)2-, —S(=O)(=NR$_{13}$)—, —S(=O)(R$_{14}$)=N—, —N=S(=O)(R$_{14}$)—, —N(R$_{62}$)—C(=O)—, —C(=O)—N(R$_{62}$)—, —N(R$_{62}$)—SO$_2$— or —SO$_2$—N(R$_{62}$)—; or $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—C$_2$-C$_{12}$alkenyl-, C$_1$-C$_6$alkyl-B—C$_2$-C$_{12}$alkynyl-, C$_2$-C$_6$alkenyl-B—C$_2$-C$_{12}$alkynyl-, C$_2$-C$_6$alkynyl-B—C$_2$-C$_{12}$alkynyl-, C$_3$-C$_8$cycloalkyl-B—C$_2$-C$_{12}$alkynyl-, benzyl-B—C$_2$-C$_{12}$alkynyl-, phenyl-B—C$_2$-C$_{12}$alkynyl-, C$_1$-C$_6$alkyl-B—C$_3$-C$_8$cycloalkyl-, C$_2$-C$_6$alkenyl-B—C$_3$-C$_8$cycloalkyl-, C$_2$-C$_6$alkynyl-B—C$_3$-C$_8$cycloalkyl-, C$_3$-C$_8$cycloalkyl-B—C$_3$-C$_8$cycloalkyl-, benzyl-B—C$_3$-C$_{12}$cycloalkyl-, phenyl-B—C$_3$-C$_{12}$cycloalkyl-, all of which, in turn, are mono- to poly-substituted by substituents independently selected from the group consisting of halogen, cyano, hydroxy, mercapto, C$_1$-C$_6$ haloalkyl, C$_1$-C$_6$ alkoxy, formyl, C$_2$-C$_6$ alkylcarbonyl, C$_1$-C$_6$ alkylthio, C$_1$-C$_6$ alkylsulfinyl and C$_1$-C$_6$ alkylsulfonyl; or R$_5$ is A-, A-(C$_1$-C$_6$alkyl)-, A-O—(C$_1$-C$_6$alkyl)-, A-(C$_3$-C$_6$alkenyl)-, A-O—(C$_4$-C$_6$alkenyl)-, A-(C$_3$-C$_6$-alkynyl)-, A-O—(C$_4$-C$_6$alkynyl)-, A-(C$_3$-C$_8$cycloalkyl)- or A-O—(C$_3$-C$_8$cycloalkyl)-;

A is a three- to ten-membered monocyclic or fused bicyclic ring system which can be aromatic, partially saturated or fully saturated and can contain 1 to 4 hetero atoms selected from the group consisting of nitrogen, oxygen and sulphur, it not being possible for each ring system to contain —O—O—, —S—S— and —O—S— fragments, and it being possible for the three- to ten-membered ring system to be itself mono- or polysubstituted A1) by substituents independently selected from the group consisting of
halogen, cyano, nitro, hydroxy, mercapto, azido, formyl, carboxy, =O, =S, C$_1$-C$_6$ alkyl, C$_2$-C$_6$ alkenyl, C$_2$-C$_6$ alkynyl, C$_3$-C$_8$ cycloalkyl, C$_1$-C$_6$ haloalkyl, C$_2$-C$_6$ haloalkenyl, C$_2$-C$_6$ haloalkynyl, C$_3$-C$_8$ halocycloalkyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkynyloxy, C$_3$-C$_8$ cycloalkyloxy, benzyl, benzyloxy, phenyl and phenoxy, where the benzyl, benzyloxy, phenyl and phenoxy, in turn, may be mono- to polysubstituted by substituents independently selected from the group consisting of halogen, cyano, nitro, hydroxy, mercapto, amino, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylsulfinyl and C$_1$-C$_6$ alkylsulfonyl; or A2) by substituents independently selected form the group consisting of (R$_{14}$)S(=O)(=NR$_{13}$)—, (R$_{14}$)(R$_{15}$)S(=O)=N—; —Si(R$_{51}$)(R$_{52}$)(R$_{53}$), —NR$_{57}$R$_{58}$, —C(=O)NR$_{57}$R$_{58}$, —C(=S)NR$_{57}$R$_{58}$, HC(=NOR$_{59}$)—, (C$_1$-C$_6$alkyl)C(=NOR$_{59}$)—, (C$_1$-C$_6$haloalkyl)C(=NOR$_{59}$)—, (C$_1$-C$_6$alkyl)C(=NOR$_{59}$)C$_1$-C$_6$alkyl-, (C$_1$-C$_6$haloalkyl)C(=NOR$_{59}$)C$_1$-C$_6$alkyl-, N(C$_1$-C$_6$alkyl)aminosulfonyl and N,N-di(C$_1$-C$_6$alkyl)aminosulfonyl; or A3) by substituents independently selected from the group consisting of
formyl, C$_2$-C$_7$ alkylcarbonyl, C$_2$-C$_7$ haloalkylcarbonyl, C$_3$-C$_7$ alkenylcarbonyl, C$_3$-C$_7$ haloalkenylcarbonyl, C$_4$-C$_9$ cycloalkylcarbonyl, C$_4$-C$_9$ halocycloalkylcarbonyl, C$_2$-C$_7$ alkoxycarbonyl, C$_2$-C$_7$ haloalkoxycarbonyl, C$_3$-C$_7$ alkenyloxycarbonyl, C$_3$-C$_7$ alkynyloxycarbonyl, C$_4$-C$_9$ cycloalkoxycarbonyl, C$_2$-C$_7$ alkylthiocarbonyl and benzyloxycarbonyl, and benzyloxycarbonyl mono- to polysubstituted by substituents independently selected from the group consisting of halogen, cyano, hydroxy, C$_1$-C$_6$ alkyl, C$_1$-C$_6$ haloalkyl and C$_1$-C$_6$ alkoxy; or A4) by substituents independently selected from the group consisting of hydroxyl, C$_1$-C$_4$ alkyl, C$_2$-C$_4$ alkenyl, C$_2$-C$_4$ alkynyl, C$_1$-C$_4$ alkoxy, halogen, C$_1$-C$_4$ haloalkyl, C$_2$-C$_4$ haloalkenyl, cyano, benzyl, phenyl, =C(R$^{36'}$)$_2$, =N—OH, =N—O—C$_1$-C$_4$-alkyl, =N—O—C$_3$-C$_4$ alkenyl, =N—O—C$_3$-C$_4$ alkynyl, =N—O—C$_1$-C$_4$ haloalkyl, =N—O—C$_3$-C$_4$ haloalkenyl, =N—O-benzyl and =N—O-phenyl, wherein the =N—O-benzyl and =N—O-phenyl are optionally substituted by one or more group selected from the group consisting of halogen, methyl, halomethyl; or R$_5$ is —N=C(R$_8$)(R$_9$); or R$_5$ is a C$_8$-C$_{11}$ spirobicyclic system containing 0, 1 or 2 O or N atoms, wherein there are no adjacent O atoms, which is optionally substituted by one or more groups independently selected from halogen, CN, NO$_2$, OH, SH, CHO, COOH, tri(C$_1$-C$_6$-alkyl)silyl, C$_1$-C$_6$ alkyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, C$_1$-C$_6$ haloalkyl, C$_3$-C$_6$ cycloalkyl, C$_3$-C$_6$ halocycloalkyl, C$_2$-C$_6$ alkenyl, C$_2$-C$_6$ haloalkenyl, C$_1$-C$_6$ alkoxy, C$_1$-C$_6$ haloalkoxy, C$_2$-C$_7$-alkylcarbonyl, C$_2$-C$_7$-alkoxycarbonyl, C$_4$-C$_7$-alkenyloxycarbonyl, C$_4$-C$_7$-alkynyloxycarbonyl, C$_1$-C$_6$ alkylthio, C$_1$-C$_6$ alkylsulfinyl, C$_1$-C$_6$ alkylsulfonyl, =O, —C(=O)NH$_2$, —C(=O)NH(CH$_3$), —C(=O)N(CH$_3$)$_2$ and —C(=S)NH$_2$; or R$^5$ is selected from G$^1$, G$^2$, G$^3$-G$^4$, G$^5$, G$^6$-G$^7$, G$^8$, G$^9$, G$^{10}$-G$^{11}$, G$^{12}$, G$^{13}$, G$^{14}$, G$^{15}$ and G$^{16}$;

R$_6$ is selected from hydrogen and SH;

R$_7$ is hydrogen, halogen or C$_1$-C$_4$ alkyl;

R$_8$ and R$_9$, independently from each other, are hydrogen, halogen, cyano, C$_1$-C$_{12}$ alkyl, C$_2$-C$_{12}$ alkenyl, C$_2$-C$_{12}$ alkynyl, C$_1$-C$_{12}$ alkoxy, formyl, C$_2$-C$_{12}$ alkylcarbonyl, C$_3$-C$_{12}$ alkenylcarbonyl, carboxy, C$_2$-C$_{12}$ alkoxycarbonyl and C$_4$-C$_{12}$ alkenyloxycarbonyl, or C$_1$-C$_{12}$ alkyl, C$_2$-C$_{12}$ alkenyl, C$_2$-C$_{12}$ alkynyl, C$_1$-C$_{12}$ alkoxy, C$_2$-C$_{12}$ alkylcarbonyl, C$_3$-C$_{12}$ alkenylcarbonyl, C$_2$-C$_{12}$ alkoxycarbonyl and C$_4$-C$_{12}$ alkenyloxycarbonyl mono- to polysubstituted by substituents independently selected from the group consisting of halogen, cyano, nitro, hydroxy, mercapto, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylsulfinyl and C$_1$-C$_6$ alkylsulfonyl; or R$_8$ and R$_9$ together from a C$_2$-C$_8$ alkylene bridge which may optionally be mono- to polysubstituted by substituents independently selected from the group consisting of halogen, cyano, C$_1$-C$_6$ alkyl and C$_1$-C$_6$ haloalkyl; or R$_8$ and R$_9$, independently from each other, are the groups A-, A-O— or A-(C$_1$-C$_6$alkyl)-;

R$_{10}$ is H, C$_1$-C$_4$ alkyl, C$_2$-C$_4$ alkenyl or C$_1$-C$_4$ haloalkyl;

R$_{13}$ is hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, C$_3$-C$_8$ cycloalkyl, C$_3$-C$_8$ halocycloalkyl, phenyl and benzyl, or is phenyl and benzyl mono- to polysubstituted by halogen, cyano, hydroxy, C$_1$-C$_6$ alkyl, C$_1$-C$_6$ haloalkyl or C$_1$-C$_6$ alkoxy;

R$_{14}$ and R$_{15}$, independently of each other, are C$_1$-C$_6$ alkyl, C$_3$-C$_8$ cycloalkyl, C$_1$-C$_6$ haloalkyl, C$_3$-C$_8$ halocycloalkyl, C$_2$-C$_6$ alkenyl, C$_2$-C$_6$ haloalkenyl, C$_2$-C$_6$ alkynyl, benzyl or phenyl, or benzyl or phenyl independently of each other, substituted by substituents selected from the group consisting of halogen, cyano, hydroxy, C$_1$-C$_6$ alkyl, C$_1$-C$_6$ haloalkyl and C$_1$-C$_6$ alkoxy;

R$_{51}$, R$_{52}$, R$_{53}$, independently of each other, are halogen, cyano, C$_1$-C$_6$ alkyl, C$_2$-C$_6$ alkenyl, C$_3$-C$_8$ cycloalkyl, C$_5$-C$_8$ cycloalkenyl, C$_2$-C$_6$ alkynyl, C$_1$-C$_6$ alkoxy, benzyl or phenyl;

$R_{54}, R_{55}, R_{56}$, independently of each other, are $C_1$-$C_6$ alkyl, $C_3$-$C_6$ alkenyl, $C_3$-$C_8$ cycloalkyl, $C_3$-$C_6$ alkynyl, benzyl or phenyl;

$R_{57}$ and $R_{58}$, independently of each other, are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_8$ cycloalkyl, $C_3$-$C_8$ halocycloalkyl, phenyl or benzyl, where phenyl or benzyl for their part may be mono- to polysubstituted on the phenyl ring by substituents independently selected from the group consisting of halogen, cyano, hydroxy, $C_1$-$C_6$ alkyl, $C_1$-$C_6$ haloalkyl and $C_1$-$C_6$ alkoxy, or $R_{57}$ and $R_{58}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano;

$R_{59}$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_8$ cycloalkyl, $C_3$-$C_8$ halocycloalkyl, benzyl and phenyl, and benzyl and phenyl mono- to polysubstituted by halogen, cyano, hydroxy, $C_1$-$C_6$ alkyl, $C_1$-$C_6$ haloalkyl or $C_1$-$C_6$ alkoxy;

$R_{60}$ is hydrogen, $C_1$-$C_6$ alkyl, $C_3$-$C_8$ cycloalkyl, $C_1$-$C_6$ haloalkyl, $C_3$-$C_8$ halocycloalkyl, $C_2$-$C_6$ alkenyl, $C_2$-$C_6$ haloalkenyl, $C_2$-$C_6$ alkynyl, benzyl or phenyl, or benzyl or phenyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy;

$R_{62}$ is hydrogen, $C_1$-$C_6$ alkyl, $C_3$-$C_8$ cycloalkyl, $C_1$-$C_6$ haloalkyl, $C_3$-$C_8$ halocycloalkyl, $C_3$-$C_6$ alkenyl, $C_3$-$C_6$ alkynyl, benzyl or phenyl, or benzyl or phenyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy;

$G^1$ is a $C_8$-$C_{10}$ fused bicyclic ring system which may be saturated or comprise one carbon-carbon double bond and is optionally substituted by one or more groups independently selected from hydroxyl, $C_1$-$C_4$ alkyl, $C_1$-$C_4$ alkoxy, halogen, $C_1$-$C_4$ haloalkyl and cyano;

$G^2$ is $C_3$-$C_6$ cycloalkenyl, which is optionally substituted by one or more groups independently selected from halogen, CN, $NO_2$, OH, SH, CHO, COOH, tri($C_1$-$C_6$-alkyl)silyl, ethyl, n-propyl, iso-propyl, n-butyl, iso-butyl, sec-butyl, tert-butyl, n-pentyl, —$CH(CH_3)$—$CH_2$—$CH_2$—$CH_3$, —CH—$CH(CH_3)$—$CH_2$—$CH_3$, —$CH_2$—$CH_2$—$CH(CH_3)$—$CH_3$, —$CH_2$—$CH_2$—$CH(CH_3)_2$, —$CH(CH_3)$—$CH(CH_3)_2$, $C_2$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, —C(=O)$NH_2$, —C(=O)NH($CH_3$), —C(=O)N($CH_3$)$_2$ and —C(=S)$NH_2$;

$G^3$ is phenyl, which is optionally substituted by one or more groups independently selected from hydroxyl, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen;

$G^4$ is $C_3$-$C_{12}$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen;

$G^5$ is $C_3$-$C_7$ cycloalkyl which is optionally substituted by one or more groups independently selected from halogen, CN, $NO_2$, OH, SH, CHO, COOH, tri($C_1$-$C_6$-alkyl)silyl, ethyl, n-propyl, iso-propyl, n-butyl, iso-butyl, sec-butyl, tert-butyl, n-pentyl, —$CH_2(CH_3)$—$CH_2$—$CH_2$—$CH_3$, —CH—$CH(CH_3)$—$CH_2$—$CH_3$, —$CH_2$—$CH_2$—$CH(CH_3)$—$CH_3$, —$CH_2$—$CH_2$—$CH(CH_3)_2$, —$CH(CH_3)$—$CH(CH_3)_2$, $C_2$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_3$-$C_6$-alkenyloxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, phenoxy, —C(=O)$NH_2$, —C(=O)NH($CH_3$), —C(=O)N($CH_3$)$_2$ and —C(=S)$NH_2$;

$G^6$ is phenyl, which must be substituted by at least one fluorine and is optionally further substituted by one or more groups independently selected from halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$G^7$ is methylene;

$G^8$ is

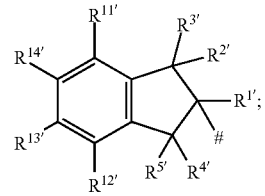

$G^9$ is

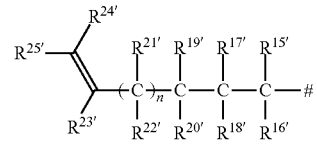

$G^{10}$ is phenyl, which is optionally substituted by one or more groups independently selected from halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$alkenyloxy, $C_3$-$C_6$ haloalkenyloxy, $C_3$-$C_6$alkynyloxy, $C_3$-$C_6$ cycloalkoxy, $C_3$-$C_6$ halocycloalkoxy, phenyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$alkylsulfonyl, $C_1$-$C_6$ haloalkylsulfonyl, phenyl, 2-phenyl-ethynyl and 2-phenyl-ethyl;

$G^{11}$ is methylene substituted by at least one group independently selected from $C_1$-$C_4$ alkyl, $C_1$-$C_4$ haloalkyl, CN, $C_1$-$C_4$ alkoxy and $C_1$-$C_4$ haloalkoxy;

$G^{12}$ is

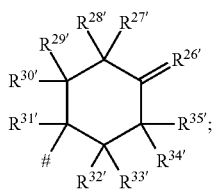

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, CN, $NO_2$, OH, SH, CHO, COOH, tri($C_1$-$C_6$-alkyl)silyl, $C_1$-$C_6$ alkyl, $C_1$-$C_6$ haloalkyl, $C_3$-$C_6$ cycloalkyl, $C_3$-$C_6$ halocycloalkyl, $C_2$-$C_6$alkenyl, $C_2$-$C_6$ haloalkenyl, $C_1$-$C_6$alkoxy, $C_1$-$C_6$ haloalkoxy, $C_2$-$C_7$ alkylcarbonyl, $C_2$-$C_7$ alkoxy carbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, =O, —C(=O)$NH_2$, —C(=O)NH($CH_3$), —C(=O)N($CH_3$)$_2$ and —C(=S)$NH_2$;

$G^{14}$ is

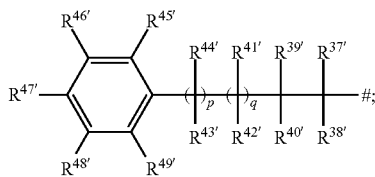

$G^{15}$ is

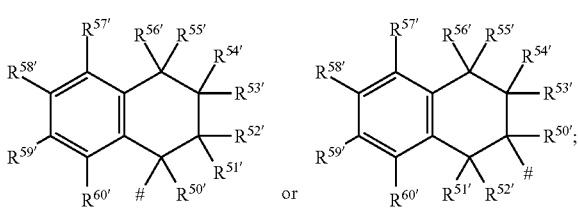

$G^{16}$ is

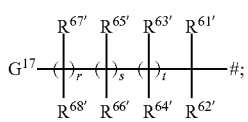

$G^{17}$ is a five- to six-membered monocyclic heteroaromatic ring system which can contain 1 to 4 members selected from the group consisting of N, N($R^{69'}$), O and S, it not being possible for each ring system to contain —O—O—, —S—S— and —O—S— fragments, and it being possible for the five- to six-membered ring system to be itself mono- or polysubstituted by groups selected from the group consisting of halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{1'}$ is selected from the group consisting of hydrogen fluorine $C_1$-$C_4$ alkyl, $C_1$-$C_4$ haloalkyl;

$R^{2'}$, $R^{3'}$, $R^{4'}$ and $R^{5'}$ are selected, independently of each other, from the group consisting of hydrogen, fluorine, $C_1$-$C_4$ alkyl, $C_1$-$C_4$ haloalkyl, $C_1$-$C_4$ alkoxy and $C_1$-$C_4$ alkylthio;

$R^{11'}$, $R^{12'}$, $R^{13'}$ and $R^{14'}$ are selected, independently of each other, from the group consisting of hydrogen, halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$alkynyl, $C_2$-$C_6$ haloalkynyl, $C_1$-$C_6$alkoxy, $C_1$-$C_6$ haloalkoxy, phenyl, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, benzyloxy, $C_1$-$C_6$alkylthio, $C_1$-$C_6$ haloalkylthio, $C_1$-$C_6$alkylsulfinyl, $C_1$-$C_6$ haloalkylsulfinyl, $C_1$-$C_6$alkylsulfonyl and $C_1$-$C_6$ haloalkylsulfonyl;

$R^{15'}$ and $R^{16'}$ are independently selected from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

$R^{26'}$ is C($R^{36'}$)$_2$, N—OH, N—O—$C_1$-$C_4$-alkyl, N—O—$C_2$-$C_4$-alkenyl, N—O—$C_2$-$C_4$ alkynyl, N—O—$C_1$-$C_4$ haloalkyl N—O—$C_2$-$C_4$ haloalkenyl, N—O-benzyl, N—O-phenyl, N—O-halophenyl, O wherein the N—O-benzyl and N—O-phenyl may be substituted by one or more groups independently selected from the group consisting of halogen, methyl and halomethyl;

$R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl and phenyl;

or $R^{28'}$ and $R^{29'}$ together with the two carbon atoms to which they are attached form a double bond;

each $R^{36'}$ is independently selected from hydrogen, halogen and $C_1$-$C_4$ alkyl;

$R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxy, C$_1$-C$_6$ haloalkoxy, C$_3$-C$_6$ alkenyloxy, C$_3$-C$_6$ haloalkenyloxy, C$_3$-C$_6$ alkyloxy, C$_3$-C$_6$ cycloalkoxy, C$_3$-C$_6$ halocycloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

$R^{50'}$ is selected from the group consisting of hydrogen fluorine C$_1$-C$_4$ alkyl, C$_1$-C$_4$ haloalkyl;

$R^{51'}$, $R^{52'}$, $R^{53'}$, $R^{54'}$, $R^{55'}$ and $R^{56'}$ are selected, independently of each other, from the group consisting of hydrogen fluorine C$_1$-C$_4$ alkyl, C$_1$-C$_4$ haloalkyl, C$_2$-C$_4$ alkoxy and C$_1$-C$_4$ alkylthio;

$R^{57'}$, $R^{58'}$, $R^{59'}$ and $R^{60'}$ are selected, independently of each other, from the group consisting of hydrogen, halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, C$_1$-C$_6$ alkyl, C$_1$-C$_6$ haloalkyl, C$_3$-C$_6$ cycloalkyl, C$_2$-C$_6$ alkenyl, C$_2$-C$_6$ haloalkenyl, C$_2$-C$_6$ alkynyl, C$_2$-C$_6$ haloalkynyl, C$_2$-C$_6$ alkoxy, C$_2$-C$_6$ haloalkoxy, phenyl, C$_3$-C$_6$ alkenyloxy, C$_3$-C$_6$ haloalkynyl, C$_3$-C$_6$ alkynyloxy, C$_3$-C$_6$ alkynyloxy, C$_3$-C$_6$ cycloalkoxy, C$_3$-C$_6$ halocycloalkoxy, benzyloxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl and C$_1$-C$_6$ haloalkylsulfonyl;

provided that at least one of $R^{57'}$, $R^{58'}$, $R^{59'}$ and $R^{60'}$ is not hydrogen;

$R^{61'}$ and $R^{62'}$ are selected independently of each other from the group consisting of hydrogen fluorine cyano C$_1$-C$_4$ alkyl and C$_1$-C$_4$ haloalkyl;

$R^{63'}$, $R^{64'}$, $R^{65'}$, $R^{66'}$, $R^{67'}$ and $R^{68'}$ are selected independently of each other from the group consisting of hydrogen, halogen, hydroxy, cyano, C$_1$-C$_4$alkyl, C$_1$-C$_4$ haloalkyl, C$_1$-C$_4$alkoxy, C$_1$-C$_4$ haloalkoxy and C$_1$-C$_4$alkylthio;

$R^{69'}$ is selected from hydrogen C$_1$-C$_4$ alkyl, C$_3$-C$_4$alkenyl and C$_1$-C$_4$ alkylcarboxy;

n is 0 or 1;

p and q are independently selected from 0 and 1; and r, s and t are independently selected from 0 and 1;

or an agronomically acceptable salt/metallic complex/metalloidic complex/isomer/structural isomer/stereo-isomer/diastereoisomer/enantiomer/tautomer/N-oxide thereof;

and component B) is a strobilurin fungicide, a sterol biosynthesis inhibitor, a triazole fungicide, a pro-triazole fungicide, a DMI fungicide, a SDHI fungicide, or a compound selected from the group consisting of Chlorothalonil, Fludioxonil, Cyprodinil, Mandipropamid, Fluazinam, Procymedone, Carbendazim, Abamectin, Clothianidin, Emamectin benzoate, Imidacloprid, Tefluthrin, Mefenoxam, Orocymedone, Thiamethoxam, Lambda-cyhalothrin, Gamma-cyhalothrin, Profenofos, Lufenuron, Diflubenzuron, Cypermethrin, Novaluron, Bifenthrin, Methomyl, Chlopyrifos, Methamidophos, Endosulfan, Betacyfluthrin, Triflumuron, Teflubenzuron, SulcotrioneAcephat, Glyphosate, Glufosinate, Mesotrione, Tembotrione, Sulcotrione, Auxins, Trinexapac-ethyl, Prohexadione-Ca, Paclobutrazol, Acibenzolar-S-methyl, Methyl-Jasmonate, Cis-Jasmone, Manganese, Cyflufenamid, Tebufloquin and Copper.

2. A fungicidal composition according to claim 1, wherein component A) is a compound of formula (I) wherein, R$_1$ and R$_2$ are each independently selected from hydrogen, C$_1$-C$_4$ alkyl, C$_3$-C$_4$ alkenyl and C$_3$-C$_4$ alkynyl;

or R$_1$ and R$_2$ together with the nitrogen atom to which they are connected form pyrrolidine or piperidine;

R$_3$ represents hydrogen, halogen, cyano, mercapto, hydroxy, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_1$-C$_4$ alkoxy, C$_1$-C$_4$ haloalkoxy, C$_3$-C$_6$ cycloalkyl, amino, C$_1$-C$_2$ alkylamino, di(C$_1$-C$_6$alkyl)amino, pyrrolidino, imidazolino, triazolino, tetrazolino, formyl, C$_2$-C$_5$ alkylcarbonyl, C$_2$-C$_5$ haloalkylcarbonyl, C$_1$-C$_6$ alkylthio, C$_1$-C$_6$ alkylsulfinyl, C$_1$-C$_6$ alkylsulfonyl, C$_1$-C$_6$ haloalkylthio, C$_1$-C$_6$ haloalkylsulfinyl, C$_1$-C$_6$ haloalkylsulfonyl or C$_1$-C$_6$ hydroxyalkyl;

R$_4$ represents hydrogen, halogen, cyano, amino, C$_1$-C$_4$ alkyl, C$_1$-C$_4$ haloalkyl, C$_3$-C$_6$ cycloalkyl, C$_2$-C$_4$ alkenyl, C$_2$-C$_4$ alkynyl, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, methylamino or dimethylamino;

R$_5$ represents hydrogen, C$_1$-C$_{12}$ alkylsulfonyl, C$_1$-C$_{12}$ alkyl, C$_3$-C$_{12}$ alkenyl, C$_3$-C$_{12}$ alkynyl, or is C$_1$-C$_{12}$ alkyl, C$_2$-C$_{12}$ alkenyl, C$_2$-C$_{12}$ alkynyl mono- to polysubstituted by substituents independently selected from the group consisting of halogen, cyano, nitro, hydroxy, mercapto, azido, formyl, C$_2$-C$_7$ alkylcarbonyl, C$_2$-C$_7$ haloalkylcarbonyl, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylsulfinyl and C$_1$-C$_6$ alkylsulfonyl; or R$_5$ is (R$_{51}$)(R$_{52}$)(R$_{53}$)Si—, (R$_{51}$)(R$_{52}$)(R$_{53}$)Si—(C$_1$-C$_{12}$alkyl)-, (R$_{51}$)(R$_{52}$)(R$_{53}$)Si—(C$_3$-C$_8$cycloalkyl)-, (R$_{54}$O)(R$_{55}$O)(R$_{56}$O)Si—, (R$_{54}$O)(R$_{55}$O)(R$_{56}$O)Si—(C$_1$-C$_{12}$alkyl)- or (R$_{54}$O)(R$_{55}$O)(R$_{56}$O)S(C$_3$-C$_8$cycloalkyl)-; or R$_5$ is C$_1$-C$_6$alkyl-B—C$_1$-C$_{12}$alkyl-, C$_2$-C$_6$alkenyl-B—C$_1$-C$_{12}$alkyl-, C$_2$-C$_6$alkynyl-B—C$_1$-C$_{12}$alkyl-, C$_3$-C$_8$cycloalkyl-B—C$_1$-C$_{12}$alkyl-, benzyl-B—C$_1$-C$_{12}$alkyl-, phenyl-B—C$_1$-C$_{12}$alkyl-, C$_1$-C$_6$alkyl-B—C$_2$-C$_{12}$alkenyl-, C$_2$-C$_6$alkenyl-B—C$_2$-C$_{12}$alkenyl-, C$_2$-C$_6$alkynyl-B—C$_2$-C$_{12}$alkenyl-, C$_3$-C$_8$cycloalkyl-B—C$_2$-C$_{12}$alkenyl-, benzyl-B—C$_2$-C$_{12}$alkenyl-, phenyl-B—C$_2$-C$_{12}$alkenyl-, C$_1$-C$_6$alkyl-B—C$_2$-C$_{12}$alkynyl-, C$_2$-C$_6$alkenyl-B—C$_2$-C$_{12}$alkynyl-, C$_2$-C$_6$alkynyl-B—C$_2$-C$_{12}$alkynyl-, C$_3$-C$_8$cycloalkyl-B—C$_2$-C$_{12}$alkynyl-, benzyl-B—C$_2$-C$_{12}$alkynyl-, phenyl-B—C$_2$-C$_{12}$alkynyl-, C$_1$-C$_6$alkyl-B—C$_3$-C$_8$cycloalkyl-, C$_2$-C$_6$alkenyl-B—C$_3$-C$_8$cycloalkyl-, C$_2$-C$_6$alkynyl-B—C$_3$-C$_8$cycloalkyl-, C$_3$-C$_8$cycloalkyl-B—C$_3$-C$_8$cycloalkyl-, benzyl-B—C$_3$-C$_{12}$cycloalkyl- or phenyl-B—C$_3$-C$_{12}$cycloalkyl-, wherein the group B is selected from —C(=O)—, —C(=S)—, —C(=NOR$_{59}$)—, —C(R$_{60}$)=NO—, —ON=C(R$_{60}$)—, —O—C(=O)—, —C(=O)—O—, —O—, —S—, —S(=O)—, —S(=O)2-, —S(=O)(=NR$_{13}$)—, —S(=O)(R$_{14}$)=N—, —N=S(=O)(R$_{14}$)—, —N(R$_{62}$)—C(=O)—, —C(=O)—N(R$_{62}$)—, —N(R$_{62}$)—SO$_2$— or —SO$_2$—N(R$_{62}$)—; or R$_5$ is C$_1$-C$_6$alkyl-B—C$_1$-C$_{12}$alkyl-, C$_2$-C$_6$alkenyl-B—C$_1$-C$_{12}$alkyl-, C$_2$-C$_6$alkynyl-B—C$_1$-C$_{12}$alkyl-, C$_3$-C$_8$cycloalkyl-B—C$_1$-C$_{12}$alkyl-, benzyl-B—C$_1$-C$_{12}$alkyl-, phenyl-B—C$_1$-C$_{12}$alkyl-, C$_1$-C$_6$alkyl-B—C$_2$-C$_{12}$alkenyl-, C$_2$-C$_6$alkenyl-B—C$_2$-C$_{12}$alkenyl-, C$_2$-C$_6$alkynyl-B—C$_2$-C$_{12}$alkenyl-, C$_3$-C$_8$cycloalkyl- B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl-, phenyl-B—$C_3$-$C_{12}$cycloalkyl-, all of which, in turn, are mono- to polysubstituted by substituents independently selected from the group consisting of halogen, cyano, hydroxy, mercapto, $C_1$-$C_6$ haloalkyl, $C_1$-$C_6$ alkoxy, formyl, $C_2$-$C_6$ alkylcarbonyl, $C_1$-$C_6$ alkylthio, $C_1$-$C_6$ alkylsulfinyl and $C_1$-$C_6$ alkylsulfonyl; or $R_5$ is selected from A-, A-($C_1$-$C_6$alkyl)-, A-O—($C_1$-$C_6$alkyl)-, A-($C_3$-$C_6$alkenyl)-, A-O—($C_4$-$C_6$alkenyl)-, A-($C_3$-$C_6$-alkynyl)-, A-O—($C_4$-$C_6$alkynyl)-, A-($C_3$-$C_8$cycloalkyl)- and A-O—($C_3$-$C_8$cycloalkyl)-;

A is a three- to ten-membered monocyclic or fused bicyclic ring system which can be aromatic, partially saturated or fully saturated and can contain 1 to 4 hetero atoms selected from the group consisting of nitrogen, oxygen and sulphur, it not being possible for each ring system to contain —O—O—, —S—S— and —O—S— fragments, and it being possible for the three- to ten-membered ring system to be itself mono- or polysubstituted A1) by substituents independently selected from the group consisting of halogen, cyano, nitro, hydroxy, mercapto, nitro, azido, formyl, carboxy, =O, =S, $C_1$-$C_6$ alkyl, $C_2$-$C_6$ alkenyl, $C_2$-$C_6$ alkynyl, $C_3$-$C_8$ cycloalkyl, $C_1$-$C_6$ haloalkyl, $C_2$-$C_6$ haloalkenyl, $C_2$-$C_6$ haloalkynyl, $C_3$-$C_8$ halocycloalkyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_8$ cycloalkyloxy, $C_3$-$C_8$ halocycloalkyloxy, $C_3$-$C_8$ cycloalkenyloxy, $C_3$-$C_8$ halocycloalkenyloxy, benzyl, benzyloxy, phenyl and phenoxy, where the benzyl, benzyloxy, phenyl and phenoxy, in turn, may be mono- to polysubstituted by substituents independently selected from the group consisting of halogen, cyano, nitro, hydroxy, mercapto, amino, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl and $C_1$-$C_6$ alkylsulfonyl; or A3) by substituents independently selected from the group consisting of formyl, $C_2$-$C_7$ alkylcarbonyl, $C_2$-$C_7$ haloalkylcarbonyl, $C_3$-$C_7$ alkenylcarbonyl, $C_3$-$C_7$ haloalkenylcarbonyl, $C_4$-$C_9$ cycloalkylcarbonyl, $C_2$-$C_7$ alkoxycarbonyl, $C_4$-$C_7$ alkenyloxycarbonyl, $C_4$-$C_7$ alkynyloxycarbonyl, $C_4$-$C_9$ cycloalkoxycarbonyl and benzyloxycarbonyl, and benzyloxycarbonyl mono- to polysubstituted by substituents independently selected from the group consisting of halogen, cyano, hydroxy, $C_1$-$C_6$ alkyl, $C_1$-$C_6$ haloalkyl and $C_1$-$C_6$ alkoxy; or A4) by substituents independently selected from the group consisting of hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl, phenyl, =C($R^{36'}$)$_2$, =N—OH, =N—O—$C_1$-$C_4$-alkyl, =N—O—$C_3$-$C_4$ alkenyl, =N—O—$C_3$-$C_4$ alkynyl, =N—O—$C_1$-$C_4$ haloalkyl, =N—O—$C_3$-$C_4$ haloalkenyl, =N—O-benzyl and =N—O-phenyl, wherein the =N—O-benzyl and =N—O-phenyl are optionally substituted by one or more group selected from the group consisting of halogen, methyl, halomethyl; or $R_5$ is a $C_8$-$C_{11}$ spirobicyclic system containing 0, 1 or 2 O, S or N atoms, wherein there are no adjacent O atoms, which is optionally substituted by one or more groups independently selected from halogen, CN, $NO_2$, OH, SH, CHO, COOH, tri($C_1$-$C_6$-alkyl)silyl, $C_1$-$C_6$ alkyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$-alkylcarbonyl, $C_2$-$C_7$-alkoxycarbonyl, $C_4$-$C_7$-alkenyloxycarbonyl, $C_4$-$C_7$-alkynyloxycarbonyl, $C_1$-$C_6$ alkylthio, $C_1$-$C_6$ alkylsulfinyl, $C_1$-$C_6$ alkylsulfonyl, =O, —C(=O)$NH_2$, —C(=O)NH($CH_3$), —C(=O)N($CH_3$)$_2$ and —C(=S)$NH_2$;

$R_6$ is hydrogen;

$R_7$ is hydrogen or $C_1$-$C_4$ alkyl.

3. A fungicidal composition according to claim 1, wherein component A) is a compound of formula (I) wherein $R_1$ and $R_2$ are each independently selected from hydrogen and $C_1$-$C_4$ alkyl;

or $R_1$ and $R_2$ together with the nitrogen atom to which they are connected form pyrrolidine or piperidine;

$R_3$ represents hydrogen, halogen, cyano, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_3$-$C_6$ cycloalkyl, amino, $C_1$-$C_2$ alkylamino, di($C_1$-$C_6$alkyl)amino, pyrrolidino, imidazolino, triazolino, formyl, phenyl, $C_2$-$C_4$ alkylcarbonyl, $C_1$-$C_6$ alkylthio, $C_1$-$C_6$ alkylsulfinyl, $C_1$-$C_6$ alkylsulfonyl or $C_1$-$C_6$ hydroxyalkyl;

$R_4$ is selected from fluorine, chlorine, bromine, $C_1$-$C_4$ alkyl, $C_1$-$C_4$ alkenyl, $C_1$-$C_4$ haloalkyl, $C_1$-$C_4$ alkoxy and $C_3$-$C_6$ cycloalkyl;

$R_5$ is selected from $G^1$, $G^2$, $G^3$-$G^4$, $G^5$, $G^6$-$G^7$, $G^8$, $G^9$, $G^{10}$-$G^{11}$, $G^{12}$, $G^{13}$, $G^{14}$, $G^{15}$ and $G^{16}$;

$R_6$ is hydrogen;

$R_7$ is selected from hydrogen and $C_1$-$C_4$ alkyl;

$G^1$ is a $C_8$-$C_{10}$ fused bicyclic ring system which may be saturated or comprise one carbon-carbon double bond and is optionally substituted by one or more groups independently selected from hydroxyl, $C_1$-$C_4$ alkyl, $C_1$-$C_4$ alkoxy, halogen, $C_1$-$C_4$ haloalkyl and cyano;

$G^2$ is $C_3$-$C_6$ cycloalkenyl, which is optionally substituted by one or more groups independently selected from halogen, CN, $NO_2$, OH, SH, CHO, COOH, tri($C_1$-$C_6$-alkyl)silyl, ethyl, n-propyl, iso-propyl, n-butyl, iso-butyl, sec-butyl, tert-butyl, n-pentyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$, $C_2$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, —C(=O)$NH_2$, —C(=O)NH($CH_3$), —C(=O)N($CH_3$)$_2$ and —C(=S)$NH_2$;

$G^3$ is phenyl, which is optionally substituted by one or more groups independently selected from hydroxyl, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen;

$G^4$ is $C_3$-$C_{12}$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy, halogen and cyano, wherein the alkyl groups are optionally substituted by one or more halogen;

$G^5$ is $C_3$-$C_7$ cycloalkyl, which is optionally substituted by one or more groups independently selected from halogen, CN, NO$_2$, OH, SH, CHO, COOH, tri($C_1$-$C_6$-alkyl) silyl, ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$, $C_2$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_3$-$C_6$-alkenyloxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, phenoxy, —C(=O)NH$_2$, —C(=O)NH(CH$_3$), —C(=O)N(CH$_3$)$_2$ and —C(=S)NH$_2$;

$G^6$ is phenyl, which must be substituted by at least one fluorine and is optionally further substituted by one or more groups independently selected from halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$G^7$ is methylene;

$G^8$ is

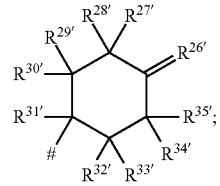

$G^9$ is

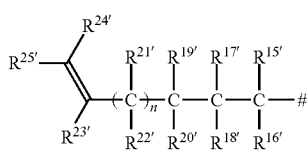

$G^{10}$ is phenyl, which is optionally substituted by one or more groups independently selected from halogen, CN, NO$_2$, OH, SH, CHO, C(=O)NH$_2$, C(=O)NH(CH$_3$), C(=O)N(CH$_3$)$_2$, C(=S)NH$_2$, C(=S)NH(CH$_3$), C(=S)N(CH$_3$)$_2$, SO$_2$NH$_2$, SO$_2$NH(CH$_3$), SO$_2$N(CH$_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, phenyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, phenyl, 2-phenyl-ethynyl and 2-phenyl-ethyl;

$G^{11}$ is methylene substituted by at least one group independently selected from $C_1$-$C_4$ alkyl, $C_1$-$C_4$ haloalkyl, CN, $C_1$-$C_4$ alkoxy and $C_1$-$C_4$ haloalkoxy;

$G^{12}$ is

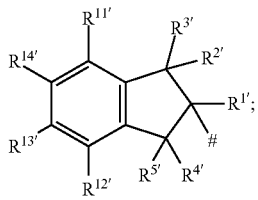

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, CN, NO$_2$, OH, SH, CHO, COOH, tri($C_1$-$C_6$-alkyl)silyl, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $C_1$-$C_6$ alkoxy, $C_1$-$C_6$ haloalkoxy, $C_2$-$C_7$ alkylcarbonyl, $C_2$-$C_7$ alkoxycarbonyl, $C_4$-$C_7$ alkenyloxycarbonyl, $C_4$-$C_7$ alkynyloxycarbonyl, $C_1$-$C_6$ alkylthio, $C_1$-$C_6$ alkylsulfinyl, $C_1$-$C_6$ alkylsulfonyl, =O, —C(=O)NH$_2$, —C(=O)NH(CH$_3$), —C(=O)N(CH$_3$)$_2$ and —C(=S)NH$_2$;

$G^{14}$ is

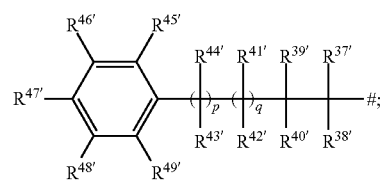

$G^{15}$ is

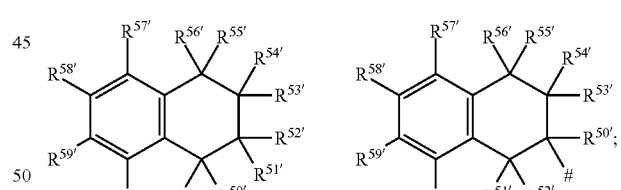

$G^{16}$ is

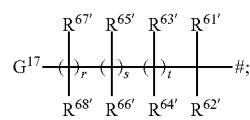

$G^{17}$ is a five- to six-membered monocyclic heteroaromatic ring system which can contain 1 to 4 members selected from the group consisting of N, N(R$^{69}$), O and S, it not being possible for each ring system to contain —O—O—, —S—S— and —O—S— fragments, and it being possible for the five- to six-membered ring system to be itself mono- or polysubstituted by groups selected from the group consisting of halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{1'}$ is selected from the group consisting of hydrogen, fluorine, $C_1$-$C_4$ alkyl, $C_1$-$C_4$ haloalkyl;

$R^{2'}$, $R^{3'}$, $R^{4'}$ and $R^{5'}$ are selected, independently of each other, from the group consisting of hydrogen, fluorine, $C_1$-$C_4$ alkyl, $C_1$-$C_4$ haloalkyl, $C_1$-$C_4$ alkoxy and $C_1$-$C_4$ alkylthio;

$R^{11'}$, $R^{12'}$, $R^{13'}$ and $R^{14'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, phenyl, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, benzyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{15'}$ and $R^{16'}$ are independently selected from the group consisting of hydrogen, halogen, cyano, $C_1$-$C_4$ alkyl, $C_1$-$C_4$ haloalkyl and $C_3$-$C_6$ cycloalkyl;

each $R^{17'}$, $R^{18'}$, $R^{19'}$, $R^{20'}$, $R^{21'}$ and $R^{22'}$ are selected independently of each other, from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $C_3$-$C_6$ cycloalkyl;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

$R^{26'}$ is $C(R^{36'})_2$, N—OH, N—O—$C_1$-$C_4$-alkyl, N—O—$C_2$-$C_4$-alkenyl, N—O—$C_2$-$C_4$ alkynyl, N—O—$C_1$-$C_4$ haloalkyl, N—O—$C_2$-$C_4$ haloalkenyl, N—O-benzyl, N—O-phenyl, N—O-halophenyl, O wherein the N—O-benzyl and N—O-phenyl may be substituted by one or more groups independently selected from the group consisting of halogen, methyl and halomethyl;

$R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, hydroxyl, $C_1$-$C_4$ alkyl, $C_2$-$C_4$ alkenyl, $C_2$-$C_4$ alkynyl, $C_1$-$C_4$ alkoxy, halogen, $C_1$-$C_4$ haloalkyl, $C_2$-$C_4$ haloalkenyl, cyano, benzyl and phenyl;

or $R^{28'}$ and $R^{29'}$ together with the two carbon atoms to which they are attached form a double bond;

each $R^{36'}$ is independently selected from hydrogen, halogen and $C_1$-$C_4$ alkyl;

$R^{37'}$ and $R^{38'}$ are selected independently of each other from the group consisting of hydrogen, halogen, cyano, $C_1$-$C_4$ alkyl and $C_1$-$C_4$ haloalkyl;

$R^{39'}$, $R^{40'}$, $R^{41'}$, $R^{42'}$, $R^{43'}$ and $R^{44'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio;

$R^{45'}$, $R^{46'}$, $R^{47'}$, $R^{48'}$ and $R^{49'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{50'}$ is selected from the group consisting of hydrogen, fluorine, $C_1$-$C_4$ alkyl, $C_1$-$C_4$ haloalkyl;

$R^{51'}$, $R^{52'}$, $R^{53'}$, $R^{54'}$, $R^{55'}$ and $R^{56'}$ are selected, independently of each other, from the group consisting of hydrogen, fluorine, $C_1$-$C_4$ alkyl, $C_1$-$C_4$ haloalkyl, $C_2$-$C_4$ alkoxy and $C_1$-$C_4$ alkylthio;

$R^{57'}$, $R^{58'}$, $R^{59'}$ and $R^{60'}$ are selected, independently of each other, from the group consisting of hydrogen, halogen, CN, $NO_2$, OH, SH, CHO, $C(=O)NH_2$, $C(=O)NH(CH_3)$, $C(=O)N(CH_3)_2$, $C(=S)NH_2$, $C(=S)NH(CH_3)$, $C(=S)N(CH_3)_2$, $SO_2NH_2$, $SO_2NH(CH_3)$, $SO_2N(CH_3)_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxy, $C_2$-$C_6$ haloalkoxy, phenyl, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, benzyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

provided that at least one of $R^{57'}$, $R^{58'}$, $R^{59'}$ and $R^{60'}$ is not hydrogen;

$R^{61'}$ and $R^{62'}$ are selected independently of each other from the group consisting of hydrogen, fluorine, cyano, $C_1$-$C_4$ alkyl and $C_1$-$C_4$ haloalkyl;

$R^{63'}$, $R^{64'}$, $R^{65'}$, $R^{66'}$, $R^{67'}$ and $R^{68'}$ are selected independently of each other from the group consisting of hydrogen, halogen, hydroxy, cyano, $C_1$-$C_4$ alkyl, $C_1$-$C_4$ haloalkyl, $C_1$-$C_4$ alkoxy, $C_1$-$C_4$ haloalkoxy and $C_1$-$C_4$ alkylthio;

$R^{69'}$ is selected from hydrogen, $C_1$-$C_4$ alkyl, $C_3$-$C_4$ alkenyl and $C_1$-$C_4$ alkylcarboxy;

n is 0 or 1;

p and q are independently selected from 0 and 1;

r, s and t are independently selected from 0 and 1.

4. A fungicidal composition according to claim 1, wherein component A) is a compound of formula (I) wherein $R_1$ and $R_2$ are each $C_1$-$C_4$ alkyl;

$R_3$ represents hydrogen, halogen, cyano, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_3$-$C_6$ cycloalkyl, $C_1$-$C_4$ alkylthio, $C_1$-$C_4$ alkylsulfinyl or $C_1$-$C_4$ alkylsulfonyl;

$R_4$ is selected from methyl, ethyl, methoxy, fluorine and chlorine;

$R_6$ is hydrogen;

$R_7$ is hydrogen or $C_1$-$C_4$ alkyl.

5. A fungicidal composition according to claim 1, wherein component A) is a compound of formula (I) wherein $R_1$ and $R_2$ are each independently selected from methyl, ethyl and isopropyl;

$R_3$ represents hydrogen, halogen, $C_1$-$C_4$ alkyl, $C_1$-$C_4$ haloalkyl, cyclopropyl, ethynyl or $C_1$-$C_4$ alkoxy;

$R_4$ is selected from methyl, methoxy, fluorine and chlorine;

$R_6$ is hydrogen;

$R_7$ is hydrogen.

6. A fungicidal composition according to claim 1, wherein component A) is a compound of formula (I) wherein
$R_1$ is methyl;
$R_2$ is ethyl;
$R_3$ is selected from hydrogen, bromine, iodine, methyl, $CHF_2$, cyclopropyl, ethynyl and methoxy;
$R_4$ is methyl;
$R_6$ is hydrogen;
$R_7$ is hydrogen.

7. A fungicidal composition according to claim 3, wherein component A) is a compound of formula (I) wherein $R_5$ is selected from $G^1$, $G^2$, $G^5$, $G^6$-$G^7$, $G^8$, $G^9$, $G^{10}$-$G^{11}$, $G^{12}$, $G^{14}$, $G^{15}$ and $G^{16}$.

8. A fungicidal composition according to claim 3, wherein component A) is a compound of formula (I) wherein $R_5$ is selected from $G^2$, $G^5$, $G^6$-$G^7$, $G^8$, $G^9$, $G^{10}$-$G^{11}$, $G^{14}$ and $G^{16}$.

9. A fungicidal composition according to claim 3, wherein component A) is a compound of formula (I) wherein $R_5$ is selected from $G^2$, $G^5$, $G^8$ and $G^{10}$-$G^{11}$.

10. A fungicidal composition according to claim 3, wherein component A) is a compound of formula (I) wherein $G^1$ is a $C_9$-$C_{10}$ fused bicyclic ring system which may be saturated or comprise one carbon-carbon double bond and is optionally substituted by one or more groups independently selected from $C_1$-$C_4$ alkyl, fluorine, methoxy and $C_1$-$C_4$ fluoroalkyl;

$G^2$ is $C_3$-$C_6$ cycloalkenyl, which is optionally substituted by one or more groups independently selected from halogen, ethyl, n-propyl, iso-propyl, n-butyl, iso-butyl, sec-butyl, tert-butyl, n-pentyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$, $C_2$-$C_6$ haloalkyl, $C_1$-$C_6$ alkoxy and $C_1$-$C_6$ alkylthio;

$G^3$ is phenyl, which is optionally substituted by one or more groups independently selected from hydroxyl, $C_1$-$C_4$ alkyl, $C_1$-$C_4$ fluoroalkyl, $C_1$-$C_4$ alkoxy and halogen;

$G^4$ is $C_5$-$C_6$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy, halogen and cyano, wherein the alkyl groups are optionally substituted by one or more halogens;

$G^5$ is $C_3$-$C_7$ cycloalkyl, which is substituted by one or more groups independently selected from ethyl, n-propyl, iso-propyl, n-butyl, iso-butyl, sec-butyl, tert-butyl, n-pentyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$, —CH($CH_3$)—CH($CH_3$)$_2$, $C_2$-$C_6$ haloalkyl, $C_1$-$C_6$ alkoxy, $C_3$-$C_4$-alkenyloxy, phenoxy and $C_1$-$C_6$ alkylthio;

$G^6$ is phenyl, which must be substituted by at least one fluorine and is optionally further substituted by one or more groups independently selected from halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_1$-$C_6$ alkoxy, $C_1$-$C_6$ haloalkoxy, $C_3$-$C_6$ alkenyloxy, $C_3$-$C_6$ alkynyloxy, $C_1$-$C_6$ alkylthio, $C_1$-$C_6$ alkylsulfinyl and $C_1$-$C_6$ alkylsulfonyl;

$G^{10}$ is phenyl, which is optionally substituted by one or more groups independently selected from halogen, CN, OH, SH, CHO, methyl, ethyl, n-propyl, iso-propyl, $CH_2F$, $CHF_2$, $CF_3$, CHF—$CH_3$, $CF_2$—$CH_3$, $CF_2$—$CF_3$, cyclopropyl, CH=$CH_2$, C($CH_3$)=$CH_2$, CH=CH($CH_3$), C($CH_3$)=CH($CH_3$), CH=C($CH_3$)$_2$, C($CH_3$)=C($CH_3$)$_2$, CH=$CF_2$, CH=$CCl_2$, C≡CH, methoxy, ethoxy, iso-propyloxy, phenyl, $OCHF_2$, $OCH_2$—C≡CH, OCH($CH_3$)—C≡CH, $SCH_3$, $SCH_2CH_3$, S(=O)$CH_3$, S(=O)$CH_2CH_3$, S(=O)$_2CH_3$ and S(=O)$_2CH_2CH_3$;

$G^{11}$ is methylene substituted by at least one group independently selected from $C_1$-$C_4$ alkyl, $C_1$-$C_4$ haloalkyl, $C_1$-$C_4$ alkoxy and $C_1$-$C_4$ haloalkoxy;

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, $C_1$-$C_6$ alkyl, $C_1$-$C_6$ haloalkyl, $C_1$-$C_6$ alkoxy, $C_1$-$C_6$ alkylthio and =O;

$G^{17}$ is a five- to six-membered monocyclic heteroaromatic ring system which can contain 1 to 4 members selected from the group consisting of N, N($R^{69'}$), O and S, it not being possible for each ring system to contain —O—O—, —S—S— and —O—S— fragments, and it being possible for the five- to six-membered ring system to be itself mono- or polysubstituted by groups selected from the group consisting of halogen, CN, $NO_2$, OH, SH, CHO, C(=O)$NH_2$, C(=O)NH($CH_3$), C(=O)N($CH_3$)$_2$, C(=S)$NH_2$, C(=S)NH($CH_3$), C(=S)N($CH_3$)$_2$, $SO_2NH_2$, $SO_2$NH($CH_3$), $SO_2$N($CH_3$)$_2$, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_3$-$C_6$ alkenyloxy, $C_3$-$C_6$ haloalkenyloxy, $C_3$-$C_6$ alkynyloxy, $C_3$-$C_6$ cycloalkoxy, $C_3$-$C_6$ halocycloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl and $C_1$-$C_6$ haloalkylsulfonyl;

$R^{1'}$ is selected from the group consisting of hydrogen, fluorine, $C_1$-$C_4$ alkyl and $C_1$-$C_4$ fluoroalkyl;

$R^{2'}$, $R^{3'}$, $R^{4'}$ and $R^{5'}$ are selected, independently of each other, from the group consisting of hydrogen, fluorine, $C_1$-$C_4$ alkyl, $C_1$-$C_4$ haloalkyl, $C_1$-$C_4$ alkoxy and $C_1$-$C_4$ alkylthio;

$R^{11'}$, $R^{12'}$, $R^{13'}$ and $R^{14'}$ are selected, independently of each other, from the group consisting of hydrogen, cyano, halogen, $C_1$-$C_6$ alkyl, $C_1$-$C_6$ haloalkyl, $C_1$-$C_6$ alkoxy and $C_1$-$C_6$ alkylthio;

$R^{15'}$, $R^{16'}$, $R^{17'}$, $R^{18'}$, $R^{19'}$, $R^{20'}$, $R^{21'}$ and $R^{22'}$ are independently selected from the group consisting of hydrogen, halogen, methyl, ethyl, isopropyl, $CH_2F$, $CHF_2$, $CF_3$, CHF—$CH_3$, $CF_2$—$CH_3$ and $CF_2CF_3$;

$R^{23'}$, $R^{24'}$ and $R^{25'}$ are independently selected from the group consisting of hydrogen, halogen, cyano, $C_1$-$C_4$ alkyl, $C_1$-$C_4$ haloalkyl, $C_1$-$C_4$ alkoxy, $C_3$-$C_6$ cycloalkyl, $C_3$-$C_6$ halocycloalkyl and $C_1$-$C_4$ alkylthio;

$R^{26'}$ is N—OH, N—O—$C_1$-$C_4$ alkyl, N—O—$C_2$-$C_4$ alkenyl, N—O—$C_2$-$C_4$ alkynyl, N—O—$C_1$-$C_4$ haloalkyl, N—O—$C_2$-$C_4$ haloalkenyl, N—O-benzyl, N—O-phenyl, N—O-halophenyl, O or C($R^{36'}$)$_2$;

$R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, hydroxyl, $C_1$-$C_4$ alkyl, $C_1$-$C_4$ alkoxy and halogen;

or $R^{28'}$ and $R^{29'}$ together with the two carbon atoms to which they are attached form a double bond;

each $R^{36'}$ is independently selected from hydrogen, halogen and $C_1$-$C_4$ alkyl;

$R^{37'}$, $R^{38'}$, $R^{39'}$, $R^{40'}$, $R^{41'}$, $R^{42'}$, $R^{43'}$ and $R^{44'}$ are selected independently of each other from a group consisting of hydrogen, halogen, methyl, ethyl, isopropyl, monofluoromethyl, polyfluoromethyl, monofluoroethyl, and polyfluoroethyl;

$R^{45'}$, $R^{46'}$, $R^{47'}$, $R^{48'}$ and $R^{49'}$ are independently selected from the group consisting of hydrogen, fluorine, chlorine, bromine, iodine, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, ethoxy, difluoromethoxy, trifluoromethoxy, methlythio, methylsulfinyl and methylsulfonyl;

$R^{50'}$ is selected from the group consisting of hydrogen, fluorine, $C_1$-$C_4$ alkyl, $C_1$-$C_4$ haloalkyl;

$R^{51'}$, $R^{52'}$, $R^{53'}$, $R^{54'}$, $R^{55'}$ and $R^{56'}$ are selected, independently of each other, from the group consisting of hydrogen, fluorine, $C_1$-$C_4$ alkyl, $C_1$-$C_4$ haloalkyl, $C_2$-$C_4$ alkoxy and $C_1$-$C_4$ haloalkoxy;

$R^{57'}$, $R^{58'}$, $R^{59'}$ and $R^{60'}$ are selected, independently of each other, from the group consisting of hydrogen, cyano, halogen, $C_1$-$C_6$ alkyl and $C_1$-$C_6$ haloalkyl;

provided that at least one of $R^{57'}$, $R^{58'}$, $R^{59'}$ and $R^{60'}$ is not hydrogen;

$R^{61'}$ and $R^{62'}$ are selected independently of each other from the group consisting of hydrogen, fluorine, cyano, $C_1$-$C_4$ alkyl and $C_1$-$C_4$ haloalkyl;

$R^{63'}$, $R^{64'}$, $R^{65'}$, $R^{66'}$, $R^{67'}$ and $R^{68'}$ are selected independently of each other from the group consisting of hydrogen, fluorine, cyano, $C_1$-$C_4$ alkyl, $C_1$-$C_4$ haloalkyl, $C_1$-$C_4$ alkoxy and $C_1$-$C_4$ haloalkoxy;

$R^{69'}$ is selected from hydrogen, $C_1$-$C_4$ alkyl and $C_1$-$C_4$ alkylcarboxy;

n is 0 or 1;

p and q are independently selected from 0 and 1;

r and s are 0 and t is 1 or 0.

11. A fungicidal composition according to claim 3, wherein component A) is a compound of formula (I) wherein $G^1$ is a saturated $C_{10}$ fused bicyclic ring system which is optionally substituted by one or more groups independently selected from $C_1$-$C_4$ alkyl, fluorine, methoxy and $C_1$-$C_4$ fluoroalkyl;

$G^2$ is a $C_5$-$C_6$ cycloalkenyl group optionally substituted by one or more fluorine atoms;

$G^3$ is phenyl, which is optionally substituted by one or more groups independently selected from hydroxyl, $C_1$-$C_4$ alkyl, CHF$_2$, CF$_3$, $C_1$-$C_4$ alkoxy and halogen;

$G^4$ is $C_5$-$C_6$ cycloalkyl which is optionally substituted by one or more groups independently selected from hydroxyl, $C_1$-$C_4$ alkyl, $C_2$-$C_4$ alkenyl, $C_2$-$C_4$ alkynyl, $C_1$-$C_4$ alkoxy and halogen;

$G^5$ is $C_5$-$C_6$ cycloalkyl, which is substituted by one or more groups independently selected from ethyl, n-propyl, iso-propyl, n-butyl, iso-butyl, sec-butyl, tert-butyl, n-pentyl, —CH(CH$_3$)—CH$_2$—CH$_2$—CH$_3$, —CH—CH(CH$_3$)—CH$_2$—CH$_3$, —CH$_2$—CH$_2$—CH(CH$_3$)—CH$_3$, —CH$_2$—CH$_2$—CH(CH$_3$)$_2$, —CH(CH$_3$)—CH(CH$_3$)$_2$ and $C_2$-$C_6$ haloalkyl;

$G^6$ is phenyl, which must be substituted by at least one fluorine and is optionally further substituted by one or more groups independently selected from halogen, CN, $C_1$-$C_4$ alkyl, $C_1$-$C_4$ haloalkyl and $C_1$-$C_4$ alkoxy;

$G^7$ is methylene;

$G^{10}$ is phenyl, which is optionally substituted by one or more groups independently selected from hydrogen, halogen, CN, OH, methyl, ethyl, n-propyl, iso-propyl, CH$_2$F, CHF$_2$, CF$_3$, CHF—CH$_3$, CF$_2$—CH$_3$, CF$_2$—CF$_3$, CH=CH$_2$, C(CH$_3$)=CH$_2$, CH=CH(CH$_3$), C(CH$_3$)=CH(CH$_3$), CH=C(CH$_3$)$_2$, C(CH$_3$)=C(CH$_3$)$_2$, CH=CF$_2$, CH=CCl$_2$, C≡CH, methoxy, ethoxy, isopropyloxy, phenyl and OCHF$_2$;

$G^{11}$ is methylene substituted by at least one group independently selected from $C_1$-$C_4$ alkyl, $C_1$-$C_4$ haloalkyl and $C_1$-$C_4$ alkoxy;

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, $C_1$-$C_6$ alkyl, $C_1$-$C_6$ haloalkyl, $C_1$-$C_6$ alkoxy, $C_1$-$C_6$ alkylthio and =O;

$G^{17}$ is a five- to six-membered monocyclic heteroaromatic ring system which can contain 1 to 4 members selected from the group consisting of N, N($R^{69'}$), O and S it not being possible for each ring system to contain —O—O—, —S—S— and —O—S— fragments, and it being possible for the five- to six-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or benzyl, wherein the phenyl or benzyl are optionally substituted by halogen, CN, $C_1$-$C_4$ alkyl or $C_1$-$C_4$ haloalkyl;

$R^{1'}$ is selected from the group consisting of hydrogen, fluorine, methyl, CH$_2$F and CF$_3$;

$R^{2'}$, $R^{3'}$, $R^{4'}$ and $R^{5'}$ are selected, independently of each other, from the group consisting of hydrogen, fluorine, methyl, CH$_2$F, CF$_3$ and methoxy;

$R^{11'}$, $R^{12'}$, $R^{13'}$ and $R^{14'}$ are selected, independently of each other, from the group consisting of hydrogen, halogen, cyano, $C_1$-$C_4$ alkyl, CHF$_2$, CF$_3$ and $C_1$-$C_4$ alkoxy;

$R^{15'}$, $R^{16'}$, $R^{17'}$, $R^{18'}$, $R^{19'}$, $R^{20'}$, $R^{21'}$ and $R^{22'}$ are each independently selected from hydrogen, fluorine, methyl, ethyl, CH$_2$F, CHF$_2$, CF$_3$ and isopropyl;

$R^{23'}$, $R^{24'}$ and $R^{25'}$ are independently selected from the group consisting of hydrogen, methyl, fluorine, chlorine, bromine, ethyl, CH$_2$F, CHF$_2$, CF$_3$ and isopropyl;

$R^{26'}$ is selected from the group consisting of N—OH, N—O— $C_1$-$C_4$ alkyl, N—O— $C_2$-$C_4$ alkenyl, N—O— $C_2$-$C_4$ alkynyl, N—O— $C_1$-$C_4$ haloalkyl, N—O—$C_2$-$C_4$ haloalkenyl, N—O-benzyl, N—O-phenyl, N—O-halophenyl, O, and C($R^{36'}$);

$R^{27'}$, $R^{28'}$, $R^{29'}$, $R^{30'}$, $R^{31'}$, $R^{32'}$, $R^{33'}$, $R^{34'}$ and $R^{35'}$ are each independently selected from the group consisting of hydrogen, $C_1$-$C_4$ alkyl and halogen;

or $R^{27'}$ and $R^{28'}$ together with the two carbon atoms to which they are attached form a double bond;

each $R^{36'}$ is independently selected from hydrogen, halogen and $C_1$-$C_4$ alkyl;

$R^{37'}$, $R^{38'}$, $R^{39'}$, $R^{40'}$, $R^{41'}$, $R^{42'}$, $R^{43'}$ and $R^{44'}$ are independently selected from the group consisting of hydrogen, fluorine, methyl and trifluoromethyl;

$R^{45'}$, $R^{46'}$, $R^{47'}$, $R^{48'}$ and $R^{49'}$ are independently selected from the group consisting of hydrogen, fluorine, chlorine, bromine, iodine, methyl, ethyl, isopropyl, cyclopropyl, C≡CH, CH=CH$_2$, C(CH$_3$)=CH$_2$, CF$_3$, CHF$_2$, CH$_2$F, —CHF—CH$_3$, —CF$_2$—CH$_3$, methoxy, difluoromethoxy, trifluoromethoxy, ethoxy, methlythio, methylsulfinyl and methylsulfonyl;

$R^{50'}$, $R^{51'}$, $R^{52'}$, $R^{53'}$, $R^{54'}$, $R^{55'}$ and $R^{56'}$ are selected, independently of each other, from the group consisting of hydrogen, fluorine, methyl, CH$_2$F and CF$_3$;

$R^{57'}$, $R^{58'}$, $R^{59'}$ and $R^{60'}$ are selected, independently of each other, from the group consisting of hydrogen, halogen, cyano, $C_1$-$C_4$ alkyl, CHF$_2$ and CF$_3$;

provided that at least one of $R^{57'}$, $R^{58'}$, $R^{59'}$ and $R^{60'}$ is not hydrogen;

$R^{61'}$ and $R^{62'}$ are selected independently of each other from the group consisting of hydrogen, fluorine, methyl, ethyl, $CHF_2$ and $CF_3$;

$R^{62'}$, $R^{63'}$, $R^{64'}$, $R^{65'}$, $R^{66'}$, $R^{67'}$ and $R^{68'}$ are selected independently of each other from the group consisting of hydrogen, fluoro, methyl, ethyl, methoxy, difluoromethoxy, trifluoromethoxy, $CHF_2$ and $CF_3$;

$R^{69'}$ is selected from hydrogen and $C_1$-$C_4$ alkyl;

n is 0 or 1;

p and q are independently selected from 0 and 1;

r and s are 0 and t is 1 or 0.

12. A fungicidal composition according to claim 3, wherein component A) is a compound of formula (I) wherein $G^1$ is a saturated $C_{10}$ fused bicyclic ring system;

$G^2$ is a $C_5$-$C_6$ cycloalkenyl group;

$G^3$ is phenyl;

$G^4$ is cyclohexyl or cyclopentyl;

$G^5$ is $C_6$ cycloalkyl, which is optionally substituted by one or more groups independently selected from ethyl, n-propyl, iso-propyl, n-butyl, iso-butyl, sec-butyl, tert-butyl, n-pentyl, —CH($CH_3$)—$CH_2$—$CH_2$—$CH_3$, —CH—CH($CH_3$)—$CH_2$—$CH_3$, —$CH_2$—$CH_2$—CH($CH_3$)—$CH_3$, —$CH_2$—$CH_2$—CH($CH_3$)$_2$ and —CH($CH_3$)—CH($CH_3$)$_2$;

$G^6$ is phenyl, which must be substituted by at least one fluorine and is optionally further substituted by one or more methyl, bromine, iodine or chlorine;

$G^7$ is methylene;

$G^{10}$ is phenyl, which is optionally substituted by one or more groups independently selected from halogen, CN, methyl, ethyl, n-propyl, iso-propyl, ethenyl, methoxy, ethoxy, iso-propyloxy, phenyl, $CHF_2$, $CF_3$, CHF—$CH_3$ and $OCHF_2$;

$G^{11}$ is methylene substituted by at least one group independently selected from methyl, $CF_3$ and ethyl;

$G^{13}$ is a $C_8$-$C_{11}$ spirobicyclic system containing 0, 1 or 2 O or N atoms, wherein there are no adjacent O atoms, which is optionally substituted by one or more groups independently selected from halogen, $C_1$-$C_4$ alkyl, $C_1$-$C_4$ alkoxy and =O;

$G^{17}$ is a five- to six-membered monocyclic heteroaromatic ring system which can contain 1 or 2 members selected from the group consisting of N, O and S, it not being possible for each ring system to contain —O—O—, —S—S— and —O—S— fragments, and it being possible for the five- to six-membered ring system to be itself mono- or polysubstituted by groups selected from the group consisting of halogen, CN, $C_1$-$C_4$ alkyl, $C_1$-$C_4$ haloalkyl, $C_1$-$C_4$ alkoxy, $C_1$-$C_4$ haloalkoxy, phenyl or fluorophenyl;

$R^{1'}$, $R^{2'}$, $R^{3'}$, $R^{4'}$ and $R^{5'}$ are each hydrogen;

$R^{11'}$, $R^{12'}$, $R^{13'}$ and $R^{14'}$ are selected, independently of each other, from the group consisting of hydrogen, halogen, cyano, $C_1$-$C_4$ alkyl and $C_1$-$C_4$ alkoxy;

$R^{15'}$, $R^{16'}$, $R^{17'}$, $R^{18'}$, $R^{19'}$, $R^{20'}$, $R^{21'}$, $R^{22'}$, $R^{23'}$, $R^{24'}$ and $R^{25'}$ are each independently selected from hydrogen, methyl, ethyl and isopropyl;

$R^{26'}$ is N—OH, N—O—$C_1$-$C_4$ alkyl, N—O—$C_2$-$C_4$ alkenyl, N—O—$C_2$-$C_4$ alkynyl, N—O—$C_1$-$C_4$ haloalkyl, N—O—$C_2$-$C_4$ haloalkenyl, N—O-benzyl, N—O-phenyl, N—O-halophenyl, O and C($R^{36'}$);

$R^{27'}$, $R^{28'}$, $R^{29'}$, $R^{30'}$, $R^{31'}$, $R^{32'}$, $R^{33'}$, $R^{34'}$ and $R^{35'}$ are each hydrogen or methyl;

or $R^{27'}$ and $R^{28'}$ together with the two carbon atoms to which they are attached form a double bond;

each $R^{36'}$ is independently selected from hydrogen, halogen and $C_1$-$C_4$ alkyl;

$R^{37'}$, $R^{38'}$, $R^{39'}$, $R^{40'}$, $R^{41'}$, $R^{42'}$, $R^{43'}$ and $R^{44'}$ are hydrogen;

$R^{45'}$, $R^{46'}$, $R^{47'}$, $R^{48'}$ and $R^{49'}$ are independently selected from the group consisting of hydrogen, fluorine, chlorine, methyl, $CF_3$, $CHF_2$, $CH_2F$, methoxy, difluoromethoxy and trifluoromethoxy;

$R^{53'}$, $R^{51'}$, $R^{52'}$, $R^{53'}$, $R^{54'}$, $R^{55'}$ and $R^{56'}$ are each hydrogen;

$R^{57'}$, $R^{58'}$, $R^{59'}$ and $R^{60'}$ are selected, independently of each other, from the group consisting of hydrogen and halogen;

provided that at least one of $R^{57'}$, $R^{58'}$, $R^{59'}$ and $R^{60'}$ is not hydrogen;

$R^{61'}$, $R^{62'}$, $R^{63'}$, $R^{64'}$, $R^{65'}$, $R^{66'}$, $R^{67'}$ and $R^{68'}$ are hydrogen;

$R^{69'}$ is hydrogen;

n is 0 or 1;

p and q are independently selected from 0 and 1;

r, s and t are each 0.

13. A compound according to formula (IV)

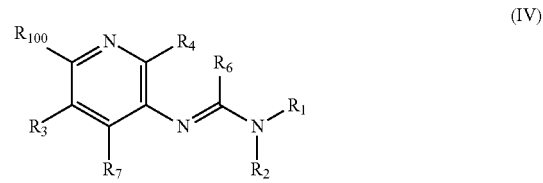

(IV)

wherein $R_{100}$ is halogen, SH, $C_1$-$C_4$ alkylthio, $C_1$-$C_4$-alkylsulfinyl, $C_1$-$C_4$ alkylsulfonyl;

$R_1$ and $R_2$ are each independently selected from hydrogen, $C_1$-$C_4$ alkyl, $C_3$-$C_4$ alkenyl, $C_3$-$C_4$ alkynyl, ($R_{10}$)carbonyl and ($R_{10}$)oxycarbonyl;

or $R_1$ and $R_2$ together with the nitrogen atom to which the are attached form a 5- or 6 membered cyclic group which may be saturated or unsaturated and may contain a further heteroatom selected from S or O;

$R^3$ represents hydrogen, halogen, cyano, nitro, mercapto, hydroxy, —C(=S)$NH_2$, —$SF_5$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$alkoxy, $C_1$-$C_6$ haloalkoxy, $C_3$-$C_6$cycloalkyl amino, $C_1$-$C_2$ alkylamino, di($C_1$-$C_6$alkyl)amino, a 5-membered heterocycle containing 1-4 nitrogen atoms, piperidino, morpholino, thiomorpholino, formyl, hydroxycarbonyl, $C_2$-$C_7$ alkoxycarbonyl, $C_2$-$C_7$ haloalkoxycarbonyl, $C_4$-$C_7$ alkenyloxycarbonyl, $C_4$-$C_7$ haloalkenyloxycarbonyl, $C_2$-$C_7$ alkylcarbonyl, $C_2$-$C_7$ haloalkylcarbonyl, $C_1$-$C_6$alkylthio, $C_1$-$C_6$alkylsulfinyl, $C_1$-$C_6$alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ hydroxyalkyl, phenyl or benzyl wherein the phenyl and benzyl are optionally substituted by one or more groups independently selected from the group consisting of halogen, cyano, hydroxy, mercapto, amino, $C_1$-$C_6$ alkyl, $C_1$-$C_6$ haloalkyl, $C_1$-$C_6$alkoxy, $C_1$-$C_6$ haloalkoxy, $C_1$-$C_6$alkylthio, $C_1$-$C_6$alkylsulfinyl and $C_1$-$C_6$alkylsulfonyl;

$R_4$ represents hydrogen, halogen, cyano, amino, $C_1$-$C_4$ alkyl, $C_1$-$C_4$ haloalkyl, $C_3$-$C_6$ cycloalkyl, $C_2$-$C_4$ alkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, methylamino or dimethylamino;

$R_6$ is selected from hydrogen and SH; and $R_7$ is hydrogen, halogen or $C_1$-$C_4$ alkyl.

14. A method of controlling phytopathogenic diseases on useful plants or on propagation material thereof, which comprises applying to the useful plants, the locus thereof or propagation material thereof a combination of components A) and B) in a synergistically effective amount according to claim 1 together with an inert carrier, and optionally an adjuvant.

15. A fungicidal composition, comprising a combination of components A) and B) according to claim 1 together with an inert carrier, and optionally an adjuvant, wherein the weight ratio of A) to B) is between 100:1 and 1:6000.

16. A method of protecting natural substances of plant origin, which have been taken from their natural life cycle, and/or their processed forms, which comprises applying to said natural substances of plant and/or animal origin or their processed forms a combination of components A) and B) according to claim 1 in a synergistically effective amount.

* * * * *